United States Patent
Suessmuth et al.

(10) Patent No.: US 10,308,595 B2
(45) Date of Patent: Jun. 4, 2019

(54) ALBICIDIN DERIVATIVES, THEIR USE AND SYNTHESIS

(71) Applicant: TECHNISCHE UNIVERSITAET BERLIN, Berlin (DE)

(72) Inventors: Roderich Suessmuth, Berlin (DE); Julian Kretz, Basel (CH); Vivien Schubert, Berlin (DE); Alexander Pesic, Berlin (DE); Manuela Huegelland, Berlin (DE); Monique Royer, Montpellier (FR); Stephane Cociancich, Ganges (FR); Philippe Rott, Wellington, FL (US); Dennis Kerwat, Berlin (DE); Stefan Graetz, Berlin (DE)

(73) Assignee: TECHNISCHE UNIVERSITÄT BERLIN, Berlin (DE)

( * ) Notice: Subject to any disclaimer, the term of this patent is extended or adjusted under 35 U.S.C. 154(b) by 0 days.

(21) Appl. No.: 14/768,323

(22) PCT Filed: Feb. 14, 2014

(86) PCT No.: PCT/EP2014/052922
§ 371 (c)(1),
(2) Date: Aug. 17, 2015

(87) PCT Pub. No.: WO2014/125075
PCT Pub. Date: Aug. 21, 2014

(65) Prior Publication Data
US 2015/0376120 A1 Dec. 31, 2015

Related U.S. Application Data

(60) Provisional application No. 61/765,056, filed on Feb. 15, 2013.

(30) Foreign Application Priority Data

| Jun. 6, 2013 | (EP) | 13170957 |
| Nov. 8, 2013 | (EP) | 13192247 |
| Dec. 31, 2013 | (EP) | 13199920 |
| Dec. 31, 2013 | (EP) | 13199921 |
| Dec. 31, 2013 | (EP) | 13199922 |

(51) Int. Cl.
| C07C 255/44 | (2006.01) |
| C07C 233/83 | (2006.01) |
| C07C 275/42 | (2006.01) |
| C07D 317/08 | (2006.01) |
| C07D 333/38 | (2006.01) |
| C07C 311/21 | (2006.01) |
| C07D 241/28 | (2006.01) |
| C07D 207/34 | (2006.01) |
| C07D 277/56 | (2006.01) |

(Continued)

(52) U.S. Cl.
CPC .......... *C07C 255/44* (2013.01); *C07C 233/83* (2013.01); *C07C 237/42* (2013.01); *C07C 255/03* (2013.01); *C07C 255/29* (2013.01); *C07C 255/57* (2013.01); *C07C 275/42* (2013.01); *C07C 311/21* (2013.01); *C07C 311/46* (2013.01); *C07C 311/47* (2013.01); *C07D 207/34* (2013.01); *C07D 209/34* (2013.01); *C07D 213/81* (2013.01); *C07D 237/24* (2013.01); *C07D 241/24* (2013.01); *C07D 241/28* (2013.01); *C07D 263/24* (2013.01); *C07D 277/56* (2013.01); *C07D 295/14* (2013.01); *C07D 295/155* (2013.01); *C07D 307/56* (2013.01); *C07D 311/12* (2013.01); *C07D 317/08* (2013.01); *C07D 317/46* (2013.01); *C07D 333/38* (2013.01); *C07F 9/062* (2013.01); *C07F 9/09* (2013.01); *C07F 9/12* (2013.01); *C07C 2601/02* (2017.05); *C07C 2601/08* (2017.05); *C07C 2601/14* (2017.05); *C07C 2601/18* (2017.05); *C07C 2603/74* (2017.05)

(58) Field of Classification Search
CPC ............................ C07C 255/44; C07C 233/83
See application file for complete search history.

(56) References Cited

U.S. PATENT DOCUMENTS

| 4,525,354 A | 6/1985 | Birch et al. |
| 2011/0178104 A1 | 7/2011 | Scott et al. |

FOREIGN PATENT DOCUMENTS

| CN | 101693763 | 4/2010 |
| JP | 2006306771 | 11/2006 |

(Continued)

OTHER PUBLICATIONS

Rott, et al. Document No. 156:631762, retrieved from STN; (2011).*
Pseudomonas [online] {retrieved on Apr. 11, 2008 from the internet} {URL; http://www.merck.com/mmhe/sect17/ch190/ch190o.html #sec17-ch 190-ch190o-262}.*
Wender et al. J. Am. Chem. Soc. 2006, vol. 126, pp. 6302-6303, "Asymmetric Catalysis of the [5+2] Cycloaddition Reaction of Vinylcyclopropanes and π-Systems".

(Continued)

*Primary Examiner* — Shawquia Jackson
(74) *Attorney, Agent, or Firm* — Brooks Kushman P.C.

(57) ABSTRACT

Antibiotically active compounds characterized by general formula (I), wherein X1, BB, BC, BD, BE and X2 are building blocks with D1, D2, D3, D4 or D5 being linkers which include carbon, sulphur, nitrogen, phosphor and/or oxygen atoms and which are covalently connecting the moieties BA and BB, BB and BC, BC and BD, BD and BE and BE and BF, respectively, and wherein in particular the building block BC comprises an amino acid derivative. The compounds for use in a method of treatment of diseases, in particular for use in a method of treatment of bacterial infections are also disclosed.

14 Claims, 13 Drawing Sheets

Figure 1:
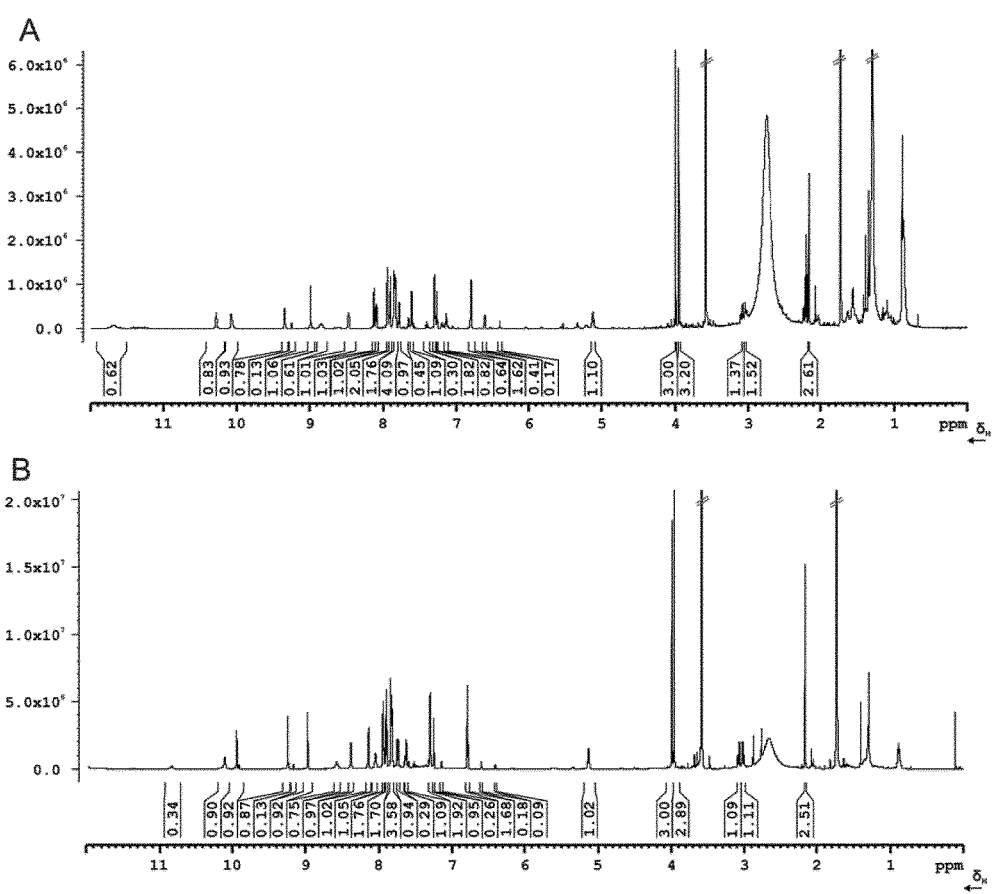

(51) Int. Cl.

| | | |
|---|---|---|
| C07D 295/14 | (2006.01) | |
| C07D 307/56 | (2006.01) | |
| C07F 9/12 | (2006.01) | |
| C07C 311/46 | (2006.01) | |
| C07C 311/47 | (2006.01) | |
| C07C 237/42 | (2006.01) | |
| C07C 255/29 | (2006.01) | |
| C07C 255/57 | (2006.01) | |
| C07C 255/03 | (2006.01) | |
| C07F 9/09 | (2006.01) | |
| C07D 209/34 | (2006.01) | |
| C07D 213/81 | (2006.01) | |
| C07D 237/24 | (2006.01) | |
| C07D 241/24 | (2006.01) | |
| C07D 263/24 | (2006.01) | |
| C07D 295/155 | (2006.01) | |
| C07D 311/12 | (2006.01) | |
| C07D 317/46 | (2006.01) | |
| C07F 9/06 | (2006.01) | |

(56) References Cited

FOREIGN PATENT DOCUMENTS

| | | |
|---|---|---|
| WO | 2004035760 | 4/2004 |
| WO | 2008112938 | 9/2008 |
| WO | 2012158672 | 11/2012 |

OTHER PUBLICATIONS

Baquero et al. Molecular Microbiology 1995, vol. 18, No. 2, pp. 301-311, "sbmC, a stationary-phase induced SOS *Escherichia coli* gene, whose product protects cells from the DNA replication inhibitor microcin B17".

Davies et al. J. Am. Chem. Soc. 1993, vol. 115, pp. 9468-9479, "a-Hydroxy Esters as Chiral Auxiliaries in Asymmetric Cyclopropanations by Rhodium (II)-Stabilized Vinylcarbenoids".

Chandrappa et al. Synlett 2010, No. 20, pp. 3019-3022, "An Efficient Method for Aryl Nitro Reduction and Cleavage of Azo Compounds Using Iron Powder/Calcium Chloride".

Perez et al. J. Med. Chem. 1992, vol. 35, pp. 4584-4588, "Dihydroxynitrobenzaldehydes and Hydroxymethoxynitrobenzaldehydes: Sythesis and Biological Activity as Catechol-O-methyltransferase Inhibitors".

Wishart et al. Biochimica et Biophysica Acta 1993, vol. 1164, pp. 36-46, "Improved synthetic methods for the selective deuteration of aromatic amino acids: applications of selective protonation towards the identification of protein biding intermediates through nuclear magnetic resonance".

Zhang et al. Organic Letters 2010, vol. 12, No. 17, pp. 3942-3945, "Synthesis of 5-Amino-oxazole-4-carboxylates from a-Chloroglycinates".

Tichenor et al. J. Am. Chem. Soc. 2004, vol. 126, pp. 8396-8398, "Total Synthesis, Structure Revision, and Absolute Configuration of (+)-Yatakemycin".

Greene et al. Part 1 of 2, Protective Groups in Organic Synthesis, Third Edition 1999, All together 815 Pages, Split into two Parts, Part 1 is 450 Pages and Part 2 is 365 Pages, "The Role of Protective Groups in Organic Synthesis".

Greene et al. Part 2 of 2, Protective Groups in Organic Synthesis, Third Edition 1999, All together 815 Pages, Split into 2 Parts, Part 1 is 450 Pages and Part 2 is 365 Pages, "Protection for the Carboxyl Group".

Chan et al. Part 1 of 2, Fmoc Solid Phase Peptide Synthesis, A Practical Approach 1989, All together 371 Pages, Split into 2 Parts, Part 1 is 160 Pages and Part 2 is 211 Pages. "Introduction—a retrospective viewpoint".

Chan et al. Part 2 of 2, Fmoc Solid Phase Peptide Synthesis, A Practical Approach 1989, All together 371 Pages, Split into 2 Parts, Part 1 is 160 Pages and Part 2 is 211 Pages. "Synthesis of Modified peptides".

Larock, Comprehensive Organic Transformations, A Guide to Functional Group Preparations, Two Volume Set, 2nd Edition, Wiley: 2010, 1 Page Abstract only, "Comprehensive Organic Transformations, A Guide to Functional Group Preparations".

Bodanszky et al. Principles of Peptide Synthesis, Springer-Verlag, Berlin 1993, 1 Page Abstract Only, "Principles of Peptide Synthesis".

Smith, March's Advanced Organic Chemistry. Reactions, Mechanisms, and Structure. 7th Edition May 2013, 1 Page Abstract Only, "March's Advanced Organic Chemistry. Reactions, Mechanisms, and Structure".

Charette et al. Organic Reactions 2001, vol. 58, 85 Pages, "Simmons-Smith Cyclopropanation Reaction".

International Search Report for PCT/EP2014/052922, Completed by the European Patent Office on Jul. 14, 2014, 5 Pages.

Coelho et al. Science Jan. 18, 2013, vol. 339, pp. 307-310, "Olefin Cyclopropanation via Carbene Transfer Catalyzed by Engineered Cytochrome P450 Enzymes".

Boucher et al. IDSA Report on Development Pipeline Jan. 2009, 12 Pages, "Bad Bugs, No Drugs: No ESKAPE! An Update from the Infectious Diseases Society of America".

Livermore et al. Journal of Antimicrobial Chemotherapy 2008, vol. 62, Suppl.2, pp. ii41-ii54, "Non susceptibility trends among Enterobacteriaceae from bacteraemias in the UK and Ireland, Jun. 2001".

Yamamoto et al. Chem. Pharm. Bull. 2002, vol. 50, No. 1, pp. 47-52, "A New Nonpeptide Tachykinin NK1 Receptor Antagonist Isolated from the Plants of Compositae".

Zhang et al. Journal of Applied Microbiology 1998, vol. 85, pp. 1023-1028, "Factors affecting biosynthesis by Xanthomonas albilineans of albicidin antibotics and phytotoxins".

Vivien et al. Antimicrobial Agents and Chemotherapy Apr. 2007, vol. 51, No. 4, pp. 1549-1552, "Heterologous Production of Albicidin: a Promising Approach to Overproducing and Characterizing This Potent Inhibitor of DNA Gyrase".

Rott et al. Journal of Bacteriology Aug. 1996, vol. 178, No. 15, pp. 4590-4596, "At Least Two Separate Gene Clusters Are Involved in Albicidin Production by Xanthomonas albilineans".

Zhang et al. PNAS USA Sep. 1997, vol. 94, pp. 9984-9989, "The gene for albicidin detoxification from Pantoea dispersa encodes an esterase and attenuates pathogenicity of Xanthomonas albilineans to sugarcane".

Bostock et al. Journal of Applied Microbiology 2006, vol. 101, pp. 151-160, "A DHA14 drug efflux gene from Xanthomonas albilineans confers high-level albicidin antibiotic resistance in *Escherichia coli*".

Hashimi et al. Antimicrobial Agents and Chemotherapy Jan. 2007, vol. 51, No. 1, pp. 181-187, "The Phytotoxin Albicidin is a Novel Inhibitor of DNA Gyrase".

Dutot et al. Chemistry a European Journal 2008, vol. 14, pp. 3154-3163, "Synthesis and Characterisation of Helical β-Peptide Architectures that Contain (S)-β3-HDOPA (Crown Ether) Derivatives".

Adamczyk et al. Organic Preparations and Procedures International 1996, vol. 28, No. 4, 6 Pages, "Synthesis of Procainamide Metabolites. N-Acetyl Desethylprocainamide and Desethylprocainamide".

Wessjohann et al. Chem. Rev. 2003, vol. 103, pp. 1625-1647, "Biosynthesis and Metabolism of Cyclopropane Rings in Natural Compounds".

Petersen et al. Organic Syntheses Inc., Organic Syntheses Coll. 1973, 4 Pages, "Working with Hazardous Chemicals".

PAC, 2007 Glossary of terms used in photochemisty, 3rd edition (IUPAC Recommendations 2006), 1 Page, "DI-PIE-methane rearrangement".

Osol et al. Remington's Pharmaceutical Sciences 15th Edition, Jun. 1976, vol. 65, No. 6, p. 933, "Remington's Pharmaceutical Sciences".

Chemical Abstract, Registry No. 1319838-00-0, XP 002727103, Dated Aug. 19, 2011, 2 Pages.

(56) References Cited

OTHER PUBLICATIONS

Chemical Abstract, Registry No. 1320744-17-9, XP 002727102, Dated Aug. 21, 2011, 2 Pages.
Chemical Abstract, Registry No. 1091978-94-7, XP 002727100, Dated Dec. 30, 2008, 2 Pages.
Chemical Abstract, Registry No. 1315923-72-8, XP 002727101, Dated Aug. 11, 2011, 2 Pages.
Chemical Abstract, Registry No. 1091978-94-7, American Chemical Society 2016, 1 Page.
Nair et al. Chemical Abstract, XP 002727097, Journal of the American Chemical Society 2013, 12 Pages, "A Synthetic Zipper Peptide Motif Orchestrated via Co-operative Interplay of Hydrogen Bonding, Aromatic Stacking, and Backbone Chirality".
Lloyd-Williams et al. CRC Press 1997, 1 Page Abstract Only, "Chemical Approaches to the Synthesis of Peptides and Proteins".
Japanese Office Action and English Translation for Japanese Application No. JP2015-557442, dated Jan. 30, 2018, All together 7 Pages.

* cited by examiner

Figure 3 A and B
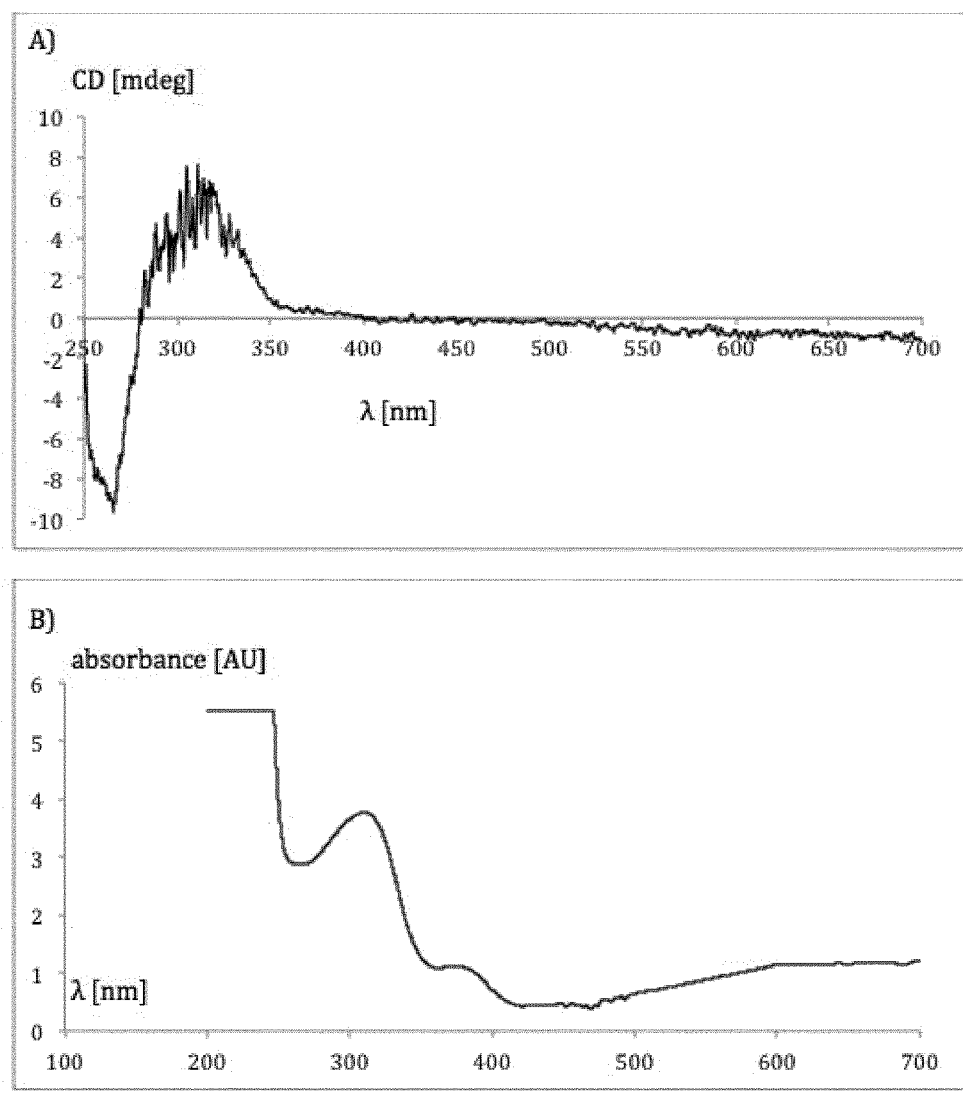

Figure 3 C and D
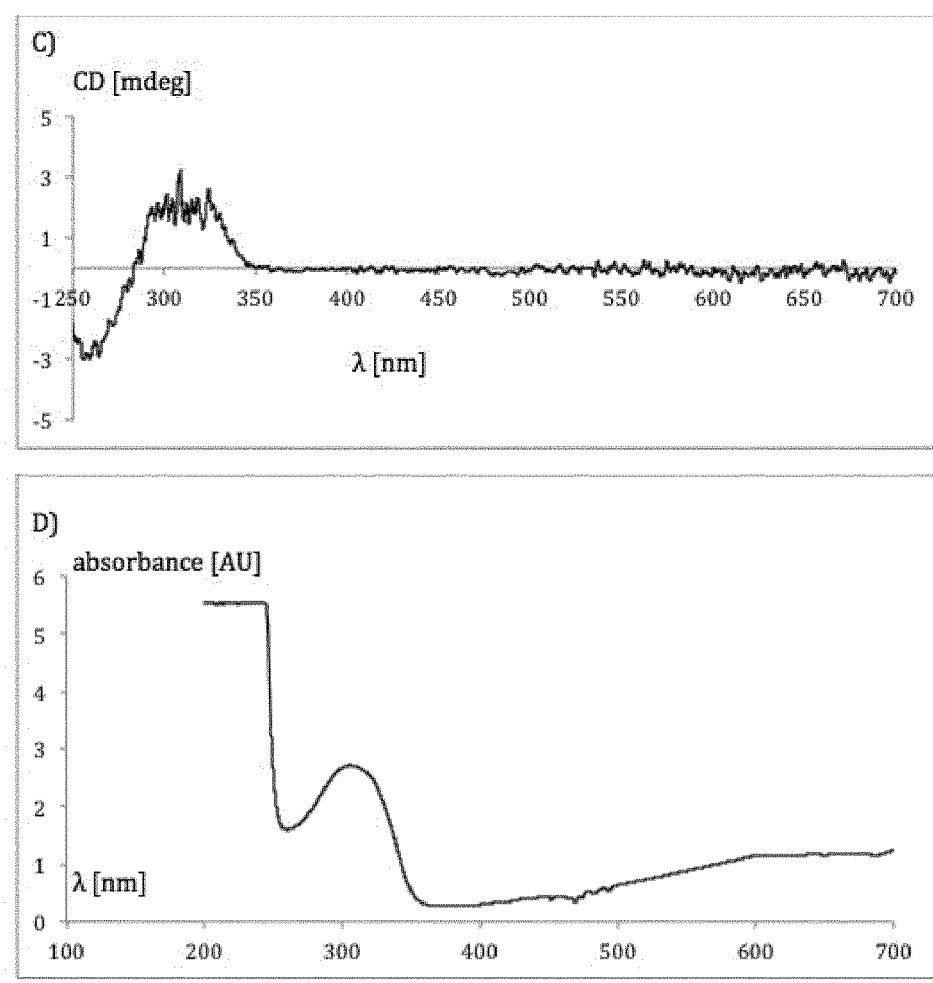

Figure 3 E and F
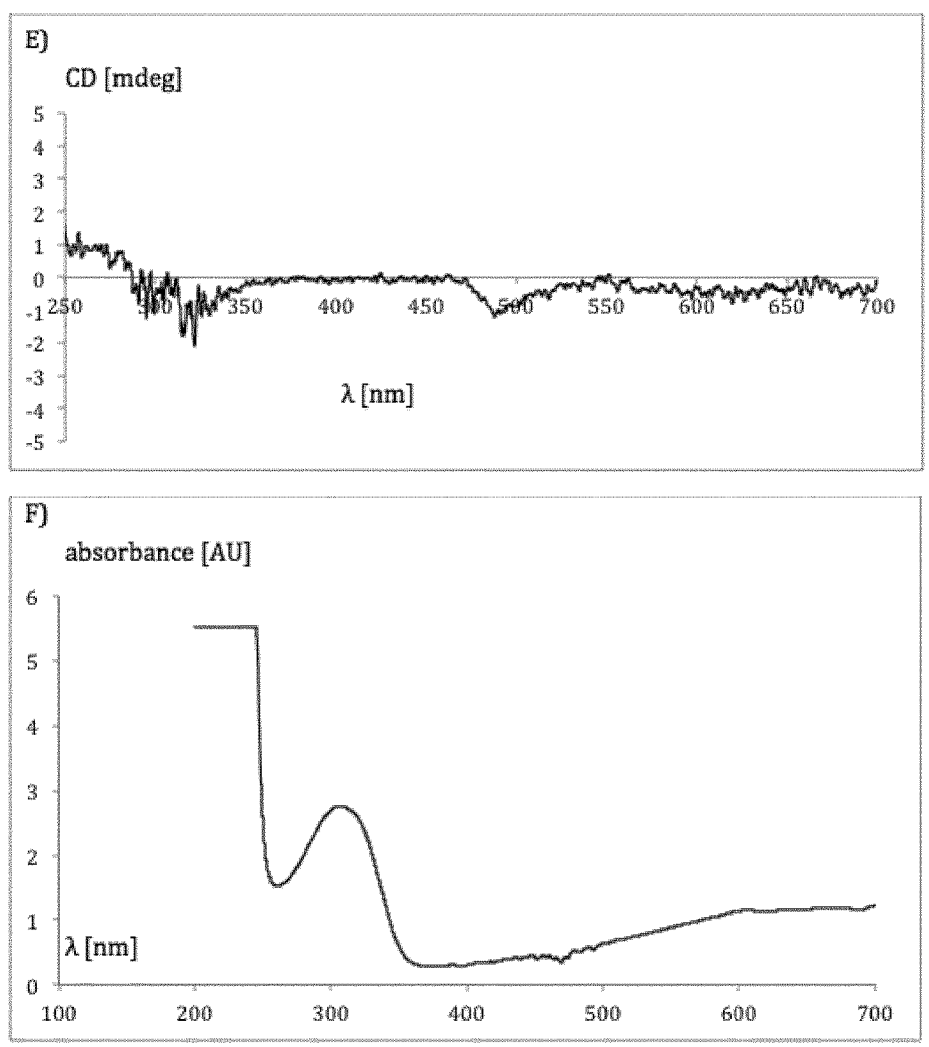

Figure 11

| sample(20 μl) | amount | Sensitive (WT DH5α strain) | Spontaneous resistant DH5α strain (probably mutated in the nucleoside transporter Tsx) | Sensistive DH5α with the empty plasmid pBC | DH5α with the plasmid pBCalb14 (albicidin pump) | DH5α with the plasmid pBCalb19 (McbG) | Sensitive (RYC1000) strain with the empty plasmid pUC19) | RYC1000 strain with the plasmid pMR100 (SbmC protein : microcin B17 resistant protein) | Sensitive (DH5α with the empty plamsid pGex4T3) | DH5α with the plasmid GST-AlbD (albicidin detoxifying hydrolase) |
|---|---|---|---|---|---|---|---|---|---|---|
| synthetic albicidin (10) | 2 ng | 8 | 0 | 8 | 7.5 | 6.5 | 8 | 6.5 | 8.5 | 0.5 |
| | 0.2 ng | 6 | 0 | 5 | 5 | 3 | 6 | 4 | 6 | 0 |
| | 0.02 ng | 2 | 0 | 2 | 1 | 0.5 | 2.5 | 0.5 | 3 | 0 |
| natural product albicidin from heterologous host | 2 ng | 7.5 | 0 | 7.5 | 7.5 | 5.5 | 7 | 6 | 8 | 0 |
| | 0.2 ng | 5.5 | 0 | 5 | 5 | 3 | 5 | 3 | 6 | 0 |
| | 0.02 ng | 2 | 0 | 2 | 0.5 | 0 | 1 | 0 | 2.5 | 0 |

ALBICIDIN DERIVATIVES, THEIR USE AND SYNTHESIS

CROSS-REFERENCE TO RELATED APPLICATION

This application is the U.S. national phase of PCT Application No. PCT/EP2014/052922 filed on Feb. 14, 2014, which claims the benefit of U.S. Provisional Application 61/765,056 filed Feb. 15, 2013 and claims priority to EP Patent Application No. 13170957.8 filed on Jun. 6, 2013, EP Patent Application No. 13192247.8 filed on Nov. 8, 2013, EP Patent Application No. 13199920.3 filed on Dec. 31, 2013, EP Patent Application No. 13199921.1 filed on Dec. 31, 2013, and EP Patent Application No. 13199922.9 filed on Dec. 31, 2013, the disclosures of which are incorporated in their entirety by reference herein.

Albicidin has been initially described as an antibiotic substance derived from *Xanthomonas albilineans*, a protobacterial sugarcane pathogen (U.S. Pat. No. 4,525,354 to Birch and Patil, incorporated by reference herein).

Since its first description in 1985, ß-albicidin has eluded structural determination in spite of its interesting properties, namely its antibiotic activity against gram-negative bacteria, a group which encompasses many medically important pathogens such as, for example, *Escherichia coli, Salmonella, Shigella, Pseudomonas, Moraxella, Helicobacter, Stenotrophomonas, Neisseria, Hemophilus* and *Legionella*.

However, the molecular structure of albicidin was determined only recently or solvates thereof. Thus, the respective salts, hydrates or solvents are not considered as impurities according to the previous definition. The "purity" of a compound may be determined using elemental analysis, HPLC analysis using UV diode array detection also in combination with mass spectrometry detection, or quantitative NMR analysis.

DIPEA is N,N-Diisopropylethylamine (CAS No. 7087-68-5). HATU is (Dimethylamino)-N,N-dimethyl(3H-[1,2,3]triazolo[4,5-b]pyridin-3-yloxy)methaniminium hexafluorophosphate (CAS No. 148893-10-1). TEA is Triethylamine (CAS No. 121-44-8). BTC is Bis(trichloromethyl) carbonate (CAS No. 32315-10-9). PFP is Pentafluorophenole (CAS No. 771-61-9). PNP is para-nitrophenol (CAS No. 100-02-7). HONB N-Hydroxy-5-norbornene-2,3-dicarboximide (CAS No. 21715-90-2). NHS is N-hydroxysuccinimidyl (CAS No. 6066-82-6). BOB is Benzotriazolyloxytris-(dimethylamino)-phosphonium hexafluorophosphate (CAS No. 56602-33-6). pyBOP is Benzotriazol-1-yl-oxy-tripyrrolidinophosphonium hexafluorophosphate (CAS No. 128625-52-5). HBTU is N,N,N',N'-Tetramethyl-O-(1H-benzotriazol-1-yl)uronium hexafluorophosphate (CAS No. 94790-37-1). DCC is N,N-Dicyclohexylcarbodiimide (CAS No. 538-75-0). DIC is N,N'-Dicyclopropylcarbodiimide (CAS No. 693-13-0), EDC is 1-Ethyl-3-(3-dimethylaminopropyl)carbodiimide (CAS No. 25952-53-8, 22572-40-3, 1892-57-5). TFFH is Fluoro-N,N,N',N'-tetramethylformamidinium hexafluorophosphate (CAS. No. 164298-23-1). DEPT is 3-(Diethoxyphosphoryloxy)-1,2,3-benzotriazin-4(3H9-one (CAS No. 165534-43-0).

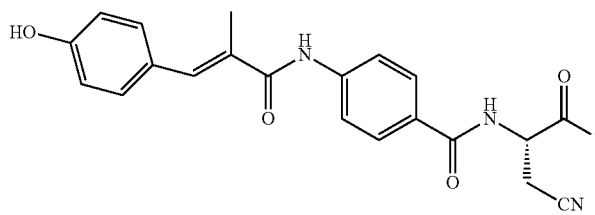
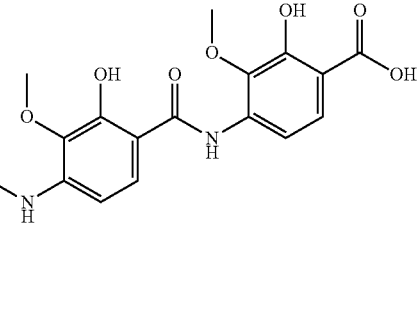

(Albicidin)

The inventors found out that a variation of one building block of albicidin provides compounds, which comprise antibiotic properties, in particular an antibiotic activity against resistant pathogens.

The problem underlying the present invention is the provision of new compounds, which comprise antibiotic properties, a method of their synthesis and their use. This problem is attained by the subject-matter of the independent claims.

TERMS AND DEFINITIONS

The term "purity" as used in the context of the present specification with respect to a preparation of a certain compound refers to the content of said compound relative to the sum of all compounds contained in the preparation. The term "compound" in this context is to be understood as a compound according to the general formula 1 (or any specific embodiments thereof) as well as any salts, hydrates A protecting group in the context of the present specification is a group employed to reduce the reactivity of a particular moiety. Protecting groups are well known to the person skilled in the art of organic chemistry. P. G. M. Wuts, "Greene's Protective Groups in Organic Synthesis," 4th ed. (2006, Wiley; ISBN 978-0-471-69754-1; 5th edition June 2013 Wiley-Blackwell).

PGH is a suitable protection group for hydroxyl groups known in the art.

PGA is a suitable protection group for carboxylic acid groups known in the art.

PGN is a suitable protection group for a $NH_2$ moiety of for example amino or amide groups known in the art. Hereinafter, due to simplicity reasons, a $NH_2$ moiety will be described as an amino moiety irrespective of the further parts of the compound.

M is a so called masked functional group such as—without being limited to—a $-NO_2$ group or a $-N_3$ group. A masked functional group can be reduced under certain conditions to an $-NH_2$ functional group but does not interfere with the coupling reactions of an acid partner with an amino partner, as discussed further below.

Protecting groups for use as PGN, PGH or PGA groups herein include, but are not limited to: (i) ethers such as methyl, substituted methyl (methoxymethyl, methylthiomethyl, (phenyidimethylsilyl) methoxymethyl, benzyloxymethyl, p-methoxybenzyloxymethyl, p-nitrobenzyloxymethyl, o-nitrobenzyloxymethyl, (4-methoxyphenoxy) methyl, guaia-colmethyl, t-butoxymethyl, 4-pentenyloxymethyl, siloxymethyl, 2-methoxyethoxymethyl, 2,2,2,-trichloroethoxymethyl, bis(2-chloroethoxymethyl), 2-(trimethylsilyl)ethoxymethyl, menthoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxide, 1-[(2-chloro-4-methyl)phenyl]-4-methoxypiperidin-4-yl, 1-(2-fluorophenyl)-4-methoxypiperidin-4-yl, 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl), substituted ethyl (1-ethoxyethyl,1-(2-chloroethoxy) ethyl, 1-[2-(trimethyl-silyl) ethoxy]ethyl, 1-methyl-1-methoxyethyl, 1-methyl-1-benzyloxyethyl, 1-methyl-1-benzyloxy-2-fluoro-ethyl, 1-methyl-1-phenoxyethyl, 2,2,2-trichloroethyl, 1,1-dianisyl-2,2,2-trichloroethyl, 1,1,1,3,3,3,-hexafluoro-2-phenylisopropyl, 2-trimethylsilylethyl, 2-(benzylthio)ethyl, 2-(phenyl-selenyl)ethyl), t-butyl, allyl, propargyl, p-chlorophenyl, p-methoxyphenyl, p-nitrophenyl, 2,4-dinitrophenyl, 2,3,5,6-tetrafluoro-4-(trifluoromethyl)phenyl, benzyl, substituted benzyl (p-methoxybenzyl, 3,4,-dimethoxybenzyl, o-nitrobenzyl, p-nitrobenzyl, p-halobenzyl, 2,6-dichlorobenzyl, p-phenylbenzyl, p-phenylenzyl, 2,6-difluorobenzyl, p-acylaminobenzyl, p-azidobenzyl, 4-azido-3-chlorobenzyl, 2-trifluoromethylbenzyl, p-(methylsulfinyl)benzyl), 2- and 4-picolyl, 3-methyl-2-picolyl-N-oxide, 2-quinolinylmethyl, 1-pyrenylmethyl, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri (p-methoxyphenyl) methyl, 4-(4-'-bromophenacyloxy)phenyldiphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)-methyl, 4,4'-dimethoxy-3"-[N-(imidazolylmethyl)]trityl, 4,4'-dimethoxy-3"-[N-(imidazolylethyl) carbamoyl]trityl, 1,1-bis(4-methoxyphenyl-l'-pyrenylmethyl, 9-Anthryl, 9-(9-phenyl) xanthenyl, 4-(17-tetrabenzo[a,c,g.lgfluorenylmethyl)-4, 4"-dimethoxytrityl, 9-(9-phenyl-10-oxo)anthryl, 1,3-benzodithiolan-2-yl, benzisothiazolyl, s,s-dioxido, silylethers (trimethylsilyl, triethylsilyl, triisopropylsilyl, dimethylisopropylsilyl, diethylisopropylsilyl, dimethylthexylsilyl, t-butyl-dimethylsilyl, t-butyidiphenylsilyl, tribenzylsilyl, tri-p-xylylsilyl, triphenylsilyl, diphenyl-methylsilyl, di-t-butylmethylsilyl, tris(t-rimethylsilyl)silyl(sisyl), (2-hydroxystyryl)dimethylsilyl, (2-hydroxystyryl)diisopropylsilyl, t-butylmethoxyphenylsilyl, t-butoxydiphenylsilyl); (ii) esters such as formate, benzoylformate, acetate, substituted acetate (chloroacetate, dichloroacetate, trichloroacetate, trifluoroacetate, methoxyacetate, triphenylmethoxyacetate, phenoxyacetate, p-chlorophenoxyacetate, phenylacetate, p-P-phenylacetate, diphenyl-acetate), nicotinate, 3-phenylpropionate, 4-pentenoate, 4-oxopentanoate (levulinate), 4,4-(ethylenedithio)pentanoate, 5-[3-bis(4-methoxyphenyl)hydroxymethylphenoxy]levulinate, pivaloate, 1-adamantoate, crotonate, 4-methoxycrotonate, benzoate, p-phenylbenzoate, 2,4,6-trimethylbenzoate(mesitoate), carbonates (methyl, methoxymethyl, 9-fluorenylmethyl, ethyl, 2,2,2-trichloroethyl, 1,1,-dimethyl-2,2,2-trichloroethyl, 2-(trimethylsilyl) ethyl, 2-(phenyl-sulfonyl)ethyl, 2-(triphenylphosphonio) ethyl, isobutyl, vinyl, allyl, p-nitrophenyl, benzyl, p-methoxybenzyl, 3,4,-dimethoxybenzyl, o-nitrobenzyl, p-nitrobenzyl, 2-dansylethyl, 2-(4-nitrophenyl)ethyl, 2-(2,4-dinitrophenyl)ethyl, 2-cyano-1-phenylethyl, S-benzylthiocarbonate, 4-ethoxy-1-naphthyl, methyldithiocarbonate), 2-iodobenzoate, 4-azidobutyrate, 4-nitro-4-methylpentanoate, o-(dibromomethyl)benzoate, 2-formylbenzenesulfonate, 2-(methylthiomethoxy)ethylcarbonate, 4-(methylthiomethoxy)butyrate, 2-(methylthiomethoxy-methyl)benzoate, 2-(chloroacetoxymethyl)benzoate, 2-[(2-chloroacetoxy)ethyl]benzoate, 2-[2-(benzyloxy)ethyl]benzoate, 2-[2-(4-methoxybenzyloxyl)ethyl]benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccionoate, (E)-2-methyl-2-butenoate (tigloate), o-(methoxycarbonyl) benzoate, p-P-benzoate, a-naphthoate, nitrate, alkyl N,N,N',N'-tetramethylphosphorodiamidate, 2-chlorobenzoate, 4-bromobenzoate, 4-nitrobenzoate, 3'5'-dimethoxybenzoin, a wild and woolly photolabile fluorescent ester, N-phenylcarbamate, borate, dimethylphosphinothioyl, 2,4-dinitrophenylsulfenate; and (iii) sulfonates (sulfate, allylsulfonate, methanesulfonate (mesylate), benzylsulfonate, tosylate, 2-[(4-nitrophenyl)ethyl]sulfonate).

An activated carboxylic acid moiety in the context of the present specification relates to a carboxylic acid (COOH) derivative that undergoes amidation (condensation with an amine moiety) with primary or secondary under conditions that allow for the preservation of other chemical functionalities present in either reaction partner. Preferred reaction conditions are pH 4-9 and temperatures in the range of about −30° C. to of about 80° C., in particular at temperatures from 25° C. to 30° C.

Examples for activated carboxylic acid moieties are pentafluorophenol (PFP) esters, para-nitrophenol (PNP) esters, 2,4,5-trichlorophenol esters, N-Hydroxy-5-norbornene-2,3-dicarboximide (HONB) esters, N-hydroxy-succinimidyl (NHS) ester, carboxylic acid chloride (acyl chloride), carboxylic acid fluoride (acyl fluoride), carboxylic acid bromide (acyl bromide), which may be produced—without being limited to—by the reaction of the carboxylic acid and thionyl chloride phosphorus pentachloride, cyanuric chloride, $SO_2Cl_2$, $SOCl_2$, triphenylphosphine and tetrachloromethane, Fluoro-N,N,N',N'-tetramethylformamidinium hexafluorophosphate (TFFH) or cyanuric fluoride, benzotriazole esters or carbodiimide esters, generated by use of the carboxylic acid and coupling agents such as Benzotriazolyloxytris-(dimethylamino)-phosphonium hexafluoro-phosphate (BOB), Benzotriazol-1-yl-oxy-tripyrrolidinophosphonium hexafluorophosphate (pyBOP), N,N,N',N'-Tetramethyl-O-(1H-benzotriazol-1-yl)uronium hexafluorophosphate (HBTU), (O-(7-azabenzotriazol-1-yl)-N,N,N',N'-tetramethyluronium hexafluorophosphate) (HATU), N,N'-Dicyclohexylmethandiimin (DCC), N,N'-Diisopropylcarbodiimide (DIC), 1-Ethyl-3-(3-dimethylaminopropyl)carbodiimide (EDC), or 3-(Diethoxyphosphoryloxy)-1,2,3-benzotriazin-4(3H)-one (DEPT) bromotri(pyrrolidino)phosphonium hexafluorophosphate (PyBrop).

Furthermore carboxylic acid moieties can be activated with chloroformates (e.g. ethyl chloroformate).

Further examples of activated carboxylic acid moieties are symmetric and mixed carbonic anhydrides. Carbonic anhydrides may be synthesized by use of coupling reagents, such as—without being limited to— 1,1'-Carbonyldiimidazol (CDl), 1,1'-carbonylbis(3-methylimidazoliumtriflate) (CB-MIT) and the before mentioned coupling agents or from carboxylic acid and acid chloride (e.g. pivaloylchloride), or from carboxylic acid and chloroformates (e.g. ethyl chloroformate). Alternatively anhydrides may be synthesized from carboxylic acid and 2-ethoxy-1-ethoxycarbonyl-1,2-dihydroquinoline (EDDQ)

Coupling agents to achieve activated carboxylic moieties may further be—without being limited to—AOP (7-Azabenzotriazol-1-yloxytris(dimethylamino)phosphonium hexafluorophosphate —CAS 156311-85-2), PyAOP ([(7-azabenzotriazol-1-yl)oxy]tris-(pyrrolidino)phosphonium hexafluorophosphate CAS-156311-83-0), Brop (bromotris(dimethylamino)phosphonium hexafluorophosphate, CAS 50296-37-2), PyBrop (bromotri(pyrrolidino)phosphonium hexafluorophosphate, CAS 132705-51-2), PyClop (chlorotri(pyrrolidino)phosphonium hexafluorophosphate, CAS 128625-52-5), BOP-Cl (N,N0-bis(2-oxo-3-oxazolidinyl)-phosphinic chloride, CAS 68641-49-6), TDBTU (2-(3,4-dihydro-4-oxo-1,2,3-benzotriazin-3-yl)-1,1,3,3-tetramethyluronium tetrafluoroborate, CAS: 125700-69-8), TNTU (2-(5-norbornene-2,3-dicarboximido)-1,1,3,3-tetramethyluronium tetrafluoroborate—CAS 125700-73-4), TSTU (2-succinimido-1,1,3,3-tetramethyluroniumtetrafluoroborate—CAS 105832-38-0), BTC (bis(trichloromethyl)carbonate—CAS 32315-10-9), BTFFH (bis(tetramethylene)fluoroformamidinium hexafluorophosphate—CAS 164298-25-3), DFIH (1,3-dimethyl-2-fluoro-4,5-dihydro-1H-imidazoliumhexafluorophosphate)

Furthermore, imidazolium agents may be employed to achieve activated carboxylic moieties, whereby examples of imidazolium agents are—without being limited to—BOI (2-(benzotriazol-1-yl)oxy-1,3-dimethylimidazolidinium hexafluorophosphate—CAS 123377-20-8) or CMBI (2-chloro-1,3-dimethyl 1H-benzimidazoliumhexafluorophosphate).

The coupling reactions may be supported by addition of bases or acylation catalysts such as—without being limited to—(N,N-Diisopropylethylamine) (DIEA), N-Methylmorpholine (NMM), 4-Dimethylaminopyridine (DMAP), 2,4,6-Trimethylpyridine (sym-collidine) or 2,6-di-tert-butyl-4-dimethylaminopyridine (DBDMAP). The addition of bases allows a deprotonation of the carboxylic acid and facilitates the reaction to the respective activated carboxylic acid.

Furthermore, bases may be added, in particular the above mentioned bases, in order to prevent a removal of the protecting group due to acidic by products. In certain cases the coupling reaction may be catalyzed by addition of acylation catalysts as DMAP.

Alternatively, the carboxylic acid moiety may be activated by using a catalytic amount of a proton acid or a Lewis acid such as—without being limited to—boronic acid catalyst.

The coupling reactions may also be achieved by the azide coupling method using diphenyl phosphorazidate (DPPA) or alternative azides.

The term "substituted" refers to the addition of a substituent group to a parent moiety.

"Substituent groups" can be protected or unprotected and can be added to one available site or to many available sites in a parent moiety. Substituent groups may also be further substituted with other substituent groups and may be attached directly or by a linking group such as an alkyl, an amide or hydrocarbyl group to a parent moiety. "Substituent groups" amenable herein include, without limitation, halogen, oxygen, nitrogen, sulphur, hydroxyl, alkyl, alkenyl, alkynyl, acyl (—C(O)$R^a$), carboxyl (—C(O)O$R^a$), aliphatic groups, alicyclic groups, alkoxy, substituted oxy (—O$R^a$), aryl, aralkyl, heterocyclic radical, heteroaryl, heteroarylalkyl, amino (—N($R^b$)($R^c$)), imino(=N$R^b$), amido (—C(O)N($R^b$)($R^c$) or —N($R^b$)C(O)$R^a$), hydrazine derivatives (—C(NH)N$R^a R^b$), tetrazole (C$N_4 H_2$), azido (—$N_3$), nitro (—$NO_2$), cyano (—CN), isocyano (—NC), cyanato (—OCN), isocyanato (—NCO), thiocyanato (—SCN); isothio-cyanato (—NCS); carbamido (—OC(O)N($R^b$)($R^c$) or —N($R^b$)C(O)O$R^a$), thiol (—S$R^b$), sulfinyl (—S(O)$R^b$), sulfonyl (—S(O)$_2 R^b$), sulfonamidyl (—S(O)$_2$N($R^b$)($R^c$) or —N($R^b$)S(O)$_2 R^b$) and fluorinated compounds —$CH_2 CF_3$, —$CHFCF_3$, —$CF_2 CF_3$, —$CHF_2$, —$CH_2 F$, —$CF_3$, —$OCF_3$, —$SCF_3$, —$SOCF_3$ or —$SO_2 CF_3$. Wherein each $R^a$, $R^b$ and $R^c$ is, independently, H or a further substituent group with a preferred list including without limitation, H, alkyl, alkenyl, alkynyl, aliphatic, alkoxy, acyl, aryl, heteroaryl, alicyclic, heterocyclic and heteroarylalkyl.

As used herein the term "alkyl," refers to a saturated straight or branched hydrocarbon moiety containing up to 8, particularly up to 4 carbon atoms. Examples of alkyl groups include, without limitation, methyl, ethyl, propyl, butyl, isopropyl, n-hexyl, octyl, and the like. Alkyl groups typically include from 1 to about 8 carbon atoms ($C_1$-$C_8$ alkyl), particularly with from 1 to about 4 carbon atoms ($C_1$-$C_4$ alkyl).

As used herein the term "cycloalkyl" refers to an interconnected alkyl group forming a saturated or unsaturated ring or polyring structure containing 3 to 10, particularly 5 to 10 carbon atoms. Examples of cycloalkyl groups include, without limitation, cyclopropane, cyclopentane, cyclohexane, norbornane, decaline or adamantan (Tricyclo [3.3.1.1]decan), and the like. Cycloalkyl groups typically include from 5 to 10 carbon atoms ($C_5$-$C_{10}$ cycloalkyl).

Alkyl or cycloalkyl groups as used herein may optionally include further substituent groups. A substitution on the cycloalkyl group also encompasses an aryl, a hetreocylce or a heteroaryl substituent, which can be connected to the cycloalkyl group via one atom or two atoms of the cycloalkyl group (like tetraline).

As used herein the term "haloalkyl," refers to a saturated straight or branched hydrocarbon moiety containing 1 to 8, particularly 1 to 4, carbon atoms and at least one halogen atom, in particular Cl or F, connected to a carbon atom. Examples of haloalkyl groups include, without limitation, $CF_3$, $CHF_2$, $CH_2 F$, $CH_2 CF_3$, $CH_2 CHF_2$, $CH_2 CH_2 F$, $CHFCF_3$, $CHFCHF_2$, $CHFCH_2 F$, $CF_2 CF_3$, $CF_2 CHF_2$, $CF_2 CH_2 F$ and the like. Haloalkyl groups typically include 1 to 4 carbon atoms ($C_1$-$C_4$ haloalkyl). More particularly haloalkyl groups comprise only F as halogen atoms.

As used herein the term "halo cycloalkyl" refers to an interconnected alkyl group forming a saturated or unsaturated ring or polyring structure containing 3 to 10, particularly 5 to 10 carbon atoms and at least one halogen atom, in particular Cl or F, connected to a carbon atom. Examples of halo cycloalkyl groups include, without limitation, fluorocyclopropane, chlorocyclohexane, dichlorocyclohexane, chloroadamantan, and the like. Halo cycloalkyl groups typically include from 5 to 10 carbon atoms ($C_5$-$C_{10}$ cycloalkyl). More particularly cyclohaloalkyl groups comprise only F as halogen atoms.

Halo alkyl or halo cycloalkyl groups as used herein may optionally include further substituent groups. A substitution on the halo cycloalkyl group also encompasses an aryl, a hetreocylce or a heteroaryl substituent, which can be connected to the halo cycloalkyl group via one atom or two atoms of the halo cycloalkyl group (like tetraline).

As used herein the term "alkenyl," refers to a straight or branched hydrocarbon chain moiety containing up to 8 carbon atoms and having at least one carbon-carbon double bond. Examples of alkenyl groups include, without limitation, ethenyl, propenyl, butenyl, 1-methyl-2-buten-1-yl, dienes such as 1,3-butadiene and the like. Alkenyl groups typically include from 2 to about 8 carbon atoms, more typically from 2 to about 4 carbon atoms. Alkenyl groups as used herein may optionally include further substituent groups.

As used herein the term "alkynyl," refers to a straight or branched hydrocarbon moiety containing up to 8 carbon atoms and having at least one carbon-carbon triple bond. Examples of alkynyl groups include, without limitation, ethynyl, 1-propynyl, 1-butynyl, and the like. Alkynyl groups typically include from 2 to about 8 carbon atoms, more typically from 2 to about 4 carbon atoms. Alkynyl groups as used herein may optionally include further substituent groups.

As used herein the term "carboxy," refers to an carboxy (—C(=O)—O— or —O—C(=O)—) alkyl moiety containing 1 to 8, particularly 1 to 4 carbon atoms comprising at least one carboxy moiety, wherein the carboxy group is used to attach the carboxy group to a parent molecule.

Examples of carboxy groups include without limitation, formate, acetate, lactate, citrate, oxalate and the like. Carboxy groups as used herein may optionally include further substituent groups. In particular "carboxy" groups include straight or branched polycarboxy groups (polyester), which comprise several interconnected momomere carboxy groups (e.g. —C(=O)—O—$CH_2$—$CH_2$—). Non limiting examples are polyehtylester or polyacrylate.

As used herein the term "alkoxy," refers to an oxygen alkyl moiety containing 1 to 8, particularly 1 to 4 carbon atoms comprising at least one oxygen moiety, wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups. In particular "alkoxy" groups include straight or branched polyalkoxy groups (polyether), which comprise several interconnected momomere alkoxy groups (e. g. —O—$CH_2$—$CH_2$—). Non limiting examples are polyehtyleneglycol (PEG) or poly-propylenglycol (PPG).

As used herein the term "heterocycle" refers to an interconnected alkyl group forming a saturated or unsaturated ring or polyring structure containing 3 to 10, particularly 5 to 10 carbon atoms in which at least one carbon atom is replaced with an oxygen, a nitrogen or a sulphur atom forming a non aromatic structure. Examples of heterocycle groups include, without limitation, oxalane, pyrrolidine or piperidine. Heterocyclic groups as used herein may optionally include further substituent groups. A substitution on the heterocyclic group also encompasses an aryl, a cycloalkyl or a heteroaryl substituent, which can be connected to the heterocyclic group via one atom or two atoms of the heterocyclic group (comparable to indole).

As used herein the term "aryl" refers to a hydrocarbon with alternating double and single bonds between the carbon atoms forming an aromatic ring structure, in particular a six ($C_6$ to ten ($C_{10}$) membered ring or polyring structure. The term "heteroaryl" refers to aromatic structures comprising a five to ten membered ring or polyring structure, comparable to aryl compounds, in which at least one member is an oxygen or a nitrogen or a sulphur atom. Due to simplicity reasons they are denominated $C_5$ to $C_{10}$ heteroaryl, wherein at least one carbon atom is replaced with an oxygen, a nitrogen or a sulphur atom forming an aromatic structure. For example a $C_5$ heteroaryl comprises a five membered ring structure with at least one carbon atom being replaced with an oxygen, a nitrogen or a sulphur atom. Examples for such a $C_5$ heteroaryl are triazole, pyrazole, imidazole, thiophen, furan or oxazole. A $C_6$ heteroaryl can be pyridine, pyrimidine or triazine. A $C_9$ heteroaryl can be indole and a $C_{10}$ heteroaryl can be quinoline. Aryl or hetero aryl groups as used herein may optionally include further substituent groups. A substitution on the hetero aryl group also encompasses an aryl, a cycloalkyl or a heterocycle substituent, which can be connected to the hetero aryl via one atom or two atoms of the hetero aryl group (comparable to indole). The same applies to an aryl group.

As used herein the term "linker" refers to a covalently connected straight chain or a ring structure of carbon, sulphur, nitrogen and/or oxygen atoms connecting a moiety comprising E or $R^4$ (as defined below) to the parent moiety (termed PM) providing a distance between these moieties. The distance may comprise between 1 up to 5 atoms, in particular 2 or 3 atoms, along the longitudinal extension direction of the parent moiety. The straight chain or the ring structure of the linker atoms may comprise further substituents. For example the linker may comprise a straight $C_4$-chain (butyl) providing a distance of 4 atoms or a methyl group providing a distance of 1 atom. The linker may further comprises a —C(=O)N($CH_3$)— or —C(=O)N(H)— group a providing a distance of 2 atoms. A —N(H)S($O_2$)— group also provides a distance of 2 atoms. A distance of three atoms may be provided by a —OC(=O)N(H)— or —N(H)C(=O)N(H)— group. The linker may further comprise a ring structure like a triazole providing a distance of 3 atoms along the longitudinal extension direction of the parent moiety.

As used herein the term "linking function" refers to a first linking function and a second linking function capable of selectively forming a covalent bond between each other (linking reaction or coupling reaction). Such linking reactions may be an organometallic coupling reaction, a Wittig reaction, an addition reaction, a condensation reaction a "click chemistry" reaction or an amide coupling reaction.

As used herein "*" indicates a stereo center of a L- or D-enantiomer, which is located on the tertiary carbon atom below the asterisk *, and wherein the compound of a general formula comprising "*" is an essentially pure L-enantiomer, an essentially pure D-enantiomer or a mixture of the L- and D-enantiomer of the same molecular formula, wherein in particular such a compound is an essentially pure L-enantiomer or an essentially pure D-enantiomer.

SUMMARY OF THE INVENTION

According to a first aspect, the invention relates to anti-biotically active compounds having a molecular structure as defined by formula 1

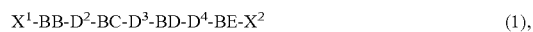

(1), a. with $X^1$ being
  i. selected from a substituent group S1 or S2, or
  ii. $R^4$-$D^1$-, with $R^4$ being selected from a substituent group S3, S4 or S5, or
  iii. BA-$D^1$- with BA-$D^1$- being selected from

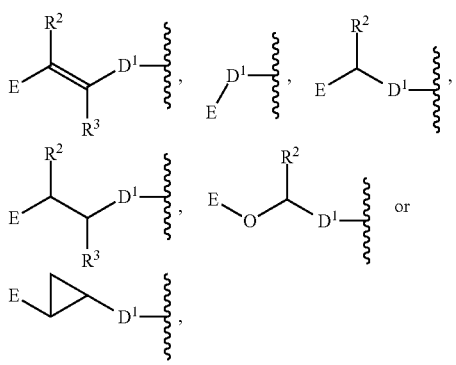

and with E being selected from a substituent group S3, S4 or S5, and b. with BB being selected from a substituent group S3 or S4, and c. with BC
 i. being selected from

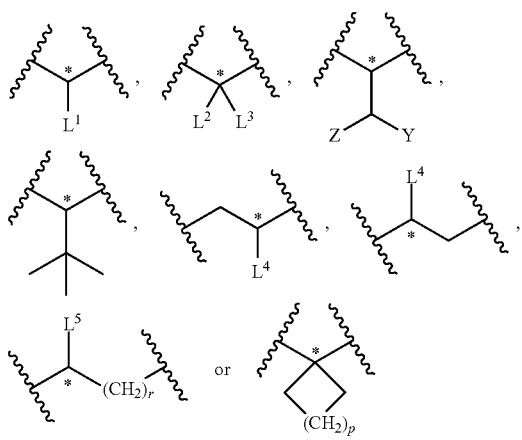

with p being 1, 2, 3, 4 or 5, in particular p being 2 or 3, and with r being 2, 3, 4 or 5, in particular r being 2, or ii. with -$D^2$-BC- being

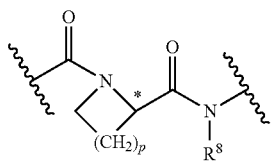

with p being 1, 2, 3, 4 or 5, in particular p being 2 or 3, and d. with BD being selected from a substituent group S3 or S4, and e. with BE being selected from a substituent group S3, and f. with $X^2$ being
 i. selected from a substituent group S1 or S2, and wherein a linker $D^5$ may be optionally situated between BE and the substituent group S1 or S2, or
 ii. being -$D^5$-BF, wherein BF is selected from a substituent group S2 with S1 being
—OH, —F, —Cl, —Br, I, —CCH, —CN, —$N_3$, —$NO_2$, —$OCH_3$, —$OCF_3$, —$NH_2$, —$NHCH_3$, —$N(CH_3)_2$, —$CH_3$, —$CH_2CH_3$ or —$CF_3$, with S2 being
—B(OR$^a$)(OR$^b$), —$(CH_2)_m$—R$^a$, —$(CH_2)_m$—OR$^a$, —$(CH_2)_m$—C(=O)R$^a$, —$(CH_2)_m$—C(=O)OR$^a$, —$(CH_2)_m$—OC(=O)R$^a$, —$(CH_2)_m$—OC(=O)OR$^a$, —$(CH_2)_m$—OC(=O)NR$^a$R$^b$, —$(CH_2)_m$—C(=O)NR$^a$R$^b$, —$(CH_2)_m$—C(=O)NR$^a$R$^b$, —$(CH_2)_m$—C(=O)NR$^b$(OR$^a$), —$(CH_2)_m$—C(=S)R$^a$, —$(CH_2)_m$—C(=S)OR$^a$, —$(CH_2)_m$—OC(=S)R$^a$, —$(CH_2)_m$—OC(=S)OR$^a$, —$(CH_2)_m$—OC(=S)NR$^a$R$^b$, —$(CH_2)_m$—C(=S)NR$^a$R$^b$, —$(CH_2)_m$—SR$^a$, —$(CH_2)_m$—S(=O)R$^a$, —$(CH_2)_m$—S($O_2$)R$^a$, —$(CH_2)_m$—S($O_2$)OR$^a$, —$(CH_2)_m$—OS($O_2$)R$^a$, —$(CH_2)_m$—OS($O_2$)OR$^a$, —$(CH_2)_m$—NR$^a$R$^b$, —$(CH_2)_m$—NR$^c$C(=O)R$^a$, —$(CH_2)_m$—NR$^c$C(=O)NR$^a$R$^b$, —$(CH_2)_m$—NR$^c$C(=O)OR$^a$, —$(CH_2)_m$—NR$^c$C(=S)R$^a$, —$(CH_2)_m$—NR$^c$C(=S)NR$^a$R$^b$, —$(CH_2)_m$—NR$^c$C(=S)OR$^a$, —$(CH_2)_m$—NR$^c$S($O_2$)R$^a$, —$(CH_2)_m$—P(=O)(OR$^b$)(OR$^a$), —$(CH_2)_m$—P(=O)(OR$^b$)(R$^a$) or —$(CH_2)_m$—S($O_2$)NR$^b$R$^a$, —$(CH_2)_m$—O—C(=O)-(M)—C(=O)OH, —$(CH_2)_m$—O—C(=O)-(M)—C(=O)OR$^a$, —$(CH_2)_m$—O—C(=O)-(M)—R$^a$, —$(CH_2)_m$—O—$(CH_2)_q$—P(=O)(R$^{ba}$)(R$^{aa}$), —$(CH_2)_m$—C(=O)O—$(CH_2)_q$—P(=O)(R$^{ba}$)(R$^{aa}$), —$(CH_2)_m$—C(=O)O—$(CH_2)_q$—S($O_2$)OH or —$(CH_2)_m$—C(=O)O—$(CH_2)_q$—S($O_2$)OR$^a$ with R$^{aa}$ being selected independently from each other from —R$^a$ or —OR$^a$, with R$^{ba}$ being selected independently from each other from —R$^b$ or —OR$^b$, with M being a substituted or unsubstituted $C_1$-$C_8$ alkyl, in particular an unsubstituted $C_1$-$C_8$ alkyl, with m being selected from 0, 1 or 2, in particular 0 or 1, with q being selected from 0, 1 or 2, in particular 0 or 1, with each R$^a$, R$^b$ or R$^c$ being selected, where applicable, independently from each other from hydrogen, —CN, a substituent group S3, a substituent group S4 or a substituent group S5, with S3 being
a substituted or unsubstituted $C_3$-$C_{10}$ cycloalkyl or a substituted or unsubstituted $C_3$-$C_{10}$ halo cycloalkyl, or a substituted or unsubstituted $C_6$-$C_{10}$ aryl, with S4 being
a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl, with S5 being
a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, with $R^2$ and $R^3$ of BA being selected, where applicable, independently from each other from —H, —F, —CN, —OH, —$NH_2$, —$NO_2$, —$NHCH_3$, —$NH(CH_3)_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —$NH_2$, —$NO_2$, —$NHCH_3$, —$NH(CH_3)_2$, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —CHFCF$_3$, —CF$_2$CF$_3$, —CHF$_2$, —CH$_2$F or —CF$_3$, more particularly with R$^2$ and R$^3$ being selected independently from each other from —H, —F or —CH$_3$, with L$^1$, L$^2$, L$^3$, L$^4$ or L$^5$ being selected independently from each other from, —H, —CH$_3$, —CH$_2$CH$_2$CH$_2$NHC(NR$^c$)N(R$^b$)(R$^a$), —CH$_2$CON(R$^b$)(R$^a$), —CH$_2$C(=O)OR$^a$, —CH$_2$SR$^a$, —CH$_2$CH$_2$C(=O)N(R$^b$)(R$^a$), —CH$_2$CH$_2$C(=O)OR$^a$, —CH$_2$(C$_3$H$_3$N$_2$), —CH$_2$CH$_2$CH$_2$—, —CH$_2$CH$_2$SCH$_3$, —CH$_2$(C$_6$H$_5$), —CH$_2$CH$_2$CH$_2$—, —CH$_2$OR$^a$, —CH(OR$^a$)CH$_3$, —CH$_2$(C$_8$H$_6$N)OR$^a$, —CH$_2$(C$_6$H$_4$)OR$^a$, —CH(CH$_3$)$_2$, —CCH, —CN, —OCH$_3$—CF$_3$, —R$^a$, —CH(R$^b$)(R$^a$), —CH$_2$C(=O)R$^a$, —C(=O)OR$^a$, —OC(=O)NR$^b$R$^a$, —C(=O)NR$^b$R$^a$, —CH$_2$C(=O)NR$^b$(OR$^a$), —CH$_2$S(O$_2$)R$^a$, —S(O$_2$)OR$^a$, —CH$_2$S(O$_2$)OR$^a$, —CH$_2$NR$^b$C(=O)R$^a$, —CH$_2$NR$^b$S(O$_2$)R$^a$, —CH$_2$P(=O)(OR$^b$)(OR$^a$), —CH$_2$P(=O)(OR$^b$)(R$^a$), —CH$_2$P(=O)(R$^b$)(R$^a$) or —CH$_2$S(O$_2$)NR$^b$R$^a$, with R$^a$ and R$^b$ being selected, where applicable, independently from each other from hydrogen, —CN, a substituent group S3, a substituent group S4 or a substituent group S5, with R$^8$ of -D$^2$-BC- being selected from —H, —CH$_3$, —CH$_2$CH$_3$, —OCH$_3$, —OCF$_3$, —CH$_2$CF$_3$, —CHFCF$_3$, —CF$_2$CF$_3$, —CHF$_2$, —CH$_2$F or —CF$_3$, in particular with R$^8$ being selected from H or CH$_3$, more particularly R$^8$ is H.

with Y being selected from —CN, —C(=O)OH, —C(=O)OCH$_3$, —C(=O)OCH$_2$CH$_3$, —C(=O)NHCH$_3$, —C(=O)NHCH$_2$CH$_3$, —C(=O)N(CH$_3$)$_2$, —C(=O)N(CH$_2$CH$_3$)$_2$, —C(=O)N(CH$_3$)(CH$_2$CH$_3$), —CF$_3$ or —C(=O)NH$_2$, and with Z being selected from —H, —OH, —CH$_3$, —CH$_2$CH$_3$, —OCH$_3$—NH$_2$—NHCH$_3$, —N(CH$_3$)$_2$ or —N(CH$_3$)$_3$$^+$, in particular Z is —H and Y is —CN or —C(=O)NH$_2$, with D$^1$, D$^2$, D$^3$, D$^4$ or D$^5$ being each, independently from each other, a linker which comprises carbon, sulphur, nitrogen, phosphor and/or oxygen atoms and which is covalently connecting the moiety, BA and BB (D$^1$), BB and BC (D$^2$), BC and BD (D$^3$), BD and BE (D$^4$) and BE and BF (D$^5$).

It is understood that a general expert will identify—on basis of his basic knowledge—combinations of the above mentioned selection, which will not lead to stable compounds. For example, concerning X the substituents —NR$^a$$_2$ and —NHR$^a$ are not possible with a C$_2$ alkynyl. Furthermore, concerning E connected to a vinyl group a C$_3$ heterocycle, like aziridine, is not a stable compound. The same applies for other combinations.

It is understood that the invention relates to compounds characterized by the general formula 1, wherein these compounds comprise no deuterium atoms in their structure. Furthermore the compounds may comprise one, two or more deuterium atoms (any hydrogen of the structure may be "exchanged") instead of hydrogen atoms. It is also possible that the compounds comprise only deuterium atoms instead of hydrogen atoms (all the H are "exchanged" with deuterium).

It is understood that the invention relates to essentially pure L- and D-enantiomers of the general formula 1 or mixtures of the L- and D-enantiomers of the same molecular formula, whereby the stereo center concerning the building block BC is indicated by an asterisk "*" and located on the tertiary carbon atom below the asterisk. Thus, the general formula 1 with the stereo center marked with an asterisk encompasses the essentially pure L- and the D-enantiomers.

A second aspect of the invention relates to the synthesis of compounds according to the general formula 1.

A further aspect of the invention relates to compounds according to the invention or obtained by a method according to the invention for use in a method of treatment of diseases, in particular for use in a method of treatment of bacterial infections.

DETAILED DESCRIPTION OF THE INVENTION

According to a first aspect, the invention relates to antibiotically active compounds having a molecular structure as defined by formula 1

$$X^1\text{-BB-}D^2\text{-BC-}D^3\text{-BD-}D^4\text{-BE-}X^2 \quad (1),$$

a. with X$^1$ being
  i. selected from a substituent group S1 or S2, or
  ii. R$^4$-D$^1$-, with R$^4$ being selected from a substituent group S3, S4 or S5, or
  iii. BA-D$^1$- with BA-D$^1$- being selected from

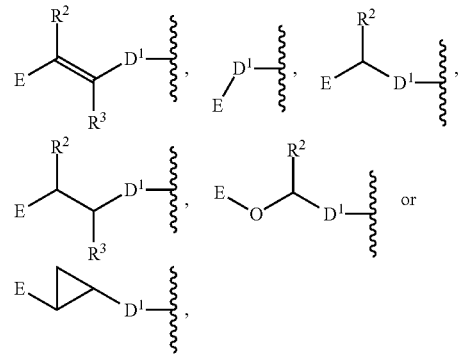

and with E being selected from a substituent group S3, S4 or S5, and b. with BB being selected from a substituent group S3 or S4, and c. with BC
  i. being selected from

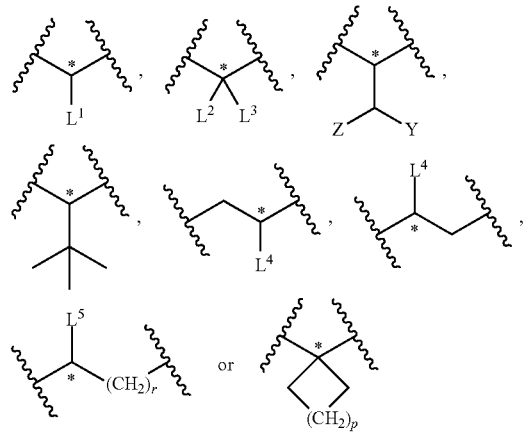

with p being 1, 2, 3, 4 or 5, in particular p being 2 or 3, and with r being 2, 3, 4 or 5, in particular r being 2, or ii. with -D²-BC- being

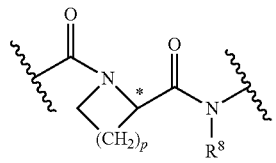

with p being 1, 2, 3, 4 or 5, in particular p being 2 or 3, and
d. with BD being selected from a substituent group S3 or S4, and
e. with BE being selected from a substituent group S3, and
f. with X² being
   i. selected from a substituent group S1 or S2, and wherein a linker D⁵ may be optionally situated between BE and the substituent group S1 or S2, or
   ii. being -D⁵-BF, wherein BF is selected from a substituent group S2
   with S1 being
      —OH, —F, —Cl, —Br, I, —CCH, —CN, —N₃, —NO₂, —OCH₃, —OCF₃, —NH₂, —NHCH₃, —N(CH₃)₂, —CH₃, —CH₂CH₃ or —CF₃,
   with S2 being
      —B(OR$^a$)(OR$^b$), —(CH₂)$_m$—R$^a$, —(CH₂)$_m$—OR$^a$, —(CH₂)$_m$—C(=O)R$^a$, —(CH₂)$_m$—C(=O)OR$^a$, —(CH₂)$_m$—OC(=O)R$^a$, —(CH₂)$_m$—OC(=O)OR$^a$, —(CH₂)$_m$—OC(=O)NR$^a$R$^b$, —(CH₂)$_m$—C(=O)NR$^a$R$^b$, —(CH₂)$_m$—C(=O)NR$^a$R$^b$, —(CH₂)$_m$—C(=O)NR$^b$(OR$^a$), —(CH₂)$_m$—C(=S)R$^a$, —(CH₂)$_m$—C(=S)OR$^a$, —(CH₂)$_m$—OC(=S)R$^a$, —(CH₂)$_m$—OC(=S)OR$^a$, —(CH₂)$_m$—OC(=S)NR$^a$R$^b$, —(CH₂)$_m$—C(=S)NR$^a$R$^b$, —(CH₂)$_m$—SR$^a$, —(CH₂)$_m$—S(=O)R$^a$, —(CH₂)$_m$—S(O₂)R$^a$, —(CH₂)$_m$—S(O₂)OR$^a$, —(CH₂)$_m$—OS(O₂)R$^a$, —(CH₂)$_m$—OS(O₂)OR$^a$, —(CH₂)$_m$—NR$^a$R$^b$, —(CH₂)$_m$—NR$^c$C(=O)R$^a$, —(CH₂)$_m$—NR$^c$C(=O)OR$^a$, —(CH₂)$_m$—NR$^c$C(=O)NR$^a$R$^b$, —(CH₂)$_m$—NR$^c$C(=S)R$^a$, —(CH₂)$_m$—NR$^c$C(=S)NR$^a$R$^b$, —(CH₂)$_m$—NR$^c$C(=S)OR$^a$, —(CH₂)$_m$—NR$^c$S(O₂)R$^a$, —(CH₂)$_m$—P(=O)(OR$^b$)(OR$^a$), —(CH₂)$_m$—P(=O)(OR$^b$)(R$^a$) or —(CH₂)$_m$—S(O₂)NR$^b$R$^a$, —(CH₂)$_m$—O—C(=O)-(M)—C(=O)OH, —(CH₂)$_m$—O—C(=O)-(M)—C(=O)OR$^a$, —(CH₂)$_m$—O—C(=O)-(M)—R$^a$, —(CH₂)$_m$—O—(CH₂)$_q$—P(=O)(R$^{ba}$)(R$^{aa}$), —(CH₂)$_m$—C(=O)O—(CH₂)$_q$—P(=O)(R$^{ba}$)(R$^{aa}$), —(CH₂)$_m$—C(=O)O—(CH₂)$_q$—S(O₂)OH or —(CH₂)$_m$—C(=O)O—(CH₂)$_q$—S(O₂)OR$^a$,
      with R$^{aa}$ being selected independently from each other from —R$^a$ or —OR$^a$,
      with R$^{ba}$ being selected independently from each other from —R$^b$ or —OR$^b$,
      with M being a substituted or unsubstituted C₁-C₈ alkyl, in particular an unsubstituted C₁-C₈ alkyl,
      with m being selected from 0, 1 or 2, in particular 0 or 1,
      with q being selected from 0, 1 or 2, in particular 0 or 1,
      with each R$^a$, R$^b$ or R$^c$ being selected, where applicable, independently from each other from hydrogen, —CN, a substituent group S3, a substituent group S4 or a substituent group S5,
   with S3 being
      a substituted or unsubstituted C₃-C₁₀ cycloalkyl or a substituted or unsubstituted C₃-C₁₀ halo cycloalkyl, or a substituted or unsubstituted C₆-C₁₀ aryl,
   with S4 being
      a substituted or unsubstituted C₃-C₁₀ heterocycle or a substituted or unsubstituted C₃-C₁₀ halo heterocycle, in particular a substituted or unsubstituted C₄-C₁₀ heterocycle or a substituted or unsubstituted C₄-C₁₀ halo heterocycle, or
      a substituted or unsubstituted C₅-C₁₀ heteroaryl,
   with S5 being
      a substituted or unsubstituted C₁-C₁₆ alkyl, a substituted or unsubstituted C₁-C₁₆ alkoxy, a substituted or unsubstituted C₁-C₁₆ carboxy, a substituted or unsubstituted C₂-C₁₆ alkenyl, a substituted or unsubstituted C₂-C₁₆ alkynyl, or a C₁-C₁₆ haloalkyl,
   with R² and R³ of BA being selected, where applicable, independently from each other from —H, —F, —CN, —OH, —NH₂, —NO₂, —NHCH₃, —NH(CH₃)₂, a substituted or unsubstituted C₁-C₃ alkyl, a substituted or unsubstituted C₁-C₃ alkoxy or a C₁-C₃ haloalkyl, in particular from —H, —F, —CN, —OH, —NH₂, —NO₂, —NHCH₃, —NH(CH₃)₂, —CH₃, —CH₂CH₃, —OCH₃, —OCH₂CH₃, —OCH₂CH₂CH₃, —OCH(CH₃)₂, —OCF₃, —CH₂CF₃, —CHFCF₃, —CF₂CF₃, —CHF₂, —CH₂F or —CF₃, more particularly with R² and R³ being selected independently from each other from —H, —F or —CH₃,
   with L¹, L², L³, L⁴ or L⁵ being selected independently from each other from, —H, —CH₃, —CH₂CH₂CH₂NHC(NR$^c$)N(R$^b$)(R$^a$), —CH₂CON(R$^b$)(R$^a$), —CH₂C(=O)OR$^a$, —CH₂SR$^a$, —CH₂CH₂C(=O)N(R$^b$)(R$^a$), —CH₂CH₂C(=O)OR$^a$, —CH₂(C₃H₃N₂), —CH₂CH₂CH₂CH₂, —CH₂CH₂SCH₃, —CH₂(C₆H₅), —CH₂CH₂CH₂—, —CH₂OR$^a$, —CH(OR$^a$)CH₃, —CH₂(C₈H₆N)OR$^a$, —CH₂(C₆H₄)OR$^a$, —CH(CH₃)₂, —CCH, —CN, —OCH₃—CF₃, —R$^a$, —CH(R$^b$)(R$^a$), —CH₂C(=O)R$^a$, —C(=O)OR$^a$, —OC(=O)NR$^b$R$^a$, —C(=O)NR$^b$R$^a$, —CH₂C(=O)NR$^b$(OR$^a$), —CH₂S(O₂)R$^a$, —S(O₂)OR$^a$, —CH₂S(O₂)OR$^a$, —CH₂NR$^b$C(=O)R$^a$, —CH₂NR$^b$S(O₂)R$^a$, —CH₂P(=O)(OR$^b$)(OR$^a$), —CH₂P(=O)(OR$^b$)(R$^a$), —CH₂P(=O)(R$^b$)(R$^a$) or —CH₂S(O₂)NR$^b$R$^a$,
      with R$^a$ and R$^b$ being selected, where applicable, independently from each other from hydrogen, —CN, a substituent group S3, a substituent group S4 or a substituent group S5,
      with R⁸ of -D²-BC- being selected from —H, —CH₃, —CH₂CH₃, —OCH₃, —OCF₃, —CH₂CF₃, —CHFCF₃, —CF₂CF₃, —CHF₂, —CH₂F or —CF₃, in particular with R⁸ being selected from H or CH₃, more particularly R⁸ is H.
   with Y being selected from —CN, —C(=O)OH, —C(=O)OCH₃, —C(=O)OCH₂CH₃, —C(=O)NHCH₃, —C(=O)NHCH₂CH₃, —C(=O)N(CH₃)₂, —C(=O)N(CH₂CH₃)₂, —C(=O)N(CH₃)(CH₂CH₃), —CF₃ or —C(=O)NH₂, and
   with Z being selected from —H, —OH, —CH₃, —CH₂CH₃, —OCH₃, —NH₂—NHCH₃, —N(CH₃)₂ or —N(CH₃)₃⁺, in particular Z is —H and Y is —CN or —C(=O)NH₂,
   with D¹, D², D³, D⁴ or D⁵ being each, independently from each other, a linker which comprises carbon, sulphur, nitrogen, phosphor and/or oxygen atoms and which is covalently connecting the moiety, BA and BB (D¹), BB and BC (D²), BC and BD (D³), BD and BE (D⁴) and BE and BF (D⁵).

In an embodiment of the present invention the compound according to the general formula 1 does not include a compound of the general formula 2a (2a)

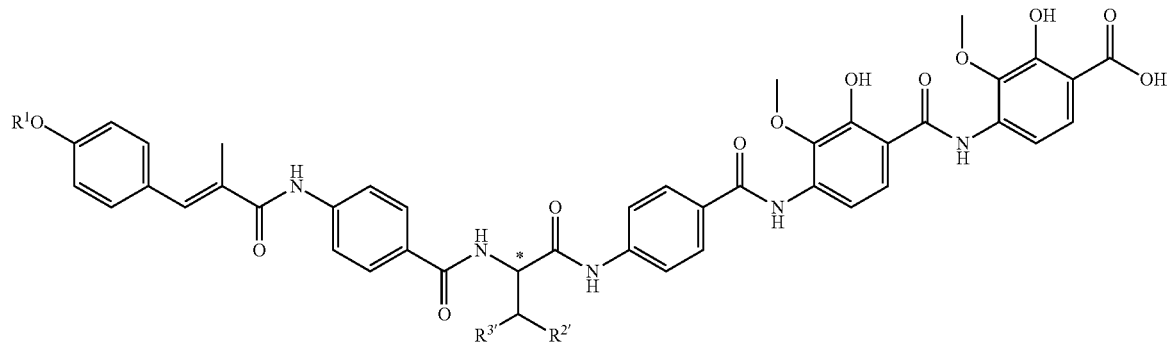

or the general formula 2b (2b)

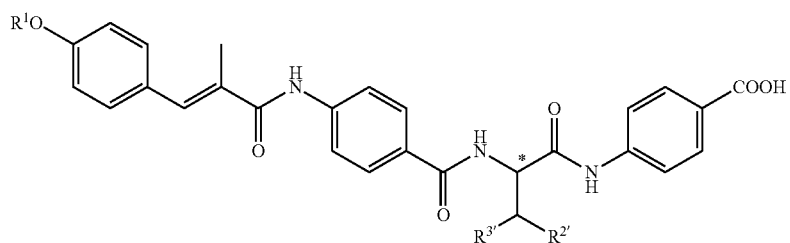

or the general formula 2c (2c)

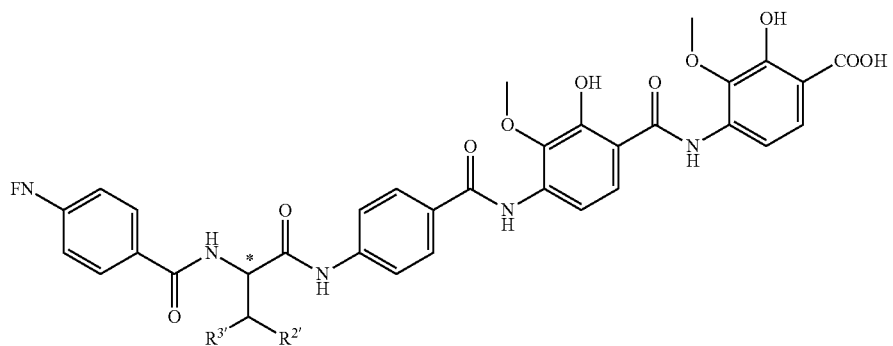

wherein $R^1$ is H or $CO(NH_2)$, $R^{2'}$ is $CO(NH_2)$ or CN, $R^{3'}$ is H or $OCH_3$, FN is $H_2N$ or Ma, wherein Ma is a masked functional group, in particular a —$NO_2$ or —$N_3$ moiety, and wherein the —$NH_2$, —NH—, —COOH or —OH moieties can comprise a removable protecting group (PGN, PGH or PGA), in particular an allyl moiety and/or an activated carboxylic acid moiety $CO^{act}$, in particular a —COCl moiety.

According to a first sub aspect (sub aspect 1) of the first aspect, the invention relates to compounds having a molecular structure as defined by a general formula (3), (formula 3)

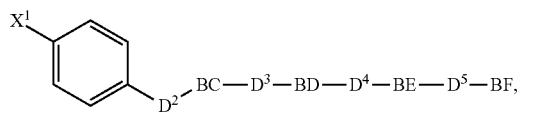

with $X^1$, $D^2$, BC, $D^3$, BD, $D^4$, BE, $D^5$ and BF having the same meaning as defined previously.

According to another sub aspect (sub aspect 2) of the first aspect, the invention relates to compounds having a molecular structure as defined by a general formula (4), (formula 4)

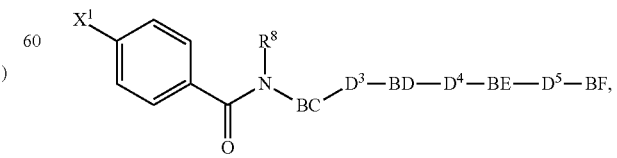

with $X^1$, $R^8$, BC, $D^3$, BD, $D^4$, BE, $D^5$ and BF having the same meaning as defined previously.

According to another sub aspect (sub aspect 3) of the first aspect, the invention relates to compounds having a molecular structure as defined by a general formula (5), (formula 5)

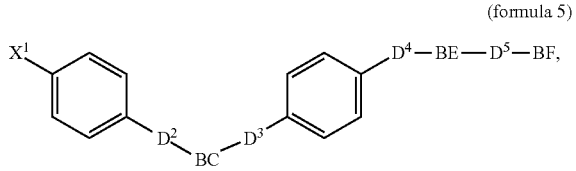

with $X^1$, $D^2$, BC, $D^3$, $D^4$, BE, $D^5$ and BF having the same meaning as defined previously.

According to another sub aspect (sub aspect 4) of the first aspect, the invention relates to compounds having a molecular structure as defined by a general formula (6), (formula 6)

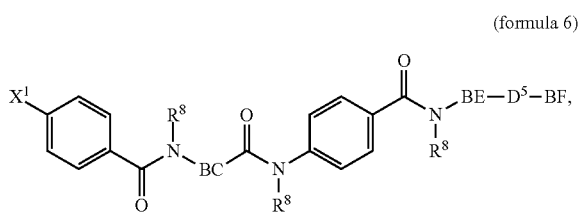

with $X^1$, $R^8$, BC, BE, $D^5$ and BF having the same meaning as defined previously.

According to another sub aspect (sub aspect 5) of the first aspect, the invention relates to compounds having a molecular structure as defined by a general formula (7), (formula 7)

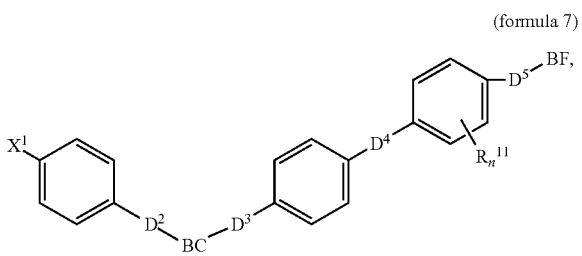

with $X^1$, $D^2$, BC, $D^3$, $D^4$, $R^{11}{}_n$, $D^5$ and BF having the same meaning as defined previously or further below.

According to another sub aspect (sub aspect 6) of the first aspect, the invention relates to compounds having a molecular structure as defined by a general formula (8), (formula 8)

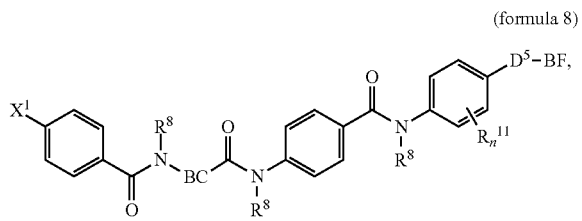

with $X^1$, $R^8$, BC, $R^{11}{}_n$, $D^5$ and BF having the same meaning as defined previously or further below.

According to another sub aspect (sub aspect 7) of the first aspect, the invention relates to compounds having a molecular structure as defined by a general formula (9), (formula 9)

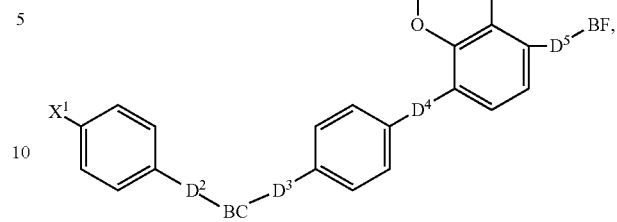

with $X^1$, $D^2$, BC, $D^3$, $D^4$, $R^{11}$, $D^5$ and BF having the same meaning as defined previously or further below.

According to another sub aspect (sub aspect 8) of the first aspect, the invention relates to compounds having a molecular structure as defined by a general formula (10), (formula 10)

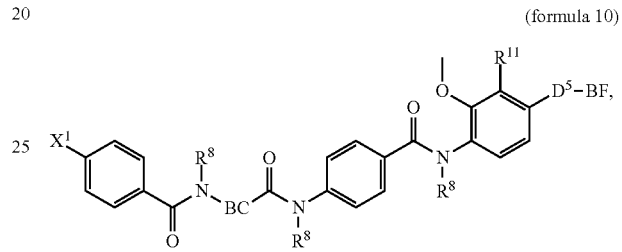

with $X^1$, $R^8$, BC, $R^{11}$, $D^5$ and BF having the same meaning as defined previously or further below.

According to another sub aspect (sub aspect 9) of the first aspect, the invention relates to compounds having a molecular structure as defined by a general formula (11), (formula 11)

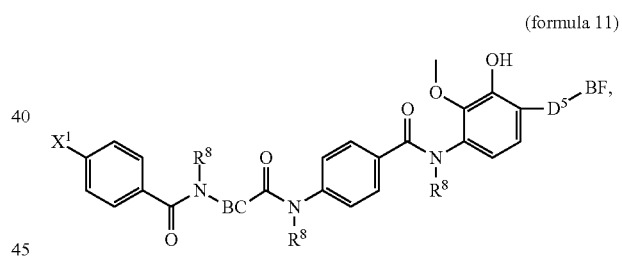

with $X^1$, $R^8$, BC, $D^5$ and BF having the same meaning as defined previously.

According to another sub aspect (sub aspect 10) of the first aspect, the invention relates to antibiotically active compounds having a molecular structure as defined by a general formula (12), (formula 12)

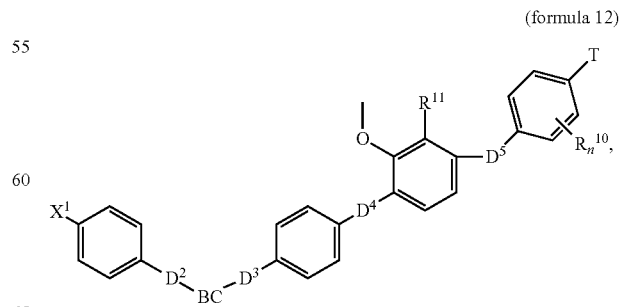

with $X^1$, $D^2$, BC, $D^3$, $D^4$, $R^{11}$, $R^{10}{}_n$, T and $D^5$ having the same meaning as defined previously or further below.

According to another sub aspect (sub aspect 11) of the first aspect, the invention relates to compounds having a molecular structure as defined by a general formula (13),

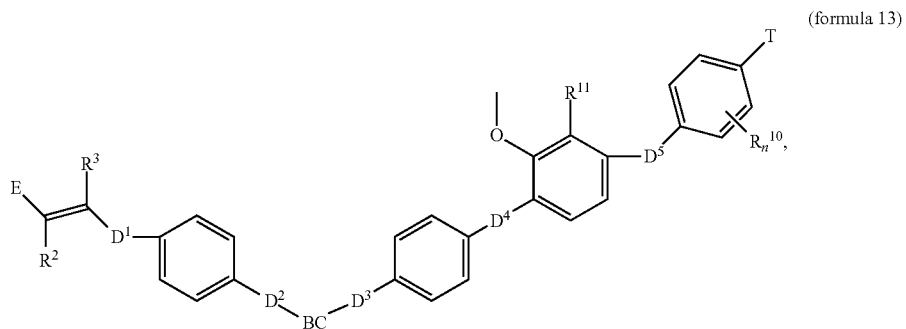
(formula 13)

with E, $R^2$, $R^3$, $D^1$, $D^2$, BC, $D^3$, $D^4$, $R^{11}$, $R^{10}_n$, T and $D^5$ having the same meaning as defined previously or further below.

According to another sub aspect (sub aspect 12) of the first aspect, the invention relates to compounds having a molecular structure as defined by a general formula (14),

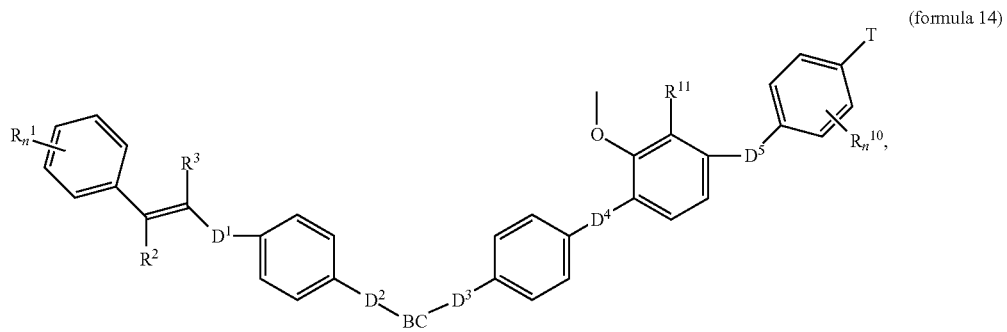
(formula 14)

with $R^2$, $R^3$, $D^1$, $D^2$, BC, $D^3$, $D^4$, $R^1_n$, $R^{11}$, $R^{10}_n$, T and $D^5$ having the same meaning as defined previously or further below.

According to another sub aspect (sub aspect 13) of the first aspect, the invention relates to compounds having a molecular structure as defined by a general formula (15),

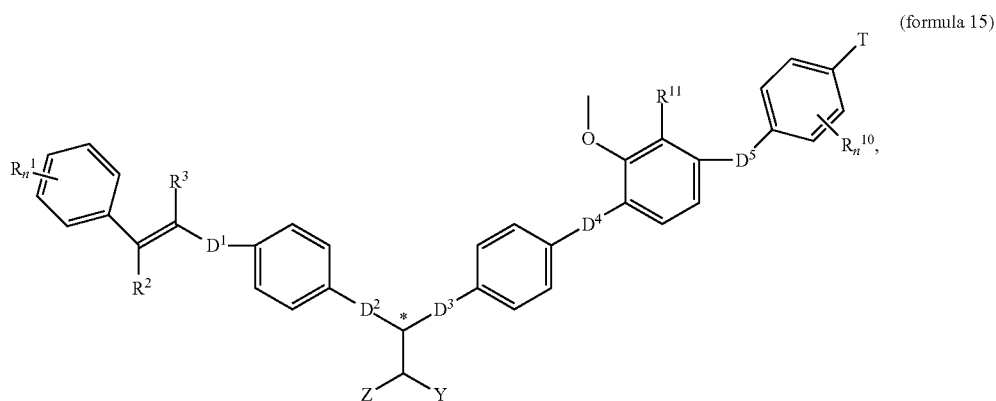
(formula 15)

with Y, Z, $R^2$, $R^3$, $D^1$, $D^2$, $D^3$, $D^4$, $R^{11}$, $R^{10}{}_n$, $R^1{}_n$, T and $D^5$ having the same meaning as defined previously or further below.

According to another sub aspect (sub aspect 14) of the first aspect, the invention relates to compounds having a molecular structure as defined by a general formula (16),

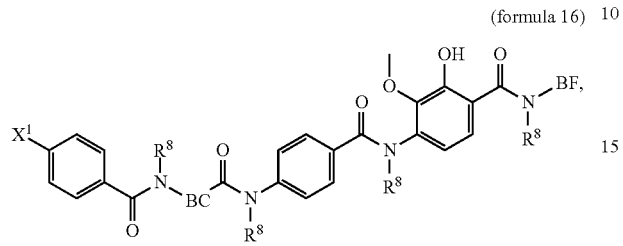

(formula 16)

with $X^1$, $R^8$, BC and BF having the same meaning as defined previously.

According to another sub aspect (sub aspect 15) of the first aspect, the invention relates to compounds having a molecular structure as defined by a general formula (17),

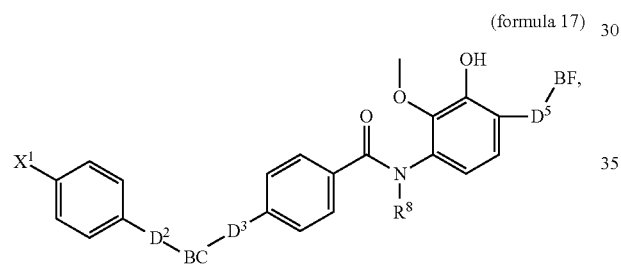

(formula 17)

with $X^1$, $R^8$, $D^2$, BC, $D^3$, $D^5$ and BF having the same meaning as defined previously.

According to another sub aspect (sub aspect 16) of the first aspect, the invention relates to compounds having a molecular structure as defined by a general formula (18),

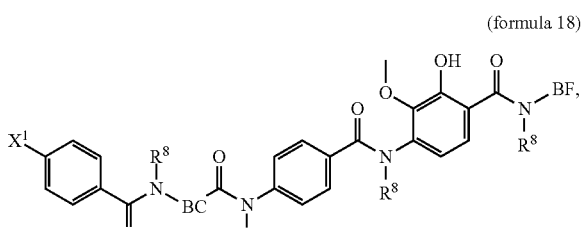

(formula 18)

with $X^1$, $R^8$, BC, $D^5$ and BF having the same meaning as defined previously.

According to another sub aspect (sub aspect 17) of the first aspect, the invention relates to compounds having a molecular structure as defined by a general formula (19),

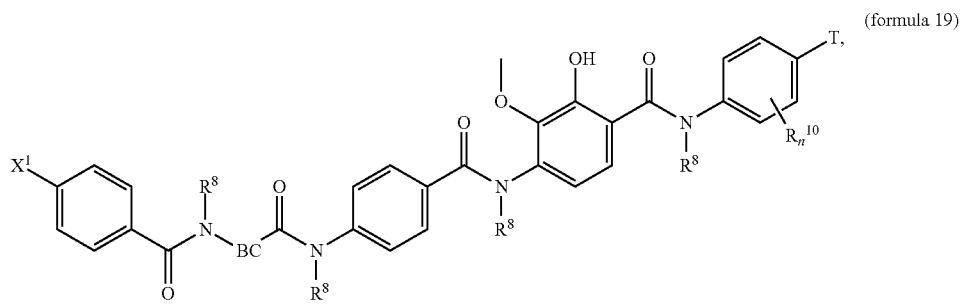

(formula 19)

with $X^1$, $R^8$, BC, $R^{10}{}_n$, and T having the same meaning as defined previously or further below.

According to another sub aspect (sub aspect 18) of the first aspect, the invention relates to compounds having a molecular structure as defined by a general formula (20),

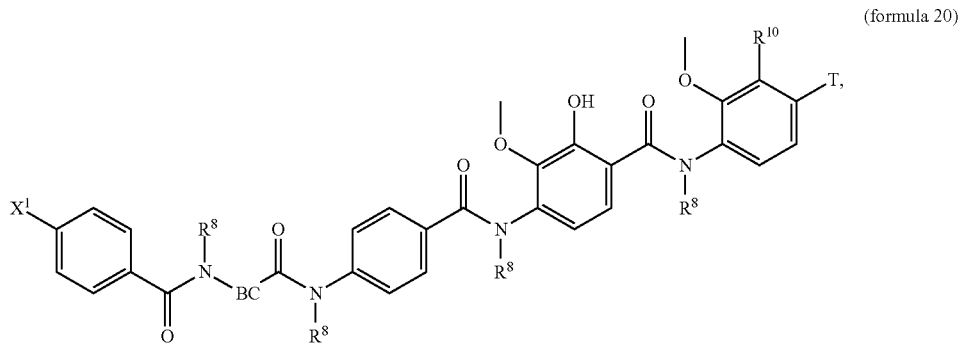

(formula 20)

with $X^1$, $R^8$, BC, $R^{10}$ and T having the same meaning as defined previously or further below.

According to another sub aspect (sub aspect 19) of the first aspect, the invention relates to compounds having a molecular structure as defined by a general formula (21),

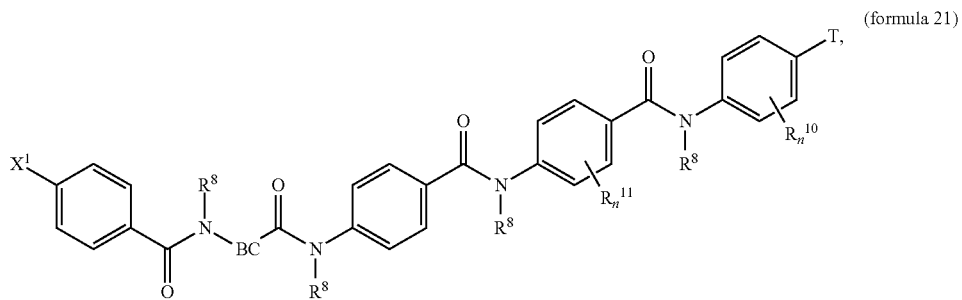

(formula 21)

with $X^1$, $R^8$, BC, $R^{11}{}_n$, $R^{10}{}_n$ and T having the same meaning as defined previously or further below.

According to another sub aspect (sub aspect 20) of the first aspect, the invention relates to compounds having a molecular structure as defined by a general formula (22),

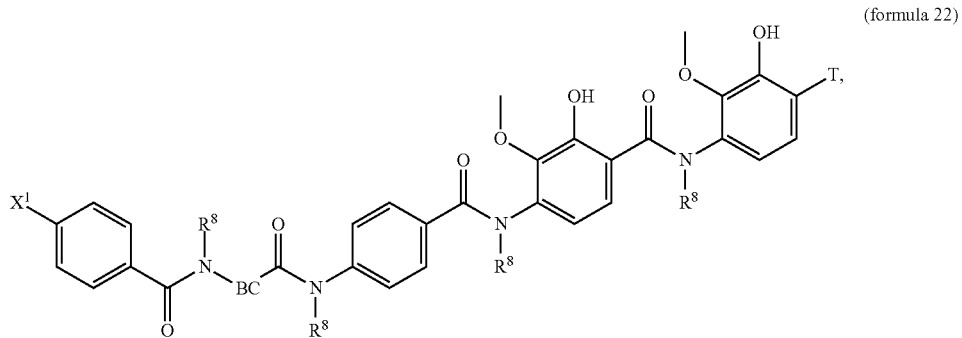

(formula 22)

with $X^1$, $R^8$, BC and T having the same meaning as defined previously or further below.

According to another sub aspect (sub aspect 21) of the first aspect, the invention relates to compounds having a molecular structure as defined by a general formula (23),

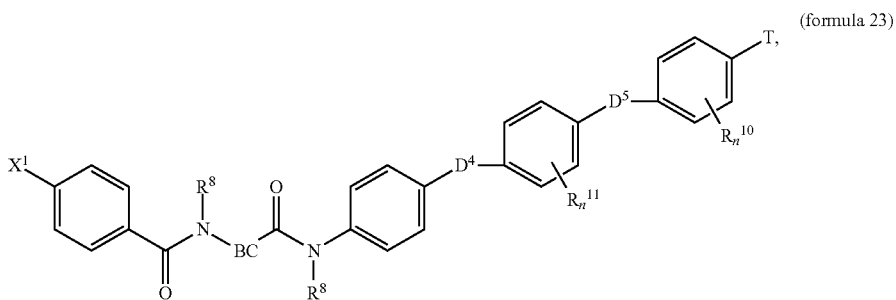

(formula 23)

with $X^1$, $R^8$, BC, $D^4$, $D^5$, $R^{11}_n$, $R^{10}_n$ and T having the same meaning as defined previously or further below.

According to another sub aspect (sub aspect 22) of the first aspect, the invention relates to compounds having a molecular structure as defined by a general formula (24),

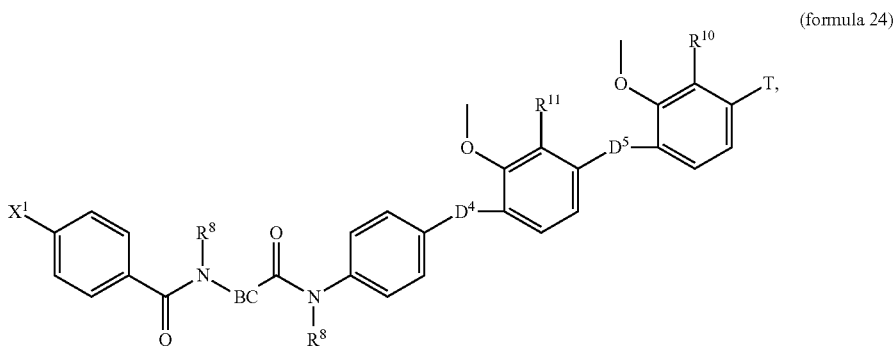

(formula 24)

with $X^1$, $R^8$, BC, $D^4$, $D^5$, $R^{11}$, $R^{10}$ and T having the same meaning as defined previously or further below.

According to another sub aspect (sub aspect 23) of the first aspect, the invention relates to compounds having a molecular structure as defined by a general formula (25),

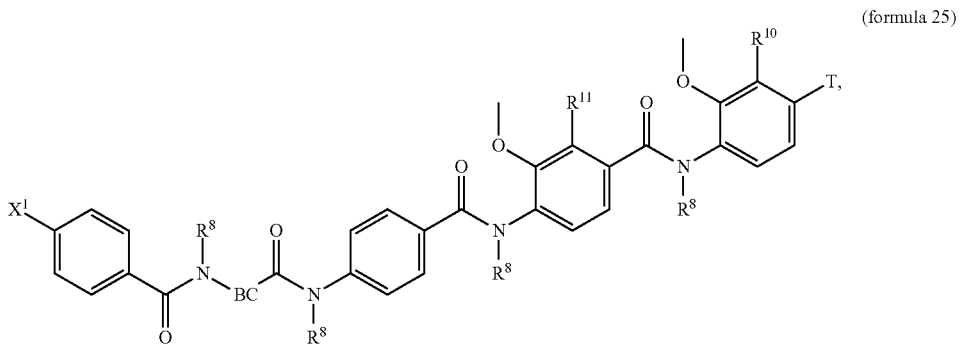

(formula 25)

with $X^1$, $R^8$, BC, $R^{11}$, $R^{10}$ and T having the same meaning as defined previously or further below.

According to another sub aspect (sub aspect 24) of the first aspect, the invention relates to compounds having a molecular structure as defined by a general formula (26),

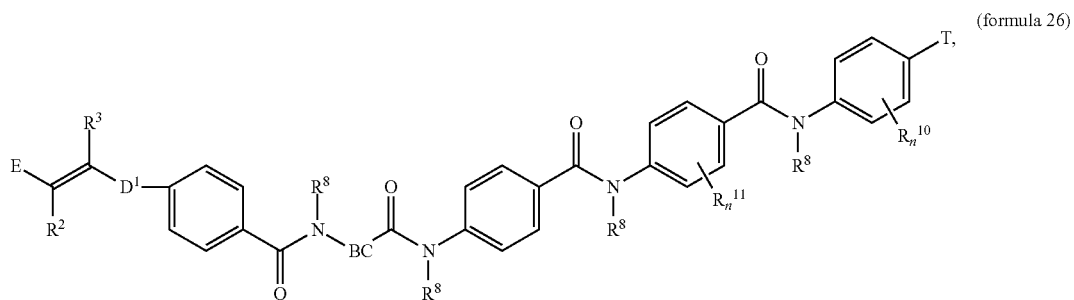

(formula 26)

with E, $R^2$, $R^3$, $D^1$, $R^8$, BC, $R^{11}_n$, $R^{10}_n$ and T having the same meaning as defined previously or further below.

According to another sub aspect (sub aspect 25) of the first aspect, the invention relates to compounds having a molecular structure as defined by a general formula (27),

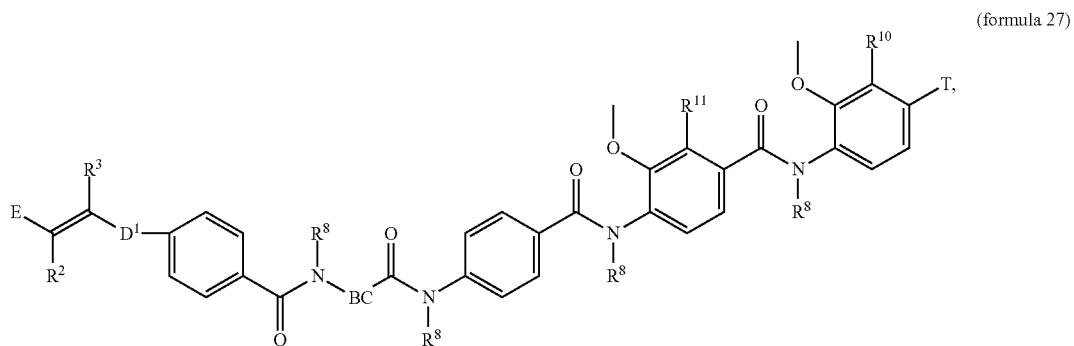

(formula 27)

with E, $R^2$, $R^3$, $D^1$, $R^8$, BC, $R^{11}$, $R^{10}$ and T having the same meaning as defined previously or further below.

According to another sub aspect (sub aspect 26) of the first aspect, the invention relates to compounds having a molecular structure as defined by a general formula (28),

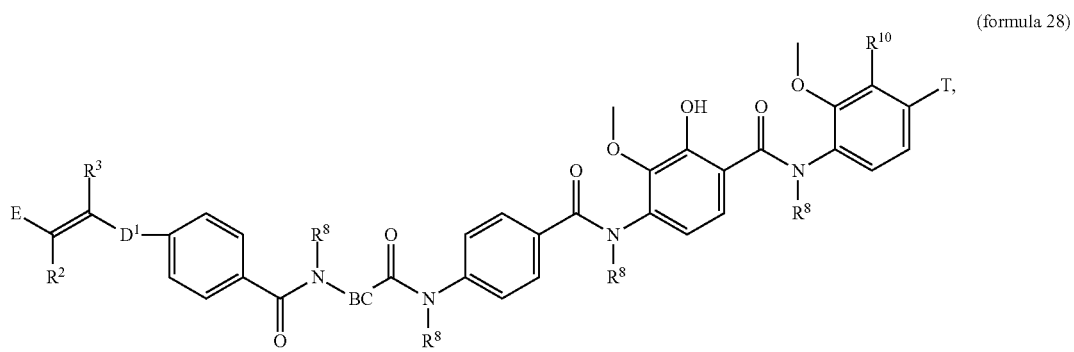

(formula 28)

with E, $R^2$, $R^3$, $D^1$, $R^8$, BC, $R^{10}$ and T having the same meaning as defined previously or further below.

According to another sub aspect (sub aspect 27) of the first aspect, the invention relates to compounds having a molecular structure as defined by a general formula (29),

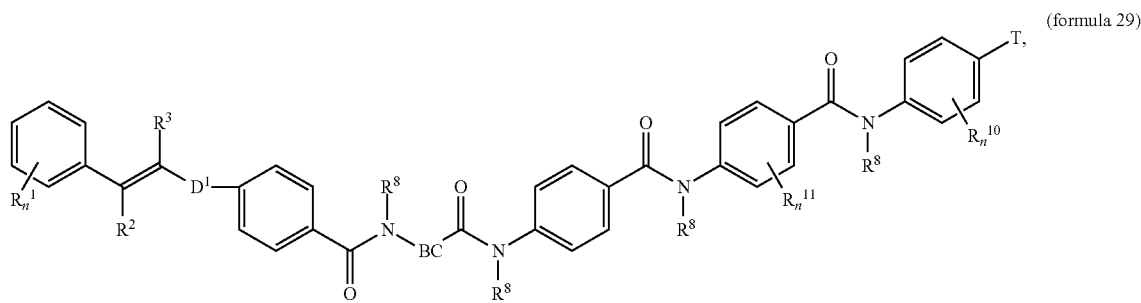

(formula 29)

with $R^1_n$, $R^{10}_n$, $R^{11}_n$, $R^2$, $R^3$, $D^1$, $R^8$, BC and T having the same meaning as defined previously or further below.

According to another sub aspect (sub aspect 28) of the first aspect, the invention relates to compounds having a molecular structure as defined by a general formula (30),

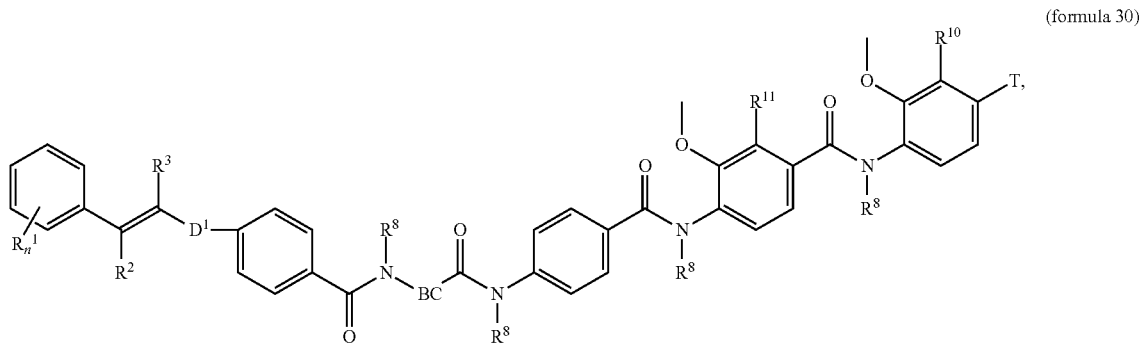

(formula 30)

with $R^1_n$, $R^{11}$, $R^{10}$, $D^1$, $R^2$, $R^3$, $R^8$, BC and T having the same meaning as defined previously or further below.

According to another sub aspect (sub aspect 29 of the first aspect, the invention relates to compounds having a molecular structure as defined by a general formula (31),

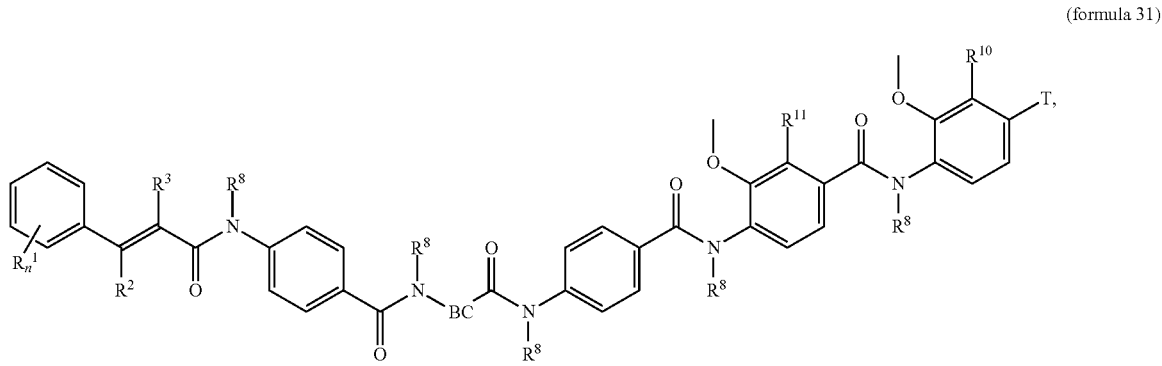

(formula 31)

with $R^1_n$, $R^{11}$, $R^{10}$, $R^2$, $R^3$, $R^8$, BC and T having the same meaning as defined previously or further below.

According to another sub aspect (sub aspect 30) of the first aspect, the invention relates to compounds having a molecular structure as defined by a general formula (32), (formula 32)

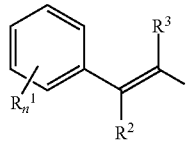 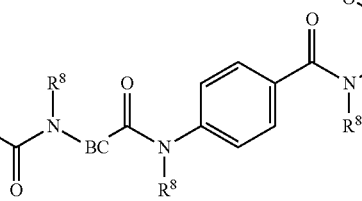

with $R^1_n$, $R^2$, $R^3$, $D^1$, $R^8$, BC and T having the same meaning as defined previously or further below.

According to another sub aspect (sub aspect 31) of the first aspect, the invention relates to compounds having a molecular structure as defined by a general formula (33), (formula 33)

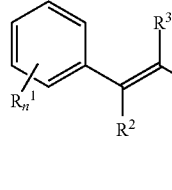 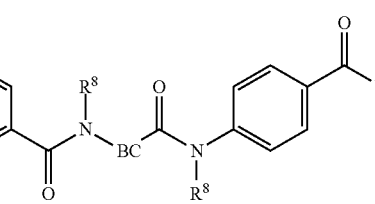

with $R^1_n$, $R^2$, $R^3$, $R^8$, BC and T having the same meaning as defined previously or further below.

According to another sub aspect (sub aspect 32) of the first aspect, the invention relates to compounds having a molecular structure as defined by a general formula (34), (formula 34)

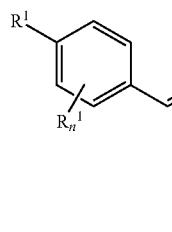 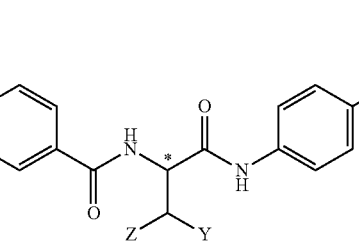

with $R^1$, $R^1_n$, $R^{11}$, $R^{10}$, Z, Y and T having the same meaning as defined previously or further below.

In some embodiments, in particular according to any one of the sub aspects 1 to 10 or 14 to 23, $X^1$ is —OH—OH, —F, —Cl, —Br, I, —CCH, —CN, —OCH$_3$, —OCF$_3$, —NH$_2$, —NHCH$_3$, —N(CH$_3$)$_2$, —CH$_3$, —CH$_2$CH$_3$ or —CF$_3$,
—B(OR$^a$)(OR$^b$), —(CH$_2$)$_m$—R$^a$, —(CH$_2$)$_m$—OR$^a$,
—(CH$_2$)$_m$—C(=O)R$^a$, —(CH$_2$)$_m$—C(=O)OR$^a$,
—(CH$_2$)$_m$—OC(=O)R$^a$, —(CH$_2$)$_m$—OC(=O)OR$^a$,
—(CH$_2$)$_m$—OC(=O)NR$^a$R$^b$, —(CH$_2$)$_m$—C(=O) NR$^a$R$^b$, —(CH$_2$)$_m$—C(=O)NR$^a$R$^b$, —(CH$_2$)$_m$—C (=O)NR$^b$(OR$^a$), —(CH$_2$)$_m$—C(=S)R$^a$, —(CH$_2$)$_m$— C(=S)OR$^a$, —(CH$_2$)$_m$—OC(=S)R$^a$, —(CH$_2$)$_m$—OC (=S)OR$^a$, —(CH$_2$)$_m$—OC(=S)NR$^a$R$^b$, —(CH$_2$)$_m$— C(=S)NR$^a$R$^b$, —(CH$_2$)$_m$—SR$^a$, —(CH$_2$)$_m$—S(=O) R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —$(CH_2)_m$—$NR^cC(=O)OR^a$, —$(CH_2)_m$—$NR^cC(=O)NR^aR^b$, —$(CH_2)_m$—$NR^cC(=S)R^a$, —$(CH_2)_m$—$NR^cC(=S)NR^aR^b$, —$(CH_2)_m$—$NR^cC(=S)OR^a$, —$(CH_2)_m$—$NR^cS(O_2)R^a$, —$(CH_2)_m$—$P(=O)(OR^b)(OR^a)$, —$(CH_2)_m$—$P(=O)(OR^b)(R^a)$ or —$(CH_2)_m$—$S(O_2)NR^bR^a$, —$(CH_2)_m$—O—$C(=O)$-(M)—$C(=O)OH$, —$(CH_2)_m$—O—$C(=O)$-(M)—$C(=O)OR^a$, —$(CH_2)_m$—O—$C(=O)$-(M)—$R^a$, —$(CH_2)_m$—O—$(CH_2)_q$—$P(=O)(R^{ba})(R^{aa})$, —$(CH_2)_m$—$C(=O)O$—$(CH_2)_q$—$P(=O)(R^{ba})(R^{aa})$, —$(CH_2)_m$—$C(=O)O$—$(CH_2)_q$—$S(O_2)OH$ or —$(CH_2)_m$—$C(=O)O$—$(CH_2)_q$—$S(O_2)OR^a$, with $R^{aa}$ being selected independently from each other from —$R^a$ or —$OR^a$,
with $R^{ba}$ being selected independently from each other from —$R^b$ or —$OR^b$,
with M being a substituted or unsubstituted $C_1$-$C_8$ alkyl, in particular an unsubstituted $C_1$-$C_8$ alkyl,
with m being selected from 0, 1 or 2, in particular 0 or 1,
with q being selected from 0, 1 or 2, in particular 0 or 1,
with each $R^a$, $R^b$ or $R^c$ being selected, where applicable, independently from each other from hydrogen, —CN,
a substituted or unsubstituted $C_3$-$C_{10}$ cycloalkyl or a substituted or unsubstituted $C_3$-$C_{10}$ halo cycloalkyl, or
a substituted or unsubstituted $C_6$-$C_{10}$ aryl,
a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl,
a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl.

In some embodiments, in particular according to any one of the sub aspects 1 to 10 or 14 to 23, $X^1$ is
—$NR^a_2$, —$NHR^a$, —$C(=O)OR^a$ or —$OR^a$,
with $R^a$ being a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or
a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl, in particular a substituted or unsubstituted 1,2,3-triazole, 1,2,4-triazole, a substituted or unsubstituted indole, a substituted or unsubstituted isoindole, a substituted or unsubstituted quinoline or a substituted or unsubstituted isoquinoline, or
—$[(CH_2)_{m1}$—O—$C(=O)$—$(CH_2)_{m2}]_{p1}$—$C(=O)OR^d$ or —$[(CH_2)_{m1}$—O—$(CH_2)_{m2}]_{p1}$—$OR^d$ with
$R^d$ being —$CH_3$, —$CH_2CH_3$, —$CH_2CH_2CH_3$, —$CH(CH_3)_2$, —$C_6H_5$
m1 and m2 being selected independently from each other form 1, 2 or 3, in particular m1 and m2 are 2, and
p1 being selected from 1 to 20, in particular from 1 to 8

In some embodiments, in particular according to any one of the sub aspects 1 to 10 or 14 to 23, $X^1$ is
—$NR^a_2$, —$NHR^a$ or —$C(=O)OR^a$, in particular X is —$NR^a_2$ or —$NHR^a$,
with $R^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl.

In some embodiments, in particular according to any one of the sub aspects 1 to 10 or 14 to 23, $X^1$ is $R^4$-$D^1$-, with $D^1$ having the same meaning as defined above, and wherein $R^4$ is
a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl.
a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl, or
a substituted or unsubstituted $C_6$-$C_{10}$ aryl.

In some embodiments, in particular according to any one of the sub aspects 1 to 10 or 14 to 23, $X^1$ is $R^4$-$D^1$-, with $D^1$ having the same meaning as defined above, and wherein $R^4$ is
a substituted or unsubstituted $C_5$-$C_6$ halo heterocycle, in particular a $C_5$-$C_6$ halo heterocycle comprising one or two halogen atoms selected from Cl of F, particularly comprising one Cl or one F,
a substituted or unsubstituted $C_5$-$C_6$ heteroaryl,
a substituted $C_6$ aryl, in particular a bicyclic $C_6$ aryl such as tetraline or indane,
a substituted or unsubstituted $C_5$-$C_6$ halo heteroaryl comprising one or two halogen atoms selected from Cl of F, particularly comprising one Cl or one F; or
$R^4$ is selected from the group of substituted or unsubstituted pyrrole, furan, thiophene, benzothiophene, chromene, thiazole, pyrazine, pyridazine, pyridine, 1,2,3-triazole, 1,2,4-triazole, imidazole, oxazol, thiazol, indole, isoindole, quinoline, isoquinoline, naphatalene, coumarin, aminocoumarin, umbelliferon, benzotriazole, psoralen, benzofurane, benzothiophene, benzimidazol, benzthiazole, benzoxazole or benzpyridazin or hydroxylated, methylated or halogenated derivatives thereof.

In some embodiments, in particular according to any one of the sub aspects 1 to 10 or 14 to 23, $X^1$ is $R^4$-$D^1$-, with $D^1$ having the same meaning as defined above, and wherein $R^4$ is a substituted or unsubstituted $C_1$-$C_5$ alkyl or a substituted or unsubstituted $C_6$-$C_{10}$ cycloalkyl, a substituted or unsubstituted $C_5$-$C_{10}$ heteroaryl or a substituted or unsubstituted $C_6$-$C_{10}$ aryl, in particular $R^4$ is selected from

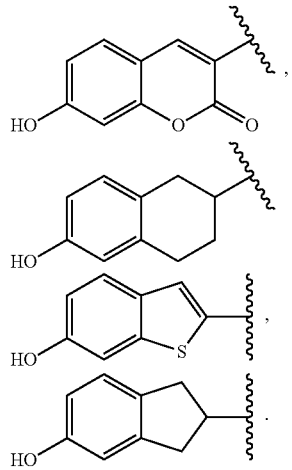

In some embodiments, in particular according to any one of the sub aspects 1 to 10 or 14 to 23, $X^1$ is $R^4$-$D^1$-, with $D^1$ having the same meaning as defined above, and wherein $R^4$ is an unsubstituted $C_1$-$C_5$ alkyl or an unsubstituted $C_6$-$C_{10}$ cycloalkyl.

In some embodiments, in particular according to any one of the sub aspects 1 to 10 or 14 to 23, $X^1$ is BA-$D^1$-, with $D^1$ having the same meaning as defined above, and BA is selected from

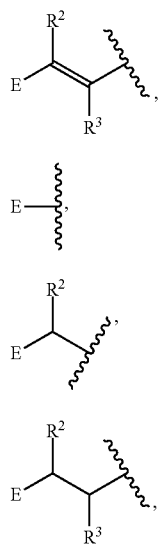

(BA1)

(BA2)

(BA3)

(BA4)

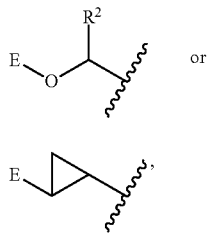

(BA5)

(BA6)

in particular BA is selected from

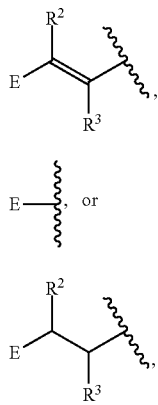

(BA1)

(BA2)

(BA4)

more particularly BA is

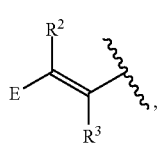

(BA1)

with $R^2$ and $R^3$ being selected, where applicable, independently from each other from —H, —F, —CN, —OH, —NH$_2$, —NO$_2$, —NHCH$_3$, —NH(CH$_3$)$_2$, a substituted or unsubstituted $C_1$-$C_3$ alkyl, a substituted or unsubstituted $C_1$-$C_3$ alkoxy or a $C_1$-$C_3$ haloalkyl, in particular with $R^2$ and $R^3$ being selected, where applicable, independently from each other from —H, —F, —CN, —OH, —NH$_2$, —NO$_2$, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with $R^2$ and $R^3$ being selected independently from each other from —H, —F or —CH$_3$, and a. E is a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl,
- a substituted or unsubstituted $C_3$-$C_{10}$ cycloalkyl or a substituted or unsubstituted $C_3$-$C_{10}$ halo cycloalkyl,
- a substituted or unsubstituted $C_3$-$C_{10}$ heterocycle or a substituted or unsubstituted $C_3$-$C_{10}$ halo heterocycle; in particular a substituted or unsubstituted $C_4$-$C_{10}$ heterocycle or a substituted or unsubstituted $C_4$-$C_{10}$ halo heterocycle,
- a substituted or unsubstituted $C_5$-$C_{10}$ heteroaryl;
- a substituted or unsubstituted $C_6$-$C_{10}$ aryl, or b. E is
- a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or c. E is
- a substituted or unsubstituted $C_1$-$C_5$ alkyl, a substituted or unsubstituted $C_6$-$C_{10}$ cycloalkyl, a substituted or unsubstituted $C_5$-$C_{10}$ heteroaryl or a substituted or unsubstituted $C_8$-$C_{10}$ aryl, or d. E is
- a substituted or unsubstituted $C_5$-$C_6$ halo heterocycle, in particular a $C_5$-$C_6$ halo heterocycle comprising one or two halogen atoms selected from Cl of F, particularly comprising one Cl or one F,
- a substituted or unsubstituted $C_5$-$C_6$ heteroaryl,
- a substituted $C_6$ aryl, in particular a bicyclic $C_6$ aryl such as tetraline or indane,
- a substituted or unsubstituted $C_5$-$C_6$ halo heteroaryl comprising one or two halogen atoms selected from Cl of F, particularly comprising one Cl or one F,
- selected from the group of substituted or unsubstituted pyrrole, furan, thiophene, benzothiophene, chromene, thiazole, pyrazine, pyridazine, pyridine, 1,2,3-triazole, 1,2,4-triazole, imidazole, oxazol, thiazol, indole, isoindole, quinoline, isoquinoline, naphatalene, coumarin, aminocoumarin, umbelliferon, benzotriazole, psoralen, benzofurane, benzothiophene, benzimidazol, benzthiazole, benzoxazole or benzpyridazin or hydroxylated, methylated or halogenated derivatives thereof, or e. E is selected from.

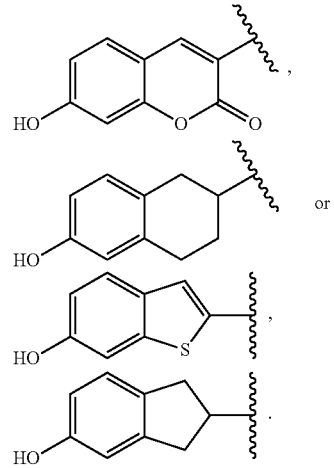

in particular from

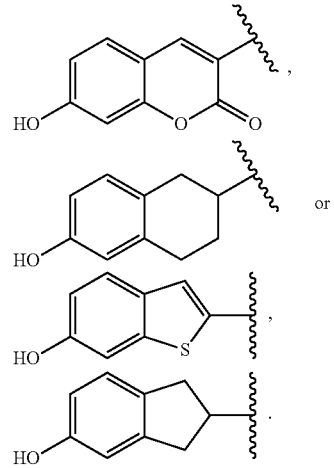

with n of $R^1_n$ being 0, 1, 2, 3, 4 or 5, in particular n of $R^1_n$ being 0, 1, 2 or 3, more particularly n of $R^1_n$ being 1, and
with each $R^1$ independently from any other $R^1$ being selected from
—OH, —F, —Cl, —Br, I, —CCH, —CN, —$N_3$, —$OCH_3$, —$OCF_3$, —$NH_2$, —$NHCH_3$, —$N(CH_3)_2$, —$CH_3$, —$CH_2$—$CH_3$, —$CF_3$, —$OCONH_2$ or —$NO_2$,
—B(OR$^a$)(OR$^b$), —$(CH_2)_m$—$R^a$, —$(CH_2)_m$—$OR^a$, —$(CH_2)_m$—C(=O)$R^a$, —$(CH_2)_m$—C(=O)$OR^a$, —$(CH_2)_m$—OC(=O)$R^a$, —$(CH_2)_m$—OC(=O) $OR^a$, —$(CH_2)_m$—OC(=O)NR$^a$R$^b$, —$(CH_2)_m$—C(=O)NR$^a$R$^b$, —$(CH_2)_m$—C(=O)NR$^a$R$^b$, —$(CH_2)_m$—C(=O)NR$^b$(OR$^a$), —$(CH_2)_m$—C(=S)$R^a$, —$(CH_2)_m$—C(=S)$OR^a$, —$(CH_2)_m$—OC(=S) $R^a$, —$(CH_2)_m$—OC(=S)$OR^a$, —$(CH_2)_m$—OC(=S)NR$^a$R$^b$, —$(CH_2)_m$—C(=S)NR$^a$R$^b$, —$(CH_2)_m$—SR$^a$, —$(CH_2)_m$—S(=O)$R^a$, —$(CH_2)_m$—S(O$_2$)$R^a$, —$(CH_2)_m$—S(O$_2$)OR$^a$, —$(CH_2)_m$—OS(O$_2$)R$^a$, —$(CH_2)_m$—OS(O$_2$)OR$^a$, —$(CH_2)_m$—NR$^a$R$^b$, —$(CH_2)_m$—NR$^c$C(=O)R$^a$, —$(CH_2)_m$—NR$^c$C(=O)OR$^a$, —$(CH_2)_m$—NR$^c$C(=O)NR$^a$R$^b$, —$(CH_2)_m$—NR$^c$C(=S)R$^a$, —$(CH_2)_m$—NR$^c$C(=S)NR$^a$R$^b$, —$(CH_2)_m$—NR$^c$C(=S)OR$^a$, —$(CH_2)_m$—NR$^c$S(O$_2$)R$^a$, —$(CH_2)_m$—P(=O)(OR$^b$)(OR$^a$), —$(CH_2)_m$—P(=O)(OR$^b$)(R$^a$) or —$(CH_2)_m$—S(O$_2$)NR$^b$R$^a$, —$(CH_2)_m$—O—C(=O)-(M)—C(=O)OH, —$(CH_2)_m$—O—C(=O)-(M)—C(=O)OR$^a$, —$(CH_2)_m$—O—C(=O)-(M)—R$^a$, —$(CH_2)_m$—O—(CH$_2$)$_q$—P(=O)(R$^{ba}$)(R$^{aa}$), —$(CH_2)_m$—C(=O)O—(CH$_2$)$_q$—P(=O)(R$^{ba}$)(R$^{aa}$), —$(CH_2)_m$—C(=O)O—(CH$_2$)$_q$—S(O$_2$)OH or —$(CH_2)_m$—C(=O)O—(CH$_2$)$_q$—S(O$_2$)OR$^a$,
with R$^{aa}$ being selected independently from each other being —R$^a$ or —OR$^a$,
with R$^{ba}$ being selected independently from each other being —R$^b$ or —OR$^b$,
with M being a substituted or unsubstituted $C_1$-$C_8$ alkyl, in particular an unsubstituted $C_1$-$C_8$ alkyl
with m being selected from 0, 1 or 2, in particular 0 or 1,
with q being selected from 0, 1 or 2, in particular 0 or 1, with each $R^a$, $R^b$ or $R^c$ being selected, where applicable, independently from each other from hydrogen, —CN
  a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl,
  a substituted or unsubstituted $C_3$-$C_{10}$ cycloalkyl or a substituted or unsubstituted $C_3$-$C_{10}$ halo cycloalkyl,
  a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle,
  a substituted or unsubstituted $C_5$-$C_{10}$ heteroaryl,
  a substituted or unsubstituted $C_6$-$C_{10}$ aryl, in particular
with each $R^1$ independently from any other $R^1$ being —OH, —F, —Cl, I, —CN, —OCH$_3$, —OCF$_3$, —OCONH$_2$ or —CF$_3$.

f. E is

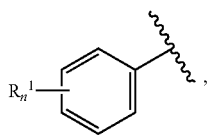

with n of $R^1_n$ being 0, 1, 2, 3, 4 or 5, in particular n of $R^1_n$ being 0, 1, 2 or 3, more particularly 1, and
each $R^1$ independently from any other $R^1$ is selected from
—OH, —F, —Cl, —Br, I, —CCH, —CN, —N$_3$, —OCH$_3$, —OCF$_3$, —NH$_2$, —NHCH$_3$, —N(CH$_3$)$_2$, —CH$_3$, —CH$_2$—CH$_3$, —CF$_3$, —OCONH$_2$ or —NO$_2$,
—B(OR$^a$)(OR$^b$), —(CH$_2$)$_m$—R$^a$, —(CH$_2$)$_m$—OR$^a$, —(CH$_2$)$_m$—C(=O)R$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O)NR$^a$R$^b$, —(CH$_2$)$_m$—C(=O)NR$^a$R$^b$, —(CH$_2$)$_m$—C(=O)NR$^b$(OR$^a$), —(CH$_2$)$_m$—C(=S)R$^a$, —(CH$_2$)$_m$—C(=S)OR$^a$, —(CH$_2$)$_m$—OC(=S)R$^a$, —(CH$_2$)$_m$—OC(=S)OR$^a$, —(CH$_2$)$_m$—OC(=S)NR$^a$R$^b$, —(CH$_2$)$_m$—C(=S)NR$^a$R$^b$, —(CH$_2$)$_m$—SR$^a$, —(CH$_2$)$_m$—S(=O)R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)OR$^a$, —(CH$_2$)$_m$—NR$^c$C(=O)NR$^a$R$^b$, —(CH$_2$)$_m$—NR$^c$C(=S)R$^a$, —(CH$_2$)$_m$—NR$^c$C(=S)NR$^a$R$^b$, —(CH$_2$)$_m$—NR$^c$C(=S)OR$^a$, —(CH$_2$)$_m$—NR$^c$S(O$_2$)R$^a$, —(CH$_2$)$_m$—P(=O)(OR$^b$)(OR$^a$), —(CH$_2$)$_m$—P(=O)(OR$^b$)(R$^a$) or —(CH$_2$)$_m$—S(O$_2$)NR$^b$R$^a$, —(CH$_2$)$_m$—O—C(=O)-(M)—C(=O)OH, —(CH$_2$)$_m$—O—C(=O)-(M)—C(=O)OR$^a$,
—(CH$_2$)$_m$—O—C(=O)-(M)—R$^a$, —(CH$_2$)$_m$—O—(CH$_2$)$_q$—P(=O)(R$^{ba}$)(R$^{aa}$), —(CH$_2$)$_m$—C(=O)O—(CH$_2$)$_q$—P(=O)(R$^{ba}$)(R$^{aa}$), —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$,
with $R^{aa}$ being selected independently from each other being —R$^a$ or —OR$^a$,
with $R^{ba}$ being selected independently from each other being —R$^b$ or —OR$^b$,
with M being a substituted or unsubstituted $C_1$-$C_8$ alkyl, in particular an unsubstituted $C_1$-$C_8$ alkyl
with m being selected from 0, 1 or 2, in particular 0 or 1,
with q being selected from 0, 1 or 2, in particular 0 or 1,
with each $R^a$, $R^b$ or $R^c$ being selected, where applicable, independently from each other from hydrogen, —CN
  a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl,
  a substituted or unsubstituted $C_3$-$C_{10}$ cycloalkyl or a substituted or unsubstituted $C_3$-$C_{10}$ halo cycloalkyl,
  a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle,
  a substituted or unsubstituted $C_5$-$C_{10}$ heteroaryl,
  a substituted or unsubstituted $C_6$-$C_{10}$ aryl, or g. E is

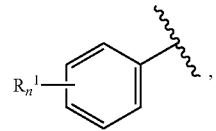

with n of $R^1_n$ being 0, 1, 2, 3, 4 or 5, in particular n of $R^1_n$ being 0, 1, 2 or 3, more particularly n of $R^1_n$ 1, and
with each $R^1$ independently from any other $R^1$ being selected from
—OH, —F, —Cl, —Br, I, —CCH, —CN, —N$_3$, —OCH$_3$, —OCF$_3$, —NH$_2$, —NH CH$_3$, —N(CH$_3$)$_2$, —CH$_3$, —CH$_2$—CH$_3$, —CF$_3$, —OCONH$_2$ or —NO$_2$,
—B(OR$^a$)(OR$^b$), —(CH$_2$)$_m$—R$^a$, —(CH$_2$)$_m$—OR$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O)NR$^a$R$^b$, —(CH$_2$)$_m$—C(=O)NR$^b$(OR$^a$), —(CH$_2$)$_m$—C(=S)R$^a$, —(CH$_2$)$_m$—C(=S)OR$^a$, —(CH$_2$)$_m$—OC(=S)R$^a$, —(CH$_2$)$_m$—OC(=S)OR$^a$, —(CH$_2$)$_m$—OC(=S)NR$^a$R$^b$, —(CH$_2$)$_m$—C(=S)

NR$^a$R$^b$, —(CH$_2$)$_m$—SR$^a$, —(CH$_2$)$_m$—S(=O)R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)NR$^a$R$^b$, —(CH$_2$)$_m$—NR$^c$C(=S)R$^a$, —(CH$_2$)$_m$—NR$^c$C(=S)NR$^a$R$^b$, —(CH$_2$)$_m$—NR$^c$C(=S)OR$^a$, —(CH$_2$)$_m$—NR$^c$S(O$_2$)R$^a$, —(CH$_2$)$_m$—P(=O)(OR$^b$)(OR$^a$), —(CH$_2$)$_m$—P(=O)(OR$^b$)(R$^a$) or —(CH$_2$)$_m$—S(O$_2$)NR$^b$R$^a$, —(CH$_2$)$_m$—O—C(=O)-(M)—C(=O)OH, —(CH$_2$)$_m$—O—C(=O)-(M)—C(=O)OR$^a$, —(CH$_2$)$_m$—O—C(=O)-(M)—R$^a$, —(CH$_2$)$_m$—O—(CH$_2$)$_q$—P(=O)(R$^{ba}$)(R$^{aa}$), —(CH$_2$)$_m$—C(=O)O—(CH$_2$)$_q$—P(=O)(R$^{ba}$)(R$^{aa}$), —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$, with R$^{aa}$ being selected independently from each other being —R$^a$ or —OR$^a$, with R$^{ba}$ being selected independently from each other being —R$^b$ or —OR$^b$, with M being a substituted or unsubstituted C$_1$-C$_8$ alkyl, in particular an unsubstituted C$_1$-C$_8$ alkyl with m being selected from 0, 1 or 2, in particular 0 or 1, with q being selected from 0, 1 or 2, in particular 0 or 1, with each R$^a$, R$^b$ or R$^c$ being selected, where applicable, independently from each other from hydrogen, —CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, —C(CH$_3$)$_3$, —C$_6$H$_5$—CH$_2$C$_6$H$_5$.

h. with E being

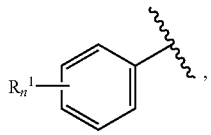

with n of R$^1_n$ being 0, 1, 2, 3, 4 or 5, in particular n of R$^1_n$ being 0, 1, 2 or 3, more particularly 1, and with each R$^1$ independently from any other R$^1$ being —OH, —F, —Cl, —Br, —I, —CCH, —CN, —N$_3$, —OCH$_3$, —OCF$_3$, —NH$_2$, —CH$_3$, —CF$_3$, —OCONH$_2$ or —NO$_2$, a substituted or unsubstituted C$_5$-C$_6$ heterocycle, a substituted or unsubstituted C$_5$-C$_6$ halo heterocycle, in particular a C$_5$-C$_6$ halo heterocycle comprising one or two halogen atoms selected from Cl of F, particularly comprising one Cl or one F, a substituted or unsubstituted C$_5$-C$_6$ heteroaryl, a substituted or unsubstituted C$_5$-C$_6$ halo heteroaryl comprising one or two halogen atoms selected from Cl of F, particularly comprising one Cl or one F, a substituted or unsubstituted C$_6$ aryl.

i. E is

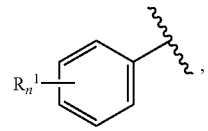

with n of R$^1_n$ being 0, 1, 2, 3, 4 or 5, in particular n of R$^1_n$ being 0, 1, 2 or 3, more particularly n of R$^1_n$ being 1, and with each R$^1$ independently from any other R$^1$ being —OH, —F, —Cl, —I, —CN, —OCH$_3$, —OCF$_3$, —OCONH$_2$ or —CF$_3$, or j. E is

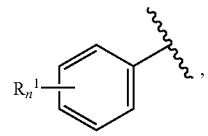

with n of R$^1_n$ being 5 and R$^1$ is F, or with n of R$^1_n$ being 5, and one to four of R$^1$ being F and the other ones of R$^1$ being selected independently from any other R$^1$ from —H, —OH, —Cl, —I, —CN, —OCH$_3$, —OCF$_3$, —OCONH$_2$ or —CF$_3$, in particular from —OH, —OCH$_3$, —OCF$_3$, —OCONH$_2$ or —CF$_3$, or with n of R$^1_n$ being 1, and R$^1$ being selected from —OH, —OCH$_3$, —OCF$_3$, —OCONH$_2$ or —CF$_3$, or with n of R$^1_n$ being 5, and one to three of R$^1$ being F and the other ones of R$^1$ being selected independently from any other R$^1$ from —H, —OH, —Cl, I, —CN, —OCH$_3$, —OCF$_3$, —OCONH$_2$ or —CF$_3$, in particular —OH, —OCH$_3$, —OCF$_3$, —OCONH$_2$ or —CF$_3$, or with n of R$^1_n$ being 2, and each R$^1$ being selected independently from any other R$^1$ from —OH, —OCH$_3$, —OCF$_3$, —OCONH$_2$ or —CF$_3$, or with n of R$^1_n$ being 5, and one or two of R$^1$ being F and the other ones of R$^1$ being selected independently from any other R$^1$ from —H, —OH, —Cl, I, —CN, —OCH$_3$, —OCF$_3$, —OCONH$_2$ or —CF$_3$, in particular —OH, —OCH$_3$, —OCF$_3$, —OCONH$_2$ or —CF$_3$, or with n of R$^1_n$ being 3, and each R$^1$ being selected independently from any other R$^1$ from —OH, —OCH$_3$, —OCF$_3$, —OCONH$_2$ or —CF$_3$, or k. E is

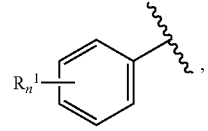

with n of R$^1_n$ being 0, 1, 2, 3, 4 or 5, in particular n of R$^1_n$ being 0, 1, 2 or 3, more particularly n of R$^1_n$ being 1, and with each R$^1$ independently from any other R$^1$ being —OH, OCH$_3$, —F or —CF$_3$.

l. E is

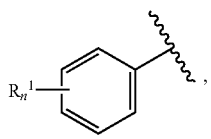

with n of R$^1_n$ being 1, 2, 3, 4 or 5, in particular n of R$^1_n$ being 1, 2 or 3, with one R$^1$ being a substituent Q, with Q being selected from —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$, —(CH$_2$)$_m$—O—S(O$_2$)OH, —(CH$_2$)$_m$—O—S(O$_2$)OR$^a$, in particular —(CH$_2$)$_m$—O—S(O$_2$)OH, —(CH$_2$)$_m$—O—S(O$_2$)OR$^a$, with m being selected from 0, 1 or 2, in particular from 0 or 1, with R$^a$ being —CH$_3$, —CH$_2$CH$_3$, —C$_6$H$_5$, —CH$_2$CH$_2$CH$_3$, —CH(CH$_3$)$_2$, —CH$_2$C$_6$H$_5$ or para-methoxybenzyl —C(=O)—O—R$^a$, —O—C(=O)—R$^a$, in particular —O—C(=O)—R$^a$, with R$^a$ being a substituted or unsubstituted C$_1$-C$_{16}$ alkyl, in particular an unsubstituted C$_1$-C$_{14}$ alkyl, —(CH$_2$)$_m$—[(CH$_2$)$_{m1}$—O—C(=O)—(CH$_2$)$_{m2}$]$_{p1}$—C(=O)OR$^d$, in particular —(CH$_2$)—[—O—C(=O)—(CH$_2$)$_2$]$_{p1}$—C(=O)OR$^d$ with
R$^d$ being —CH$_3$, —CH$_2$CH$_3$, —CH$_2$CH$_2$CH$_3$, —CH(CH$_3$)$_2$, —C$_6$H$_5$
m1 and m2 being selected independently from each other form 1, 2 or 3, in particular m1 and m2 are 2, and
p1 being selected from 1 to 20, in particular from 1 to 8, —(CH$_2$)$_m$—[(CH$_2$)$_{m1}$—O—(CH$_2$)$_{m2}$]$_{p1}$—OR$^d$, in particular —[—O—(CH$_2$)$_2$]$_{p1}$—OR$^d$, with
R$^d$ being —CH$_3$, —CH$_2$CH$_3$, —CH$_2$CH$_2$CH$_3$, —CH(CH$_3$)$_2$, —C$_6$H$_5$
m1 and m2 being selected independently from each other form 1, 2 or 3, in particular m1 and m2 are 2, and
p1 being selected from 1 to 20, in particular from 1 to 8, —(CH$_2$)$_m$—C(=O)O—(CH$_2$)$_q$—P(=O)(R$^{ba}$)(R$^{aa}$), —(CH$_2$)$_m$—O—(CH$_2$)$_q$—P(=O)(R$^{ba}$)(R$^{aa}$), in particular from —(CH$_2$)$_m$—O—(CH$_2$)$_q$—P(=O)(R$^{ba}$)(R$^{aa}$),
with R$^{aa}$ and R$^{ba}$ being selected, where applicable, independently from each other from —R$^a$ or —OR$^a$ and
with R$^a$ being hydrogen, —OCH$_3$, —OCH$_2$CH$_3$, —CH$_3$, —CH$_2$CH$_3$, —C$_6$H$_5$—CH$_2$CH$_2$CH$_3$, —CH(CH$_3$)$_2$, —CH$_2$C$_6$H$_5$ or para-methoxybenzyl,
with m being selected from 0, 1 or 2, in particular 0 or 1,
with q being selected from 0, 1 or 2, in particular 0 or 1,
and with the other R$^1$ being selected independently from each other R$^1$ from —OH, —F, —Cl, I, —CN, —OCH$_3$, —OCF$_3$, —OCONH$_2$ or —CF$_3$, in particular from —OH, —F, —OCH$_3$, —OCF$_3$, —OCONH$_2$ or —CF$_3$, or m. E is

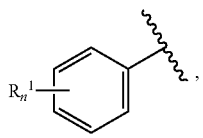

with n of R$^1_n$ being 5, and one to four of R$^1$ being F, one R$^1$ being the substituent Q, and, where applicable, the other ones of R$^1$ being selected independently from any other R$^1$ from —H, —OH, —Cl, I, —CN, —OCH$_3$, —OCF$_3$, —OCONH$_2$ or —CF$_3$, in particular from —OH, —OCH$_3$, —OCF$_3$, —OCONH$_2$ or —CF$_3$, or with n of R$^1_n$ being 5, and one to three of R$^1$ being F, one R$^1$ being the substituent Q, and, where applicable, the other ones of R$^1$ being selected independently from any other R$^1$ from —H, —OH, —Cl, I, —CN, —OCH$_3$, —OCF$_3$, —OCONH$_2$ or —CF$_3$, in particular —OH, —OCH$_3$, —OCF$_3$, —OCONH$_2$ or —CF$_3$, or with n of R$^1_n$ being 5, and one or two of R$^1$ being F, one R$^1$ being the substituent Q, and, where applicable, the other ones of R$^1$ being selected independently from any other R$^1$ from —H, —OH, —Cl, I, —CN, —OCH$_3$, —OCF$_3$, —OCONH$_2$ or —CF$_3$, in particular —OH, —OCH$_3$, —OCF$_3$, —OCONH$_2$ or —CF$_3$, or with n of R$^1_n$ being 5, and one of R$^1$ being F, one R$^1$ being the substituent Q, and, where applicable, the other ones of R$^1$ being selected independently from any other R$^1$ from —H, —OH, —Cl, I, —CN, —OCH$_3$, —OCF$_3$, —OCONH$_2$ or —CF$_3$, in particular —OH, —OCH$_3$, —OCF$_3$, —OCONH$_2$ or —CF$_3$, or with n of R$^1_n$ being 3, one R$^1$ being the substituent Q, and the other R$^1$ being selected independently from each other R$^1$ from —OH, —OCH$_3$, —OCF$_3$, —OCONH$_2$ or —CF$_3$, or with n of R$^1_n$ being 2, one R$^1$ being the substituent Q and the other R$^1$ being —H, —OH, —OCH$_3$, —OCF$_3$, —OCONH$_2$ or —CF$_3$, or with n of R$^1_n$ being 1 with R$^1$ being the substituent Q, with Q having the same meaning as defined previously, and wherein in particular Q is in para position with respect to the attachment position of the phenyl moiety of E to the parent moiety, and wherein in particular any hydrogen of the phenyl group may be substituted with F, or n. E is

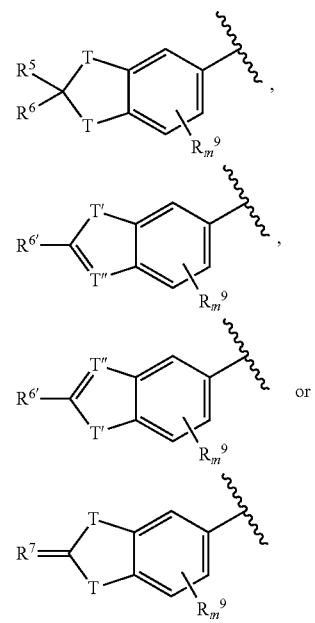

with each T being selected independently from each other from —CH$_2$, —NH, —S or —O, —CHCH$_3$, —C(CH$_3$)$_2$ or —NR$^c$,
with R$^c$ being —OH, —CH$_3$, —CH$_2$CH$_3$, —CH$_2$CH$_2$CH$_3$, —CH(CH$_3$)$_2$, and
with T' being selected from —CH$_2$, —NH, —S or —O, —CHCH$_3$, —C(CH$_3$)$_2$ or —NR$^c$, and with T" being selected from —CH or =N, and
with R⁵ and R⁶ being selected independently from each other from —H, —F, —CH₃, —CH₂CH₃, —OCH₃, —CH₂CF₃, —CHFCF₃, —CF₂CF₃, —CHF₂, —CH₂F or —CF₃, in particular with R⁵ and R⁶ being selected independently from each other from H, —F or —CH₃, and
with R⁶' being selected from —CH₃, —OH, —OCH₃ or —OCH₂CH₃
with R⁷ being selected from =NH, =S or =O, and
with m of R⁹ₘ being selected from 0, 1, 2 or 3, and each R⁹ being selected independently from each other —Cl, —F, Br, I, —OH, —CCH, —CN —CH₃, —CH₂CH₃, —OCH₃, —COOH, —COOR^b, —C(O)NH₂, —C(O)NH(R^b); —C(O)N(R^b)₂, —NHC(=O)OR^b, —NR^bC(=O)OR^b, —NR^bC(=O)OH, —CH₂CF₃, —CHFCF₃, —CF₂CF₃, —CHF₂, —CH₂F or —CF₃
with R^b being a substituted or unsubstituted C₁-C₅ alkyl, a substituted or unsubstituted C₂-C₅ alkenyl, a substituted or unsubstituted C₂-C₅ alkynyl, or a C₁-C₅ haloalkyl, or o. E is

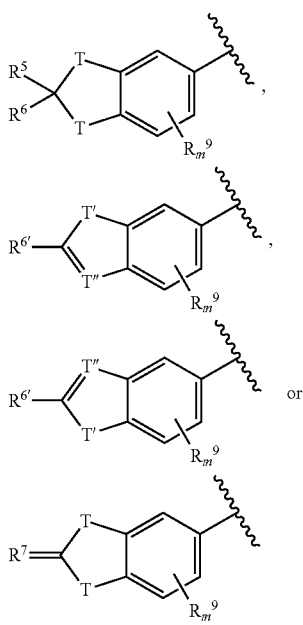

with m of R⁹ₘ being 0, and
with each T being selected independently from each other from —CH₂, —CHCH₃, —C(CH₃)₂, —NH, NR^c, —S or —O, in particular form —C(CH₃)₂, —NH, —S or —O,
with R^c being —CH₂OH, —CH₃, —CH₂CH₃, —CH₂CH₂CH₃, —CH(CH₃)₂, —CH₂CF₃, —CHFCF₃, —CF₂CF₃, —CHF₂, —CH₂F, —CF₃
with T' being selected from —CH₂, —NH, —S or —O, —CHCH₃, —C(CH₃)₂ or —NR^c, in particular from —O, —S or —NH, and
with T" being selected from —CH or =N, in particular T" is =N, and
with R⁵ and R⁶ being selected independently from each other from —H, —F —CH₃, —CH₂CH₃, —OCH₃, —CH₂CF₃, —CHFCF₃, —CF₂CF₃, —CHF₂, —CH₂F or —CF₃, in particular with R⁵ and R⁶ being selected independently from each other from H, —F or CH₃, and with R⁶' being selected from OH, —OCH₃, —OCH₂CH₃ or —CH₃,
with R⁷ being selected from =NH, =S or =O, in particular R⁷ is =O, or p. E is selected from

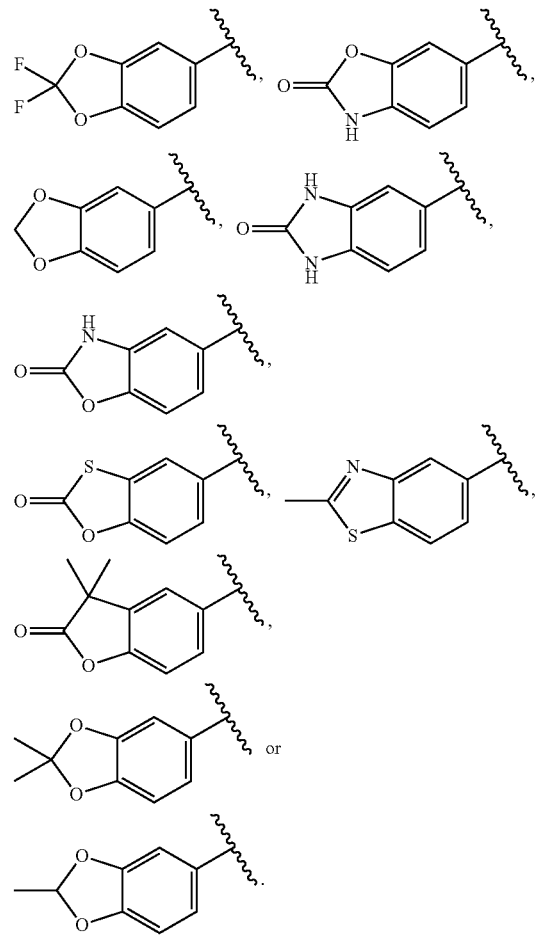

In some embodiments, in particular according to any one of the sub aspects 11 or 24 to 26, E is
a substituted or unsubstituted C₁-C₁₆ alkyl, a substituted or unsubstituted C₁-C₁₆ alkoxy, a substituted or unsubstituted C₁-C₁₆ carboxy, a substituted or unsubstituted C₂-C₁₆ alkenyl, a substituted or unsubstituted C₂-C₁₆ alkynyl, or a C₁-C₁₆ haloalkyl, in particular a substituted or unsubstituted C₁-C₈ alkyl, a substituted or unsubstituted C₁-C₈ alkoxy, a substituted or unsubstituted C₂-C₈ alkenyl, a substituted or unsubstituted C₂-C₈ alkynyl, or a substituted or unsubstituted C₁-C₈ haloalkyl, a substituted or unsubstituted C₃-C₁₀ cycloalkyl, or a substituted or unsubstituted C₃-C₁₀ halo cycloalkyl,
a substituted or unsubstituted C₃-C₁₀ cycloalkyl or a substituted or unsubstituted C₃-C₁₀ halo cycloalkyl,
a substituted or unsubstituted C₃-C₁₀ heterocycle or a substituted or unsubstituted C₃-C₁₀ halo heterocycle; in particular a substituted or unsubstituted C₄-C₁₀ heterocycle or a substituted or unsubstituted C₄-C₁₀ halo heterocycle,
a substituted or unsubstituted C₅-C₁₀ heteroaryl;
a substituted or unsubstituted C₆-C₁₀ aryl.

In some embodiments, in particular according to any one of the sub aspects 11 or 24 to 26, E is a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, or a substituted or unsubstituted $C_1$-$C_8$ haloalkyl.

In some embodiments, in particular according to any one of the sub aspects 11 or 24 to 26, E is a substituted or unsubstituted $C_1$-$C_5$ alkyl, a substituted or unsubstituted $C_6$-$C_{10}$ cycloalkyl, a substituted or unsubstituted $C_5$-$C_{10}$ heteroaryl or a substituted or unsubstituted $C_8$-$C_{10}$ aryl.

In some embodiments, in particular according to any one of the sub aspects 11 or 24 to 26, E is a substituted or unsubstituted $C_5$-$C_6$ halo heterocycle, in particular a $C_5$-$C_6$ halo heterocycle comprising one or two halogen atoms selected from Cl of F, particularly comprising one Cl or one F, a substituted or unsubstituted $C_5$-$C_6$ heteroaryl, a substituted $C_6$ aryl, in particular a bicyclic $C_6$ aryl such as tetraline or indane, a substituted or unsubstituted $C_5$-$C_6$ halo heteroaryl comprising one or two halogen atoms selected from Cl of F, particularly comprising one Cl or one F, selected from the group of substituted or unsubstituted pyrrole, furan, thiophene, benzothiophene, chromene, thiazole, pyrazine, pyridazine, pyridine, 1,2,3-triazole, 1,2,4-triazole, imidazole, oxazol, thiazol, indole, isoindole, quinoline, isoquinoline, naphatalene, coumarin, aminocoumarin, umbelliferon, benzotriazole, psoralen, benzofurane, benzothiophene, benzimidazol, benzthiazole, benzoxazole or benzpyridazin or hydroxylated, methylated or halogenated derivatives thereof selected from.

with n of $R^1_n$ being 0, 1, 2, 3, 4 or 5, in particular n of $R^1_n$ being 0, 1, 2 or 3, more particularly n of $R^1_n$ being 1, and with each $R^1$ independently from any other $R^1$ being selected from —OH, —F, —Cl, —Br, I, —CCH, —CN, —$N_3$, —$OCH_3$, —$OCF_3$, —$NH_2$, —$NHCH_3$, —N$(CH_3)_2$, —$CH_3$, —$CH_2$—$CH_3$, —$CF_3$, —$OCONH_2$ or —$NO_2$, —B($OR^a$)($OR^b$), —$(CH_2)_m$—$R^a$, —$(CH_2)_m$—$OR^a$, —$(CH_2)_m$—C(=O)$R^a$, —$(CH_2)_m$—C(=O)$OR^a$, —$(CH_2)_m$—OC(=O)$R^a$, —$(CH_2)_m$—OC(=O)$OR^a$, —$(CH_2)_m$—OC(=O)$NR^aR^b$, —$(CH_2)_m$—C(=O)$NR^aR^b$, —$(CH_2)_m$—C(=O)$NR^aR^b$, —$(CH_2)_m$—C(=O)$NR^b(OR^a)$, —$(CH_2)_m$—C(=S)$R^a$, —$(CH_2)_m$—C(=S)$OR^a$, —$(CH_2)_m$—OC(=S)$R^a$, —$(CH_2)_m$—OC(=S)$OR^a$, —$(CH_2)_m$—OC(=S)$NR^aR^b$, —$(CH_2)_m$—C(=S)$NR^aR^b$, —$(CH_2)_m$—$SR^a$, —$(CH_2)_m$—S(=O)$R^a$, —$(CH_2)_m$—S($O_2$)$R^a$, —$(CH_2)_m$—S($O_2$)$OR^a$, —$(CH_2)_m$—OS($O_2$)$R^a$, —$(CH_2)_m$—OS($O_2$)$OR^a$, —$(CH_2)_m$—$NR^aR^b$, —$(CH_2)_m$—$NR^cC(=O)R^a$, —$(CH_2)_m$—$NR^cC(=O)OR^a$, —$(CH_2)_m$—$NR^cC(=O)NR^aR^b$, —$(CH_2)_m$—$NR^cC(=S)R^a$, —$(CH_2)_m$—$NR^cC(=S)NR^aR^b$, —$(CH_2)_m$—$NR^cC(=S)OR^a$, —$(CH_2)_m$—$NR^cS(O_2)R^a$, —$(CH_2)_m$—P(=O)($OR^b$)($OR^a$), —$(CH_2)_m$—P(=O)($OR^b$)($R^a$) or —$(CH_2)_m$—S($O_2$)$NR^bR^a$, —$(CH_2)_m$—O—C(=O)-(M)—C(=O)OH, —$(CH_2)_m$—O—C(=O)-(M)—C(=O)$OR^a$, —$(CH_2)_m$—O—C(=O)-(M)—$R^a$, —$(CH_2)_m$—O—$(CH_2)_q$—P(=O)($R^{ba}$)($R^{aa}$), —$(CH_2)_m$—C(=O)O—$(CH_2)_q$—P(=O)($R^{ba}$)($R^{aa}$), —$(CH_2)_m$—C(=O)O—$(CH_2)_q$—S($O_2$)OH, —$(CH_2)_m$—C(=O)O—$(CH_2)_q$—S($O_2$)$OR^a$, with $R^{aa}$ being selected independently from each other being —$R^a$ or —$OR^a$, with $R^{ba}$ being selected independently from each other being —$R^b$ or —$OR^b$, with M being a substituted or unsubstituted $C_1$-$C_8$ alkyl, in particular an unsubstituted $C_1$-$C_8$ alkyl with m being selected from 0, 1 or 2, in particular 0 or 1, with q being selected from 0, 1 or 2, in particular 0 or 1, with each $R^a$, $R^b$ or $R^c$ being selected, where applicable, independently from each other from hydrogen, —CN a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl, a substituted or unsubstituted $C_3$-$C_{10}$ cycloalkyl or a substituted or unsubstituted $C_3$-$C_{10}$ halo cycloalkyl, a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, a substituted or unsubstituted $C_5$-$C_{10}$ heteroaryl, a substituted or unsubstituted $C_6$-$C_{10}$ aryl, in particular with each $R^1$ independently from any other $R^1$ being —OH, —F, —Cl, I, —CN, —OCH$_3$, —OCF$_3$, —OCONH$_2$ or —CF$_3$.

In some embodiments, in particular according to any one of the sub aspects 11 or 24 to 26, E is

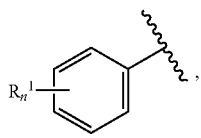

with n of $R^1_n$ being 0, 1, 2, 3, 4 or 5, in particular n of $R^1_n$ being 0, 1, 2 or 3, more particularly 1, and with each $R^1$ independently from any other $R^1$ being selected from —OH, —F, —Cl, —Br, I, —CCH, —CN, —N$_3$, —OCH$_3$, —OCF$_3$, —NH$_2$, —NHCH$_3$, —N(CH$_3$)$_2$, —CH$_3$, —CH$_2$—CH$_3$, —CF$_3$, —OCONH$_2$ or —NO$_2$, —B(OR$^a$)(OR$^b$), —(CH$_2$)$_m$—R$^a$, —(CH$_2$)$_m$—OR$^a$, —(CH$_2$)$_m$—C(=O)R$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O)NR$^a$R$^b$, —(CH$_2$)$_m$—C(=O)NR$^a$R$^b$, —(CH$_2$)$_m$—C(=O)NR$^b$(OR$^a$), —(CH$_2$)$_m$—C(=S)R$^a$, —(CH$_2$)$_m$—C(=S)OR$^a$, —(CH$_2$)$_m$—OC(=S)R$^a$, —(CH$_2$)$_m$—OC(=S)OR$^a$, —(CH$_2$)$_m$—OC(=S)NR$^a$R$^b$, —(CH$_2$)$_m$—C(=S)NR$^a$R$^b$, —(CH$_2$)$_m$—SR$^a$, —(CH$_2$)$_m$—S(=O)R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)NR$^a$R$^b$, —(CH$_2$)$_m$—NR$^c$C(=S)R$^a$, —(CH$_2$)$_m$—NR$^c$C(=S)NR$^a$R$^b$, —(CH$_2$)$_m$—NR$^c$C(=S)OR$^a$, —(CH$_2$)$_m$—NR$^c$S(O$_2$)R$^a$, —(CH$_2$)$_m$—P(=O)(OR$^b$)(C)R$^a$), —(CH$_2$)$_m$—P(=O)(OR$^b$)(R$^a$) or —(CH$_2$)$_m$—S(O$_2$)NR$^b$R$^a$, —(CH$_2$)$_m$—O—C(=O)-(M)—C(=O)OH, —(CH$_2$)$_m$—O—C(=O)-(M)—C(=O)OR$^a$, —(CH$_2$)$_m$—O—C(=O)-(M)—R$^a$, —(CH$_2$)$_m$—O—(CH$_2$)$_q$—P(=O)(R$^{ba}$)(R$^{aa}$), —(CH$_2$)$_m$—C(=O)O—(CH$_2$)$_q$—P(=O)(R$^{ba}$)(R$^{aa}$—(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$, with R$^{aa}$ being selected independently from each other being —R$^a$ or —OR$^a$, with R$^{ba}$ being selected independently from each other being —R$^b$ or —OR$^b$, with M being a substituted or unsubstituted $C_1$-$C_8$ alkyl, in particular an unsubstituted $C_1$-$C_8$ alkyl with m being selected from 0, 1 or 2, in particular 0 or 1, with q being selected from 0, 1 or 2, in particular 0 or 1, with each R$^a$, R$^b$ or R$^c$ being selected, where applicable, independently from each other from hydrogen, —CN a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl, a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, a substituted or unsubstituted $C_5$-$C_{10}$ heteroaryl, a substituted or unsubstituted $C_6$-$C_{10}$ aryl.

In some embodiments, in particular according to any one of the sub aspects 11 or 24 to 26, E is

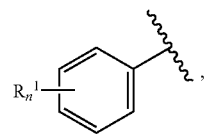

with n of $R^1_n$ being 0, 1, 2, 3, 4 or 5, in particular n of $R^1_n$ being 0, 1, 2 or 3, more particularly n of $R^1_n$ 1, and with each $R^1$ independently from any other $R^1$ being selected from OH, —F, —Cl, —Br, I, —CCH, —CN, —N$_3$, —OCH$_3$, —OCF$_3$, —NH$_2$, —NHCH$_3$, —N(CH$_3$)$_2$, —CH$_3$, —CH$_2$—CH$_3$, —CF$_3$, —OCONH$_2$ or —NO$_2$, —B(OR$^a$)(OR$^b$), —(CH$_2$)$_m$—R$^a$, —(CH$_2$)$_m$—OR$^a$, —(CH$_2$)$_m$—C(=O)R$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O)NR$^a$R$^b$, —(CH$_2$)$_m$—C(=O)NR$^a$R$^b$, —(CH$_2$)$_m$—C(=O)NR$^b$(OR$^a$), —(CH$_2$)$_m$—C(=S)R$^a$, —(CH$_2$)$_m$—C(=S)OR$^a$, —(CH$_2$)$_m$—OC(=S)R$^a$, —(CH$_2$)$_m$—OC(=S)OR$^a$, —(CH$_2$)$_m$—OC(=S)NR$^a$R$^b$, —(CH$_2$)$_m$—C(=S)NR$^a$R$^b$, —(CH$_2$)$_m$—SR$^a$, —(CH$_2$)$_m$—S(=O)R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)NR$^a$R$^b$, —(CH$_2$)$_m$—NR$^c$C(=S)R$^a$, —(CH$_2$)$_m$—NR$^c$C(=S)NR$^a$R$^b$, —(CH$_2$)$_m$—NR$^c$C(=S)OR$^a$, —(CH$_2$)$_m$—

$NR^cS(O_2)R^a$, —$(CH_2)_m$—$P(=O)(OR^b)(R^a)$, —$(CH_2)_m$—$P(=O)(OR^b)(R^a)$ or —$(CH_2)_m$—$S(O_2)NR^bR^a$, —$(CH_2)_m$—O—$C(=O)$-(M)—$C(=O)OH$, —$(CH_2)_m$—O—$C(=O)$-(M)—$C(=O)OR^a$, —$(CH_2)_m$—O—$C(=O)$-(M)—$R^a$, —$(CH_2)_m$—O—$(CH_2)_q$—$P(=O)(R^{ba})(R^{aa})$, —$(CH_2)_m$—$C(=O)O$—$(CH_2)_q$—$P(=O)(R^{ba})(R^{aa})$, —$(CH_2)_m$—$C(=O)O$—$(CH_2)_q$—$S(O_2)OH$ or —$(CH_2)_m$—$C(=O)O$—$(CH_2)_q$—$S(O_2)OR^a$, with $R^{aa}$ being selected independently from each other being —$R^a$ or —$OR^a$, with $R^{ba}$ being selected independently from each other being —$R^b$ or —$OR^b$, with M being a substituted or unsubstituted $C_1$-$C_8$ alkyl, in particular an unsubstituted $C_1$-$C_8$ alkyl with m being selected from 0, 1 or 2, in particular 0 or 1, with q being selected from 0, 1 or 2, in particular 0 or 1, with each $R^a$, $R^b$ or $R^c$ being selected, where applicable, independently from each other from hydrogen, —CN a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl, a substituted or unsubstituted $C_3$-$C_{10}$ cycloalkyl or a substituted or unsubstituted $C_3$-$C_{10}$ halo cycloalkyl, a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, a substituted or unsubstituted $C_5$-$C_{10}$ heteroaryl, a substituted or unsubstituted $C_6$-$C_{10}$ aryl, or q. E is

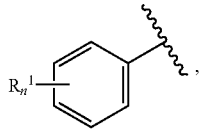

with n of $R^1_n$ being 0, 1, 2, 3, 4 or 5, in particular n of $R^1_n$ being 0, 1, 2 or 3, more particularly n of $R^1_n$ 1, and with each $R^1$ independently from any other $R^1$ being selected from —OH, —F, —Cl, —Br, I, —CCH, —CN, —$N_3$, —$OCH_3$, —$OCF_3$, —$NH_2$, —$NHCH_3$, —$N(CH_3)_2$, —$CH_3$, —$CH_2$—$CH_3$, —$CF_3$, —$OCONH_2$ or —$NO_2$, —$B(OR^a)(OR^b)$, —$(CH_2)_m$—$R^a$, —$(CH_2)_m$—$OR^a$, —$(CH_2)_m$—$C(=O)OR^a$, —$(CH_2)_m$—$OC(=O)R^a$, —$(CH_2)_m$—$OC(=O)OR^a$, —$(CH_2)_m$—$OC(=O)NR^aR^b$, —$(CH_2)_m$—$C(=O)NR^aR^b$, —$(CH_2)_m$—$C(=O)NR^aR^b$, —$(CH_2)_m$—$C(=O)NR^b(OR^a)$, —$(CH_2)_m$—$C(=S)R^a$, —$(CH_2)_m$—$C(=S)OR^a$, —$(CH_2)_m$—$OC(=S)R^a$, —$(CH_2)_m$—$OC(=S)OR^a$, —$(CH_2)_m$—$OC(=S)NR^aR^b$, —$(CH_2)_m$—$C(=S)NR^aR^b$, —$(CH_2)_m$—$SR^a$, —$(CH_2)_m$—$S(=O)R^a$, —$(CH_2)_m$—$S(O_2)R^a$, —$(CH_2)_m$—$S(O_2)OR^a$, —$(CH_2)_m$—$OS(O_2)R^a$, —$(CH_2)_m$—$OS(O_2)OR^a$, —$(CH_2)_m$—$NR^aR^b$, —$(CH_2)_m$—$NR^cC(=O)R^a$, —$(CH_2)_m$—$NR^cC(=O)OR^a$, —$(CH_2)_m$—$NR^cC(=O)NR^aR^b$, —$(CH_2)_m$—$NR^cC(=S)R^a$, —$(CH_2)_m$—$NR^cC(=S)NR^aR^b$, —$(CH_2)_m$—$NR^cC(=S)OR^a$, —$(CH_2)_m$—$NR^cS(O_2)R^a$, —$(CH_2)_m$—$P(=O)(OR^b)(OR^a)$, —$(CH_2)_m$—$P(=O)(OR^b)(R^a)$ or —$(CH_2)_m$—$S(O_2)NR^bR^a$, —$(CH_2)_m$—O—$C(=O)$-(M)—$C(=O)OH$, —$(CH_2)_m$—O—$C(=O)$-(M)—$C(=O)OR^a$, —$(CH_2)_m$—O—$C(=O)$-(M)—$R^a$, —$(CH_2)_m$—O—$(CH_2)_q$—$P(=O)(R^{ba})(R^{aa})$, —$(CH_2)_m$—$C(=O)O$—$(CH_2)_q$—$P(=O)(R^{ba})(R^{aa})$, —$(CH_2)_m$—$C(=O)O$—$(CH_2)_q$—$S(O_2)OH$ or —$(CH_2)_m$—$C(=O)O$—$(CH_2)_q$—$S(O_2)OR^a$, with $R^{aa}$ being selected independently from each other being —$R^a$ or —$OR^a$, with $R^{ba}$ being selected independently from each other being —$R^b$ or —$OR^b$, with M being a substituted or unsubstituted $C_1$-$C_8$ alkyl, in particular an unsubstituted $C_1$-$C_8$ alkyl with m being selected from 0, 1 or 2, in particular 0 or 1, with q being selected from 0, 1 or 2, in particular 0 or 1, with each $R^a$, $R^b$ or $R^c$ being selected, where applicable, independently from each other from hydrogen, —$CH_3$, —$CH_2CH_3$, —$CH_2CH_2CH_3$, —$CH_2CH_2CH_2CH_3$, —$CH(CH_3)_2$, —$CH_2CH(CH_3)_2$, —$C(CH_3)_3$, —$C_6H_5$—$CH_2C_6H_5$ In some embodiments, in particular according to any one of the sub aspects 11 or 24 to 26, E is

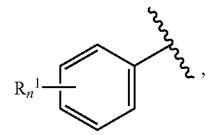

with n of $R^1_n$ being 0, 1, 2, 3, 4 or 5, in particular n of $R^1_n$ being 0, 1, 2 or 3, more particularly 1, and with each $R^1$ independently from any other $R^1$ being —OH, —F, —Cl, Br, I, CCH, —CN, —$N_3$, —$OCH_3$, —$OCF_3$, —$NH_2$, —$CH_3$, —$CF_3$, —$OCONH_2$ or —$NO_2$, a substituted or unsubstituted $C_5$-$C_6$ heterocycle, a substituted or unsubstituted $C_5$-$C_6$ halo heterocycle, in particular a $C_5$-$C_6$ halo heterocycle comprising one or two halogen atoms selected from Cl of F, particularly comprising one Cl or one F, a substituted or unsubstituted $C_5$-$C_6$ heteroaryl, a substituted or unsubstituted $C_5$-$C_6$ halo heteroaryl comprising one or two halogen atoms selected from Cl of F, particularly comprising one Cl or one F, a substituted or unsubstituted $C_6$ aryl.

In some embodiments, in particular according to any one of the sub aspects 11 or 24 to 26, E is

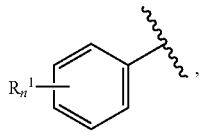

with n of $R^1_n$ being 0, 1, 2, 3, 4 or 5, in particular n of $R^1_n$ being 0, 1, 2 or 3, more particularly n of $R^1_n$ being 1, and with each $R^1$ independently from any other $R^1$ being —OH, —F, —Cl, I, —CN, —OCH$_3$, —OCF$_3$, —CONH$_2$ or —CF$_3$.

In some embodiments, in particular according to any one of the sub aspects 11 or 24 to 26, E is

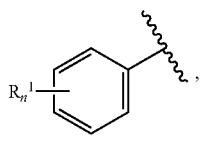

with n of $R^1_n$ being 5 and $R^1$ is F, or with n of $R^1_n$ being 5, and one to four of $R^1$ being F and the other ones of $R^1$ being selected independently from any other $R^1$ from —H, —OH, —Cl, I, —CN, —OCH$_3$, —OCF$_3$, —OCONH$_2$ or —CF$_3$, in particular from —OH, —OCH$_3$, —OCF$_3$, —OCONH$_2$ or —CF$_3$, or with n of $R^1_n$ being 1, and $R^1$ being selected from —OH, —OCH$_3$, —OCF$_3$, —OCONH$_2$ or —CF$_3$, or with n of $R^1_n$ being 5, and one to three of $R^1$ being F and the other ones of $R^1$ being selected independently from any other $R^1$ from —H, —OH, —Cl, I, —CN, —OCH$_3$, —OCF$_3$, —OCONH$_2$ or —CF$_3$, in particular —OH, —OCH$_3$, —OCF$_3$, —OCONH$_2$ or —CF$_3$, or with n of $R^1_n$ being 2, and each $R^1$ being selected independently from any other $R^1$ from —OH, —OCH$_3$, —OCF$_3$, —OCONH$_2$ or —CF$_3$, or with n of $R^1_n$ being 5, and one or two of $R^1$ being F and the other ones of $R^1$ being selected independently from any other $R^1$ from —H, —OH, —Cl, I, —CN, —OCH$_3$, —OCF$_3$, —OCONH$_2$ or —CF$_3$, in particular —OH, —OCH$_3$, —OCF$_3$, —OCONH$_2$ or —CF$_3$, or with n of $R^1_n$ being 3, and each $R^1$ being selected independently from any other $R^1$ from —OH, —OCH$_3$, —OCF$_3$, —OCONH$_2$ or —CF$_3$.

In some embodiments, in particular according to any one of the sub aspects 11 or 24 to 26, E is

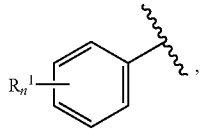

with n of $R^1_n$ being 0, 1, 2, 3, 4 or 5, in particular n of $R^1_n$ being 0, 1, 2 or 3, more particularly n of $R^1_n$ being 1, and with each $R^1$ independently from any other $R^1$ being —OH, OCH$_3$, —F, —OCONH$_2$ or —CF$_3$.

In some embodiments, in particular according to any one of the sub aspects 11 or 24 to 26, E is

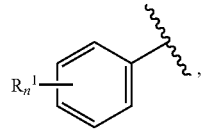

with n of $R^1_n$ being 1, 2, 3, 4 or 5, in particular n of $R^1_n$ being 1, 2 or 3, with one $R^1$ being a substituent Q, with Q being selected from —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$, —(CH$_2$)$_m$—O—S(O$_2$)OH, —(CH$_2$)$_m$—O—S(O$_2$)OR$^a$, in particular —(CH$_2$)$_m$—O—S(O$_2$)OH, —(CH$_2$)$_m$—O—S(O$_2$)OR$^a$, with m being selected from 0, 1 or 2, in particular from 0 or 1, with R$^a$ being —CH$_3$, —CH$_2$CH$_3$, —C$_6$H$_5$—CH$_2$CH$_2$CH$_3$, —CH(CH$_3$)$_2$, —CH$_2$C$_6$H$_5$ or para-methoxybenzyl —C(=O)—O—R$^a$, —O—C(=O)—R$^a$, in particular —O—C(=O)—R$^a$, with R$^a$ being a substituted or unsubstituted C$_1$-C$_{16}$ alkyl, in particular an unsubstituted C$_1$-C$_{14}$ alkyl, —(CH$_2$)$_m$—[(CH$_2$)$_{m1}$—O—C(=O)—(CH$_2$)$_{m2}$]$_{p1}$—C(=O)OR$^d$, in particular —(CH$_2$)—[—O—C(=O)—(CH$_2$)$_2$]$_{p1}$—C(=O)OR$^d$ with R$^d$ being —CH$_3$, —CH$_2$CH$_3$, —CH$_2$CH$_2$CH$_3$, —CH(CH$_3$)$_2$, —C$_6$H$_5$ m1 and m2 being selected independently from each other form 1, 2 or 3, in particular m1 and m2 are 2, and p1 being selected from 1 to 20, in particular from 1 to 8, —(CH$_2$)$_m$—[(CH$_2$)$_{m1}$—O—(CH$_2$)$_{m2}$]$_{p1}$—OR$^d$, in particular —[—O—(CH$_2$)$_2$]$_{p1}$—OR$^d$, with R$^d$ being —CH$_3$, —CH$_2$CH$_3$, —CH$_2$CH$_2$CH$_3$, —CH(CH$_3$)$_2$, —C$_6$H$_5$ m1 and m2 being selected independently from each other form 1, 2 or 3, in particular m1 and m2 are 2, and p1 being selected from 1 to 20, in particular from 1 to 8, —(CH$_2$)$_m$—C(=O)O—(CH$_2$)$_q$—P(=O)(R$^{ba}$)(R$^{aa}$), —(CH$_2$)$_m$—O—(CH$_2$)$_q$—P(=O)(R$^{ba}$)(R$^{aa}$), in particular from —(CH$_2$)$_m$—O—(CH$_2$)$_q$—P(=O)(R$^{ba}$)(R$^{aa}$), with R$^{aa}$ and R$^{ba}$ being selected, where applicable, independently from each other from —R$^a$ or —OR$^a$ and with R$^a$ being hydrogen, —OCH$_3$, —OCH$_2$CH$_3$, —CH$_3$, —CH$_2$CH$_3$, —C$_6$H$_5$—CH$_2$CH$_2$CH$_3$, —CH(CH$_3$)$_2$, —CH$_2$C$_6$H$_5$ or para-methoxybenzyl with m being selected from 0, 1 or 2, in particular 0 or 1, with q being selected from 0, 1 or 2, in particular 0 or 1, and with the other $R^1$ being selected independently from each other $R^1$ from —OH, —F, —Cl, —I, —CN, —OCH$_3$, —OCF$_3$, —OCONH$_2$ or —CF$_3$, in particular from —OH, —F, —OCH$_3$, —OCF$_3$, —OCONH$_2$ or —CF$_3$.

In some embodiments, in particular according to any one of the sub aspects 11 or 24 to 26, E is

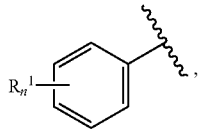

with n of $R^1_n$ being 5, and one to four of $R^1$ being F, one $R^1$ being the substituent Q, and, where applicable, the other ones of $R^1$ being selected independently from any other $R^1$ from —H, —OH, —Cl, —I, —CN, —OCH$_3$, —OCF$_3$, —OCONH$_2$ or —CF$_3$, in particular from —OH, —OCH$_3$, —OCF$_3$, —OCONH$_2$ or —CF$_3$, or with n of $R^1_n$ being 5, and one to three of $R^1$ being F, one $R^1$ being the substituent Q, and, where applicable, the other ones of $R^1$ being selected independently from any other $R^1$ from —H, —OH, —Cl, —I, —CN, —OCH$_3$, —OCF$_3$, —OCONH$_2$ or —CF$_3$, in particular —OH, —OCH$_3$, —OCF$_3$, —OCONH$_2$ or —CF$_3$, or with n of $R^1_n$ being 5, and one or two of $R^1$ being F, one $R^1$ being the substituent Q, and, where applicable, the other ones of $R^1$ being selected independently from any other $R^1$ from —H, —OH, —Cl, —I, —CN, —OCH$_3$, —OCF$_3$, —OCONH$_2$ or —CF$_3$, in particular —OH, —OCH$_3$, —OCF$_3$, —OCONH$_2$ or —CF$_3$, or with n of $R^1_n$ being 5, and one of $R^1$ being F, one $R^1$ being the substituent Q, and, where applicable, the other ones of $R^1$ being selected independently from any other $R^1$ from —H, —OH, —Cl, —I, —CN, —OCH$_3$, —OCF$_3$, —OCONH$_2$ or —CF$_3$, in particular —OH, —OCH$_3$, —OCF$_3$, —OCONH$_2$ or —CF$_3$, or with n of $R^1_n$ being 3, one $R^1$ being the substituent Q, and the other $R^1$ being selected independently from each other $R^1$ from —OH, —OCH$_3$, —OCF$_3$, —OCONH$_2$ or —CF$_3$, or with n of $R^1_n$ being 2, one $R^1$ being the substituent Q and the other $R^1$ being —H, —OH, —OCH$_3$, —OCF$_3$, —OCONH$_2$ or —CF$_3$, or with n of $R^1_n$ being 1 with $R^1$ being the substituent Q, with Q having the same meaning as defined previously, and wherein in particular Q is in para position with respect to the attachment position of the phenyl moiety of E to the parent moiety, and wherein in particular any hydrogen of the phenyl group may be substituted with F.

In some embodiments, in particular according to any one of the sub aspects 11 or 24 to 26, E is

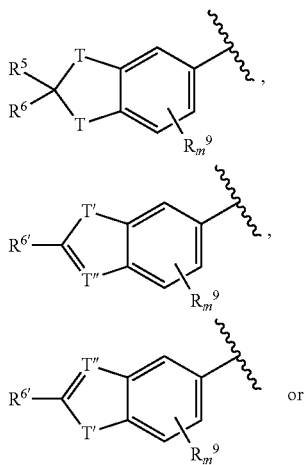

-continued

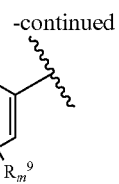

with each T being selected independently from each other from —CH$_2$, —NH, —S or —O, —CHCH$_3$, —C(CH$_3$)$_2$ or —NR$^c$, with R$^c$ being —OH, —CH$_3$, —CH$_2$CH$_3$, —CH$_2$CH$_2$CH$_3$, —CH(CH$_3$)$_2$, and with T' being selected from —CH$_2$, —NH, —S or —O, —CHCH$_3$, —C(CH$_3$)$_2$ or —NR$^c$, and with T'' being selected from —CH or =N, and with R$^5$ and R$^6$ being selected independently from each other from —H, —F, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular with R$^5$ and R$^6$ being selected independently from each other from H, —F or —CH$_3$, and with R$^{6'}$ being selected from —OH, —OCH$_3$, —OCH$_2$CH$_3$ or —CH$_3$, with R$^7$ being selected from =NH, =S or =O, and with m of $R^9_m$ being selected from 0, 1, 2 or 3, and each R$^9$ being selected independently from each other from —Cl, —F, Br, —I, —OH, —CCH, —CN —CH$_3$, —CH$_2$CH$_3$, —OCH$_3$, —COOH, —COOR$^b$, —C(O)NH$_2$, —C(O)NH(R$^b$); —NHC(=O)OR$^b$, —NR$^b$C(=O)OR$^b$, —NR$^b$C(=O)OH, —C(O)N(R$^b$)$_2$— CH$_2$CF$_3$, —CHFCF$_3$, —CF$_2$CF$_3$, —CHF$_2$, —CH$_2$F or —CF$_3$, with R$^b$ being a substituted or unsubstituted C$_1$-C$_5$ alkyl, a substituted or unsubstituted C$_2$-C$_5$ alkenyl, a substituted or unsubstituted C$_2$-C$_5$ alkynyl, or a C$_1$-C$_5$ haloalkyl.

In some embodiments, in particular according to any one of the sub aspects 11 or 24 to 26, E is

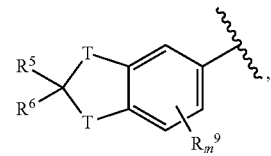

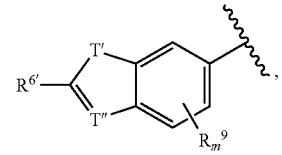

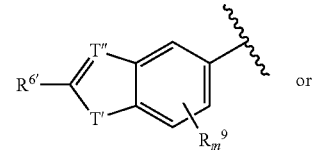 or

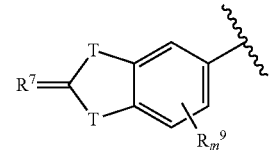

with m of $R^9_m$ being 0, and
with each T being selected independently from each other from —CH$_2$, —CHCH$_3$, —C(CH$_3$)$_2$, —NH, NR$^c$, —S or —O, in particular form —C(CH$_3$)$_2$, —NH, —S or —O,
with $R^c$ being —CH$_2$OH, —CH$_3$, —CH$_2$CH$_3$, —CH$_2$CH$_2$CH$_3$, —CH(CH$_3$)$_2$,
with T' being selected from —CH$_2$, —NH, —S or —O, —CHCH$_3$, —C(CH$_3$)$_2$ or —NR$^c$, in particular from —O, —S or —NH, and
with T" being selected from —CH or =N, in particular T" is =N, and
with $R^5$ and $R^6$ being selected independently from each other from —H, —F —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular with $R^5$ and $R^6$ being selected independently from each other from H, —F or CH$_3$, and
with $R^{6'}$ being selected from OH, —OCH$_3$, —OCH$_2$CH$_3$ or —CH$_3$,
with $R^7$ being selected from =NH, =S or =O, in particular $R^7$ is =O.

In some embodiments, in particular according to any one of the sub aspects 11 or 24 to 26, E is selected from

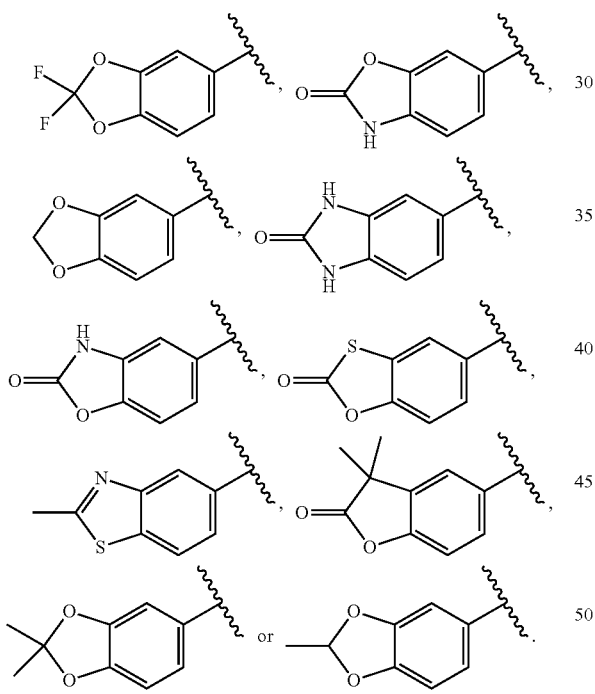

In some embodiments, in particular according to any one of the sub aspects 12, 13 or 27 to 32,
n of $R^1_n$ is 0, 1, 2, 3, 4 or 5, in particular n of $R^1_n$ being 0, 1, 2 or 3, more particularly 1, and
each $R^1$ independently from any other $R^1$ is selected from —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$—CH$_3$, —CF$_3$, —OCONH$_2$ or —NO$_2$, —B(OR$^a$)(OR$^b$), —(CH$_2$)$_m$—R$^a$, —(CH$_2$)$_m$—OR$^a$, —(CH$_2$)$_m$—C(=O)R$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O) NR$^a$R$^b$, —(CH$_2$)$_m$—C(=O)NR$^a$R$^b$, —(CH$_2$)$_m$—C(=O)NR$^b$(OR$^a$), —(CH$_2$)$_m$—C(=S)R$^a$, —(CH$_2$)$_m$—C(=S)OR$^a$, —(CH$_2$)$_m$—OC(=S)R$^a$, —(CH$_2$)$_m$—OC(=S)OR$^a$, —(CH$_2$)$_m$—OC(=S)NR$^a$R$^b$, —(CH$_2$)$_m$—C(=S)NR$^a$R$^b$, —(CH$_2$)$_m$—SR$^a$, —(CH$_2$)$_m$—S(=O) R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)OR$^a$, —(CH$_2$)$_m$—NR$^c$C(=O) NR$^a$R$^b$, —(CH$_2$)$_m$—NR$^c$C(=S)R$^a$, —(CH$_2$)$_m$—NR$^c$C(=S)NR$^a$R$^b$, —(CH$_2$)$_m$—NR$^c$C(=S)OR$^a$, —(CH$_2$)$_m$—NR$^c$S(O$_2$)R$^a$, —(CH$_2$)$_m$—P(=O)(OR$^b$)(OR$^a$), —(CH$_2$)$_m$—P(=O)(OR$^b$)(R$^a$) or —(CH$_2$)$_m$—S(O$_2$)NR$^b$R$^a$, —(CH$_2$)$_m$—O—C(=O)-(M)—C(=O)OH, —(CH$_2$)$_m$—O—C(=O)-(M)—C(=O)OR$^a$, —(CH$_2$)$_m$—O—C(=O)-(M)—R$^a$, —(CH$_2$)$_m$—O—(CH$_2$)$_q$—P(=O)(R$^{ba}$)(R$^{aa}$), —(CH$_2$)$_m$—C(=O)O—(CH$_2$)$_q$—P(=O)(R$^{ba}$)(R$^{aa}$), —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$,
with $R^{aa}$ being selected independently from each other being —R$^a$ or —OR$^a$,
with $R^{ba}$ being selected independently from each other being —R$^b$ or —OR$^b$,
with M being a substituted or unsubstituted C$_1$-C$_8$ alkyl, in particular an unsubstituted C$_1$-C$_8$ alkyl
with m being selected from 0, 1 or 2, in particular 0 or 1, with q being selected from 0, 1 or 2, in particular 0 or 1,
with each R$^a$, R$^b$ or R$^c$ being selected, where applicable, independently from each other from hydrogen, —CN
a substituted or unsubstituted C$_1$-C$_{16}$ alkyl, a substituted or unsubstituted C$_1$-C$_{16}$ alkoxy, a substituted or unsubstituted C$_1$-C$_{16}$ carboxy, a substituted or unsubstituted C$_2$-C$_{16}$ alkenyl, a substituted or unsubstituted C$_2$-C$_{16}$ alkynyl, or a C$_1$-C$_{16}$ haloalkyl, in particular a substituted or unsubstituted C$_1$-C$_8$ alkyl, a substituted or unsubstituted C$_1$-C$_8$ alkoxy, a substituted or unsubstituted C$_2$-C$_8$ alkenyl, a substituted or unsubstituted C$_2$-C$_8$ alkynyl, a substituted or unsubstituted C$_1$-C$_8$ haloalkyl, a substituted or unsubstituted C$_3$-C$_{10}$ cycloalkyl, or a substituted or unsubstituted C$_3$-C$_{10}$ halo cycloalkyl,
a substituted or unsubstituted C$_3$-C$_{10}$ cycloalkyl or a substituted or unsubstituted C$_3$-C$_{10}$ halo cycloalkyl,
a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle,
a substituted or unsubstituted C$_5$-C$_{10}$ heteroaryl,
a substituted or unsubstituted C$_6$-C$_{10}$ aryl.

In some embodiments, in particular according to any one of the sub aspects 12, 13 or 27 to 32, with n of $R^1_n$ of BA being 0, 1, 2, 3, 4 or 5, in particular n of $R^1_n$ being 0, 1, 2 or 3, more particularly n of $R^1_n$ 1, and
with each $R^1$ independently from any other $R^1$ being selected from
—OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$—CH$_3$, —CF$_3$, —OCONH$_2$ or —NO$_2$, —B(OR$^a$)(OR$^b$), —(CH$_2$)$_m$—R$^a$, —(CH$_2$)$_m$—OR$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)

$NR^aR^b$, —$(CH_2)_m$—C(═O)$NR^aR^b$, —$(CH_2)_m$—C(═O)$NR^aR^b$, —$(CH_2)_m$—C(═O)$NR^b(OR^a)$, —$(CH_2)_m$—C(═S)$R^a$, —$(CH_2)_m$—C(═S)$OR^a$, —$(CH_2)_m$—OC(═S)$R^a$, —$(CH_2)_m$—OC(═S)$OR^a$, —$(CH_2)_m$—OC(═S)$NR^aR^b$, —$(CH_2)_m$—C(═S)$NR^aR^b$, —$(CH_2)_m$—$SR^a$, —$(CH_2)_m$—S(═O)$R^a$, —$(CH_2)_m$—S($O_2$)$R^a$, —$(CH_2)_m$—S($O_2$)$OR^a$, —$(CH_2)_m$—OS($O_2$)$R^a$, —$(CH_2)_m$—OS($O_2$)$OR^a$, —$(CH_2)_m$—$NR^aR^b$, —$(CH_2)_m$—$NR^cC$(═O)$R^a$, —$(CH_2)_m$—$NR^cC$(═O)$OR^a$, —$(CH_2)_m$—$NR^cC$(═O)$NR^aR^b$, —$(CH_2)_m$—$NR^cC$(═S)$R^a$, —$(CH_2)_m$—$NR^cC$(═S)$NR^aR^b$, —$(CH_2)_m$—$NR^cC$(═S)$OR^a$, —$(CH_2)_m$—$NR^cS(O_2)R^a$, —$(CH_2)_m$—P(═O)($OR^b$)($OR^a$), —$(CH_2)_m$—P(═O)($OR^b$)($R^a$) or —$(CH_2)_m$—S($O_2$)$NR^bR^a$, —$(CH_2)_m$—O—C(═O)-(M)—C(═O)OH, —$(CH_2)_m$—O—C(═O)-(M)—C(═O)$OR^a$, —$(CH_2)_m$—O—C(═O)-(M)—$R^a$, —$(CH_2)_m$—O—$(CH_2)_q$—P(═O)($R^{ba}$)($R^{aa}$), —$(CH_2)_m$—C(═O)O—$(CH_2)_q$—P(═O)($R^{ba}$)($R^{aa}$), —$(CH_2)_m$—C(═O)O—$(CH_2)_q$—S($O_2$)OH or —$(CH_2)_m$—C(═O)O—$(CH_2)_q$—S($O_2$)$OR^a$, with $R^{aa}$ being selected independently from each other being —$R^a$ or —$OR^a$,
with $R^{ba}$ being selected independently from each other being —$R^b$ or —$OR^b$,
with M being a substituted or unsubstituted $C_1$-$C_8$ alkyl, in particular an unsubstituted $C_1$-$C_8$ alkyl,
with m being selected from 0, 1 or 2, in particular 0 or 1,
with q being selected from 0, 1 or 2, in particular 0 or 1,
with each $R^a$, $R^b$ or $R^c$ being selected, where applicable, independently from each other from hydrogen, —$CH_3$, —$CH_2CH_3$, —$CH_2CH_2CH_3$, —$CH_2CH_2CH_2CH_3$, —CH($CH_3$)$_2$, —$CH_2CH(CH_3)_2$, —C($CH_3$)$_3$, —$C_6H_5$—$CH_2C_6H_5$.

In some embodiments, in particular according to any one of the sub aspects 12, 13 or 27 to 32,
n of $R^1_n$ is 0, 1, 2, 3, 4 or 5, in particular n of $R^1_n$ is 0, 1, 2 or 3, more particularly 1, and with each $R^1$ independently from any other $R^1$ being
—OH, —F, —Cl, —Br, —I, —CCH, —CN, —$N_3$, —$OCH_3$, —$OCF_3$, —$NH_2$, —$CH_3$, —$CF_3$—$OCONH_2$ or —$NO_2$,
a substituted or unsubstituted $C_5$-$C_6$ heterocycle,
a substituted or unsubstituted $C_5$-$C_6$ halo heterocycle, in particular a $C_5$-$C_6$ halo heterocycle comprising one or two halogen atoms selected from Cl of F, particularly comprising one Cl or one F,
a substituted or unsubstituted $C_5$-$C_6$ heteroaryl,
a substituted or unsubstituted $C_5$-$C_6$ halo heteroaryl comprising one or two halogen atoms selected from Cl of F, particularly comprising one Cl or one F,
a substituted or unsubstituted $C_6$ aryl.

In some embodiments, in particular according to any one of the sub aspects 12, 13 or 27 to 32,
n of $R^1_n$ is 0, 1, 2, 3, 4 or 5, in particular n of $R^1_n$ is 0, 1, 2 or 3, more particularly 1, and
with each $R^1$ independently from any other $R^1$ being —OH, —F, —Cl, —I, —CN, —$OCH_3$, —$OCF_3$, —$OCONH_2$ or —$CF_3$.

In some embodiments, in particular according to any one of the sub aspects 12, 13 or 27 to 32,
n of $R^1_n$ is 5 and $R^1$ is F, or
n of $R^1_n$ is 5, and one to four of $R^1$ being F and the other ones of $R^1$ are selected independently from any other $R^1$ from —H, —OH, —Cl, —I, —CN, —$OCH_3$, —$OCF_3$, —$OCONH_2$ or —$CF_3$, in particular from —OH, —$OCH_3$, —$OCF_3$, —$OCONH_2$ or —$CF_3$, or n of $R^1_n$ is 1, and $R^1$ are selected from —OH, —$OCH_3$, —$OCF_3$, —$OCONH_2$ or —$CF_3$, or n of $R^1_n$ is 5, and one to three of $R^1$ are F and the other ones of $R^1$ are selected independently from any other $R^1$ from —H, —OH, —Cl, —I, —CN, —$OCH_3$, —$OCF_3$, —$OCONH_2$ or —$CF_3$, in particular from —OH, —$OCH_3$, —$OCF_3$ or —$CF_3$, or n of $R^1_n$ is 2, and each $R^1$ is selected independently from any other $R^1$ from —OH, —$OCH_3$, —$OCF_3$, —$OCONH_2$ or —$CF_3$, or n of $R^1_n$ is 5, and one or two of $R^1$ are F and the other ones of $R^1$ are selected independently from any other $R^1$ from —H, —OH, —Cl, I, —CN, —$OCH_3$, —$OCF_3$, —$OCONH_2$ or —$CF_3$, in particular from —OH, —$OCH_3$, —$OCF_3$, —$OCONH_2$ or —$CF_3$, or n of $R^1_n$ is 3, and each $R^1$ is selected independently from any other $R^1$ from —OH, —$OCH_3$, —$OCF_3$, —$OCONH_2$ or —$CF_3$.

In some embodiments, in particular according to any one of the sub aspects 12, 13 or 27 to 32,
n of $R^1_n$ is 0, 1, 2, 3, 4 or 5, in particular n of $R^1_n$ is 0, 1, 2 or 3, more particularly n of $R^1_n$ is 1, and with each $R^1$ independently from any other $R^1$ being —OH, $OCH_3$, —F or —$CF_3$.

In some embodiments, in particular according to any one of the sub aspects 12, 13 or 27 to 32,
n of $R^1_n$ is 1, 2, 3, 4 or 5, in particular n of $R^1_n$ is 1, 2 or 3,
with one $R^1$ being a substituent Q, with Q being selected from
—$(CH_2)_m$—C(═O)O—$(CH_2)_q$—S($O_2$)OH or —$(CH_2)_m$—C(═O)O—$(CH_2)_q$—S($O_2$)$OR^a$, —$(CH_2)_m$—O—S($O_2$)OH, —$(CH_2)_m$—O—S($O_2$)$OR^a$, in particular —$(CH_2)_m$—O—S($O_2$)OH, —$(CH_2)_m$—O—S($O_2$)$OR^a$, with m being selected from 0, 1 or 2, in particular from 0 or 1, with $R^a$ being —$CH_3$, —$CH_2CH_3$, —$C_6H_5$—$CH_2CH_2CH_3$, —CH($CH_3$)$_2$, —$CH_2C_6H_5$ or para-methoxybenzyl —C(═O)—O—$R^a$, —O—C(═O)—$R^a$, in particular —O—C(═O)—$R^a$, with $R^a$ being a substituted or unsubstituted $C_1$-$C_{16}$ alkyl, in particular an unsubstituted $C_1$-$C_{14}$ alkyl, —$(CH_2)_m$—[$(CH_2)_{m1}$—O—C(═O)—$(CH_2)_{m2}$]$_{p1}$—C(═O)$OR^d$, in particular —$(CH_2)$—[—O—C(═O)—$(CH_2)_2$]$_{p1}$—C(═O)$OR^d$ with
$R^d$ being —$CH_3$, —$CH_2CH_3$, —$CH_2CH_2CH_3$, —CH($CH_3$)$_2$, —$C_6H_5$
m1 and m2 being selected independently from each other form 1, 2 or 3, in particular m1 and m2 are 2, and
p1 being selected from 1 to 20, in particular from 1 to 8, —$(CH_2)_m$—[$(CH_2)_{m1}$—O—$(CH_2)_{m2}$]$_{p1}$—$OR^d$, in particular —[—O—$(CH_2)_2$]$_{p1}$—$OR^d$, with
$R^d$ being —$CH_3$, —$CH_2CH_3$, —$CH_2CH_2CH_3$, —CH($CH_3$)$_2$, —$C_6H_5$
m1 and m2 being selected independently from each other form 1, 2 or 3, in particular m1 and m2 are 2, and
p1 being selected from 1 to 20, in particular from 1 to 8, —(CH$_2$)$_m$—C(=O)O—(CH$_2$)$_q$—P(=O)(R$^{ba}$)(R$^{aa}$),
—(CH$_2$)$_m$—O—(CH$_2$)$_q$—P(=O)(R$^{ba}$)(R$^{aa}$), in particular from —(CH$_2$)$_m$—O—(CH$_2$)$_q$—P(=O)(R$^{ba}$)(R$^{aa}$), with R$^{aa}$ and R$^{ba}$ being selected, where applicable, independently from each other from —R$^a$ or —OR$^a$ and with R$^a$ being hydrogen, —OCH$_3$, —OCH$_2$CH$_3$, —CH$_3$, —CH$_2$CH$_3$, —C$_6$H$_5$—CH$_2$CH$_2$CH$_3$, —CH(CH$_3$)$_2$, —CH$_2$C$_6$H$_5$ or para-methoxybenzyl with m being selected from 0, 1 or 2, in particular 0 or 1, with q being selected from 0, 1 or 2, in particular 0 or 1, and with the other R$^1$ being selected independently from each other R$^1$ from —OH, —F, —Cl, I, —CN, —OCH$_3$, —OCF$_3$, —OCONH$_2$ or —CF$_3$, in particular from —OH, —F, —OCH$_3$, —OCF$_3$, —OCONH$_2$ or —CF$_3$.

In some embodiments, in particular according to any one of the sub aspects 12, 13 or 27 to 32, n of R$^1_n$ is 5, and one to four of R$^1$ are F, one R$^1$ is the substituent Q, and, where applicable, the other ones of R$^1$ are selected independently from any other R$^1$ from —H, —OH, —Cl, I, —CN, —OCH$_3$, —OCF$_3$, —OCONH$_2$ or —CF$_3$, in particular from —OH, —OCH$_3$, —OCF$_3$, —OCONH$_2$ or —CF$_3$, or n of R$^1_n$ is 5, and one to three of R$^1$ are F, one R$^1$ is the substituent Q, and, where applicable, the other ones of R$^1$ are selected independently from any other R$^1$ from —H, —OH, —Cl, I, —CN, —OCH$_3$, —OCF$_3$, —OCONH$_2$ or —CF$_3$, in particular —OH, —OCH$_3$, —OCF$_3$, —OCONH$_2$ or —CF$_3$, or n of R$^1_n$ is 5, and one or two of R$^1$ are F, one R$^1$ is the substituent Q, and, where applicable, the other ones of R$^1$ are selected independently from any other R$^1$ from —H, —OH, —Cl, I, —CN, —OCH$_3$, —OCF$_3$, —OCONH$_2$ or —CF$_3$, in particular —OH, —OCH$_3$, —OCF$_3$, —OCONH$_2$ or —CF$_3$, or n of R$^1_n$ is 5, and one of R$^1$ is F, one R$^1$ is the substituent Q, and, where applicable, the other ones of R$^1$ are selected independently from any other R$^1$ from —H, —OH, —Cl, I, —CN, —OCH$_3$, —OCF$_3$, —OCONH$_2$ or —CF$_3$, in particular from —OH, —OCH$_3$, —OCF$_3$, —OCONH$_2$ or —CF$_3$, or n of R$^1_n$ is 3, one R$^1$ is the substituent Q, and the other R$^1$ are selected independently from each other R$^1$ from —OH, —OCH$_3$, —OCF$_3$, —OCONH$_2$ or —CF$_3$, or n of R$^1_n$ is 2, one R$^1$ is the substituent Q and the other R$^1$ is —H, —OH, —OCH$_3$, —OCF$_3$, —OCONH$_2$ or —CF$_3$, or n of R$^1_n$ is 1, with R$^1$ being the substituent Q, with Q having the same meaning as defined previously, and wherein in particular Q is in para position with respect to the attachment position of the phenyl moiety of E to the parent moiety, and wherein in particular any hydrogen of the phenyl group may be substituted with F.

In some embodiments, in particular according to any one of the sub aspects 11 to 13 or 24 to 31, R$^2$ and R$^3$ are selected, where applicable, independently from each other from —H, —F, —CN, —OH, —NH$_2$, —NO$_2$, —NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl.

In some embodiments, in particular according to any one of the sub aspects 11 to 13 or 24 to 31, R$^2$ and R$^3$ are selected, where applicable, independently from each other from —H, —F, —CN, —OH, —NH$_2$, —NO$_2$, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$.

In some embodiments, in particular according to any one of the sub aspects 11 to 13 or 24 to 31, R$^2$ and R$^3$ are selected independently from each other from —H, —F or —CH$_3$.

In some embodiments, X$^1$ is selected from

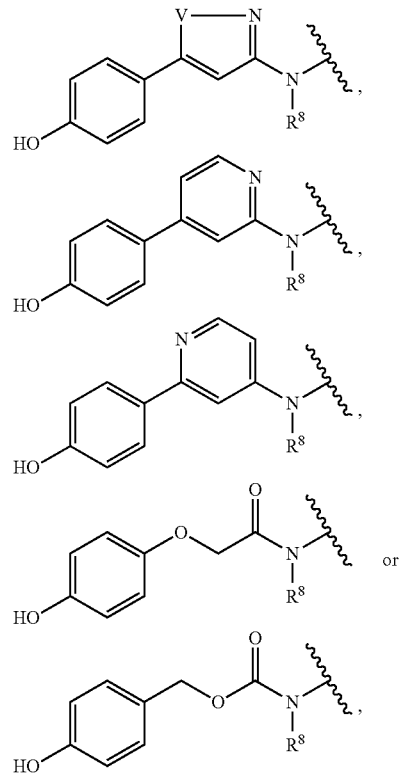

with R$^8$ being selected from H or CH$_3$, in particular R$^8$ is H and with V being selected from O, NH or S, in particular from O or NH.

In some embodiments, X$^1$ is selected from

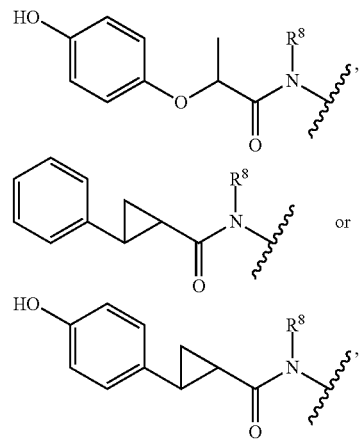

with R$^8$ being selected from H or CH$_3$, in particular R$^8$ is H.

In some embodiments, $X^1$ is selected from
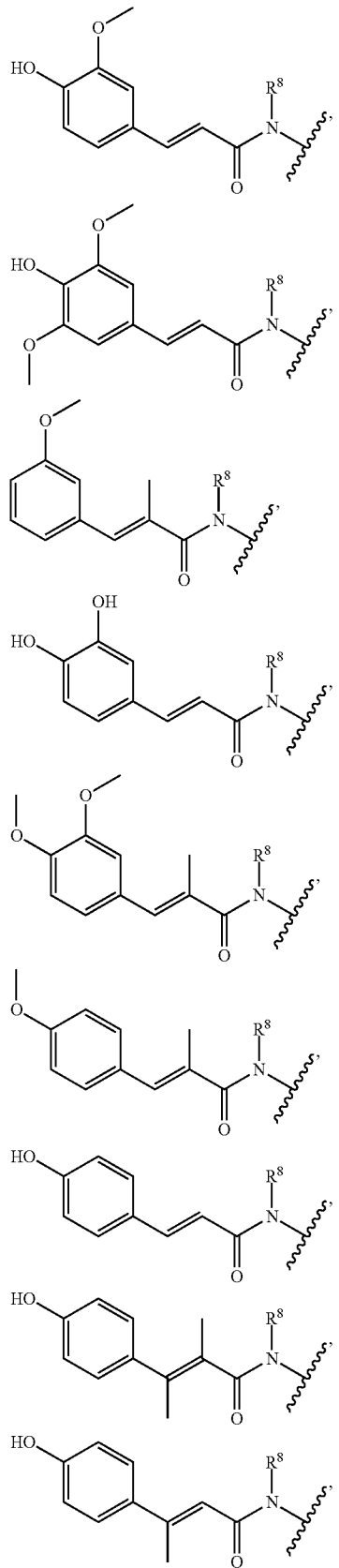
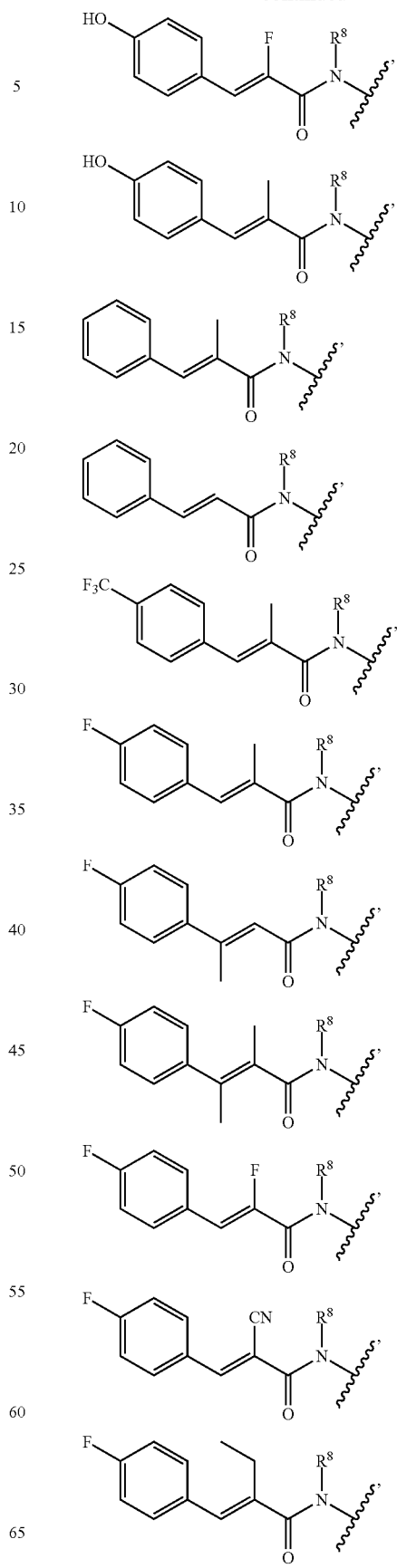

-continued
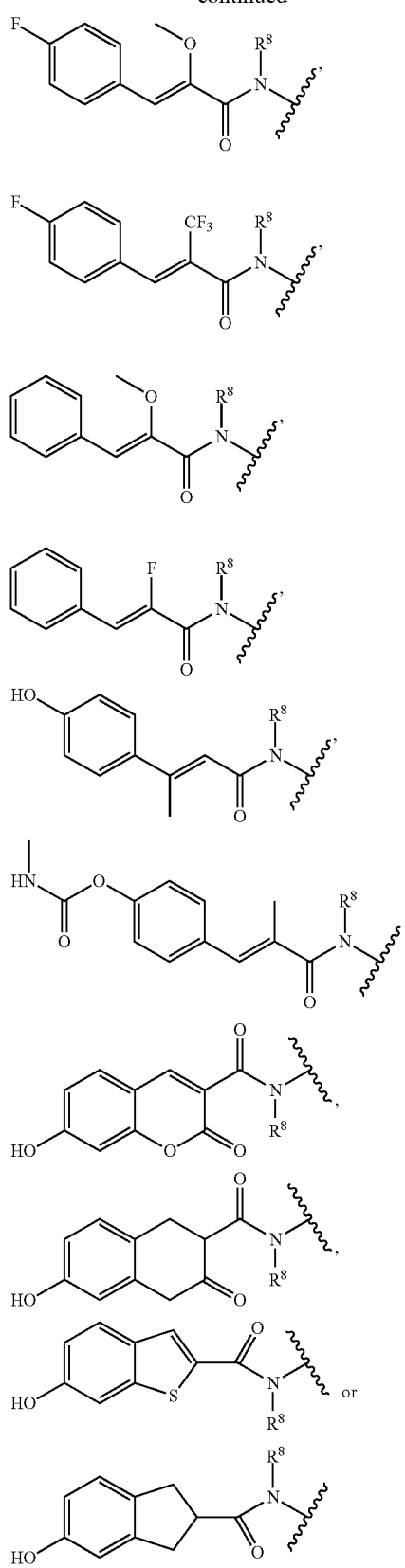
with R[8] being selected from H or CH$_3$, in particular R[8] is H.
In some embodiments, X[1] is selected from

In some embodiments, BB is

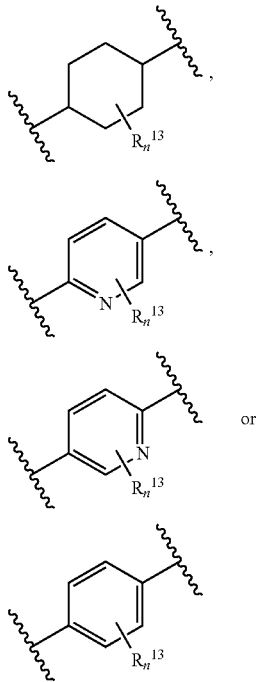

with n of $R^{13}_n$ being 0, 1, 2, 3 or 4, in particular n of $R^{13}_n$ being 0, 1 or 2, with each $R^{13}$ independently from any other $R^{13}$ being —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CF$_3$ or —NO$_2$, in particular —OH, —F, —Cl, —Br, —I, —CCH, —CN, —N$_3$, —OCH$_3$, —OCF$_3$, -, —CH$_3$, —CH$_2$CH$_3$ or —CF$_3$, with each $R^{13}$ independently from any other $R^{13}$ being —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_3$, —CF$_3$ or —NO$_2$, in particular —OH, —F, —Cl, —Br, —I, —CCH, —CN, —N$_3$, —OCH$_3$, —OCF$_3$, -, —CH$_3$, —CH$_2$CH$_3$ or —CF$_3$, wherein, each carbon atom of the cyclic system which comprises no substituent $R^{13}$ comprises F instead of H.

In some embodiments, BB is

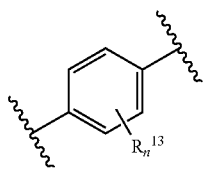

with n of $R^{13}_n$ being 0, or with n of $R^{13}_n$ being 1, 2, 3 or 4 with each $R^{13}$ being F, in particular n is 4 and each $R^{13}$ is F.

In some embodiments, in particular according to any one of the sub aspects 1 to 12 or 14 to 38, BC is selected from

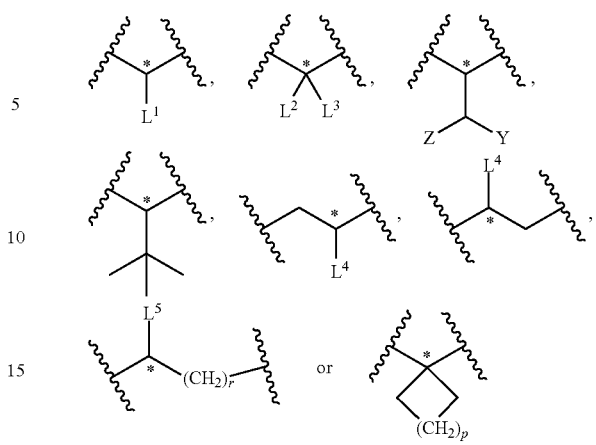

with p being 1, 2, 3, 4 or 5, in particular p being 2 or 3, and with r being 2, 3, 4 or 5, in particular r being 2, with $L^1$, $L^2$, $L^4$, $L^5$ being selected independently from each other from side chains of amino acids such as —H (Gly), —CH$_3$ (Ala), —CH$_2$CH$_2$CH$_2$NHC(NR$^c$)N(R$^b$)(R$^a$) (Arg), —CH$_2$CON(R$^b$)(R$^a$) (Asn), —CH$_2$C(=O)OR$^a$ (Asp), —CH$_2$SR$^a$ (Cys), —CH$_2$CH$_2$C(=O)N(R$^b$)(R$^a$) (Gln), —CH$_2$CH$_2$C(=O)OR$^a$ (Glu), —CH$_2$(C$_3$H$_3$N$_2$) (His), —CH$_2$CH$_2$CH$_2$CH$_2$ (Lys), —CH$_2$CH$_2$SCH$_3$ (Met), —CH$_2$(C$_6$H$_5$) (Phe), —CH$_2$CH$_2$CH$_2$— (Pro), —CH$_2$OR$^a$ (Ser), —CH(OR$^a$)CH$_3$ (Thr), —CH$_2$(C$_8$H$_6$N)OR$^a$ (Trp), —CH$_2$(C$_6$H$_4$)OR$^a$ (Tyr), —CH(CH$_3$)$_2$ (Val), or from —CCH, —CN, —OCH$_3$, —CH$_3$, —CF$_3$, —R$^a$, —CH(R$^b$)(R$^a$), —CH$_2$OR$^a$, —CH$_2$C(=O)R$^a$, —C(=O)OR$^a$, —OC(=O)NR$^b$R$^a$, —C(=O)NR$^b$R$^a$, —CH$_2$C(=O)NR$^b$(OR$^a$), —CH$_2$S(O$_2$)R$^a$, —S(O$_2$)OR$^a$, —CH$_2$S(O$_2$)OR$^a$, —CH$_2$NHC(=O)R$^a$, —CH$_2$NR$^b$S(O$_2$)R$^a$, —CH$_2$P(=O)(OR$^b$)(OR$^a$), —CH$_2$P(=O)(OR$^b$)(R$^a$),), —CH$_2$P(=O)(R$^b$)(R$^a$) or —CH$_2$S(O$_2$)NR$^b$R$^a$, with R$^a$ and R$^b$ being selected, where applicable, independently from each other from a substituted or unsubstituted C$_1$-C$_4$ alkyl, a substituted or unsubstituted C$_1$-C$_4$ alkoxy, a substituted or unsubstituted C$_1$-C$_4$ carboxy, a substituted or unsubstituted C$_2$-C$_4$ alkenyl, a substituted or unsubstituted C$_2$-C$_4$ alkynyl, or a C$_1$-C$_4$ haloalkyl, or a substituted or unsubstituted C$_3$-C$_{10}$ cycloalkyl or a substituted or unsubstituted C$_3$-C$_{10}$ halo cycloalkyl, or a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle, or a substituted or unsubstituted C$_5$-C$_{10}$ heteroaryl, or a substituted or unsubstituted C$_6$-C$_{10}$ aryl, and with $L^3$ being selected from —CH$_3$, —CH$_2$CH$_3$, —OCH$_3$, —OCH$_2$CH$_3$, a C$_1$-C$_2$-fluoro alkyl, with Y being —CN, —C(=O)OH, —C(=O)OCH$_3$, —C(=O)OCH$_2$CH$_3$, —C(=O)NHCH$_3$, —C(=O)NHCH$_2$CH$_3$, —C(=O)N(CH$_3$)$_2$, —C(=O)N(CH$_2$CH$_3$)$_2$, —C(=O)N(CH$_3$)(CH$_2$CH$_3$) or —C(=O)NH$_2$, in particular Z is H and Y is CN and —C(=O)NH$_2$, and wherein with Z being —H, —OH, —CH$_3$, —CH$_2$CH$_3$, —OCH$_3$—NH$_2$NHCH$_3$, N(CH$_3$)$_2$N(CH$_3$)$_3^+$.

In some embodiments L¹, L², L³, L⁴ and L⁵ comprise the structure elements of amino acids and their derivatives. The respective amino acid is named in brackets.

In some embodiments, in particular according to any one of the sub aspects 1 to 12 or 14 to 38, BC is selected from

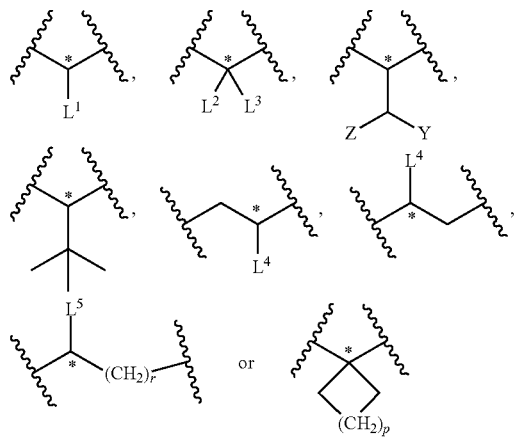

with p being 1, 2, 3, 4 or 5, in particular p being 2 or 3, and with r being 2, 3, 4 or 5, in particular r being 2, with $L^1$, $L^2$, $L^4$, $L^5$ being selected independently from each other from side chains of amino acids such as —H (Gly), —CH₃ (Ala), —CH₂CH₂CH₂NHC(NR$^c$)N(R$^b$)(R$^a$) (Arg), —CH₂CON(R$^b$)(R$^a$) (Asn), —CH₂C(═O)OR$^a$ (Asp), —CH₂SR$^a$ (Cys), —CH₂CH₂C(═O)N(R$^b$)(R$^a$) (Gln), —CH₂CH₂C(═O)OR$^a$ (Glu), —CH₂(C₃H₃N₂) (His), —CH₂CH₂CH₂CH₂ (Lys), —CH₂CH₂SCH₃ (Met), —CH₂(C₆H₅) (Phe), —CH₂CH₂CH₂— (Pro), —CH₂OR$^a$ (Ser), —CH(OR$^a$)CH₃ (Thr), —CH₂(C₈H₆N)OR$^a$ (Trp), —CH₂(C₆H₄)OR$^a$ (Tyr), —CH(CH₃)₂ (Val), or from —CCH, —CN, —OCH₃, —CH₃, —CF₃, —R$^a$, —CH₂OR$^a$, —CH₂C(═O)R$^a$, —C(═O)OR$^a$, —OC(═O)NR$^b$R$^a$, —C(═O)NR$^b$R$^a$, —CH₂C(═O)NR$^b$(OR$^a$), —CH₂S(O₂)R$^a$, —S(O₂)OR$^a$, —CH₂S(O₂)OR$^a$, —CH₂NHC(═O)R$^a$, —CH₂NR$^b$S(O₂)R$^a$, —CH₂P(═O)(OR$^b$)(OR$^a$), —CH₂P(═O)(OR$^b$)(R$^a$), —CH₂P(═O)(R$^b$)(R$^a$) or —CH₂S(O₂)NR$^b$R$^a$, with R$^a$ and R$^b$ being selected, where applicable, independently from each other from CH₃, —CH₂CH₃, —CH₂CH₂CH₃, —CH₂CH₂CH₂CH₃, —CH(CH₃)₂, —CH₂CH(CH₃)₂, —C(CH₃)₃, —C₆H₅, —CH₂C₆H₅, mono methoxybenzyl, in particular para-methoxybenzyl, or dimethoxybenzyl or trimethoxybenzyl L³ being selected from —CH₃, —CH₂CH₃, —OCH₃, —OCH₂CH₃, a C₁-C₂-fluoro alkyl, with Y being —CN, —C(═O)OH, —C(═O)OCH₃, —C(═O)OCH₂CH₃, —C(═O)NHCH₃, —C(═O)NHCH₂CH₃, —C(═O)N(CH₃)₂, —C(═O)N(CH₂CH₃)₂, —C(═O)N(CH₃)(CH₂CH₃) or —C(═O)NH₂, in particular Z is H and Y is CN and —C(═O)NH₂, and wherein with Z being —H, —OH, —CH₃, —CH₂CH₃, —OCH₃, —NH₂NHCH₃, N(CH₃)₂ or N(CH₃)₃⁺.

In some embodiments, in particular according to any one of the sub aspects 1 to 12 or 14 to 38, BC is selected from

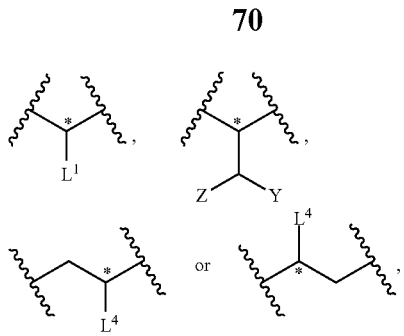

with L¹ or L⁴ being selected independently from each other from side chains of amino acids such as —H (Gly), —CH₃ (Ala), —CH₂CH₂CH₂NHC(NR$^c$)N(R$^b$)(R$^a$) (Arg), —CH₂CON(R$^b$)(R$^a$) (Asn), —CH₂C(═O)OR$^a$ (Asp), —CH₂SR$^a$ (Cys), —CH₂CH₂C(═O)N(R$^b$)(R$^a$) (Gln), —CH₂CH₂C(═O)OR$^a$ (Glu), —CH₂(C₃H₃N₂) (His), —CH₂CH₂CH₂CH₂ (Lys), —CH₂CH₂SCH₃ (Met), —CH₂(C₆H₅) (Phe), —CH₂CH₂CH₂— (Pro), —CH₂OR$^a$ (Ser), —CH(OR$^a$)CH₃ (Thr), —CH₂(C₈H₆N)OR$^a$ (Trp), —CH₂(C₆H₄)OR$^a$ (Tyr), —CH(CH₃)₂ (Val), or from —CCH, —CN, —OCH₃, —CH₃, —CF₃, —R$^a$, —CH(R$^b$)(R$^a$), —CH₂OR$^a$, —CH₂C(═O)R$^a$, —C(═O)OR$^a$, —OC(═O)NR$^b$R$^a$, —C(═O)NR$^b$R$^a$, —CH₂C(═O)NR$^b$(OR$^a$), —CH₂S(O₂)R$^a$, —S(O₂)OR$^a$, —CH₂S(O₂)OR$^a$, —CH₂NHC(═O)R$^a$, —CH₂NR$^b$S(O₂)R$^a$, —CH₂P(═O)(OR$^b$)(OR$^a$), —CH₂P(═O)(OR$^b$)(R$^a$), —CH₂P(═O)(R$^b$)(R$^a$) or —CH₂S(O₂)NR$^b$R$^a$, with R$^a$ and R$^b$ being selected, where applicable, independently from each other from
- a substituted or unsubstituted C₁-C₄ alkyl, a substituted or unsubstituted C₁-C₄ alkoxy, a substituted or unsubstituted C₁-C₄ carboxy, a substituted or unsubstituted C₂-C₄ alkenyl, a substituted or unsubstituted C₂-C₄ alkynyl, or a C₁-C₄ haloalkyl, or
- a substituted or unsubstituted C₃-C₁₀ cycloalkyl or a substituted or unsubstituted C₃-C₁₀ halo cycloalkyl, or
- a substituted or unsubstituted C₃-C₁₀ heterocycle or a substituted or unsubstituted C₃-C₁₀ halo heterocycle, in particular a substituted or unsubstituted C₄-C₁₀ heterocycle or a substituted or unsubstituted C₄-C₁₀ halo heterocycle, or
- a substituted or unsubstituted C₅-C₁₀ heteroaryl, or
- a substituted or unsubstituted C₆-C₁₀ aryl, and with with Y being —CN, —C(═O)OH, —C(═O)OCH₃, —C(═O)OCH₂CH₃, —C(═O)NHCH₃, —C(═O)NHCH₂CH₃, —C(═O)N(CH₃)₂, —C(═O)N(CH₂CH₃)₂, —C(═O)N(CH₃)(CH₂CH₃) or —C(═O)NH₂, in particular Z is H and Y is CN and —C(═O)NH₂, and wherein with Z being —H, —OH, —CH₃, —CH₂CH₃, —OCH₃—NH₂NHCH₃, N(CH₃)₂N(CH₃)₃⁺.

In some embodiments, in particular according to any one of the sub aspects 1 to 12 or 14 to 38, BC is selected from

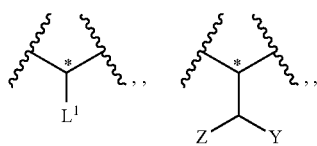

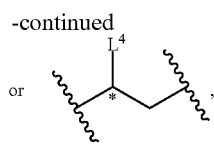 or 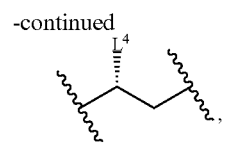

with $L^1$ or $L^4$ being selected independently from each other from side chains of amino acids such as —H (Gly), —CH$_3$ (Ala), —CH$_2$CH$_2$CH$_2$NHC(NR$^c$)N(R$^b$)(R$^a$) (Arg), —CH$_2$CON(R$^b$)(R$^a$) (Asn), —CH$_2$C(=O)OR$^a$ (Asp), —CH$_2$SR$^a$ (Cys), —CH$_2$CH$_2$C(=O)N(R$^b$)(R$^a$) (Gln), —CH$_2$CH$_2$C(=O)OR$^a$ (Glu), —CH$_2$(C$_3$H$_3$N$_2$) (His), —CH$_2$CH$_2$CH$_2$CH$_2$ (Lys), —CH$_2$CH$_2$SCH$_3$ (Met), —CH$_2$(C$_6$H$_5$) (Phe), —CH$_2$CH$_2$CH$_2$— (Pro), —CH$_2$OR$^a$ (Ser), —CH(OR$^a$)CH$_3$ (Thr), —CH$_2$(C$_8$H$_6$N)OR$^a$ (Trp), —CH$_2$(C$_6$H$_4$)OR$^a$ (Tyr), —CH(CH$_3$)$_2$ (Val), or from —CCH, —CN, —OCH$_3$, —CH$_3$, —CF$_3$, —R$^a$, —CH$_2$OR$^a$, —CH$_2$C(=O)R$^a$, —C(=O)OR$^a$, —OC(=O)NR$^b$R$^a$, —C(=O)NR$^b$R$^a$, —CH$_2$C(=O)NR$^b$(OR$^a$), —CH$_2$S(O$_2$)R$^a$, —S(O$_2$)OR$^a$, —CH$_2$S(O$_2$)OR$^a$, —CH$_2$NHC(=O)R$^a$, —CH$_2$NR$^b$S(O$_2$)R$^a$, —CH$_2$P(=O)(OR$^b$)(OR$^a$), —CH$_2$P(=O)(OR$^b$)(R$^a$), —CH$_2$P(=O)(R$^b$)(R$^a$) or —CH$_2$S(O$_2$)NR$^b$R$^a$, with $R^a$ and $R^b$ being selected, where applicable, independently from each other from CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, —C(CH$_3$)$_3$, —C$_6$H$_5$, —CH$_2$C$_6$H$_5$, mono methoxybenzyl, in particular para methoxybenzyl, or dimethoxybenzyl or trimethoxybenzyl.

In some embodiments, in particular according to any one of the sub aspects 1 to 12 or 14 to 38, BC is selected from

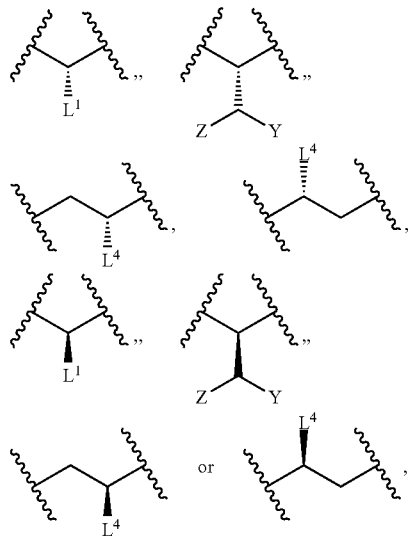

in particular

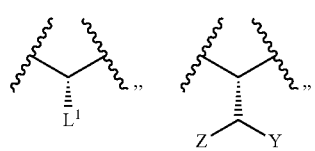

with $L^1$ or $L^4$ being selected independently from each other from side chains of amino acids such as —H (Gly), —CH$_3$ (Ala), —CH$_2$CH$_2$CH$_2$NHC(NR$^c$)N(R$^b$)(R$^a$) (Arg), —CH$_2$CON(R$^b$)(R$^a$) (Asn), —CH$_2$C(=O)OR$^a$ (Asp), —CH$_2$SR$^a$ (Cys), —CH$_2$CH$_2$C(=O)N(R$^b$)(R$^a$) (Gln), —CH$_2$CH$_2$C(=O)OR$^a$ (Glu), —CH$_2$(C$_3$H$_3$N$_2$) (His), —CH$_2$CH$_2$CH$_2$CH$_2$ (Lys), —CH$_2$CH$_2$SCH$_3$ (Met), —CH$_2$(C$_6$H$_5$) (Phe), —CH$_2$CH$_2$CH$_2$— (Pro), —CH$_2$OR$^a$ (Ser), —CH(OR$^a$)CH$_3$ (Thr), —CH$_2$(C$_8$H$_6$N)OR$^a$ (Trp), —CH$_2$(C$_6$H$_4$)OR$^a$ (Tyr), —CH(CH$_3$)$_2$ (Val), or from —CCH, —CN, —OCH$_3$, —CH$_3$, —CF$_3$, —R$^a$, —CH(R$^b$)(R$^a$), —CH$_2$OR$^a$, —CH$_2$C(=O)R$^a$, —C(=O)OR$^a$, —OC(=O)NR$^b$R$^a$, —C(=O)NR$^b$R$^a$, —CH$_2$C(=O)NR$^b$(OR$^a$), —CH$_2$S(O$_2$)R$^a$, —S(O$_2$)OR$^a$, —CH$_2$S(O$_2$)OR$^a$, —CH$_2$NHC(=O)R$^a$, —CH$_2$NR$^b$S(O$_2$)R$^a$, —CH$_2$P(=O)(OR$^b$)(OR$^a$), —CH$_2$P(=O)(OR$^b$)(R$^a$), —CH$_2$P(=O)(R$^b$)(R$^a$) or —CH$_2$S(O$_2$)NR$^b$R$^a$, with $R^a$ and $R^b$ being selected, where applicable, independently from each other from a substituted or unsubstituted C$_1$-C$_4$ alkyl, a substituted or unsubstituted C$_1$-C$_4$ alkoxy, a substituted or unsubstituted C$_1$-C$_4$ carboxy, a substituted or unsubstituted C$_2$-C$_4$ alkenyl, a substituted or unsubstituted C$_2$-C$_4$ alkynyl, or a C$_1$-C$_4$ haloalkyl, or a substituted or unsubstituted C$_3$-C$_{10}$ cycloalkyl or a substituted or unsubstituted C$_3$-C$_{10}$ halo cycloalkyl, or a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle, or a substituted or unsubstituted C$_5$-C$_{10}$ heteroaryl, or a substituted or unsubstituted C$_6$-C$_{10}$ aryl, and with with Y being —CN, —C(=O)OH, —C(=O)OCH$_3$, —C(=O)OCH$_2$CH$_3$, —C(=O)NHCH$_3$, —C(=O)NHCH$_2$CH$_3$, —C(=O)N(CH$_3$)$_2$, —C(=O)N(CH$_2$CH$_3$)$_2$, —C(=O)N(CH$_3$)(CH$_2$CH$_3$) or —C(=O)NH$_2$, in particular Z is H and Y is CN and —C(=O)NH$_2$, and wherein with Z being —H, —OH, —CH$_3$, —CH$_2$CH$_3$, —OCH$_3$—NH$_2$NHCH$_3$, N(CH$_3$)$_2$N(CH$_3$)$_3^+$.

In some embodiments, in particular according to any one of the sub aspects 1 to 12 or 14 to 38, BC is selected from

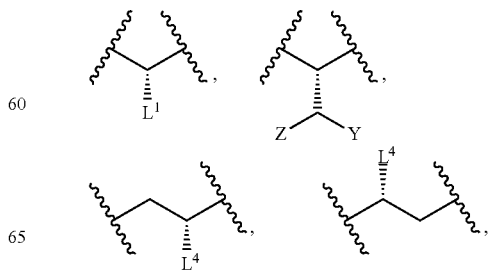

-continued

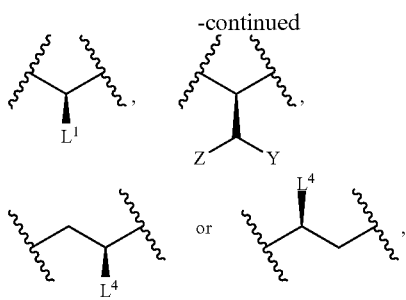

in particular

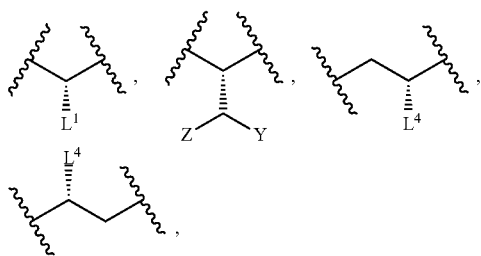

with $L^1$ or $L^4$ being selected independently from each other from side chains of amino acids such as H (Gly), —$CH_3$ (Ala), —$CH_2CH_2CH_2NHC(NR^c)N(R^b)(R^a)$ (Arg), —$CH_2CON(R^b)(R^a)$ (Asn), —$CH_2C(=O)OR^a$ (Asp), —$CH_2SR^a$ (Cys), —$CH_2CH_2C(=O)N(R^b)(R^a)$ (Gln), —$CH_2CH_2C(=O)OR^a$ (Glu), —$CH_2(C_3H_3N2)$ (His), —$CH_2CH_2CH_2CH_2$ (Lys), —$CH_2CH_2SCH_3$ (Met), —$CH_2(C_6H_5)$ (Phe), —$CH_2CH_2CH_2$— (Pro), —$CH_2OR^a$ (Ser), —$CH(OR^a)CH_3$ (Thr), —$CH_2(C_8H_6N)OR^a$ (Trp), —$CH_2(C_6H_4)OR^a$ (Tyr), —$CH(CH_3)_2$ (Val), or from —CCH, —CN, —$OCH_3$, —$CH_3$, —$CF_3$, —$R^a$, —$CH_2OR^a$, —$CH_2C(=O)R^a$, —$C(=O)OR^a$, —$OC(=O)NR^bR^a$, —$C(=O)NR^bR^a$, —$CH_2C(=O)NR^b(OR^a)$, —$CH_2S(O_2)R^a$, —$S(O_2)OR^a$, —$CH_2S(O_2)OR^a$, —$CH_2NHC(=O)R^a$, —$CH_2NR^bS(O_2)R^a$, —$CH_2P(=O)(OR^b)(OR^a)$, —$CH_2P(=O)(OR^b)(R^a)$, —$CH_2P(=O)(R^b)(R^a)$ or —$CH_2S(O_2)NR^bR^a$, with $R^a$ and $R^b$ being selected, where applicable, independently from each other from $CH_3$, —$CH_2CH_3$, —$CH_2CH_2CH_3$, —$CH_2CH_2CH_2CH_3$, —$CH(CH_3)_2$, —$CH_2CH(CH_3)_2$, —$C(CH_3)_3$, —$C_6H_5$, —$CH_2C_6H_5$, mono methoxybenzyl, in particular para methoxybenzyl, or dimethoxybenzyl or trimethoxybenzyl.

In some embodiments, in particular according to any one of the sub aspects 1 to 12 or 14 to 38, BC is selected from

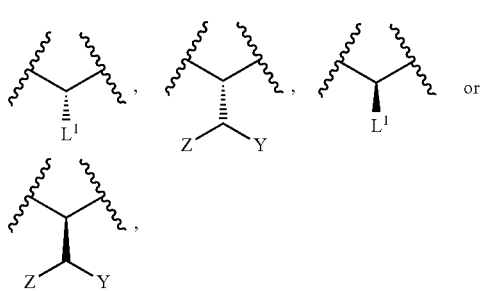

in particular

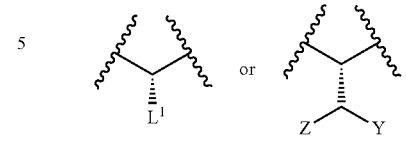

with $L^1$ or $L^4$ being selected independently from each other from side chains of amino acids such as —H (Gly), —$CH_3$ (Ala), —$CH_2CH_2CH_2NHC(NR^c)N(R^b)(R^a)$ (Arg), —$CH_2CON(R^b)(R^a)$ (Asn), —$CH_2C(=O)OR^a$ (Asp), —$CH_2SR^a$ (Cys), —$CH_2CH_2C(=O)N(R^b)(R^a)$ (Gln), —$CH_2CH_2C(=O)OR^a$ (Glu), —$CH_2(C_3H_3N_2)$ (His), —$CH_2CH_2CH_2CH_2$ (Lys), —$CH_2CH_2SCH_3$ (Met), —$CH_2(C_6H_5)$ (Phe), —$CH_2CH_2CH_2$— (Pro), —$CH_2OR^a$ (Ser), —$CH(OR^a)CH_3$ (Thr), —$CH_2(C_8H_6N)OR^a$ (Trp), —$CH_2(C_6H_4)OR^a$ (Tyr), —$CH(CH_3)_2$ (Val), or from —CCH, —CN, —$OCH_3$, —$CH_3$, —$CF_3$, —$R^a$, —$CH(R^b)(R^a)$, —$CH_2OR^a$, —$CH_2C(=O)R^a$, —$C(=O)OR^a$, —$OC(=O)NR^bR^a$, —$C(=O)NR^bR^a$, —$CH_2C(=O)NR^b(OR^a)$, —$CH_2S(O_2)R^a$, —$S(O_2)OR^a$, —$CH_2S(O_2)OR^a$, —$CH_2NHC(=O)R^a$, —$CH_2NR^bS(O_2)R^a$, —$CH_2P(=O)(OR^b)(OR^a)$, —$CH_2P(=O)(OR^b)(R^a)$, —$CH_2P(=O)(R^b)(R^a)$ or —$CH_2S(O_2)NR^bR^a$, with $R^a$ and $R^b$ being selected, where applicable, independently from each other from
a substituted or unsubstituted $C_1$-$C_4$ alkyl, a substituted or unsubstituted $C_1$-$C_4$ alkoxy, a substituted or unsubstituted $C_1$-$C_4$ carboxy, a substituted or unsubstituted $C_2$-$C_4$ alkenyl, a substituted or unsubstituted $C_2$-$C_4$ alkynyl, or a $C_1$-$C_4$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl, and with with Y being —CN, —$C(=O)OH$, —$C(=O)OCH_3$, —$C(=O)OCH_2CH_3$, —$C(=O)NHCH_3$, —$C(=O)NHCH_2CH_3$, —$C(=O)N(CH_3)_2$, —$C(=O)N(CH_2CH_3)_2$, —$C(=O)N(CH_3)(CH_2CH_3)$ or —$C(=O)NH_2$, in particular Z is H and Y is CN and —$C(=O)NH_2$, and wherein with Z being —H, —OH, —$CH_3$, —$CH_2CH_3$, —$OCH_3$—$NH_2NHCH_3$, $N(CH_3)_2N(CH_3)_3^+$.

In some embodiments, in particular according to any one of the sub aspects 1 to 12 or 14 to 38, BC is selected from

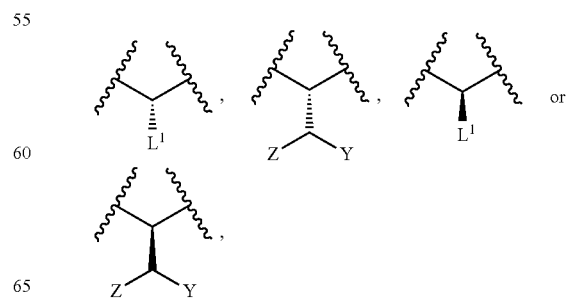

in particular

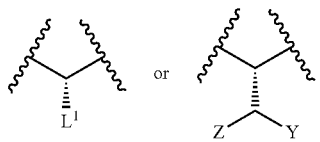

with L$^1$ or L$^4$ being selected independently from each other from side chains of amino acids such as H (Gly), —CH$_3$ (Ala), —CH$_2$CH$_2$CH$_2$NHC(NR$^c$)N(R$^b$)(R$^a$) (Arg), —CH$_2$CON(R$^b$)(R$^a$) (Asn), —CH$_2$C(=O)OR$^a$ (Asp), —CH$_2$SR$^a$ (Cys), —CH$_2$CH$_2$C(=O)N(R$^b$)(R$^a$) (Gln), —CH$_2$CH$_2$C(=O)OR$^a$ (Glu), —CH$_2$(C$_3$H$_3$N2) (His), —CH$_2$CH$_2$CH$_2$CH$_2$ (Lys), —CH$_2$CH$_2$SCH$_3$ (Met), —CH$_2$(C$_6$H$_5$) (Phe), —CH$_2$CH$_2$CH$_2$— (Pro), —CH$_2$OR$^a$ (Ser), —CH(OR$^a$)CH$_3$ (Thr), —CH$_2$(C$_8$H$_6$N)OR$^a$ (Trp), —CH$_2$(C$_6$H$_4$)OR$^a$ (Tyr), —CH(CH$_3$)$_2$ (Val), or from —CCH, —CN, —OCH$_3$, —CH$_3$, —CF$_3$, —R$^a$, —CH$_2$OR$^a$, —CH$_2$C(=O)R$^a$, —C(=O)OR$^a$, —OC(=O)NR$^b$R$^a$, —C(=O)NR$^b$R$^a$, —CH$_2$C(=O)NR$^b$(OR$^a$), —CH$_2$S(O$_2$)R$^a$, —S(O$_2$)OR$^a$, —CH$_2$S(O$_2$)OR$^a$, —CH$_2$NHC(=O)R$^a$, —CH$_2$NR$^b$S(O$_2$)R$^a$, —CH$_2$P(=O)(OR$^b$)(OR$^a$), —CH$_2$P(=O)(OR$^b$)(R$^a$), —CH$_2$P(=O)(R$^b$)(R$^a$) or —CH$_2$S(O$_2$)NR$^b$R$^a$, with R$^a$ and R$^b$ being selected, where applicable, independently from each other from CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, —C(CH$_3$)$_3$, —C$_6$H$_5$, —CH$_2$C$_6$H$_5$, mono methoxybenzyl, in particular para methoxybenzyl, or dimethoxybenzyl or trimethoxybenzyl.

In some embodiments, in particular according to any one of the sub aspects 1 to 12 or 14 to 38, -D$^2$-BC- is

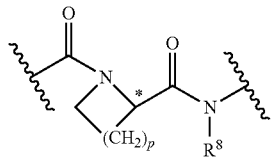

with p being 1, 2, 3, 4 or 5, in particular p being 2 or 3, and with, where applicable, each R$^8$ being selected independently from each other from —H, —CH$_3$, —CH$_2$CH$_3$, —OCH$_3$, —OCF$_3$, —CH$_2$CF$_3$, —CHFCF$_3$, —CF$_2$CF$_3$, —CHF$_2$, —CH$_2$F or —CF$_3$, in particular with each R$^8$ being selected independently from each other from H or CH$_3$, more particularly each R$^8$ being H.

In some embodiments, in particular according to any one of the sub aspects 1 to 12 or 14 to 38, -D$^2$-BC- is

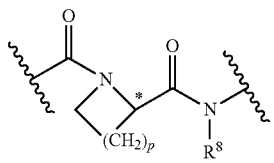

with p being 1, 2, 3, 4 or 5, in particular p being 2 or 3, and with R$^8$ being H or CH$_3$.

In some embodiments, in particular according to any one of the sub aspects 1 or 2, BD is

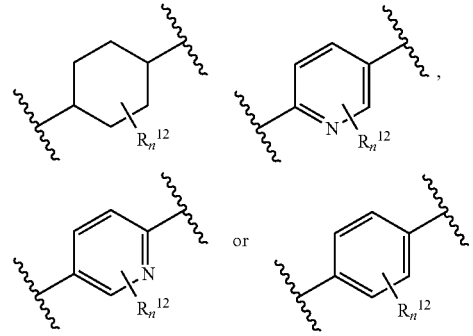

with n of R$^{12}_n$ being 0, 1, 2, 3 or 4, in particular n of R$^{12}_n$ being 0, 1 or 2, with each R$^{12}$ independently from any other R$^{12}$ being —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CF$_3$ or —NO$_2$, in particular —OH, —F, —Cl, —Br, —I, —CCH, —CN, —N$_3$, —OCH$_3$, —OCF$_3$, -, —CH$_3$, —CH$_2$CH$_3$ or —CF$_3$, or with each R$^{12}$ independently from any other R$^{12}$ being —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_3$, —CF$_3$ or —NO$_2$, in particular —OH, —F, —Cl, —Br, —I, —CCH, —CN, —N$_3$, —OCH$_3$, —OCF$_3$, -, —CH$_3$, —CH$_2$CH$_3$ or —CF$_3$, wherein each carbon atom of the cyclic system which comprises no substituent R$^{12}$ comprises F instead of H.

In some embodiments, in particular according to any one of the sub aspects 1 or 2, BD is

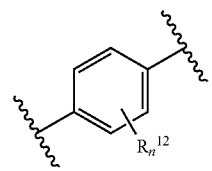

with n of R$^{12}_n$ being 0, or with n of R$^{12}_n$ being 1, 2, 3 or 4 with each R$^{12}$ being F, in particular n is 4 and each R$^{13}$ is F.

In some embodiments, in particular according to any one of the sub aspects 1 to 6, 19, 21, 24 or 27, BE is

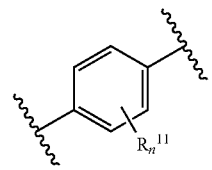

with n of R$^{11}_n$ being 0, 1, 2, 3 or 4, in particular of R$^{11}_n$ being 0, 1, 2 or 3, with each $R^{11}$ being selected independently from any other $R^{11}$ from —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$, or with each $R^{11}$ being selected independently from any other $R^{11}$ from —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$, wherein, each carbon atom of the cyclic system which comprises no substituent $R^{11}$ comprises F instead of H.

In some embodiments, in particular according to any one of the sub aspects 1 to 6, 19, 21, 24 or 27, BE is

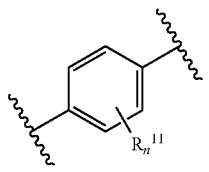

with n of $R^{11}_n$ being 2, and with each $R^{11}$ independently from any other $R^{11}$ being —OH, —OCH$_3$ or —OCF$_3$, in particular —OCH$_3$ or —OCF$_3$, more particularly with one $R^{11}$ being —OH and the other $R^{11}$ being —OCH$_3$ or —OCF$_3$, in particular —OCH$_3$, wherein more particularly OH is in ortho and OCH$_3$ or —OCF$_3$ in meta position with respect to the attachment position of the phenyl moiety of BE to $D^5$, or with n of $R^{11}_n$ being 1, and with $R^{11}$ being —OH, wherein in particular OH is in ortho position with respect to the attachment position of the phenyl of BE to $D^5$ or with n of $R^{11}_n$ being 1, and with $R^{11}$ being —OCH$_3$ or —OCF$_3$, in particular or —OCH$_3$, wherein more particularly —OCH$_3$ or —OCF$_3$ is in meta position with respect to the attachment position of the phenyl of BE to $D^5$, or with n of $R^{11}_n$ being 0, or with n of $R^{11}_n$ being 4 and each $R^{11}$ is F.

In some embodiments, in particular according to any one of the sub aspects 1 to 6, 19, 21, 24 or 27, BE is

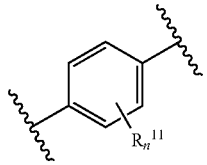

with n of $R^{11}_n$ being 1, 2, 3 or 4, in particular n of $R^{11}_n$ being 1, 2 or 3, with one $R^{11}$ being a substituent Q, with Q being selected from —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$, —(CH$_2$)$_m$—O—S(O$_2$)OH, —(CH$_2$)$_m$—O—S(O$_2$)OR$^a$, in particular —(CH$_2$)$_m$—O—S(O$_2$)OH, —(CH$_2$)$_m$—O—S(O$_2$)OR$^a$, with m being selected from 0, 1 or 2, in particular from 0 or 1, with R$^a$ being —CH$_3$, —CH$_2$CH$_3$, —C$_6$H$_5$, —CH$_2$CH$_2$CH$_3$, —CH(CH$_3$)$_2$, —CH$_2$C$_6$H$_5$ or para-methoxybenzyl —C(=O)—O—R$^a$, —O—C(=O)—R$^a$, in particular —O—C(=O)—R$^a$, with R$^a$ being a substituted or unsubstituted C$_1$-C$_{16}$ alkyl, in particular an unsubstituted C$_1$-C$_{14}$ alkyl, —(CH$_2$)$_m$—[(CH$_2$)$_{m1}$—O—C(=O)—(CH$_2$)$_{m2}$]$_{p1}$—C(=O)OR$^d$, in particular —(CH$_2$)—[—O—C(=O)—(CH$_2$)$_2$]$_{p1}$—C(=O)OR$^d$ with R$^d$ being —CH$_3$, —CH$_2$CH$_3$, —CH$_2$CH$_2$CH$_3$, —CH(CH$_3$)$_2$, —C$_6$H$_5$ m1 and m2 being selected independently from each other form 1, 2 or 3, in particular m1 and m2 are 2, and p1 being selected from 1 to 20, in particular from 1 to 8, —(CH$_2$)$_m$—[(CH$_2$)$_{m1}$—O—(CH$_2$)$_{m2}$]$_{p1}$—OR$^d$, in particular —[—O—(CH$_2$)$_2$]$_{p1}$—OR$^d$, with R$^d$ being —CH$_3$, —CH$_2$CH$_3$, —CH$_2$CH$_2$CH$_3$, —CH(CH$_3$)$_2$, —C$_6$H$_5$ m1 and m2 being selected independently from each other form 1, 2 or 3, in particular m1 and m2 are 2, and p1 being selected from 1 to 20, in particular from 1 to 8, —(CH$_2$)$_m$—C(=O)O—(CH$_2$)$_q$—P(=O)(R$^{ba}$)(R$^{aa}$), —(CH$_2$)$_m$—O—(CH$_2$)$_q$—P(=O)(R$^{ba}$)(R$^{aa}$), in particular from —(CH$_2$)$_m$—O—(CH$_2$)$_q$—P(=O)(R$^{ba}$)(R$^{aa}$), with R$^{aa}$ and R$^{ba}$ being selected, where applicable, independently from each other from —R$^a$ or —OR$^a$ and with R$^a$ being hydrogen, —OCH$_3$, —OCH$_2$CH$_3$, —CH$_3$, —CH$_2$CH$_3$, —C$_6$H$_5$, —CH$_2$CH$_2$CH$_3$, —CH(CH$_3$)$_2$, —CH$_2$C$_6$H$_5$ or para-methoxybenzyl with m being selected from 0, 1 or 2, in particular 0 or 1, with q being selected from 0, 1 or 2, in particular 0 or 1, and i. with the other $R^{11}$ being selected independently from any other $R^{11}$ from —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$, or ii. with the other $R^{11}$ being selected independently from any other $R^{11}$ from —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$, wherein, each carbon atom of the cyclic system which comprises no substituent $R^{11}$ comprises F instead of H.

In some embodiments, in particular according to any one of the sub aspects 1 to 6, 19, 21, 24 or 27, BE is

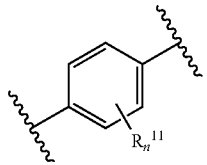

with n of $R^{11}{}_n$ being 0 or 2, and with one $R^{11}$ being Q and the other $R^{11}$ being —OCH$_3$ or —OCF$_3$, more particularly Q is in ortho and OCH$_3$ or —OCF$_3$ is in meta position with respect to the attachment position of the phenyl moiety of BB to D$^5$, with Q having the same meaning as defined above.

In some embodiments, in particular according to any one of the sub aspects 1 to 3,
-D$^4$-BE is

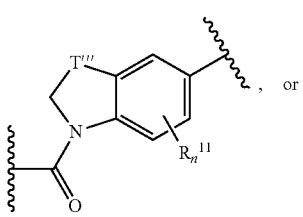

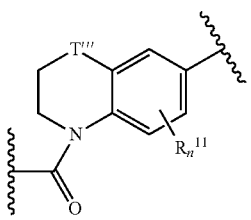

with each T''' being selected from —CH$_2$, —NH, —S, —O, or —NR$^c$, in particular T''' is O,
with R$^c$ being —OH, —CH$_3$, —CH$_2$CH$_3$, —CH$_2$CH$_2$CH$_3$, —CH(CH$_3$)$_2$,
with n of $R^{11}{}_n$ being 0, 1, 2 or 3, in particular n of $R^{11}{}_n$ being 0, 1, or 2,
i. with each $R^{11}$ being selected independently from any other $R^{11}$ from —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$, or
ii. with each $R^{11}$ being selected independently from any other $R^{11}$ from —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$, wherein, each carbon atom of the cyclic system which comprises no substituent $R^{11}$ comprises F instead of H.

In some embodiments, in particular according to any one of the sub aspects 1 to 3,
-D$^4$-BE is

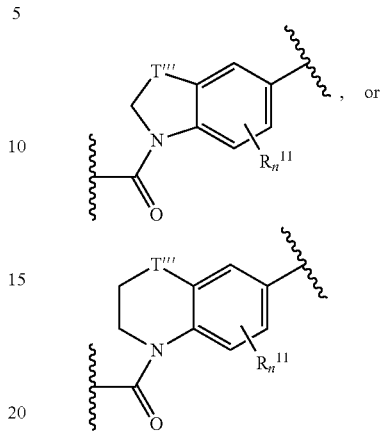

with each T''' being selected from —CH$_2$, —NH, —S, —O, or —NR$^c$, in particular T''' is O,
with R$^c$ being —OH, —CH$_3$, —CH$_2$CH$_3$, —CH$_2$CH$_2$CH$_3$, —CH(CH$_3$)$_2$,
with n of $R^{11}{}_n$ being 2, and with each $R^{11}$ independently from any other $R^{11}$ being —OH, —OCH$_3$ or —OCF$_3$, in particular —OCH$_3$ or —OCF$_3$, more particularly with one $R^{11}$ being —OH and the other $R^{11}$ being —OCH$_3$ or —OCF$_3$, in particular —OCH$_3$, wherein more particularly OH is in ortho and OCH$_3$ or —OCF$_3$ in meta position with respect to the attachment position of the phenyl moiety of BE to D$^5$, or
with n of $R^{11}{}_n$ being 1, and with $R^{11}$ being —OH, wherein in particular OH is in ortho position with respect to the attachment position of the phenyl of BE to D$^5$ or
with n of $R^{11}{}_n$ being 1, and with $R^{11}$ being —OCH$_3$ or —OCF$_3$, in particular or —OCH$_3$, wherein more particularly —OCH$_3$ or —OCF$_3$ is in meta position with respect to the attachment position of the phenyl of BE to D$^5$, or
with n of $R^{11}{}_n$ being 0, or
with n of $R^{11}{}_n$ being 4 and each $R^{11}$ is F.

In some embodiments, in particular according to any one of the sub aspects 1 to 3,
-D$^4$-BE is

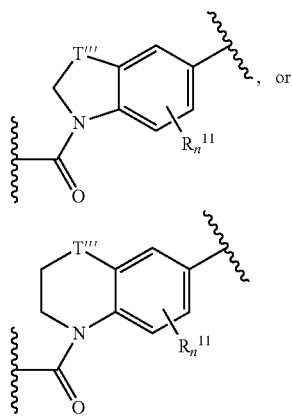

with each T''' being selected from —CH$_2$, —NH, —S, —O, or —NR$^c$, in particular T''' is O,
  with R$^c$ being —OH, —CH$_3$, —CH$_2$CH$_3$, —CH$_2$CH$_2$CH$_3$, —CH(CH$_3$)$_2$,
  with n of R$^{11}_n$ being 1, 2 or 3, in particular n of R$^{11}_n$ being 1 or 2,
  with one R$^{11}$ being a substituent Q, with Q being selected from
    —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$, —(CH$_2$)$_m$—O—S(O$_2$)OH, —(CH$_2$)$_m$—O—S(O$_2$)OR$^a$, in particular —(CH$_2$)$_m$—O—S(O$_2$)OH, —(CH$_2$)$_m$—O—S(O$_2$)OR$^a$, with m being selected from 0, 1 or 2, in particular from 0 or 1, with R$^a$ being —CH$_3$, —CH$_2$CH$_3$, —C$_6$H$_5$, —CH$_2$CH$_2$CH$_3$, —CH(CH$_3$)$_2$, —CH$_2$C$_6$H$_5$ or para-methoxybenzyl
    —C(=O)—O—R$^a$, —O—C(=O)—R$^a$, in particular —O—C(=O)—R$^a$, with R$^a$ being a substituted or unsubstituted C$_1$-C$_{16}$ alkyl, in particular an unsubstituted C$_1$-C$_{14}$ alkyl,
    —(CH$_2$)$_m$—[(CH$_2$)$_{m1}$—O—C(=O)—(CH$_2$)$_{m2}$]$_{p1}$—C(=O)OR$^d$, in particular —(CH$_2$)—[—O—C(=O)—(CH$_2$)$_2$]$_{p1}$—C(=O)OR$^d$ with
      R$^d$ being —CH$_3$, —CH$_2$CH$_3$, —CH$_2$CH$_2$CH$_3$, —CH(CH$_3$)$_2$, —C$_6$H$_5$
      m1 and m2 being selected independently from each other form 1, 2 or 3, in particular m1 and m2 are 2, and
      p1 being selected from 1 to 20, in particular from 1 to 8,
    —(CH$_2$)$_m$—[(CH$_2$)$_{m1}$—O—(CH$_2$)$_{m2}$]$_{p1}$—OR$^d$, in particular —[—O—(CH$_2$)$_2$]$_{p1}$—OR$^d$, with
      R$^d$ being —CH$_3$, —CH$_2$CH$_3$, —CH$_2$CH$_2$CH$_3$, —CH(CH$_3$)$_2$, —C$_6$H$_5$
      m1 and m2 being selected independently from each other form 1, 2 or 3, in particular m1 and m2 are 2, and
      p1 being selected from 1 to 20, in particular from 1 to 8,
    —(CH$_2$)$_m$—C(=O)O—(CH$_2$)$_q$—P(=O)(R$^{ba}$)(R$^{aa}$), —(CH$_2$)$_m$—O—(CH$_2$)$_q$—P(=O)(R$^{ba}$)(R$^{aa}$), in particular from —(CH$_2$)$_m$—O—(CH$_2$)$_q$—P(=O)(R$^{ba}$)(R$^{aa}$),
      with R$^{aa}$ and R$^{ba}$ being selected, where applicable, independently from each other from —R$^a$ or —OR$^a$ and
      with R$^a$ being hydrogen, —OCH$_3$, —OCH$_2$CH$_3$, —CH$_3$, —CH$_2$CH$_3$, —C$_6$H$_5$, —CH$_2$CH$_2$CH$_3$, —CH(CH$_3$)$_2$, —CH$_2$C$_6$H$_5$ or para-methoxybenzyl
      with m being selected from 0, 1 or 2, in particular 0 or 1,
      with q being selected from 0, 1 or 2, in particular 0 or 1, and
  i. with the other R$^{11}$ being selected independently from any other R$^{11}$ from —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$, or
  ii. with the other R$^{11}$ being selected independently from any other R$^{11}$ from —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$, wherein, each carbon atom of the cyclic system which comprises no substituent R$^{11}$ comprises F instead of H.

In some embodiments, in particular according to any one of the sub aspects 1 to 3,
-D$^4$-BE is

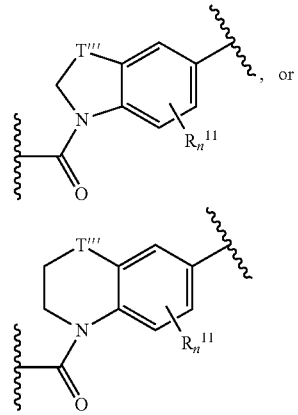
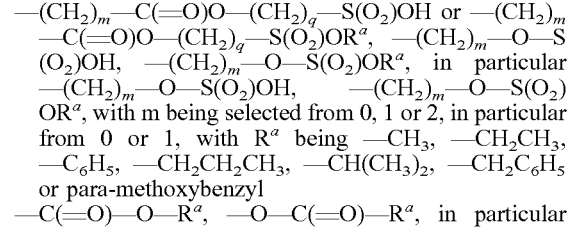

with each T''' being selected from —CH$_2$, —NH, —S, —O, or —NR$^c$, in particular T''' is O,
  with R$^c$ being —OH, —CH$_3$, —CH$_2$CH$_3$, —CH$_2$CH$_2$CH$_3$, —CH(CH$_3$)$_2$,
  with n of R$^{11}_n$ being 0 or 2, and with one R$^{11}$ being Q and the other R$^{11}$ being —OCH$_3$ or —OCF$_3$, more particularly Q is in ortho and OCH$_3$ or —OCF$_3$ is in meta position with respect to the attachment position of the phenyl moiety of BB to D$^5$, with Q having the same meaning as defined above.

In some embodiments, in particular according to any one of the sub aspects 7, 8, 10 to 13, 22, 23, 25, 28, 29 or 32,
  R$^{11}$ is a substituent Q, with Q being selected from
    —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$, —(CH$_2$)$_m$—O—S(O$_2$)OH, —(CH$_2$)$_m$—O—S(O$_2$)OR$^a$, in particular —(CH$_2$)$_m$—O—S(O$_2$)OH, —(CH$_2$)$_m$—O—S(O$_2$)OR$^a$, with m being selected from 0, 1 or 2, in particular from 0 or 1, with R$^a$ being —CH$_3$, —CH$_2$CH$_3$, —C$_6$H$_5$, —CH$_2$CH$_2$CH$_3$, —CH(CH$_3$)$_2$, —CH$_2$C$_6$H$_5$ or para-methoxybenzyl
    —C(=O)—O—R$^a$, —O—C(=O)—R$^a$, in particular —O—C(=O)—R$^a$, with R$^a$ being a substituted or unsubstituted C$_1$-C$_{16}$ alkyl, in particular an unsubstituted C$_1$-C$_{14}$ alkyl,
    —(CH$_2$)$_m$—[(CH$_2$)$_{m1}$—O—C(=O)—(CH$_2$)$_{m2}$]$_{p1}$—C(=O)OR$^d$, in particular —(CH$_2$)—[—O—C(=O)—(CH$_2$)$_2$]$_{p1}$—C(=O)OR$^d$ with
      R$^d$ being —CH$_3$, —CH$_2$CH$_3$, —CH$_2$CH$_2$CH$_3$, —CH(CH$_3$)$_2$, —C$_6$H$_5$
      m1 and m2 being selected independently from each other form 1, 2 or 3, in particular m1 and m2 are 2, and
      p1 being selected from 1 to 20, in particular from 1 to 8,
    —(CH$_2$)$_m$—[(CH$_2$)$_{m1}$—O—(CH$_2$)$_{m2}$]$_{p1}$—OR$^d$, in particular —[—O—(CH$_2$)$_2$]$_{p1}$—OR$^d$, with
      R$^d$ being —CH$_3$, —CH$_2$CH$_3$, —CH$_2$CH$_2$CH$_3$, —CH(CH$_3$)$_2$, —C$_6$H$_5$
      m1 and m2 being selected independently from each other form 1, 2 or 3, in particular m1 and m2 are 2, and p1 being selected from 1 to 20, in particular from 1 to 8,
—(CH$_2$)$_m$—C(=O)O—(CH$_2$)$_q$—P(=O)(R$^{ba}$)(R$^{aa}$),
—(CH$_2$)$_m$—O—(CH$_2$)$_q$—P(=O)(R$^{ba}$)(R$^{aa}$), in particular from —(CH$_2$)$_m$—O—(CH$_2$)$_q$—P(=O)(R$^{ba}$)(R$^{aa}$), with R$^{aa}$ and R$^{ba}$ being selected, where applicable, independently from each other from —R$^a$ or —OR$^a$ and with R$^a$ being hydrogen, —OCH$_3$, —OCH$_2$CH$_3$, —CH$_3$, —CH$_2$CH$_3$, —C$_6$H$_5$, —CH$_2$CH$_2$CH$_3$, —CH(CH$_3$)$_2$, —CH$_2$C$_6$H$_5$ or para-methoxybenzyl with m being selected from 0, 1 or 2, in particular 0 or 1, with q being selected from 0, 1 or 2, in particular 0 or 1.

In some embodiments, X$^2$ is
—OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_3$, —CF$_3$ or —NO$_2$, —B(OR$^a$)(OR$^b$), —(CH$_2$)$_m$—R$^a$, —(CH$_2$)$_m$—OR$^a$, —(CH$_2$)$_m$—C(=O)R$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O)NR$^a$R$^b$, —(CH$_2$)$_m$—C(=O)NR$^b$(OR$^a$), —(CH$_2$)$_m$—C(=S)R$^a$, —(CH$_2$)$_m$—C(=S)OR$^a$, —(CH$_2$)$_m$—OC(=S)R$^a$, —(CH$_2$)$_m$—OC(=S)OR$^a$, —(CH$_2$)$_m$—OC(=S)NR$^a$R$^b$, —(CH$_2$)$_m$—C(=S)NR$^a$R$^b$, —(CH$_2$)$_m$—SR$^a$, —(CH$_2$)$_m$—S(=O)R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)OR$^a$, —(CH$_2$)$_m$—NR$^c$C(=O)NR$^a$R$^b$, —(CH$_2$)$_m$—NR$^c$C(=S)R$^a$, —(CH$_2$)$_m$—NR$^c$C(=S)NR$^a$R$^b$, —(CH$_2$)$_m$—NR$^c$C(=S)OR$^a$, —(CH$_2$)$_m$—NR$^c$S(O$_2$)R$^a$, —(CH$_2$)$_m$—P(=O)(OR$^b$)(OR$^a$), —(CH$_2$)$_m$—P(=O)(OR$^b$)(R$^a$) or —(CH$_2$)$_m$—S(O$_2$)NR$^b$R$^a$, —(CH$_2$)$_m$—O—C(=O)-(M)—C(=O)OH, —(CH$_2$)$_m$—O—C(=O)-(M)—C(=O)OR$^a$, —(CH$_2$)$_m$—O—C(=O)-(M)—R$^a$, —(CH$_2$)$_m$—O—(CH$_2$)$_q$—P(=O)(R$^{ba}$)(R$^{aa}$), —(CH$_2$)$_m$—C(=O)O—(CH$_2$)$_q$—P(=O)(R$^{ba}$)(R$^{aa}$), —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$, with R$^{aa}$ being selected independently from each other from —R$^a$ or —OR$^a$, with R$^{ba}$ being selected independently from each other from —R$^b$ or —OR$^b$, with M being a substituted or unsubstituted C$_1$-C$_8$ alkyl, in particular an unsubstituted C$_1$-C$_8$ alkyl, with m being selected from 0, 1 or 2, in particular 0 or 1, with q being selected from 0, 1 or 2, in particular 0 or 1, with each R$^a$, R$^b$ or R$^c$ being selected independently from each other from hydrogen, —CN, a substituted or unsubstituted C$_3$-C$_{10}$ cycloalkyl or a substituted or unsubstituted C$_3$-C$_{10}$ halo cycloalkyl, or a substituted or unsubstituted C$_6$-C$_{10}$ aryl, a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle, or a substituted or unsubstituted C$_5$-C$_{10}$ heteroaryl, a substituted or unsubstituted C$_1$-C$_{16}$ alkyl, a substituted or unsubstituted C$_1$-C$_{16}$ alkoxy, a substituted or unsubstituted C$_1$-C$_{16}$ carboxy, a substituted or unsubstituted C$_2$-C$_{16}$ alkenyl, a substituted or unsubstituted C$_2$-C$_{16}$ alkynyl, or a C$_1$-C$_{16}$ haloalkyl, and wherein a linker D$^5$ may be optionally situated between BE and X$^2$ In some embodiments, X$^2$ is
—OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_3$, —CF$_3$ or —NO$_2$, —B(OR$^a$)(OR$^b$), —(CH$_2$)$_m$—R$^a$, —(CH$_2$)$_m$—OR$^a$, —(CH$_2$)$_m$—C(=O)R$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O)NR$^a$R$^b$, —(CH$_2$)$_m$—C(=O)NR$^b$(OR$^a$), —(CH$_2$)$_m$—C(=S)R$^a$, —(CH$_2$)$_m$—C(=S)OR$^a$, —(CH$_2$)$_m$—OC(=S)R$^a$, —(CH$_2$)$_m$—OC(=S)OR$^a$, —(CH$_2$)$_m$—OC(=S)NR$^a$R$^b$, —(CH$_2$)$_m$—C(=S)NR$^a$R$^b$, —(CH$_2$)$_m$—SR$^a$, —(CH$_2$)$_m$—S(=O)R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)OR$^a$, —(CH$_2$)$_m$—NR$^c$C(=O)NR$^a$R$^b$, —(CH$_2$)$_m$—NR$^c$C(=S)R$^a$, —(CH$_2$)$_m$—NR$^c$C(=S)NR$^a$R$^b$, —(CH$_2$)$_m$—NR$^c$C(=S)OR$^a$, —(CH$_2$)$_m$—NR$^c$S(O$_2$)R$^a$, —(CH$_2$)$_m$—P(=O)(OR$^b$)(OR$^a$), —(CH$_2$)$_m$—P(=O)(OR$^b$)(R$^a$) or —(CH$_2$)$_m$—S(O$_2$)NR$^b$R$^a$, —(CH$_2$)$_m$—O—C(=O)-(M)—C(=O)OH, —(CH$_2$)$_m$—O—C(=O)-(M)—C(=O)OR$^a$, —(CH$_2$)$_m$—O—C(=O)-(M)—R$^a$, —(CH$_2$)$_m$—O—(CH$_2$)$_q$—P(=O)(R$^{ba}$)(R$^{aa}$), —(CH$_2$)$_m$—C(=O)O—(CH$_2$)$_q$—P(=O)(R$^{ba}$)(R$^{aa}$), —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$, with R$^{aa}$ being selected independently from each other from —R$^a$ or —OR$^a$, with R$^{ba}$ being selected independently from each other from —R$^b$ or —OR$^b$, with M being a substituted or unsubstituted C$_1$-C$_8$ alkyl, in particular an unsubstituted C$_1$-C$_8$ alkyl, with m being selected from 0, 1 or 2, in particular 0 or 1, with q being selected from 0, 1 or 2, in particular 0 or 1, with each R$^a$, R$^b$ or R$^c$ being selected independently from each other from hydrogen, —CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, —C(CH$_3$)$_3$, —C$_6$H$_5$, —CH$_2$C$_6$H$_5$, wherein a linker D$^5$ may be optionally situated between BE and X$^2$ In some embodiments, in particular according to any one of the sub aspects 1 to 9 or 14 to 16, BF is a substituted or unsubstituted C$_3$-C$_{10}$ cycloalkyl or a substituted or unsubstituted C$_3$-C$_{10}$ halo cycloalkyl, or a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle, or a substituted or unsubstituted C$_5$-C$_{10}$ heteroaryl, or a substituted or unsubstituted C$_6$-C$_{10}$ aryl.

In some embodiments, in particular according to any one of the sub aspects 1 to 17, 19, 21, 24 or 27, BF is

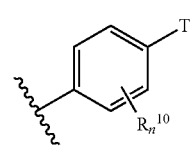

wherein $D^5$ has the same meaning as defined previously, and with T being selected from —OH, —F, —Cl, —Br, I, —CCH, —CN, —$N_3$, —$OCH_3$, —$OCF_3$, —$NH_2$, —$NHCH_3$, —$N(CH_3)_2$, —$CH_3$, —$CH_2$—$CH_3$, —$CF_3$ or —$NO_2$, —$B(OR^a)(OR^b)$, —$(CH_2)_m$—$R^a$, —$(CH_2)_m$—$OR^a$, —$(CH_2)_m$—$C(=O)R^a$, —$(CH_2)_m$—$C(=O)OR^a$, —$(CH_2)_m$—$OC(=O)R^a$, —$(CH_2)_m$—$OC(=O)OR^a$, —$(CH_2)_m$—$OC(=O)NR^aR^b$, —$(CH_2)_m$—$C(=O)NR^aR^b$, —$(CH_2)_m$—$C(=O)NR^aR^b$, —$(CH_2)_m$—$C(=O)NR^b(OR^a)$, —$(CH_2)_m$—$C(=S)R^a$, —$(CH_2)_m$—$C(=S)OR^a$, —$(CH_2)_m$—$OC(=S)R^a$, —$(CH_2)_m$—$OC(=S)OR^a$, —$(CH_2)_m$—$OC(=S)NR^aR^b$, —$(CH_2)_m$—$C(=S)NR^aR^b$, —$(CH_2)_m$—$SR^a$, —$(CH_2)_m$—$S(=O)R^a$, —$(CH_2)_m$—$S(O_2)R^a$, —$(CH_2)_m$—$S(O_2)OR^a$, —$(CH_2)_m$—$OS(O_2)R^a$, —$(CH_2)_m$—$OS(O_2)OR^a$, —$(CH_2)_m$—$NR^aR^b$, —$(CH_2)_m$—$NR^cC(=O)R^a$, —$(CH_2)_m$—$NR^cC(=O)NR^aR^b$, —$(CH_2)_m$—$NR^cC(=O)OR^a$, —$(CH_2)_m$—$NR^cC(=S)R^a$, —$(CH_2)_m$—$NR^cC(=S)NR^aR^b$, —$(CH_2)_m$—$NR^cC(=S)OR^a$, —$(CH_2)_m$—$NR^cS(O_2)R^a$, —$(CH_2)_m$—$P(=O)(OR^b)(OR^a)$, —$(CH_2)_m$—$P(=O)(OR^b)(R^a)$ or —$(CH_2)_m$—$S(O_2)NR^bR^a$, —$(CH_2)_m$—O—$C(=O)$-(M)—$C(=O)OH$, —$(CH_2)_m$—O—$C(=O)$-(M)-$C(=O)OR^a$, —$(CH_2)_m$—O—$C(=O)$-(M)—$R^a$, —$(CH_2)_m$—O—$(CH_2)_q$—$P(=O)(R^{ba})(R^{aa})$, —$(CH_2)_m$—$C(=O)$O—$(CH_2)_q$—$P(=O)(R^{ba})(R^{aa})$, —$(CH_2)_m$—$C(=O)O$—$(CH_2)_q$—$S(O_2)OH$ or —$(CH_2)_m$—$C(=O)O$—$(CH_2)_q$—$S(O_2)OR^a$, with $R^{aa}$ being selected independently from each other being —$R^a$ or —$OR^a$, with $R^{ba}$ being selected independently from each other being —$R^b$ or —$OR^b$, with M being a substituted or unsubstituted $C_1$-$C_8$ alkyl, in particular an unsubstituted $C_1$-$C_8$ alkyl with m being selected from 0, 1 or 2, in particular 0 or 1, with q being selected from 0, 1 or 2, in particular 0 or 1, with each $R^a$, $R^b$ or $R^c$ being selected, where applicable, independently from each other from hydrogen, —CN a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl, with n of $R^{10}_n$ being 0, 1, 2, 3 or 4, in particular n of $R^{10}_n$ being 0, 1, 2 or 3, 4, and with each $R^{10}$ independently from any other $R^{10}$ being selected from —OH, —F, —Cl, —Br, I, —CCH, —CN, —$N_3$, —$OCH_3$, —$OCF_3$, —$NH_2$, —$NHCH_3$, —$N(CH_3)_2$, —$CH_3$, —$CH_2$—$CH_3$, —$CF_3$ or —$NO_2$, —$B(OR^a)(OR^b)$, —$(CH_2)_m$—$R^a$, —$(CH_2)_m$—$OR^a$, —$(CH_2)_m$—$C(=O)R^a$, —$(CH_2)_m$—$C(=O)OR^a$, —$(CH_2)_m$—$OC(=O)R^a$, —$(CH_2)_m$—$OC(=O)OR^a$, —$(CH_2)_m$—$OC(=O)NR^aR^b$, —$(CH_2)_m$—$C(=O)NR^aR^b$, —$(CH_2)_m$—$C(=O)NR^aR^b$, —$(CH_2)_m$—$C(=O)NR^b(OR^a)$, —$(CH_2)_m$—$C(=S)R^a$, —$(CH_2)_m$—$C(=S)OR^a$, —$(CH_2)_m$—$OC(=S)R^a$, —$(CH_2)_m$—$OC(=S)OR^a$, —$(CH_2)_m$—$OC(=S)NR^aR^b$, —$(CH_2)_m$—$C(=S)NR^aR^b$, —$(CH_2)_m$—$SR^a$, —$(CH_2)_m$—$S(=O)R^a$, —$(CH_2)_m$—$S(O_2)R^a$, —$(CH_2)_m$—$S(O_2)OR^a$, —$(CH_2)_m$—$OS(O_2)R^a$, —$(CH_2)_m$—$OS(O_2)OR^a$, —$(CH_2)_m$—$NR^aR^b$, —$(CH_2)_m$—$NR^cC(=O)R^a$, —$(CH_2)_m$—$NR^cC(=O)NR^aR^b$, —$(CH_2)_m$—$NR^cC(=O)OR^a$, —$(CH_2)_m$—$NR^cC(=S)R^a$, —$(CH_2)_m$—$NR^cC(=S)NR^aR^b$, —$(CH_2)_m$—$NR^cC(=S)OR^a$, —$(CH_2)_m$—$NR^cS(O_2)R^a$, —$(CH_2)_m$—$P(=O)(OR^b)(OR^a)$, —$(CH_2)_m$—$P(=O)(OR^b)(R^a)$ or —$(CH_2)_m$—$S(O_2)NR^bR^a$, —$(CH_2)_m$—O—$C(=O)$-(M)—$C(=O)OH$, —$(CH_2)_m$—O—$C(=O)$-(M)-$C(=O)OR^a$, —$(CH_2)_m$—O—$C(=O)$-(M)—$R^a$, —$(CH_2)_m$—O—$(CH_2)_q$—$P(=O)(R^{ba})(R^{aa})$, —$(CH_2)_m$—$C(=O)$O—$(CH_2)_q$—$P(=O)(R^{ba})(R^{aa})$, —$(CH_2)_m$—$C(=O)O$—$(CH_2)_q$—$S(O_2)OH$ or —$(CH_2)_m$—$C(=O)O$—$(CH_2)_q$—$S(O_2)OR^a$, with $R^{aa}$ being selected independently from each other being —$R^a$ or —$OR^a$, with $R^{ba}$ being selected independently from each other being —$R^b$ or —$OR^b$, with M being a substituted or unsubstituted $C_1$-$C_8$ alkyl, in particular an unsubstituted $C_1$-$C_8$ alkyl with m being selected from 0, 1 or 2, in particular 0 or 1, with q being selected from 0, 1 or 2, in particular 0 or 1, with each $R^a$, $R^b$ or $R^c$ being selected, where applicable, independently from each other from hydrogen, —CN a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl, a substituted or unsubstituted $C_3$-$C_{10}$ cycloalkyl or a substituted or unsubstituted $C_3$-$C_{10}$ halo cycloalkyl, a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, a substituted or unsubstituted $C_5$-$C_{10}$ heteroaryl, a substituted or unsubstituted $C_6$-$C_{10}$ aryl.

In some embodiments, in particular according to any one of the sub aspects 1 to 17, 19, 21, 24 or 27, BF is

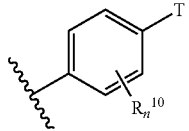

wherein $D^5$ and T have the same meaning as defined previously,
with n of $R^1{}_n$ being 0, 1, 2, 3 or 4, in particular n of $R^1{}_n$ being 0, 1, 2 or 3, and
with each $R^1$ independently from any other $R^1$ being selected from
—OH, —F, —Cl, —Br, I, —CCH, —CN, —N$_3$, —OCH$_3$, —OCF$_3$, —NH$_2$, —NHCH$_3$, —N(CH$_3$)$_2$, —CH$_3$, —CH$_2$—CH$_3$, —CF$_3$ or —NO$_2$, —B(OR$^a$)(OR$^b$), —(CH$_2$)$_m$—R$^a$, —(CH$_2$)$_m$—OR$^a$, —(CH$_2$)$_m$—C(=O)R$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O)NR$^a$R$^b$, —(CH$_2$)$_m$—C(=O)NR$^a$R$^b$, —(CH$_2$)$_m$—C(=O)NR$^b$(OR$^a$), —(CH$_2$)$_m$—C(=S)R$^a$, —(CH$_2$)$_m$—C(=S)OR$^a$, —(CH$_2$)$_m$—OC(=S)R$^a$, —(CH$_2$)$_m$—OC(=S)OR$^a$, —(CH$_2$)$_m$—OC(=S)NR$^a$R$^b$, —(CH$_2$)$_m$—C(=S)NR$^a$R$^b$, —(CH$_2$)$_m$—SR$^a$, —(CH$_2$)$_m$—S(=O)R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)NR$^a$R$^b$, —(CH$_2$)$_m$—NR$^c$C(=O)OR$^a$, —(CH$_2$)$_m$—NR$^c$C(=S)R$^a$, —(CH$_2$)$_m$—NR$^c$C(=S)NR$^a$R$^b$, —(CH$_2$)$_m$—NR$^c$C(=S)OR$^a$, —(CH$_2$)$_m$—NR$^c$S(O$_2$)R$^a$, —(CH$_2$)$_m$—P(=O)(OR$^b$)(OR$^a$), —(CH$_2$)$_m$—P(=O)(OR$^b$)(R$^a$) or —(CH$_2$)$_m$—S(O$_2$)NR$^b$R$^a$, —(CH$_2$)$_m$—O—C(=O)-(M)—C(=O)OH, —(CH$_2$)$_m$—O—C(=O)-(M)—C(=O)OR$^a$, —(CH$_2$)$_m$—O—C(=O)-(M)—R$^a$, —(CH$_2$)$_m$—O—(CH$_2$)$_q$—P(=O)(R$^{ba}$)(R$^{aa}$), —(CH$_2$)$_m$—C(=O)O—(CH$_2$)$_q$—P(=O)(R$^{ba}$)(R$^{aa}$), —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$,
with R$^{aa}$ being selected independently from each other being —R$^a$ or —OR$^a$,
with R$^{ba}$ being selected independently from each other being —R$^b$ or —OR$^b$,
with M being a substituted or unsubstituted C$_1$-C$_8$ alkyl, in particular an unsubstituted C$_1$-C$_8$ alkyl, in particular C$_1$ to C$_2$ alkyl,
with m being selected from 0, 1 or 2, in particular 0 or 1,
with q being selected from 0, 1 or 2, in particular 0 or 1,
with each R$^a$, R$^b$ or R$^c$ being selected, where applicable, independently from each other from
hydrogen, —CH$_3$, —CH$_2$CH$_3$, —CH$_2$CH$_2$CH$_3$, —CH$_2$CH$_2$CH$_2$CH$_3$, —CH(CH$_3$)$_2$, —CH$_2$CH(CH$_3$)$_2$, —C(CH$_3$)$_3$, —C$_6$H$_5$, —CH$_2$C$_6$H$_5$.

In some embodiments, in particular according to any one of the sub aspects 1 to 17, 19, 21, 24 or 27,
BF is

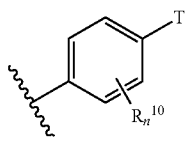

wherein $D^5$ and T have the same meaning as defined previously,
with n of $R^{10}{}_n$ being 0, 1, 2, 3 or 4, in particular n of $R^{10}{}_n$ being 0, 1, 2 or 3, and
with each $R^{10}$ independently from any other $R^{10}$ being
—OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$,
a substituted or unsubstituted C$_5$-C$_6$ heterocycle,
a substituted or unsubstituted C$_5$-C$_6$ halo heterocycle, in particular a C$_5$-C$_6$ halo heterocycle comprising one or two halogen atoms selected from Cl of F, particularly comprising one Cl or one F,
a substituted or unsubstituted C$_5$-C$_6$ heteroaryl,
a substituted or unsubstituted C$_5$-C$_6$ halo heteroaryl comprising one or two halogen atoms selected from Cl of F, particularly comprising one Cl or one F,
a substituted or unsubstituted C$_6$ aryl.

In some embodiments, in particular according to any one of the sub aspects 1 to 17, 19, 21, 24 or 27,
BF is

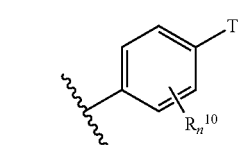

wherein $D^5$ and T have the same meaning as defined previously,
with n of $R^{10}{}_n$ being 0, 1, 2, 3 or 4, in particular n of $R^{10}{}_n$ being 0, 1, 2 or 3, and with each $R^{10}$ independently from any other $R^{10}$ being —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$.

In some embodiments, in particular according to any one of the sub aspects 1 to 17, 19, 21, 24 or 27,
BF is

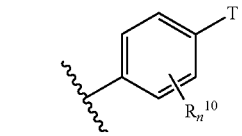

wherein $D^5$ and T have the same meaning as defined previously,
with n of $R^{10}{}_n$ being 2, and with each $R^{10}$ independently from any other $R^{10}$ being —OH, —OCH$_3$ or —OCF$_3$, in particular OH or —OCH$_3$, more particularly with one $R^{10}$ being —OH and the other $R^{10}$ being —OCH$_3$, wherein further in particular OH is in meta and OCH$_3$ or —OCF$_3$ in ortho position with respect to the attachment position of the phenyl moiety of BF to $D^5$, or
with n of $R^{10}{}_n$ being 1, and with $R^{10}$ being —OH, wherein in particular OH is in meta position with respect to the attachment position of the phenyl of BF to $D^5$ or with n of $R^{10}{}_n$ being 1, and with $R^{10}$ being —OCH$_3$ or —OCF$_3$, in particular or —OCH$_3$, wherein more particularly —OCH$_3$ or —OCF$_3$ is in ortho position with respect to the attachment position of the phenyl of BF to $D^5$, or
  with n of $R^{10}{}_n$ being 0, or
  with n of $R^{10}{}_n$ being 4 and each $R^{10}$ is F.

In some embodiments, in particular according to any one of the sub aspects 1 to 17, 19, 21, 24 or 27,
BF is

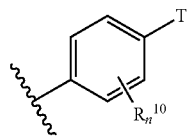

wherein $D^5$ and T have the same meaning as defined previously,
  with n of $R^{10}{}_n$ being 0, 1, 2, 3 or 4, in particular n of $R^1{}_n$ being 0, 1, 2 or 3, and with each $R^{10}$ independently from any other $R^{10}$ being —OH, OCH$_3$, —F or —CF$_3$.

In some embodiments, in particular according to any one of the sub aspects 1 to 17, 19, 21, 24 or 27,
BF is

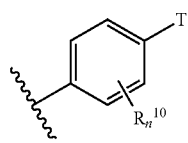

wherein $D^5$ and T have the same meaning as defined previously,
  with n of $R^{10}{}_n$ being 1, 2, 3 or 4, in particular n of $R^{10}{}_n$ being 1, 2 or 3,
  with one $R^{10}$ being a substituent Q, with Q being selected from
    —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$, —(CH$_2$)$_m$—O—S(O$_2$)OH, —(CH$_2$)$_m$—O—S(O$_2$)OR$^a$, in particular —(CH$_2$)$_m$—O—S(O$_2$)OH, —(CH$_2$)$_m$—O—S(O$_2$)OR$^a$, with m being selected from 0, 1 or 2, in particular from 0 or 1, with R$^a$ being —CH$_3$, —CH$_2$CH$_3$, —C$_6$H$_5$, —CH$_2$CH$_2$CH$_3$, —CH(CH$_3$)$_2$, —CH$_2$C$_6$H$_5$ or para-methoxybenzyl
    —C(=O)—O—R$^a$, —O—C(=O)—R$^a$, in particular —O—C(=O)—R$^a$, with R$^a$ being a substituted or unsubstituted $C_1$-$C_{16}$ alkyl, in particular an unsubstituted $C_1$-$C_{14}$ alkyl,
    —(CH$_2$)$_m$—[(CH$_2$)$_{m1}$—O—C(=O)—(CH$_2$)$_{m2}$]$_{p1}$—C(=O)OR$^d$, in particular —(CH$_2$)—[—O—C(=O)—(CH$_2$)$_2$]$_{p1}$—C(=O)OR$^d$ with
      R$^d$ being —CH$_3$, —CH$_2$CH$_3$, —CH$_2$CH$_2$CH$_3$, —CH(CH$_3$)$_2$, —C$_6$H$_5$
      m1 and m2 being selected independently from each other form 1, 2 or 3, in particular m1 and m2 are 2, and
      p1 being selected from 1 to 20, in particular from 1 to 8,
    —(CH$_2$)$_m$—[(CH$_2$)$_{m1}$—O—(CH$_2$)$_{m2}$]$_{p1}$—OR$^d$, in particular —[—O—(CH$_2$)$_2$]$_{p1}$—OR$^d$, with
      R$^d$ being —CH$_3$, —CH$_2$CH$_3$, —CH$_2$CH$_2$CH$_3$, —CH(CH$_3$)$_2$, —C$_6$H$_5$
      m1 and m2 being selected independently from each other form 1, 2 or 3, in particular m1 and m2 are 2, and
      p1 being selected from 1 to 20, in particular from 1 to 8,
    —(CH$_2$)$_m$—C(=O)O—(CH$_2$)$_q$—P(=O)(R$^{ba}$)(R$^{aa}$),
    —(CH$_2$)$_m$—O—(CH$_2$)$_q$—P(=O)(R$^{ba}$)(R$^{aa}$), in particular from —(CH$_2$)$_m$—O—(CH$_2$)$_q$—P(=O)(R$^{ba}$)(R$^{aa}$),
      with R$^{aa}$ and R$^{ba}$ being selected, where applicable, independently from each other from —R$^a$ or —OR$^a$ and
      with R$^a$ being hydrogen, —OCH$_3$, —OCH$_2$CH$_3$, —CH$_3$, —CH$_2$CH$_3$, —C$_6$H$_5$—CH$_2$CH$_2$CH$_3$, —CH(CH$_3$)$_2$, —CH$_2$C$_6$H$_5$ or para-methoxybenzyl
        with m being selected from 0, 1 or 2, in particular 0 or 1,
        with q being selected from 0, 1 or 2, in particular 0 or 1,
  and with the other $R^{10}$ being selected independently from each other $R^{10}$ from —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$.

In some embodiments, in particular according to any one of the sub aspects 1 to 17, 19, 21, 24 or 27,
BF is

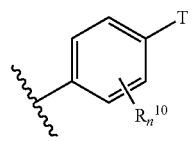

wherein $D^5$ and T have the same meaning as defined previously,
  with n of $R^{10}{}_n$ being 5, and one to four of $R^1$ being F, one $R^{10}$ being the substituent Q, and, where applicable, the other ones of $R^{10}$ being selected independently from any other $R^1$ from —H, —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$, or
  with n of $R^{10}{}_n$ being 5, and one to three of $R^{10}$ being F, one $R^{10}$ being the substituent Q, and, where applicable, the other ones of $R^{10}$ being selected independently from any other $R^{10}$ from —H, —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH$_2$OCH$_3$, —CHCH$_2$, —CH$_2$OH, —SO$_2$NH$_2$, —SO$_2$N(CH$_3$)$_2$, —SO$_2$NHCH$_3$, —CH$_3$, —CF$_3$ or —NO$_2$, in particular from —OH, —F, —OCH$_3$, —OCF$_3$ or —CF$_3$, or
  with n of $R^{10}{}_n$ being 5, and one or two of $R^{10}$ being F, one $R^{10}$ being the substituent Q, and, where applicable, the other ones of $R^{10}$ being selected independently from any other $R^{10}$ from —H, —OH, —F, —Cl, —Br, —I, —CCH, —CN, —N$_3$, —OCH$_3$, —OCF$_3$, —NH$_2$, —NHCH$_3$, —N(CH$_3$)$_2$, —CH$_3$, —CH$_2$CH$_3$, —CH₂OCH₃, —CHCH₂, —CH₂OH, —SO₂NH₂, —SO₂N(CH₃)₂, —SO₂NHCH₃, —CH₃, —CF₃ or —NO₂, in particular from —OH, —F, —OCH₃, —OCF₃ or —CF₃, or with n of $R^{10}{}_n$ being 5, and one of $R^{10}$ being F, one $R^{10}$ being the substituent Q, and, where applicable, the other ones of $R^{10}$ being selected independently from any other $R^{10}$ from —H, —OH, —F, —Cl, —Br, —I, —CCH, —CN, —N₃, —OCH₃, —OCF₃, —NH₂, —NHCH₃, —N(CH₃)₂, —CH₃, —CH₂CH₃, —CH₂OCH₃, —CHCH₂, —CH₂OH, —SO₂NH₂, —SO₂N(CH₃)₂, —SO₂NHCH₃, —CH₃, —CF₃ or —NO₂, in particular from —OH, —F, —OCH₃, —OCF₃ or —CF₃, or with n of $R^{10}{}_n$ being 3, one $R^{10}$ being the substituent Q, and the other $R^{10}$ being selected independently from each other $R^{10}$ from —H, —OH, —F, —Cl, —Br, —I, —CCH, —CN, —N₃, —OCH₃, —OCF₃, —NH₂, —NHCH₃, —N(CH₃)₂, —CH₃, —CH₂CH₃, —CH₂OCH₃, —CHCH₂, —CH₂OH, —SO₂NH₂, —SO₂N(CH₃)₂, —SO₂NHCH₃, —CH₃, —CF₃ or —NO₂, in particular from —OH, —F, —OCH₃, —OCF₃ or —CF₃, or with n of $R^{10}{}_n$ being 2, one $R^{10}$ being the substituent Q and the other $R^{10}$ being —H, —OH, —F, —Cl, —Br, —I, —CCH, —CN, —N₃, —OCH₃, —OCF₃, —NH₂, —NHCH₃, —N(CH₃)₂, —CH₃, —CH₂CH₃, —CH₂OCH₃, —CHCH₂, —CH₂OH, —SO₂NH₂, —SO₂N(CH₃)₂, —SO₂NHCH₃, —CH₃, —CF₃ or —NO₂, in particular from —OH, —F, —OCH₃, —OCF₃ or —CF₃, or with n of $R^{10}{}_n$ being 1 with $R^{10}$ being the substituent Q, with Q having the same meaning as defined previously, and wherein in particular Q is in ortho position with respect to the attachment position of the phenyl moiety to the parent moiety, and wherein in particular any hydrogen of the phenyl group may be substituted with F.

In some embodiments, in particular according to any one of the sub aspects 1 to 17, 19, 21, 24 or 27, BF is

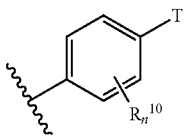

with n of $R^{10}{}_n$ being 2, and with one $R^{10}$ being Q and the other $R^{10}$ being —OCH₃ or —OCF₃, more particularly Q is in meta and OCH₃ or —OCF₃ is in ortho position with respect to the attachment position of the phenyl moiety of BB to $D^4$, with Q and T having the same meaning as defined above.

In some embodiments, in particular according to any one of the sub aspects 1 to 17, 19, 21, 24 or 27, -$D^5$-BF is

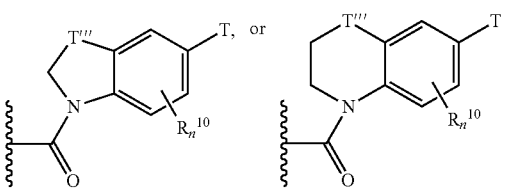

with T having the same meaning as defined above, with each T''' being selected from —CH₂, —NH, —S, —O, or —NR$^c$, in particular T''' is O, with R$^c$ being —OH, —CH₃, —CH₂CH₃, —CH₂CH₂CH₃, —CH(CH₃)₂, with n of $R^{10}{}_n$ being 0, 1, 2 or 3, in particular n of $R^{11}{}_n$ being 0, 1 or 2, with each $R^{10}$ being selected independently from any other $R^{10}$ from —OH, —F, —Cl, —Br, —I, —CCH, —CN, —N₃, —OCH₃, —OCF₃, —NH₂, —NHCH₃, —N(CH₃)₂, —CH₃, —CH₂CH₃, —CH₂OCH₃, —CHCH₂, —CH₂OH, —SO₂NH₂, —SO₂N(CH₃)₂, —SO₂NHCH₃, —CH₃, —CF₃ or —NO₂, in particular from —OH, —F, —OCH₃, —OCF₃ or —CF₃, or with each $R^{10}$ being selected independently from any other $R^{10}$ from —OH, —F, —Cl, —Br, —I, —CCH, —CN, —N₃, —OCH₃, —OCF₃, —NH₂, —NHCH₃, —N(CH₃)₂, —CH₃, —CH₂CH₃, —CH₂OCH₃, —CHCH₂, —CH₂OH, —SO₂NH₂, —SO₂N(CH₃)₂, —SO₂NHCH₃, —CH₃, —CF₃ or —NO₂, in particular from —OH, —F, —OCH₃, —OCF₃ or —CF₃, wherein, each carbon atom of the cyclic system which comprises no substituent $R^{10}$ comprises F instead of H In some embodiments, in particular according to any one of the sub aspects 1 to 17, 19, 21, 24 or 27, -$D^5$-BF is

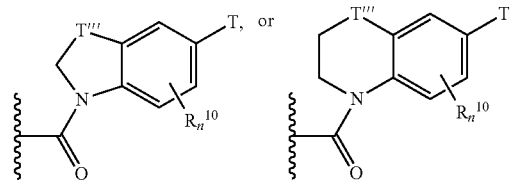

with T having the same meaning as defined above, with each T''' being selected from —CH₂, —NH, —S, —O, or —NR$^c$, in particular T''' is O, with R$^c$ being —OH, —CH₃, —CH₂CH₃, —CH₂CH₂CH₃, —CH(CH₃)₂ with n of $R^{10}{}_n$ being 2, and with each $R^{10}$ independently from any other $R^{10}$ being —OH, —OCH₃ or —OCF₃, in particular —OCH₃ or —OCF₃, more particularly with one $R^{10}$ being —OH and the other $R^{10}$ being —OCH₃ or —OCF₃, in particular —OCH₃, wherein more particularly OH is in ortho and OCH₃ or —OCF₃ in meta position with respect to the attachment position of T, or with n of $R^{10}{}_n$ being 1, and with $R^{10}$ being —OH, wherein in particular OH is in ortho position with respect to the attachment position of T, or with n of $R^{10}{}_n$ being 1, and with $R^{10}$ being —OCH₃ or —OCF₃, in particular or —OCH₃, wherein more particularly —OCH₃ or —OCF₃ is in meta position with respect to the attachment position of T, or with n of $R^{10}{}_n$ being 0, or with n of $R^{10}{}_n$ being 4 and each $R^{10}$ is F.

In some embodiments, in particular according to any one of the sub aspects 1 to 17, 19, 21, 24 or 27,
-$D^5$-BF is

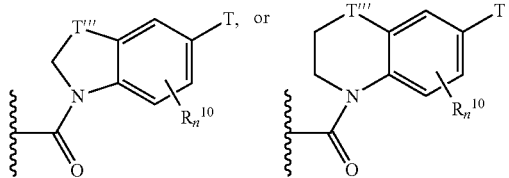

with T having the same meaning as defined above,
with each T''' being selected from —$CH_2$, —NH, —S, —O, or —$NR^c$, in particular T''' is O,
with $R^c$ being —OH, —$CH_3$, —$CH_2CH_3$, —$CH_2CH_2CH_3$, —$CH(CH_3)_2$,
with n of $R^{10}{}_n$ being 1, 2 or 3, in particular n of $R^{10}{}_n$ being 1 or 2,
with one $R^{10}$ being a substituent Q, with Q being selected from

- —$(CH_2)_m$—C(=O)O—$(CH_2)_q$—S($O_2$)OH or —$(CH_2)_m$—C(=O)O—$(CH_2)_q$—S($O_2$)$OR^a$, —$(CH_2)_m$—O—S($O_2$)OH, —$(CH_2)_m$—O—S($O_2$)$OR^a$, in particular —$(CH_2)_m$—O—S($O_2$)OH, —$(CH_2)_m$—O—S($O_2$)$OR^a$, with m being selected from 0, 1 or 2, in particular from 0 or 1, with $R^a$ being —$CH_3$, —$CH_2CH_3$, —$C_6H_5$, —$CH_2CH_2CH_3$, —$CH(CH_3)_2$, —$CH_2C_6H_5$ or para-methoxybenzyl
- —C(=O)—O—$R^a$, —O—C(=O)—$R^a$, in particular —O—C(=O)—$R^a$, with $R^a$ being a substituted or unsubstituted $C_1$-$C_{16}$ alkyl, in particular an unsubstituted $C_1$-$C_{14}$ alkyl,
- —$(CH_2)_m$—[$(CH_2)_{m1}$—O—C(=O)—$(CH_2)_{m2}]_{p1}$—C(=O)$OR^d$, in particular —$(CH_2)$—[—O—C(=O)—$(CH_2)_2]_{p1}$—C(=O)$OR^d$ with
  $R^d$ being —$CH_3$, —$CH_2CH_3$, —$CH_2CH_2CH_3$, —$CH(CH_3)_2$, —$C_6H_5$
  m1 and m2 being selected independently from each other form 1, 2 or 3, in particular m1 and m2 are 2, and
  p1 being selected from 1 to 20, in particular from 1 to 8,
- —$(CH_2)_m$—[$(CH_2)_{m1}$—O—$(CH_2)_{m2}]_{p1}$—$OR^d$, in particular —[—O—$(CH_2)_2]_{p1}$—$OR^d$, with
  $R^d$ being —$CH_3$, —$CH_2CH_3$, —$CH_2CH_2CH_3$, —$CH(CH_3)_2$, —$C_6H_5$
  m1 and m2 being selected independently from each other form 1, 2 or 3, in particular m1 and m2 are 2, and
  p1 being selected from 1 to 20, in particular from 1 to 8,
- —$(CH_2)_m$—C(=O)O—$(CH_2)_q$—P(=O)($R^{ba}$)($R^{aa}$), —$(CH_2)_m$—O—$(CH_2)_q$—P(=O)($R^{ba}$)($R^{aa}$), in particular from —$(CH_2)_m$—O—$(CH_2)_q$—P(=O)($R^{ba}$)($R^{aa}$),
  with $R^{aa}$ and $R^{ba}$ being selected, where applicable, independently from each other from —$R^a$ or —$OR^a$ and
    with $R^a$ being hydrogen, —$OCH_3$, —$OCH_2CH_3$, —$CH_3$, —$CH_2CH_3$, —$C_6H_5$, —$CH_2CH_2CH_3$, —$CH(CH_3)_2$, —$CH_2C_6H_5$ or para-methoxybenzyl
    with m being selected from 0, 1 or 2, in particular 0 or 1,
    with q being selected from 0, 1 or 2, in particular 0 or 1, i. with the other $R^{11}$ being selected independently from any other $R^{11}$ from —OH, —F, —Cl, —Br, —I, —CCH, —CN, —$N_3$, —$OCH_3$, —$OCF_3$, —$NH_2$, —$NHCH_3$, —$N(CH_3)_2$, —$CH_3$, —$CH_2CH_3$, —$CH_2OCH_3$, —$CHCH_2$, —$CH_2OH$, —$SO_2NH_2$, —$SO_2N(CH_3)_2$, —$SO_2NHCH_3$, —$CH_3$, —$CF_3$ or —$NO_2$, in particular from —OH, —F, —$OCH_3$, —$OCF_3$ or —$CF_3$, or ii. with the other $R^{11}$ being selected independently from any other $R^{11}$ from —OH, —F, —Cl, —Br, —I, —CCH, —CN, —$N_3$, —$OCH_3$, —$OCF_3$, —$NH_2$, —$NHCH_3$, —$N(CH_3)_2$, —$CH_3$, —$CH_2CH_3$, —$CH_2OCH_3$, —$CHCH_2$, —$CH_2OH$, —$SO_2NH_2$, —$SO_2N(CH_3)_2$, —$SO_2NHCH_3$, —$CH_3$, —$CF_3$ or —$NO_2$, in particular from —OH, —F, —$OCH_3$, —$OCF_3$ or —$CF_3$, wherein, each carbon atom of the cyclic system which comprises no substituent $R^{11}$ comprises F instead of H.

In some embodiments, in particular according to any one of the sub aspects 1 to 17, 19, 21, 24 or 27,
-$D^5$-BF is

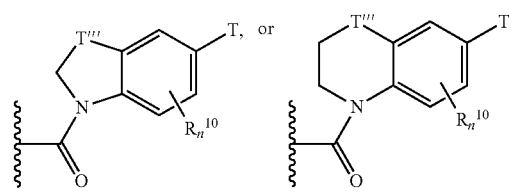

with T having the same meaning as defined above,
with each T''' being selected from —$CH_2$, —NH, —S, —O, or —$NR^c$, in particular T''' is O,
with $R^c$ being —OH, —$CH_3$, —$CH_2CH_3$, —$CH_2CH_2CH_3$, —$CH(CH_3)_2$,
with n of $R^{11}{}_n$ being 0 or 2, and with one $R^{11}$ being Q and the other $R^{11}$ being —$OCH_3$ or —$OCF_3$, more particularly Q is in ortho and $OCH_3$ or —$OCF_3$ is in meta position with respect to the attachment position of T, with Q having the same meaning as defined above.

In some embodiments, in particular according to the sub aspect 32, with $R^1$ being a substituent Q, Q is selected from
- —$(CH_2)_m$—C(=O)O—$(CH_2)_q$—S($O_2$)OH or —$(CH_2)_m$—C(=O)O—$(CH_2)_q$—S($O_2$)$OR^a$, —$(CH_2)_m$—O—S($O_2$)OH, —$(CH_2)_m$—O—S($O_2$)$OR^a$, in particular —$(CH_2)_m$—O—S($O_2$)OH, —$(CH_2)_m$—O—S($O_2$)$OR^a$, with $R^a$ being —$CH_3$, —$CH_2CH_3$, —$C_6H_5$, —$CH_2CH_2CH_3$, —$CH(CH_3)_2$, —$CH_2C_6H_5$ or para-methoxybenzyl
- —C(=O)—O—$R^a$, —O—C(=O)—$R^a$, in particular —O—C(=O)—$R^a$, with $R^a$ being a substituted or unsubstituted $C_1$-$C_{16}$ alkyl, in particular an unsubstituted $C_1$-$C_{14}$ alkyl, —[$(CH_2)_{m1}$—O—C(=O)—$(CH_2)_{m2}]_{p1}$—C(=O)$OR^d$ or —[$(CH_2)_{m1}$—O—$(CH_2)_{m2}]_{p1}$—$OR^d$, in particular —[$(CH_2)_{m1}$—O—$(CH_2)_{m2}]_{p1}$—$OR^d$ with
  $R^d$ being —$CH_3$, —$CH_2CH_3$, —$CH_2CH_2CH_3$, —$CH(CH_3)_2$, —$C_6H_5$
  m1 and m2 being selected independently from each other form 1, 2 or 3, in particular m1 and m2 are 2, and
  p1 being selected from 1 to 20, in particular from 1 to 8,
- —[$(CH_2)_{m1}$—O—$(CH_2)_{m2}]_{p1}$—$OR^d$, in particular —[—O—$(CH_2)_2]_{p1}$—$OR^d$, with $R^d$ being —$CH_3$, —$CH_2CH_3$, —$CH_2CH_2CH_3$, —$CH(CH_3)_2$, —$C_6H_5$ m1 and m2 being selected independently from each other form 1, 2 or 3, in particular m1 and m2 are 2, and p1 being selected from 1 to 20, in particular from 1 to 8, —$(CH_2)_m$—$C(=O)O$—$(CH_2)_q$—$P(=O)(R^{ba})(R^{aa})$, —$(CH_2)_m$—$O$—$(CH_2)_q$—$P(=O)(R^{ba})(R^{aa})$, in particular from —$(CH_2)_m$—$O$—$(CH_2)_q$—$P(=O)(R^{ba})(R^{aa})$, with $R^{aa}$ and $R^{ba}$ being selected, where applicable, independently from each other from —$R^a$ or —$OR^a$ and with $R^a$ being hydrogen, —$OCH_3$, —$OCH_2CH_3$, —$CH_3$, —$CH_2CH_3$, —$C_6H_5$, —$CH_2CH_2CH_3$, —$CH(CH_3)_2$, —$CH_2C_6H_5$ or para-methoxybenzyl with m being selected from 0, 1 or 2, in particular 0 or 1, with q being selected from 0, 1 or 2, in particular 0 or 1, In some embodiments, in particular according to the sub aspect 32, with n of $R^1_n$ being 5, and one to four of $R^1$ being F, one $R^1$ being the substituent Q, and, where applicable, the other ones of $R^1$ being selected independently from any other $R^1$ from —OH, —Cl, I, —CN, —$OCH_3$, —$OCF_3$ or —$CF_3$, in particular from —OH, —$OCH_3$, —$OCF_3$ or —$CF_3$, or with n of $R^1_n$ being 5, and one to three of $R^1$ being F, one $R^1$ being the substituent Q, and, where applicable, the other ones of $R^1$ being selected independently from any other $R^1$ from —OH, —Cl, I, —CN, —$OCH_3$, —$OCF_3$ or —$CF_3$, in particular —OH, —$OCH_3$, —$OCF_3$ or —$CF_3$, or with n of $R^1_n$ being 5, and one or two of $R^1$ being F, one $R^1$ being the substituent Q, and, where applicable, the other ones of $R^1$ being selected independently from any other $R^1$ from —OH, —Cl, I, —CN, —$OCH_3$, —$OCF_3$ or —$CF_3$, in particular —OH, —$OCH_3$, —$OCF_3$ or —$CF_3$, or with n of $R^1_n$ being 5, and one of $R^1$ being F, one $R^1$ being the substituent Q, and, where applicable, the other ones of $R^1$ being selected independently from any other $R^1$ from —OH, —Cl, I, —CN, —$OCH_3$, —$OCF_3$ or —$CF_3$, in particular —OH, —$OCH_3$, —$OCF_3$ or —$CF_3$, or with n of $R^1_n$ being 3, one $R^1$ being the substituent Q, and the other $R^1$ being selected independently from each other $R^1$ from —OH, —$OCH_3$, —$OCF_3$ or —$CF_3$.

with n of $R^1_n$ being 2, one $R^1$ being the substituent Q and the other $R^1$ being —OH, —$OCH_3$, —$OCF_3$ or —$CF_3$, or with n of $R^1_n$ being 1 with $R^1$ being the substituent Q, and with Q having the same meaning as defined previously, and wherein in particular Q is in para position with respect to the attachment position of the phenyl moiety of E to the parent moiety.

In some embodiments, in particular according to any one of the sub aspects 7, 8, 10, 11 to 13, 22, 23, 25, 28, 29 or 32, $R^{11}$ is a substituent Q, with Q being selected from —$(CH_2)_m$—$C(=O)O$—$(CH_2)_q$—$S(O_2)OH$ or —$(CH_2)_m$—$C(=O)O$—$(CH_2)_q$—$S(O_2)OR^a$, —$(CH_2)_m$—$O$—$S(O_2)OH$, —$(CH_2)_m$—$O$—$S(O_2)OR^a$, in particular —$(CH_2)_m$—$O$—$S(O_2)OH$, —$(CH_2)_m$—$O$—$S(O_2)OR^a$, with $R^a$ being —$CH_3$, —$CH_2CH_3$, —$C_6H_5$, —$CH_2CH_2CH_3$, —$CH(CH_3)_2$, —$CH_2C_6H_5$ or para-methoxybenzy —$C(=O)$—$O$—$R^a$, —$O$—$C(=O)$—$R^a$, in particular —$O$—$C(=O)$—$R^a$, with $R^a$ being a substituted or unsubstituted $C_1$-$C_{16}$ alkyl, in particular an unsubstituted $C_1$-$C_{14}$ alkyl, —$[(CH_2)_{m1}$—$O$—$C(=O)$—$(CH_2)_{m2}]_{p1}$—$C(=O)OR^d$ or —$[(CH_2)_{m1}$—$O$—$(CH_2)_{m2}]_{p1}$—$OR^d$, in particular —$[(CH_2)_{m1}$—$O$—$(CH_2)_{m2}]_{p1}$—$OR^d$ with $R^d$ being —$CH_3$, —$CH_2CH_3$, —$CH_2CH_2CH_3$, —$CH(CH_3)_2$, —$C_6H_5$ m1 and m2 being selected independently from each other form 1, 2 or 3, in particular m1 and m2 are 2, and p1 being selected from 1 to 20, in particular from 1 to 8, —$[(CH_2)_{m1}$—$O$—$(CH_2)_{m2}]_{p1}$—$OR^d$, in particular —$[$—$O$—$(CH_2)_2]_{p1}$—$OR^d$, with $R^d$ being —$CH_3$, —$CH_2CH_3$, —$CH_2CH_2CH_3$, —$CH(CH_3)_2$, —$C_6H_5$ m1 and m2 being selected independently from each other form 1, 2 or 3, in particular m1 and m2 are 2, and p1 being selected from 1 to 20, in particular from 1 to 8, —$(CH_2)_m$—$C(=O)O$—$(CH_2)_q$—$P(=O)(R^{ba})(R^{aa})$, —$(CH_2)_m$—$O$—$(CH_2)_q$—$P(=O)(R^{ba})(R^{aa})$, in particular from —$(CH_2)_m$—$O$—$(CH_2)_q$—$P(=O)(R^{ba})(R^{aa})$, with $R^{aa}$ and $R^{ba}$ being selected, where applicable, independently from each other from —$R^a$ or —$OR^a$ and with $R^a$ being hydrogen, —$OCH_3$, —$OCH_2CH_3$, —$CH_3$, —$CH_2CH_3$, —$C_6H_5$, —$CH_2CH_2CH_3$, —$CH(CH_3)_2$, —$CH_2C_6H_5$ or para-methoxybenzyl with m being selected from 0, 1 or 2, in particular 0 or 1, with q being selected from 0, 1 or 2, in particular 0 or 1, and, in particular, wherein, each carbon atom of the cyclic system which comprises no substituent $R^{13}$ comprises F instead of H.

In some embodiments, in particular according to any one of the sub aspects 7, 8, 10, 11 to 13, 22, 23, 25, 28, 29 or 32, $R^{10}$ is a substituent Q, with Q being selected from —$(CH_2)_m$—$C(=O)O$—$(CH_2)_q$—$S(O_2)OH$ or —$(CH_2)_m$—$C(=O)O$—$(CH_2)_q$—$S(O_2)OR^a$, —$(CH_2)_m$—$O$—$S(O_2)OH$, —$(CH_2)_m$—$O$—$S(O_2)OR^a$, in particular —$(CH_2)_m$—$O$—$S(O_2)OH$, —$(CH_2)_m$—$O$—$S(O_2)OR^a$, with $R^a$ being —$CH_3$, —$CH_2CH_3$, —$C_6H_5$, —$CH_2CH_2CH_3$, —$CH(CH_3)_2$, —$CH_2C_6H_5$ or para-methoxybenzy —$C(=O)$—$O$—$R^a$, —$O$—$C(=O)$—$R^a$, in particular —$O$—$C(=O)$—$R^a$, with $R^a$ being a substituted or unsubstituted $C_1$-$C_{16}$ alkyl, in particular an unsubstituted $C_1$-$C_{14}$ alkyl, —$[(CH_2)_{m1}$—$O$—$C(=O)$—$(CH_2)_{m2}]_{p1}$—$C(=O)OR^d$ or —$[(CH_2)_{m1}$—$O$—$(CH_2)_{m2}]_{p1}$—$OR^d$, in particular —$[(CH_2)_{m1}$—$O$—$(CH_2)_{m2}]_{p1}$—$OR^d$ with $R^d$ being —$CH_3$, —$CH_2CH_3$, —$CH_2CH_2CH_3$, —$CH(CH_3)_2$, —$C_6H_5$ m1 and m2 being selected independently from each other form 1, 2 or 3, in particular m1 and m2 are 2, and p1 being selected from 1 to 20, in particular from 1 to 8, —$[(CH_2)_{m1}$—$O$—$(CH_2)_{m2}]_{p1}$—$OR^d$, in particular —$[$—$O$—$(CH_2)_2]_{p1}$—$OR^d$, with $R^d$ being —$CH_3$, —$CH_2CH_3$, —$CH_2CH_2CH_3$, —$CH(CH_3)_2$, —$C_6H_5$ m1 and m2 being selected independently from each other form 1, 2 or 3, in particular m1 and m2 are 2, and p1 being selected from 1 to 20, in particular from 1 to 8, —$(CH_2)_m$—C(=O)O—$(CH_2)_q$—P(=O)($R^{ba}$)($R^{aa}$),
—$(CH_2)_m$—O—$(CH_2)_q$—P(=O)($R^{ba}$)($R^{aa}$), in particular from —$(CH_2)_m$—O—$(CH_2)_q$—P(=O)($R^{ba}$)($R^{aa}$), with $R^{aa}$ and $R^{ba}$ being selected, where applicable, independently from each other from —$R^a$ or —$OR^a$ and with $R^a$ being hydrogen, —$OCH_3$, —$OCH_2CH_3$, —$CH_3$, —$CH_2CH_3$, —$C_6H_5$, —$CH_2CH_2CH_3$, —$CH(CH_3)_2$, —$CH_2C_6H_5$ or para-methoxybenzyl with m being selected from 0, 1 or 2, in particular 0 or 1, with q being selected from 0, 1 or 2, in particular 0 or 1, and, in particular, wherein, each carbon atom of the cyclic system which comprises no substituent $R^{13}$ comprises F instead of H.

In some embodiments, in particular according to any one of the sub aspects 10 to 13, 18 to 32, T is selected from —OH, —F, —Cl, —Br, I, —CCH, —CN, —$N_3$, —$OCH_3$, —$OCF_3$, —$NH_2$, —$NHCH_3$, —$N(CH_3)_2$, —$CH_3$, —$CH_2$—$CH_3$, —$CF_3$ or —$NO_2$, —B($OR^a$)($OR^b$), —$(CH_2)_m$—$R^a$, —$(CH_2)_m$—$OR^a$, —$(CH_2)_m$—C(=O)$R^a$, —$(CH_2)_m$—C(=O)$OR^a$, —$(CH_2)_m$—OC(=O)$R^a$, —$(CH_2)_m$—OC(=O)$OR^a$, —$(CH_2)_m$—OC(=O)$NR^aR^b$, —$(CH_2)_m$—C(=O)$NR^aR^b$, —$(CH_2)_m$—C(=O)$NR^aR^b$, —$(CH_2)_m$—C(=O)$NR^b(OR^a)$, —$(CH_2)_m$—C(=S)$R^a$, —$(CH_2)_m$—C(=S)$OR^a$, —$(CH_2)_m$—OC(=S)$R^a$, —$(CH_2)_m$—OC(=S)$OR^a$, —$(CH_2)_m$—OC(=S)$NR^aR^b$, —$(CH_2)_m$—C(=S)$NR^aR^b$, —$(CH_2)_m$—$SR^a$, —$(CH_2)_m$—S(=O)$R^a$, —$(CH_2)_m$—S($O_2$)$R^a$, —$(CH_2)_m$—S($O_2$)$OR^a$, —$(CH_2)_m$—OS($O_2$)$R^a$, —$(CH_2)_m$—OS($O_2$)$OR^a$, —$(CH_2)_m$—$NR^aR^b$, —$(CH_2)_m$—$NR^aC$(=O)$R^a$, —$(CH_2)_m$—$NR^cC$(=O)$NR^aR^b$, —$(CH_2)_m$—$NR^cC$(=O)$OR^a$, —$(CH_2)_m$—$NR^cC$(=S)$R^a$, —$(CH_2)_m$—$NR^cC$(=S)$NR^aR^b$, —$(CH_2)_m$—$NR^cC$(=S)$OR^a$, —$(CH_2)_m$—$NR^cS$($O_2$)$R^a$, —$(CH_2)_m$—P(=O)($OR^b$)($OR^a$), —$(CH_2)_m$—P(=O)($OR^b$)($R^a$) or —$(CH_2)_m$—S($O_2$)$NR^bR^a$, —$(CH_2)_m$—O—C(=O)-(M)—C(=O)OH, —$(CH_2)_m$—O—C(=O)-(M)—C(=O)$OR^a$, —$(CH_2)_m$—O—C(=O)-(M)—$R^a$, —$(CH_2)_m$—O—$(CH_2)_q$—P(=O)($R^{ba}$)($R^{aa}$), —$(CH_2)_m$—C(=O)O—$(CH_2)_q$—P(=O)($R^{ba}$)($R^{aa}$), —$(CH_2)_m$—C(=O)O—$(CH_2)_q$—S($O_2$)OH or —$(CH_2)_m$—C(=O)O—$(CH_2)_q$—S($O_2$)$OR^a$, with $R^{aa}$ being selected independently from each other being —$R^a$ or —$OR^a$, with $R^{ba}$ being selected independently from each other being —$R^b$ or —$OR^b$, with M being a substituted or unsubstituted $C_1$-$C_8$ alkyl, in particular an unsubstituted $C_1$-$C_8$ alkyl with m being selected from 0, 1 or 2, in particular 0 or 1, with q being selected from 0, 1 or 2, in particular 0 or 1, with each $R^a$, $R^b$ or $R^c$ being selected, where applicable, independently from each other from hydrogen,
—CN a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl, In some embodiments, in particular according to any one of the sub aspects 10 to 13, 18 to 32, T is selected from a. —B(OH)$_2$, —CN, —$NH_2$, —OH, —$OCH_3$, —C(=O)$NH_2$, —C(=O)NH(CN), —C(=O)NH(OH), —$CH_2OH$, —$CH_2C$(=O)OH, —$CH_2C$(=O)NH(OH), —$CH_2C$(=O)$NH_2$, —$CH_2NHS$($O_2$)OH, —$CH_2NHC$(=O)OH, —P(=O)(OH)(OH), —$CH_2P$(=O)(OH)(OH), —$CH_2S$($O_2$)OH, —S($O_2$)OH or —S($O_2$)$NH_2$ or b. —$R^a$, —$CH_2R^a$, —$SR^a$, —$CH_2SR^a$, —S(=O)$R^a$, —C(=O)$NHR^a$, —$CH_2C$(=O)$NHR^a$, —$CH_2NHS$($O_2$)$R^a$, —C(=O)$OR^a$, —$OR^a$ or —$NHR^a$, —C(=O)$OR^a$, —$CH_2C$(=O)NH($OR^a$), —C(=O)NH$OR^a$, —C(=O)$NHR^a$, —$(CH_2)_m$—NHC(=O)$OR^a$, —$CH_2NHS$($O_2$)$R^a$, —$CH_2OR^a$, —$CH_2NHC$(=O)$R^a$, —P(=O)(OH)($OR^a$), —$CH_2P$(=O)(OH)($OR^a$), —P(=O)(OH)($R^a$), —$CH_2P$(=O)(OH)($R^a$), —$CH_2S$($O_2$)$OR^a$, —S($O_2$)$OR^a$, —S($O_2$)$R^a$ or —$CH_2S$($O_2$)$R^a$, or —S($O_2$)$NHR^a$, with $R^a$ being selected from a substituted or unsubstituted $C_1$-$C_{16}$ alkyl, a substituted or unsubstituted $C_1$-$C_{16}$ alkoxy, a substituted or unsubstituted $C_2$-$C_{14}$ alkenyl, a substituted or unsubstituted $C_2$-$C_{14}$ alkynyl, or a $C_1$-$C_{14}$ haloalkyl, in particular a substituted or unsubstituted $C_1$-$C_5$ alkyl, more particularly $R^a$ is —$CH_3$—$CF_3$, —$CH_2CH_3$, —$CH_2CF_3$, —CN, —$CH_2CH_2CH_3$, —$CH(CH_3)_2$, —$CH_2C_6H_5$ or para-methoxybenzy —[$(CH_2)_{m1}$—O—$(CH_2)_{m2}$]$_{p1}$—$OR^d$, —[$(CH_2)_{m1}$—C(=O)O—$(CH_2)_{m2}$]$_{p1}$—$OR^d$ in particular —[—O—$(CH_2)_2$]$_{p1}$—$OR^d$, —[—C(=O)O—$(CH_2)_2$]$_{p1}$—$OR^d$, with $R^d$ being —$CH_3$, —$CH_2CH_3$, —$CH_2CH_2CH_3$, —$CH(CH_3)_2$, —$C_6H_5$ m1 and m2 being selected independently from each other form 1, 2 or 3, in particular m1 and m2 are 2, and p1 being selected from 1 to 20, in particular from 1 to 8, c. —$R^a$, —$CH_2R^a$, —$SR^a$, —$CH_2SR^a$, —S(=O)$R^a$, —C(=O)$NHR^a$, —$CH_2C$(=O)$NHR^a$, —$CH_2NHS$($O_2$)$R^a$, —C(=O)$OR^a$, —$OR^a$ or —$NHR^a$, with $R^a$ being a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl.

In some embodiments, in particular according to any one of the sub aspects 10 to 13, 18 to 32, T is selected from —(CH$_2$)$_m$—C(═O)O—(CH$_2$)$_q$—S(O$_2$)OH or —(CH$_2$)$_m$—C(═O)O—(CH$_2$)$_q$—S(O$_2$)OR$^a$, —(CH$_2$)$_m$—O—S(O$_2$)OH, —(CH$_2$)$_m$—O—S(O$_2$)OR$^a$, in particular —(CH$_2$)$_m$—O—S(O$_2$)OH, —(CH$_2$)$_m$—O—S(O$_2$)OR$^a$, with R$^a$ being —CH$_3$, —CH$_2$CH$_3$, —C$_6$H$_5$, —CH$_2$CH$_2$CH$_3$, —CH(CH$_3$)$_2$, —CH$_2$C$_6$H$_5$ or para-methoxybenzy —C(═O)—O—R$^a$, —O—C(═O)—R$^a$, in particular —O—C(═O)—R$^a$, with R$^a$ being a substituted or unsubstituted C$_1$-C$_{16}$ alkyl, in particular an unsubstituted C$_1$-C$_{14}$ alkyl, —[(CH$_2$)$_{m1}$—O—C(═O)—(CH$_2$)$_{m2}$]$_{p1}$—C(═O)OR$^d$ or —[(CH$_2$)$_{m1}$—O—(CH$_2$)$_{m2}$]$_{p1}$—OR$^d$, in particular —[(CH$_2$)$_{m1}$—O—(CH$_2$)$_{m2}$]$_{p1}$—OR$^d$ with R$^d$ being —CH$_3$, —CH$_2$CH$_3$, —CH$_2$CH$_2$CH$_3$, —CH(CH$_3$)$_2$, —C$_6$H$_5$ m1 and m2 being selected independently from each other form 1, 2 or 3, in particular m1 and m2 are 2, and p1 being selected from 1 to 20, in particular from 1 to 8, —[(CH$_2$)$_{m1}$—O—(CH$_2$)$_{m2}$]$_{p1}$—OR$^d$, in particular —[—O—(CH$_2$)$_2$]$_{p1}$—OR$^d$, with R$^d$ being —CH$_3$, —CH$_2$CH$_3$, —CH$_2$CH$_2$CH$_3$, —CH(CH$_3$)$_2$, —C$_6$H$_5$ m1 and m2 being selected independently from each other form 1, 2 or 3, in particular m1 and m2 are 2, and p1 being selected from 1 to 20, in particular from 1 to 8, —(CH$_2$)$_m$—C(═O)O—(CH$_2$)$_q$—P(═O)(R$^{ba}$)(R$^{aa}$), —(CH$_2$)$_m$—O—(CH$_2$)$_q$—P(═O)(R$^{ba}$)(R$^{aa}$), in particular from —(CH$_2$)$_m$—O—(CH$_2$)$_q$—P(═O)(R$^{ba}$)(R$^{aa}$), with R$^{aa}$ and R$^{ba}$ being selected, where applicable, independently from each other from —R$^a$ or —OR$^a$ and with R$^a$ being hydrogen, —OCH$_3$, —OCH$_2$CH$_3$, —CH$_3$, —CH$_2$CH$_3$, —C$_6$H$_5$, —CH$_2$CH$_2$CH$_3$, —CH(CH$_3$)$_2$, —CH$_2$C$_6$H$_5$ or para-methoxybenzyl with m being selected from 0, 1 or 2, in particular 0 or 1, with q being selected from 0, 1 or 2, in particular 0 or 1, In some embodiments, in particular according to any one of the sub aspects 10 to 13, 18 to 32, T is —C(═O)OR$^a$ with R$^a$ being a substituted or unsubstituted C$_1$-C$_{16}$ alkyl, in particular an unsubstituted C$_1$-C$_{16}$ alkyl, —[(CH$_2$)$_{m1}$—O—(CH$_2$)$_{m2}$]$_{p1}$—OR$^d$, —[(CH$_2$)$_{m1}$—C(═O)O—(CH$_2$)$_{m2}$]$_{p1}$—OR$^d$, in particular —[—O—(CH$_2$)$_2$]$_{p1}$—OR$^d$, —[—C(═O)O—(CH$_2$)$_2$]$_{p1}$, with R$^d$ being —CH$_3$, —CH$_2$CH$_3$, —CH$_2$CH$_2$CH$_3$, —CH(CH$_3$)$_2$, —C$_6$H$_5$ m1 and m2 being selected independently from each other form 1, 2 or 3, in particular m1 and m2 are 2, and p1 being selected from 1 to 20, in particular from 1 to 8.

In some embodiments, in particular according to any one of the sub aspects 10 to 13, 18 to 32, T is selected from the following compounds —B(OH)$_2$, —CN, —OH, —CH$_2$OH, —CH$_2$OCH$_3$, —OCH$_3$, —C(═O)NH$_2$, —C(═O)NH(CN), —C(═O)OH, —C(═O)NH(CH$_3$), —C(═O)NH(OH), —S(O$_2$)NH$_2$, —CH$_2$C(═O)OH, —CH$_2$C(═O)NHOH, —CH$_2$—NH—S(O)$_2$CF$_3$, —CH$_2$—C(═O)—NH—OCH$_3$, —P(═O)(OH)$_2$, —CH$_2$P(═O)(OH)$_2$, —P(═O)(OH)(OCH$_2$CH$_3$), —P(═O)(OH)(CH$_3$), —CH$_2$P(═O)(OH)(CH$_3$), —CH$_2$S(O)$_2$(OH), —S(O)$_2$(OH),

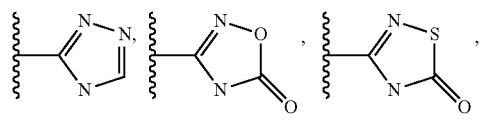

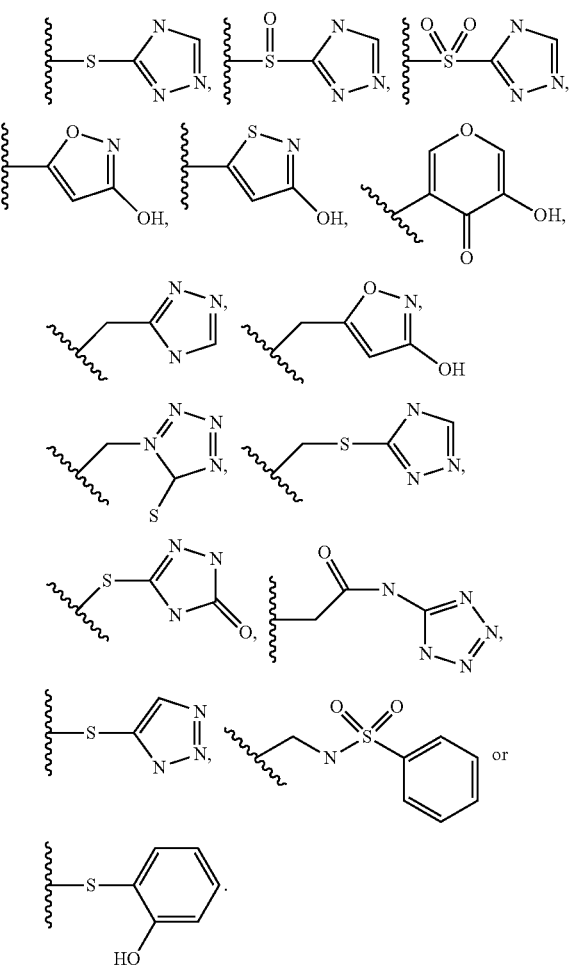

In some embodiments, in particular according to any one of the sub aspects, each D$^1$ to D$^5$ is selected independently from each other from

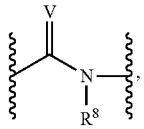
(D1)

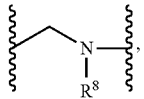
(D2)

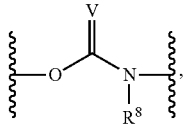
(D3)

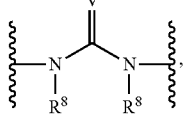
(D4)

-continued (D5) 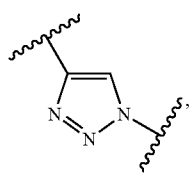

(D6) 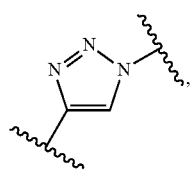

(D7) 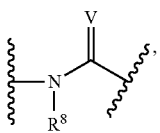

(D8) 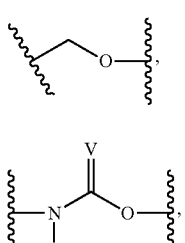

(D9) 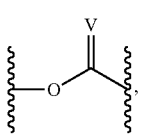

(D10) 

(D11) 

(D12) 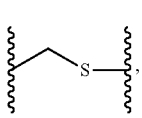

(D13) 

(D13′) 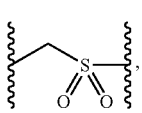

(D13″)

-continued (D14) 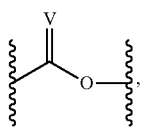

(D15) 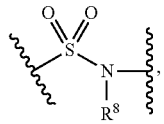

(D16) 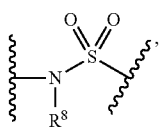

(D17) 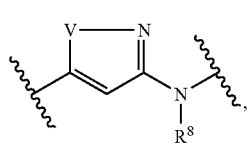

(D18) 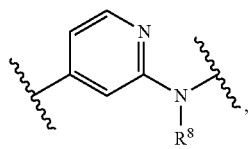

(D19) 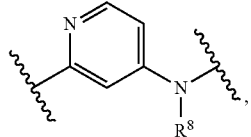

(D20) 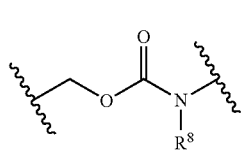

(D21) 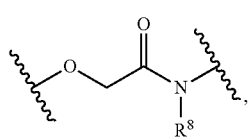

with each $R^8$ being —H, or, where applicable, with each $R^8$ being selected independently from each other from —H, —CH$_3$, —CH$_2$CH$_3$, —OCH$_3$, —OCF$_3$, —CH$_2$CF$_3$, —CHFCF$_3$, —CF$_2$CF$_3$, —CHF$_2$, —CH$_2$F or —CF$_3$, in particular with each $R^8$ being selected independently from each other from H or CH$_3$, more particularly $R^8$ being H, and with V being, where applicable, S, NH or O, in particular V being O.

D1 to D5 may also be a phosphor containing groups, in particular a O—P containing functionality such as —OP(O)$_2$—NH— or alike.

In some embodiments, in particular according to any one of the sub aspects, each $D^1$ to $D^5$ is selected independently from each other from

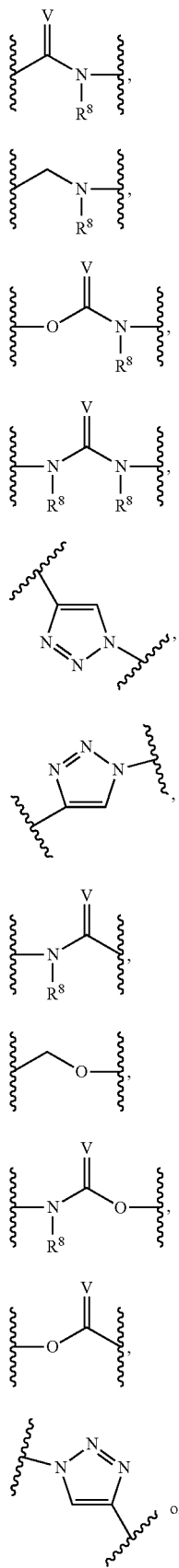

-continued (D12)

with each R⁸ being —H, or, where applicable, with each R⁸ being selected independently from each other from —H, —CH₃, —CH₂CH₃, —OCH₃, —OCF₃, —CH₂CF₃, —CHFCF₃, —CF₂CF₃, —CHF₂, —CH₂F or —CF₃, in particular with each R⁸ being selected independently from each other from H or CH₃, more particularly R⁸ being H, and with V being, where applicable, S, NH or O, in particular V being O.

In some embodiments, in particular according to any one of the sub aspects, each D¹ to D⁵ is selected independently from each other from (D1)

(D2)

(D3)

(D4)

(D5)

(D6)

with each R⁸ being —H, or, where applicable, with each R⁸ being selected independently from each other from —H, —CH₃, —CH₂CH₃, —OCH₃, —OCF₃, —CH₂CF₃, —CHFCF₃, —CF₂CF₃, —CHF₂, —CH₂F or —CF₃, in particular with each R⁸ being selected independently from each other from H or CH₃, more particularly R⁸ being H, and with V being, where applicable, S, NH or O, in particular V being O.

In some embodiments, in particular according to any one of the sub aspects, each $D^1$ to $D^5$ is selected independently from each other from

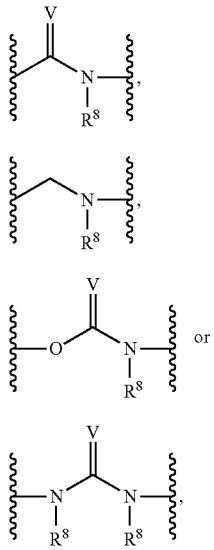

(D1)

(D2)

(D3)

(D4)

with each $R^8$ being —H, or, where applicable, with each $R^8$ being selected independently from each other from —H, —CH$_3$, —CH$_2$CH$_3$, —OCH$_3$, —OCF$_3$, —CH$_2$CF$_3$, —CHFCF$_3$, —CF$_2$CF$_3$, —CHF$_2$, —CH$_2$F or —CF$_3$, in particular with each $R^8$ being selected independently from each other from H or CH$_3$, more particularly $R^8$ being H, and with V being, where applicable, S, NH or O, in particular V being O.

In some embodiments, in particular according to any one of the sub aspects, each $D^1$ to $D^5$ is selected independently from each other from

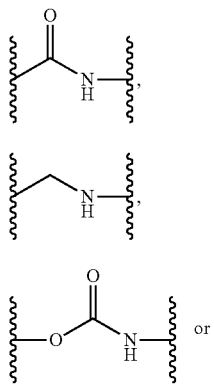

(D1a)

(D2a)

(D3a)

-continued

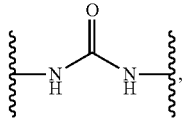

(D4a)

in particular from

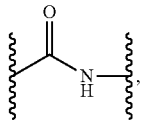

(D1a)

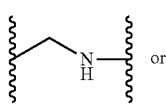

(D2a)

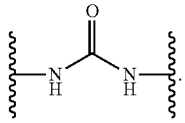

(D4a)

In some embodiments, in particular according to any one of the sub aspects 11 to 13, 24 to 31, $R^2$ and $R^3$ of BA are selected, where applicable, independently from each other from —H, —F, —CN, —OH, —NH$_2$, —NO$_2$, —NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl, in particular from —H, —F, —CN, —OH, —NH$_2$, —NO$_2$, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with $R^2$ and $R^3$ being selected independently from each other from —H, —F or —CH$_3$.

In some embodiments, in particular according to any one of the sub aspects 2, 4, 6, 8, 9, 14 to 31 each $R^8$ is, where applicable, selected independently from each other from —H, —CH$_3$, —CH$_2$CH$_3$, —OCH$_3$, —OCF$_3$, —CH$_2$CF$_3$, —CHFCF$_3$, —CF$_2$CF$_3$, —CHF$_2$, —CH$_2$F or —CF$_3$, in particular with each $R^8$ being selected independently from each other from H or CH$_3$, more particularly each $R^8$ being H.

According to a sub aspect (sub aspect 32) of the first aspect, the invention relates to antibiotically active compounds having a molecular structure as defined by a general formula (34), (formula 34)

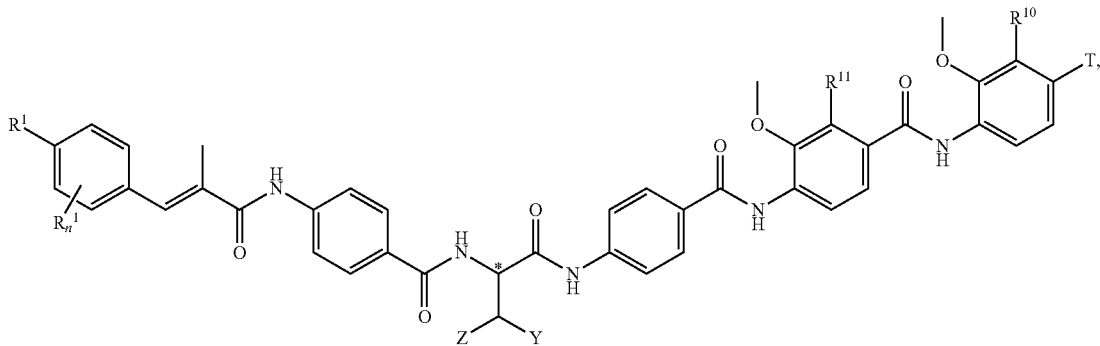

a. with n of $R^1_n$ being 1, 2, 3, 4 or 5, in particular n of $R^1_n$ being 1, 2 or 3, with $R^1$ of BA being a substituent Q, with Q being selected from
- $-(CH_2)_m-C(=O)O-(CH_2)_q-S(O_2)OH$ or $-(CH_2)_m-C(=O)O-(CH_2)_q-S(O_2)OR^a$, $-(CH_2)_m-O-S(O_2)OH$, $-(CH_2)_m-O-S(O_2)OR^a$, in particular $-(CH_2)_m-O-S(O_2)OH$, $-(CH_2)_m-O-S(O_2)OR^a$, with $R^a$ being $-CH_3$, $-CH_2CH_3$, $-C_6H_5$, $-CH_2CH_2CH_3$, $-CH(CH_3)_2$, $-CH_2C_6H_5$ or para-methoxybenzyl
- $-C(=O)-O-R^a$, $-O-C(=O)-R^a$, in particular $-O-C(=O)-R^a$, with $R^a$ being a substituted or unsubstituted $C_1$-$C_{16}$ alkyl, in particular an unsubstituted $C_1$-$C_{14}$ alkyl, $-[(CH_2)_{m1}-O-C(=O)-(CH_2)_{m2}]_{p1}-C(=O)OR^d$ or $-[(CH_2)_{m1}-O-(CH_2)_{m2}]_{p1}-OR^d$, in particular $-[(CH_2)_{m1}-O-(CH_2)_{m2}]_{p1}-OR^d$ with
  - $R^d$ being $-CH_3$, $-CH_2CH_3$, $-CH_2CH_2CH_3$, $-CH(CH_3)_2$, $-C_6H_5$
  - m1 and m2 being selected independently from each other form 1, 2 or 3, in particular m1 and m2 are 2, and
  - p1 being selected from 1 to 20, in particular from 1 to 8,
- $-[(CH_2)_{m1}-O-(CH_2)_{m2}]_{p1}-OR^d$, in particular $-[-O-(CH_2)_2]_{p1}-OR^d$, with
  - $R^d$ being $-CH_3$, $-CH_2CH_3$, $-CH_2CH_2CH_3$, $-CH(CH_3)_2$, $-C_6H_5$
  - m1 and m2 being selected independently from each other form 1, 2 or 3, in particular m1 and m2 are 2, and
  - p1 being selected from 1 to 20, in particular from 1 to 8,
- $-(CH_2)_m-C(=O)O-(CH_2)_q-P(=O)(R^{ba})(R^{aa})$, $-(CH_2)_m-O-(CH_2)_q-P(=O)(R^{ba})(R^{aa})$, in particular from $-(CH_2)_m-O-(CH_2)_q-P(=O)(R^{ba})(R^{aa})$,
  - with $R^{aa}$ and $R^{ba}$ being selected, where applicable, independently from each other from $-R^a$ or $-OR^a$ and
    - with $R^a$ being hydrogen, $-OCH_3$, $-OCH_2CH_3$, $-CH_3$, $-CH_2CH_3$, $-C_6H_5$, $-CH_2CH_2CH_3$, $-CH(CH_3)_2$, $-CH_2C_6H_5$ or para-methoxybenzyl
  - with m being selected from 0, 1 or 2, in particular 0 or 1,
  - with q being selected from 0, 1 or 2, in particular 0 or 1, and with the other $R^1$ being selected independently from each other $R^1$ from $-OH$, $-F$, $-Cl$, $-I$, $-CN$, $-OCH_3$, $-OCF_3$, $-OCONH_2$ or $-CF_3$, in particular from $-OH$, $-F$, $-OCH_3$, $-OCF_3$, $-OCONH_2$ or $-CF_3$, or with n of $R^1_n$ being 5, and one to four of $R^1$ being F, one $R^1$ being the substituent Q, and, where applicable, the other ones of $R^1$ being selected independently from any other $R^1$ from $-OH$, $-Cl$, $-I$, $-CN$, $-OCH_3$, $-OCF_3$, $-OCONH_2$ or $-CF_3$, in particular from $-OH$, $-OCH_3$, $-OCF_3$, $-OCONH_2$ or $-CF_3$, or with n of $R^1_n$ being 5, and one to three of $R^1$ being F, one $R^1$ being the substituent Q, and, where applicable, the other ones of $R^1$ being selected independently from any other $R^1$ from $-OH$, $-Cl$, $-I$, $-CN$, $-OCH_3$, $-OCF_3$, $-OCONH_2$ or $-CF_3$, in particular $-OH$, $-OCH_3$, $-OCF_3$, $-OCONH_2$ or $-CF_3$, or with n of $R^1_n$ being 5, and one or two of $R^1$ being F, one $R^1$ being the substituent Q, and, where applicable, the other ones of $R^1$ being selected independently from any other $R^1$ from $-OH$, $-Cl$, $-I$, $-CN$, $-OCH_3$, $-OCF_3$, $-OCONH_2$ or $-CF_3$, in particular $-OH$, $-OCH_3$, $-OCF_3$, $-OCONH_2$ or $-CF_3$, or with n of $R^1_n$ being 5, and one of $R^1$ being F, one $R^1$ being the substituent Q, and, where applicable, the other ones of $R^1$ being selected independently from any other $R^1$ from $-OH$, $-Cl$, I, $-CN$, $-OCH_3$, $-OCF_3$, $-OCONH_2$ or $-CF_3$, in particular $-OH$, $-OCH_3$, $-OCF_3$, $-OCONH_2$ or $-CF_3$, or with n of $R^1_n$ being 3, one $R^1$ being the substituent Q, and the other $R^1$ being selected independently from each other $R^1$ from $-OH$, $-OCH_3$, $-OCF_3$, $-OCONH_2$ or $-CF_3$.

with n of $R^1_n$ being 2, one $R^1$ being the substituent Q and the other $R^1$ being $-OH$, $-OCH_3$, $-OCF_3$, $-OCONH_2$ or $-CF_3$, or with n of $R^1_n$ being 1 with $R^1$ being the substituent Q, and with Q having the same meaning as defined previously, and wherein in particular Q is in para position with respect to the attachment position of the phenyl moiety of E to the parent moiety, and b. $R^{11}$ is a substituent Q, with Q being selected from
- $-(CH_2)_m-C(=O)O-(CH_2)_q-S(O_2)OH$ or $-(CH_2)_m-C(=O)O-(CH_2)_q-S(O_2)OR^a$, $-(CH_2)_m-O-S(O_2)OH$, $-(CH_2)_m-O-S(O_2)OR^a$, in particular $-(CH_2)_m-O-S(O_2)OH$, $-(CH_2)_m-O-S(O_2)OR^a$, with $R^a$ being $-CH_3$, $-CH_2CH_3$, $-C_6H_5$, $-CH_2CH_2CH_3$, $-CH(CH_3)_2$, $-CH_2C_6H_5$ or para-methoxybenzyl
- $-C(=O)-O-R^a$, $-O-C(=O)-R^a$, in particular $-O-C(=O)-R^a$, with $R^a$ being a substituted or unsubstituted $C_1$-$C_{16}$ alkyl, in particular an unsubstituted $C_1$-$C_{14}$ alkyl, —[$(CH_2)_{m1}$—O—C(=O)—$(CH_2)_{m2}]_{p1}$—C(=O)OR$^d$ or —[$(CH_2)_{m1}$—O—$(CH_2)_{m2}]_{p1}$—OR$^d$, in particular —[$(CH_2)_{m1}$—O—$(CH_2)_{m2}]_{p1}$—OR$^d$ with R$^d$ being —$CH_3$, —$CH_2CH_3$, —$CH_2CH_2CH_3$, —CH$(CH_3)_2$, —$C_6H_5$ m1 and m2 being selected independently from each other form 1, 2 or 3, in particular m1 and m2 are 2, and p1 being selected from 1 to 20, in particular from 1 to 8, —[$(CH_2)_{m1}$—O—$(CH_2)_{m2}]_{p1}$—OR$^d$, in particular —[—O—$(CH_2)_2]_{p1}$—OR$^d$, with R$^d$ being —$CH_3$, —$CH_2CH_3$, —$CH_2CH_2CH_3$, —CH$(CH_3)_2$, —$C_6H_5$ m1 and m2 being selected independently from each other form 1, 2 or 3, in particular m1 and m2 are 2, and p1 being selected from 1 to 20, in particular from 1 to 8, —$(CH_2)_m$—C(=O)O—$(CH_2)_q$—P(=O)(R$^{ba}$)(R$^{aa}$), —$(CH_2)_m$—O—$(CH_2)_q$—P(=O)(R$^{ba}$)(R$^{aa}$), in particular from —$(CH_2)_m$—O—$(CH_2)_q$—P(=O)(R$^{ba}$)(R$^{aa}$), with R$^{aa}$ and R$^{ba}$ being selected, where applicable, independently from each other from —R$^a$ or —OR$^a$ and with R$^a$ being hydrogen, —$OCH_3$, —$OCH_2CH_3$, —$CH_3$, —$CH_2CH_3$, —$C_6H_5$, —$CH_2CH_2CH_3$, —CH$(CH_3)_2$, —$CH_2C_6H_5$ or para-methoxybenzyl with m being selected from 0, 1 or 2, in particular 0 or 1, with q being selected from 0, 1 or 2, in particular 0 or 1, and, in particular, wherein, each carbon atom of the cyclic system which comprises no substituent R$^{11}$ comprises F instead of H, and c. with T being selected from —OH, —F, —Cl, —Br, I, —CCH, —CN, —$N_3$, —$OCH_3$, —$OCF_3$, —$NH_2$, —$NHCH_3$, —$N(CH_3)_2$, —$CH_3$, —$CH_2$—$CH_3$, —$CF_3$ or —$NO_2$,
—B(OR$^a$)(OR$^b$), —$(CH_2)_m$—R$^a$, —$(CH_2)_m$—OR$^a$, —$(CH_2)_m$—C(=O)R$^a$, —$(CH_2)_m$—C(=O)OR$^a$, —$(CH_2)_m$—OC(=O)R$^a$, —$(CH_2)_m$—OC(=O)OR$^a$, —$(CH_2)_m$—OC(=O)NR$^aR^b$, —$(CH_2)_m$—C(=O)NR$^aR^b$, —$(CH_2)_m$—C(=O)NR$^aR^b$, —$(CH_2)_m$—C(=O)NR$^b$(OR$^a$), —$(CH_2)_m$—C(=S)R$^a$, —$(CH_2)_m$—C(=S)OR$^a$, —$(CH_2)_m$—OC(=S)R$^a$, —$(CH_2)_m$—OC(=S)OR$^a$, —$(CH_2)_m$—OC(=S)NR$^aR^b$, —$(CH_2)_m$—C(=S)NR$^aR^b$, —$(CH_2)_m$—SR$^a$, —$(CH_2)_m$—S(=O)R$^a$, —$(CH_2)_m$—S(O$_2$)R$^a$, —$(CH_2)_m$—S(O$_2$)OR$^a$, —$(CH_2)_m$—OS(O$_2$)R$^a$, —$(CH_2)_m$—OS(O$_2$)OR$^a$, —$(CH_2)_m$—NR$^aR^b$, —$(CH_2)_m$—NR$^aC$(=O)R$^a$, —$(CH_2)_m$—NR$^cC$(=O)NR$^aR^b$, —$(CH_2)_m$—NR$^cC$(=O)OR$^a$, —$(CH_2)_m$—NR$^cC$(=S)R$^a$, —$(CH_2)_m$—NR$^cC$(=S)NR$^aR^b$, —$(CH_2)_m$—NR$^cC$(=S)OR$^a$, —$(CH_2)_m$—NR$^cS$(O$_2$)R$^a$, —$(CH_2)_m$—P(=O)(OR$^b$)(OR$^a$), —$(CH_2)_m$—P(=O)(OR$^b$)(R$^a$) or —$(CH_2)_m$—S(O$_2$)NR$^bR^a$, —$(CH_2)_m$—O—C(=O)-(M)—C(=O)OH, —$(CH_2)_m$—O—C(=O)-(M)—C(=O)OR$^a$, —$(CH_2)_m$—O—C(=O)-(M)—R$^a$, —$(CH_2)_m$—O—$(CH_2)_q$—P(=O)(R$^{ba}$)(R$^{aa}$), —$(CH_2)_m$—C(=O)O—$(CH_2)_q$—P(=O)(R$^{ba}$)(R$^{aa}$), —$(CH_2)_m$—C(=O)O—$(CH_2)_q$—S(O$_2$)OH or —$(CH_2)_m$—C(=O)O—$(CH_2)_q$—S(O$_2$)OR$^a$, with R$^{aa}$ being selected independently from each other being —R$^a$ or —OR$^a$, with R$^{ba}$ being selected independently from each other being —R$^b$ or —OR$^b$, with M being a substituted or unsubstituted $C_1$-$C_8$ alkyl, in particular an unsubstituted $C_1$-$C_8$ alkyl with m being selected from 0, 1 or 2, in particular 0 or 1, with q being selected from 0, 1 or 2, in particular 0 or 1, with each R$^a$, R$^b$ or R$^c$ being selected, where applicable, independently from each other from hydrogen,

—CN a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl, or with T being selected from —$(CH_2)_m$—C(=O)O—$(CH_2)_q$—S(O$_2$)OH or —$(CH_2)_m$—C(=O)O—$(CH_2)_q$—S(O$_2$)OR$^a$, —$(CH_2)_m$—O—S(O$_2$)OH, —$(CH_2)_m$—O—S(O$_2$)OR$^a$, in particular —$(CH_2)_m$—O—S(O$_2$)OH, —$(CH_2)_m$—O—S(O$_2$)OR$^a$, with R$^a$ being —$CH_3$, —$CH_2CH_3$, —$C_6H_5$, —$CH_2CH_2CH_3$, —CH$(CH_3)_2$, —$CH_2C_6H_5$ or para-methoxybenzyl —C(=O)—O—R$^a$, —O—C(=O)—R$^a$, in particular —O—C(=O)—R$^a$, with R$^a$ being a substituted or unsubstituted $C_1$-$C_{16}$ alkyl, in particular an unsubstituted $C_1$-$C_{14}$ alkyl, —[$(CH_2)_{m1}$—O—C(=O)—$(CH_2)_{m2}]_{p1}$—C(=O)OR$^d$ or —[$(CH_2)_{m1}$—O—$(CH_2)_{m2}]_{p1}$—OR$^d$, in particular —[$(CH_2)_{m1}$—O—$(CH_2)_{m2}]_{p1}$—OR$^d$ with R$^d$ being —$CH_3$, —$CH_2CH_3$, —$CH_2CH_2CH_3$, —CH$(CH_3)_2$, —$C_6H_5$ m1 and m2 being selected independently from each other form 1, 2 or 3, in particular m1 and m2 are 2, and p1 being selected from 1 to 20, in particular from 1 to 8, —[$(CH_2)_{m1}$—O—$(CH_2)_{m2}]_{p1}$—OR$^d$, in particular —[—O—$(CH_2)_2]_{p1}$—OR$^d$, with R$^d$ being —$CH_3$, —$CH_2CH_3$, —$CH_2CH_2CH_3$, —CH$(CH_3)_2$, —$C_6H_5$ m1 and m2 being selected independently from each other form 1, 2 or 3, in particular m1 and m2 are 2, and p1 being selected from 1 to 20, in particular from 1 to 8, —$(CH_2)_m$—C(=O)O—$(CH_2)_q$—P(=O)(R$^{ba}$)(R$^{aa}$), —$(CH_2)_m$—O—$(CH_2)_q$—P(=O)(R$^{ba}$)(R$^{aa}$), in particular from —$(CH_2)_m$—O—$(CH_2)_q$—P(=O)(R$^{ba}$)(R$^{aa}$), with R$^{aa}$ and R$^{ba}$ being selected, where applicable, independently from each other from —R$^a$ or —OR$^a$ and with $R^a$ being hydrogen, —$OCH_3$, —$OCH_2CH_3$, —$CH_3$, —$CH_2CH_3$, —$C_6H_5$—$CH_2CH_2CH_3$, —$CH(CH_3)_2$, —$CH_2C_6H_5$ or para-methoxybenzyl with m being selected from 0, 1 or 2, in particular 0 or 1, with q being selected from 0, 1 or 2, in particular 0 or 1, or with T being selected from
—$B(OH)_2$, —CN, —$NH_2$, —OH, —$OCH_3$, —C(=O)$NH_2$, —C(=O)NH(CN), —C(=O)NH(OH), —$CH_2$OH, —$CH_2$C(=O)OH, —$CH_2$C(=O)NH(OH), —$CH_2$C(=O)$NH_2$, —$CH_2$NHS($O_2$)OH, —$CH_2$NHC(=O)OH, —P(=O)(OH)(OH), —$CH_2$P(=O)(OH)(OH), —$CH_2$S($O_2$)OH, —S($O_2$)OH or —S($O_2$)$NH_2$ or —$R^a$, —$CH_2R^a$, —$SR^a$, —$CH_2SR^a$, —S(=O)$R^a$, —C(=O)$NHR^a$, —$CH_2$C(=O)$NHR^a$, —$CH_2$NHS($O_2$)$R^a$, —C(=O)$OR^a$, —$OR^a$ or —$NHR^a$, —C(=O)$OR^a$, —$CH_2$C(=O)NH($OR^a$), —C(=O)$NHOR^a$, —C(=O)$NHR^a$, —$CH_2$NHS($O_2$)$R^a$, —($CH_2$)—NHC(=O)$OR^a$, —$CH_2OR^a$, —$CH_2$NHC(=O)$R^a$, —P(=O)(OH)($OR^a$), —$CH_2$P(=O)(OH)($OR^a$), —P(=O)(OH)($R^a$), —$CH_2$P(=O)(OH)($R^a$), —$CH_2$S($O_2$)$OR^a$, —S($O_2$)$OR^a$, —S($O_2$)$R^a$ or —$CH_2$S($O_2$)$R^a$, or —S($O_2$)$NHR^a$, with $R^a$ being selected from
a substituted or unsubstituted $C_1$-$C_{16}$ alkyl, a substituted or unsubstituted $C_1$-$C_{16}$ alkoxy, a substituted or unsubstituted $C_2$-$C_{14}$ alkenyl, a substituted or unsubstituted $C_2$-$C_{14}$ alkynyl, or a $C_1$-$C_{14}$ haloalkyl, in particular a substituted or unsubstituted $C_1$-$C_5$ alkyl, more particularly $R^a$ is —$CH_3$—$CF_3$, —$CH_2CH_3$, —$CH_2CF_3$, —CN, —$CH_2CH_2CH_3$, —$CH(CH_3)_2$, —$CH_2C_6H_5$ or para-methoxybenzy —[($CH_2$)$_{m1}$—O—($CH_2$)$_{m2}$]$_{p1}$—$OR^d$, —[($CH_2$)$_{m1}$—C(=O)O—($CH_2$)$_{m2}$]$_{p1}$—$OR^d$ in particular —[—O—($CH_2$)$_2$]$_{p1}$—$OR^d$, —[—C(=O)O—($CH_2$)$_2$]$_{p1}$—$OR^d$, with
$R^d$ being —$CH_3$, —$CH_2CH_3$, —$CH_2CH_2CH_3$, —$CH(CH_3)_2$, —$C_6H_5$ m1 and m2 being selected independently from each other form 1, 2 or 3, in particular m1 and m2 are 2, and p1 being selected from 1 to 20, in particular from 1 to 8, —$R^a$, —$CH_2R^a$, —$SR^a$, —$CH_2SR^a$, —S(=O)$R^a$, —C(=O)$NHR^a$, —$CH_2$C(=O)$NHR^a$, —$CH_2$NHS($O_2$)$R^a$, —C(=O)$OR^a$, —$OR^a$ or —$NHR^a$, with $R^a$ being
a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl, or
a substituted or unsubstituted $C_6$-$C_{10}$ aryl, or with T being is —C(=O)$OR^a$
with $R^a$ being
a substituted or unsubstituted $C_1$-$C_{16}$ alkyl, in particular an unsubstituted $C_1$-$C_{16}$ alkyl, —[($CH_2$)$_{m1}$—O—($CH_2$)$_{m2}$]$_{p1}$—$OR^d$, —[($CH_2$)$_{m1}$—C(=O)O—($CH_2$)$_{m2}$]$_{p1}$—$OR^d$, in particular —[—O—($CH_2$)$_2$]$_{p1}$—$OR^d$, —[—C(=O)O—($CH_2$)$_2$]$_{p1}$, with
$R^d$ being —$CH_3$, —$CH_2CH_3$, —$CH_2CH_2CH_3$, —$CH(CH_3)_2$, —$C_6H_5$ m1 and m2 being selected independently from each other form 1, 2 or 3, in particular m1 and m2 are 2, and p1 being selected from 1 to 20, in particular from 1 to 8, or T is selected from the following compounds
—$B(OH)_2$, —CN, —OH, —$CH_2OH$, —$CH_2OCH_3$, —$OCH_3$, —C(=O)$NH_2$, —C(=O)NH(CN), —C(=O)OH, —C(=O)NH($CH_3$), —C(=O)NH(OH), —S($O_2$)$NH_2$, —$CH_2$C(=O)OH, —$CH_2$C(=O)NHOH, —$CH_2$—NH—S($O_2$)$CF_3$, —$CH_2$—C(=O)—NH—$OCH_3$, —P(=O)(OH)$_2$, —$CH_2$P(=O)(OH)$_2$, —P(=O)(OH)(O$CH_2CH_3$), —P(=O)(OH)($CH_3$), —$CH_2$P(=O)(OH)($CH_3$), —$CH_2$S($O_2$)(OH), —S($O_2$)(OH),

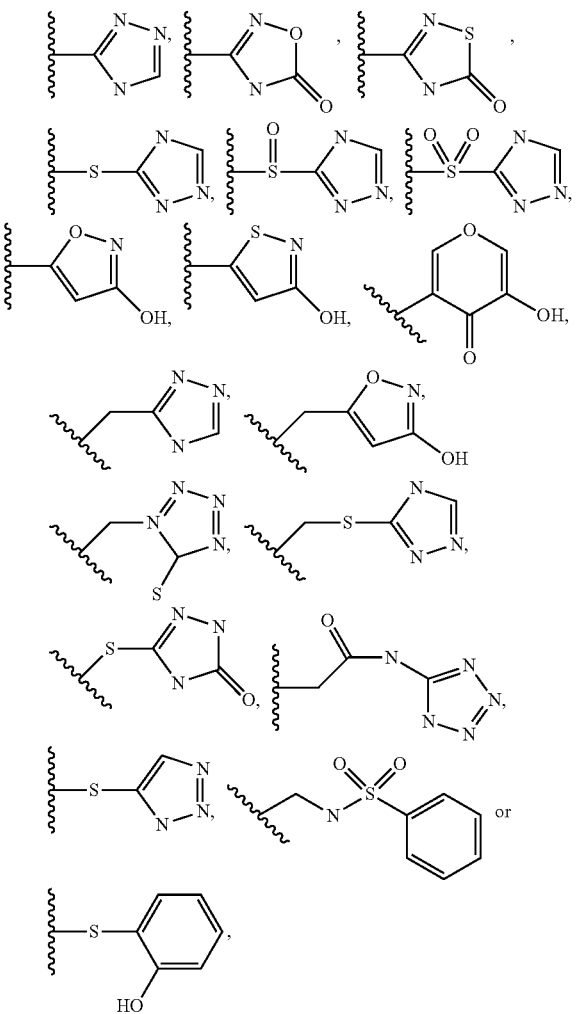

and
d. $R^{10}$ is a substituent Q, with Q being selected from
—($CH_2$)$_m$—C(=O)O—($CH_2$)$_q$—S($O_2$)OH or —($CH_2$)$_m$—C(=O)O—($CH_2$)$_q$—S($O_2$)$OR^a$, —($CH_2$)$_m$—O—S($O_2$)OH, —($CH_2$)$_m$—O—S($O_2$)$OR^a$, in particular —($CH_2$)$_m$—O—S($O_2$)OH, —($CH_2$)$_m$—O—S($O_2$)$OR^a$, with $R^a$ being —$CH_3$, —$CH_2CH_3$, —$C_6H_5$, —$CH_2CH_2CH_3$, —$CH(CH_3)_2$, —$CH_2C_6H_5$ or para-methoxybenzyl
—C(=O)—O—$R^a$, —O—C(=O)—$R^a$, in particular —O—C(=O)—$R^a$, with $R^a$ being a substituted or unsubstituted $C_1$-$C_{16}$ alkyl, in particular an unsubstituted $C_1$-$C_{14}$ alkyl, —[(CH$_2$)$_{m1}$—O—C(=O)—(CH$_2$)$_{m2}$]$_{p1}$—C(=O)OR$^d$ or —[(CH$_2$)$_{m1}$—O—(CH$_2$)$_{m2}$]$_{p1}$—OR$^d$, in particular —[(CH$_2$)$_{m1}$—O—(CH$_2$)$_{m2}$]$_{p1}$—OR$^d$ with
R$^d$ being —CH$_3$, —CH$_2$CH$_3$, —CH$_2$CH$_2$CH$_3$, —CH(CH$_3$)$_2$, —C$_6$H$_5$
m1 and m2 being selected independently from each other form 1, 2 or 3, in particular m1 and m2 are 2, and
p1 being selected from 1 to 20, in particular from 1 to 8,
—[(CH$_2$)$_{m1}$—O—(CH$_2$)$_{m2}$]$_{p1}$—OR$^d$, in particular —[—O—(CH$_2$)$_2$]$_{p1}$—OR$^d$, with
R$^d$ being —CH$_3$, —CH$_2$CH$_3$, —CH$_2$CH$_2$CH$_3$, —CH(CH$_3$)$_2$, —C$_6$H$_5$
m1 and m2 being selected independently from each other form 1, 2 or 3, in particular m1 and m2 are 2, and
p1 being selected from 1 to 20, in particular from 1 to 8,
—(CH$_2$)$_m$—C(=O)O—(CH$_2$)$_q$—P(=O)(R$^{ba}$)(R$^{aa}$), —(CH$_2$)$_m$—O—(CH$_2$)$_q$—P(=O)(R$^{ba}$)(R$^{aa}$), in particular from —(CH$_2$)$_m$—O—(CH$_2$)$_q$—P(=O)(R$^{ba}$)(R$^{aa}$),
with R$^{aa}$ and R$^{ba}$ being selected, where applicable, independently from each other from —R$^a$ or —OR$^a$ and
with R$^a$ being hydrogen, —OCH$_3$, —OCH$_2$CH$_3$, —CH$_3$, —CH$_2$CH$_3$, —C$_6$H$_5$, —CH$_2$CH$_2$CH$_3$, —CH(CH$_3$)$_2$, —CH$_2$C$_6$H$_5$ or para-methoxybenzyl
with m being selected from 0, 1 or 2, in particular 0 or 1,
with q being selected from 0, 1 or 2, in particular 0 or 1,
and, in particular, wherein, each carbon atom of the cyclic system which comprises no substituent R$^{10}$ comprises F instead of H, and
e. with Y being selected from —CN, —C(=O)OH, —C(=O)OCH$_3$, —C(=O)OCH$_2$CH$_3$, —C(=O)NHCH$_3$, —C(=O)NHCH$_2$CH$_3$, —C(=O)N(CH$_3$)$_2$, —C(=O)N(CH$_2$CH$_3$)$_2$, —C(=O)N(CH$_3$)(CH$_2$CH$_3$) or —C(=O)NH$_2$, and
f. with Z being selected from —H, —OH, —CH$_3$, —CH$_2$CH$_3$ or —OCH$_3$, in particular Z is H and Y is CN or —C(=O)NH$_2$.

In some embodiments, the compounds of the invention comprise the following formula (1A)

wherein
Z is —H, —OH, —CH$_3$, —CH$_2$CH$_3$ or —OCH$_3$ and Y is —CN, —C(=O)OH, —C(=O)OCH$_3$, —C(=O)OCH$_2$CH$_3$, —C(=O)NHCH$_3$, —C(=O)NHCH$_2$CH$_3$, —C(=O)N(CH$_3$)$_2$, —C(=O)N(CH$_2$CH$_3$)$_2$, —C(=O)N(CH$_3$)(CH$_2$CH$_3$) or —C(=O)NH$_2$, in particular Z is H and Y is CN and —C(=O)NH$_2$, and more particularly Z is H and Y is CN, and wherein
a. X is
—OH, —F, —Cl, —Br, I, —CCH, —CN, —N$_3$, —NO$_2$, —OCH$_3$, —OCF$_3$, —NH$_2$, —NHCH$_3$, —N(CH$_3$)$_2$, —CH$_3$, —CH$_2$CH$_3$ or —CF$_3$, or
—B(OR$^a$)(OR$^b$), —(CH$_2$)$_m$—R$^a$, —(CH$_2$)$_m$—OR$^a$, —(CH$_2$)$_m$—C(=O)R$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O)NR$^a$R$^b$, —(CH$_2$)$_m$—C(=O)NR$^a$R$^b$, —(CH$_2$)$_m$—C(=O)NR$^b$(OR$^a$), —(CH$_2$)$_m$—NR$^c$C(=O)OR$^a$, —(CH$_2$)$_m$—C(=S)R$^a$, —(CH$_2$)$_m$—C(=S)OR$^a$, —(CH$_2$)$_m$—OC(=S)R$^a$, —(CH$_2$)$_m$—OC(=S)OR$^a$, —(CH$_2$)$_m$—OC(=S)NR$^a$R$^b$, —(CH$_2$)$_m$—C(=S)NR$^a$R$^b$, —(CH$_2$)$_m$—SR$^a$, —(CH$_2$)$_m$—S(=O)R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)NR$^a$R$^b$, —(CH$_2$)$_m$—NR$^c$C(=O)OR$^a$, —(CH$_2$)$_m$—NR$^c$C(=S)R$^a$, —(CH$_2$)$_m$—NR$^c$C(=S)NR$^a$R$^b$, —(CH$_2$)$_m$—NR$^c$C(=S)OR$^a$, —(CH$_2$)$_m$—NR$^c$S(O$_2$)R$^a$, —(CH$_2$)$_m$—P(=O)(OR$^b$)(OR$^a$), —(CH$_2$)$_m$—P(=O)(OR$^b$)(R$^a$) or —(CH$_2$)$_m$—S(O$_2$)NR$^b$R$^a$, —(CH$_2$)$_m$—O—C(=O)-(M)—C(=O)OH, —(CH$_2$)$_m$—O—C(=O)-(M)—C(=O)OR$^a$, —(CH$_2$)$_m$—O—C(=O)-(M)—R$^a$, —(CH$_2$)$_m$—O—(CH$_2$)$_q$—P(=O)(R$^{ba}$)(R$^{aa}$), —(CH$_2$)$_m$—C(=O)O—(CH$_2$)$_q$—P(=O)(R$^{ba}$)(R$^{aa}$), —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$,
with R$^{aa}$ being selected independently from each other from —R$^a$ or —OR$^a$,
with R$^{ba}$ being selected independently from each other from —R$^b$ or —OR$^b$,
with M being a substituted or unsubstituted $C_1$-$C_8$ alkyl, in particular an unsubstituted $C_1$-$C_8$ alkyl,
with m being selected from 0, 1 or 2,
with q being selected from 0, 1 or 2,
with each R$^a$, R$^b$ or R$^c$ being selected, where applicable, independently from each other from hydrogen, —CN,

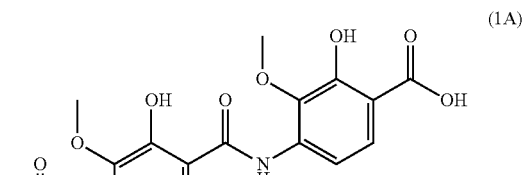

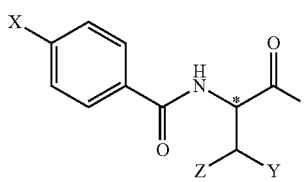

a substituted or unsubstituted C$_3$-C$_{10}$ cycloalkyl or a substituted or unsubstituted C$_3$-C$_{10}$ halo cycloalkyl, or a substituted or unsubstituted C$_6$-C$_{10}$ aryl, a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle, or a substituted or unsubstituted C$_5$-C$_{10}$ heteroaryl, a substituted or unsubstituted C$_1$-C$_{16}$ alkyl, a substituted or unsubstituted C$_1$-C$_{16}$ alkoxy, a substituted or unsubstituted C$_1$-C$_{16}$ carboxy, a substituted or unsubstituted C$_2$-C$_{16}$ alkenyl, a substituted or unsubstituted C$_2$-C$_{16}$ alkynyl, or a C$_1$-C$_{16}$ haloalkyl, in particular a substituted or unsubstituted C$_1$-C$_8$ alkyl, a substituted or unsubstituted C$_2$-C$_8$ alkenyl, a substituted or unsubstituted C$_2$-C$_8$ alkynyl, or a substituted or unsubstituted C$_1$-C$_8$ haloalkyl; or wherein b. X is

with D being a linker which comprises carbon, sulphur, nitrogen and/or oxygen atoms and which is covalently connecting R$^4$ and the parent moiety PM, and with R$^4$ being a substituted or unsubstituted C$_1$-C$_8$ alkyl, a substituted or unsubstituted C$_1$-C$_8$ alkoxy, a substituted or unsubstituted C$_2$-C$_8$ alkenyl, a substituted or unsubstituted C$_2$-C$_8$ alkynyl, or a substituted or unsubstituted C$_1$-C$_8$ haloalkyl, or a substituted or unsubstituted C$_3$-C$_{10}$ cycloalkyl or a substituted or unsubstituted C$_3$-C$_{10}$ halo cycloalkyl, or a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle, or a substituted or unsubstituted C$_5$-C$_{10}$ heteroaryl, or a substituted or unsubstituted C$_6$-C$_{10}$ aryl; or wherein c. X is

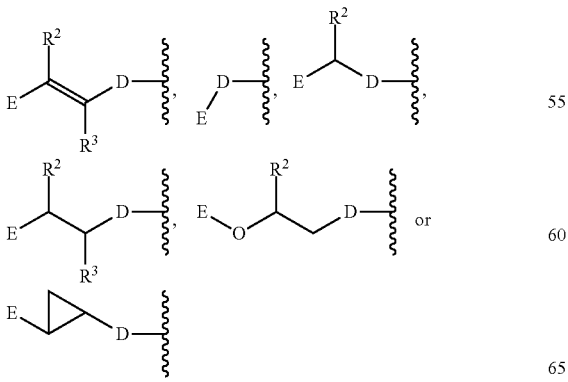

with R$^2$ and R$^3$ being selected, where applicable, independently from each other from —H, —F, —CN, —OH, —NH$_2$, —NO$_2$, —NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl, in particular from —H, —F, —CN, —OH, —NH$_2$, —NO$_2$, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with R$^2$ and R$^3$ being selected independently from each other from H, F or CH$_3$, and with D being a linker which comprises carbon, sulphur, nitrogen and/or oxygen atoms and which is covalently connecting the moiety comprising E and the parent moiety, with E being a substituted or unsubstituted C$_1$-C$_8$ alkyl, a substituted or unsubstituted C$_1$-C$_8$ alkoxy, a substituted or unsubstituted C$_2$-C$_8$ alkenyl, a substituted or unsubstituted C$_2$-C$_8$ alkynyl, or a substituted or unsubstituted C$_1$-C$_8$ haloalkyl, or a substituted or unsubstituted C$_3$-C$_{10}$ cycloalkyl or a substituted or unsubstituted C$_3$-C$_{10}$ halo cycloalkyl, or a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle, or a substituted or unsubstituted C$_5$-C$_{10}$ heteroaryl, or a substituted or unsubstituted C$_8$-C$_{10}$ aryl; or with E being

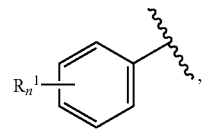

with n of R$^1_n$ being 0, 1, 2, 3, 4 or 5, in particular n of R$^1_n$ being 0, 1, 2, more particularly n being 1, and with each R$^1$ independently from any other R$^1$ being —OH, —F, —Cl, —Br, —I, —CCH, —CN, —N$_3$, —NO$_2$, —OCH$_3$, —OCF$_3$, —NH$_2$, —NHCH$_3$, —N(CH$_3$)$_2$, —CH$_3$, —CH$_2$CH$_3$, —OCONH$_2$ or —CF$_3$, or —B(OR$^a$)(OR$^b$), —(CH$_2$)$_m$—R$^a$, —(CH$_2$)$_m$—OR$^a$, —(CH$_2$)$_m$—C(=O)R$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O)NR$^a$R$^b$, —(CH$_2$)$_m$—C(=O)NR$^a$R$^b$, —(CH$_2$)$_m$—C(=O)NR$^b$(OR$^a$), —(CH$_2$)$_m$—C(=S)R$^a$, —(CH$_2$)$_m$—C(=S)OR$^a$, —(CH$_2$)$_m$—OC(=S)R$^a$, —(CH$_2$)$_m$—OC(=S)OR$^a$, —(CH$_2$)$_m$—OC(=S)NR$^a$R$^b$, —(CH$_2$)$_m$—C(=S)NR$^a$R$^b$, —(CH$_2$)$_m$—SR$^a$, —(CH$_2$)$_m$—S(=O)R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)NR$^a$R$^b$, —(CH$_2$)$_m$—NR$^c$C(=O)OR$^a$, —(CH$_2$)$_m$—NR$^c$C(=S)R$^a$, —(CH$_2$)$_m$—NR$^c$C(=S)NR$^a$R$^b$, —(CH$_2$)$_m$—NR$^c$C(=S)OR$^a$, —(CH$_2$)$_m$—NR$^c$S(O$_2$)R$^a$, —(CH$_2$)$_m$—P(=O)(OR$^b$)(OR$^a$), —(CH$_2$)$_m$—P $(=O)(OR^b)(R^a)$ or $-(CH_2)_m-S(O_2)NR^bR^a$,
$-(CH_2)_m-O-C(=O)-(M)-C(=O)OH$,
$-(CH_2)_m-O-C(=O)-(M)-C(=O)OR^a$,
$-(CH_2)_m-O-C(=O)-(M)-R^a$, $-(CH_2)_m-O-(CH_2)_q-P(=O)(R^{ba})(R^{aa})$, $-(CH_2)_m-C(=O)O-(CH_2)_q-P(=O)(R^{ba})(R^{aa})$, $-(CH_2)_m-C(=O)O-(CH_2)_q-S(O_2)OH$ or $-(CH_2)_m-C(=O)O-(CH_2)_q-S(O_2)OR^a$, with $R^{aa}$ being selected independently from each other from $-R^a$ or $-OR^a$, with $R^{ba}$ being selected independently from each other from $-R^b$ or $-OR^b$, with M being a substituted or unsubstituted $C_1$-$C_8$ alkyl, in particular an unsubstituted $C_1$-$C_8$ alkyl, with m being selected from 0, 1 or 2, with q being selected from 0, 1 or 2, with each $R^a$, $R^b$ or $R^c$ being selected, where applicable, independently from each other from hydrogen, —CN, a substituted or unsubstituted $C_3$-$C_{10}$ cycloalkyl or a substituted or unsubstituted $C_3$-$C_{10}$ halo cycloalkyl, or a substituted or unsubstituted $C_6$-$C_{10}$ aryl, a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl; or with E being selected from

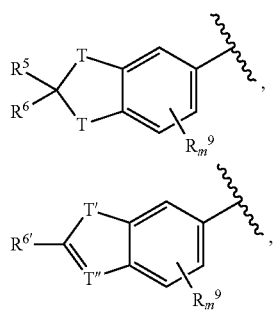

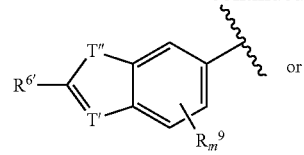

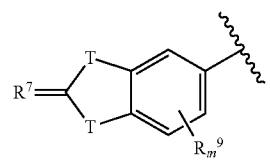

with each T being selected independently from each other from $-CH_2$, $-NH$, $-S$ or $-O$, $-CHCH_3$, $-C(CH_3)_2$ or $-NR^c$, with $R^c$ being $-OH$, $-CH_3$, $-CH_2CH_3$, $-CH_2CH_2CH_3$, $-CH(CH_3)_2$, and with T' being selected from $-CH_2$, $-NH$, $-S$ or $-O$, $-CHCH_3$, $-C(CH_3)_2$ or $-NR^c$, and with T" being selected from $-CH$ or $=N$, and with $R^5$ and $R^6$ being selected independently from each other from $-H$, $-F$, $-CH_3$, $-CH_2CH_3$, $-OCH_3$, $-CH_2CF_3$, $-CHFCF_3$, $-CF_2CF_3$, $-CHF_2$, $-CH_2F$ or $-CF_3$, in particular with $R^5$ and $R^6$ being selected independently from each other from H, $-F$ or $-CH_3$, and with $R^{6'}$ being selected from OH, $-OCH_3$, $-OCH_2CH_3$, $-CH_3$, with $R^7$ being selected from $=NH$, $=S$ or $=O$, and with m of $R^9_m$ being selected from 0, 1, 2 or 3, and each $R^9$ being selected independently from each other from $-Cl$, $-F$, Br, I, $-OH$, $-CCH$, $-CN$, $-CH_3$, $-CH_2CH_3$, $-OCH_3$, $-COOH$, $-COOR^b$, $-C(O)NH_2$, $-C(O)NH(CH_3)$; $-C(O)N(CH_3)_2$, $-NHC(=O)OCH_3$, $-NCH_3C(=O)OCH_3$, $-CH_2CF_3$, $-CHFCF_3$, $-CF_2CF_3$, $-CHF_2$, $-CH_2F$ or $-CF_3$, with $R^b$ being a substituted or unsubstituted $C_1$-$C_5$ alkyl, a substituted or unsubstituted $C_2$-$C_5$ alkenyl, a substituted or unsubstituted $C_2$-$C_5$ alkynyl, or a $C_1$-$C_5$ haloalkyl, wherein \* indicates a stereo center of a L- or D-enantiomer, which is located on the tertiary carbon atom below the asterisk \*, and wherein the compound of the general formula 1 is an essentially pure L-enantiomer, an essentially pure D-enantiomer or a mixture of the L- and D-enantiomer of the same molecular formula.

In some embodiments, the compounds of the invention are characterized by the formula 1L

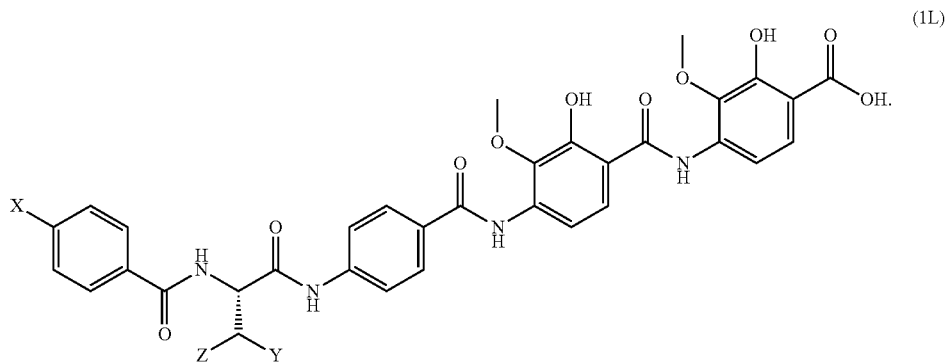

(1L)

In some embodiments, the compounds of the invention are characterized by the formula 1D

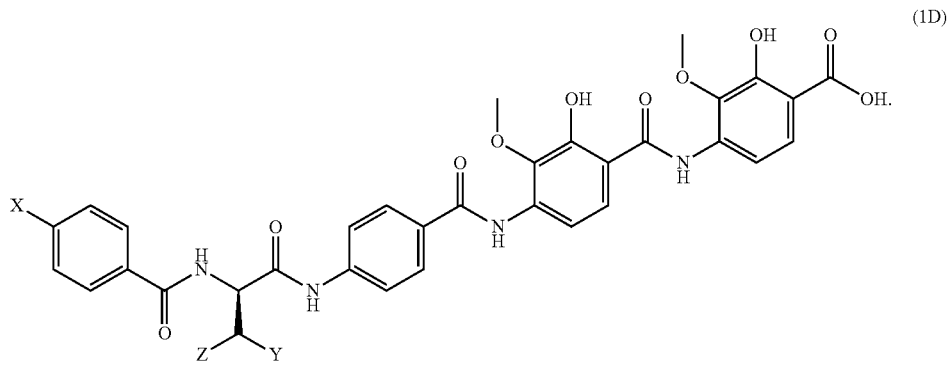

(1D)

In some embodiments, the compounds of the invention relates to a mixture of the L- and D-enantiomer of the same molecular formula.

In some embodiments, Z of the general formula 1 is —H, —OH, —CH$_3$, —CH$_2$CH$_3$ or —OCH$_3$ and Y is —CN, —C(=O)OH, —C(=O)OCH$_3$, —C(=O)OCH$_2$CH$_3$, —C(=O)NHCH$_3$, —C(=O)NHCH$_2$CH$_3$, —C(=O)N(CH$_3$)$_2$, —C(=O)N(CH$_2$CH$_3$)$_2$, —C(=O)N(CH$_3$)(CH$_2$CH$_3$) or —C(=O)NH$_2$.

In some embodiments, Z of the general formula 1 is —H and Y is CN or —C(=O)NH$_2$.

In some embodiments, Z of the general formula 1 is —H and Y is —CN.

In some embodiments, the compounds of the invention are characterized by a general formula 1,
with X being
—H, —OH, —F, —Cl, —Br, I, —NH$_2$, —CN, —COOH, —N$_3$ or —NO$_2$, or
—NR$^a$$_2$, —NHR$^a$, —R$^a$, —C(=O)R$^a$, —C(=O)OR$^a$, —OR$^a$, —OC(=O)R$^a$—OC(=O)OR$^a$, —OC(=O)NHR$^a$, —NHC(=O)R$^a$, —NHC(=O)NHR$^a$, —C(=O)NHR$^a$, —NHC(=O)OR$^a$, —C(=S)R$^a$, —C(=S)OR$^a$, —SR$^a$, —OC(=S)R$^a$, —OC(=S)OR$^a$, —OC(=S)NHR$^a$, —NHC(=S)R$^a$, —NHC(=S)NHR$^a$, —C(=S)NHR$^a$ or —NHC(=S)OR$^a$,
with R$^a$ being a substituted or unsubstituted C$_1$-C$_8$ alkyl, a substituted or unsubstituted C$_2$-C$_8$ alkenyl, a substituted or unsubstituted C$_2$-C$_8$ alkynyl, or a substituted or unsubstituted C$_1$-C$_8$ haloalkyl, or
a substituted or unsubstituted C$_3$-C$_{10}$ cycloalkyl or a substituted or unsubstituted C$_3$-C$_{10}$ halo cycloalkyl, or
a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle, or
a substituted or unsubstituted C$_5$-C$_{10}$ heteroaryl, or
a substituted or unsubstituted C$_6$-C$_{10}$ aryl, wherein
Z is —H, —OH, —CH$_3$, —CH$_2$CH$_3$ or —OCH$_3$ and Y is —CN, —C(=O)OH, —C(=O)OCH$_3$, —C(=O)OCH$_2$CH$_3$, —C(=O)NHCH$_3$, —C(=O)NHCH$_2$CH$_3$, —C(=O)N(CH$_3$)$_2$, —C(=O)N(CH$_2$CH$_3$)$_2$, —C(=O)N(CH$_3$)(CH$_2$CH$_3$) or —C(=O)NH$_2$, in particular Z is H and Y is CN and —C(=O)NH$_2$, more particularly Z is H and Y is CN.

In some embodiments, the compounds of the invention are characterized by a general formula 1A,
with X being
—H, —OH, —F, —Cl, —Br, I, —NH$_2$, —CN, —COOH, —N$_3$ or —NO$_2$, or
—NR$^a$$_2$, —NHR$^a$, —R$^a$, —C(=O)R$^a$, —C(=O)OR$^a$, —OR$^a$ or —OC(=O)R$^a$
with R$^a$ being a substituted or unsubstituted C$_1$-C$_8$ alkyl, a substituted or unsubstituted C$_2$-C$_8$ alkenyl, a substituted or unsubstituted C$_2$-C$_8$ alkynyl, or a substituted or unsubstituted C$_1$-C$_8$ haloalkyl, or
a substituted or unsubstituted C$_3$-C$_{10}$ cycloalkyl or a substituted or unsubstituted C$_3$-C$_{10}$ halo cycloalkyl, or
a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle, or a substituted or unsubstituted $C_5$-$C_{10}$ heteroaryl, wherein
Z is —H, —OH, —$CH_3$, —$CH_2CH_3$ or —$OCH_3$ and Y is —CN, —C(═O)OH, —C(═O)$OCH_3$, —C(═O)$OCH_2CH_3$, —C(═O)$NHCH_3$, —C(═O)$NHCH_2CH_3$, —C(═O)$N(CH_3)_2$, —C(═O)$N(CH_2CH_3)_2$, —C(═O)N($CH_3$)($CH_2CH_3$) or —C(═O)$NH_2$, in particular Z is H and Y is CN and —C(═O)$NH_2$, more particularly Z is H and Y is CN.

In some embodiments, X of the general formula 1A is —$NR^a_2$, —$NHR^a$ —C(═O)$OR^a$ or —$OR^a$,
  with $R^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or
  a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
  a substituted or unsubstituted $C_5$-$C_{10}$ heteroaryl, in particular a substituted or unsubstituted 1,2,3-triazole, a substituted or unsubstituted 1.2.4-triazole, a substituted or unsubstituted indole, a substituted or unsubstituted isoindole, a substituted or unsubstituted quinoline or a substituted or unsubstituted isoquinoline, wherein
Z is —H, —OH, —$CH_3$, —$CH_2CH_3$ or —$OCH_3$ and Y is —CN, —C(═O)OH, —C(═O)$OCH_3$, —C(═O)$OCH_2CH_3$, —C(═O)$NHCH_3$, —C(═O)$NHCH_2CH_3$, —C(═O)$N(CH_3)_2$, —C(═O)$N(CH_2CH_3)_2$, —C(═O)N($CH_3$)($CH_2CH_3$) or —C(═O)$NH_2$, in particular Z is H and Y is CN and —C(═O)$NH_2$, more particularly Z is H and Y is CN.

In some embodiments, X of the general formula 1A is —$NR^a_2$, —$NHR^a$ or —C(═O)$OR^a$, in particular X is —$NR^a_2$ or —$NHR^a$,
  with $R^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, wherein
Z is —H, —OH, —$CH_3$, —$CH_2CH_3$ or —$OCH_3$ and Y is —CN, —C(═O)OH, —C(═O)$OCH_3$, —C(═O)$OCH_2CH_3$, —C(═O)$NHCH_3$, —C(═O)$NHCH_2CH_3$, —C(═O)$N(CH_3)_2$, —C(═O)$N(CH_2CH_3)_2$, —C(═O)N($CH_3$)($CH_2CH_3$) or —C(═O)$NH_2$, in particular Z is H and Y is CN and —C(═O)$NH_2$, more particularly Z is H and Y is CN.

In some embodiments, the compound of the general formula 1 is an essentially pure L-enantiomer, an essentially pure D-enantiomer or a mixture of the L- and D-enantiomer of the same molecular formula, wherein in particular the compound of the general formula 1 is an essentially pure L-enantiomer or an essentially pure D-enantiomer, more particularly an essentially pure L-enantiomer.

In some embodiments, the compound of the invention is characterized by the formula 1, wherein
Z is —H, —OH, —$CH_3$, —$CH_2CH_3$ or —$OCH_3$ and Y is —CN, —C(═O)OH, —C(═O)$OCH_3$, —C(═O)$OCH_2CH_3$, —C(═O)$NHCH_3$, —C(═O)$NHCH_2CH_3$, —C(═O)$N(CH_3)_2$, —C(═O)$N(CH_2CH_3)_2$, —C(═O)N($CH_3$)($CH_2CH_3$) or —C(═O)$NH_2$, in particular Z is H and Y is CN and —C(═O)$NH_2$, and wherein
the compound of the general formula 1A is an essentially pure L-enantiomer, an essentially pure D-enantiomer or a mixture of the L- and D-enantiomer of the same molecular formula, and wherein X is

with D being a linker which comprises carbon, sulphur, nitrogen and/or oxygen atoms and which is covalently connecting $R^4$ and the parent moiety PM, and
with $R^4$ being
  a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or
  a substituted or unsubstituted $C_3$-$C_{10}$ cycloalkyl or a substituted or unsubstituted $C_3$-$C_{10}$ halo cycloalkyl, or
  a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
  a substituted or unsubstituted $C_5$-$C_{10}$ heteroaryl, or
  a substituted or unsubstituted $C_6$-$C_{10}$ aryl; or wherein
X is

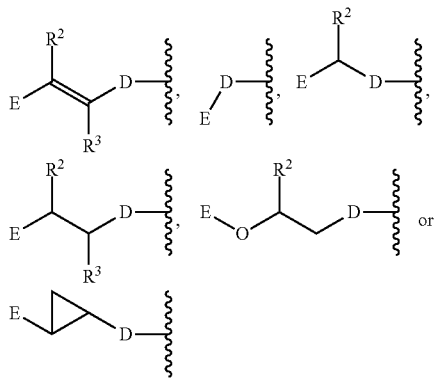

with $R^2$ and $R^3$ being selected, where applicable, independently from each other from —H, —F, —CN, —OH, —$NH_2$, —$NO_2$, —$NHCH_3$, —$NH(CH_3)_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —$NH_2$, —$NO_2$, —$NHCH_3$, —$NH(CH_3)_2$, —$CH_3$, —$CH_2CH_3$, —$OCH_3$, —$OCH_2CH_3$, —$OCH_2CH_2CH_3$, —OCH($CH_3$)$_2$, —$OCF_3$, —$CH_2CF_3$, —$CHFCF_3$, —$CF_2CF_3$, —$CHF_2$, —$CH_2F$ or —$CF_3$, more particularly with $R^2$ and $R^3$ being selected independently from each other from H, F or $CH_3$, and
with D being a linker which comprises carbon, sulphur, nitrogen and/or oxygen atoms and which is covalently connecting the moiety comprising E and the parent moiety PM,
with E being
  a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_8$-$C_{10}$ aryl; or with E being

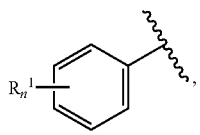

—OH, —F, —Cl, —Br, I, —CCH, —CN, —$N_3$, —$NO_2$, —$OCH_3$, —$OCF_3$, —$NH_2$, —$NHCH_3$, —$N(CH_3)_2$, —$CH_3$, —$CH_2CH_3$, —$OCONH_2$ or —$CF_3$, or

—B($OR^a$)($OR^b$), —$(CH_2)_m$—$R^a$, —$(CH_2)_m$—$OR^a$, —$(CH_2)_m$—C(=O)$R^a$, —$(CH_2)_m$—C(=O)$OR^a$, —$(CH_2)_m$—OC(=O)$R^a$, —$(CH_2)_m$—OC(=O)$OR^a$, —$(CH_2)_m$—OC(=O)$NR^aR^b$, —$(CH_2)_m$—C(=O)$NR^aR^b$, —$(CH_2)_m$—C(=O)$NR^aR^b$, —$(CH_2)_m$—C(=O)$NR^b(OR^a)$, —$(CH_2)_m$—C(=S)$R^a$, —$(CH_2)_m$—C(=S)$OR^a$, —$(CH_2)_m$—OC(=S)$R^a$, —$(CH_2)_m$—OC(=S)$OR^a$, —$(CH_2)_m$—OC(=S)$NR^aR^b$, —$(CH_2)_m$—C(=S)$NR^aR^b$, —$(CH_2)_m$—$SR^a$, —$(CH_2)_m$—S(=O)$R^a$, —$(CH_2)_m$—$S(O_2)R^a$, —$(CH_2)_m$—$S(O_2)OR^a$, —$(CH_2)_m$—$OS(O_2)R^a$, —$(CH_2)_m$—$OS(O_2)OR^a$, —$(CH_2)_m$—$NR^aR^b$, —$(CH_2)_m$—$NR^cC(=O)R^a$, —$(CH_2)_m$—$NR^cC(=O)NR^aR^b$, —$(CH_2)_m$—$NR^cC(=O)OR^a$, —$(CH_2)_m$—$NR^cC(=S)R^a$, —$(CH_2)_m$—$NR^cC(=S)NR^aR^b$, —$(CH_2)_m$—$NR^cC(=S)OR^a$, —$(CH_2)_m$—$NR^cS(O_2)R^a$, —$(CH_2)_m$—P(=O)($OR^b$)($OR^a$), —$(CH_2)_m$—P(=O)($OR^b$)($R^a$) or —$(CH_2)_m$—$S(O_2)NR^bR^a$, —$(CH_2)_m$—O—C(=O)-(M)—C(=O)OH, —$(CH_2)_m$—O—C(=O)-(M)—C(=O)$OR^a$, —$(CH_2)_m$—O—C(=O)-(M)—$R^a$, —$(CH_2)_m$—O—$(CH_2)_q$—P(=O)($R^{ba}$)($R^{aa}$), —$(CH_2)_m$—C(=O)O—$(CH_2)_q$—P(=O)($R^{ba}$)($R^{aa}$), —$(CH_2)_m$—C(=O)O—$(CH_2)_q$—$S(O_2)OH$ or —$(CH_2)_m$—C(=O)O—$(CH_2)_q$—$S(O_2)OR^a$, with $R^{aa}$ being selected independently from each other from —$R^a$ or —$OR^a$, with $R^{ba}$ being selected independently from each other from —$R^b$ or —$OR^b$, with M being a substituted or unsubstituted $C_1$-$C_8$ alkyl, in particular an unsubstituted $C_1$-$C_8$ alkyl, with m being selected from 0, 1 or 2, with q being selected from 0, 1 or 2, with each $R^a$, $R^b$ or $R^c$ being selected, where applicable, independently from each other from hydrogen, —CN, a substituted or unsubstituted $C_3$-$C_{10}$ cycloalkyl or a substituted or unsubstituted $C_3$-$C_{10}$ halo cycloalkyl, or a substituted or unsubstituted $C_6$-$C_{10}$ aryl, a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl;

with E being

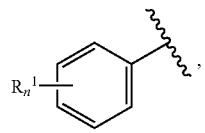

with n of $R^1_n$ being 0, 1, 2, 3, 4 or 5, in particular n of $R^1_n$ being 0, 1 or 2, more particularly n being 1, and with each $R^1$ independently from any other $R^1$ being —OH, —F, —Cl, —Br, I, CCH, —CN, —$N_3$, —$OCH_3$, —$OCF_3$, —$NH_2$, —$CH_3$, —$CF_3$, —$OCONH_2$ or —$NO_2$, or —$NR^a_2$, —$NHR^a$, —$R^a$, —C(=O)$R^a$, —C(=O)$OR^a$, $OR^a$, —OC(=O)$R^a$, —OC(=O)$OR^a$, —OC(=O)$NHR^a$, —NHC(=O)$R^a$, —NHC(=O)$NHR^a$, —C(=O)$NHR^a$ or —NHC(=O)$OR^a$, with $R^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl, or with E being

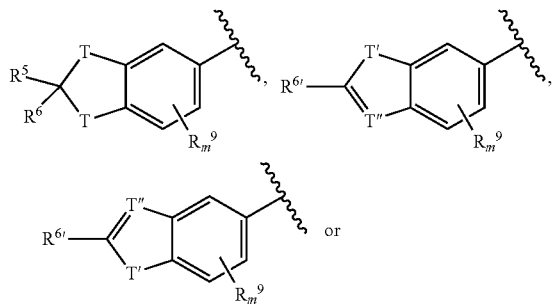

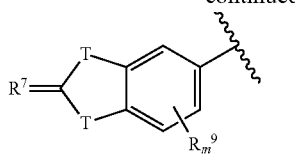

with each T being selected independently from each other from —CH$_2$, —NH, —S or —O, —CHCH$_3$, —C(CH$_3$)$_2$ or —NR$^c$,
  with R$^c$ being —OH, —CH$_3$, —CH$_2$CH$_3$, —CH$_2$CH$_2$CH$_3$, —CH(CH$_3$)$_2$, and
with T' being selected from —CH$_2$, —NH, —S or —O, —CHCH$_3$, —C(CH$_3$)$_2$ or —NR$^c$, and
with T" being selected from —CH or =N, and
with R$^5$ and R$^6$ being selected independently from each other from —H, —F, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular with R$^5$ and R$^6$ being selected independently from each other from H, —F or —CH$_3$, and
with R$^{6\prime}$ being selected from —OH, —OCH$_3$, —OCH$_2$CH$_3$, —CH$_3$,
with R$^7$ being selected from =NH, =S or =O, and
with m of R$^9_m$ being selected from 0, 1, 2 or 3, and each R$^9$ being selected independently from each other from —OH, —F, —Br, —I, —OH, —CCH, —CN—CH$_3$, —CH$_2$CH$_3$, —OCH$_3$, —COOH, —COOR$^b$, —C(O)NH$_2$, —C(O)NH(CH$_3$); —C(O)N(CH$_3$)$_2$, —NHC(=O)OCH$_3$, —NCH$_3$C(=O)OCH$_3$, —CH$_2$CF$_3$, —CHFCF$_3$, —CF$_2$CF$_3$, —CHF$_2$, —CH$_2$F or —CF$_3$,
with R$^b$ being a substituted or unsubstituted C$_1$-C$_5$ alkyl, a substituted or unsubstituted C$_2$-C$_5$ alkenyl, a substituted or unsubstituted C$_2$-C$_5$ alkynyl, or a C$_1$-C$_5$ haloalkyl.

In some embodiments, D of the general formula 1A is selected from

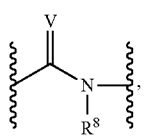
(D1)

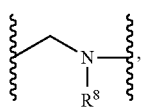
(D2)

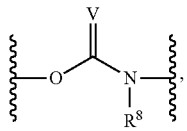
(D3)

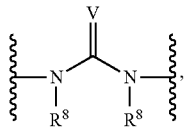
(D4)

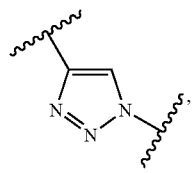
(D5)

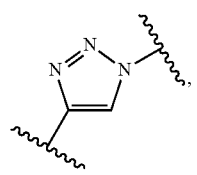
(D6)

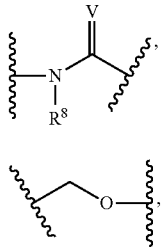
(D7)

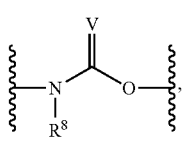
(D8)

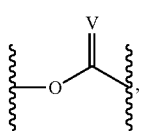
(D9)

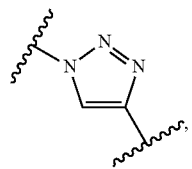
(D10)

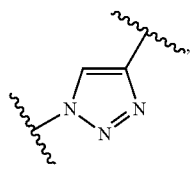
(D11)

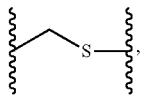
(D12)

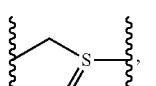
(D13)

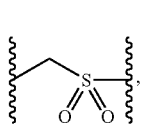
(D13')

(D13")

-continued

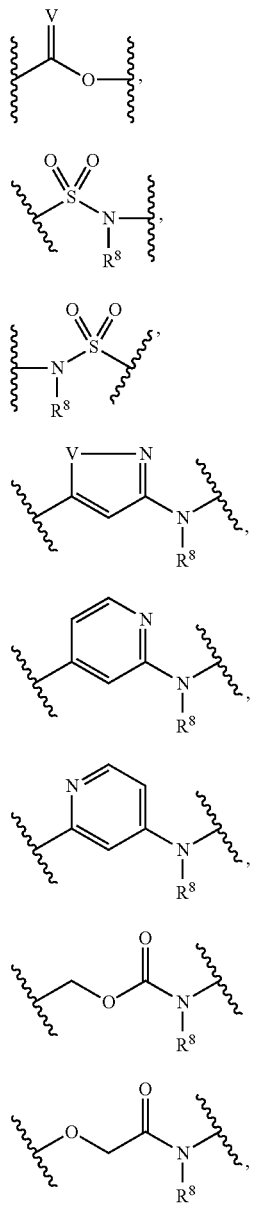

with each R[8] being —H, or, where applicable, with each R[8] being selected independently from each other from —H, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular each R[8] is selected independently from each other from H or CH$_3$, and with V being, where applicable, S, NH or O, in particular V being O.

In some embodiments, D of the general formula 1A is selected from

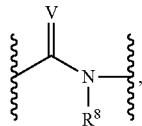

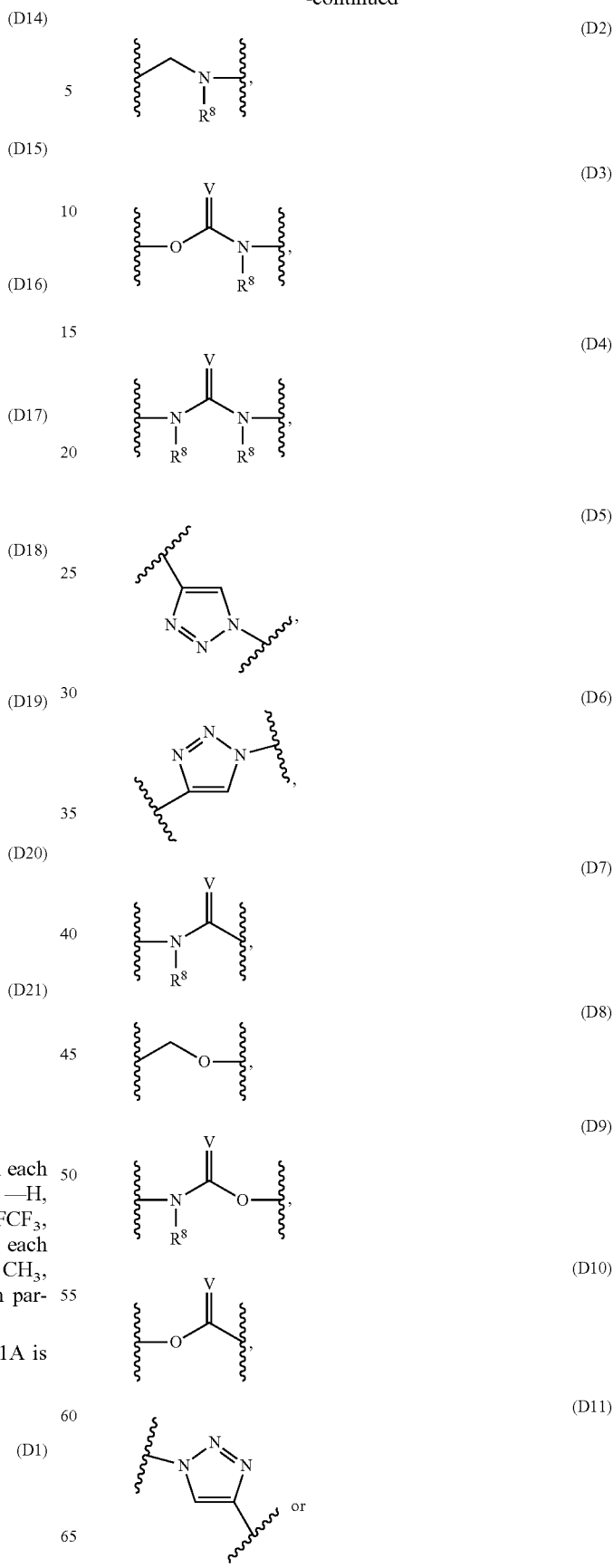

(D12)

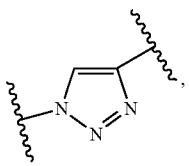

with each $R^8$ being —H, or, where applicable, with each $R^8$ being selected independently from each other from —H, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular each $R^8$ is selected independently from each other from H or CH$_3$, more particularly $R^8$ is —H, and with V being, where applicable, S, NH or O, in particular V being O.

In some embodiments, D of the general formula 1A is selected from (D1)

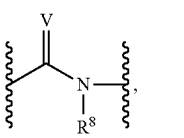

(D2)

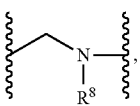

(D3)

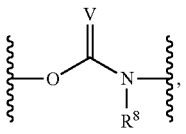

(D4)

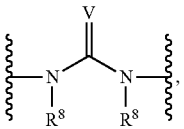

(D5)

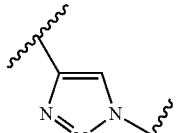  or (D6)

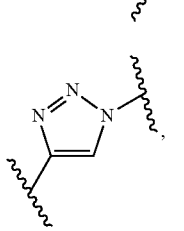

with each $R^8$ being —H, or, where applicable, with each $R^8$ being selected independently from each other from —H, —CH$_3$, —CH$_2$CH$_3$, —OCF$_3$, —CH$_2$CF$_3$, —CHFCF$_3$, —CF$_2$CF$_3$, —CHF$_2$, —CH$_2$F or —CF$_3$, in particular each $R^8$ is selected independently from each other from H or CH$_3$, more particularly $R^8$ is —H, and with V being, where applicable, S, NH or O, in particular V being O.

In some embodiments, D of the general formula 1A is selected from (D1)

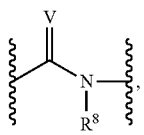

(D2)

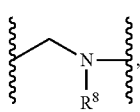

(D3)

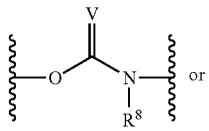 or (D4)

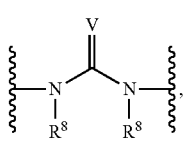

with each $R^8$ being —H, or, where applicable, with each $R^8$ being selected independently from each other from —H, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular each $R^8$ is selected independently from each other from H or CH$_3$, more particularly $R^8$ is —H, and with V being, where applicable, S, NH or O, in particular V being O.

In some embodiments, $R^4$ of the general formula 1A is a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, or a substituted or unsubstituted $C_1$-$C_8$ haloalkyl; or a substituted or unsubstituted $C_3$-$C_{10}$ cycloalkyl or a substituted or unsubstituted $C_3$-$C_{10}$ halo cycloalkyl; or a substituted or unsubstituted $C_3$-$C_{10}$ heterocycle or a substituted or unsubstituted $C_3$-$C_{10}$ halo heterocycle; in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl; or a substituted or unsubstituted $C_6$-$C_{10}$ aryl.

In some embodiments, $R^4$ of the general formula 1A is a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl.

In some embodiments, $R^4$ of the general formula 1A is a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a $C_1$-$C_8$ haloalkyl, a substituted or unsubstituted $C_3$-$C_{10}$ cycloalkyl, or a substituted or unsubstituted $C_3$-$C_{10}$ halo cycloalkyl, or In some embodiments, $R^4$ of the general formula 1A is
a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the D moiety, or a substituted or unsubstituted $C_5$-$C_6$ heteroaryl, a substituted $C_6$ aryl, in particular a bicyclic $C_6$ aryl such as tetralin or indane, a substituted or unsubstituted halo heteroaryl comprising one or two halogen atoms selected from Cl of F, particularly comprising one Cl or one F in para position (in case of a $C_6$ halo heteroaryl) in relation to the attachment position of the heterocycle to the D moiety; or $R^4$ is selected from the group of substituted or unsubstituted pyrrole, furan, thiophene, benzothiophene, chromene, thiazole, pyrazine, pyridazine, pyridine, 1,2,3-triazole, 1,2,4-triazole, imidazole, oxazol, thiazol, indole, isoindole, quinoline, isoquinoline, naphatalene, coumarin, aminocoumarin, umbelliferon, benzotriazole, psoralen, benzofurane, benzothiophene, benzimidazol, benzthiazole, benzoxazole or benzpyridazin or hydroxylated, methylated or halogenated derivatives thereof.

In some embodiments, $R^4$ of the general formula 1A is selected from

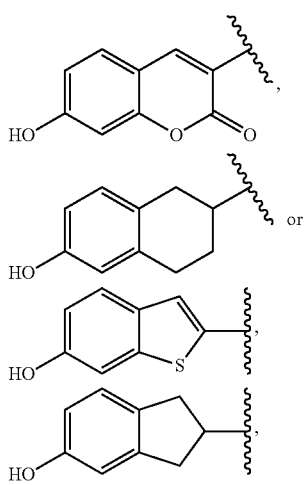

In some embodiments, $R^4$ of the general formula 1A is
a substituted or unsubstituted $C_1$-$C_5$ alkyl or a substituted or unsubstituted $C_6$-$C_{10}$ cycloalkyl, a substituted or unsubstituted $C_5$-$C_{10}$ heteroaryl or a substituted or unsubstituted $C_6$-$C_{10}$ aryl.

In some embodiments, $R^4$ of the general formula 1A is a straight or branched $C_1$-$C_5$ alkyl or a $C_6$-$C_{10}$ cycloalkyl ring or polyring structure In some embodiments, X of the general formula 1A is

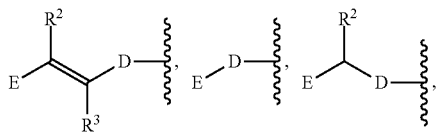

-continued

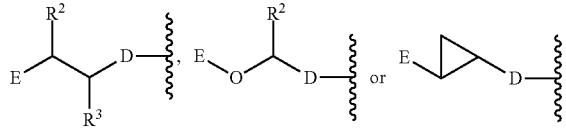

with $R^2$ and $R^3$ being selected, where applicable, independently from each other from —H, —F, —CN, —OH, —NH$_2$, —NO$_2$, —NHCH$_3$, —NH(CH$_3$)$_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —NH$_2$, —NO$_2$, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with $R^2$ and $R^3$ being selected independently from each other from H, F or CH$_3$.

It is understood that a general expert will identify—on basis of his basic knowledge -combinations of the above mentioned selection, which will not lead to stable compounds. For example, the first mentioned structure will lead to stable compounds if $R^2$ or $R^3$ are selected from —H or —CH$_3$ but not if they are chosen from —OH or NH$_2$. However, the third mentioned structure will lead to stable compounds if $R^2$ is —OH or NH$_2$.

In some embodiments, X of the general formula 1A is

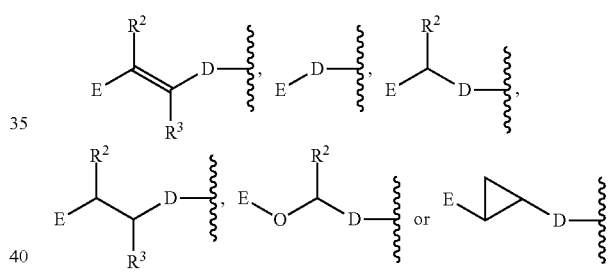

with $R^2$ and $R^3$ being selected independently from each other from H or CH$_3$, in particular with $R^2$ being H and $R^3$ being CH$_3$ or $R^2$ being H and $R^3$ being H.

In some embodiments, E of the general formula 1A is
a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_8$-$C_{10}$ aryl.

In some embodiments, E of the general formula 1A is
a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a $C_1$-$C_8$ haloalkyl, a substituted or unsubstituted $C_3$-$C_{10}$ cycloalkyl, or a substituted or unsubstituted $C_3$-$C_{10}$ halo cycloalkyl, or In some embodiments, E of the general formula 1A is
a substituted or unsubstituted $C_1$-$C_5$ alkyl, a substituted or unsubstituted $C_6$-$C_{10}$ cycloalkyl, or a substituted or unsubstituted $C_5$-$C_{10}$ heteroaryl or a substituted or unsubstituted $C_8$-$C_{10}$ aryl, or In some embodiments, E of the general formula 1A is
a substituted or unsubstituted $C_3$-$C_{10}$ heterocycle or $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl, or
a substituted or unsubstituted $C_6$-$C_{10}$ aryl.

In some embodiments, E of the general formula 1A is
a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the D moiety, or
a substituted or unsubstituted $C_5$-$C_6$ heteroaryl,
a substituted or unsubstituted $C_5$-$C_6$ halo heteroaryl comprising one or two halogen atoms selected from Cl of F, particularly comprising one Cl or one F in para position in relation to the attachment position of the heteroaryl to the D moiety; or
E is selected from the group of substituted or unsubstituted pyrrole, furan, thiophene, benzothiophene, chromene, thiazole, pyrazine, pyridazine, pyridine, 1,2,3-triazole, 1,2,4-triazole, imidazole, oxazol, thiazol, indole, isoindole, quinoline, isoquinoline, naphatalene, coumarin, aminocoumarin, umbelliferon, benzotriazole, psoralen, benzofurane, benzothiophene, benzimidazol, benzthiazole, benzoxazole or benzpyridazin or hydroxylated, methylated or halogenated derivatives thereof, or
E is selected from.

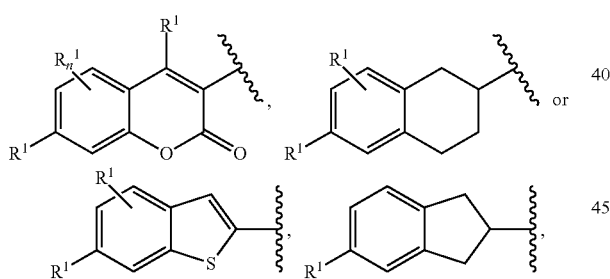

in particular from

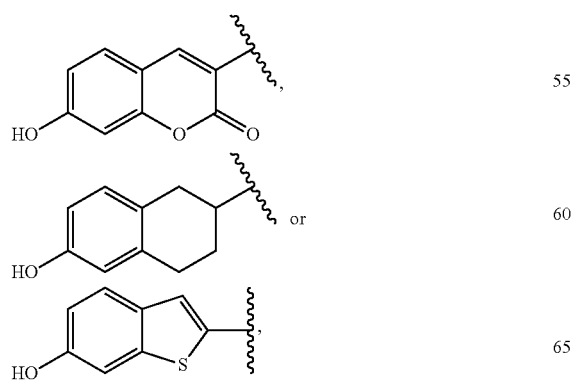

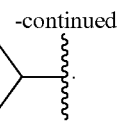

with n of $R^1_n$ being 0, 1, 2, 3, 4 or 5, in particular n of $R^1_n$ being 0, 1, 2 or 3, more particularly n of $R^1_n$ being 1, and with each $R^1$ independently from any other $R^1$ being selected from
—OH, —F, —Cl, —Br, I, —CCH, —CN, —$N_3$, —$OCH_3$, —$OCF_3$, —$NH_2$, —$NHCH_3$, —$N(CH_3)_2$, —$CH_3$, —$CH_2$—$CH_3$, —$CF_3$, —$OCONH_2$ or —$NO_2$,
—$B(OR^a)(OR^b)$, —$(CH_2)_m$—$R^a$, —$(CH_2)_m$—$OR^a$, —$(CH_2)_m$—$C(=O)R^a$, —$(CH_2)_m$—$C(=O)OR^a$, —$(CH_2)_m$—$OC(=O)R^a$, —$(CH_2)_m$—$OC(=O)OR^a$, —$(CH_2)_m$—$OC(=O)NR^aR^b$, —$(CH_2)_m$—$C(=O)NR^aR^b$, —$(CH_2)_m$—$C(=O)NR^aR^b$, —$(CH_2)_m$—$C(=O)NR^b(OR^a)$, —$(CH_2)_m$—$C(=S)R^a$, —$(CH_2)_m$—$C(=S)OR^a$, —$(CH_2)_m$—$OC(=S)R^a$, —$(CH_2)_m$—$OC(=S)OR^a$, —$(CH_2)_m$—$OC(=S)NR^aR^b$, —$(CH_2)_m$—$C(=S)NR^aR^b$, —$(CH_2)_m$—$SR^a$, —$(CH_2)_m$—$S(=O)R^a$, —$(CH_2)_m$—$S(O_2)R^a$, —$(CH_2)_m$—$S(O_2)OR^a$, —$(CH_2)_m$—$OS(O_2)R^a$, —$(CH_2)_m$—$OS(O_2)OR^a$, —$(CH_2)_m$—$NR^aR^b$, —$(CH_2)_m$—$NR^cC(=O)OR^a$, —$(CH_2)_m$—$NR^cC(=O)R^a$, —$(CH_2)_m$—$NR^cC(=O)NR^aR^b$, —$(CH_2)_m$—$NR^cC(=S)R^a$, —$(CH_2)_m$—$NR^cC(=S)NR^aR^b$, —$(CH_2)_m$—$NR^cC(=S)OR^a$, —$(CH_2)_m$—$NR^cS(O_2)R^a$, —$(CH_2)_m$—$P(=O)(OR^b)(OR^a)$, —$(CH_2)_m$—$P(=O)(OR^b)(R^a)$ or —$(CH_2)_m$—$S(O_2)NR^bR^a$,
—$(CH_2)_m$—O—$C(=O)$-(M)—$C(=O)OH$,
—$(CH_2)_m$—O—$C(=O)$-(M)—$C(=O)OR^a$,
—$(CH_2)_m$—O—$C(=O)$-(M)—$R^a$, —$(CH_2)_m$—O—$(CH_2)_q$—$P(=O)(R^{ba})(R^{aa})$, —$(CH_2)_m$—$C(=O)$O—$(CH_2)_q$—$P(=O)(R^{ba})(R^{aa})$, —$(CH_2)_m$—$C(=O)O$—$(CH_2)_q$—$S(O_2)OH$ or —$(CH_2)_m$—$C(=O)O$—$(CH_2)_q$—$S(O_2)OR^a$, with $R^{aa}$ being selected independently from each other being —$R^a$ or —$OR^a$,
with $R^{ba}$ being selected independently from each other being —$R^b$ or —$OR^b$,
with M being a substituted or unsubstituted $C_1$-$C_8$ alkyl, in particular an unsubstituted $C_1$-$C_8$ alkyl
with m being selected from 0, 1 or 2,
with q being selected from 0, 1 or 2,
with each $R^a$, $R^b$ or $R^c$ being selected, where applicable, independently from each other from
hydrogen, —CN
a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl, a substituted or unsubstituted $C_3$-$C_{10}$ cycloalkyl or a substituted or unsubstituted $C_3$-$C_{10}$ halo cycloalkyl, a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, a substituted or unsubstituted $C_5$-$C_{10}$ heteroaryl, a substituted or unsubstituted $C_6$-$C_{10}$ aryl, in particular with each $R^1$ independently from any other $R^1$ being —OH, —F, —Cl, I, —CN, —OCH$_3$, —OCF$_3$ or —CF$_3$.

In some embodiments, E of the general formula 1A is

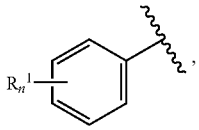

with n of $R^1_n$ being 0, 1, 2, 3, 4 or 5, or
with n of $R^1_n$ being 0, 1 or 2, or
with n of $R^1_n$ being 0 or 1, or
with n of $R^1_n$ being 1, or
with n of $R^1_n$ being 0.

In some embodiments, E of the general formula 1A is

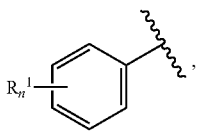

with n of $R^1_n$ being 0, 1, 2, 3, 4 or 5, in particular n of $R^1_n$ being 0, 1 or 2, more particularly 1, and with each $R^1$ independently from any other $R^1$ being —OH, —F, —Cl, —Br, I, —CCH, —CN, —N$_3$, —NO$_2$, —OCH$_3$, —OCF$_3$, —NH$_2$, —NHCH$_3$, —N(CH$_3$)$_2$, —CH$_3$, —CH$_2$CH$_3$, —OCONH$_2$ or —CF$_3$, or —B(OR$^a$)(OR$^b$), —(CH$_2$)$_m$—R$^a$, —(CH$_2$)$_m$—OR$^a$, —(CH$_2$)$_m$—C(=O)R$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O)NR$^a$R$^b$, —(CH$_2$)$_m$—C(=O)NR$^a$R$^b$, —(CH$_2$)$_m$—C(=O)NR$^b$(OR$^a$), —(CH$_2$)$_m$—C(=S)R$^a$, —(CH$_2$)$_m$—C(=S)OR$^a$, —(CH$_2$)$_m$—OC(=S)R$^a$, —(CH$_2$)$_m$—OC(=S)OR$^a$, —(CH$_2$)$_m$—OC(=S)NR$^a$R$^b$, —(CH$_2$)$_m$—C(=S)NR$^a$R$^b$, —(CH$_2$)$_m$—SR$^a$, —(CH$_2$)$_m$—S(=O)R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)OR$^a$, —(CH$_2$)$_m$—NR$^c$C(=O)NR$^a$R$^b$, —(CH$_2$)$_m$—NR$^c$C(=S)R$^a$, —(CH$_2$)$_m$—NR$^c$C(=S)NR$^a$R$^b$, —(CH$_2$)$_m$—NR$^c$C(=S)OR$^a$, —(CH$_2$)$_m$—NR$^c$S(O$_2$)R$^a$, —(CH$_2$)$_m$—P(=O)(OR$^b$)(OR$^a$), —(CH$_2$)$_m$—P(=O)(OR$^b$)(R$^a$) or —(CH$_2$)$_m$—S(O$_2$)NR$^b$R$^a$, —(CH$_2$)$_m$—O—C(=O)-(M)—C(=O)OH, —(CH$_2$)$_m$—O—C(=O)-(M)—C(=O)OR$^a$, —(CH$_2$)$_m$—O—C(=O)-(M)—R$^a$, —(CH$_2$)$_m$—O—(CH$_2$)$_q$—P(=O)(R$^{ba}$)(R$^{aa}$), —(CH$_2$)$_m$—C(=O)O—(CH$_2$)$_q$—P(=O)(R$^{ba}$)(R$^{aa}$), —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$, with $R^{aa}$ being selected independently from each other from —R$^a$ or —OR$^a$, with $R^{ba}$ being selected independently from each other from —R$^b$ or —OR$^b$, with M being a substituted or unsubstituted $C_1$-$C_8$ alkyl, in particular an unsubstituted $C_1$-$C_8$ alkyl, with m being selected from 0, 1 or 2, with q being selected from 0, 1 or 2, with each $R^a$, $R^b$ or $R^c$ being selected, where applicable, independently from each other from
hydrogen, —CN,
a substituted or unsubstituted $C_3$-$C_{10}$ cycloalkyl or a substituted or unsubstituted $C_3$-$C_{10}$ halo cycloalkyl, or
a substituted or unsubstituted $C_6$-$C_{10}$ aryl,
a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl,
a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl.

In some embodiments, E of the general formula 1A is

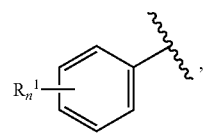

with n of $R^1_n$ being 0, 1, 2, 3, 4 or 5, in particular n of $R^1_n$ being 0, 1 or 2, more particularly 0 or 1, and with each $R^1$ independently from any other $R^1$ being —OH, —F, —Cl, —Br, —I, —CCH, —CN, —N$_3$, —OCH$_3$, —OCF$_3$, —NH$_2$, —CH$_3$, —CF$_3$, —OCONH$_2$ or —NO$_2$, or
—NR$^a_2$, —NHR$^a$, —R$^a$, —C(=O)R$^a$, —C(=O)OR$^a$, OR$^a$, —OC(=O)R$^a$, —OC(=O)OR$^a$, —OC(=O)NHR$^a$, —NHC(=O)R$^a$, —NHC(=O)NHR$^a$, —C(=O)NHR$^a$, —NHC(=O)OR$^a$, —C(=S)R$^a$, —C(=S)OR$^a$, —SR$^a$, —OC(=S)R$^a$, —OC(=S)OR$^a$, —OC(=S)NHR$^a$, —NHC(=S)R$^a$, —NHC(=S)NHR$^a$, —C(=S)NHR$^a$ or —NHC(=S)OR$^a$, in particular —NR$^a_2$, —NHR$^a$, —R$^a$, —C(=O)R$^a$, —C(=O)OR$^a$, OR$^a$, —OC(=O)R$^a$, —OC(=O)OR$^a$, —OC(=O)NHR$^a$, —NHC(=O)R$^a$, —NHC(=O)NHR$^a$, —C(=O)NHR$^a$ or —NHC(=O)OR$^a$ with $R^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle; in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl, or
a substituted or unsubstituted $C_6$-$C_{10}$ aryl; or
In some embodiments, E of the general formula 1A is

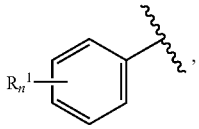

with n of $R^1_n$ being 0, 1, 2, 3, 4 or 5, in particular n of $R^1_n$ being 0, 1 or 2, more particularly 0 or 1, and
a. with each $R^1$ independently from any other $R^1$ being
—OH, —F, —Cl, —I, —CCH, —CN, —$N_3$, —$OCH_3$, —$OCF_3$, —$NH_2$, —$CH_3$, —$CF_3$, —$OCONH_2$ or —$NO_2$, or
a substituted or unsubstituted $C_5$-$C_6$ heterocycle
a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or
a substituted or unsubstituted $C_5$-$C_6$ heteroaryl,
a substituted or unsubstituted $C_5$-$C_6$ halo heteroaryl comprising one or two halogen atoms selected from Cl of F, particularly comprising one Cl or one F in para position in relation to the attachment position of the heteroaryl to the benzene moiety, or
a substituted or unsubstituted $C_6$ aryl; or
b. with each $R^1$ independently from any other $R^1$ being —OH, —F, —Cl, I, —CN, —$OCH_3$, —$OCF_3$ or —$CF_3$; or
c. with each $R^1$ independently from any other $R^1$ being —OH, —F or —$CF_3$,
wherein in particular $R^1$ is in para position in relation to the attachment position of the benzene moiety to the remaining structure.
In some embodiments, E of the general formula 1A is

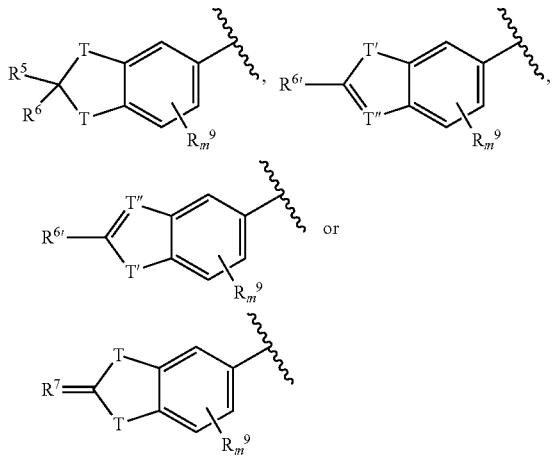

with each T being selected independently from each other from —$CH_2$, —NH, —S or —O, —$CHCH_3$, —$C(CH_3)_2$ or —$NR^c$,
with $R^c$ being —OH, —$CH_3$, —$CH_2CH_3$, —$CH_2CH_2CH_3$, —$CH(CH_3)_2$, and
with T' being selected from —$CH_2$, —NH, —S or —O, —$CHCH_3$, —$C(CH_3)_2$ or —$NR^c$, and
with T" being selected from —CH or =N, and
with $R^5$ and $R^6$ being selected independently from each other from —H, —F, —$CH_3$, —$CH_2CH_3$, —$OCH_3$, —$CH_2CF_3$, —$CHFCF_3$, —$CF_2CF_3$, —$CHF_2$, —$CH_2F$ or —$CF_3$, in particular with $R^5$ and $R^6$ being selected independently from each other from H, —F or —$CH_3$, and
with $R^{6'}$ being selected from OH, —$OCH_3$, —$OCH_2CH_3$, —$CH_3$,
with $R^7$ being selected from =NH, =S or =O, and
with m of $R^9_m$ being selected from 0, 1, 2 or 3, and each $R^9$ being selected independently from each other from —OH, —F, —Br, —I, —OH, —CCH, —CN—$CH_3$, —$CH_2CH_3$, —$OCH_3$, —COOH, —$COOR^b$, —C(O)$NH_2$, —C(O)NH($CH_3$); —C(O)N($CH_3$)$_2$, —NHC(=O)$OCH_3$, —$NCH_3$C(=O)$OCH_3$, —$CH_2CF_3$, —$CHFCF_3$, —$CF_2CF_3$, —$CHF_2$, —$CH_2F$ or —$CF_3$,
with $R^b$ being a substituted or unsubstituted $C_1$-$C_5$ alkyl, a substituted or unsubstituted $C_2$-$C_5$ alkenyl, a substituted or unsubstituted $C_2$-$C_5$ alkynyl, or a $C_1$-$C_5$ haloalkyl.
In some embodiments, E of the general formula 1A is

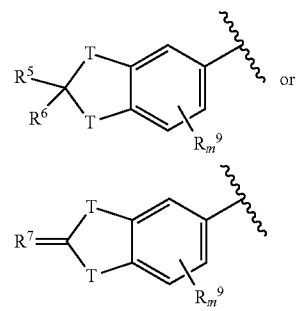

with each T being selected independently from each other from —CH, —$CH_2$, —NH, —S or —O, and —$CHCH_3$, —$C(CH_3)_2$, =N, —$NR^c$,
with $R^c$ being —$CH_2OH$, —$CH_3$, —$CH_2CH_3$, —$CH_2CH_2CH_3$, —$CH(CH_3)_2$, —$CH_2CF_3$, —$CHFCF_3$, —$CF_2CF_3$, —$CHF_2$, —$CH_2F$, —$CF_3$
with $R^5$ and $R^6$ being selected independently from each other from —H, —F, —$CH_3$, —$CH_2CH_3$, —$OCH_3$, —$CH_2CF_3$, —$CHFCF_3$, —$CF_2CF_3$, —$CHF_2$, —$CH_2F$ or —$CF_3$, in particular $R^5$ and $R^6$ are selected independently from each other from H, F or $CH_3$, and
with $R^7$ being selected from =NH, =S or =O, and with m of $R^9_m$ being selected from 0, 1, 2 or 3, and each $R^9$ being selected independently from each other from —Cl, —F, Br, I, —OH, —CCH, —$CH_3$, —$CH_2CH_3$, —$OCH_3$, —COOH, —$COOR^b$, —C(O)$NH_2$, —NHC(=O)$OCH_3$, —$NCH_3$C(=O)$OCH_3$, —C(O)NH($CH_3$); —C(O)N($CH_3$)$_2$—$CH_2CF_3$, —$CHFCF_3$, —$CF_2CF_3$, —$CHF_2$, —$CH_2F$ or —$CF_3$, $R_2$N—COOH
with $R^b$ being a substituted or unsubstituted $C_1$-$C_5$ alkyl, a substituted or unsubstituted $C_2$-$C_5$ alkenyl, a substituted or unsubstituted $C_2$-$C_5$ alkynyl, or a $C_1$-$C_5$ haloalkyl.

In some embodiments, E of the general formula 1A is

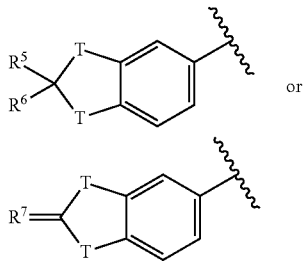 or with m of $R^9{}_m$ being 0, and with each T being selected independently from each other from —CH, —CH$_2$, —NH, —S or —O, —CHCH$_3$, —C(CH$_3$)$_2$, =N, —NR$^c$, with R$^c$ being —CH$_2$OH, —CH$_3$, —CH$_2$CH$_3$, —CH$_2$CH$_2$CH$_3$, —CH(CH$_3$)$_2$, —CH$_2$CF$_3$, —CHFCF$_3$, —CF$_2$CF$_3$, —CHF$_2$, —CH$_2$F, —CF$_3$ and with R$^5$ and R$^6$ being selected independently from each other from —H, —F, —CH$_3$, —CH$_2$CH$_3$, —OCH$_3$, —CH$_2$CH$_3$, —CHFCF$_3$, —CF$_2$CF$_3$, —CHF$_2$, —CH$_2$F or —CF$_3$, in particular R$^5$ and R$^6$ are selected independently from each other from H, F or CH$_3$, and with R$^7$ being selected from =NH, =S or =O.

In some embodiments, E of the general formula 1A is selected from

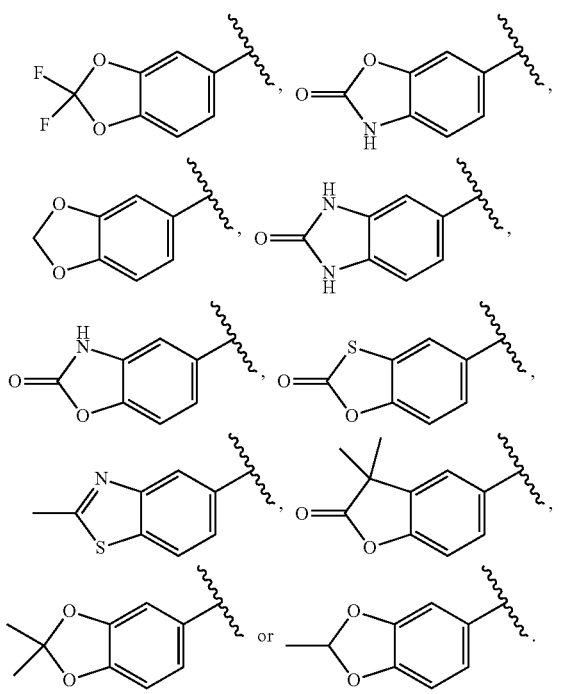

In some embodiments, X of the general formula 1A is

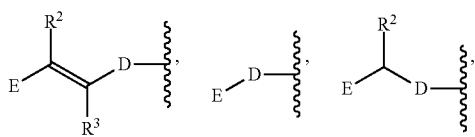

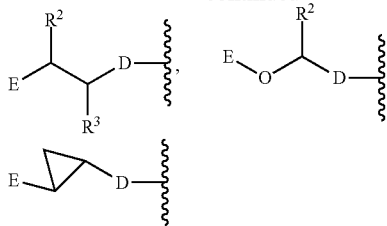

with R$^2$ and R$^3$ being selected, where applicable, independently from each other from —H, —F, —CN, —OH, —NH$_2$, —NO$_2$, —NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl, in particular from —H, —F, —CN, —OH, —NH$_2$, —NO$_2$, —NHCH$_3$, —NH (CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with R$^2$ and R$^3$ being selected independently from each other from H, F or CH$_3$, and with D being a linker which comprises carbon, sulphur, nitrogen and/or oxygen atoms and which is covalently connecting the moiety comprising R$^1$ and the parent moiety, in particular D is a linker selected from the linkers characterized by general formula D1 to D21, D1 to D12, D1 to D6 or D1 to D4, and E being

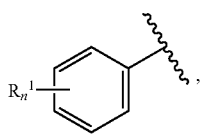

with n of $R^1{}_n$ being 0, 1, 2, 3, 4 or 5, in particular n of $R^1{}_n$ being 0, 1 or 2, more particularly n being 0 or 1, and a. with each R$^1$ independently from any other R$^1$ being
—OH, —F, —Cl, —Br, —I, —CCH, —CN, —N$_3$, —NO$_2$, —OCH$_3$, —OCF$_3$, —NH$_2$, —NHCH$_3$, —N(CH$_3$)$_2$, —CH$_3$, —CH$_2$CH$_3$, —OCONH$_2$ or —CF$_3$, or
—B(OR$^a$)(OR$^b$), —(CH$_2$)$_m$—R$^a$, —(CH$_2$)$_m$—OR$^a$, —(CH$_2$)$_m$—C(=O)R$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O) NR$^a$R$^b$, —(CH$_2$)$_m$—C(=O)NR$^a$R$^b$, —(CH$_2$)$_m$—C (=O)NR$^b$(OR$^a$), —(CH$_2$)$_m$—C(=S)R$^a$, —(CH$_2$)$_m$— C(=S)OR$^a$, —(CH$_2$)$_m$—OC(=S)R$^a$, —(CH$_2$)$_m$—OC (=S)OR$^a$, —(CH$_2$)$_m$—OC(=S)NR$^a$R$^b$, —(CH$_2$)$_m$— C(=S)NR$^a$R$^b$, —(CH$_2$)$_m$—SR$^a$, —(CH$_2$)$_m$—S(=O) R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)OR$^a$, —(CH$_2$)$_m$—NR$^c$C(=O) NR$^a$R$^b$, —(CH$_2$)$_m$—NR$^c$C(=S)R$^a$, —(CH$_2$)$_m$—NR$^c$C (=S)NR$^a$R$^b$, —(CH$_2$)$_m$—NR$^c$C(=S)OR$^a$, —(CH$_2$)$_m$ —NR$^c$S(O$_2$)R$^a$, —(CH$_2$)$_m$—P(=O)(OR$^b$)(OR$^a$), —(CH$_2$)$_m$—P(=O)(OR$^b$)(R$^a$) or —(CH$_2$)$_m$—S(O$_2$) NR$^b$R$^a$, —(CH$_2$)$_m$—O—C(=O)-(M)—C(=O)OH, —(CH$_2$)$_m$—O—C(=O)-(M)—C(=O)OR$^a$, —(CH$_2$)$_m$ —O—C(=O)-(M)—R$^a$, —(CH$_2$)$_m$—O—(CH$_2$)$_q$—P (=O)(R$^{ba}$)(R$^{aa}$), —(CH$_2$)$_m$—C(=O)O—(CH$_2$)$_q$—P $(=O)(R^{ba})(R^{aa})$, $-(CH_2)_m-C(=O)O-(CH_2)_q-S(O_2)OH$ or $-(CH_2)_m-C(=O)O-(CH_2)_q-S(O_2)OR^a$, with $R^{aa}$ being selected independently from each other from $-R^a$ or $-OR^a$, with $R^{ba}$ being selected independently from each other from $-R^b$ or $-OR^b$, with M being a substituted or unsubstituted $C_1$-$C_8$ alkyl, in particular an unsubstituted $C_1$-$C_8$ alkyl, with m being selected from 0, 1 or 2, with q being selected from 0, 1 or 2, with each $R^a$, $R^b$ or $R^c$ being selected, where applicable, independently from each other from hydrogen, $-CN$,

- a substituted or unsubstituted $C_3$-$C_{10}$ cycloalkyl or a substituted or unsubstituted $C_3$-$C_{10}$ halo cycloalkyl, or
- a substituted or unsubstituted $C_6$-$C_{10}$ aryl,
- a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
- a substituted or unsubstituted $C_5$-$C_{10}$ heteroaryl,
- a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl;

b. with each $R^1$ independently from any other $R^1$ being
—OH, —F, —Cl, —Br, —I, —CCH, —CN, —N$_3$, —OCH$_3$, —OCF$_3$, —NH$_2$, —CH$_3$, —CF$_3$, —OCONH$_2$ or —NO$_2$, or
—NR$^a_2$, —NHR$^a$, —R$^a$, —C(=O)R$^a$, —C(=O)OR$^a$, OR$^a$, —OC(=O)R$^a$, —OC(=O)OR$^a$, —OC(=O)NHR$^a$, —NHC(=O)R$^a$, —NHC(=O)NHR$^a$, —C(=O)NHR$^a$, —NHC(=O)OR$^a$, —C(=S)R$^a$, —C(=S)OR$^a$, —SR$^a$, —OC(=S)R$^a$, —OC(=S)OR$^a$, —OC(=S)NHR$^a$, —NHC(=S)R$^a$, —NHC(=S)NHR$^a$, —C(=S)NHR$^a$ or —NHC(=S)OR$^a$, in particular —NR$^a_2$, —NHR$^a$, —R$^a$, —C(=O)R$^a$, —C(=O)OR$^a$, OR$^a$, —OC(=O)R$^a$, —OC(=O)OR$^a$, —OC(=O)NHR$^a$, —NHC(=O)R$^a$, —NHC(=O)NHR$^a$, —C(=O)NHR$^a$ or —NHC(=O)OR$^a$ with $R^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle; in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl; or c. with each $R^1$ independently from any other $R^1$ being
—OH, —F, —Cl, —I, —CCH, —CN, —N$_3$, —OCH$_3$, —OCF$_3$, —NH$_2$, —CH$_3$, —CF$_3$, —OCONH$_2$ or —NO$_2$, or a substituted or unsubstituted $C_5$-$C_6$ heterocycle a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or a substituted or unsubstituted $C_5$-$C_6$ heteroaryl, a substituted or unsubstituted halo heteroaryl comprising one or two halogen atoms selected from Cl of F, particularly comprising one Cl or one F in para position (in case of a $C_6$ halo heteroaryl) in relation to the attachment position of the heterocycle to the benzene moiety, or a substituted or unsubstituted $C_6$ aryl; or d. with each $R^1$ independently from any other $R^1$ being
—OH, —F, —Cl, —I, —CN, —OCH$_3$, —OCF$_3$ or —CF$_3$; or e. with each $R^1$ independently from any other $R^1$ being
—OH, —F or —CF$_3$, wherein in particular $R^1$ is in para position in relation to the attachment position of the benzene moiety to the remaining structure.

In some embodiments, X of the general formula 1A is

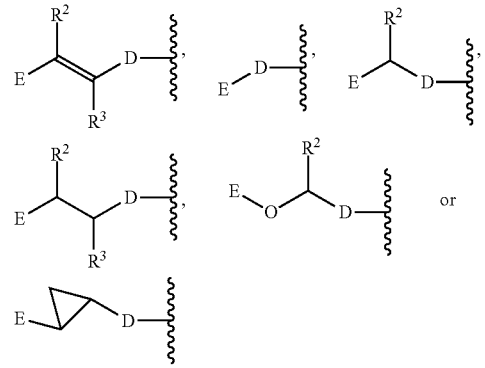

with $R^2$ and $R^3$ being selected, where applicable, independently from each other from —H, —F, —CN, —OH, —NH$_2$, —NO$_2$, —NHCH$_3$, —NH(CH$_3$)$_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —NH$_2$, —NO$_2$, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with $R^2$ and $R^3$ being selected independently from each other from H, F or CH$_3$, and with D being

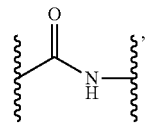

and with
E being

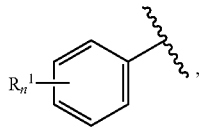

with n of $R^1_n$ being 0, 1, 2, 3, 4 or 5, in particular n of $R^1_n$ being 0, 1 or 2, more particularly n being 0 or 1, and a. with each $R^1$ independently from any other $R^1$ being
—OH, —F, —Cl, —Br, —I, —CCH, —CN, —N$_3$, —NO$_2$, —OCH$_3$, —OCF$_3$, —NH$_2$, —NHCH$_3$, —N(CH$_3$)$_2$, —CH$_3$, —CH$_2$CH$_3$, —OCONH$_2$ or —CF$_3$, or
—B(OR$^a$)(OR$^b$), —(CH$_2$)$_m$—R$^a$, —(CH$_2$)$_m$—OR$^a$, —(CH$_2$)$_m$—C(=O)R$^a$, —(CH$_2$)$_m$—C(=O)OR$^a$, —(CH$_2$)$_m$—OC(=O)R$^a$, —(CH$_2$)$_m$—OC(=O)OR$^a$, —(CH$_2$)$_m$—OC(=O)NR$^a$R$^b$, —(CH$_2$)$_m$—C(=O)NR$^a$R$^b$, —(CH$_2$)$_m$—C(=O)NR$^a$R$^b$, —(CH$_2$)$_m$—C(=O)NR$^b$(OR$^a$), —(CH$_2$)$_m$—C(=S)R$^a$, —(CH$_2$)$_m$—C(=S)OR$^a$, —(CH$_2$)$_m$—OC(=S)R$^a$, —(CH$_2$)$_m$—OC(=S)OR$^a$, —(CH$_2$)$_m$—OC(=S)NR$^a$R$^b$, —(CH$_2$)$_m$—C(=S)NR$^a$R$^b$, —(CH$_2$)$_m$—SR$^a$, —(CH$_2$)$_m$—S(=O)R$^a$, —(CH$_2$)$_m$—S(O$_2$)R$^a$, —(CH$_2$)$_m$—S(O$_2$)OR$^a$, —(CH$_2$)$_m$—OS(O$_2$)R$^a$, —(CH$_2$)$_m$—OS(O$_2$)OR$^a$, —(CH$_2$)$_m$—NR$^a$R$^b$, —(CH$_2$)$_m$—NR$^c$C(=O)R$^a$, —(CH$_2$)$_m$—NR$^c$C(=O)OR$^a$, —(CH$_2$)$_m$—NR$^c$C(=O)NR$^a$R$^b$, —(CH$_2$)$_m$—NR$^c$C(=S)R$^a$, —(CH$_2$)$_m$—NR$^c$C(=S)NR$^a$R$^b$, —(CH$_2$)$_m$—NR$^c$C(=S)OR$^a$, —(CH$_2$)$_m$—NR$^c$S(O$_2$)R$^a$, —(CH$_2$)$_m$—P(=O)(OR$^b$)(OR$^a$), —(CH$_2$)$_m$—P(=O)(OR$^b$)(R$^a$) or —(CH$_2$)$_m$—S(O$_2$)NR$^b$R$^a$, —(CH$_2$)$_m$—O—C(=O)-(M)—C(=O)OH, —(CH$_2$)$_m$—O—C(=O)-(M)—C(=O)OR$^a$, —(CH$_2$)$_m$—O—C(=O)-(M)—R$^a$, —(CH$_2$)$_m$—O—(CH$_2$)$_q$—P(=O)(R$^{ba}$)(R$^{aa}$), —(CH$_2$)$_m$—C(=O)O—(CH$_2$)$_q$—P(=O)(R$^{ba}$)(R$^{aa}$), —(CH$_2$)$_m$—C(=O)O—(CH$_2$)$_q$—S(O$_2$)OH or —(CH$_2$)$_m$—C(=O)O—(CH$_2$)$_q$—S(O$_2$)OR$^a$, with $R^{aa}$ being selected independently from each other from —R$^a$ or —OR$^a$, with $R^{ba}$ being selected independently from each other from —R$^b$ or —OR$^b$, with M being a substituted or unsubstituted $C_1$-$C_8$ alkyl, in particular an unsubstituted $C_1$-$C_8$ alkyl, with m being selected from 0, 1 or 2, with q being selected from 0, 1 or 2, with each $R^a$, $R^b$ or $R^c$ being selected, where applicable, independently from each other from hydrogen, —CN,
a substituted or unsubstituted $C_3$-$C_{10}$ cycloalkyl or a substituted or unsubstituted $C_3$-$C_{10}$ halo cycloalkyl, or
a substituted or unsubstituted $C_6$-$C_{10}$ aryl,
a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl,
a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl;

b. with each $R^1$ independently from any other $R^1$ being
—OH, —F, —Cl, —Br, —I, —CCH, —CN, —N$_3$, —OCH$_3$, —OCF$_3$, —NH$_2$, —CH$_3$, —CF$_3$, —OCONH$_2$ or —NO$_2$, or
—NR$^a_2$, —NHR$^a$, —R$^a$, —C(=O)R$^a$, —C(=O)OR$^a$, OR$^a$, —OC(=O)R$^a$, —OC(=O)OR$^a$, —OC(=O)NHR$^a$, —NHC(=O)R$^a$, —NHC(=O)NHR$^a$, —C(=O)NHR$^a$, —NHC(=O)OR$^a$, —C(=S)R$^a$, —C(=S)OR$^a$, —SR$^a$, —OC(=S)R$^a$, —OC(=S)OR$^a$, —OC(=S)NHR$^a$, —NHC(=S)R$^a$, —NHC(=S)NHR$^a$, —C(=S)NHR$^a$ or —NHC(=S)OR$^a$, in particular —NR$^a_2$, —NHR$^a$, —R$^a$, —C(=O)R$^a$, —C(=O)OR$^a$, OR$^a$, —OC(=O)R$^a$, —OC(=O)OR$^a$, —OC(=O)NHR$^a$, —NHC(=O)R$^a$, —NHC(=O)NHR$^a$, —C(=O)NHR$^a$ or —NHC(=O)OR$^a$, with $R^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or
a substituted or unsubstituted $C_3$-$C_{10}$ cycloalkyl or a substituted or unsubstituted $C_3$-$C_{10}$ halo cycloalkyl, or
a substituted or unsubstituted $C_3$-$C_{10}$ heterocycle or a substituted or unsubstituted $C_3$-$C_{10}$ halo heterocycle; in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl, or
a substituted or unsubstituted $C_6$-$C_{10}$ aryl; or c. with each $R^1$ independently from any other $R^1$ being
—OH, —F, —Cl, I, CCH, —CN, —N$_3$, —OCH$_3$, —OCF$_3$, —NH$_2$, —CH$_3$, —CF$_3$, —OCONH$_2$ or —NO$_2$, or
a substituted or unsubstituted $C_5$-$C_6$ heterocycle
a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or
a substituted or unsubstituted $C_5$-$C_6$ heteroaryl,
a substituted or unsubstituted halo heteroaryl comprising one or two halogen atoms selected from Cl of F, particularly comprising one Cl or one F in para position (in case of a $C_6$ halo heteroaryl) in relation to the attachment position of the heterocycle to the benzene moiety, or
a substituted or unsubstituted $C_6$ aryl; or d. with each $R^1$ independently from any other $R^1$ being
—OH, —F, —Cl, I, —CN, —OCH$_3$, —OCF$_3$ or —CF$_3$; or e. with each $R^1$ independently from any other $R^1$ being
—OH, —F or —CF$_3$, wherein in particular $R^1$ is in para position in relation to the attachment position of the benzene moiety to the remaining structure.

In some embodiments, X of the general formula 1A is

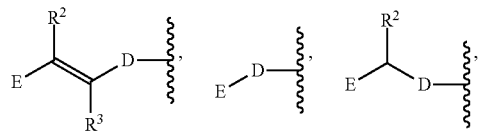

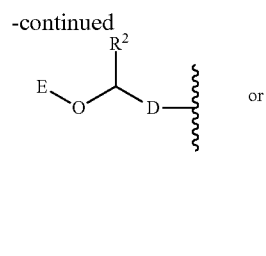

with $R^2$ and $R^3$ being selected, where applicable, independently from each other from —H, —F, —CN, —OH, —NO$_2$, —NH$_2$, —NHCH$_3$, —NH(CH$_3$)$_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —NH$_2$, —NO$_2$, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with $R^2$ and $R^3$ being selected independently from each other from H, F or CH$_3$, and with D being a linker which comprises carbon, sulphur, nitrogen and/or oxygen atoms and which is covalently connecting the moiety comprising $R^1$ and the parent moiety, in particular D is a linker selected from the linkers characterized by general formula D1 to D21, D1 to D12, D1 to D6 or D1 to D4, and a. E is
- a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or
- a substituted or unsubstituted $C_3$-$C_{10}$ cycloalkyl or a substituted or unsubstituted $C_3$-$C_{10}$ halo cycloalkyl, or
- a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or
- a substituted or unsubstituted $C_4$-$C_{10}$ halo heterocycle, or
- a substituted or unsubstituted $C_5$-$C_{10}$ heteroaryl, or
- a substituted or unsubstituted $C_8$-$C_{10}$ aryl, or b. E is
- a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl, or c. E is
- a substituted or unsubstituted $C_1$-$C_5$ alkyl, a substituted or unsubstituted $C_6$-$C_{10}$ cycloalkyl, or a substituted or unsubstituted $C_5$-$C_{10}$ heteroaryl or a substituted or unsubstituted $C_8$-$C_{10}$ aryl, or d. E is
- a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
- a substituted or unsubstituted $C_5$-$C_{10}$ heteroaryl, or
- a substituted or unsubstituted $C_8$-$C_{10}$ aryl, or e. E is
- a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the 'D moiety, or
- a substituted or unsubstituted $C_5$-$C_6$ heteroaryl,
- a substituted or unsubstituted $C_5$-$C_6$ halo heteroaryl comprising one or two halogen atoms selected from Cl of F, particularly comprising one Cl or one F in para position in relation to the attachment position of the heteroaryl to the D moiety; or
- E is selected from the group of substituted or unsubstituted pyrrole, furan, thiophene, benzothiophene, chromene, thiazole, pyrazine, pyridazine, pyridine, 1,2,3-triazole, 1,2,4-triazole, imidazole, oxazol, thiazol, indole, isoindole, quinoline, isoquinoline, naphatalene, coumarin, aminocoumarin, umbelliferon, benzotriazole, psoralen, benzofurane, benzothiophene, benzimidazol, benzthiazole, benzoxazole or benzpyridazin or hydroxylated, methylated or halogenated derivatives thereof, or f. E is selected from.

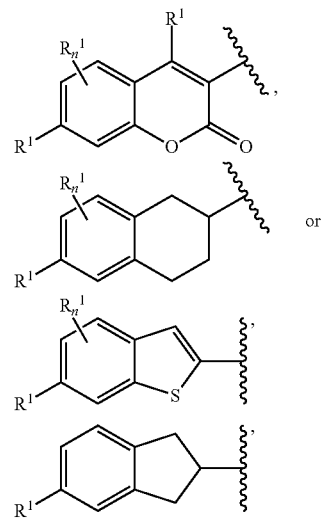

in particular from

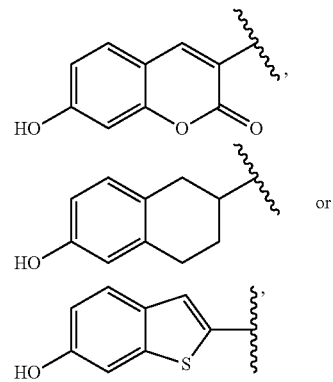

-continued

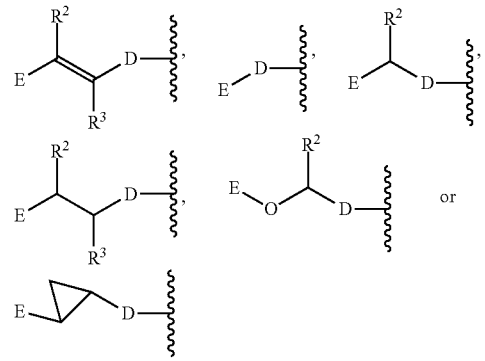

with n of $R^1_n$ being 0, 1, 2, 3, 4 or 5, in particular n of $R^1_n$ being 0, 1, 2 or 3, more particularly n of $R^1_n$ being 1, and with each $R^1$ independently from any other $R^1$ being selected from —OH, —F, —Cl, —Br, —I, —CCH, —CN, —$N_3$, —$OCH_3$, —$OCF_3$, —$NH_2$, —$NHCH_3$, —$N(CH_3)_2$, —$CH_3$, —$CH_2$—$CH_3$, —$CF_3$, —$OCONH_2$ or —$NO_2$, —$B(OR^a)(OR^b)$, —$(CH_2)_m$—$R^a$, —$(CH_2)_m$—$OR^a$, —$(CH_2)_m$—$C(=O)R^a$, —$(CH_2)_m$—$C(=O)OR^a$, —$(CH_2)_m$—$OC(=O)R^a$, —$(CH_2)_m$—$OC(=O)OR^a$, —$(CH_2)_m$—$OC(=O)NR^aR^b$, —$(CH_2)_m$—$C(=O)NR^aR^b$, —$(CH_2)_m$—$C(=O)NR^aR^b$, —$(CH_2)_m$—$C(=O)NR^b(OR^a)$, —$(CH_2)_m$—$C(=S)R^a$, —$(CH_2)_m$—$C(=S)OR^a$, —$(CH_2)_m$—$OC(=S)R^a$, —$(CH_2)_m$—$OC(=S)OR^a$, —$(CH_2)_m$—$OC(=S)NR^aR^b$, —$(CH_2)_m$—$C(=S)NR^aR^b$, —$(CH_2)_m$—$SR^a$, —$(CH_2)_m$—$S(=O)R^a$, —$(CH_2)_m$—$S(O_2)R^a$, —$(CH_2)_m$—$S(O_2)OR^a$, —$(CH_2)_m$—$OS(O_2)R^a$, —$(CH_2)_m$—$OS(O_2)OR^a$, —$(CH_2)_m$—$NR^aR^b$, —$(CH_2)_m$—$NR^cC(=O)R^a$, —$(CH_2)_m$—$NR^cC(=O)NR^aR^b$, —$(CH_2)_m$—$NR^cC(=O)OR^a$, —$(CH_2)_m$—$NR^cC(=S)R^a$, —$(CH_2)_m$—$NR^cC(=S)NR^aR^b$, —$(CH_2)_m$—$NR^cC(=S)OR^a$, —$(CH_2)_m$—$NR^cS(O_2)R^a$, —$(CH_2)_m$—$P(=O)(OR^b)(OR^a)$, —$(CH_2)_m$—$P(=O)(OR^b)(R^a)$ or —$(CH_2)_m$—$S(O_2)NR^bR^a$, —$(CH_2)_m$—O—C(=O)-(M)—C(=O)OH, —$(CH_2)_m$—O—C(=O)-(M)—C(=O)$OR^a$, —$(CH_2)_m$—O—C(=O)-(M)—$R^a$, —$(CH_2)_m$—O—$(CH_2)_q$—$P(=O)(R^{ba})(R^{aa})$, —$(CH_2)_m$—C(=O)O—$(CH_2)_q$—$P(=O)(R^{ba})(R^{aa})$, —$(CH_2)_m$—C(=O)O—$(CH_2)_q$—$S(O_2)$OH or —$(CH_2)_m$—C(=O)O—$(CH_2)_q$—$S(O_2)OR^a$, with $R^{aa}$ being selected independently from each other being —$R^a$ or —$OR^a$, with $R^{ba}$ being selected independently from each other being —$R^b$ or —$OR^b$, with M being a substituted or unsubstituted $C_1$-$C_8$ alkyl, in particular an unsubstituted $C_1$-$C_8$ alkyl with m being selected from 0, 1 or 2, with q being selected from 0, 1 or 2, with each $R^a$, $R^b$ or $R^c$ being selected, where applicable, independently from each other from hydrogen, —CN a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl, a substituted or unsubstituted $C_3$-$C_{10}$ cycloalkyl or a substituted or unsubstituted $C_3$-$C_{10}$ halo cycloalkyl, a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, a substituted or unsubstituted $C_5$-$C_{10}$ heteroaryl, a substituted or unsubstituted $C_6$-$C_{10}$ aryl, in particular with each $R^1$ independently from any other $R^1$ being —OH, —F, —Cl, I, —CN, —$OCH_3$, —$OCF_3$, —$OCONH_2$ or —$CF_3$ In some embodiments, X of the general formula 1A is

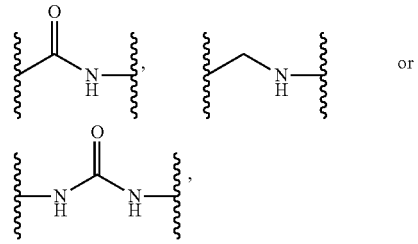

with $R^2$ and $R^3$ being selected, where applicable, independently from each other from —H, —F, —CN, —$NO_2$, —OH, —$NH_2$, —$NHCH_3$, —$NH(CH_3)_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —$NH_2$, —$NO_2$, —$NHCH_3$, —$NH(CH_3)_2$, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —$CHFCF_3$, —$CF_2CF_3$, —$CHF_2$, —$CH_2F$ or —$CF_3$, more particularly with $R^2$ and $R^3$ being selected independently from each other from H, F or $CH_3$, and with D being and with
a. E being
a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_8$-$C_{10}$ aryl, or b. E being a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl, or c. E being a substituted or unsubstituted $C_1$-$C_5$ alkyl, a substituted or unsubstituted $C_6$-$C_{10}$ cycloalkyl, or a substituted or unsubstituted $C_5$-$C_{10}$ heteroaryl or a substituted or unsubstituted $C_6$-$C_{10}$ aryl, or d. E being a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl, or e. E being a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the D moiety, or a substituted or unsubstituted $C_5$-$C_6$ heteroaryl, a substituted or unsubstituted $C_5$-$C_6$ halo heteroaryl comprising one or two halogen atoms selected from Cl of F, particularly comprising one Cl or one F in para position in relation to the attachment position of the heteroaryl to the D moiety; or E is selected from the group of substituted or unsubstituted pyrrole, furan, thiophene, benzothiophene, chromene, thiazole, pyrazine, pyridazine, pyridine, 1,2,3-triazole, 1,2,4-triazole, imidazole, oxazol, thiazol, indole, isoindole, quinoline, isoquinoline, naphatalene, coumarin, aminocoumarin, umbelliferon, benzotriazole, psoralen, benzofurane, benzothiophene, benzimidazol, benzthiazole, benzoxazole or benzpyridazin or hydroxylated, methylated or halogenated derivatives thereof, or E is selected from.

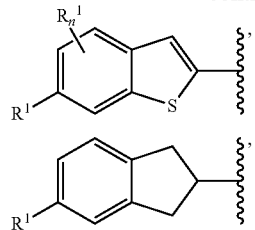

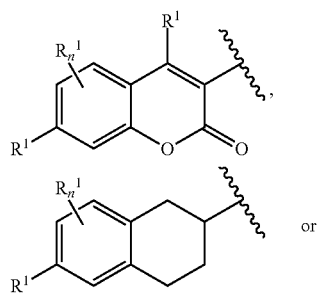

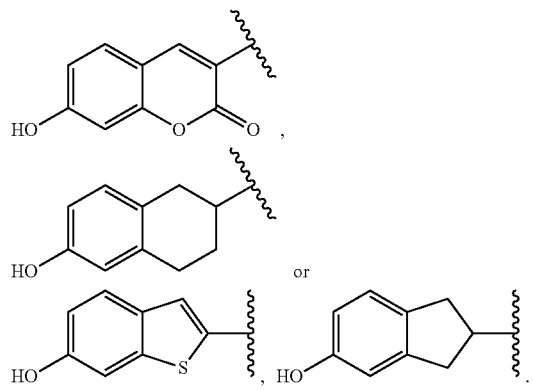

in particular from

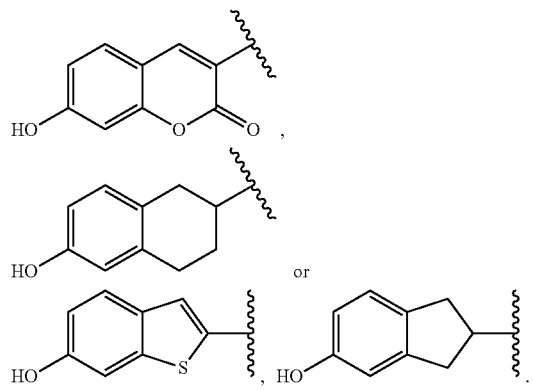

with n of $R^1_n$ being 0, 1, 2, 3, 4 or 5, in particular n of $R^1_n$ being 0, 1, 2 or 3, more particularly n of $R^1_n$ being 1, and with each $R^1$ independently from any other $R^1$ being selected from —OH, —F, —Cl, —Br, —I, —CCH, —CN, —$N_3$, —$OCH_3$, —$OCF_3$, —$NH_2$, —$NHCH_3$, —$N(CH_3)_2$, —$CH_3$, —$CH_2$—$CH_3$, —$CF_3$, —$OCONH_2$ or —$NO_2$, —$B(OR^a)(OR^b)$, —$(CH_2)_m$—$R^a$, —$(CH_2)_m$—$OR^a$, —$(CH_2)_m$—$C(=O)R^a$, —$(CH_2)_m$—$C(=O)OR^a$, —$(CH_2)_m$—$OC(=O)R^a$, —$(CH_2)_m$—$OC(=O)OR^a$, —$(CH_2)_m$—$OC(=O)NR^aR^b$, —$(CH_2)_m$—$C(=O)NR^aR^b$, —$(CH_2)_m$—$C(=O)NR^aR^b$, —$(CH_2)_m$—$C(=O)NR^b(OR^a)$, —$(CH_2)_m$—$C(=S)R^a$, —$(CH_2)_m$—$C(=S)OR^a$, —$(CH_2)_m$—$OC(=S)R^a$, —$(CH_2)_m$—$OC(=S)OR^a$, —$(CH_2)_m$—$OC(=S)NR^aR^b$, —$(CH_2)_m$—$C(=S)NR^aR^b$, —$(CH_2)_m$—$SR^a$, —$(CH_2)_m$—$S(=O)R^a$, —$(CH_2)_m$—$S(O_2)R^a$, —$(CH_2)_m$—$S(O_2)OR^a$, —$(CH_2)_m$—$OS(O_2)R^a$, —$(CH_2)_m$—$OS(O_2)OR^a$, —$(CH_2)_m$—$NR^aR^b$, —$(CH_2)_m$—$NR^cC(=O)R^a$, —$(CH_2)_m$—$NR^cC(=O)NR^aR^b$, —$(CH_2)_m$—$NR^cC(=O)OR^a$, —$(CH_2)_m$—$NR^cC(=S)R^a$, —$(CH_2)_m$—$NR^cC(=S)NR^aR^b$, —$(CH_2)_m$—$NR^cC(=S)OR^a$, —$(CH_2)_m$—$NR^cS(O_2)R^a$, —$(CH_2)_m$—$P(=O)(OR^b)(OR^a)$, —$(CH_2)_m$—$P(=O)(OR^b)(R^a)$ or —$(CH_2)_m$—$S(O_2)NR^bR^a$, —$(CH_2)_m$—O—$C(=O)$-(M)—$C(=O)OH$, —$(CH_2)_m$—O—$C(=O)$-(M)—$C(=O)OR^a$, —$(CH_2)_m$—O—$C(=O)$-(M)—$R^a$, —$(CH_2)_m$—O—$(CH_2)_q$—$P(=O)(R^{ba})(R^{aa})$, —$(CH_2)_m$—$C(=O)$O—$(CH_2)_q$—$P(=O)(R^{ba})(R^{aa})$, —$(CH_2)_m$—$C(=O)O$—$(CH_2)_q$—$S(O_2)OH$ or —$(CH_2)_m$—$C(=O)O$—$(CH_2)_q$—$S(O_2)OR^a$, with $R^{aa}$ being selected independently from each other being —$R^a$ or —$OR^a$, with $R^{ba}$ being selected independently from each other being —$R^b$ or —$OR^b$, with M being a substituted or unsubstituted $C_1$-$C_8$ alkyl, in particular an unsubstituted $C_1$-$C_8$ alkyl with m being selected from 0, 1 or 2, with q being selected from 0, 1 or 2, with each $R^a$, $R^b$ or $R^c$ being selected, where applicable, independently from each other from hydrogen, —CN
- a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, in particular a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl,
- a substituted or unsubstituted $C_3$-$C_{10}$ cycloalkyl or a substituted or unsubstituted $C_3$-$C_{10}$ halo cycloalkyl,
- a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle,
- a substituted or unsubstituted $C_5$-$C_{10}$ heteroaryl,
- a substituted or unsubstituted $C_6$-$C_{10}$ aryl, in particular with each $R^1$ independently from any other $R^1$ being —OH, —F, —Cl, I, —CN, —$OCH_3$, —$OCF_3$, —$OCONH_2$ or —$CF_3$.

In some embodiments, X of the general formula 1A is

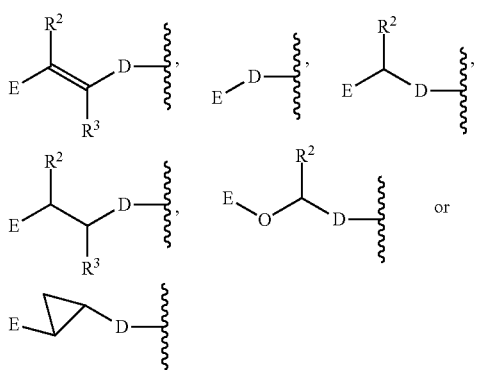

with $R^2$ and $R^3$ being selected, where applicable, independently from each other from —H, —F, —CN, —OH, —$NH_2$, —$NO_2$, —$NHCH_3$, —$NH(CH_3)_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —$NH_2$, —$NO_2$, —$NHCH_3$, —$NH(CH_3)_2$, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —$CHFCF_3$, —$CF_2CF_3$, —$CHF_2$, —$CH_2F$ or —$CF_3$, more particularly with $R^2$ and $R^3$ being selected independently from each other from H, F or $CH_3$, and with D being a linker which comprises carbon, sulphur, nitrogen and/or oxygen atoms and which is covalently connecting the moiety comprising $R^1$ and the parent moiety, in particular D is a linker selected from the linkers characterized by general formula D1 to D21, D1 to D12, D1 to D6 or D1 to D4, and

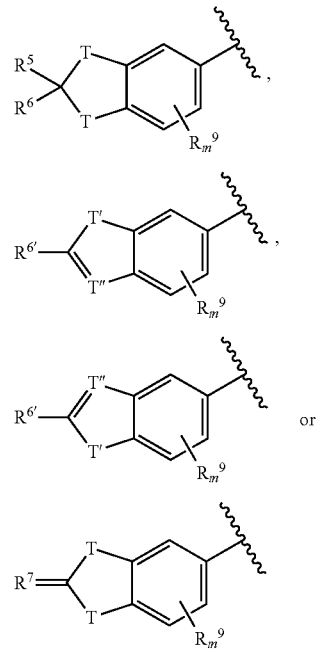

with each T being selected independently from each other from —$CH_2$, —NH, —S or —O, —$CHCH_3$, —$C(CH_3)_2$ or —$NR^c$, with $R^c$ being —OH, —$CH_3$, —$CH_2CH_3$, —$CH_2CH_2CH_3$, —$CH(CH_3)_2$, and with T' being selected from —$CH_2$, —NH, —S or —O, —$CHCH_3$, —$C(CH_3)_2$ or —$NR^c$, and with T" being selected from —CH or =N, and with $R^5$ and $R^6$ being selected independently from each other from —H, —F, —$CH_3$, —$CH_2CH_3$, —$OCH_3$, —$CH_2CF_3$, —$CHFCF_3$, —$CF_2CF_3$, —$CHF_2$, —$CH_2F$ or —$CF_3$, in particular with $R^5$ and $R^6$ being selected independently from each other from H, —F or —$CH_3$, and with $R^{6'}$ being selected from —OH, —$OCH_3$, —$OCH_2CH_3$, —$CH_3$, with $R^7$ being selected from =NH, =S or =O, and with m of $R^9_m$ being selected from 0, 1, 2 or 3, and each $R^9$ being selected independently from each other from —Cl, —F, Br, I, —OH, —CCH, —CN—$CH_3$, —$CH_2CH_3$, —$OCH_3$, —COOH, —$COOR^b$, —C(O)$NH_2$, —C(O)NH($CH_3$); —C(O)N($CH_3)_2$, —NHC(=O)$OCH_3$, —$NCH_3C(=O)OCH_3$, —$CH_2CF_3$, —$CHFCF_3$, —$CF_2CF_3$, —$CHF_2$, —$CH_2F$ or —$CF_3$, with $R^b$ being a substituted or unsubstituted $C_1$-$C_5$ alkyl, a substituted or unsubstituted $C_2$-$C_5$ alkenyl, a substituted or unsubstituted $C_2$-$C_5$ alkynyl, or a $C_1$-$C_5$ haloalkyl In some embodiments, X of the general formula 1A is

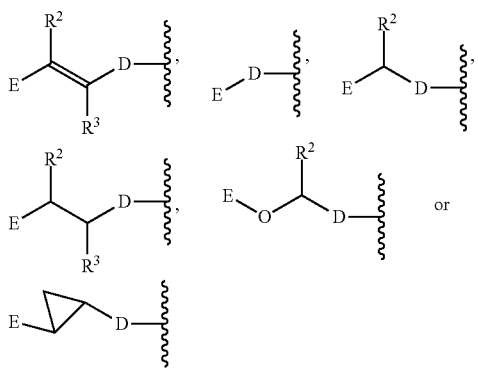

with $R^2$ and $R^3$ being selected, where applicable, independently from each other from —H, —F, —CN, —OH, —NH$_2$, —NO$_2$, —NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl, in particular from —H, —F, —CN, —OH, —NH$_2$, —NO$_2$, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with $R^2$ and $R^3$ being selected independently from each other from H, F or CH$_3$, and with D being a linker which comprises carbon, sulphur, nitrogen and/or oxygen atoms and which is covalently connecting the moiety comprising $R^1$ and the parent moiety, in particular D is a linker selected from the linkers characterized by general formula D1 to D21, D1 to D12, D1 to D6 or D1 to D4, and E is

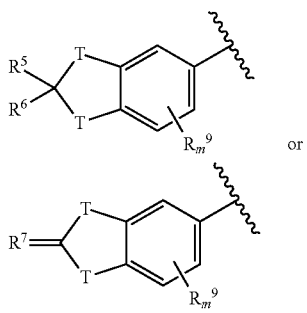

a. with each T being selected independently from each other from —CH, —CH$_2$, —NH, —S or —O, —CHCH$_3$, —C(CH$_3$)$_2$, =N, —NR$^c$, with R$^c$ being —CH$_2$OH, —CH$_3$, —CH$_2$CH$_3$, —CH$_2$CH$_2$CH$_3$, —CH(CH$_3$)$_2$, —CH$_2$CF$_3$, —CHFCF$_3$, —CF$_2$CF$_3$, —CHF$_2$, —CH$_2$F, —CF$_3$ and with $R^5$ and $R^6$ being selected independently from each other from —H, —F, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular $R^5$ and $R^6$ are selected independently from each other from H, F or CH$_3$, and with $R^7$ being selected from =NH, =S or =O, and with m of $R^9_m$ being selected from 0, 1, 2 or 3, and each $R^9$ being selected independently from each other from —Cl, —F, Br, I, —OH, —CCH, —CH$_3$, —CH$_2$CH$_3$, —OCH$_3$, —COOH, —COOR$^b$, —C(O)NH$_2$, —C(O)NH(CH$_3$); —C(O)N(CH$_3$)$_2$, —NHC(=O)OCH$_3$, —NCH$_3$C(=O)OCH$_3$, —CH$_2$CF$_3$, —CHFCF$_3$, —CF$_2$CF$_3$, —CHF$_2$, —CH$_2$F or —CF$_3$, with R$^b$ being a substituted or unsubstituted C$_1$-C$_5$ alkyl, a substituted or unsubstituted C$_2$-C$_5$ alkenyl, a substituted or unsubstituted C$_2$-C$_5$ alkynyl, or a C$_1$-C$_5$ haloalkyl, or b. with m of $R^9_m$ being 0, and with each T being selected independently from each other from —CH, —CH$_2$, —NH, —S or —O, —CHCH$_3$, —C(CH$_3$)$_2$, =N, —NR$^c$, with R$^c$ being —CH$_2$OH, —CH$_3$, —CH$_2$CH$_3$, —CH$_2$CH$_2$CH$_3$, —CH(CH$_3$)$_2$, —CH$_2$CF$_3$, —CHFCF$_3$, —CF$_2$CF$_3$, —CHF$_2$, —CH$_2$F, —CF$_3$ and with $R^5$ and $R^6$ being selected independently from each other from —H, —F, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular $R^5$ and $R^6$ are selected independently from each other from H, F or CH$_3$, and with $R^7$ being selected from =NH, =S or =O, or c. with E being selected from

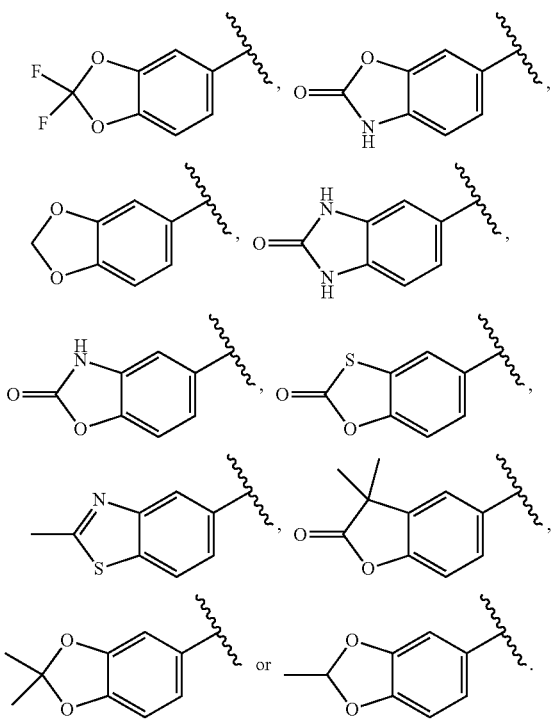

In some embodiments, X of the general formula 1A is

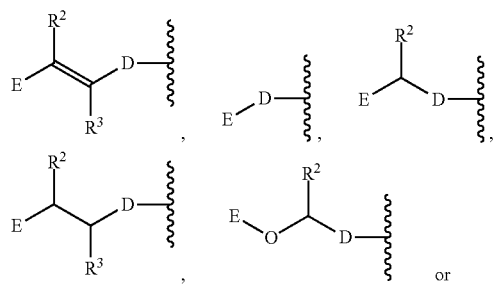

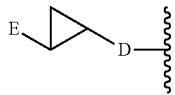

with $R^2$ and $R^3$ being selected, where applicable, independently from each other from —H, —F, —CN, —OH, —NH$_2$, —NO$_2$, —NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl, in particular from —H, —F, —CN, —OH, —NH$_2$, —NO$_2$, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with $R^2$ and $R^3$ being selected independently from each other from H, F or CH$_3$, and with D being

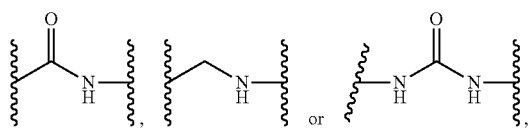

and with

E being

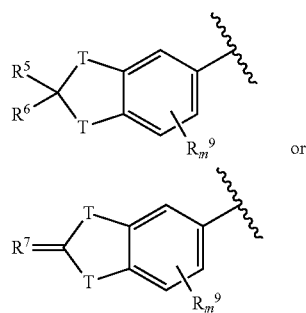

a. with each T being selected independently from each other from —CH, —CH$_2$, —NH, —S or —O, —CHCH$_3$, —C(CH$_3$)$_2$, =N, —NR$^c$, with R$^c$ being —CH$_2$OH, —CH$_3$, —CH$_2$CH$_3$, —CH$_2$CH$_2$CH$_3$, —CH(CH$_3$)$_2$, —CH$_2$CF$_3$, —CHFCF$_3$, —CF$_2$CF$_3$, —CHF$_2$, —CH$_2$F, —CF$_3$ and with R$^5$ and R$^6$ being selected independently from each other from —H, —F, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular R$^5$ and R$^6$ are selected independently from each other from H, F or CH$_3$, and with R$^7$ being selected from =NH, =S or =O, and with m of R$^9{}_m$ being selected from 0, 1, 2 or 3, and each R$^9$ being selected independently from each other from —Cl, —F, Br, I, —OH, —CCH, —CH$_3$, —CH$_2$CH$_3$, —OCH$_3$, —COOH, —COOR$^b$, —C(O)NH$_2$, —C(O)NH(CH$_3$); —C(O)N(CH$_3$)$_2$, —NHC(=O)OCH$_3$, —NCH$_3$C(=O)OCH$_3$, —CH$_2$CF$_3$, —CHFCF$_3$, —CF$_2$CF$_3$, —CHF$_2$, —CH$_2$F or —CF$_3$, with R$^b$ being a substituted or unsubstituted C$_1$-C$_5$ alkyl, a substituted or unsubstituted C$_2$-C$_5$ alkenyl, a substituted or unsubstituted C$_2$-C$_5$ alkynyl, or a C$_1$-C$_5$ haloalkyl, or b. with m of R$^9{}_m$ being 0, and with each T being selected independently from each other from —CH, —CH$_2$, —NH, —S or —O, —CHCH$_3$, —C(CH$_3$)$_2$, =N, —NR$^c$, with R$^c$ being —CH$_2$OH, —CH$_3$, —CH$_2$CH$_3$, —CH$_2$CH$_2$CH$_3$, —CH(CH$_3$)$_2$, —CH$_2$CF$_3$, —CHFCF$_3$, —CF$_2$CF$_3$, —CHF$_2$, —CH$_2$F, —CF$_3$ and with R$^5$ and R$^6$ being selected independently from each other from —H, —F, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular R$^5$ and R$^6$ are selected independently from each other from H, F or CH$_3$, and with R$^7$ being selected from =NH, =S or =O, or c. with E being selected from

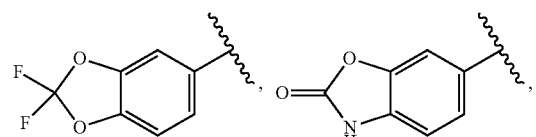

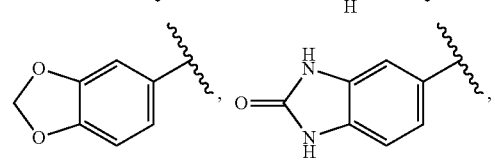

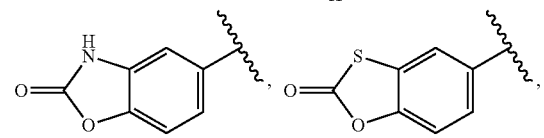

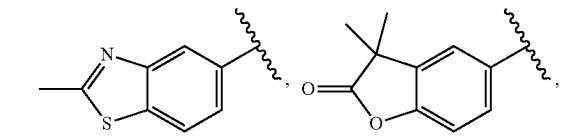

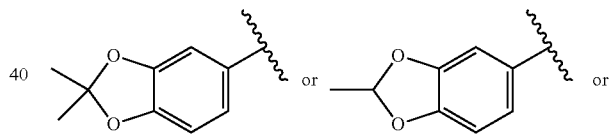

or d. with E being selected from

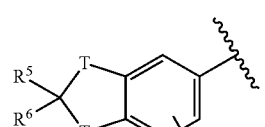

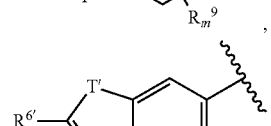

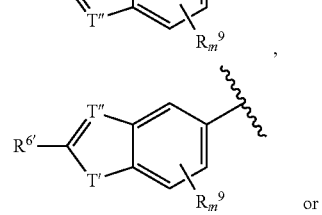

or

-continued

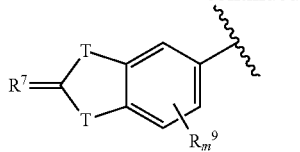

with each T being selected independently from each other from —CH₂, —NH, —S or —O, —CHCH₃, —C(CH₃)₂ or —NR$^c$,
  with R$^c$ being —OH, —CH₃, —CH₂CH₃, —CH₂CH₂CH₃, —CH(CH₃)₂, and
with T' being selected from —CH₂, —NH, —S or —O, —CHCH₃, —C(CH₃)₂ or —NR$^c$, and
with T" being selected from —CH or =N, and
with R⁵ and R⁶ being selected independently from each other from —H, —F, —CH₃, —CH₂CH₃, —OCH₃, —CH₂CF₃, —CHFCF₃, —CF₂CF₃, —CHF₂, —CH₂F or —CF₃, in particular with R⁵ and R⁶ being selected independently from each other from H, —F or —CH₃, and
with R⁶' being selected from OH, —OCH₃, —OCH₂CH₃, —CH₃,
with R⁷ being selected from =NH, =S or =O, and
with m of R⁹$_m$ being selected from 0, 1, 2 or 3, and each R⁹ being selected independently from each other from —Cl, —F, Br, I, —OH, —CCH, —CN—CH₃, —CH₂CH₃, —OCH₃, —COOH, —COOR$^b$, —C(O)NH₂, —C(O)NH(CH₃); —C(O)N(CH₃)₂, —NHC(=O)OCH₃, —NCH₃C(=O)OCH₃, —CH₂CF₃, —CHFCF₃, —CF₂CF₃, —CHF₂, —CH₂F or —CF₃,
  with R$^b$ being a substituted or unsubstituted C₁-C₅ alkyl, a substituted or unsubstituted C₂-C₅ alkenyl, a substituted or unsubstituted C₂-C₅ alkynyl, or a C₁-C₅ haloalkyl In some embodiments, X of the general formula 1A is

with E-D- being selected from

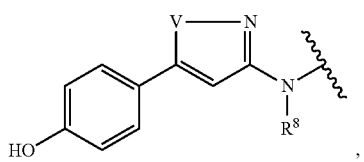

,

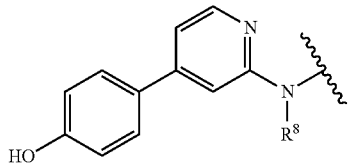

,

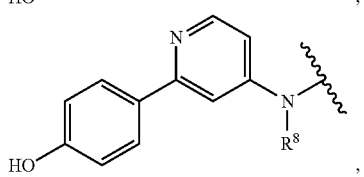

,

-continued

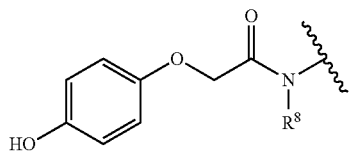

or

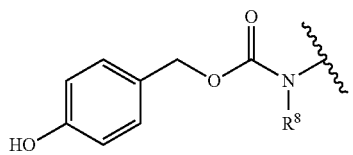

, with R⁸ being selected from H or CH₃, in particular R⁸ is H and with V being selected from O, NH or S, in particular from O or NH.

In some embodiments, X is

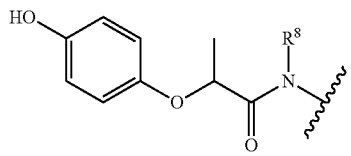

,

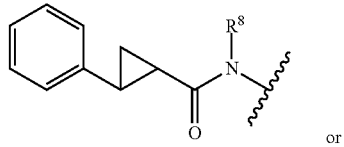

or

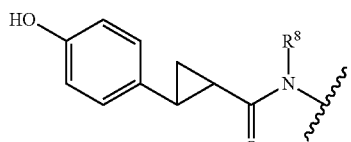

, with R⁸ being selected from H or CH₃, in particular R⁸ is H.

In some embodiments, X of the general formula 1A is

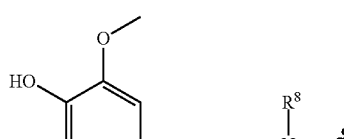

,

,

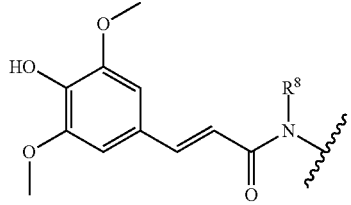

,

159
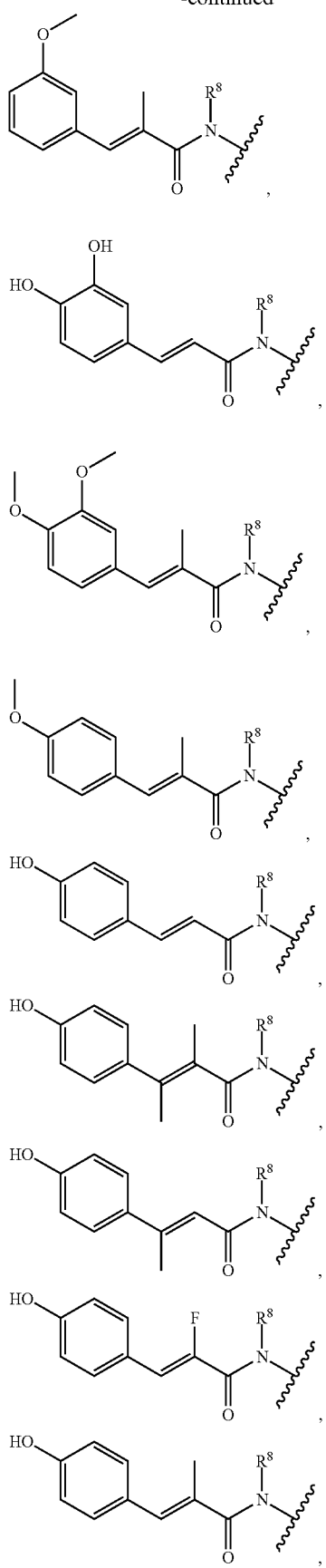
160
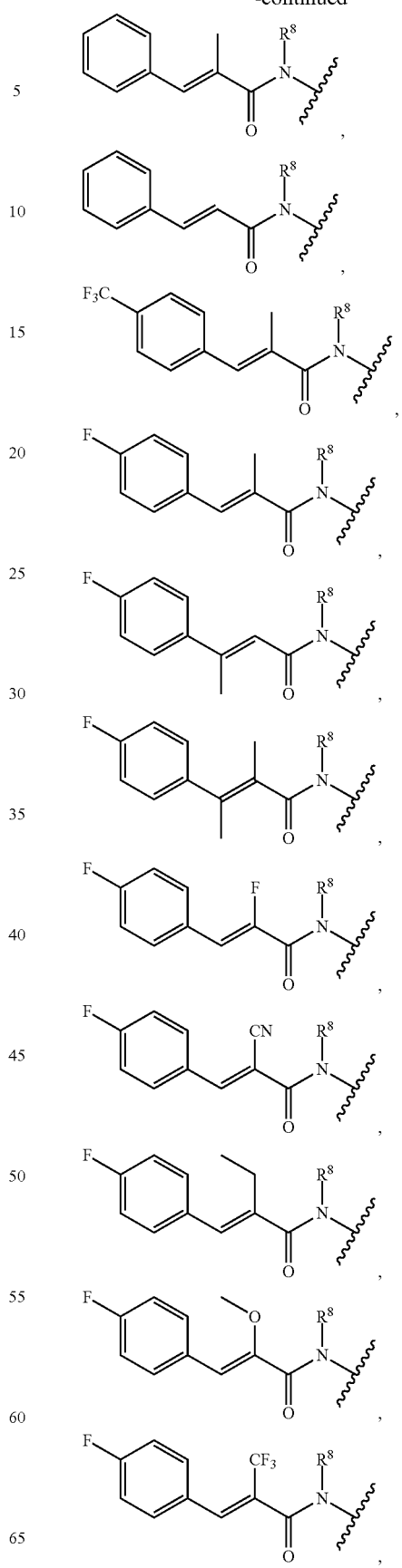

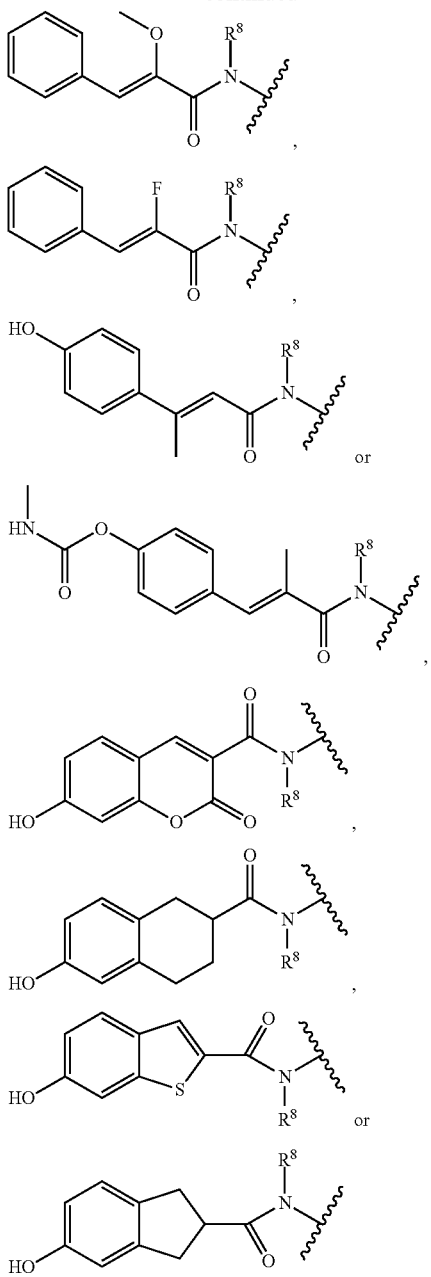

with R⁸ being selected from H or CH₃, in particular R⁸ is H.

In some embodiments, X of the general formula 1A is

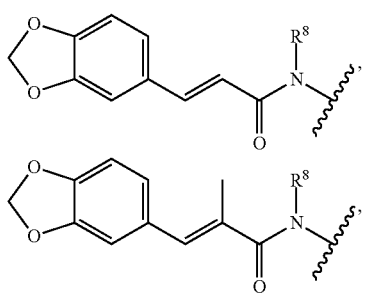

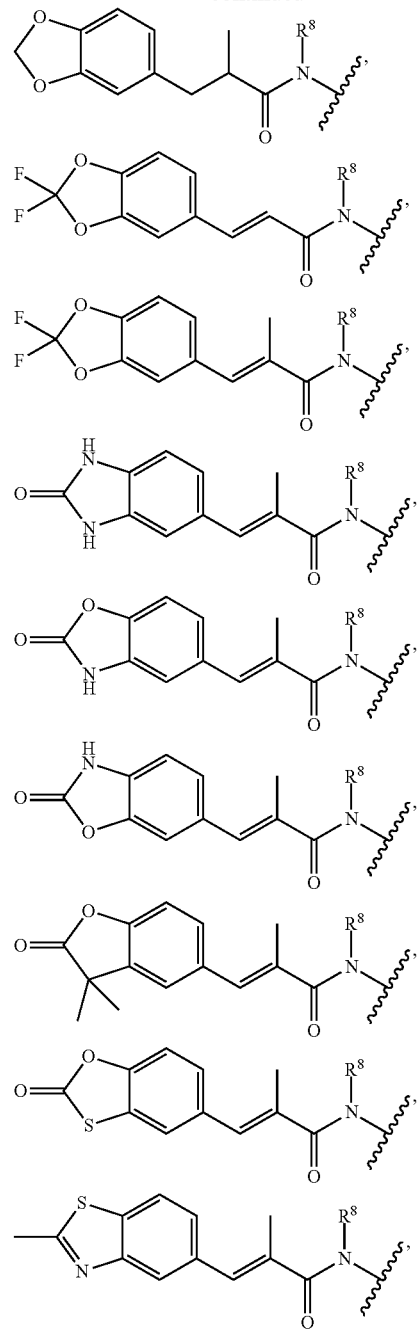

with R⁸ being selected from H or CH₃, in particular R⁸ is H.

In some embodiments, X of the general formula 1A is

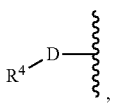

with D being a linker which comprises carbon, sulphur, nitrogen and/or oxygen atoms and which is covalently connecting the moiety comprising R¹ and the parent moiety, in particular D is a linker selected from the linkers characterized by general formula D1 to D21, D1 to D12, D1 to D6 or D1 to D4, and with
a. $R^4$ being
   a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, or a substituted or unsubstituted $C_1$-$C_8$ haloalkyl; or
   a substituted or unsubstituted $C_3$-$C_{10}$ cycloalkyl or a substituted or unsubstituted $C_3$-$C_{10}$ halo cycloalkyl; or
   a substituted or unsubstituted $C_3$-$C_{10}$ heterocycle or a substituted or unsubstituted $C_3$-$C_{10}$ halo heterocycle; in particular a substituted or unsubstituted $C_4$-$C_{10}$ heterocycle or
   a substituted or unsubstituted $C_4$-$C_{10}$ halo heterocycle, or
   a substituted or unsubstituted $C_5$-$C_{10}$ heteroaryl; or
   a substituted or unsubstituted $C_6$-$C_{10}$ aryl, or
b. $R^4$ being
   a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or
   a substituted or unsubstituted $C_4$-$C_{10}$ halo heterocycle, or
   a substituted or unsubstituted $C_5$-$C_{10}$ heteroaryl, or
   a substituted or unsubstituted $C_6$-$C_{10}$ aryl, or
c. $R^4$ being
   a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl, or
d. $R^4$ being
   a straight or branched $C_1$-$C_5$ alkyl or a $C_6$-$C_{10}$ cycloalkyl ring or polyring structure
e. $R^4$ being
   a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the D moiety, or
   a substituted or unsubstituted $C_5$-$C_6$ heteroaryl,
   a substituted $C_6$ aryl, in particular a bicyclic $C_6$ aryl such as tetralin or indane,
   a substituted or unsubstituted halo heteroaryl comprising one or two halogen atoms selected from Cl of F, particularly comprising one Cl or one F in para position (in case of a $C_6$ halo heteroaryl) in relation to the attachment position of the heterocycle to the D moiety; or
   $R^4$ is selected from the group of substituted or unsubstituted pyrrole, furan, thiophene, benzothiophene, chromene, thiazole, pyrazine, pyridazine, pyridine, 1,2,3-triazole, 1,2,4-triazole, imidazole, oxazol, thiazol, indole, isoindole, quinoline, isoquinoline, naphatalene, coumarin, aminocoumarin, umbelliferon, benzotriazole, psoralen, benzofurane, benzothiophene, benzimidazol, benzthiazole, benzoxazole or benzpyridazin or hydroxylated, methylated or halogenated derivatives thereof, or
f. $R^4$ being
   a substituted or unsubstituted $C_1$-$C_5$ alkyl or a substituted or unsubstituted $C_6$-$C_{10}$ cycloalkyl, a substituted or unsubstituted $C_5$-$C_{10}$ heteroaryl or a substituted or unsubstituted $C_6$-$C_{10}$ aryl, or
g. $R^4$ is selected from

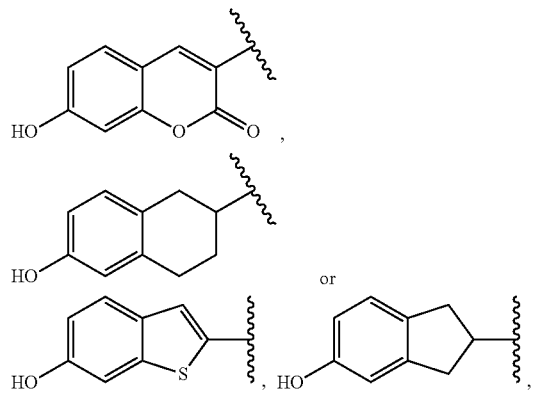

In some embodiments, X of the general formula 1A is

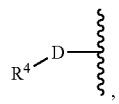

with D being

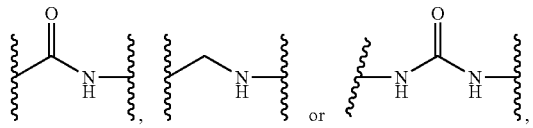

and with
a. $R^4$ being
   a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, or a substituted or unsubstituted $C_1$-$C_8$ haloalkyl; or
   a substituted or unsubstituted $C_3$-$C_{10}$ cycloalkyl or a substituted or unsubstituted $C_3$-$C_{10}$ halo cycloalkyl; or
   a substituted or unsubstituted $C_3$-$C_{10}$ heterocycle or a substituted or unsubstituted $C_3$-$C_{10}$ halo heterocycle; in particular a substituted or unsubstituted $C_4$-$C_{10}$ heterocycle or a substituted or unsubstituted $C_4$-$C_{10}$ halo heterocycle, or
   a substituted or unsubstituted $C_5$-$C_{10}$ heteroaryl; or
   a substituted or unsubstituted $C_6$-$C_{10}$ aryl, or
b. $R^4$ being
   a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
   a substituted or unsubstituted $C_5$-$C_{10}$ heteroaryl, or
   a substituted or unsubstituted $C_6$-$C_{10}$ aryl, or
c. $R^4$ being
   a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, a substituted or unsubstituted $C_1$-$C_8$ haloalkyl, a substituted or unsubstituted $C_3$-$C_{10}$ cycloalkyl, or a substituted or unsubstituted $C_3$-$C_{10}$ halo cycloalkyl, or d. $R^4$ being
   a straight or branched $C_1$-$C_5$ alkyl or a $C_6$-$C_{10}$ cycloalkyl ring or polyring structure e. $R^4$ being
   a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the D moiety, or
   a substituted or unsubstituted $C_5$-$C_6$ heteroaryl,
   a substituted $C_6$ aryl, in particular a bicyclic $C_6$ aryl such as tetralin or indane,
   a substituted or unsubstituted $C_5$-$C_6$ halo heteroaryl comprising one or two halogen atoms selected from Cl of F, particularly comprising one Cl or one F in para position in relation to the attachment position of the heteroaryl to the D moiety; or
   $R^4$ is selected from the group of substituted or unsubstituted pyrrole, furan, thiophene, benzothiophene, chromene, thiazole, pyrazine, pyridazine, pyridine, 1,2,3-triazole, 1,2,4-triazole, imidazole, oxazol, thiazol, indole, isoindole, quinoline, isoquinoline, naphatalene, coumarin, aminocoumarin, umbelliferon, benzotriazole, psoralen, benzofurane, benzothiophene, benzimidazol, benzthiazole, benzoxazole or benzpyridazin or hydroxylated, methylated or halogenated derivatives thereof, f. $R^4$ being
   a substituted or unsubstituted $C_1$-$C_5$ alkyl or a substituted or unsubstituted $C_6$-$C_{10}$ cycloalkyl, a substituted or unsubstituted $C_5$-$C_{10}$ heteroaryl or a substituted or unsubstituted $C_6$-$C_{10}$ aryl.

In some embodiments, X of the general formula 1A is

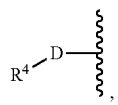

with $R^4$-D- being selected from

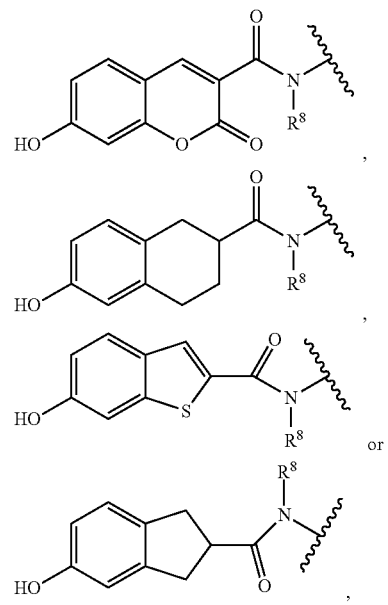

with $R^8$ being selected from H or $CH_3$, in particular $R^8$ is H.

In some embodiments, the compound of the invention is characterised by the general formula CAa

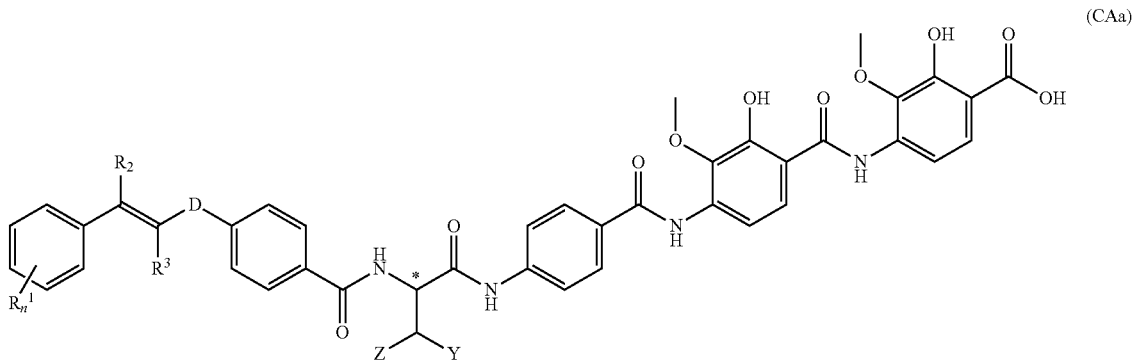

(CAa)

with $R^2$ and $R^3$ being selected, where applicable, independently from each other from —H, —F, —CN, —NHCH$_3$, —NH(CH$_3$)$_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with $R^2$ and $R^3$ being selected independently from each other from H, F or CH$_3$, and with D being a linker which comprises carbon, sulphur, nitrogen and/or oxygen atoms and which is covalently connecting the moiety comprising $R^1$ and the parent moiety, in particular D is a linker selected from the linkers characterized by general formula D1 to D21, D1 to D12, D1 to D6 or D1 to D4, and with n of $R^1{}_n$ being 0, 1, 2, 3, 4 or 5, in particular n of $R^1{}_n$ being 0, 1 or 2, more particularly 0 or 1, and with each $R^1$ independently from any other $R^1$ being —OH, —F, —Cl, —Br, —I, —CCH, —CN, —$N_3$, —$OCH_3$, —$OCF_3$, —$NH_2$, —$CH_3$, —$CF_3$, —$OCONH_2$ or —$NO_2$, or
—$NR^a{}_2$, —$NHR^a$, —$R^a$, —C(=O)$R^a$, —C(=O)$OR^a$, $OR^a$, —OC(=O)$R^a$, —OC(=O)$OR^a$, —OC(=O)$NHR^a$, —NHC(=O)$R^a$, —NHC(=O)$NHR^a$, —C(=O)$NHR^a$ or —NHC(=O)$OR^a$,
  with $R^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or
a substituted or unsubstituted $C_3$-$C_{10}$ cycloalkyl or a substituted or unsubstituted $C_3$-$C_{10}$ halo cycloalkyl, or
a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl, or
a substituted or unsubstituted $C_6$-$C_{10}$ aryl,
wherein in particular $R^1$ is in para position in relation to the attachment position of the benzene moiety to the double bond.

In some embodiments, the compound of the invention is characterised by the general formula CAa with $R^2$ and $R^3$ being selected, where applicable, independently from each other from —H, —F, —CN, —$NHCH_3$, —$NH(CH_3)_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —$NHCH_3$, —$NH(CH_3)_2$, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —$CHFCF_3$, —$CF_2CF_3$, —$CHF_2$, —$CH_2F$ or —$CF_3$, more particularly with $R^2$ and $R^3$ being selected independently from each other from H, F or $CH_3$, in particular $R^2$ and $R^3$ are selected independently from each other from H, F or $CH_3$, and with D being a linker as defined above, in particular D is a linker selected from the linkers characterized by general formula D1 to D21, D1 to D12, D1 to D6 or D1 to D4, and with n of $R^1{}_n$ being 0, 1, 2, 3, 4 or 5, in particular n of $R^1{}_n$ being 0, 1 or 2, more particularly 0 or 1, and
  with each $R^1$ independently from any other $R^1$ being
    —OH, —F, —Cl, —I, —CCH, —CN, —$N_3$, —$OCH_3$, —$OCF_3$, —$NH_2$, —$CH_3$, —$CF_3$, —$OCONH_2$ or —$NO_2$, or
  a substituted or unsubstituted $C_5$-$C_6$ heterocycle
  a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or
  a substituted or unsubstituted $C_5$-$C_6$ heteroaryl,
  a substituted or unsubstituted $C_5$-$C_6$ halo heteroaryl comprising one or two halogen atoms selected from Cl of F, particularly comprising one Cl or one F in para position in relation to the attachment position of the heteroaryl to the benzene moiety, or
  a substituted or unsubstituted $C_6$ aryl; or
with each $R^1$ independently from any other $R^1$ being
  —OH, —F, —Cl, I, —CN, —$OCH_3$, —$OCF_3$ or —$CF_3$; or
with each $R^1$ independently from any other $R^1$ being
  —OH, —F or —$CF_3$,
wherein in particular $R^1$ is in para position in relation to the attachment position of the benzene moiety to the double bond.

In some embodiments, the compound of the invention is characterised by the general formula CAa with $R^2$ being H and $R^3$ being $CH_3$ or $R^2$ being H and $R^3$ being H, and with D being a linker as defined above, in particular D is a linker selected from the linkers characterized by general formula D1 to D21, D1 to D12, D1 to D6 or D1 to D4, and with n of $R^1{}_n$ being 0 or 1, in particular n of $R^1{}_n$ being 1, and
  with $R^1$ being
    —OH, —F, —Cl, —I, —CCH, —CN, —$N_3$, —$OCH_3$, —$OCF_3$, —$NH_2$, —$CH_3$, —$CF_3$, —$OCONH_2$ or —$NO_2$, or
  a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or
  a substituted or unsubstituted $C_5$-$C_6$ heteroaryl,
  a substituted or unsubstituted $C_5$-$C_6$ halo heteroaryl comprising one or two halogen atoms selected from Cl of F, particularly comprising one Cl or one F in para position in relation to the attachment position of the heteroaryl to the benzene moiety,
  a substituted or unsubstituted $C_6$ aryl; or
with $R^1$ being
  —OH, —F, —Cl, I, —CN, —$OCH_3$, —$OCF_3$ or —$CF_3$; or
with $R^1$ being
  —OH, —F or —$CF_3$,
wherein in particular $R^1$ is in para position in relation to the attachment position of the benzene moiety to the double bond.

In some embodiments, the compound of the invention is characterised by the general formula CAb (CAb)

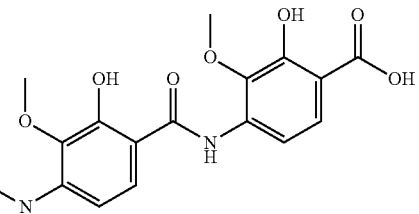
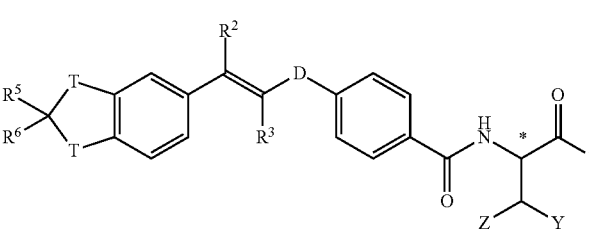

with $R^2$ and $R^3$ being selected, where applicable, independently from each other from —H, —F, —CN, —NHCH$_3$, —NH(CH$_3$)$_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with $R^2$ and $R^3$ being selected independently from each other from H, F or CH$_3$, in particular $R^2$ and $R^3$ are selected independently from each other from H, F or CH$_3$, and with D being a linker which comprises carbon, sulphur, nitrogen and/or oxygen atoms and which is covalently connecting the moiety comprising T and the parent moiety, in particular D is a linker selected from the linkers characterized by general formula D1 to D21, D1 to D12, D1 to D6 or D1 to D4, and with each T being selected independently from each other from —CH, —CH$_2$, —NH, —S or —O, —CHCH$_3$, —C(CH$_3$)$_2$, =N, —NR$^c$, with R$^c$ being —CH$_2$OH, —CH$_3$, —CH$_2$CH$_3$, —CH$_2$CH$_2$CH$_3$, —CH(CH$_3$)$_2$, —CH$_2$CF$_3$, —CHFCF$_3$, —CF$_2$CF$_3$, —CHF$_2$, —CH$_2$F, —CF$_3$ and with $R^5$ and $R^6$ being selected independently from each other from —H, —F, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular $R^5$ and $R^6$ are selected independently from each other from H, F or CH$_3$.

In some embodiments, the compound of the invention is characterised by the general formula CAb with $R^2$ and $R^3$ being selected, where applicable, independently from each other from —H, —F, —CN, —NHCH$_3$, —NH(CH$_3$)$_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with $R^2$ and $R^3$ being selected independently from each other from H, F or CH$_3$, in particular $R^2$ and $R^3$ are selected independently from each other from H, F or CH$_3$, and with D being a linker as defined above, in particular D is a linker selected from the linkers characterized by general formula D1 to D21, D1 to D12, D1 to D6 or D1 to D4, and with $R^5$ and $R^6$ being selected independently from each other from —H, —F, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular $R^5$ and $R^6$ are selected independently from each other from H, F or CH$_3$, more particularly $R^5$ and $R^6$ are H, and with each T being selected independently from each other from —CH, —CH$_2$, —NH, —S or —O; —CHCH$_3$, —C(CH$_3$)$_2$, =N, —NR$^c$, with R$^c$ being —CH$_2$OH, —CH$_3$, —CH$_2$CH$_3$, —CH$_2$CH$_2$CH$_3$, —CH(CH$_3$)$_2$, —CH$_2$CF$_3$, —CHFCF$_3$, —CF$_2$CF$_3$, —CHF$_2$, —CH$_2$F, —CF$_3$ or with each T being O.

In some embodiments, the compound of the invention is characterised by the general formula CAb with $R^2$ being H and $R^3$ being CH$_3$ or $R^2$ being H and $R^3$ being H, and with D being a linker as defined above, in particular D is a linker selected from the linkers characterized by general formula D1 to D21, D1 to D12, D1 to D6 or D1 to D4, and with $R^5$ and $R^6$ being selected independently from each other from —H, —F or —CH$_3$, in particular $R^5$ and $R^6$ are H, and with each T being selected independently from each other from —CH, —CH$_2$, —NH, —S or —O; or —CHCH$_3$, —C(CH$_3$)$_2$, =N, —NR$^c$, with R$^c$ being —CH$_2$OH, —CH$_3$, —CH$_2$CH$_3$, —CH$_2$CH$_2$CH$_3$, —CH(CH$_3$)$_2$, —CH$_2$CF$_3$, —CHFCF$_3$, —CF$_2$CF$_3$, —CHF$_2$, —CH$_2$F, —CF$_3$ with each T being O.

In some embodiments, the compound of the invention is characterised by the general formula CAc, with D being a linker of the formula D1

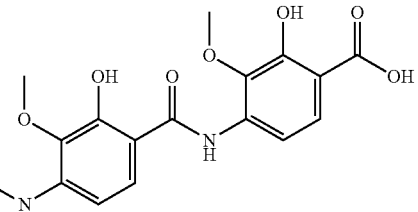

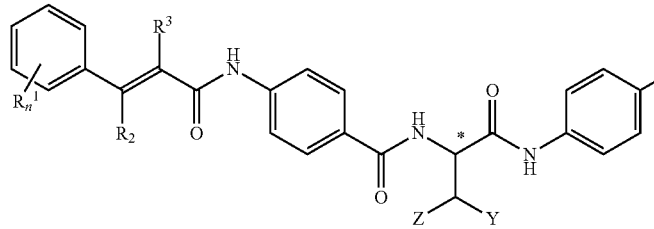

(CAc)

with $R^2$ and $R^3$ being selected, where applicable, independently from each other from —H, —F, —CN, —NHCH$_3$, —NH(CH$_3$)$_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with $R^2$ and $R^3$ being selected independently from each other from H, F or CH$_3$, in particular $R^2$ and $R^3$ are selected independently from each other from H, F or CH$_3$, and with n of $R^1_n$ being 0, 1, 2, 3, 4 or 5, in particular n of $R^1_n$ being 0, 1 or 2, more particularly 1, and with each $R^1$ independently from any other $R^1$ being —OH, —F, —Cl, —Br, I, CCH, —CN, —N$_3$, —OCH$_3$, —OCF$_3$, —NH$_2$, —CH$_3$, —CF$_3$, —OCONH$_2$ or —NO$_2$, or —NR$^a_2$, —NHR$^a$, —R$^a$, —C(=O)R$^a$, —C(=O)OR$^a$, OR$^a$, —OC(=O)R$^a$, —OC(=O)OR$^a$, —OC(=O)NHR$^a$, —NHC(=O)R$^a$, —NHC(=O)NHR$^a$, —C(=O)NHR$^a$ or —NHC(=O)OR$^a$, with R$^a$ being a substituted or unsubstituted C$_1$-C$_8$ alkyl, a substituted or unsubstituted C$_2$-C$_8$ alkenyl, a substituted or unsubstituted C$_2$-C$_8$ alkynyl, or a substituted or unsubstituted C$_1$-C$_8$ haloalkyl, or
a substituted or unsubstituted C$_3$-C$_{10}$ cycloalkyl or a substituted or unsubstituted C$_3$-C$_{10}$ halo cycloalkyl, or
a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle, or
a substituted or unsubstituted C$_5$-C$_{10}$ heteroaryl, or
a substituted or unsubstituted C$_6$-C$_{10}$ aryl,
wherein in particular R$^1$ is in para position in relation to the attachment position of the benzene moiety to the double bond.

In some embodiments, the compound of the invention is characterised by the general formula CAc with R$^2$ and R$^3$ being selected, where applicable, independently from each other from —H, —F, —CN, —NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl, in particular from —H, —F, —CN, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with R$^2$ and R$^3$ being selected independently from each other from H, F or CH$_3$, in particular R$^2$ and R$^3$ are selected independently from each other from H, F or CH$_3$, and with n of R$^1_n$ being 0, 1, 2, 3, 4 or 5, in particular n of R$^1_n$ being 0, 1 or 2, more particularly 1, and
with each R$^1$ independently from any other R$^1$ being
—OH, —F, —Cl, —Br, —I, —CCH, —CN, —N$_3$, —OCH$_3$, —OCF$_3$, —NH$_2$, —CH$_3$, —CF$_3$, —OCONH$_2$ or —NO$_2$, or
a substituted or unsubstituted C$_5$-C$_6$ halo heterocycle, in particular a C$_5$-C$_6$ halo heterocycle comprising one or two halogen atoms selected from Cl of F, particularly comprising one Cl or one F in para position in relation to the attachment position of the heterocycle to the benzene moiety, or
a substituted or unsubstituted C$_5$-C$_6$ heteroaryl,
a substituted or unsubstituted C$_5$-C$_6$ halo heteroaryl comprising one or two halogen atoms selected from Cl of F, particularly comprising one Cl or one F in para position in relation to the attachment position of the heteroaryl to the benzene moiety, or
a substituted or unsubstituted C$_6$ aryl; or
with each R$^1$ independently from any other R$^1$ being
—OH, —F, —Cl, I, —CN, —OCH$_3$, —OCF$_3$ or —CF$_3$; or
with each R$^1$ independently from any other R$^1$ being
—OH, —F or —CF$_3$,
wherein in particular R$^1$ is in para position in relation to the attachment position of the benzene moiety to the double bond.

In some embodiments, the compound of the invention is characterised by the general formula CAc with R$^2$ being H and R$^3$ being CH$_3$ or R$^2$ being H and R$^3$ being H, and with n of R$^1_n$ being 0 or 1, in particular n of R$^1_n$ being 1, and
with R$^1$ being
—OH, —F, —Cl, —I, —CCH, —CN, —N$_3$, —OCH$_3$, —OCF$_3$, —NH$_2$, —CH$_3$, —CF$_3$, —OCONH$_2$ or —NO$_2$, or
a substituted or unsubstituted C$_5$-C$_6$ halo heterocycle, in particular a C$_5$-C$_6$ halo heterocycle comprising one or two halogen atoms selected from Cl of F, particularly comprising one Cl or one F in para position in relation to the attachment position of the heterocycle to the benzene moiety, or
a substituted or unsubstituted C$_5$-C$_6$ heteroaryl,
a substituted or unsubstituted C$_5$-C$_6$ halo heteroaryl comprising one or two halogen atoms selected from Cl of F, particularly comprising one Cl or one F in para position in relation to the attachment position of the heteroaryl to the benzene moiety, or
a substituted or unsubstituted C$_6$ aryl; or
with each R$^1$ independently from any other R$^1$ being
—OH, —F, —Cl, I, —CN, —OCH$_3$, —OCF$_3$ or —CF$_3$; or
with each R$^1$ independently from any other R$^1$ being
—OH, —F or —CF$_3$,
wherein in particular R$^1$ is in para position in relation to the attachment position of the benzene moiety to the double bond.

In some embodiments, the compound of the invention is characterised by the general formula CAd, with D being a linker of the formula D1

(CAd)

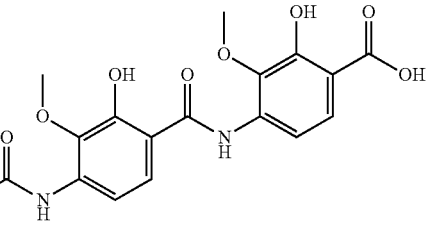

position in relation to the attachment position of the heterocycle to the benzene moiety, or
a substituted or unsubstituted C$_5$-C$_6$ heteroaryl,
a substituted or unsubstituted C$_5$-C$_6$ halo heteroaryl comprising one or two halogen atoms selected from Cl of F, particularly comprising one Cl or one F in para position in relation to the attachment position of the heteroaryl to the benzene moiety, or
a substituted or unsubstituted C$_6$ aryl; or with R$^2$ and R$^3$ being selected, where applicable, independently from each other from —H, —F, —CN, —NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl, in particular from —H, —F, —CN, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with R$^2$ and R$^3$ being selected independently from each other from H, F or CH₃, in particular R² and R³ are selected independently from each other from H, F or CH₃, and with each T being selected independently from each other from —CH, —CH₂, —NH, —S or —O, —CHCH₃, —C(CH₃)₂, =N, —NR$^c$, with R$^c$ being —CH₂OH, —CH₃, —CH₂CH₃, —CH₂CH₂CH₃, —CH(CH₃)₂, —CH₂CF₃, —CHFCF₃, —CF₂CF₃, —CHF₂, —CH₂F, —CF₃ or with each T being O.

In some embodiments, the compound of the invention is characterised by the general formula BAa

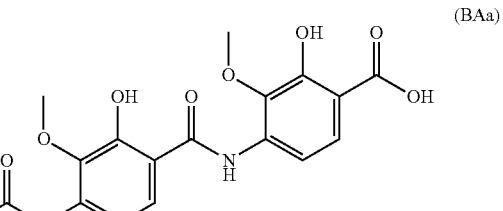
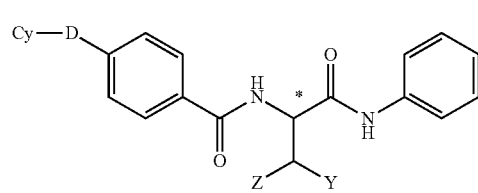

(BAa)

—CH₂CH₃, —CH₂CH₂CH₃, —CH(CH₃)₂, —CH₂CF₃, —CHFCF₃, —CF₂CF₃, —CHF₂, —CH₂F, —CF₃ and with R⁵ and R⁶ being selected independently from each other from —H, —F, —CH₃, —CH₂CH₃, —OCH₃, —CH₂CF₃, —CHFCF₃, —CF₂CF₃, —CHF₂, —CH₂F or —CF₃, in particular R⁵ and R⁶ are selected independently from each other from H, F or CH₃.

In some embodiments, the compound of the invention is characterised by the general formula CAd with R² and R³ being selected, where applicable, independently from each other from —H, —F, —CN, —NHCH₃, —NH(CH₃)₂, a substituted or unsubstituted C₁-C₃ alkyl, a substituted or unsubstituted C₁-C₃ alkoxy or a C₁-C₃ haloalkyl, in particular from —H, —F, —CN, —NHCH₃, —NH(CH₃)₂, —CH₃, —CH₂CH₃, —OCH₃, —OCH₂CH₃, —OCH₂CH₂CH₃, —OCH(CH₃)₂, —OCF₃, —CH₂CF₃, —CHFCF₃, —CF₂CF₃, —CHF₂, —CH₂F or —CF₃, more particularly with R² and R³ being selected independently from each other from H, F or CH₃, in particular R² and R³ are selected independently from each other from H, F or CH₃, and with R⁵ and R⁶ being selected independently from each other from —H, —F, —CH₃, —CH₂CH₃, —OCH₃, —CH₂CF₃, —CHFCF₃, —CF₂CF₃, —CHF₂, —CH₂F or —CF₃, in particular R⁵ and R⁶ are selected independently from each other from H, F or CH₃, more particularly R⁵ and R⁶ are H, and with each T being selected independently from each other from CH, —CH₂, —NH, —S or —O; —CHCH₃, —C(CH₃)₂, =N, —NR$^c$, with R$^c$ being —CH₂OH, —CH₃, —CH₂CH₃, —CH₂CH₂CH₃, —CH(CH₃)₂, —CH₂CF₃, —CHFCF₃, —CF₂CF₃, —CHF₂, —CH₂F, —CF₃ or with each T being O.

In some embodiments, the compound of the invention is characterised by the general formula CAd with R² being H and R³ being CH₃ or R² being H and R³ being H, and with R⁵ and R⁶ being selected independently from each other from —H, —F or —CH₃, in particular R⁵ and R⁶ are H, and with each T being selected independently from each other from CH, —CH₂, —NH, —S or —O; —CHCH₃, —C(CH₃)₂, =N, —NR$^c$, with R$^c$ being —CH₂OH, with D being a linker which comprises carbon, sulphur, nitrogen and/or oxygen atoms and which is covalently connecting the moiety comprising Cy and the parent moiety, in particular D is a linker selected from the linkers characterized by general formula D1 to D21, D1 to D12, D1 to D6 or D1 to D4, and with Cy being a substituted or unsubstituted C₃-C₁₀ heterocycle or a substituted or unsubstituted C₃-C₁₀ halo heterocycle, in particular a substituted or unsubstituted C₄-C₁₀ heterocycle or a substituted or unsubstituted C₄-C₁₀ halo heterocycle, or a substituted or unsubstituted C₅-C₁₀ heteroaryl, or a substituted or unsubstituted C₆-C₁₀ aryl.

In some embodiments, the compound of the invention is characterised by the general formula BAa with D being a linker as defined above, in particular D is a linker selected from the linkers characterized by general formula D1 to D21, D1 to D12, D1 to D6 or D1 to D4, and with Cy being a substituted or unsubstituted C₅-C₆ halo heterocycle, in particular a C₅-C₆ halo heterocycle comprising one or two halogen atoms selected from Cl of F, particularly comprising one Cl or one F in para position in relation to the attachment position of the heterocycle to the D moiety, or a substituted or unsubstituted C₅-C₆ heteroaryl, a substituted C₆ aryl, in particular a bicyclic C₆ aryl such as tetralin or indane, a substituted or unsubstituted C₅-C₆ halo heteroaryl comprising one or two halogen atoms selected from Cl of F, particularly comprising one Cl or one F in para position in relation to the attachment position of the heteroaryl to the D moiety; or Cy being selected from the group of substituted or unsubstituted pyrrole, furan, thiophene, benzothiophene, chromene, thiazole, pyrazine, pyridazine, pyridine, 1,2,3-triazole, 1,2,4-triazole, imidazole, oxazol, thiazol, indole, isoindole, quinoline, isoquinoline, naphatalene, coumarin, aminocoumarin, umbelliferon, benzotriazole, psoralen, benzofurane, benzothiophene, benzimidazol, benzthiazole, benzoxazole or benzpyridazin or hydroxylated, methylated or halogenated derivatives thereof.

In some embodiments, the compound of the invention is characterised by the general formula BAb

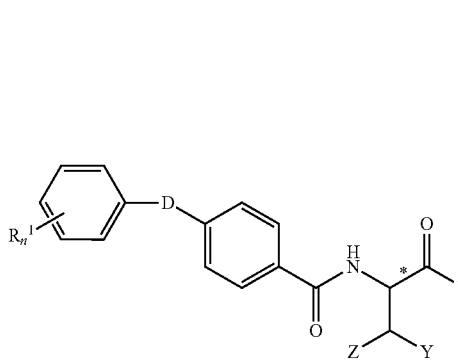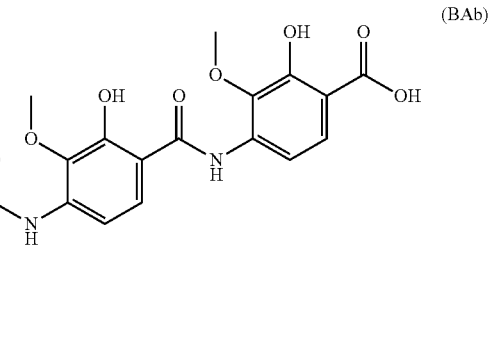

(BAb)

with D being a linker which comprises carbon, sulphur, nitrogen and/or oxygen atoms and which is covalently connecting the moiety comprising $R^1$ and the parent moiety, in particular D is a linker selected from the linkers characterized by general formula D1 to D21, D1 to D12, D1 to D6 or D1 to D4, and with n of $R^1_n$ being 0, 1, 2, 3, 4 or 5, in particular n of $R^1_n$ being 0, 1 or 2, more particularly 1, and with each $R^1$ independently from any other $R^1$ being
- —H, —OH, —F, —Cl, —Br, I, CCH, —CN, —N$_3$, —OCH$_3$, —OCF$_3$, —NH$_2$, —CH$_3$, —CF$_3$, —OCONH$_2$ or —NO$_2$, or
- —NR$^a_2$, —NHR$^a$, —R$^a$, —C(=O)R$^a$, —C(=O)OR$^a$, OR$^a$, —OC(=O)R$^a$, —OC(=O)OR$^a$, —OC(=O)NHR$^a$, —NHC(=O)R$^a$, —NHC(=O)NHR$^a$, —C(=O)NHR$^a$ or —NHC(=O)OR$^a$,
    - with R$^a$ being a substituted or unsubstituted C$_1$-C$_8$ alkyl, a substituted or unsubstituted C$_2$-C$_8$ alkenyl, a substituted or unsubstituted C$_2$-C$_8$ alkynyl, or a substituted or unsubstituted C$_1$-C$_8$ haloalkyl, or
- a substituted or unsubstituted C$_3$-C$_{10}$ cycloalkyl or a substituted or unsubstituted C$_3$-C$_{10}$ halo cycloalkyl, or
- a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle, or
- a substituted or unsubstituted C$_5$-C$_{10}$ heteroaryl, or
- a substituted or unsubstituted C$_6$-C$_{10}$ aryl, wherein in particular $R^1$ is in para position in relation to the attachment position of the benzene moiety to the D moiety.

In some embodiments, the compound of the invention is characterised by the general formula BAb with D being a linker as defined above, in particular D is a linker selected from the linkers characterized by general formula D1 to D21, D1 to D12, D1 to D6 or D1 to D4, and with n of $R^1_n$ being 0, 1, 2, 3, 4 or 5, in particular n of $R^1_n$ being 0, 1 or 2, more particularly 1, and
- with each $R^1$ independently from any other $R^1$ being
    - —OH, —F, —Cl, Br, I, CCH, —CN, —N$_3$, —OCH$_3$, —OCF$_3$, —NH$_2$, —CH$_3$, —CF$_3$, —OCONH$_2$ or —NO$_2$, or
- a substituted or unsubstituted C$_5$-C$_6$ heterocycle
- a substituted or unsubstituted C$_5$-C$_6$ halo heterocycle, in particular a C$_5$-C$_6$ halo heterocycle comprising one or two halogen atoms selected from Cl of F, particularly comprising one Cl or one F in para position in relation to the attachment position of the heterocycle to the D moiety, or
- a substituted or unsubstituted C$_5$-C$_6$ heteroaryl,
- a substituted or unsubstituted C$_5$-C$_6$ halo heteroaryl comprising one or two halogen atoms selected from Cl of F, particularly comprising one Cl or one F in para position in relation to the attachment position of the heteroaryl to the D moiety, or
- a substituted or unsubstituted C$_6$ aryl; or
with each $R^1$ independently from any other $R^1$ being
    - —OH, —F, —Cl, I, —CN, —OCH$_3$, —OCF$_3$ or —CF$_3$; or
with each $R^1$ independently from any other $R^1$ being
    - —OH, —F or —CF$_3$, wherein in particular $R^1$ is in para position in relation to the attachment position of the benzene moiety to the D moiety.

In some embodiments, the compound of the invention is characterised by the general formula BAb with D being a linker as defined above, in particular D is a linker selected from the linkers characterized by general formula D1 to D21, D1 to D12, D1 to D6 or D1 to D4, and with n of $R^1_n$ being 0 or 1, in particular n of $R^1_n$ being 1, and
with $R^1$ being
- —OH, —F, —Cl, Br, I, CCH, —CN, —N$_3$, —OCH$_3$, —OCF$_3$, —NH$_2$, —CH$_3$, —CF$_3$, —OCONH$_2$ or —NO$_2$, or
- a substituted or unsubstituted C$_5$-C$_6$ heterocycle
- a substituted or unsubstituted C$_5$-C$_6$ halo heterocycle, in particular a C$_5$-C$_6$ halo heterocycle comprising one or two halogen atoms selected from Cl of F, particularly comprising one Cl or one F in para position in relation to the attachment position of the heterocycle to the D moiety, or
- a substituted or unsubstituted C$_5$-C$_6$ heteroaryl,
- a substituted or unsubstituted C$_5$-C$_6$ halo heteroaryl comprising one or two halogen atoms selected from Cl of F, particularly comprising one Cl or one F in para position in relation to the attachment position of the heteroaryl to the D moiety, or
- a substituted or unsubstituted C$_6$ aryl; or
with each $R^1$ independently from any other $R^1$ being
    - —OH, —F, —Cl, I, —CN, —OCH$_3$, —OCF$_3$ or —CF$_3$; or
with each $R^1$ independently from any other $R^1$ being
    - —OH, —F or —CF$_3$, wherein in particular $R^1$ is in para position in relation to the attachment position of the benzene moiety to the D moiety.

In some embodiments, the compound of the invention is characterised by the general formula BAc with D being a linker of the formula D1

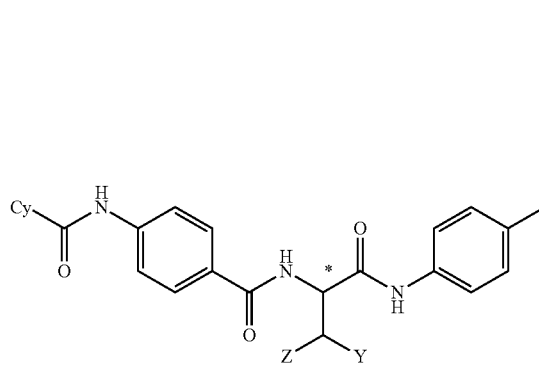
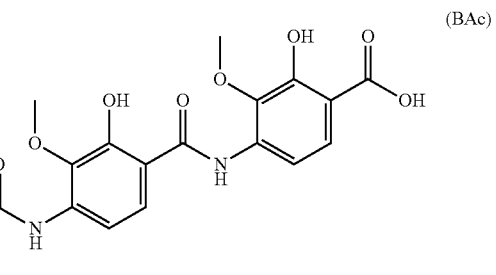

(BAc)

with Cy being
a substituted or unsubstituted $C_3$-$C_{10}$ heterocycle or substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl, or
a substituted or unsubstituted $C_6$-$C_{10}$ aryl.

In some embodiments, the compound of the invention is characterised by the general formula BAc with
Cy being
a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the —C(=O)—NH— moiety, or a substituted or unsubstituted $C_5$-$C_6$ heteroaryl, a substituted $C_6$ aryl, in particular a bicyclic $C_6$ aryl such as tetralin or indane, a substituted or unsubstituted $C_5$-$C_6$ halo heteroaryl comprising one or two halogen atoms selected from Cl of F, particularly comprising one Cl or one F in para position in relation to the attachment position of the heteroaryl to the —C(=O)—NH— moiety; or Cy being selected from the group of substituted or unsubstituted pyrrole, furan, thiophene, benzothiophene, chromene, thiazole, pyrazine, pyridazine, pyridine, 1,2,3-triazole, 1,2,4-triazole, imidazole, oxazol, thiazol, indole, isoindole, quinoline, isoquinoline, naphatalene, coumarin, aminocoumarin, umbelliferon, benzotriazole, psoralen, benzofurane, benzothiophene, benzimidazol, benzthiazole, benzoxazole or benzpyridazin or hydroxylated, methylated or halogenated derivatives thereof.

In some embodiments, the compound of the invention is characterised by the general formula BAd with D being a linker of the formula D1

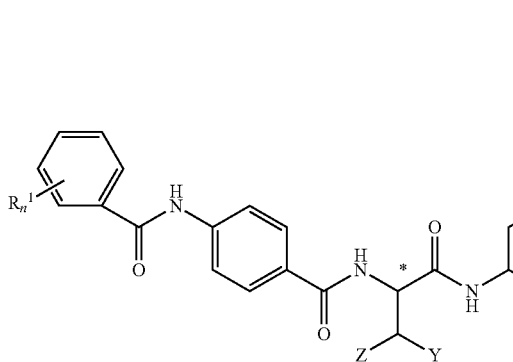

(BAd)

with n of $R^1_n$ being 0, 1, 2, 3, 4 or 5, in particular n of $R^1_n$ being 0, 1 or 2, more particularly 1, and with each $R^1$ independently from any other $R^1$ being
—OH, —F, —Cl, —Br, I, CCH, —CN, —N$_3$, —OCH$_3$, —OCF$_3$, —NH$_2$, —CH$_3$, —CF$_3$, —OCONH$_2$ or —NO$_2$, or
—NR$^a_2$, —NHR$^a$, —R$^a$, —C(=O)R$^a$, —C(=O)OR$^a$, OR$^a$, —OC(=O)R$^a$, —OC(=O)OR$^a$, —OC(=O) NHR$^a$, —NHC(=O)R$^a$, —NHC(=O)NHR$^a$, —C(=O)NHR$^a$ or —NHC(=O)OR$^a$,
with R$^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or
a substituted or unsubstituted $C_3$-$C_{10}$ cycloalkyl or a substituted or unsubstituted $C_3$-$C_{10}$ halo cycloalkyl, or
a substituted or unsubstituted $C_3$-$C_{10}$ heterocycle or substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted C$_5$-C$_{10}$ heteroaryl, or
a substituted or unsubstituted C$_6$-C$_{10}$ aryl,
wherein in particular R$^1$ is in para position in relation to the attachment position of the benzene moiety to the —C(═O)NH— moiety.

In some embodiments, the compound of the invention is characterised by the general formula BAd with n of R$^1_n$ being 0, 1, 2, 3, 4 or 5, in particular n of R$^1_n$ being 0, 1 or 2, more particularly 1, and
with each R$^1$ independently from any other R$^1$ being
—OH, —F, —Cl, Br, I, CCH, —CN, —N$_3$, —OCH$_3$, —OCF$_3$, —NH$_2$, —CH$_3$, —CF$_3$, —OCONH$_2$ or —NO$_2$, or
a substituted or unsubstituted C$_5$-C$_6$ heterocycle
a substituted or unsubstituted C$_5$-C$_6$ halo heterocycle, in particular a C$_5$-C$_6$ halo heterocycle comprising one or two halogen atoms selected from Cl of F, particularly comprising one Cl or one F in para position in relation to the attachment position of the heterocycle to the —C(═O)NH— moiety, or
a substituted or unsubstituted C$_5$-C$_6$ heteroaryl,
a substituted or unsubstituted C$_5$-C$_6$ halo heteroaryl comprising one or two halogen atoms selected from Cl of F, particularly comprising one Cl or one F in para position in relation to the attachment position of the heteroaryl to the —C(═O)NH— moiety, or
a substituted or unsubstituted C$_6$ aryl; or
with each R$^1$ independently from any other R$^1$ being
—OH, —F, —Cl, —CN, I, —OCH$_3$, —OCF$_3$ or —CF$_3$; or
with each R$^1$ independently from any other R$^1$ being
—OH, —F or —CF$_3$,
wherein in particular R$^1$ is in para position in relation to the attachment position of the benzene moiety to th —C(═O)NH— moiety.

In some embodiments, the compound of the invention is characterised by the general formula BAd with n of R$^1_n$ being 0 or 1, in particular n of R$^1_n$ being 1, and
with R$^1$ being
—OH, —F, —Cl, —Br, —I, —CCH, —CN, —N$_3$, —OCH$_3$, —OCF$_3$, —NH$_2$, —CH$_3$, —CF$_3$, —OCONH$_2$ or —NO$_2$, or
a substituted or unsubstituted C$_5$-C$_6$ heterocycle
a substituted or unsubstituted C$_5$-C$_6$ halo heterocycle, in particular a C$_5$-C$_6$ halo heterocycle comprising one or two halogen atoms selected from Cl of F, particularly comprising one Cl or one F in para position in relation to the attachment position of the heterocycle to the —C(═O)NH— moiety, or
a substituted or unsubstituted C$_5$-C$_6$ heteroaryl,
a substituted or unsubstituted C$_5$-C$_6$ halo heteroaryl comprising one or two halogen atoms selected from Cl of F, particularly comprising one Cl or one F in para position in relation to the attachment position of the heteroaryl to the —C(═O)NH— moiety, or
a substituted or unsubstituted C$_6$ aryl; or
with each R$^1$ independently from any other R$^1$ being
—OH, —F, —Cl, I, —CN, —OCH$_3$, —OCF$_3$ or —CF$_3$; or
with each R$^1$ independently from any other R$^1$ being
—OH, —F or —CF$_3$,
wherein in particular R$^1$ is in para position in relation to the attachment position of the benzene moiety to the —C(═O)NH— moiety.

In some embodiments, the compound of the invention is characterised by the general formula PAa

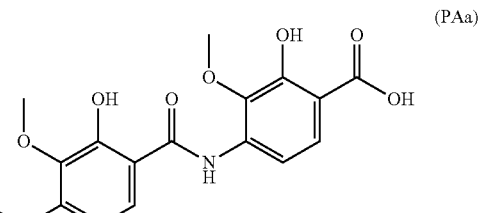
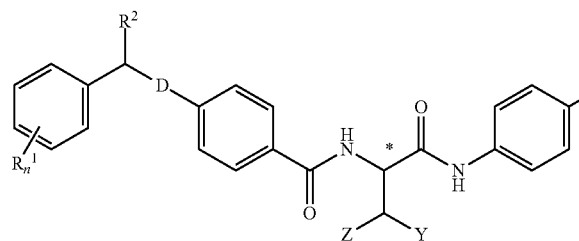

(PAa)

with R$^2$ being selected, where applicable, from —H, —OH, —NH$_2$, —NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl, in particular from —H, —OH, —NH$_2$, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with R$^2$ being selected from H or CH$_3$, with D being a linker which comprises carbon, sulphur, nitrogen and/or oxygen atoms and which is covalently connecting the moiety comprising R$^1$ and the parent moiety, in particular D is a linker selected from the linkers characterized by general formula D1 to D21, D1 to D12, D1 to D6 or D1 to D4, and with n of R$^1_n$ being 0, 1, 2, 3, 4 or 5, in particular n of R$^1_n$ being 0, 1 or 2, more particularly 1, and with each R$^1$ independently from any other R$^1$ being
—OH, —F, —Cl, —Br, —I, —CCH, —CN, —N$_3$, —OCH$_3$, —OCF$_3$, —NH$_2$, —CH$_3$, —CF$_3$, —OCONH$_2$ or —NO$_2$, or
—NR$^a_2$, —NHR$^a$, —R$^a$, —C(═O)R$^a$, —C(═O)OR$^a$, OR$^a$, —OC(═O)R$^a$, —OC(═O)OR$^a$, —OC(═O)NHR$^a$, —NHC(═O)R$^a$, —NHC(═O)NHR$^a$, —C(═O)NHR$^a$ or —NHC(═O)OR$^a$,
with R$^a$ being a substituted or unsubstituted C$_1$-C$_8$ alkyl, a substituted or unsubstituted C$_2$-C$_8$ alkenyl, a substituted or unsubstituted C$_2$-C$_8$ alkynyl, or a substituted or unsubstituted C$_1$-C$_8$ haloalkyl, or
a substituted or unsubstituted C$_3$-C$_{10}$ cycloalkyl or a substituted or unsubstituted C$_3$-C$_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl, wherein in particular $R^1$ is in para position in relation to the attachment position of the benzene moiety to the —$CR^2$-D moiety In some embodiments, the compound of the invention is characterised by the general formula PAa, with $R^2$ being selected, where applicable, from —H, —OH, —$NH_2$, —$NHCH_3$, —$NH(CH_3)_2$, a substituted or unsubstituted $C_1$-$C_3$ alkyl, a substituted or unsubstituted $C_1$-$C_3$ alkoxy or a $C_1$-$C_3$ haloalkyl, in particular from —H, —OH, —$NH_2$, —$NHCH_3$, —$NH(CH_3)_2$, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —$CHFCF_3$, —$CF_2CF_3$, —$CHF_2$, —$CH_2F$ or —$CF_3$, more particularly with $R^2$ being selected from H or $CH_3$, with D being a linker as defined above, in particular D is a linker selected from the linkers characterized by general formula D1 to D21, D1 to D12, D1 to D6 or D1 to D4, and with n of $R^1{}_n$ being 0, 1, 2, 3, 4 or 5, in particular n of $R^1{}_n$ being 0, 1 or 2, more particularly 1, and with each $R^1$ independently from any other $R^1$ being
—OH, —F, —Cl, —Br, —I, —CCH, —CN, —$N_3$, —$OCH_3$, —$OCF_3$, —$NH_2$, —$CH_3$, —$CF_3$, —$OCONH_2$ or —$NO_2$, or a substituted or unsubstituted $C_5$-$C_6$ heterocycle a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or a substituted or unsubstituted $C_5$-$C_6$ heteroaryl, a substituted or unsubstituted $C_5$-$C_6$ halo heteroaryl comprising one or two halogen atoms selected from Cl of F, particularly comprising one Cl or one F in para position in relation to the attachment position of the heteroaryl to the -benzene moiety, or a substituted or unsubstituted $C_6$ aryl; or with each $R^1$ independently from any other $R^1$ being
—OH, —F, —Cl, I, —CN, —$OCH_3$, —$OCF_3$ or —$CF_3$; or with each $R^1$ independently from any other $R^1$ being
—OH, —F or —Cl, wherein in particular $R^1$ is in para position in relation to the attachment position of the benzene moiety to the —$CR^2$-D moiety.

In some embodiments, the compound of the invention is characterised by the general formula PAa, with $R^2$ being selected —H or —$CH_3$, in particular with $R^2$ being —H, with D being a linker as defined above, in particular D is a linker selected from the linkers characterized by general formula D1 to D21, D1 to D12, D1 to D6 or D1 to D4, and with n of $R^1{}_n$ being 0 or 1, in particular n of $R^1{}_n$ being 1, and with $R^1$ being
—OH, —F, —Cl, —Br, —I, —CCH, —CN, —$N_3$, —$OCH_3$, —$OCF_3$, —$NH_2$, —$CH_3$, —$CF_3$, —$OCONH_2$ or —$NO_2$, or a substituted or unsubstituted $C_5$-$C_6$ heterocycle a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or a substituted or unsubstituted $C_5$-$C_6$ heteroaryl, a substituted or unsubstituted $C_5$-$C_6$ halo heteroaryl comprising one or two halogen atoms selected from Cl of F, particularly comprising one Cl or one F in para position in relation to the attachment position of the heteroaryl to the benzene moiety, or a substituted or unsubstituted $C_6$ aryl; or with each $R^1$ independently from any other $R^1$ being
—OH, —F, —Cl, I, —CN, —$OCH_3$, —$OCF_3$ or —$CF_3$; or with each $R^1$ independently from any other $R^1$ being
—OH, —F or —Cl, wherein in particular $R^1$ is in para position in relation to the attachment position of the benzene moiety to the —$CR^2$-D moiety.

In some embodiments, the compound of the invention is characterised by the general formula PAb with D being a linker of the formula D1

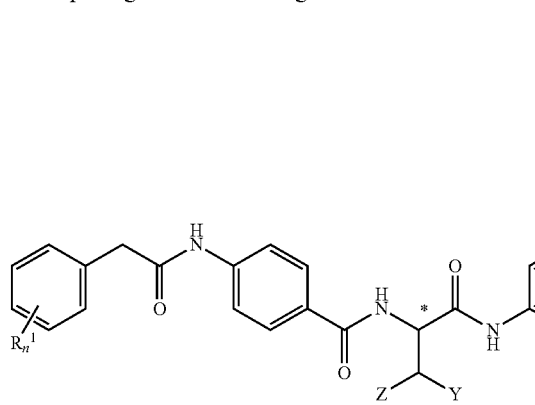
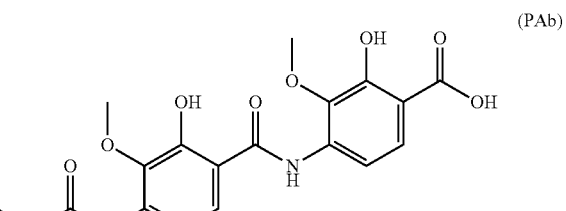

(PAb)

with n of $R^1{}_n$ being 0, 1, 2, 3, 4 or 5, in particular n of $R^1{}_n$ being 0, 1 or 2, more particularly 1, and with each $R^1$ independently from any other $R^1$ being —OH, —F, —Cl, —Br, I, CCH, —CN, —$N_3$, —$OCH_3$, —$OCF_3$, —$NH_2$, —$CH_3$, —$CF_3$, —$OCONH_2$ or —$NO_2$, or —$NR^a{}_2$, —$NHR^a$, —$R^a$, —C(=O)$R^a$, —C(=O)O$R^a$, O$R^a$, —OC(=O)$R^a$, —OC(=O)O$R^a$, —OC(=O) NH$R^a$, —NHC(=O)$R^a$, —NHC(=O)NH$R^a$, —C(=O)NH$R^a$ or —NHC(=O)O$R^a$, with $R^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl, wherein in particular $R^1$ is in para position in relation to the attachment position of the benzene moiety to the —$CH_2$-D- moiety.

In some embodiments, the compound of the invention is characterised by the general formula PAb with n of $R^1_n$ being 0, 1, 2, 3, 4 or 5, in particular n of $R^1_n$ being 0, 1 or 2, more particularly 1, and with each $R^1$ independently from any other $R^1$ being
—OH, —F, —Cl, Br, I, CCH, —CN, —$N_3$, —$OCH_3$, —$OCF_3$, —$NH_2$, —$CH_3$, —$CF_3$, —$OCONH_2$ or —$NO_2$, or a substituted or unsubstituted $C_5$-$C_6$ heterocycle a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or a substituted or unsubstituted $C_5$-$C_6$ heteroaryl, a substituted or unsubstituted $C_5$-$C_6$ halo heteroaryl comprising one or two halogen atoms selected from Cl of F, particularly comprising one Cl or one F in para position in relation to the attachment position of the heteroaryl to the benzene moiety, or a substituted or unsubstituted $C_6$ aryl; or with each $R^1$ independently from any other $R^1$ being
—OH, —F, —Cl, I, —CN, —$OCH_3$, —$OCF_3$ or —$CF_3$; or with each $R^1$ independently from any other $R^1$ being
—OH, —F or —Cl, wherein in particular $R^1$ is in para position in relation to the attachment position of the benzene moiety to the —$CH_2$-D- moiety.

In some embodiments, the compound of the invention is characterised by the general formula PPa with $R^2$ and $R^3$ being selected, where applicable, independently from each other from —H, —F, —CN, —OH, —$NH_2$, —$NO_2$, —$NHCH_3$, —$NH(CH_3)_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —$NH_2$, —$NO_2$, —$NHCH_3$, —NH($CH_3)_2$, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —$CHFCF_3$, —$CF_2CF_3$, —$CHF_2$, —$CH_2F$ or —$CF_3$, more particularly with $R^2$ and $R^3$ being selected independently from each other from H, F or $CH_3$, in particular $R^2$ and $R^3$ are selected independently from each other from H, F or $CH_3$, and with D being a linker which comprises carbon, sulphur, nitrogen and/or oxygen atoms and which is covalently connecting the moiety comprising $R^1$ and the parent moiety, in particular D is a linker selected from the linkers characterized by general formula D1 to D21, D1 to D12, D1 to D6 or D1 to D4, and with n of $R^1_n$ being 0, 1, 2, 3, 4 or 5, in particular n of $R^1_n$ being 0, 1 or 2, more particularly 1, and with each $R^1$ independently from any other $R^1$ being
—OH, —F, —Cl, —Br, I, CCH, —CN, —$N_3$, —$OCH_3$, —$OCF_3$, —$NH_2$, —$CH_3$, —$CF_3$, —$OCONH_2$ or —$NO_2$, or —$NR^a_2$, —$NHR^a$, —$R^a$, —C(=O)$R^a$, —C(=O)O$R^a$, O$R^a$, —OC(=O)$R^a$, —OC(=O)O$R^a$, —OC(=O)NH$R^a$, —NHC(=O)$R^a$, —NHC(=O)NH$R^a$, —C(=O)NH$R^a$ or —NHC(=O)O$R^a$, with $R^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or a substituted or unsubstituted $C_3$-$C_{10}$ cycloalkyl or a substituted or unsubstituted $C_3$-$C_{10}$ halo cycloalkyl, or a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or a substituted or unsubstituted $C_5$-$C_{10}$ heteroaryl, or a substituted or unsubstituted $C_6$-$C_{10}$ aryl, wherein in particular $R^1$ is in para position in relation to the attachment position of the benzene moiety to the —C($R^2$) moiety.

In some embodiments, the compound of the invention is characterised by the general formula PPa with $R^2$ and $R^3$ being selected, where applicable, independently from each other from —H, —F, —CN, —OH, —$NO_2$, —$NH_2$,

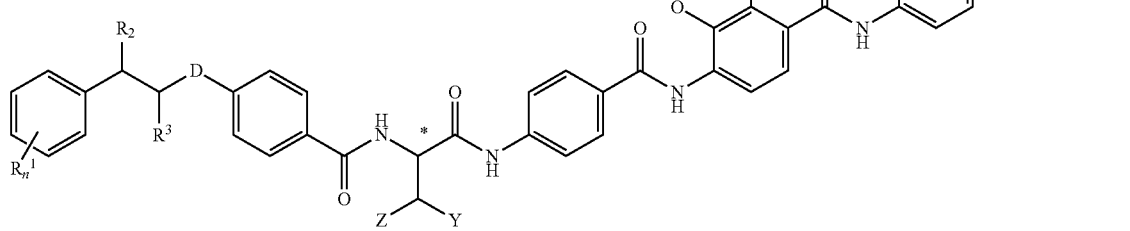

(PPa)

—NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl, in particular from —H, —F, —CN, —OH, —NH$_2$, —NO$_2$, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with R$^2$ and R$^3$ being selected independently from each other from H, F or CH$_3$, in particular R$^2$ and R$^3$ are selected independently from each other from H, F or CH$_3$, and with D being a linker as defined above, in particular D is a linker selected from the linkers characterized by general formula D1 to D21, D1 to D12, D1 to D6 or D1 to D4, and with n of R$^1_n$ being 0, 1, 2, 3, 4 or 5, in particular n of R$^1_n$ being 0, 1 or 2, more particularly 1, and with each R$^1$ independently from any other R$^1$ being
—OH, —F, —Cl, —Br, —I, —CCH, —CN, —N$_3$, —OCH$_3$, —OCF$_3$, —NH$_2$, —CH$_3$, —CF$_3$, —OCONH$_2$ or —NO$_2$, or
a substituted or unsubstituted C$_5$-C$_6$ heterocycle
a substituted or unsubstituted C$_5$-C$_6$ halo heterocycle, in particular a C$_5$-C$_6$ halo heterocycle comprising one or two halogen atoms selected from Cl of F, particularly comprising one Cl or one F in para position in relation to the attachment position of the heterocycle to the benzene moiety, or
a substituted or unsubstituted C$_5$-C$_6$ heteroaryl,
a substituted or unsubstituted C$_5$-C$_6$ halo heteroaryl comprising one or two halogen atoms selected from Cl of F, particularly comprising one Cl or one F in para position in relation to the attachment position of the heteroaryl to the benzene moiety, or
a substituted or unsubstituted C$_6$ aryl; or
with each R$^1$ independently from any other R$^1$ being
—OH, —F, —Cl, —I, —CN, —OCH$_3$, —OCF$_3$ or —CF$_3$; or
with each R$^1$ independently from any other R$^1$ being
—OH, —F or —CF$_3$,
wherein in particular R$^1$ is in para position in relation to the attachment position of the benzene moiety to the —C(R$^2$) moiety.

In some embodiments, the compound of the invention is characterised by the general formula PPa with R$^2$ being H and R$^3$ being CH$_3$ or R$^2$ being H and R$^3$ being H, and with D being a linker as defined above, in particular D is a linker selected from the linkers characterized by general formula D1 to D21, D1 to D12, D1 to D6 or D1 to D4, and with n of R$^1_n$ being 0 or 1, in particular n of R$^1_n$ being 1, and with R$^1$ being
—OH, —F, —Cl, —Br, —I, —CCH, —CN, —N$_3$, —OCH$_3$, —OCF$_3$, —NH$_2$, —CH$_3$, —CF$_3$, —OCONH$_2$ or —NO$_2$, or
a substituted or unsubstituted C$_5$-C$_6$ heterocycle
a substituted or unsubstituted C$_5$-C$_6$ halo heterocycle, in particular a C$_5$-C$_6$ halo heterocycle comprising one or two halogen atoms selected from Cl of F, particularly comprising one Cl or one F in para position in relation to the attachment position of the heterocycle to the benzene moiety, or
a substituted or unsubstituted C$_5$-C$_6$ heteroaryl,
a substituted or unsubstituted C$_5$-C$_6$ halo heteroaryl comprising one or two halogen atoms selected from Cl of F, particularly comprising one Cl or one F in para position in relation to the attachment position of the heteroaryl to the benzene moiety, or
a substituted or unsubstituted C$_6$ aryl; or
with each R$^1$ independently from any other R$^1$ being
—OH, —F, —Cl, I, —CN, —OCH$_3$, —OCF$_3$ or —CF$_3$; or
with each R$^1$ independently from any other R$^1$ being
—OH, —F or —CF$_3$,
wherein in particular R$^1$ is in para position in relation to the attachment position of the benzene moiety to the —C(R$^2$) moiety.

In some embodiments, the compound of the invention is characterised by the general formula PPb, with D being a linker of the formula D1

(PPb)

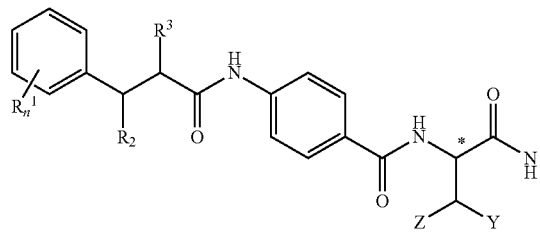
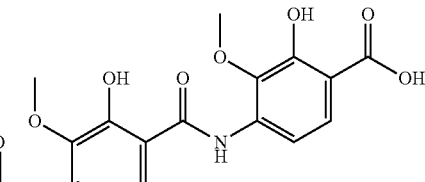

with R$^2$ and R$^3$ being selected, where applicable, independently from each other from —H, —F, —CN, —OH, —NH$_2$, —NO$_2$, —NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl, in particular from —H, —F, —CN, —OH, —NH$_2$, —NO$_2$, —NHCH$_3$, —NH (CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with R$^2$ and R$^3$ being selected independently from each other from H, F or CH$_3$, in particular R$^2$ and R$^3$ are selected independently from each other from H, F or CH$_3$, and with n of R$^1_n$ being 0, 1, 2, 3, 4 or 5, in particular n of R$^1_n$ being 0, 1 or 2, more particularly 1, and with each R$^1$ independently from any other R$^1$ being
—OH, —F, —Cl, —Br, I, CCH, —CN, —N$_3$, —OCH$_3$, —OCF$_3$, —NH$_2$, —CH$_3$, —CF$_3$, —OCONH$_2$ or —NO$_2$, or —NR$^a_2$, —NHR$^a$, —R$^a$, —C(=O)R$^a$, —C(=O)OR$^a$, OR$^a$, —OC(=O)R$^a$, —OC(=O)OR$^a$, —OC(=O)NHR$^a$, —NHC(=O)R$^a$, —NHC(=O)NHR$^a$, —C(=O)NHR$^a$ or —NHC(=O)OR$^a$,
  with R$^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or
a substituted or unsubstituted $C_3$-$C_{10}$ cycloalkyl or a substituted or unsubstituted $C_3$-$C_{10}$ halo cycloalkyl, or
a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
a substituted or unsubstituted $C_5$-$C_{10}$ heteroaryl, or
a substituted or unsubstituted $C_6$-$C_{10}$ aryl,
wherein in particular R$^1$ is in para position in relation to the attachment position of the benzene moiety to the —C(R$^2$) moiety.

In some embodiments, the compound of the invention is characterised by the general formula PPb with R$^2$ and R$^3$ being selected, where applicable, independently from each other from —H, —F, —CN, —OH, —NH$_2$, —NO$_2$, —NHCH$_3$, —NH(CH$_3$)$_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —NH$_2$, —NO$_2$, —NHCH$_3$, —NH(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with R$^2$ and R$^3$ being selected independently from each other from H, F or CH$_3$, in particular R$^2$ and R$^3$ are selected independently from each other from H, F or CH$_3$, and with n of R$^1_n$ being 0, 1, 2, 3, 4 or 5, in particular n of R$^1_n$ being 0, 1 or 2, more particularly 1, and
  with each R$^1$ independently from any other R$^1$ being
    —OH, —F, —Cl, —Br, —I, —CCH, —CN, —N$_3$, —OCH$_3$, —OCF$_3$, —NH$_2$, —CH$_3$, —CF$_3$, —OCONH$_2$ or —NO$_2$, or
  a substituted or unsubstituted $C_5$-$C_6$ heterocycle
  a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or
  a substituted or unsubstituted $C_5$-$C_6$ heteroaryl,
  a substituted or unsubstituted $C_5$-$C_6$ halo heteroaryl comprising one or two halogen atoms selected from Cl of F, particularly comprising one Cl or one F in para position in relation to the attachment position of the heteroaryl to the benzene moiety, or
  a substituted or unsubstituted $C_6$ aryl; or
  with each R$^1$ independently from any other R$^1$ being
    —OH, —F, —Cl, I, —CN, —OCH$_3$, —OCF$_3$ or —CF$_3$; or
  with each R$^1$ independently from any other R$^1$ being
    —OH, —F or —CF$_3$,
wherein in particular R$^1$ is in para position in relation to the attachment position of the benzene moiety to the —C(R$^2$) moiety.

In some embodiments, the compound of the invention is characterised by the general formula PPb with R$^2$ being H and R$^3$ being CH$_3$ or R$^2$ being H and R$^3$ being H, and with n of R$^1_n$ being 0 or 1, in particular n of R$^1_n$ being 1, and
  with R$^1$ being
    —OH, —F, —Cl, —Br, —I, —CCH, —CN, —N$_3$, —OCH$_3$, —OCF$_3$, —NH$_2$, —CH$_3$, —CF$_3$, —OCONH$_2$ or —NO$_2$, or
  a substituted or unsubstituted $C_5$-$C_6$ heterocycle
  a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or
  a substituted or unsubstituted $C_5$-$C_6$ heteroaryl,
  a substituted or unsubstituted $C_5$-$C_6$ halo heteroaryl comprising one or two halogen atoms selected from Cl of F, particularly comprising one Cl or one F in para position in relation to the attachment position of the heteroaryl to the benzene moiety, or
  a substituted or unsubstituted $C_6$ aryl; or
  with each R$^1$ independently from any other R$^1$ being
    —OH, —F, —Cl, I, —CN, —OCH$_3$, —OCF$_3$ or —CF$_3$; or
  with each R$^1$ independently from any other R$^1$ being
    —OH, —F or —CF$_3$,
wherein in particular R$^1$ is in para position in relation to the attachment position of the benzene moiety to the —C(R$^2$) moiety.

In some embodiments, the compound of the invention is characterised by the general formula PPc and comprises a benzoic acid structural element or a similar element

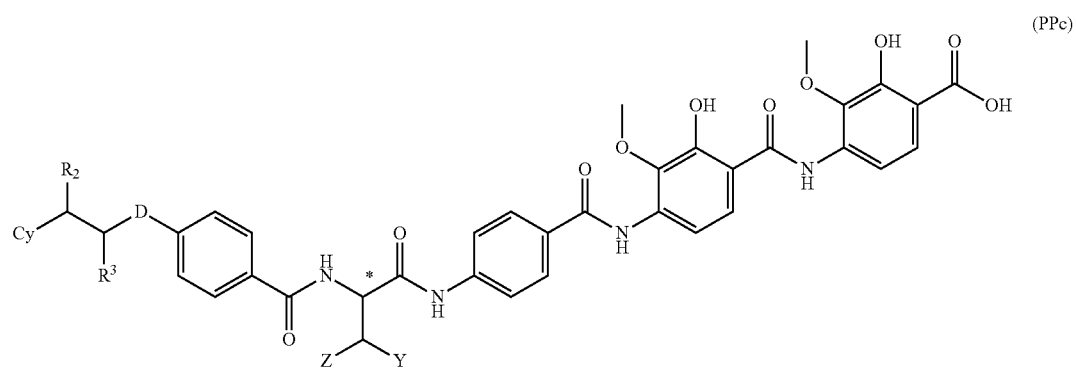
(PPc)

with $R^2$ and $R^3$ being selected, where applicable, independently from each other from —H, —F, —CN, —OH, —$NH_2$, —$NO_2$, —$NHCH_3$, —$NH(CH_3)_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —$NH_2$, —$NO_2$, —$NHCH_3$, —$NH(CH_3)_2$, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —$CHFCF_3$, —$CF_2CF_3$, —$CHF_2$, —$CH_2F$ or —$CF_3$, more particularly with $R^2$ and $R^3$ being selected independently from each other from H, F or $CH_3$, with D being a linker which comprises carbon, sulphur, nitrogen and/or oxygen atoms and which is covalently connecting the moiety comprising Cy and the parent moiety, in particular D is a linker selected from the linkers characterized by general formula D1 to D21, D1 to D12, D1 to D6 or D1 to D4, and a substituted or unsubstituted $C_5$-$C_6$ heteroaryl, a substituted $C_6$ aryl, in particular a bicyclic $C_6$ aryl such as tetralin or indane, a substituted or unsubstituted $C_5$-$C_6$ halo heteroaryl comprising one or two halogen atoms selected from Cl of F, particularly comprising one Cl or one F in para position in relation to the attachment position of the heteroaryl to the —$C(R^2)$ moiety; or Cy being selected from the group of substituted or unsubstituted pyrrole, furan, thiophene, thiazole, benzothiophene, chromene, pyrazine, pyridazine, pyridine or halogenated derivatives thereof.

In some embodiments, the compound of the invention is characterised by the general formula PPd

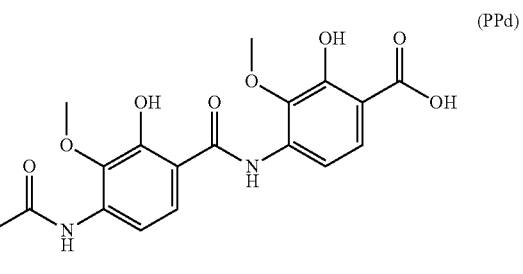

(PPd)

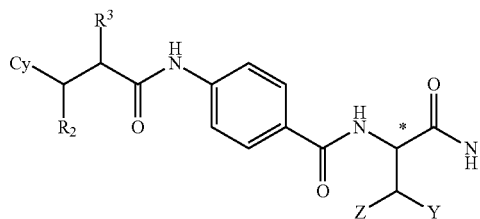

with Cy being
  a substituted or unsubstituted $C_3$-$C_{10}$ cycloalkyl or a substituted or unsubstituted $C_3$-$C_{10}$ halo cycloalkyl, or
  a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
  a substituted or unsubstituted $C_5$-$C_{10}$ heteroaryl, or
  a substituted or unsubstituted $C_6$-$C_{10}$ aryl.

In some embodiments, the compound of the invention is characterised by the general formula PPc, with $R^2$ and $R^3$ being selected, where applicable, independently from each other from —H, —F, —CN, —OH, —$NH_2$, —$NO_2$, —$NHCH_3$, —$NH(CH_3)_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —$NH_2$, —$NO_2$, —$NHCH_3$, —$NH(CH_3)_2$, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —$CHFCF_3$, —$CF_2CF_3$, —$CHF_2$, —$CH_2F$ or —$CF_3$, more particularly with $R^2$ and $R^3$ being selected independently from each other from H, F or $CH_3$, with D being a linker as defined above, in particular D is a linker selected from the linkers characterized by general formula D1 to D21, D1 to D12, D1 to D6 or D1 to D4, and with
  Cy being
  a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the —$C(R^2)$ moiety, or with $R^2$ and $R^3$ being selected, where applicable, independently from each other from —H, —F, —CN, —OH, —$NH_2$, —$NO_2$, —$NHCH_3$, —$NH(CH_3)_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —$NH_2$, —$NO_2$, —$NHCH_3$, —$NH(CH_3)_2$, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —$CHFCF_3$, —$CF_2CF_3$, —$CHF_2$, —$CH_2F$ or —$CF_3$, more particularly with $R^2$ and $R^3$ being selected independently from each other from H, F or $CH_3$,
  with Cy being
  a substituted or unsubstituted $C_3$-$C_{10}$ cycloalkyl or a substituted or unsubstituted $C_3$-$C_{10}$ halo cycloalkyl, or
  a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
  a substituted or unsubstituted $C_5$-$C_{10}$ heteroaryl, or
  a substituted or unsubstituted $C_6$-$C_{10}$ aryl.

In some embodiments, the compound of the invention is characterised by the general formula PPd with $R^2$ and $R^3$ being selected, where applicable, independently from each other from —H, —F, —CN, —OH, —$NH_2$, —$NO_2$, —$NHCH_3$, —$NH(CH_3)_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —$NH_2$, —$NO_2$, —$NHCH_3$, —$NH(CH_3)_2$, —$CH_3$, —$CH_2CH_3$, —$OCH_3$, —$OCH_2CH_3$, —$OCH_2CH_2CH_3$, —$OCH(CH_3)_2$, —$OCF_3$, —$CH_2CF_3$, —$CHFCF_3$, —CF$_2$CF$_3$, —CHF$_2$, —CH$_2$F or —CF$_3$, more particularly with R$^2$ and R$^3$ being selected independently from each other from H, F or CH$_3$, with Cy being
  a substituted or unsubstituted C$_5$-C$_6$ halo heterocycle, in particular a C$_5$-C$_6$ halo heterocycle comprising one or two halogen atoms selected from Cl of F, particularly comprising one Cl or one F in para position in relation to the attachment position of the heterocycle to the —C(R$^2$) moiety, or
  a substituted or unsubstituted C$_5$-C$_6$ heteroaryl,
  a substituted C$_6$ aryl, in particular a bicyclic C$_6$ aryl such as tetralin or indane,
  a substituted or unsubstituted C$_5$-C$_6$ halo heteroaryl comprising one or two halogen atoms selected from Cl of F, particularly comprising one Cl or one F in para position in relation to the attachment position of the heteroaryl to the —C(R$^2$) moiety; or Cy being selected from the group of substituted or unsubstituted pyrrole, furan, thiophene, thiazole, benzothiophene, chromene, pyrazine, pyridazine, pyridine or halogenated derivatives thereof.

In some embodiments, the compound of the invention is characterised by the general formula P,

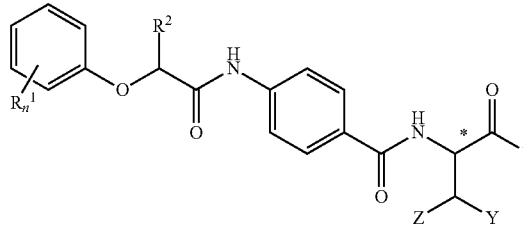
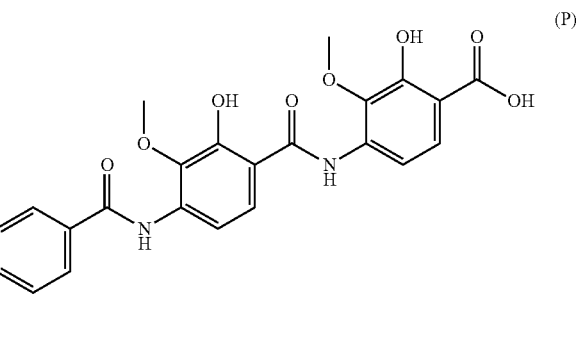

with R$^2$ being selected, where applicable, from —H, —OH, —NH$_2$, —NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl, in particular from —H, —OH, —CH$_2$OH, —NH$_2$, —NHCH$_3$, —NH(CH$_3$)$_2$, —CH$_3$, —CH$_2$CH$_3$, —CH$_2$CH$_2$CH$_3$, —CH(CH$_3$)$_2$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with R$^2$ being selected from H or CH$_3$—, and
with n of R$^1_n$ being 0, 1, 2, 3, 4 or 5, in particular n of R$^1_n$ being 0, 1 or 2, more particularly 1, and with each R$^1$ independently from any other R$^1$ being
  —H, —OH, —F, —Cl, —Br, I, CCH, —CN, —N$_3$, —OCH$_3$, —OCF$_3$, —NH$_2$, —CH$_3$, —CF$_3$, —OCONH$_2$ or —NO$_2$, or
  —NR$^a_2$, —NHR$^a$, —R$^a$, —C(=O)R$^a$, —C(=O)OR$^a$, OR$^a$, —OC(=O)R$^a$, —OC(=O)OR$^a$, —OC(=O)NHR$^a$, —NHC(=O)R$^a$, —NHC(=O)NHR$^a$, —C(=O)NHR$^a$ or —NHC(=O)OR$^a$,
    with R$^a$ being a substituted or unsubstituted C$_1$-C$_8$ alkyl, a substituted or unsubstituted C$_2$-C$_8$ alkenyl, a substituted or unsubstituted C$_2$-C$_8$ alkynyl, or a substituted or unsubstituted C$_1$-C$_8$ haloalkyl, or
  a substituted or unsubstituted C$_3$-C$_{10}$ cycloalkyl or a substituted or unsubstituted C$_3$-C$_{10}$ halo cycloalkyl, or
  a substituted or unsubstituted C$_3$-C$_{10}$ heterocycle or a substituted or unsubstituted C$_3$-C$_{10}$ halo heterocycle, in particular a substituted or unsubstituted C$_4$-C$_{10}$ heterocycle or a substituted or unsubstituted C$_4$-C$_{10}$ halo heterocycle, or
  a substituted or unsubstituted C$_5$-C$_{10}$ heteroaryl, or
  a substituted or unsubstituted C$_6$-C$_{10}$ aryl,
wherein in particular R$^1$ is in para position in relation to the attachment position of the benzene moiety to the —OC(R$^2$) moiety.

In some embodiments, the compound of the invention is characterised by the general formula P with R$^2$ being selected, where applicable, from —H, —OH, —NH$_2$, —NHCH$_3$, —NH(CH$_3$)$_2$, a substituted or unsubstituted C$_1$-C$_3$ alkyl, a substituted or unsubstituted C$_1$-C$_3$ alkoxy or a C$_1$-C$_3$ haloalkyl, in particular from —H, —OH, —CH$_2$OH, —NH$_2$, —NHCH$_3$, —NH(CH$_3$)$_2$, —CH$_3$, —CH$_2$CH$_3$, —CH$_2$CH$_2$CH$_3$, —CH(CH$_3$)$_2$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with R$^2$ being selected from H or CH$_3$, in particular R$^3$ is selected from H or CH$_3$, and with n of R$^1_n$ being 0, 1, 2, 3, 4 or 5, in particular n of R$^1_n$ being 0, 1 or 2, more particularly 1, and
  with each R$^1$ independently from any other R$^1$ being
    —OH, —F, —Cl, Br, I, CCH, —CN, —N$_3$, —OCH$_3$, —OCF$_3$, —NH$_2$, —CH$_3$, —CF$_3$, —OCONH$_2$ or —NO$_2$, or
  a substituted or unsubstituted C$_5$-C$_6$ heterocycle
  a substituted or unsubstituted C$_5$-C$_6$ halo heterocycle, in particular a C$_5$-C$_6$ halo heterocycle comprising one or two halogen atoms selected from Cl of F, particularly comprising one Cl or one F in para position in relation to the attachment position of the heterocycle to the benzene moiety, or
  a substituted or unsubstituted C$_5$-C$_6$ heteroaryl,
  a substituted or unsubstituted C$_5$-C$_6$ halo heteroaryl comprising one or two halogen atoms selected from Cl of F, particularly comprising one Cl or one F in para position in relation to the attachment position of the heteroaryl to the benzene moiety, or
  a substituted or unsubstituted C$_6$ aryl; or
  with each R$^1$ independently from any other R$^1$ being
    —OH, —F, —Cl, I, —CN, —OCH$_3$, —OCF$_3$ or —CF$_3$; or
  with each R$^1$ independently from any other R$^1$ being
    —OH, —F or —CF$_3$,
wherein in particular R$^1$ is in para position in relation to the attachment position of the benzene moiety to the —OC(R$^3$) moiety.

In some embodiments, the compound of the invention is characterised by the general formula P with R$^2$ being CH$_3$ or R$^3$ being H, and with n of R$^1_n$ being 0 or 1, in particular n of R$^1_n$ being 1, and
  with R$^1$ being
    —OH, —F, —Cl, Br, I, CCH, —CN, —N$_3$, —OCH$_3$, —OCF$_3$, —NH$_2$, —CH$_3$, —CF$_3$, —OCONH$_2$ or —NO$_2$, or

- a substituted or unsubstituted $C_5$-$C_6$ heterocycle
- a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or
- a substituted or unsubstituted $C_5$-$C_6$ heteroaryl,
- a substituted or unsubstituted $C_5$-$C_6$ halo heteroaryl comprising one or two halogen atoms selected from Cl of F, particularly comprising one Cl or one F in para position in relation to the attachment position of the heteroaryl to the benzene moiety, or
- a substituted or unsubstituted $C_6$ aryl; or
- with each $R^1$ independently from any other $R^1$ being —OH, —F, —Cl, I, —CN, —OCH$_3$, —OCF$_3$ or —CF$_3$; or
- with each $R^1$ independently from any other $R^1$ being —OH, —F or —CF$_3$, wherein in particular $R^1$ is in para position in relation to the attachment position of the benzene moiety to the —OC(R$^2$) moiety.

In some embodiments, the compound of the invention is characterised by the general formula FAa

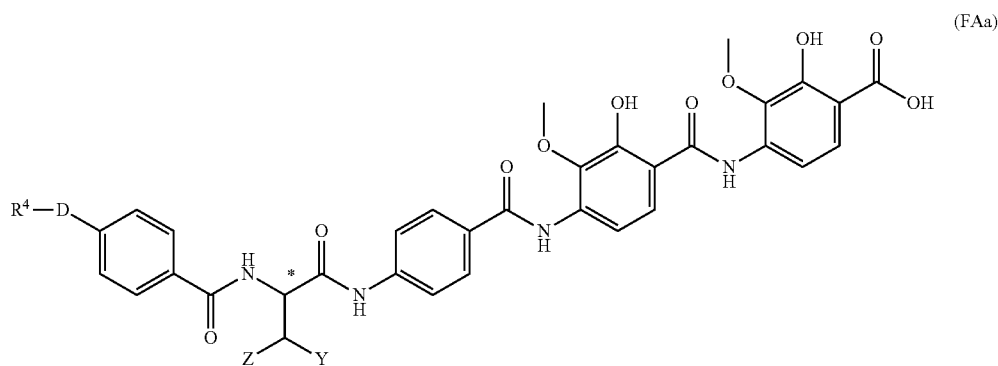

(FAa)

with D being a linker which comprises carbon, sulphur, nitrogen and/or oxygen atoms and which is covalently connecting the moiety comprising $R^4$ and the parent moiety, in particular D is a linker selected from the linkers characterized by general formula D1 to D21, D1 to D12, D1 to D6 or D1 to D4, and with $R^4$ being
- a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, or a substituted or unsubstituted $C_1$-$C_8$ haloalkyl; or
- a substituted or unsubstituted $C_3$-$C_{10}$ cycloalkyl or a substituted or unsubstituted $C_3$-$C_{10}$ halo cycloalkyl.

In some embodiments, the compound of the invention is characterised by the general formula FAa with D being a linker as defined above, in particular D is a linker selected from the linkers characterized by general formula D1 to D21, D1 to D12, D1 to D6 or D1 to D4, and with $R^4$ being a straight or branched $C_1$-$C_5$ alkyl or a $C_6$-$C_{10}$ cycloalkyl ring or polyring structure.

In some embodiments, the compound of the invention is characterised by the general formula FAb with D being a linker of the formula D1

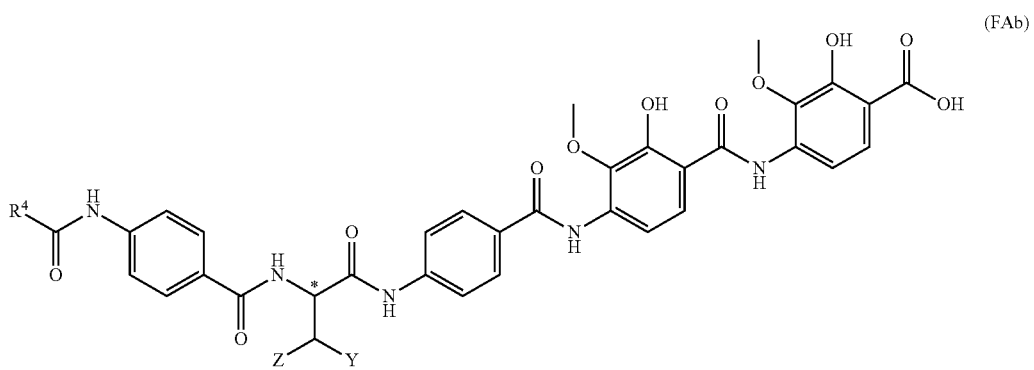

(FAb)

with R⁴ being
  a substituted or unsubstituted $C_1$-$C_8$ alkyl, a substituted or unsubstituted $C_1$-$C_8$ alkoxy, a substituted or unsubstituted $C_2$-$C_8$ alkenyl, a substituted or unsubstituted $C_2$-$C_8$ alkynyl, or a substituted or unsubstituted $C_1$-$C_8$ haloalkyl; or
  a substituted or unsubstituted $C_3$-$C_{10}$ cycloalkyl or a substituted or unsubstituted $C_3$-$C_{10}$ halo cycloalkyl.

In some embodiments, the compound of the invention is characterised by the general formula FAb with D being a linker as defined above, in particular D is a linker selected from the linkers characterized by general formula D1 to D21, D1 to D12, D1 to D6 or D1 to D4, and with R⁴ being a straight or branched $C_1$-$C_5$ alkyl or a $C_6$-$C_{10}$ cycloalkyl ring or polyring structure.

In some embodiments, the compound of the invention is characterised by the general formula UAa

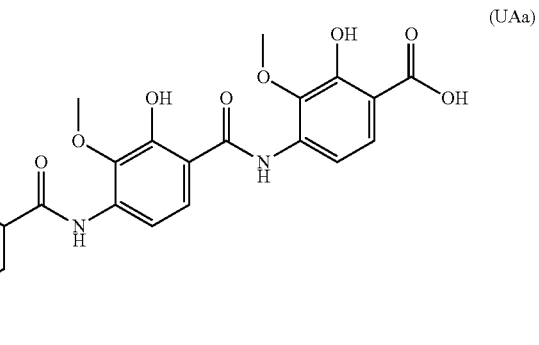

(UAa)

with n of $R^1_n$ being 0, 1, 2, 3, 4 or 5, in particular n of $R^1_n$ being 0, 1 or 2, more particularly 0 or 1, and with each $R^1$ independently from any other $R^1$ being
  —OH, —F, —Cl, —Br, I, CCH, —CN, —N₃, —OCH₃, —OCF₃, —NH₂, —CH₃, —CF₃, —OCONH₂ or —NO₂, or
  —NR$^a_2$, —NHR$^a$, —R$^a$, —C(=O)R$^a$, —C(=O)OR$^a$, OR$^a$, —OC(=O)R$^a$, —OC(=O)OR$^a$, —OC(=O)NHR$^a$, —NHC(=O)R$^a$, —NHC(=O)NHR$^a$, —C(=O)NHR$^a$ or —NHC(=O)OR$^a$,
    with R$^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or
  a substituted or unsubstituted $C_3$-$C_{10}$ cycloalkyl or a substituted or unsubstituted $C_3$-$C_{10}$ halo cycloalkyl, or
  a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
  a substituted or unsubstituted $C_5$-$C_{10}$ heteroaryl, or
  a substituted or unsubstituted $C_6$-$C_{10}$ aryl,
wherein in particular $R^1$ is in para position in relation to the attachment position of the benzene moiety to the —HNC(=O)NH— moiety.

In some embodiments, the compound of the invention is characterised by the general formula UAa with n of $R^1_n$ being 0, 1, 2, 3, 4 or 5, in particular n of $R^1_n$ being 0, 1 or 2, more particularly 0 or 1, and with each $R^1$ independently from any other $R^1$ being
  —OH, —F, —Cl, Br, I, CCH, —CN, —N₃, —OCH₃, —OCF₃, —NH₂, —CH₃, —CF₃, —OCONH₂ or —NO₂, or
  a substituted or unsubstituted $C_5$-$C_6$ heterocycle
  a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or
  a substituted or unsubstituted $C_5$-$C_6$ heteroaryl,
  a substituted or unsubstituted $C_5$-$C_6$ halo heteroaryl comprising one or two halogen atoms selected from Cl of F, particularly comprising one Cl or one F in para position in relation to the attachment position of the heteroaryl to the benzene moiety, or
  a substituted or unsubstituted $C_6$ aryl; or
with each $R^1$ independently from any other $R^1$ being
  —OH, —F, —Cl, I, —CN, —OCH₃, —OCF₃ or —CF₃; or
with each $R^1$ independently from any other $R^1$ being
  —OH, —F or —CF₃,
wherein in particular $R^1$ is in para position in relation to the attachment position of the benzene moiety to the —HNC(=O)NH moiety.

In some embodiments, the compound of the invention is characterised by the general formula UAa with n of $R^1_n$ being 0 or 1, and
  with $R^1$ being
    —OH, —F, —Cl, Br, I, CCH, —CN, —N₃, —OCH₃, —OCF₃, —NH₂, —CH₃, —CF₃, —OCONH₂ or —NO₂, or
    a substituted or unsubstituted $C_5$-$C_6$ heterocycle
    a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or
    a substituted or unsubstituted $C_5$-$C_6$ heteroaryl,
    a substituted or unsubstituted $C_5$-$C_6$ halo heteroaryl comprising one or two halogen atoms selected from Cl of F, particularly comprising one Cl or one F in para position in relation to the attachment position of the heteroaryl to the benzene moiety, or
    a substituted or unsubstituted $C_6$ aryl; or
with each $R^1$ independently from any other $R^1$ being
  —OH, —F, —Cl, I, —CN, —OCH₃, —OCF₃ or —CF₃; or with each R¹ independently from any other R¹ being
—OH, —F or —CF₃,
wherein in particular R¹ is in para position in relation to the attachment position of the benzene moiety to the —HNC(=O)NH moiety.

In some embodiments, the compound of the invention is characterised by the general formula UAa with n of R¹$_n$ being 0.

In some embodiments, the compound of the invention is characterised by the general formula AMa

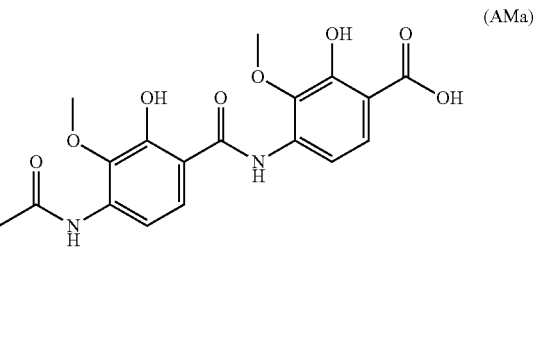

(AMa)

with n of R¹$_n$ being 0, 1, 2, 3, 4 or 5, in particular n of R¹$_n$ being 0, 1 or 2, more particularly 1, and with each R¹ independently from any other R¹ being
—OH, —F, —Cl, —Br, I, CCH, —CN, —N₃, —OCH₃, —OCF₃, —NH₂, —CH₃, —CF₃, —OCONH₂ or —NO₂, or
—NR$^a$₂, —NHR$^a$, —R$^a$, —C(=O)R$^a$, —C(=O)OR$^a$, OR$^a$, —OC(=O)R$^a$, —OC(=O)OR$^a$, —OC(=O)NHR$^a$, —NHC(=O)R$^a$, —NHC(=O)NHR$^a$, —C(=O)NHR$^a$ or —NHC(=O)OR$^a$,
with R$^a$ being a substituted or unsubstituted C₁-C₈ alkyl, a substituted or unsubstituted C₂-C₈ alkenyl, a substituted or unsubstituted C₂-C₈ alkynyl, or a substituted or unsubstituted C₁-C₈ haloalkyl, or
a substituted or unsubstituted C₃-C₁₀ cycloalkyl or a substituted or unsubstituted C₃-C₁₀ halo cycloalkyl, or
a substituted or unsubstituted C₃-C₁₀ heterocycle or a substituted or unsubstituted C₃-C₁₀ halo heterocycle, in particular a substituted or unsubstituted C₄-C₁₀ heterocycle or a substituted or unsubstituted C₄-C₁₀ halo heterocycle, or
a substituted or unsubstituted C₅-C₁₀ heteroaryl, or
a substituted or unsubstituted C₆-C₁₀ aryl,
wherein in particular R¹ is in para position in relation to the attachment position of the benzene moiety to the —CH₂NH— moiety.

In some embodiments, the compound of the invention is characterised by the general formula BAd with n of R¹$_n$ being 0, 1, 2, 3, 4 or 5, in particular n of R¹$_n$ being 0, 1 or 2, more particularly 1, and
with each R¹ independently from any other R¹ being
—OH, —F, —Cl, Br, I, CCH, —CN, —N₃, —OCH₃, —OCF₃, —NH₂, —CH₃, —CF₃, —OCONH₂ or —NO₂, or
a substituted or unsubstituted C₅-C₆ heterocycle
a substituted or unsubstituted C₅-C₆ halo heterocycle, in particular a C₅-C₆ halo heterocycle comprising one or two halogen atoms selected from Cl of F, particularly comprising one Cl or one F in para position in relation to the attachment position of the heterocycle to the benzene moiety, or
a substituted or unsubstituted C₅-C₆ heteroaryl,
a substituted or unsubstituted C₅-C₆ halo heteroaryl comprising one or two halogen atoms selected from Cl of F, particularly comprising one Cl or one F in para position in relation to the attachment position of the heteroaryl to the benzene moiety, or
a substituted or unsubstituted C₆ aryl; or
with each R¹ independently from any other R¹ being
—OH, —F, —Cl, I, —CN, —OCH₃, —OCF₃ or —CF₃; or
with each R¹ independently from any other R¹ being
—OH, —F or —CF₃,
wherein in particular R¹ is in para position in relation to the attachment position of the benzene moiety to the —CH₂NH— moiety.

In some embodiments, the compound of the invention is characterised by the general formula AMa with n of R¹$_n$ being 0 or 1, in particular n of R¹$_n$ being 1, and
with R¹ being
—OH, —F, —Cl, Br, I, CCH, —CN, —N₃, —OCH₃, —OCF₃, —NH₂, —CH₃, —CF₃, —OCONH₂ or —NO₂, or
a substituted or unsubstituted C₅-C₆ heterocycle
a substituted or unsubstituted C₅-C₆ halo heterocycle, in particular a C₅-C₆ halo heterocycle comprising one or two halogen atoms selected from Cl of F, particularly comprising one Cl or one F in para position in relation to the attachment position of the heterocycle to the benzene moiety, or
a substituted or unsubstituted C₅-C₆ heteroaryl,
a substituted or unsubstituted C₅-C₆ halo heteroaryl comprising one or two halogen atoms selected from Cl of F, particularly comprising one Cl or one F in para position in relation to the attachment position of the heteroaryl to the benzene moiety, or
a substituted or unsubstituted C₆ aryl; or
with each R¹ independently from any other R¹ being
—OH, —F, —Cl, I, —CN, —OCH₃, —OCF₃ or —CF₃; or
with each R¹ independently from any other R¹ being
—OH, —F or —CF₃,
wherein in particular R¹ is in para position in relation to the attachment position of the benzene moiety to the —CH₂NH— moiety.

In some embodiments, the compound of the invention is characterised by the general formula SAa

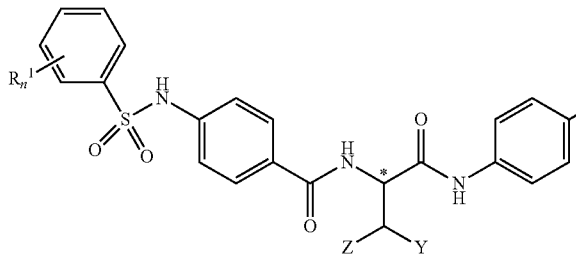
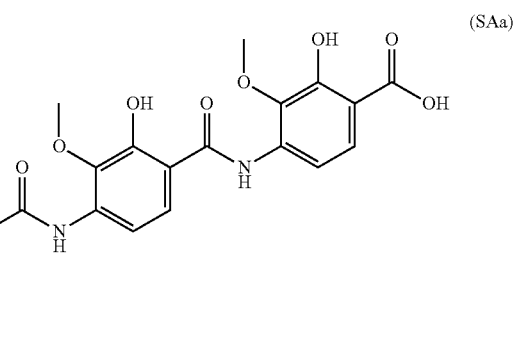

(SAa)

with n of $R^1_n$ being 0, 1, 2, 3, 4 or 5, in particular n of $R^1_n$ being 0, 1 or 2, more particularly 1, and with each $R^1$ independently from any other $R^1$ being
- —OH, —F, —Cl, —Br, I, CCH, —CN, —$N_3$, —$OCH_3$, —$OCF_3$, —$NH_2$, —$CH_3$, —$CF_3$, —$OCONH_2$ or —$NO_2$, or
- —$NR^a_2$, —$NHR^a$, —$R^a$, —C(=O)$R^a$, —C(=O)O$R^a$, O$R^a$, —OC(=O)$R^a$, —OC(=O)O$R^a$, —OC(=O)NH$R^a$, —NHC(=O)$R^a$, —NHC(=O)NH$R^a$, —C(=O)NH$R^a$ or —NHC(=O)O$R^a$,
  - with $R^a$ being a substituted or unsubstituted $C_1$-$C_8$ alkyl, a substituted or unsubstituted $C_2$-$C_8$ alkenyl, a substituted or unsubstituted $C_2$-$C_8$ alkynyl, or a substituted or unsubstituted $C_1$-$C_8$ haloalkyl, or
- a substituted or unsubstituted $C_3$-$C_{10}$ cycloalkyl or a substituted or unsubstituted $C_3$-$C_{10}$ halo cycloalkyl, or
- a substituted or unsubstituted $C_3$-$C_{10}$ heterocycle or a substituted or unsubstituted $C_3$-$C_{10}$ halo heterocycle, in particular a substituted or unsubstituted $C_4$-$C_{10}$ heterocycle or a substituted or unsubstituted $C_4$-$C_{10}$ halo heterocycle, or
- a substituted or unsubstituted $C_5$-$C_{10}$ heteroaryl, or
- a substituted or unsubstituted $C_6$-$C_{10}$ aryl, wherein in particular $R^1$ is in para position in relation to the attachment position of the benzene moiety to the —$S(O_2)$NH— moiety.

In some embodiments, the compound of the invention is characterised by the general formula SAa with n of $R^1_n$ being 0, 1, 2, 3, 4 or 5, in particular n of $R^1_n$ being 0, 1 or 2, more particularly 1, and
- with each $R^1$ independently from any other $R^1$ being
  - —OH, —F, —Cl, Br, I, CCH, —CN, —$N_3$, —$OCH_3$, —$OCF_3$, —$NH_2$, —$CH_3$, —$CF_3$, —$OCONH_2$ or —$NO_2$, or
  - a substituted or unsubstituted $C_5$-$C_6$ heterocycle
  - a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or
  - a substituted or unsubstituted $C_5$-$C_6$ heteroaryl,
  - a substituted or unsubstituted $C_5$-$C_6$ halo heteroaryl comprising one or two halogen atoms selected from Cl of F, particularly comprising one Cl or one F in para position in relation to the attachment position of the heteroaryl to the benzene moiety, or
  - a substituted or unsubstituted $C_6$ aryl; or
- with each $R^1$ independently from any other $R^1$ being
  - —OH, —F, —Cl, I, —CN, —$OCH_3$, —$OCF_3$ or —$CF_3$; or
- with each $R^1$ independently from any other $R^1$ being
  - —OH, —F or —$CF_3$, wherein in particular $R^1$ is in para position in relation to the attachment position of the benzene moiety to the —$S(O_2)$NH— moiety.

In some embodiments, the compound of the invention is characterised by the general formula SAa with n of $R^1_n$ being 0 or 1, in particular n of $R^1_n$ being 1, and
- with $R^1$ being
  - —OH, —F, —Cl, Br, I, CCH, —CN, —$N_3$, —$OCH_3$, —$OCF_3$, —$NH_2$, —$CH_3$, —$CF_3$, —$OCONH_2$ or —$NO_2$, or
  - a substituted or unsubstituted $C_5$-$C_6$ heterocycle
  - a substituted or unsubstituted $C_5$-$C_6$ halo heterocycle, in particular a $C_5$-$C_6$ halo heterocycle comprising one or two halogen atoms selected from Cl of F, particularly comprising one Cl or one F in para position in relation to the attachment position of the heterocycle to the benzene moiety, or
  - a substituted or unsubstituted $C_5$-$C_6$ heteroaryl,
  - a substituted or unsubstituted $C_5$-$C_6$ halo heteroaryl comprising one or two halogen atoms selected from Cl of F, particularly comprising one Cl or one F in para position in relation to the attachment position of the heteroaryl to the benzene moiety, or
  - a substituted or unsubstituted $C_6$ aryl; or
- with each $R^1$ independently from any other $R^1$ being
  - —OH, —F, —Cl, I, —CN, —$OCH_3$, —$OCF_3$ or —$CF_3$; or
- with each $R^1$ independently from any other $R^1$ being
  - —OH, —F or —$CF_3$, wherein in particular $R^1$ is in para position in relation to the attachment position of the benzene moiety to the —$S(O_2)$NH— moiety.

Particular embodiments of the invention are the compounds 1 to 50, 70 to 76 as depicted in the experimental section and the following compounds 78 to 117.

Compound 78:
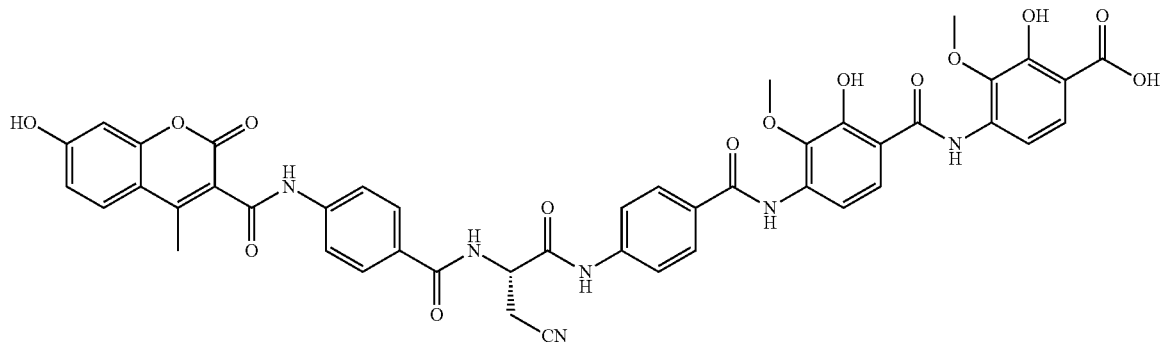 [SMILES: COc1c(NC(=O)c2ccc(NC(=O)c3ccc(NC(=O)[C@H](CC#N)NC(=O)c4ccc(NC(=O)c5c(C)c6ccc(O)cc6oc5=O)cc4)cc3)c(OC)c2O)ccc(C(=O)O)c1O]
Chemical Formula: $C_{45}H_{36}N_6O_{14}$
Exact Mass: 884,2289
Compound 79:
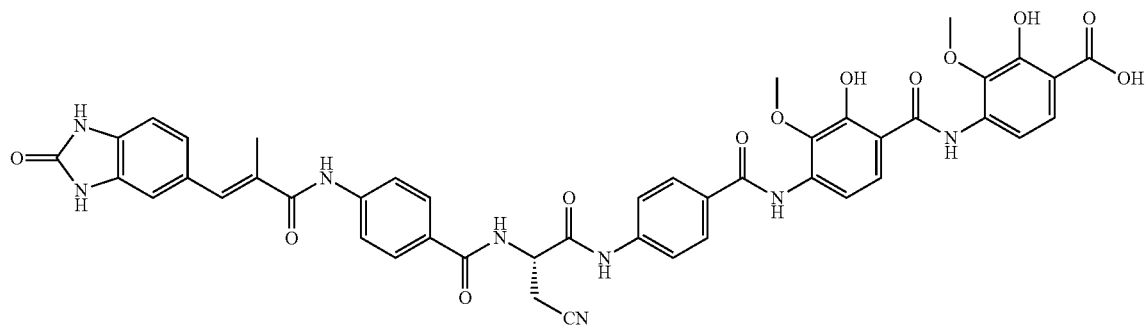
Chemical Formula: $C_{45}H_{38}N_8O_{12}$
Exact Mass: 882,2609
Compound 80:
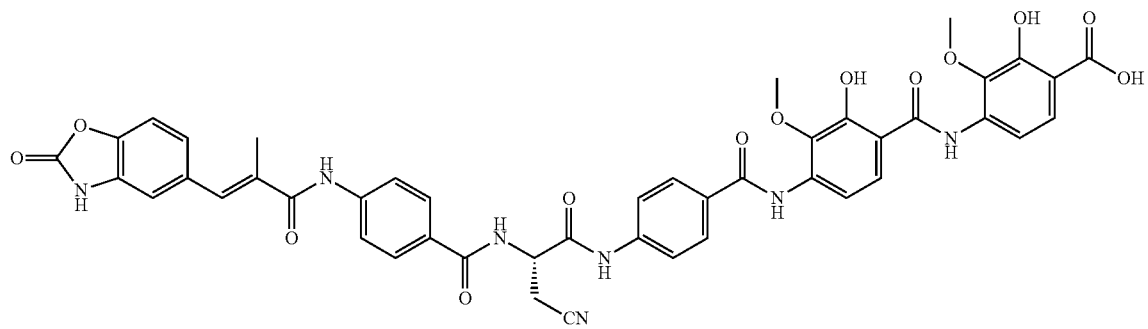 [SMILES: COc1c(NC(=O)c2ccc(NC(=O)c3ccc(NC(=O)[C@H](CC#N)NC(=O)c4ccc(NC(=O)/C(C)=C/c5ccc6oc(=O)[nH]c6c5)cc4)cc3)c(OC)c2O)ccc(C(=O)O)c1O]
Chemical Formula: $C_{45}H_{37}N_7O_{13}$
Exact Mass: 883,2449

Compound 81:
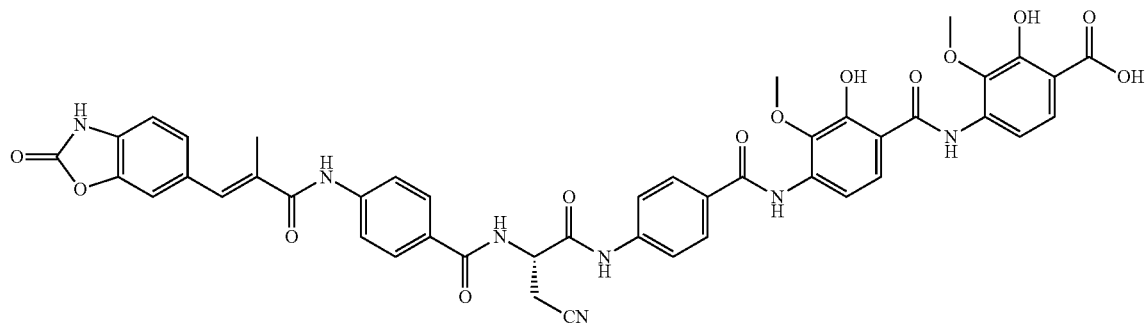 [SMILES: COc1c(NC(=O)c2ccc(NC(=O)c3ccc(NC(=O)[C@H](CC#N)NC(=O)c4ccc(NC(=O)/C(C)=C/c5ccc6[nH]c(=O)oc6c5)cc4)cc3)c(OC)c2O)ccc(C(=O)O)c1O]
Chemical Formula: $C_{45}H_{37}N_7O_{13}$
Exact Mass: 883.2449
Compound 82:
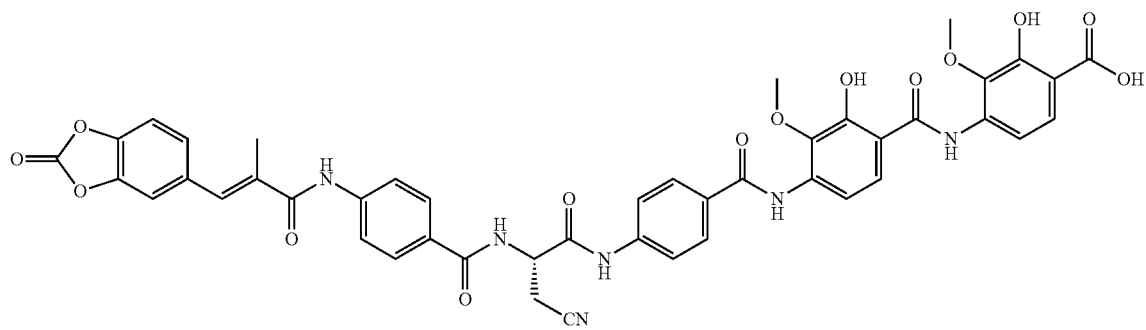 [SMILES: COc1c(NC(=O)c2ccc(NC(=O)c3ccc(NC(=O)[C@H](CC#N)NC(=O)c4ccc(NC(=O)/C(C)=C/c5ccc6oc(=O)oc6c5)cc4)cc3)c(OC)c2O)ccc(C(=O)O)c1O]
Chemical Formula: $C_{45}H_{36}N_6O_{14}$
Exact Mass: 884.2289
Compound 83:
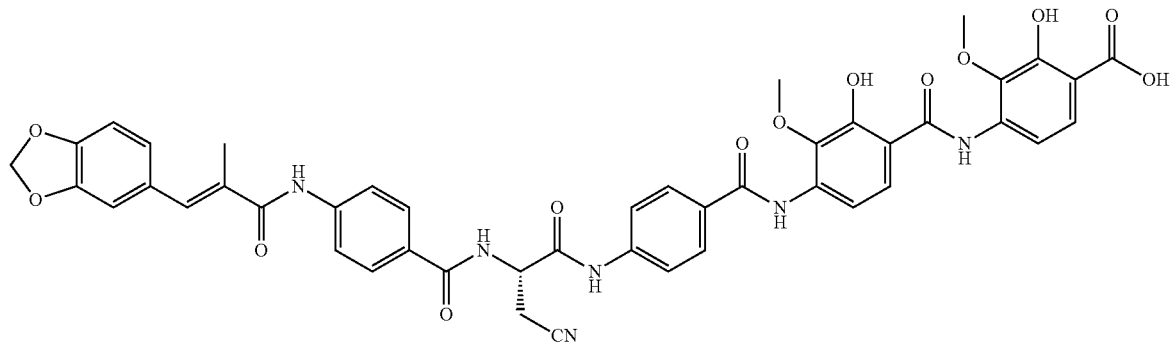 [SMILES: COc1c(NC(=O)c2ccc(NC(=O)c3ccc(NC(=O)[C@H](CC#N)NC(=O)c4ccc(NC(=O)/C(C)=C/c5ccc6c(c5)OCO6)cc4)cc3)c(OC)c2O)ccc(C(=O)O)c1O]
Chemical Formula: $C_{45}H_{38}N_6O_{13}$
Exact Mass: 870.2497

Compound 84:
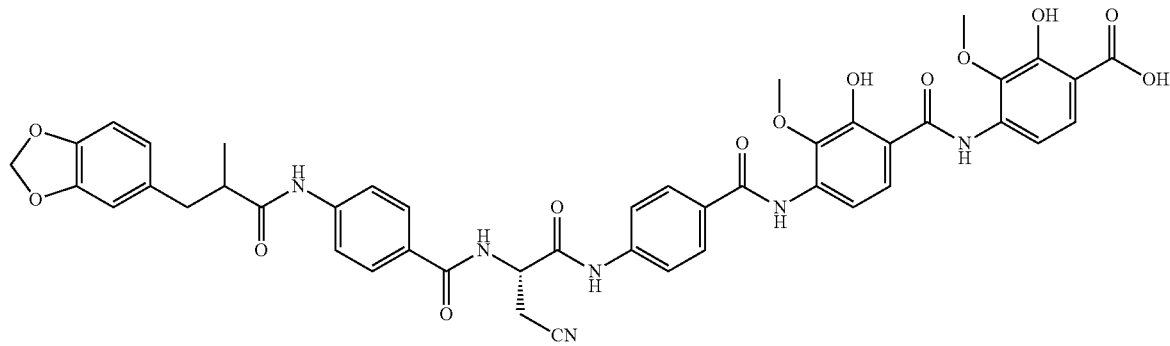 [SMILES: COc1c(NC(=O)c2ccc(NC(=O)c3ccc(NC(=O)[C@H](CC#N)NC(=O)c4ccc(NC(=O)C(C)Cc5ccc6c(c5)OCO6)cc4)cc3)c(OC)c2O)ccc(C(=O)O)c1O]
Chemical Formula: C$_{45}$H$_{40}$N$_6$O$_{13}$
Exact Mass: 872,2653
Compound 85:
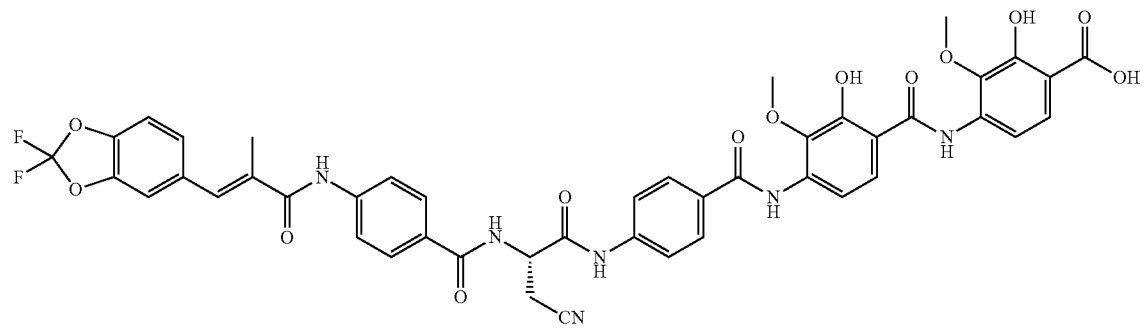 [SMILES: COc1c(NC(=O)c2ccc(NC(=O)c3ccc(NC(=O)[C@H](CC#N)NC(=O)c4ccc(NC(=O)/C(C)=C/c5ccc6c(c5)OC(F)(F)O6)cc4)cc3)c(OC)c2O)ccc(C(=O)O)c1O]
Chemical Formula: C$_{45}$H$_{36}$F$_2$N$_6$O$_{13}$
Exact Mass: 906,2308
Compound 86:
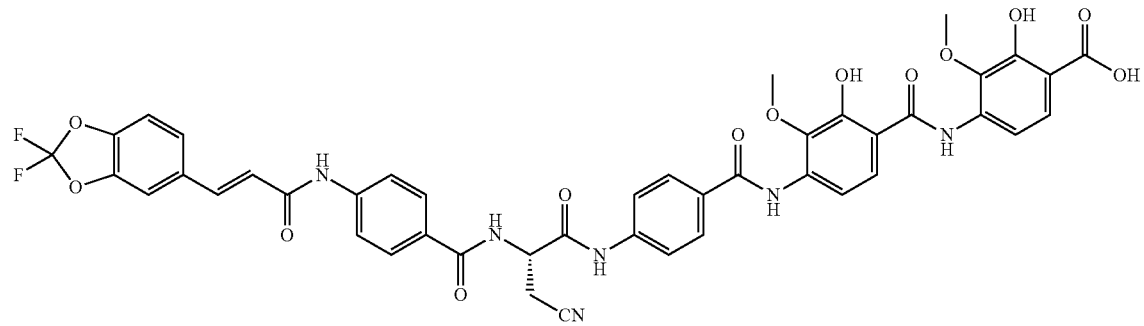 [SMILES: COc1c(NC(=O)c2ccc(NC(=O)c3ccc(NC(=O)[C@H](CC#N)NC(=O)c4ccc(NC(=O)/C=C/c5ccc6c(c5)OC(F)(F)O6)cc4)cc3)c(OC)c2O)ccc(C(=O)O)c1O]
Chemical Formula: C$_{44}$H$_{34}$F$_2$N$_6$O$_{13}$
Exact Mass: 892,2152

Compound 87:
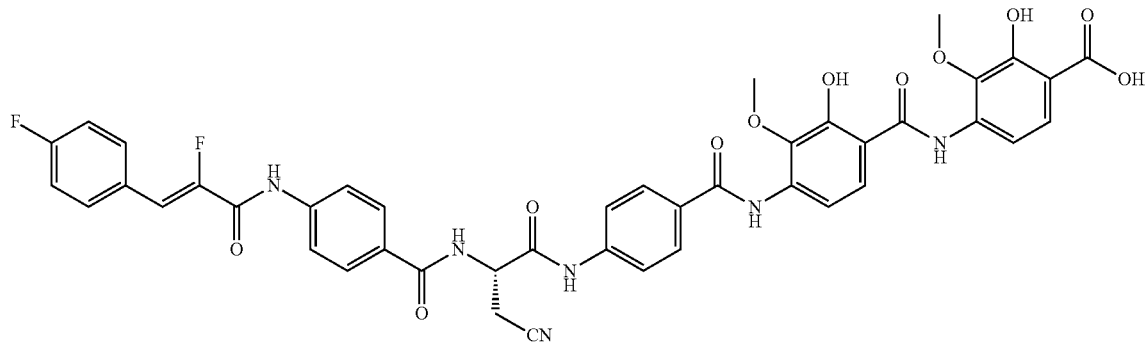 [SMILES: COc1c(NC(=O)c2ccc(NC(=O)c3ccc(NC(=O)[C@H](CC#N)NC(=O)c4ccc(NC(=O)/C(F)=C/c5ccc(F)cc5)cc4)cc3)c(OC)c2O)ccc(C(=O)O)c1O]
Chemical Formula: C₄₃H₃₄F₂N₆O₁₁
Exact Mass: 848.2254
Compound 88:
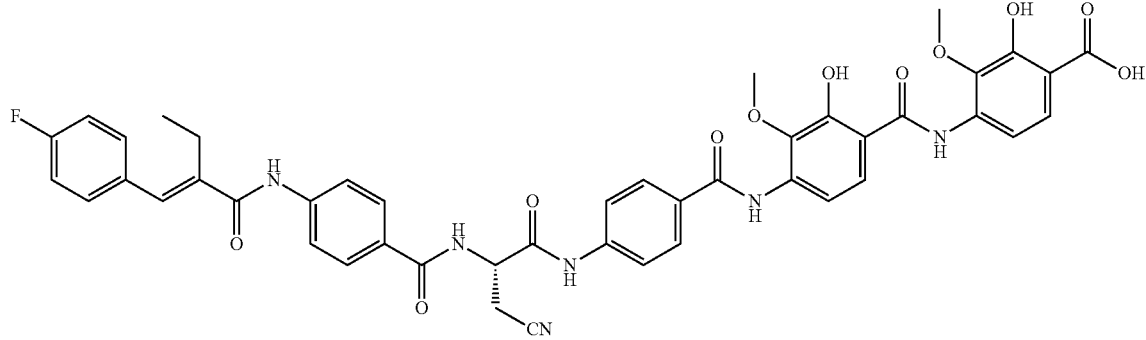 [SMILES: CC/C(=C\c1ccc(F)cc1)C(=O)Nc1ccc(C(=O)N[C@@H](CC#N)C(=O)Nc2ccc(C(=O)Nc3ccc(C(=O)Nc4ccc(C(=O)O)c(O)c4OC)c(O)c3OC)cc2)cc1]
Chemical Formula: C₄₅H₃₉FN₆O₁₁
Exact Mass: 858.2661
Compound 89:
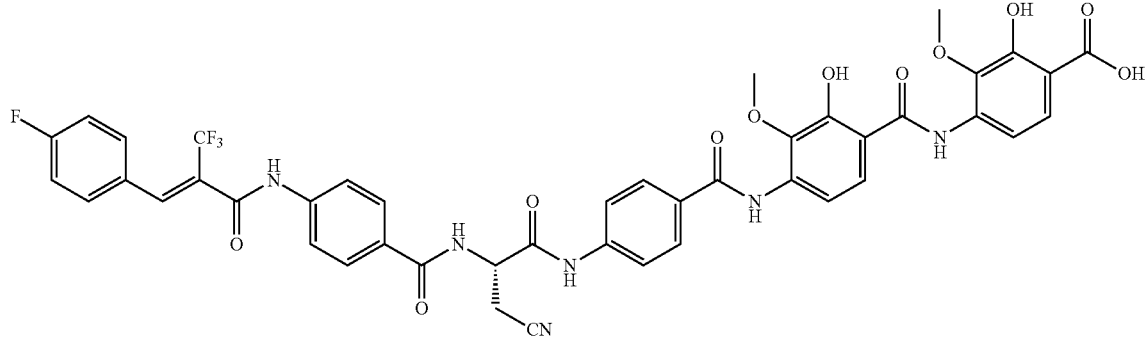
Chemical Formula: C₄₄H₃₄F₄N₆O₁₁
Exact Mass: 898.2222

Compound 90:
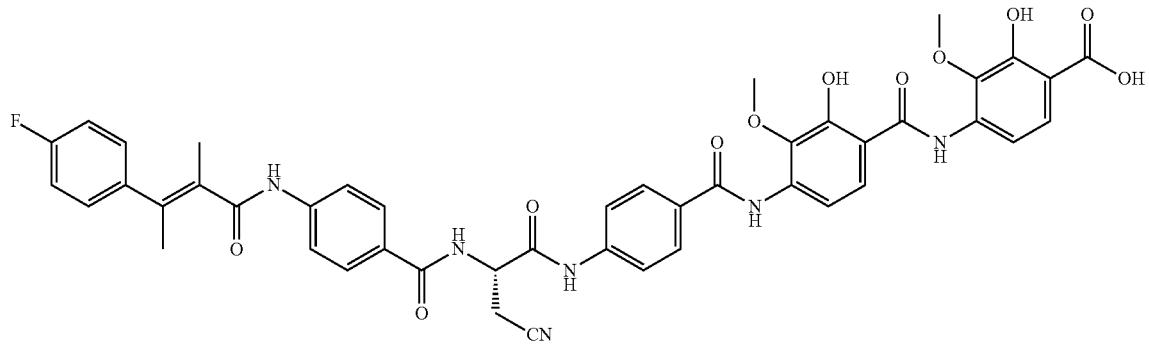 [SMILES: COc1c(NC(=O)c2ccc(NC(=O)c3ccc(NC(=O)[C@H](CC#N)NC(=O)c4ccc(NC(=O)/C(C)=C(\C)c5ccc(F)cc5)cc4)cc3)c(OC)c2O)ccc(C(=O)O)c1O]
Chemical Formula: $C_{45}H_{39}FN_6O_{11}$
Exact Mass: 858,2661
Compound 91:
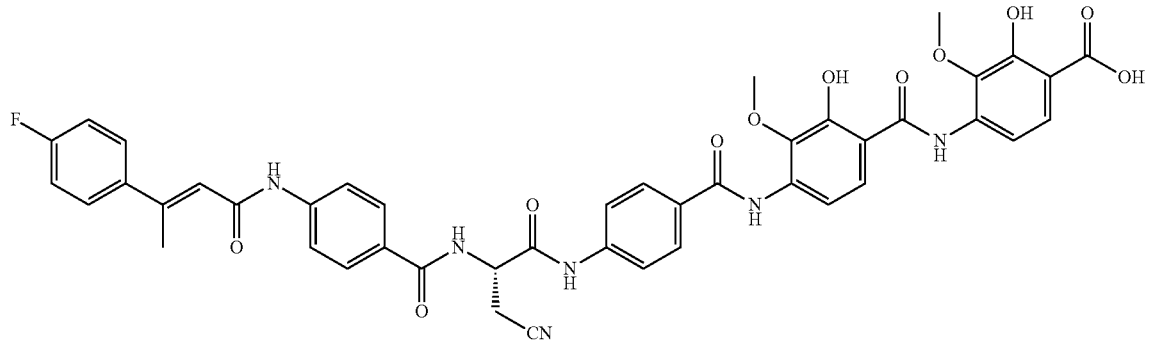 [SMILES: COc1c(NC(=O)c2ccc(NC(=O)c3ccc(NC(=O)[C@H](CC#N)NC(=O)c4ccc(NC(=O)/C=C(\C)c5ccc(F)cc5)cc4)cc3)c(OC)c2O)ccc(C(=O)O)c1O]
Chemical Formula: $C_{44}H_{37}FN_6O_{11}$
Exact Mass: 844,2504
Compound 92:
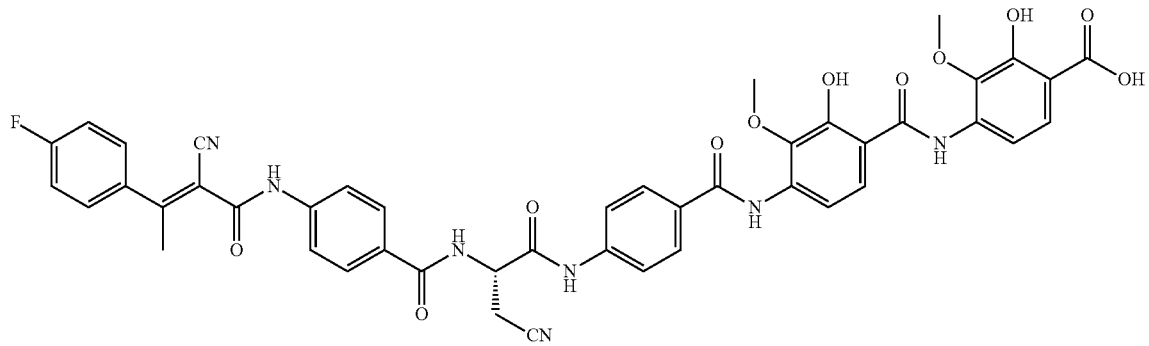
Chemical Formula: $C_{45}H_{36}FN_7O_{11}$
Exact Mass: 869,2457

Compound 93:
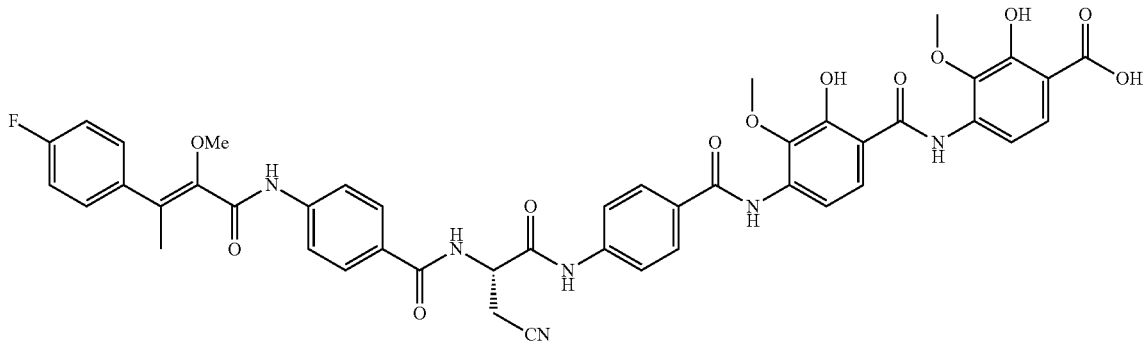 [SMILES: CO/C(C(=O)Nc1ccc(C(=O)N[C@@H](CC#N)C(=O)Nc2ccc(C(=O)Nc3ccc(C(=O)Nc4ccc(C(=O)O)c(O)c4OC)c(O)c3OC)cc2)cc1)=C(/C)c1ccc(F)cc1]
Chemical Formula: $C_{45}H_{39}FN_6O_{12}$
Exact Mass: 874.2610
Compound 94:
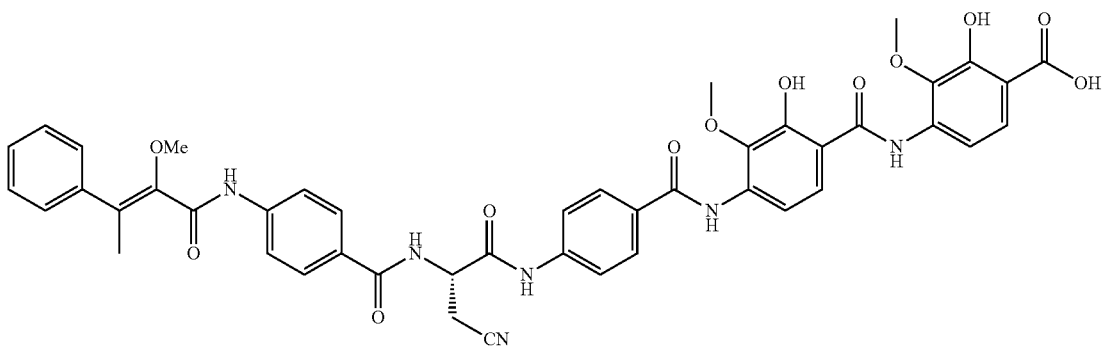 [SMILES: CO/C(C(=O)Nc1ccc(C(=O)N[C@@H](CC#N)C(=O)Nc2ccc(C(=O)Nc3ccc(C(=O)Nc4ccc(C(=O)O)c(O)c4OC)c(O)c3OC)cc2)cc1)=C(/C)c1ccccc1]
Chemical Formula: $C_{44}H_{38}N_6O_{12}$
Exact Mass: 842.2548
Compound 95:
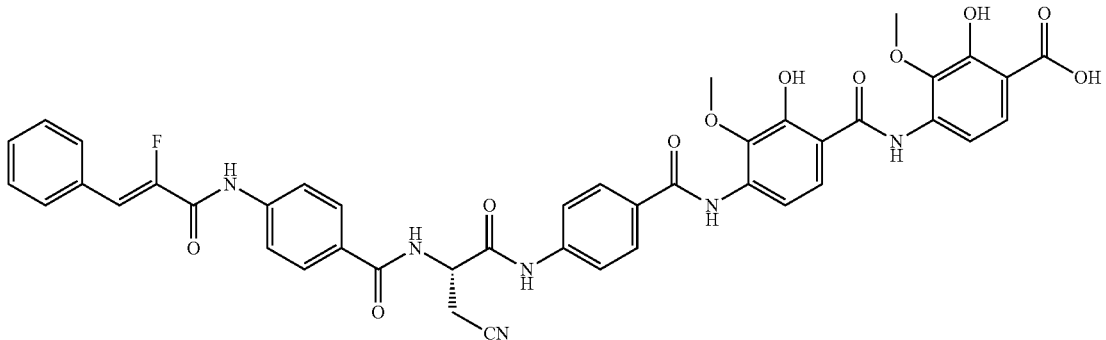 [SMILES: COc1c(NC(=O)c2ccc(NC(=O)c3ccc(NC(=O)[C@H](CC#N)NC(=O)c4ccc(NC(=O)/C(F)=C/c5ccccc5)cc4)cc3)c(OC)c2O)ccc(C(=O)O)c1O]
Chemical Formula: $C_{43}H_{35}FN_6O_{11}$
Exact Mass: 830.2348

Compound 96:
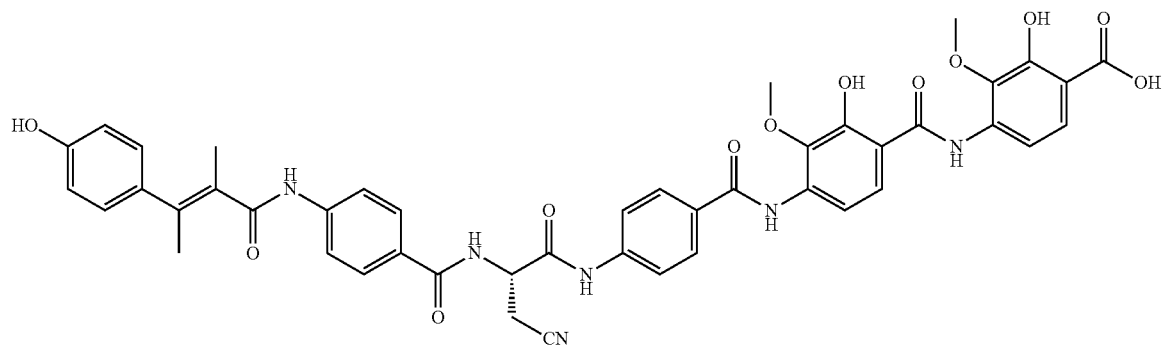 [SMILES: COc1c(NC(=O)c2ccc(NC(=O)c3ccc(NC(=O)[C@H](CC#N)NC(=O)c4ccc(NC(=O)/C(C)=C(\C)c5ccc(O)cc5)cc4)cc3)c(OC)c2O)ccc(C(=O)O)c1O]
Chemical Formula: $C_{45}H_{40}N_6O_{12}$
Exact Mass: 856,2704
Compound 97:
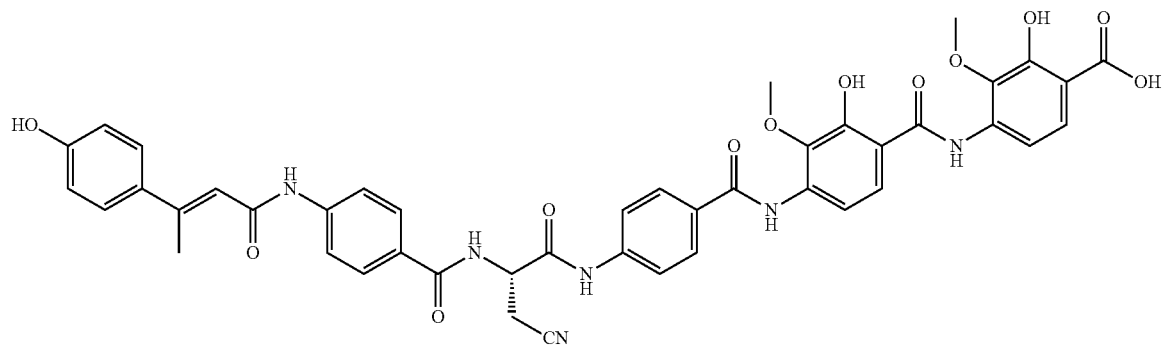 [SMILES: COc1c(NC(=O)c2ccc(NC(=O)c3ccc(NC(=O)[C@H](CC#N)NC(=O)c4ccc(NC(=O)/C=C(\C)c5ccc(O)cc5)cc4)cc3)c(OC)c2O)ccc(C(=O)O)c1O]
Chemical Formula: $C_{44}H_{38}N_6O_{12}$
Exact Mass: 842,2548
Compound 98:
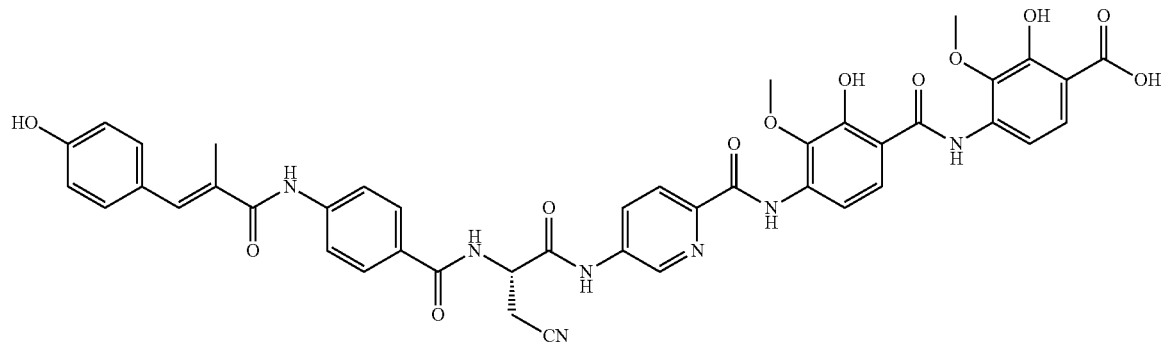 [SMILES: COc1c(NC(=O)c2ccc(NC(=O)c3ccc(NC(=O)[C@H](CC#N)NC(=O)c4ccc(NC(=O)/C(C)=C/c5ccc(O)cc5)cc4)cn3)c(OC)c2O)ccc(C(=O)O)c1O]

Compound 99:
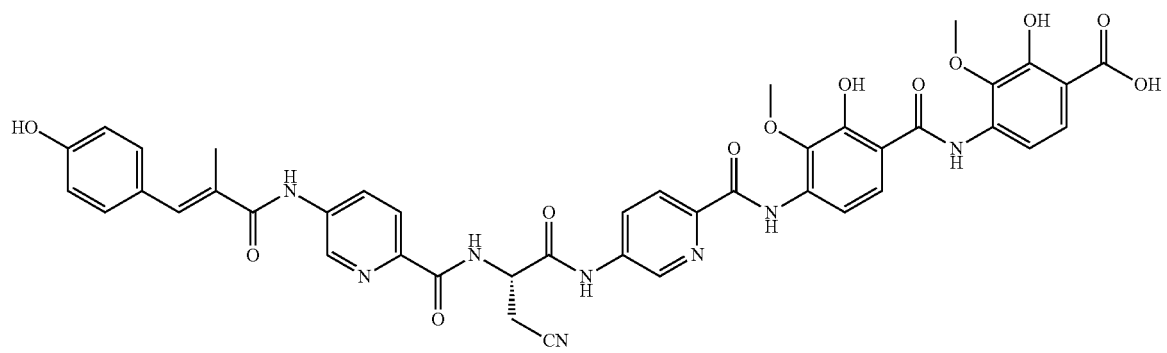 [SMILES: COc1c(NC(=O)c2ccc(NC(=O)c3ccc(NC(=O)[C@H](CC#N)NC(=O)c4ccc(NC(=O)/C(C)=C/c5ccc(O)cc5)cn4)cn3)c(OC)c2O)ccc(C(=O)O)c1O]
Chemical Formula: $C_{42}H_{36}N_8O_{12}$
Exact Mass: 844,24527
Compound 100:
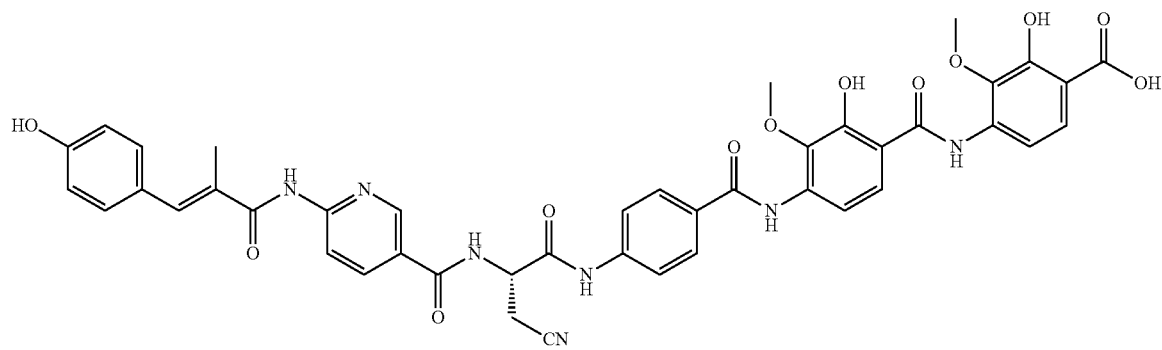 [SMILES: COc1c(NC(=O)c2ccc(NC(=O)c3ccc(NC(=O)[C@H](CC#N)NC(=O)c4ccc(NC(=O)/C(C)=C/c5ccc(O)cc5)nc4)cc3)c(OC)c2O)ccc(C(=O)O)c1O]
Chemical Formula: $C_{43}H_{37}N_7O_{12}$
Exact Mass: 843,25002
Compound 101:
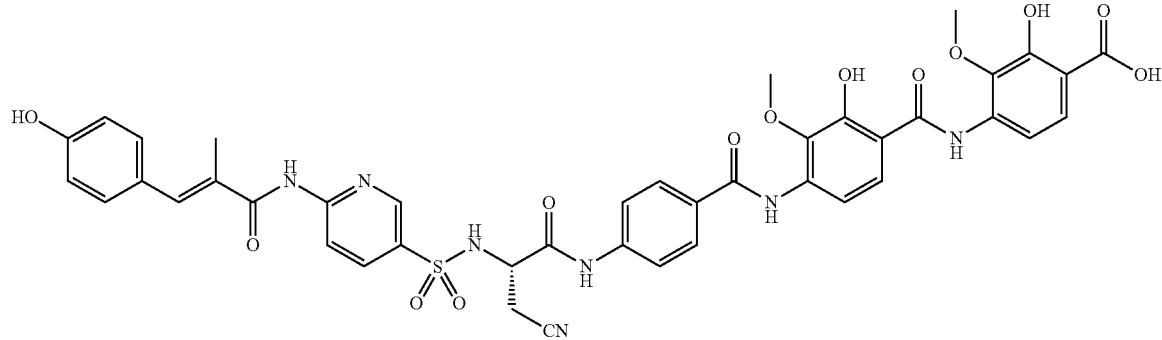 [SMILES: COc1c(NC(=O)c2ccc(NC(=O)c3ccc(NC(=O)[C@H](CC#N)NS(=O)(=O)c4ccc(NC(=O)/C(C)=C/c5ccc(O)cc5)nc4)cc3)c(OC)c2O)ccc(C(=O)O)c1O]
Chemical Formula: $C_{43}H_{38}N_6O_{13}S$
Exact Mass: 878,22176

Compound 102:
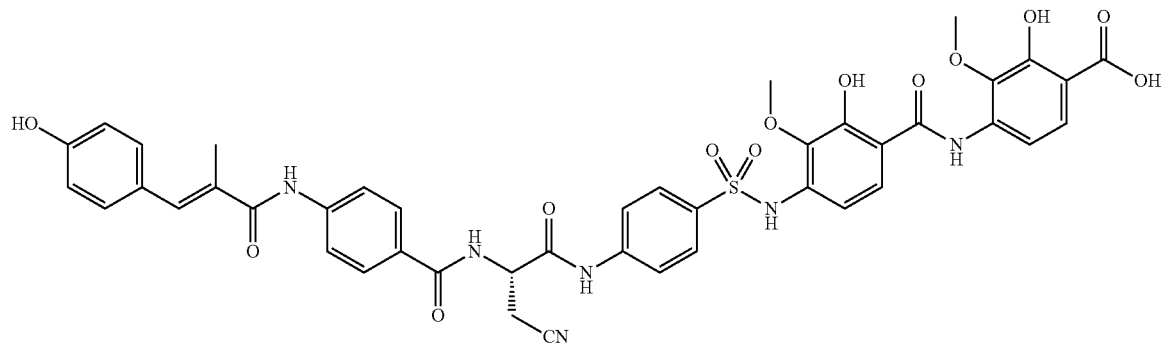 [SMILES: COc1c(NC(=O)c2ccc(NS(=O)(=O)c3ccc(NC(=O)[C@H](CC#N)NC(=O)c4ccc(NC(=O)/C(C)=C/c5ccc(O)cc5)cc4)cc3)c(OC)c2O)ccc(C(=O)O)c1O]
Chemical Formula: $C_{43}H_{38}N_6O_{13}S$
Exact Mass: 878,22176
Compound 103:
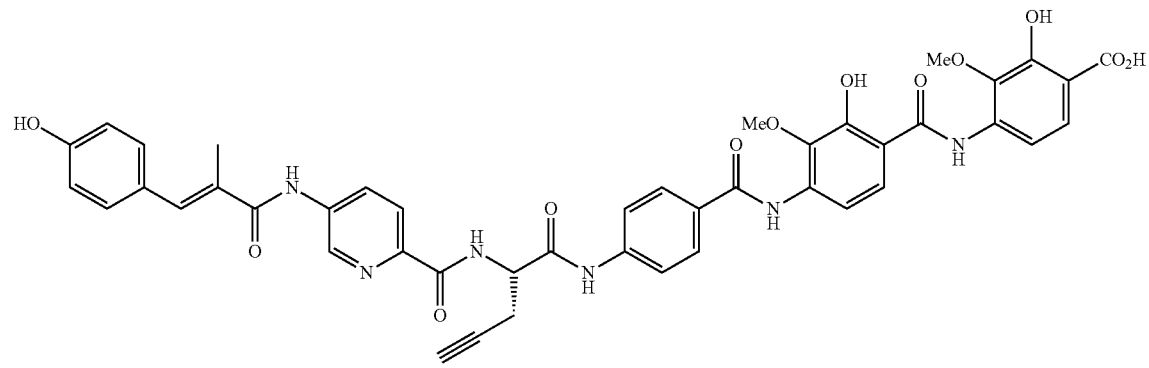
Chemical Formula: $C_{44}H_{38}N_6O_{12}$
Exact Mass: 842,25477
Compound 104:
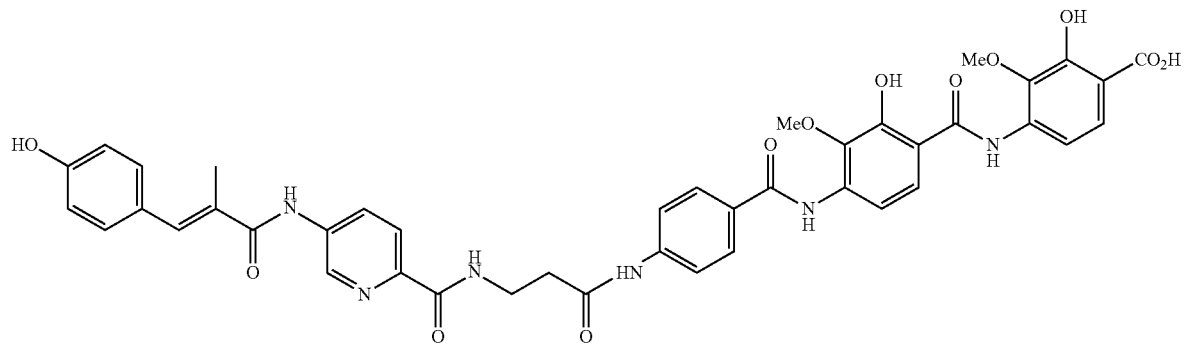 [SMILES: COc1c(NC(=O)c2ccc(NC(=O)c3ccc(NC(=O)CCNC(=O)c4ccc(NC(=O)/C(C)=C/c5ccc(O)cc5)cn4)cc3)c(OC)c2O)ccc(C(=O)O)c1O]
Chemical Formula: $C_{42}H_{38}N_6O_{12}$
Exact Mass: 818,25477

Compound 105:
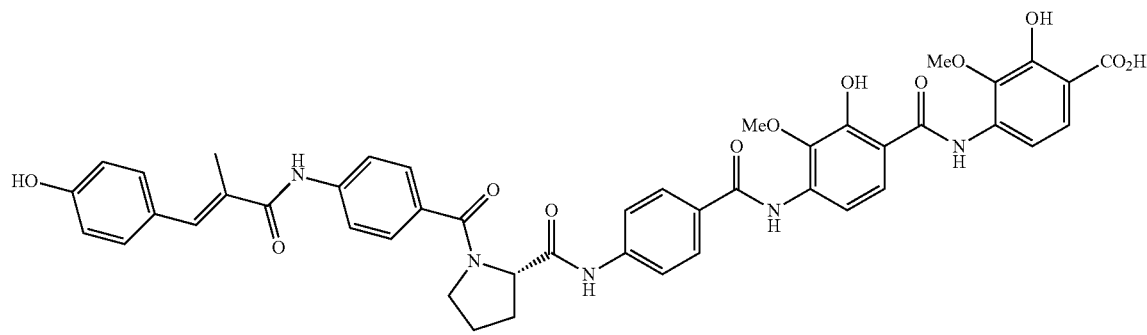 [SMILES: COc1c(NC(=O)c2ccc(NC(=O)c3ccc(NC(=O)[C@@H]4CCCN4C(=O)c4ccc(NC(=O)/C(C)=C/c5ccc(O)cc5)cc4)cc3)c(OC)c2O)ccc(C(=O)O)c1O]
Chemical Formula: $C_{45}H_{41}N_5O_{12}$
Exact Mass: 843,27517
Compound 106:
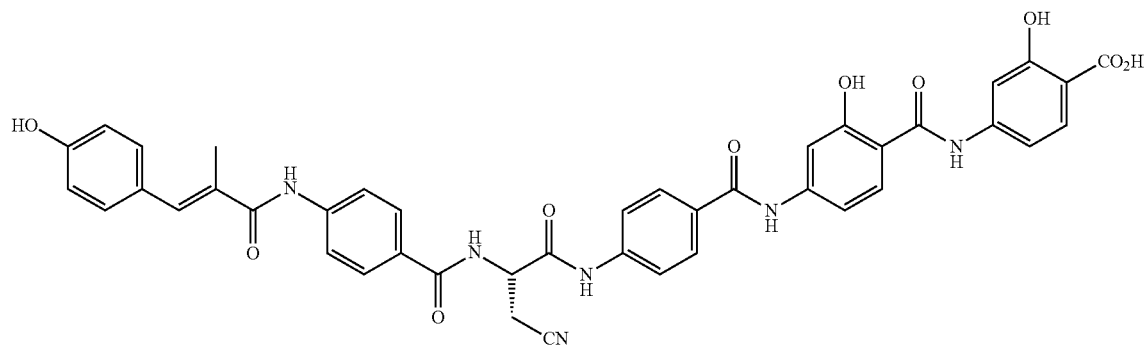
Chemical Formula: $C_{42}H_{34}N_6O_{10}$
Exact Mass: 782,2336
Compound 107:
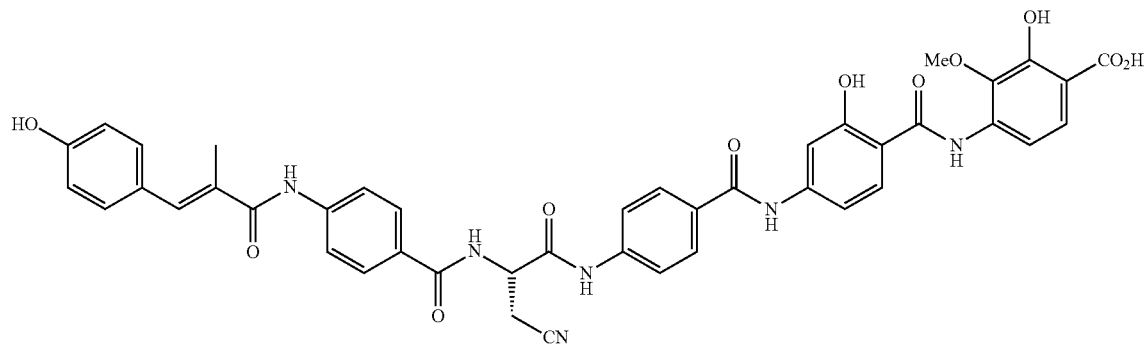
Chemical Formula: $C_{43}H_{36}N_6O_{11}$
Exact Mass: 812,2442

Compound 108:
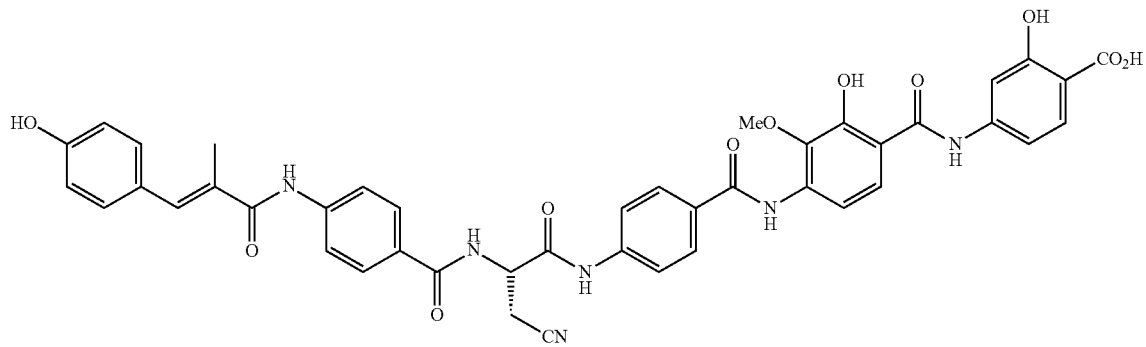
Chemical Formula: $C_{43}H_{36}N_6O_{11}$
Exact Mass: 812,2442
Compound 109:
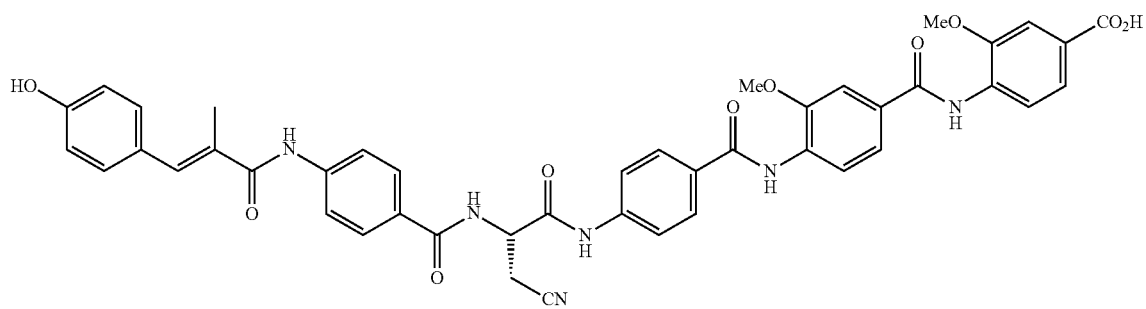
Chemical Formula: $C_{44}H_{38}N_6O_{10}$
Exact Mass: 810,2649
Compound 110:
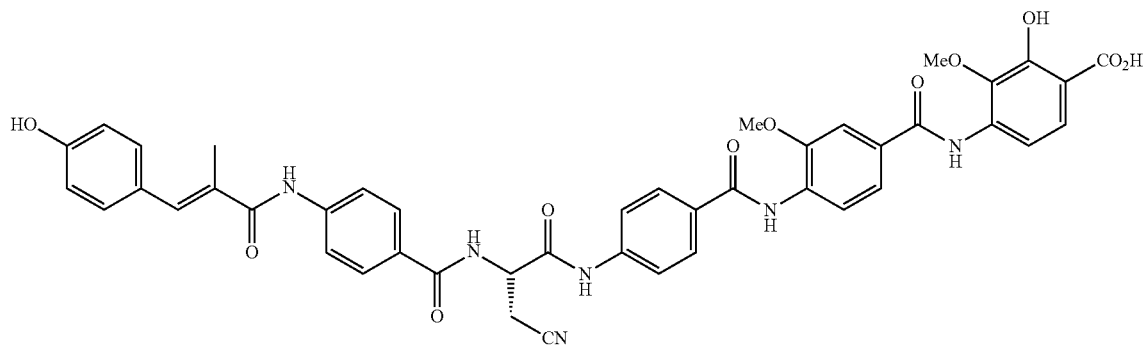
Chemical Formula: $C_{44}H_{38}N_6O_{11}$
Exact Mass: 826,2599

Compound 111:
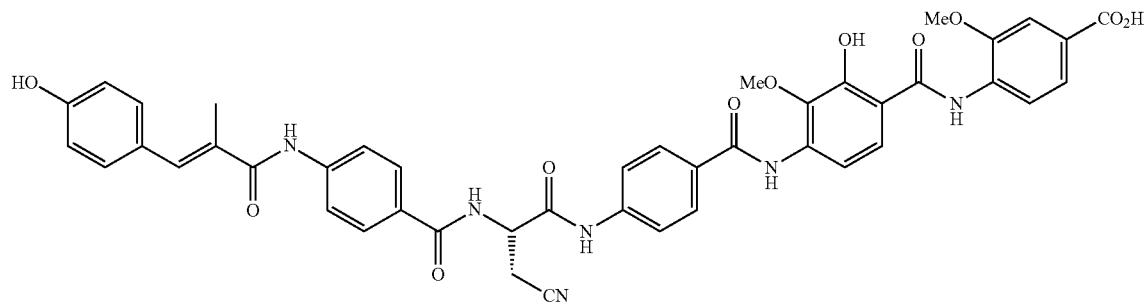
Chemical Formula: C$_{44}$H$_{38}$N$_6$O$_{11}$
Exact Mass: 826.2599
Compound 112:
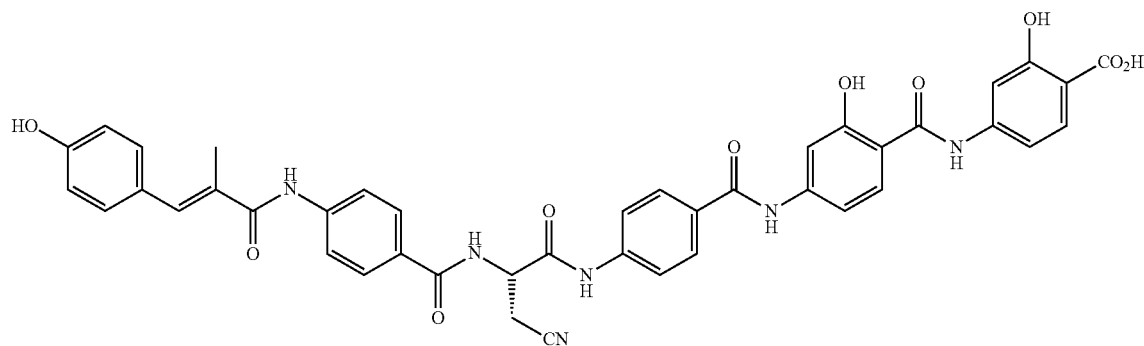
Compound 113:
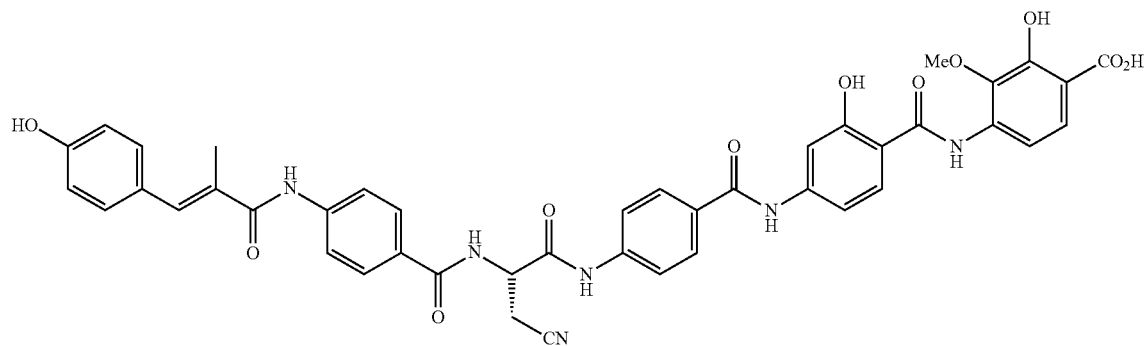

Compound 114:
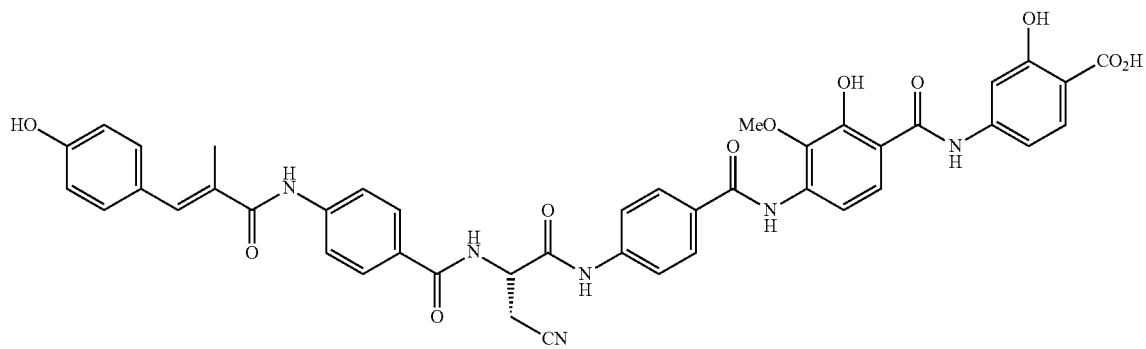
Compound 115:
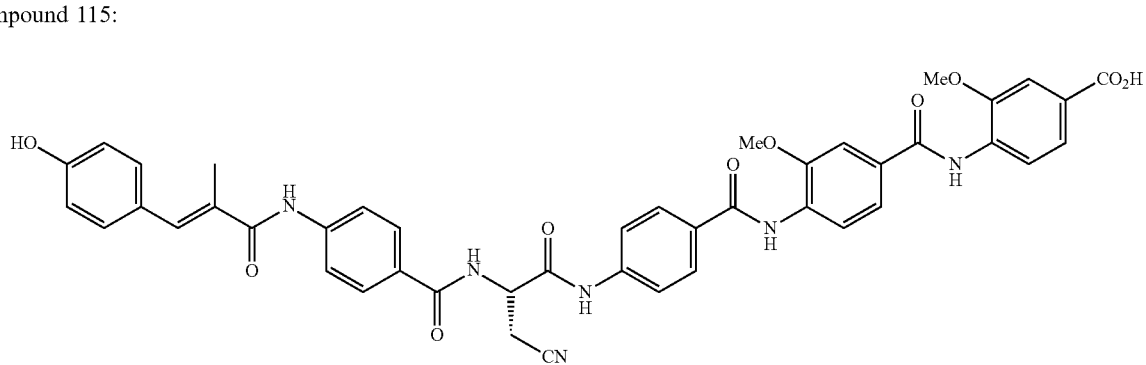
Compound 116:
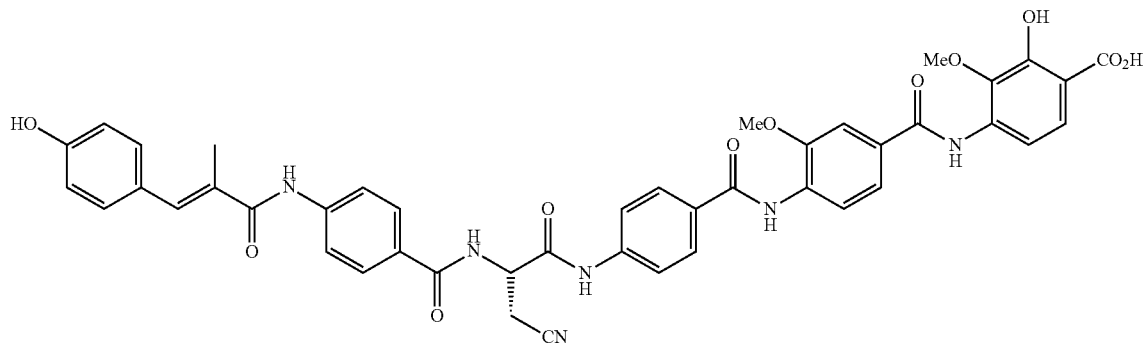
Compound 117:
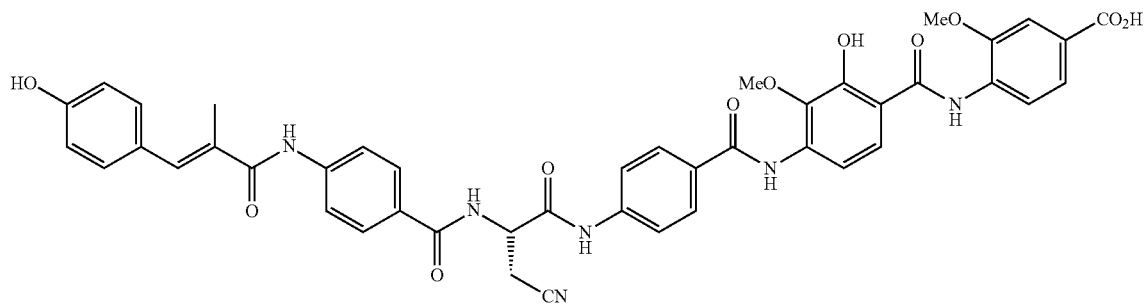

In some embodiments the compounds 1 to 50, 70 to 76 and 78 to 117 comprise an essentially pure L-enantiomer structure, an essentially pure D-enantiomer structure or a mixture of the L- and D-enantiomer of the same molecular formula, wherein in particular the compounds 1 to 50, 70 to 76 and 78 to 117 comprise an essentially pure L-enantiomer structure.
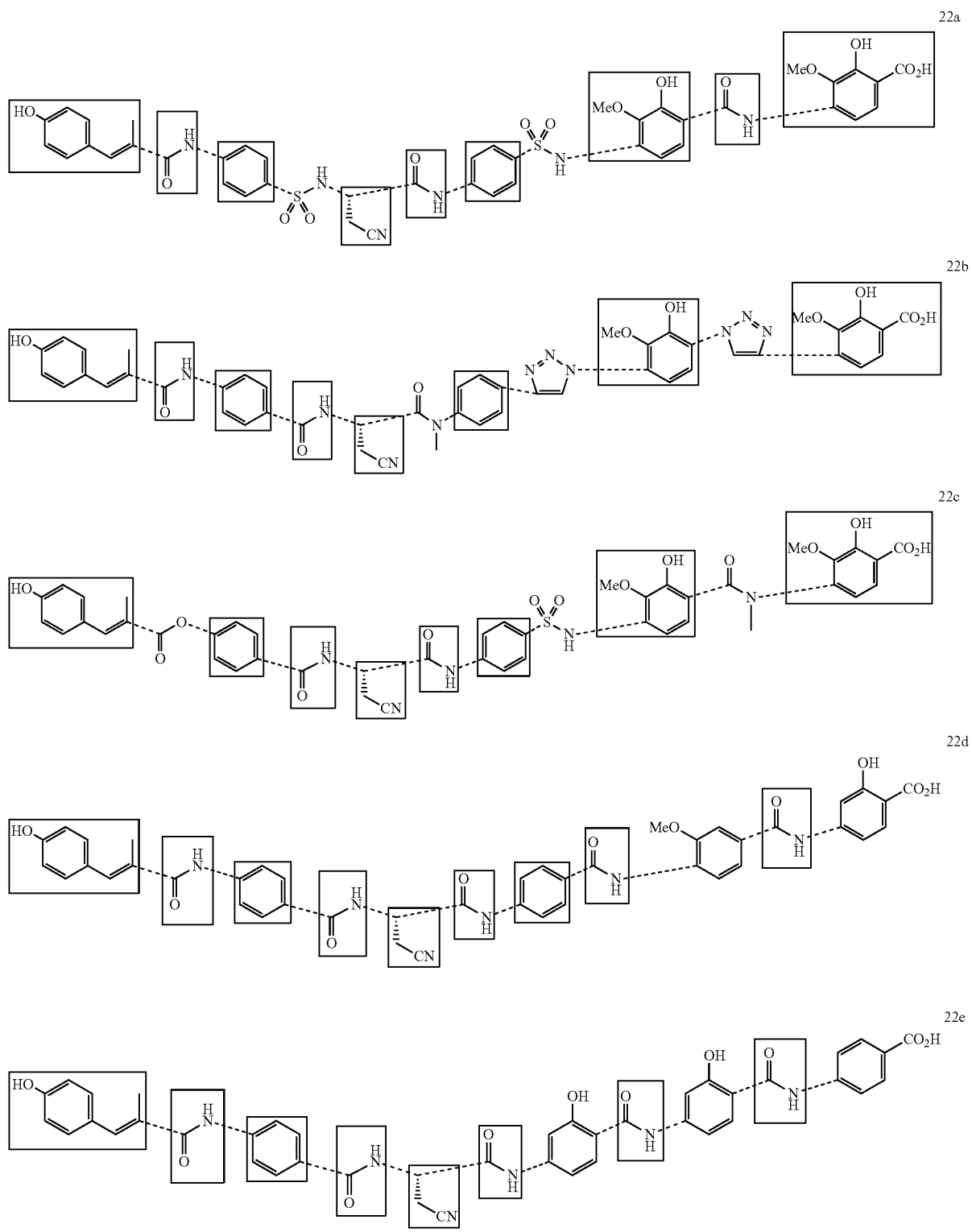

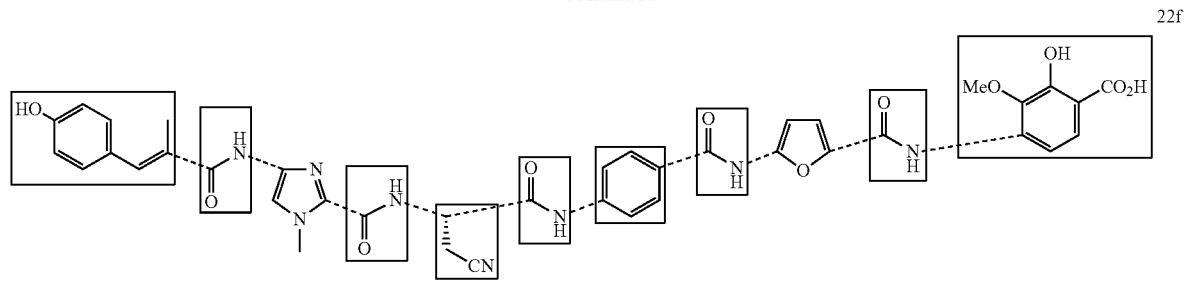
22f
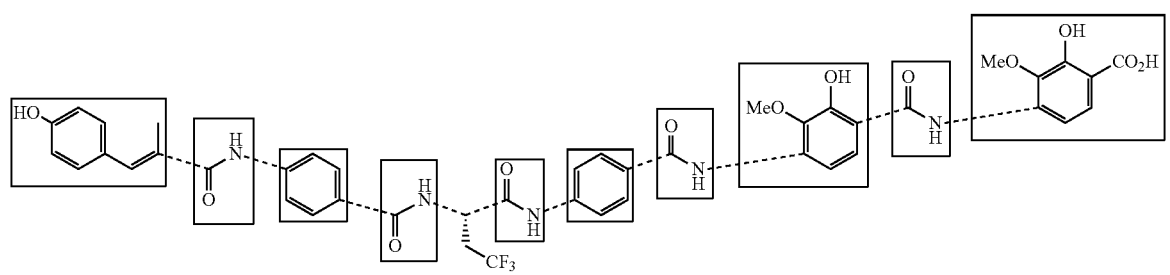
22g
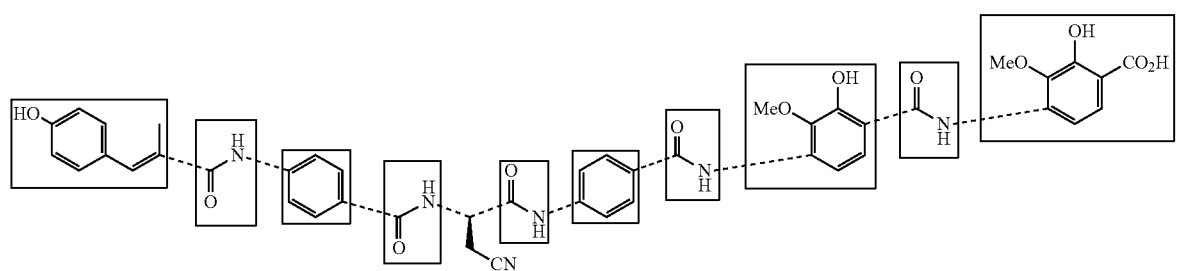
22h
Further embodiments of the present compounds are compounds 22a-22h.
Yet further embodiments of the present compounds may comprise one of the following structures according to formula (1L)
(1L)

and formula (1D),
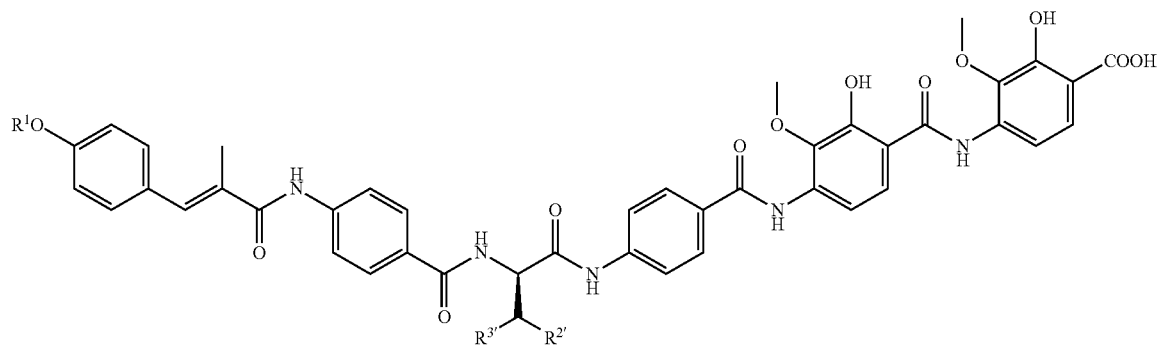
(1D)
wherein
R¹ is H or CO(NH₂),
R²' is CO(NH₂) or CN,
R³' is H or OCH₃.
In case of the compounds of formula (1L) and (1D) comprising a —OCH₃ moiety as R3' the following stereoisomers of formula (1L1), (1L2), (1D1) and (1D2) are possible:
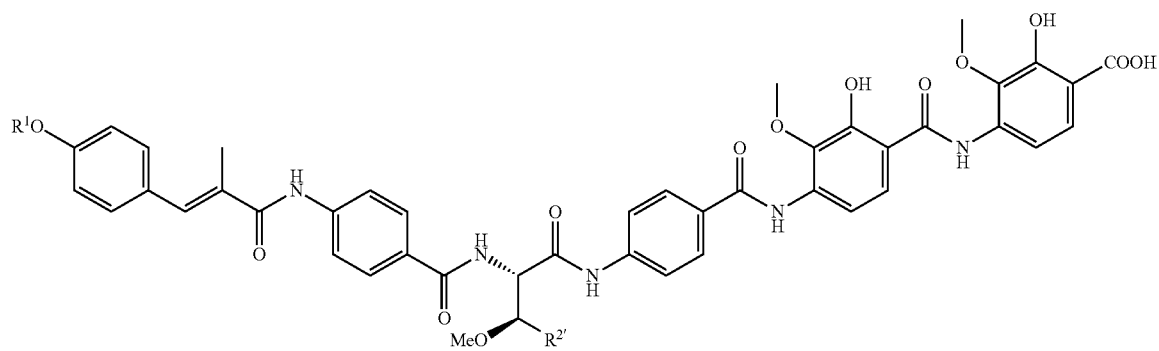
(1L1)
formula (1L2)
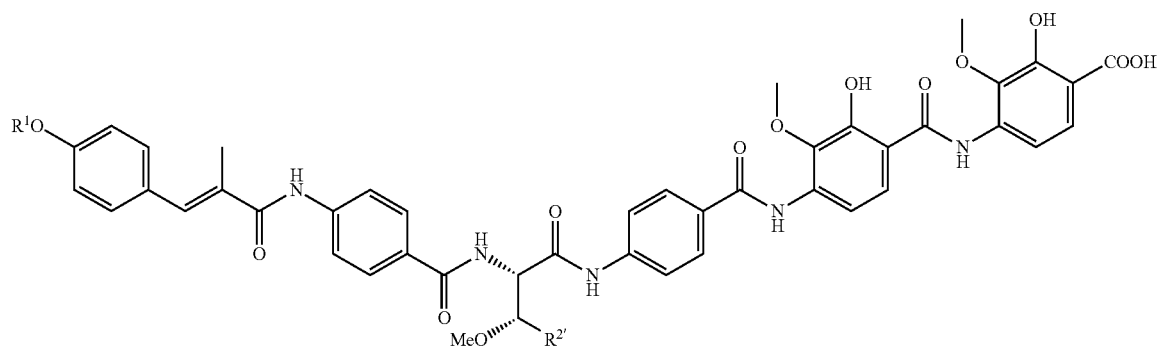
(1L2)

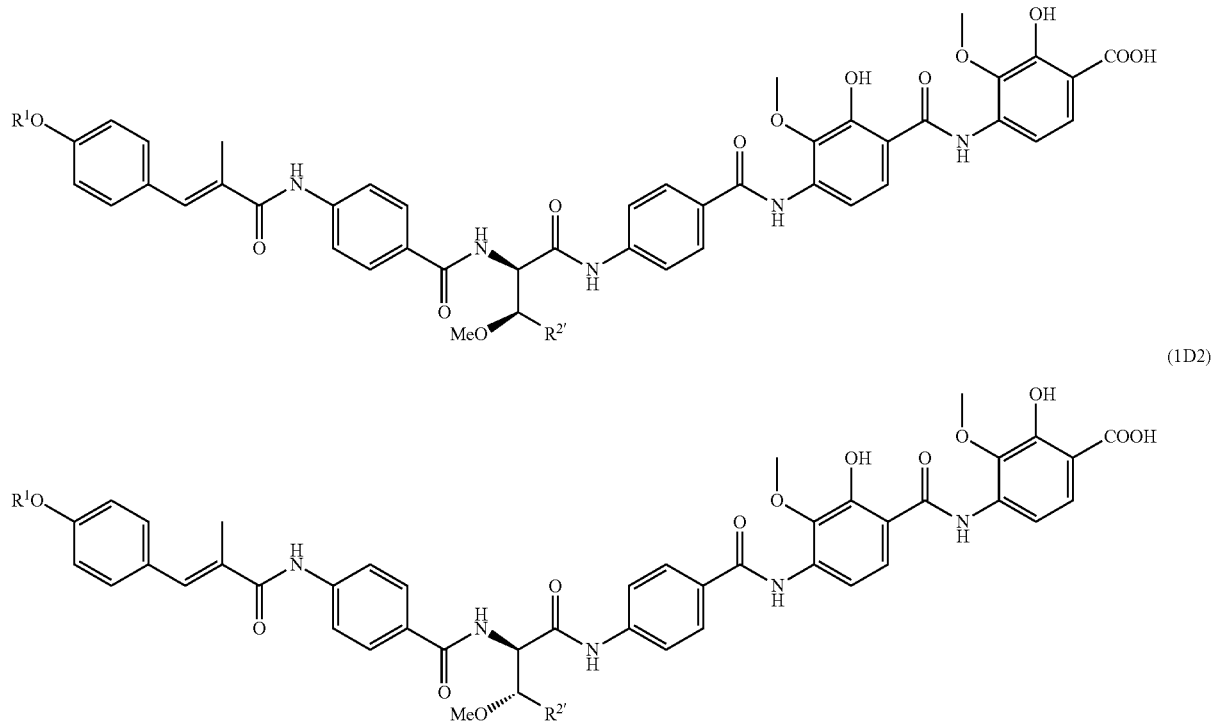

wherein
R¹ is H or CO(NH₂),
R²' is CO(NH₂) or CN,

In some embodiments, concerning antibiotically active natural occurring L-albicidin compounds of the formula (1L),
a. R¹ is H, R³' is H and R²' is CN (beta-Albicidin), or
b. R¹ is H, R³' is H and R²' is CO(NH₂) (Asn-Albicidin), or
c. R¹ is CO(NH₂), R³' is H and R²' is CN (Carbamoyl-Albicidin), or
d. R¹ is CO(NH₂), R³' is H and R²' is CO(NH₂) (Carbamoyl-Asn-Albicidin), or
e. R¹ is H, R³' is OCH₃ and R²' is CN (beta-OMe-Albicidin), or
f. R¹ is H, R³' is OCH₃ and R²' is CO(NH₂) (Asn-OMe-Albicidin), or
g. R¹ is CO(NH₂), R³' is OCH₃ and R²' is CN (Carbamoyl-OMe-Albicidin), or
h. R¹ is CO(NH₂), R³' is OCH₃ and R²' is CO(NH₂) (Carbamoyl-OMe-Asn-Albicidin).

In some embodiments, concerning antibiotically active synthetic D-albicidin compounds of the formula (1D),
a. R¹ is H and R²' is CN (Enantio-beta-Albicidin), or
b. R¹ is H, and R²' is CO(NH₂) (Enantio-Asn-Albicidin), or
c. R¹ is CO(NH₂), and R²' is CN (Enantio-Carbamoyl-Albicidin), or
d. R¹ is CO(NH₂), and R²' is CO(NH₂) (Enantio-Carbamoyl-Asn-Albicidin), or
e. R¹ is H, R³' is OCH₃ and R²' is CN (Enantio-beta-OMe-Albicidin), or
f. R¹ is H, R³' is OCH₃ and R²' is CO(NH₂) (Enantio-Asn-OMe-Albicidin), or
g. R¹ is CO(NH₂), R³' is OCH₃ and R²' is CN (Enantio-Carbamoyl-OMe-Albicidin), or
h. R¹ is CO(NH₂), R³' is OCH₃ and R²' is CO(NH₂) (Enantio-Carbamoyl-OMe-Asn-Albicidin).

In some embodiments, concerning antibiotically active natural occurring L-albicidin compounds of the formula (1L),
a. R¹ is H and R²' is CN (beta-Albicidin), or
b. R¹ is H, and R²' is CO(NH₂) (Asn-Albicidin).

In some embodiments, concerning antibiotically active synthetic D-albicidin compounds of the formula (1D),
a. R¹ is H and R²' is CN (Enantio-beta-Albicidin), or
b. R¹ is H, and R²' is CO(NH₂) (Enantio-Asn-Albicidin).

In some embodiments, concerning antibiotically active natural occurring L-albicidin compounds of the formula (1L),
a. R¹ is H and R²' is CN (beta-Albicidin).

In some embodiments, concerning antibiotically active synthetic D-albicidin compounds of the formula (1D),
a. R¹ is H and R²' is CN (Enantio-beta-Albicidin).

In some embodiments, the compounds of the invention relates to a mixture of the L- and D-enantiomer of the same molecular formula.

In some embodiments, the compounds of the invention relates to a mixture of
beta-Albicidin and Enantio-beta-Albicidin, or
Asn-Albicidin and Enantio-Asn-Albicidin, or
Carbamoyl-Albicidin and Enantio-Carbamoyl-Albicidin, or
Carbamoyl-Asn-Albicidin and Enantio-Carbamoyl-Asn-Albicidin, or
beta-OMe-Albicidin and Enantio-beta-OMe-Albicidin, or
Asn-OMe-Albicidin and Enantio-Asn-OMe-Albicidin, or
Carbamoyl-OMe-Albicidin and Enantio-Carbamoyl-OMe-Albicidin, or Carbamoyl-OMe-Asn-Albicidin and Enantio-OMe-Carbamoyl-Asn-Albicidin In some embodiments, the compounds of the invention relates to a mixture of beta-Albicidin and Enantio-beta-Albicidin, or Asn-Albicidin and Enantio-Asn-Albicidin.

In some embodiments, the compounds of the invention relates to a mixture of beta-Albicidin and Enantio-beta-Albicidin.

In a another embodiment the compounds according to formula 1L, 1D, 1L1, 1L2, 1D1 and/or 1D2 may be exempted from the general formula (1). In particular the natural occurring L-albicidin compounds of formula 1L may be exempted from the general formula I.

It is understood that all the compounds of the general formulae 1 and embodiments thereof may comprise—depending on the selected substituents—at least one further stereocenter with an L- or D-configuration. Thus, the embodiments of the invention encompass a pure compound with the same stereo centers (e.g. a compound only with an L and a D stereo center or two L stereo centers) or a mixture of the respective enantiomers of the same molecular formula.

The compounds of the general formula 1 can also be obtained in the form of their hydrates and/or also can include other solvents used for example for the crystallization of compounds present in the solid form. Depending on the method and/or the reaction conditions, compounds of the general formula 1 can be obtained in the free form or in the form of salts. Particularly in the form of salts of alkali metals, alkaline earth metals, ammonium or alkylammonium.

Pharmaceutically acceptable salts of compounds of the formula (I) mean both their organic and inorganic salts as described in Remington's Pharmaceutical Sciences (17th edition, page 1418 (1985)). Because of the physical and chemical stability and the solubility, preference is given for acidic groups inter alia to sodium, potassium, calcium and ammonium salts; preference is given for basic groups inter alia to salts of maleic acid, fumaric acid, succinic acid, malic acid, tartaric acid, methylsulfonic acid, hydrochloric acid, sulfuric acid, phosphoric acid or of carboxylic acids or sulfonic acids, for example as hydrochlorides, hydrobromides, phosphates, sulfates, methanesulfonates, acetates, lactates, maleates, fumarates, malates, gluconates, and salts of amino acids, of natural bases or carboxylic acids. The preparation of pharmaceutically acceptable salts from compounds of the formula (I) which are capable of salt formation, including their stereoisomeric forms, takes place in a manner known per se. The compounds of the formula (I) form stable alkali metal, alkaline earth metal or optionally substituted ammonium salts with basic reagents such as hydroxides, carbonates, bicarbonates, alcoholates and ammonia or organic bases, for example trimethyl- or triethylamine, ethanolamine, diethanolamine or triethanolamine, trometamol or else basic amino acids, for example lysine, ornithine or arginine. Where the compounds of the formula (I) have basic groups, stable acid addition salts can also be prepared with strong acids. Suitable pharmaceutically acceptable acid addition salts of the compounds of the invention are salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. The hydrochloride salt is a preferred salt.

Salts with a pharmaceutically unacceptable anion such as, for example, trifluoroacetate likewise belong within the framework of the invention as useful intermediates for the preparation or purification of pharmaceutically acceptable salts and/or for use in nontherapeutic, for example in vitro, applications.

The present invention furthermore relates to pharmaceutical preparations (or pharmaceutical compositions) which contain an effective amount of at least one compound of the formula (I) and/or its pharmaceutically acceptable salts and a pharmaceutically acceptable carrier, i. e. one or more pharmaceutically acceptable carrier substances (or vehicles) and/or additives (or excipients). The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays.

The pharmaceutical preparations according to the invention are prepared in a manner known per se and familiar to one skilled in the art, pharmaceutically acceptable inert inorganic and/or organic carrier substances and/or additives being used in addition to the compound(s) of the formula (I) and/or its (their) pharmaceutically acceptable salts and/or its (their) prodrugs. For the production of pills, tablets, coated tablets and hard gelatin capsules it is possible to use, for example, lactose, corn starch or derivatives thereof, talc, stearic acid or its salts, etc. Carrier substances for soft gelatin capsules and suppositories are, for example, fats, waxes, semisolid and liquid polyols, natural or hardened oils, etc. Suitable carrier substances for the production of solutions, for example injection solutions, or of emulsions or syrups are, for example, water, saline, alcohols, glycerol, polyols, sucrose, invert sugar, glucose, vegetable oils, etc. Suitable carrier substances for microcapsules, implants or rods are, for example, copolymers of glycolic acid and lactic acid. The pharmaceutical preparations normally contain about 0.5 to about 90% by weight of the compounds of the formula (I) and/or their pharmaceutically acceptable salts and/or their prodrugs. The amount of the active ingredient of the formula (I) and/or its pharmaceutically acceptable salts and/or its prodrugs in the pharmaceutical preparations normally is from about 0.5 to about 1000 mg, preferably from about 1 to about 500 mg.

A prodrug within the meaning of the present invention is a precursor chemical compound of an biological active compound of general formula (1). Instead of administering the active compound or drug, a prodrug might be used instead to improve the absorption, distribution, metabolization and excretion. Prodrugs are often designed to improve bioavailability when a drug itself is poorly absorbed from the gastrointestinal tract. A prodrug may also be used to improve the selectively of the drug. This reduces adverse or unintended effects of a drug, especially important in treatments like chemotherapy, which can have severe unintended and undesirable side effects.

An example of a prodrug withing the context of the present invention is shown below:

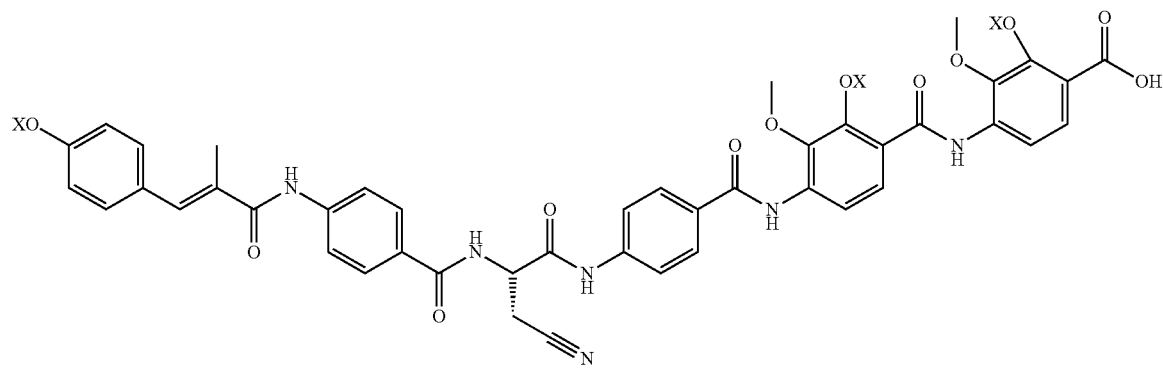
wherein X can be a —OPO$_3$H or —OSO$_3$H moiety each with single or multiple substituents.
A typical reaction scheme for such a prodrug compound is depicted exemplarily in the following:
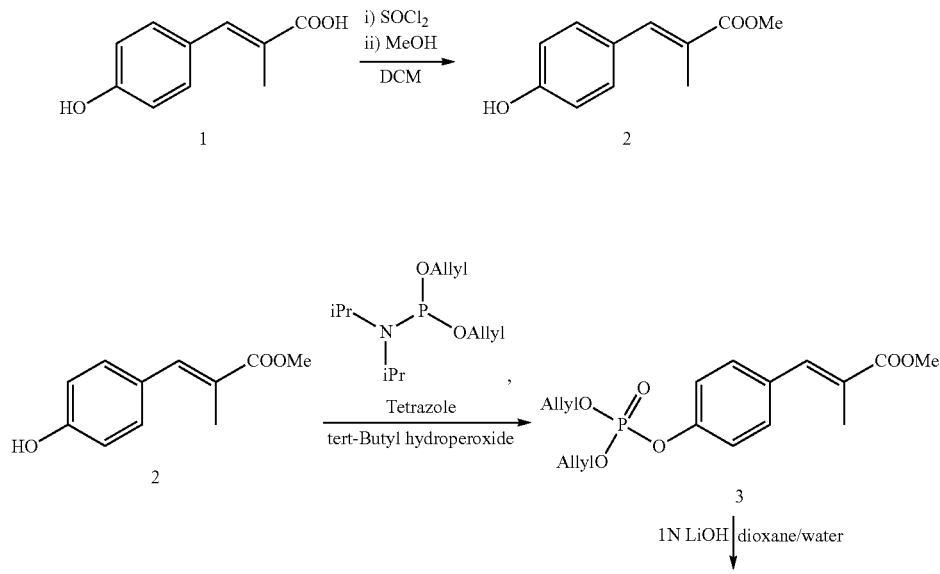
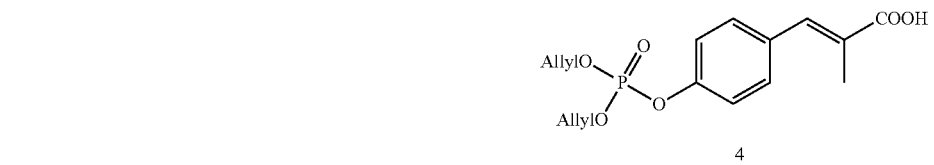
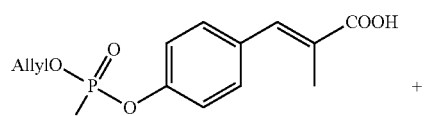

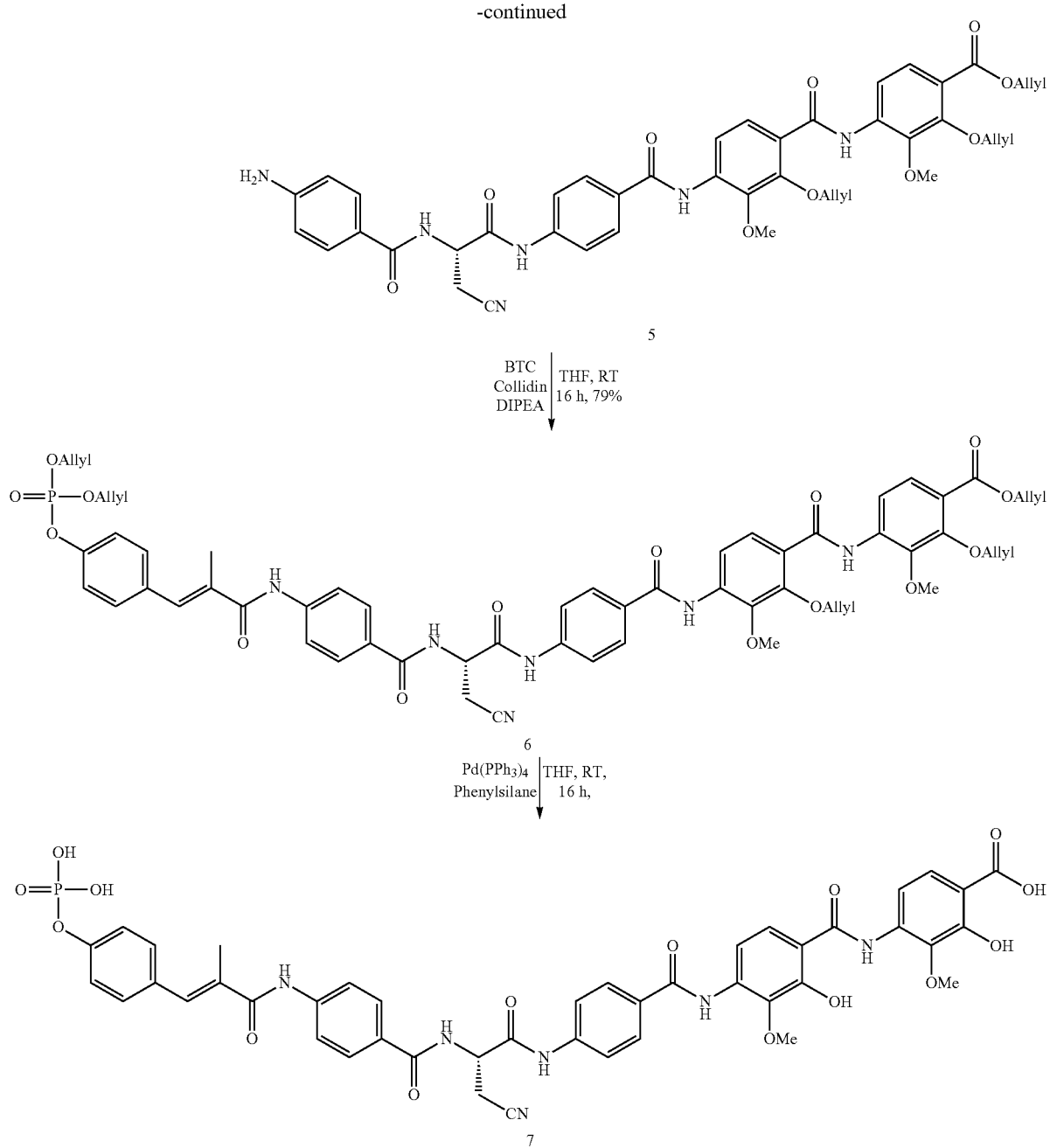

In addition to the active ingredients of the formula (I) and/or their pharmaceutically acceptable salts and to carrier substances, the pharmaceutical preparations can contain one or more additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formula (I) and/or their pharmaceutically acceptable salts. In case a pharmaceutical preparation contains two or more compounds of the formula (I) the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formula (I) allows a great deal of control over the biological and physico-chemical properties of the compounds and thus allows the selection of such desired compounds. Furthermore, in addition to at least one compound of the formula (I) and/or its pharmaceutically acceptable salts, the pharmaceutical preparations can also contain one or more other therapeutically or prophylactically active ingredients. When using the compounds of the formula (I) the dose can vary within wide limits and, as is customary and is known to the physician, is to be suited to the individual conditions in each individual case. It depends, for example, on the specific compound employed, on the nature and severity of the disease to be treated, on the mode and the schedule of administration, or on whether an acute or chronic condition is treated or whether prophylaxis is carried out. An appropriate dosage can be established using clinical approaches well known in the medical art. In general, the daily dose for achieving the desired results in an adult weighing about 75 kg is from about 0.01 to about 100 mg/kg, preferably from about 0.1 to about 50 mg/kg, in particular from about 0.1 to about 10 mg/kg, (in each case in mg per kg of body weight). The daily dose can be divided, in particular in the case of the administration of relatively large amounts, into several, for example 2, 3 or 4, part administrations. As usual, depending on individual behavior it may be necessary to deviate upwards or downwards from the daily dose indicated.

Furthermore, the compounds of the formula (I) can be used as synthesis intermediates for the preparation of other compounds, in particular of other pharmaceutical active ingredients, which are obtainable from the compounds of the formula I1 for example by introduction of substituents or modification of functional groups.

The compounds of the invention may also exist in various polymorphous forms, for example as amorphous and crystalline polymorphous forms. All polymorphous forms of the compounds of the invention belong within the framework of the invention and are a further aspect of the invention.

The compounds of the general formula 1 may be present as optical isomers or as mixtures thereof. The invention relates both to the pure isomers and all possible isomeric mixtures and is hereinafter understood as doing so, even if stereochemical details are not specifically mentioned in every case. Enantiomeric mixtures of compounds of the general formula 1, which are obtainable by the process or any other way, may be separated in known manner—on the basis of the physical-chemical differences of their components—into pure enantiomers, for example by fractional crystallisation, distillation and/or chromatography, in particular by preparative HPLC using a chiral HPLC column.

According to the invention, apart from separation of corresponding isomer mixtures, generally known methods of diastereoselective or enantioselective synthesis can also be applied to obtain pure diastereoisomers or enantiomers, e.g. by carrying out the method described hereinafter and using educts with correspondingly suitable stereochemistry.

It is advantageous to isolate or synthesise the biologically more active isomer, provided that the individual compounds have different biological activities.

Methods of Synthesis

A compound of the general formula (1) can generally be regarded as a chain of up to six building blocks a-b-c-d-e-f, each block being linked to the next by a linker group, for example a peptide (amide) bond.

The six building blocks are a: BA-J or $X^1$-J b: G-BB-J or $X^1$-BB-J; c: G-BC-J;
d: G-BD-J e: G-BE-J, or G-BE-$X^2$; f: G-BF or G-$X^2$, with G being a second linking function capable of selectively forming a covalent bond by a reaction with a first linking function J yielding the respective and with $X^1$, BA, BB, BC, BD, BE, BF and $X^2$ having the same meaning as defined previously.

Thus, derivatives of the six building blocks are employed as intermediates in the synthesis of the invention as building blocks of the general formula a: (a-J): BA-J; ($X^1$-J): $X^1$-J;
b: (b-J): G-BB-J; ($X^1$-b-J): $X^1$-BB-J;
c: (c-J): G-BC-J;
d: (d-J): G-BD-J;
e: (e-J): G-BE-J; (e-$X^2$): G-BE-$X^2$
f: (G-$X^2$): G-$X^2$ wherein J or G may be activated before a linking reaction ($J^{act}$ or $G^{act}$) or may be reversibly inactivated by a removable protecting group ($J^p$ or $G^p$)

wherein a removable protecting group is employed, if necessary, to suppress unwanted side reaction. For example, if a first building block employed in a reaction comprise a COOH moiety, which is destined to react specifically with a $NH_2$ moiety of a second building block, wherein said second building block comprises also a COOH moiety, the COOH moiety of said second building block is protected for avoiding a coupling reaction of said second building block with itself. The use of protecting group is a standard procedure for a skilled person and a skilled person will easily determine the necessity of a protecting group and will employ a suitable protecting group.

There are different reaction pathways for providing a compound of the general formula 1 using the above mentioned building blocks.

It is apparent to the skilled person that a suitable reaction pathway will not necessarily involve the isolated building blocks in each case, but will take place between combinations of the above mentioned building blocks in order to arrive at the full sequence of six blocks (a-b-c-d-e-f). Therefore, the above is to be understood as a teaching regarding the sequence of blocks, i.e. which block links to which other one through the linking functions J and G.

For example, the reaction of the building block b with the building block c will yield a building compound b-c. This compound b-c can react as a further building block in subsequent reactions by removing or adding a protection group, if necessary. The further building block b-c can react with a building block a, yielding a compound a-b-c. Said compound a-b-c can function as a reaction partner for the building block d. The same applies to further subsequent reactions in order to arrive at the full sequence of six blocks.

Many ways to achieve the full sequence a-b-c-d-e-f are possible. The following examples show—without being limited to these combinations—three further possible combinations such as e+f yielding (e-f), d+(e-f) yielding (d-e-f), c+(d-e-f) yielding (c-d-e-f), a+b yielding (a-b), (a-b)+(c-d-e-f) yielding (a-b-c-d-e-f), b+c yielding (b-c), (b-c)+d yielding (b-c-d), e+f yielding (e-f), (b-c-d)+(e-f) yielding (b-c-d-e-f), a+(b-c-d-e-f) yielding (a-b-c-d-e-f) or c+d yielding (c-d), b+(c-d) yielding (b-c-d), e+f yielding (e-f), (b-c-d)+(e-f) yielding a+(b-c-d-e-f) yielding (a-b-c-d-e-f).

In embodiments of the synthesis of the invention where one last coupling step is made to arrive at the backbone of the compound of the formula 1 (this "last step" may be followed by subsequent reactions to remove protecting groups or to introduce modifications of the reactive groups), this last step of backbone formation can be:

a+b-c-d-e-f, or
a-b+c-d-e-f, or
a-b-c+d-e-f, or
a-b-c-d+e-f, or
a-b-c-d-e+f.

In embodiments of the synthesis of the invention where one coupling step is made to arrive at the intermediate a-b-c-d-e this step can be:

a+b-c-d-e, or
a-b+c-d-e, or
a-b-c+d-e, or
a-b-c-d+e.

In embodiments of the synthesis of the invention where one coupling step is made to arrive at the intermediate b-c-d-e-f, this step can be:
b-c-d-e+f, or
b-c-d+e-f, or
b-c+d-e-f, or
b+c-d-e-f.

In embodiments of the synthesis of the invention where one coupling step is made to arrive at the intermediate b-c-d-e, this step can be:
b-c-d+e, or
b-c+d-e, or
b+c-d-e.

In the following some of these possible pathways are explained in more detail. Other pathways may be employed in a similar manner.

Thus, a building block G-BC-J (c-J) is reacted with a building block G-BD-J (d-J) yielding a building block
G-BC-$D^3$-BD-J (BZ1-J).

Furthermore, a building block $X^1$-BB-J ($X^1$-b-J) is reacted with a building block G-BC-$D^3$-BD-$J^P$ (BZ1-J) yielding a building block
$X^1$-BB-$D^2$-BC-$D^3$-BD-J (BZ2a-J).

Alternatively a building block G-BB-J (b-J) is reacted with a building block G-BC-$D^3$-BD-J (BZ1-J) yielding a building block
G-BB-$D^2$-BC-$D^3$-BD-J (BZ2b-J).

Furthermore, a building block G-BE-J (e-J) is reacted with a building block G-$X^2$ (G-$X^2$) yielding a building block
G-BE-$D^5$-$X^2$ (BZ3a)

Alternatively, a building block G-BE-J (e-J) is reacted with a building block G-BF-J (BF-J) yielding a building block
G-BE-$D^5$-BF (BZ3b).

The building block $X^1$-BB-$D^2$-BC-$D^3$-BD-J (BZ2a-J) is reacted with a building block G-BE-$X^2$ (BE-$X^2$), wherein after an eventual removal of possible protecting groups the compound with a molecular structure as defined in formula 1

$X^1$-BB-$D^2$-BC-$D^3$-BD-$D^4$-BE-$X^2$ is provided.

Alternatively, the building block $X^1$-BB-$D^2$-BC-$D^3$-BD-J (BZ2a-J) is reacted with a building block G-BE-$D^5$-$X^2$ (BZ3a), wherein after an eventual removal of possible protecting groups the compound with a molecular structure as defined in formula 1, $X^1$-BB-$D^2$-BC-$D^3$-BD-$D^4$-BE-$D^5$-$X^2$ is provided.

In another alternative, the building block $X^1$-BB-$D^2$-BC-$D^3$-BD-J (BZ2a-J) is reacted with a building block G-BE-$D^5$-BF (BZ3b), wherein after an eventual removal of possible protecting groups the compound with a molecular structure as defined in formula 1, with $X^2$ being -$D^5$-BF, $X^1$-BB-$D^2$-BC-$D^3$-BD-$D^4$-BE-$D^5$-BF is provided.

In a further alternative, the building block G-BB-$D^2$-BC-$D^3$-BD-J (BZ2b-J) is reacted with a building block G-BE-$X^2$ (BE-$X^2$), wherein a building block
G-BB-$D^2$-BC-$D^3$-BD-$D^4$-BE-$X^2$ (BZ4a)
is provided.

The building block G-BB-$D^2$-BC-$D^3$-BD-$D^4$-BE-$X^2$ (BZ4a) is then reacted with a building block BA-J (a-J), wherein after an eventual removal of possible protecting groups the compound with a molecular structure as defined in formula 1, with $X^1$ being BA-$D^1$-

BA-$D^1$-BB-$D^2$-BC-$D^3$-BD-$D^4$-BE-$X^2$ is provided.

Alternatively, the building block G-BB-$D^2$-BC-$D^3$-BD-J (BZ2b-J) is reacted with a building block G-BE-$D^5$-$X^2$ (BZ3a), yielding a building block
G-BB-$D^2$-BC-$D^3$-BD-$D^4$-BE-$D^5$-$X^2$ (BZ4b).

The building block G-BB-$D^2$-BC-$D^3$-BD-$D^4$-BE-$D^5$-$X^2$ (BZ4b) is reacted with BA-J (a-J), wherein after an eventual removal of possible protecting groups the compound with a molecular structure as defined in formula 1, with $X^1$ being BA-$D^1$-

BA-$D^1$-BB-$D^2$-BC-$D^3$-BD-$D^4$-BE-$D^5$-$X^2$ is provided.

Alternatively, the building block G-BB-$D^2$-BC-$D^3$-BD-J (BZ2b-J) is reacted with a building block G-BE-$D^5$-BF (BZ3b) yielding a building block
G-BB-$D^2$-BC-$D^3$-BD-$D^4$-BE-$D^5$-BF (BZ4c)

The building block G-BB-$D^2$-BC-$D^3$-BD-$D^4$-BE-$D^5$-BF (BZ4c) is reacted with BA-J (a-J), wherein after an eventual removal of possible protecting groups the compound with a molecular structure as defined in formula 1, with $X^1$ being BA-$D^1$- and $X^2$ being $D^5$-BF,

BA-$D^1$-BB-$D^2$-BC-$D^3$-BD-$D^4$-BE-$D^5$-BF is provided.

The method of synthesis is explained in the following with more specific building blocks, without being limited to these specific building blocks.

In most cases J refers to a COOH moiety, wherein said first linking function may be, if necessary, activated ($CO^{act}$) or protected ($COO^{PGA}$), and G refers to a $NH_2$ moiety, wherein said second linking function may be, if necessary, protected (FN).

Thus, derivatives of the six building blocks are employed as intermediates in the synthesis of the invention as building blocks of the general formula (a-COOH): BA-COOH, (a-$CO^{act}$): BA-$CO^{act}$,     a ($X^1$-J):     $X^1$-J;

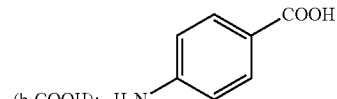     b (b-COOH): $H_2N$

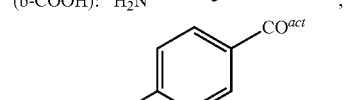

(b-$CO^{act}$): FN

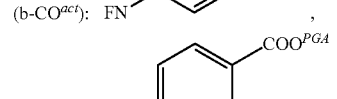

($H_2N$-b): $H_2N$

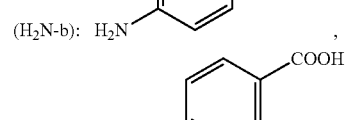

($X^1$-b-COOH): $X^1$

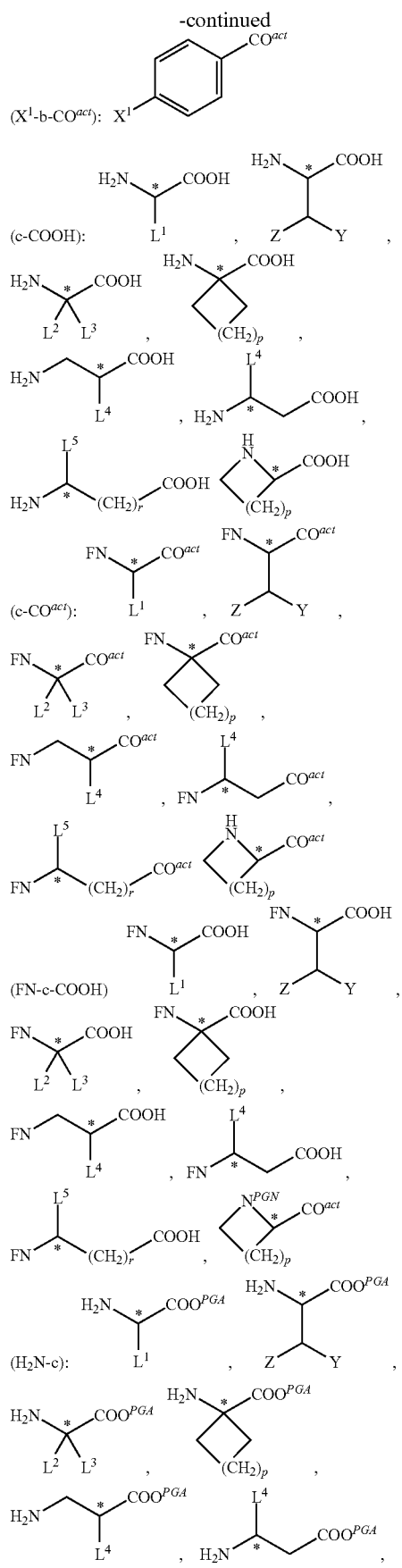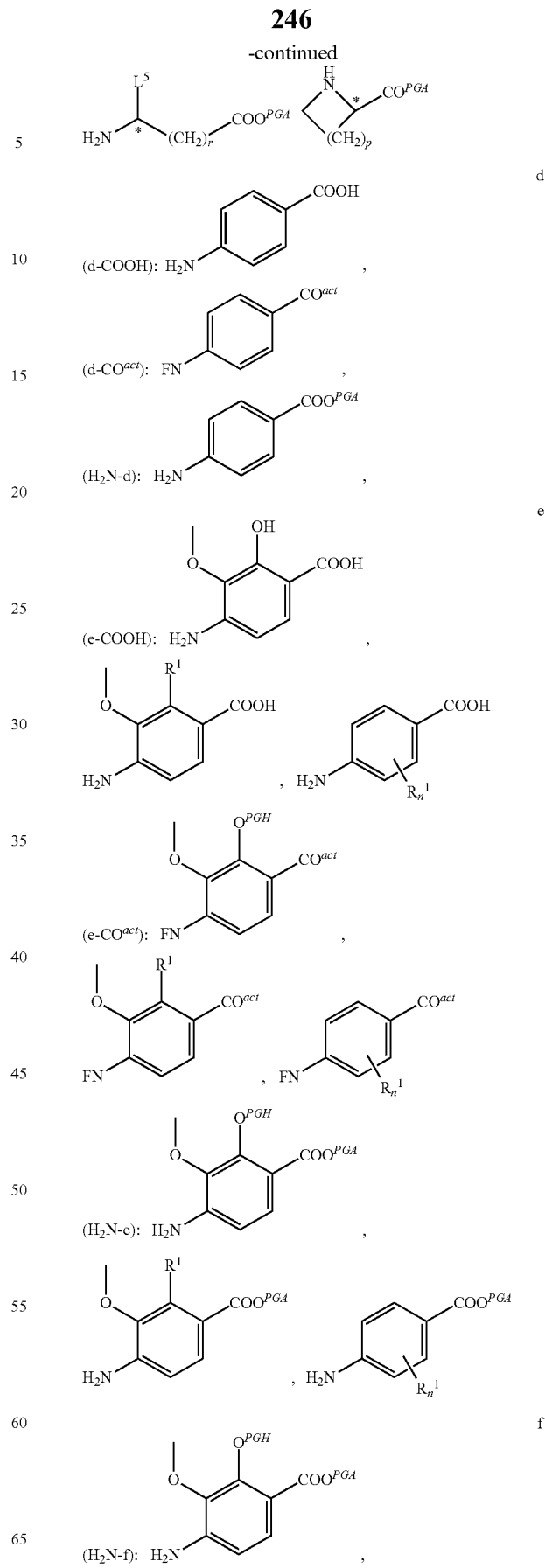

-continued

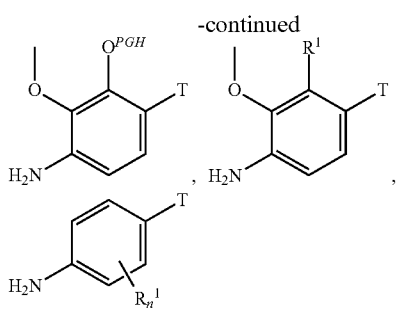

wherein
FN is $N^{PGN}$ or M, wherein
  M is a masked functional group, in particular M is —$NO_2$ or —$N_3$, and wherein,
$N^{PGN}$, $COO^{PGA}$ or $O^{PGH}$ signifies an $NH_2$, COOH or OH moiety reversibly inactivated by a removable protecting group, and $CO^{act}$ signifies an activated carboxylic acid moiety,
A building block c-COOH

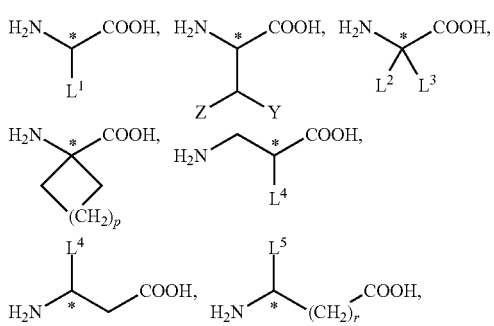

or
a building block FN-c-$CO^{act}$

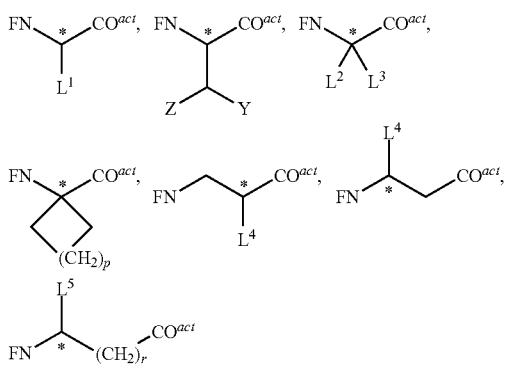

is reacted with a building block ($H_2$N-d):

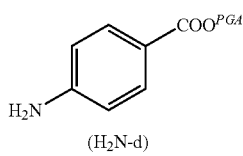

yielding a building block BZ1a

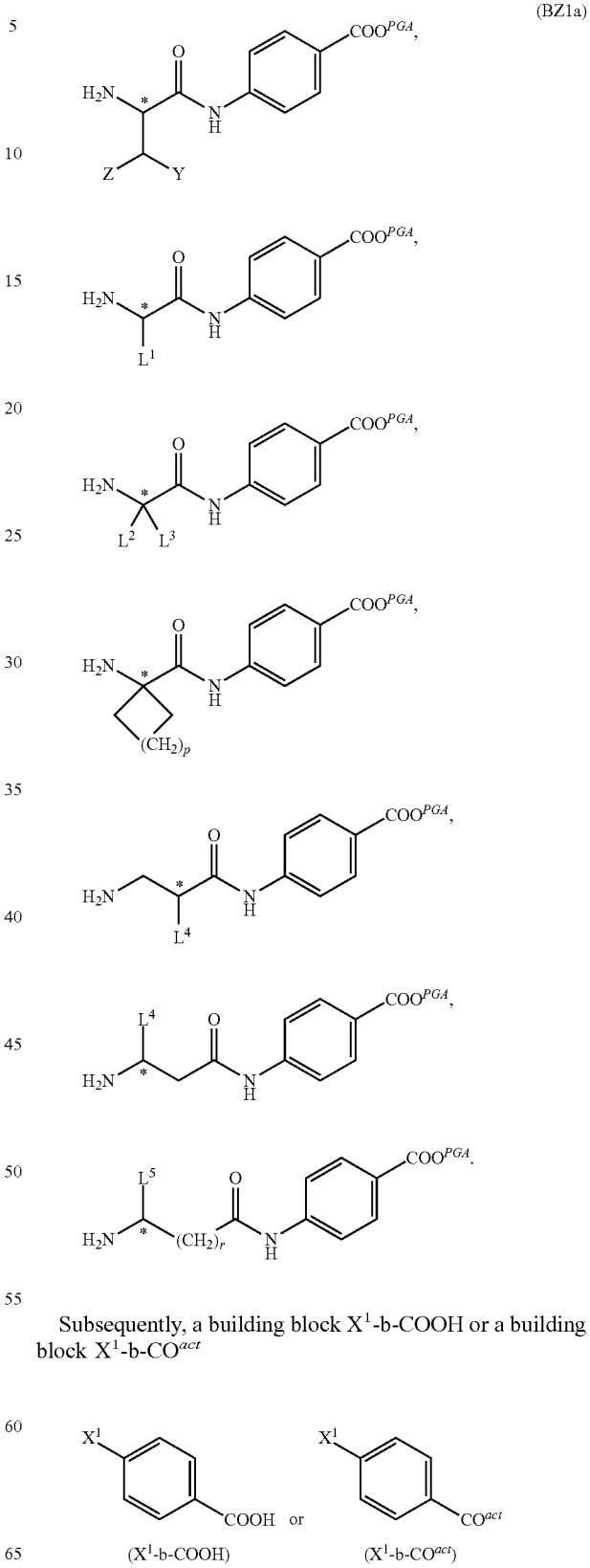

Subsequently, a building block $X^1$-b-COOH or a building block $X^1$-b-$CO^{act}$ is reacted with the building block (BZa1) yielding a building block BZ2a

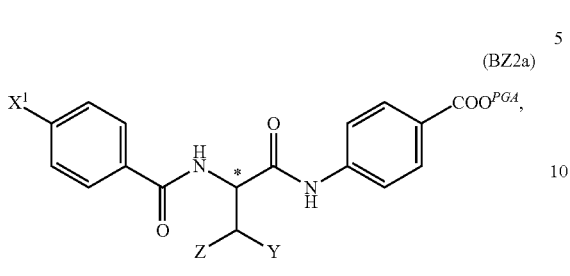

(BZ2a)

wherein the depicted building block is representative for the other similar building blocks BZ2a derived from a reaction with the building block BZa1, which may be used in an analogue reaction yielding to analogue compounds. This building block is used further below to describe the further reactions, the other building blocks may be used in a similar manner.

Subsequently the protecting group PGA may be removed and a building block BZ2a-COOH

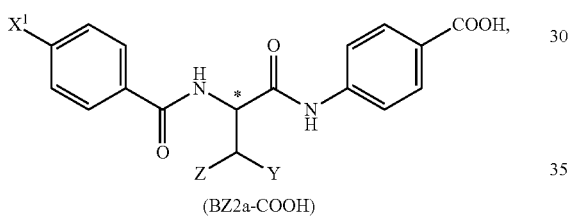

(BZ2a-COOH)

is provided, which can be optionally activated to provide a building block BZ2a-CO$^{act}$

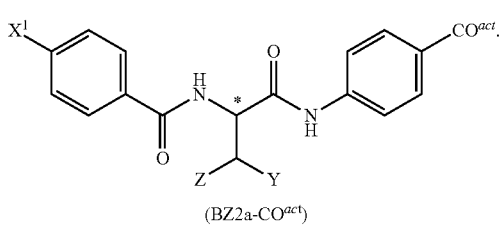

(BZ2a-CO$^{act}$)

Alternatively a building block HN-c

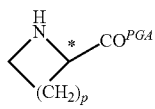

is reacted with a building block X$^1$-b-COOH or a building block X$^1$-b-CO$^{act}$, the protecting group PGA is removed and the reaction product is reacted with a building block H$_2$N-d yielding a compound BZ2a-COOH

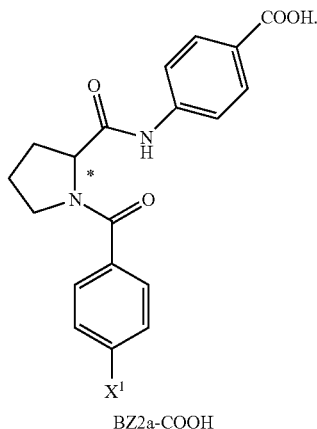

BZ2a-COOH

Similar further reactions as discussed concerning BZ2a-COOH

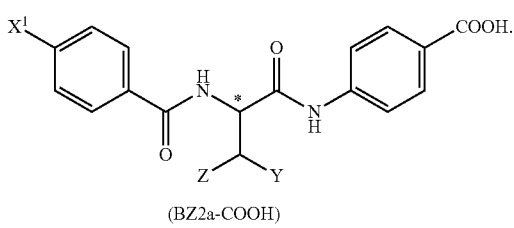

(BZ2a-COOH)

apply

Furthermore, a building block e-COOH or a building block e-CO$^{act}$

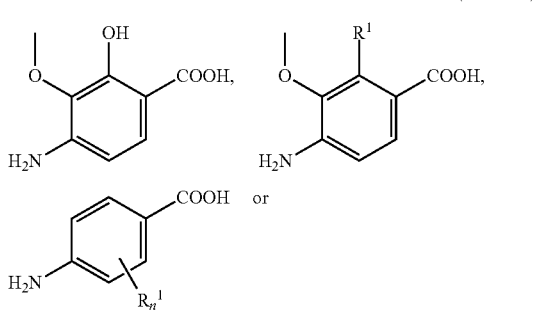

(e-COOH)

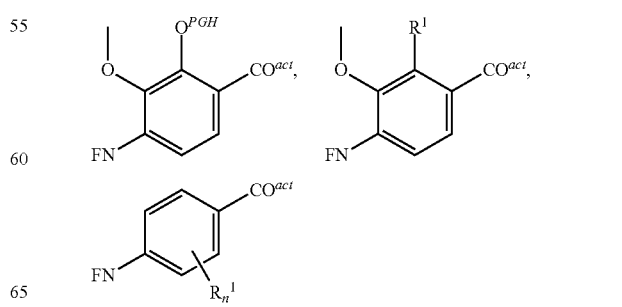

(e-COact)

251 is reacted with the building block H₂N-f

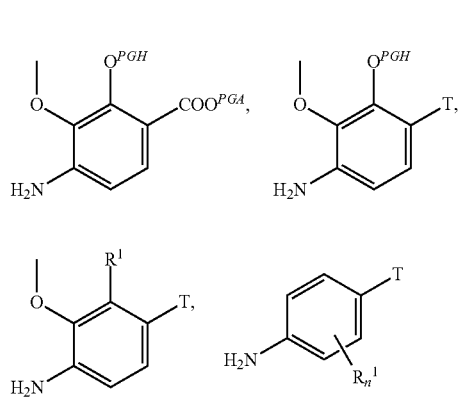
(H2N-f)

yielding a building block BZ3b

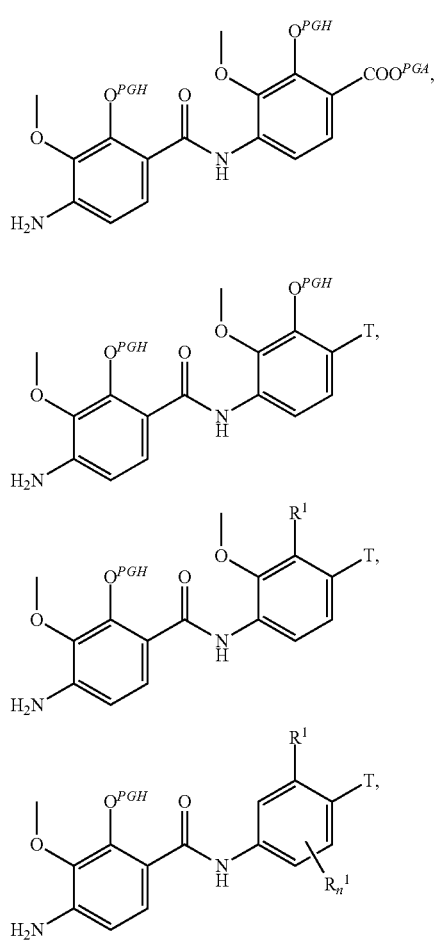
(BZ3b)

wherein variants of the block BE are not depicted due to simplicity reasons. These variants may be used in a similar manner, yielding analogue building blocks BZ3b. The depicted building blocks BZ3b are used further below to describe the further reactions, the other building blocks may be used in a similar manner

252

The building block BZ2a-COOH or the building block BZ2a-CO$^{act}$

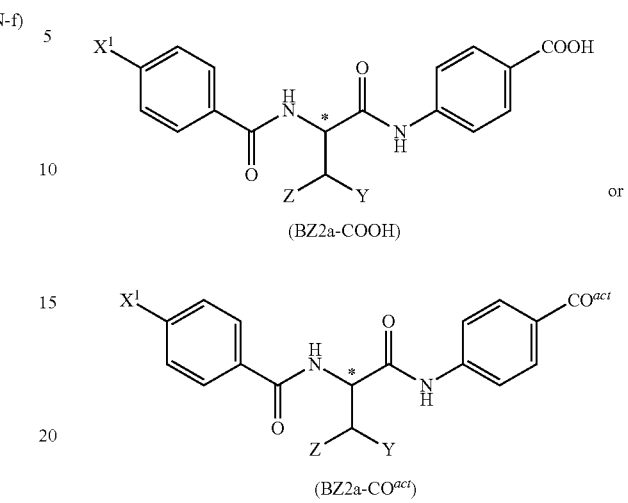
(BZ2a-COOH) or
(BZ2a-CO$^{act}$)

is reacted with a building block BZ3b

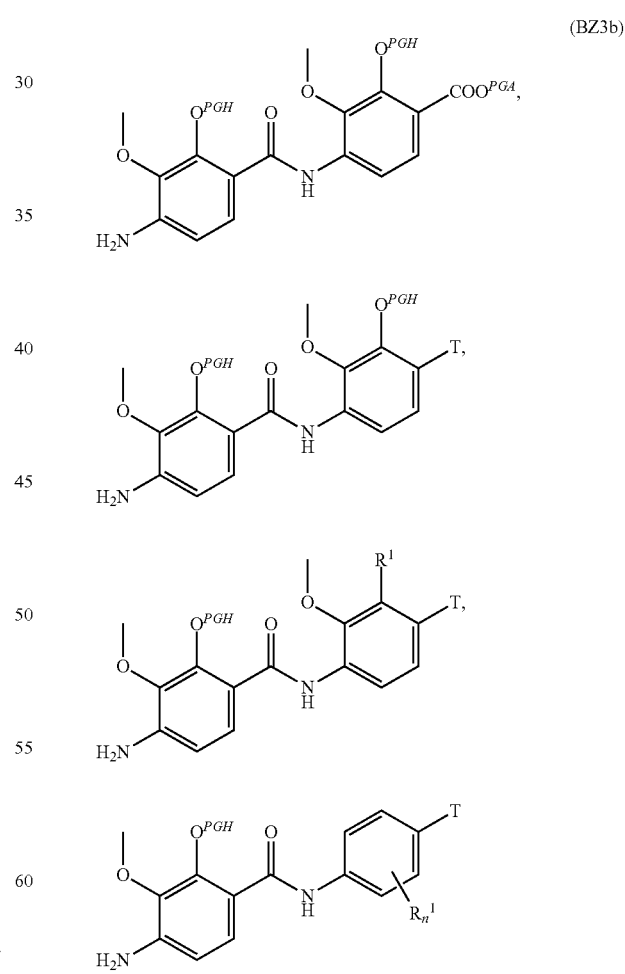
(BZ3b)

wherein after removal of the protecting groups the compound with a molecular structure as defined in formula 1

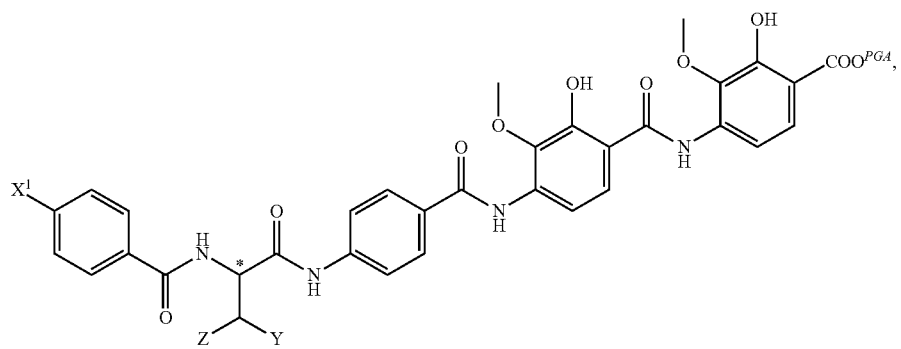
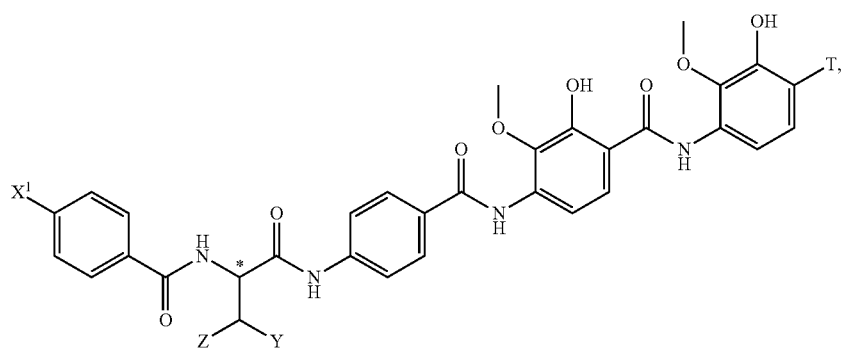
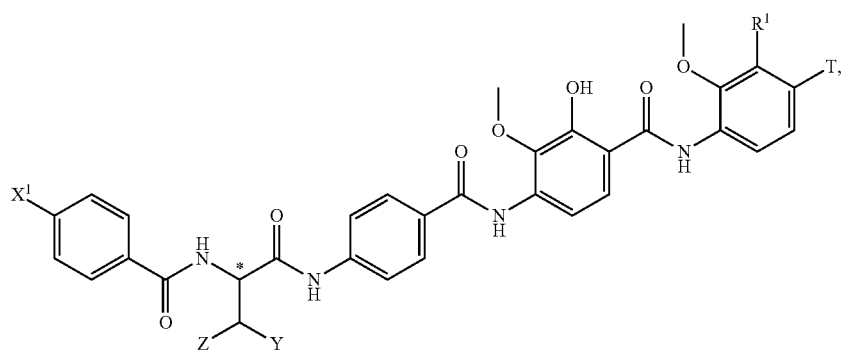
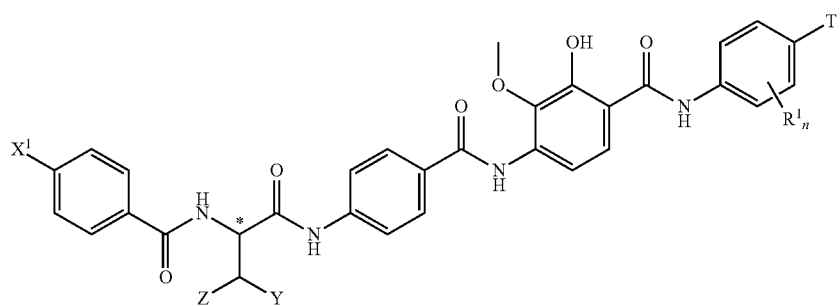

is provided

An alternative of the second aspect of the invention relates to the synthesis of compounds according to the general formula 1, wherein a. $X^1$ is

with $D^1$ being a linker derived from a reaction of J and G and which comprises carbon, sulphur, nitrogen and/or oxygen atoms and which is covalently connecting $R^4$ and the parent moiety, and with $R^4$ being selected from a substituent group S3, S4 or S5, or b. $X^1$ is

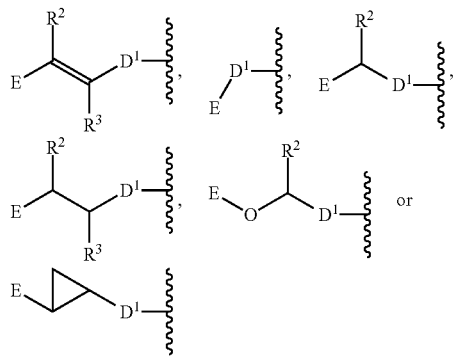

with $R^2$ and $R^3$ of BA being selected, where applicable, independently from each other from —H, —F, —CN, —OH, —NH$_2$, —NO$_2$, —NHCH$_3$, —N(CH$_3$)$_2$, a substituted or unsubstituted $C_1$-$C_3$ alkyl, a substituted or unsubstituted $C_1$-$C_3$ alkoxy or a $C_1$-$C_3$ haloalkyl, in particular from —H, —F, —CN, —OH, —NH$_2$, —NO$_2$, —NHCH$_3$, —N(CH$_3$)$_2$, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$, more particularly with $R^2$ and $R^3$ being selected independently from each other from —H, —F or —CH$_3$, and with $D^1$ being a linker derived from a reaction of J and G and which comprises carbon, sulphur, nitrogen and/or oxygen atoms and which is covalently connecting the moiety comprising E and the parent moiety, with E being selected from a substituent group S3, S4 or S5, or with E being

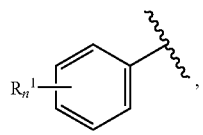

with n of $R^1_n$ being 0, 1, 2, 3, 4 or 5, in particular n of $R^1_n$ being 0, 1, 2 or 3, more particularly n of $R^1_n$ being 1, with each $R^1$ independently from any other $R^1$ being selected from a substituent group S1 or S2, or with E being

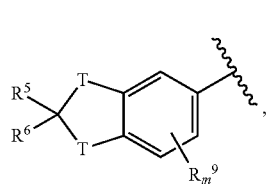

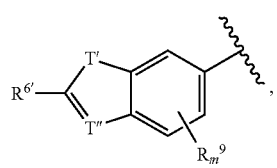

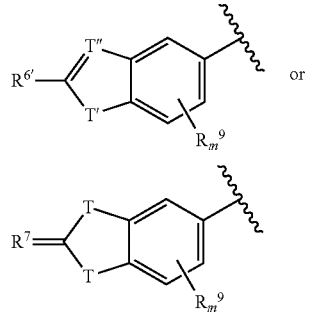

with each T being selected independently from each other from —CH$_2$, —NH, —S or —O, —CHCH$_3$, —C(CH$_3$)$_2$ or —NR$^c$, with $R^c$ being —CH$_2$OH, —CH$_3$, —CH$_2$CH$_3$, —CH$_2$CH$_2$CH$_3$, and with T' being selected from —CH$_2$, —NH, —S or —O, —CHCH$_3$, —C(CH$_3$)$_2$ or —NR$^c$, and with T" being selected from —CH or =N, and with $R^5$ and $R^6$ being selected independently from each other from —H, —F, —CH$_3$, —CH$_2$CH$_3$, —OCH$_3$, —CH$_2$CF$_3$, —CHFCF$_3$, —CF$_2$CF$_3$, —CHF$_2$, —CH$_2$F or —CF$_3$, in particular with $R^5$ and $R^6$ being selected independently from each other from H, —F or —CH$_3$, and with $R^{6'}$ being selected from —OH, —OCH$_3$, —OCH$_2$CH$_3$ or —CH$_3$ with $R^7$ being selected from =NH, =S or =O, and with m of $R^9_m$ being selected from 0, 1, 2 or 3, and each $R^9$ being selected independently from each other from —Cl, —F, Br, I, —OH, —CCH, —CH$_3$, —CH$_2$CH$_3$, —OCH$_3$, —COOH, —COOR$^b$, —C(O)NH$_2$, —C(O)NH(R$^b$); —C(O)N(R$^b$)$_2$, —NHC(=O)OR$^b$, —NR$^b$C(=O)OR$^b$, —NR$^b$C(=O)OH—CH$_2$CF$_3$, —CHFCF$_3$, —CF$_2$CF$_3$, —CHF$_2$, —CH$_2$F or —CF$_3$, with $R^b$ being a substituted or unsubstituted $C_1$-$C_5$ alkyl, a substituted or unsubstituted $C_2$-$C_5$ alkenyl, a substituted or unsubstituted $C_2$-$C_5$ alkynyl, or a $C_1$-$C_5$ haloalkyl.

In some embodiments, a building block BB1

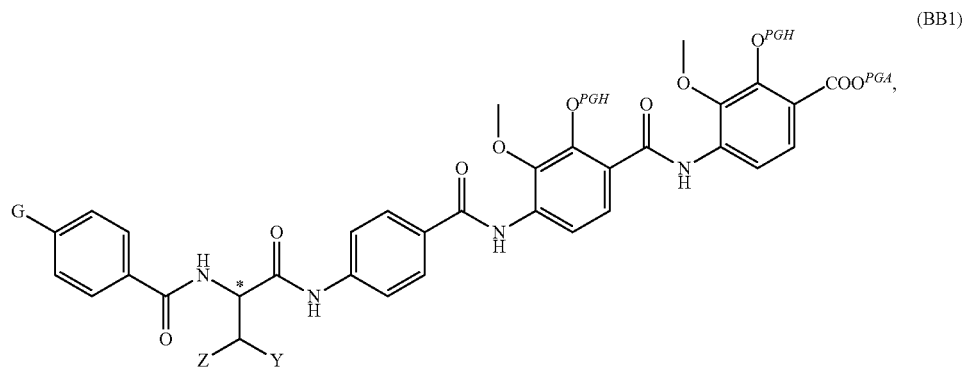
(BB1)
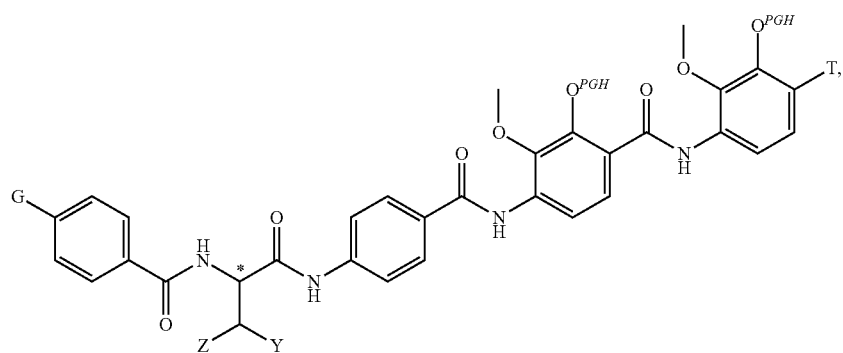
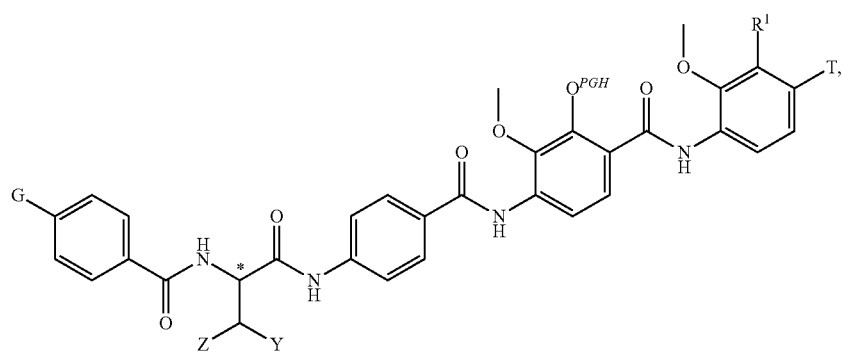
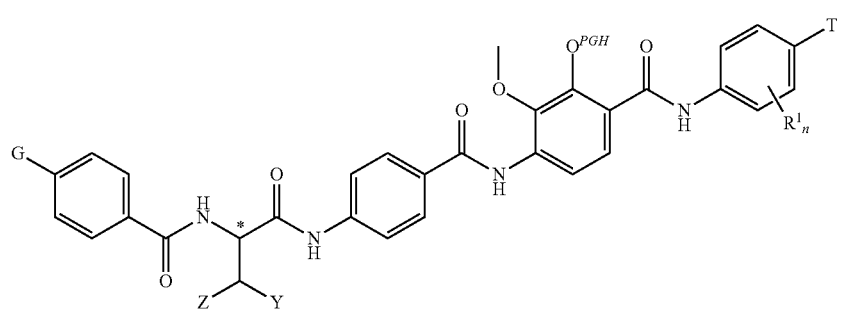

may be employed, which may be provided analogously to the previously described synthesis, is provided. Said building block BB1 may be described by the general formula GBB1
G-PPM       (GBB1),
with PPM being the protected parent moiety
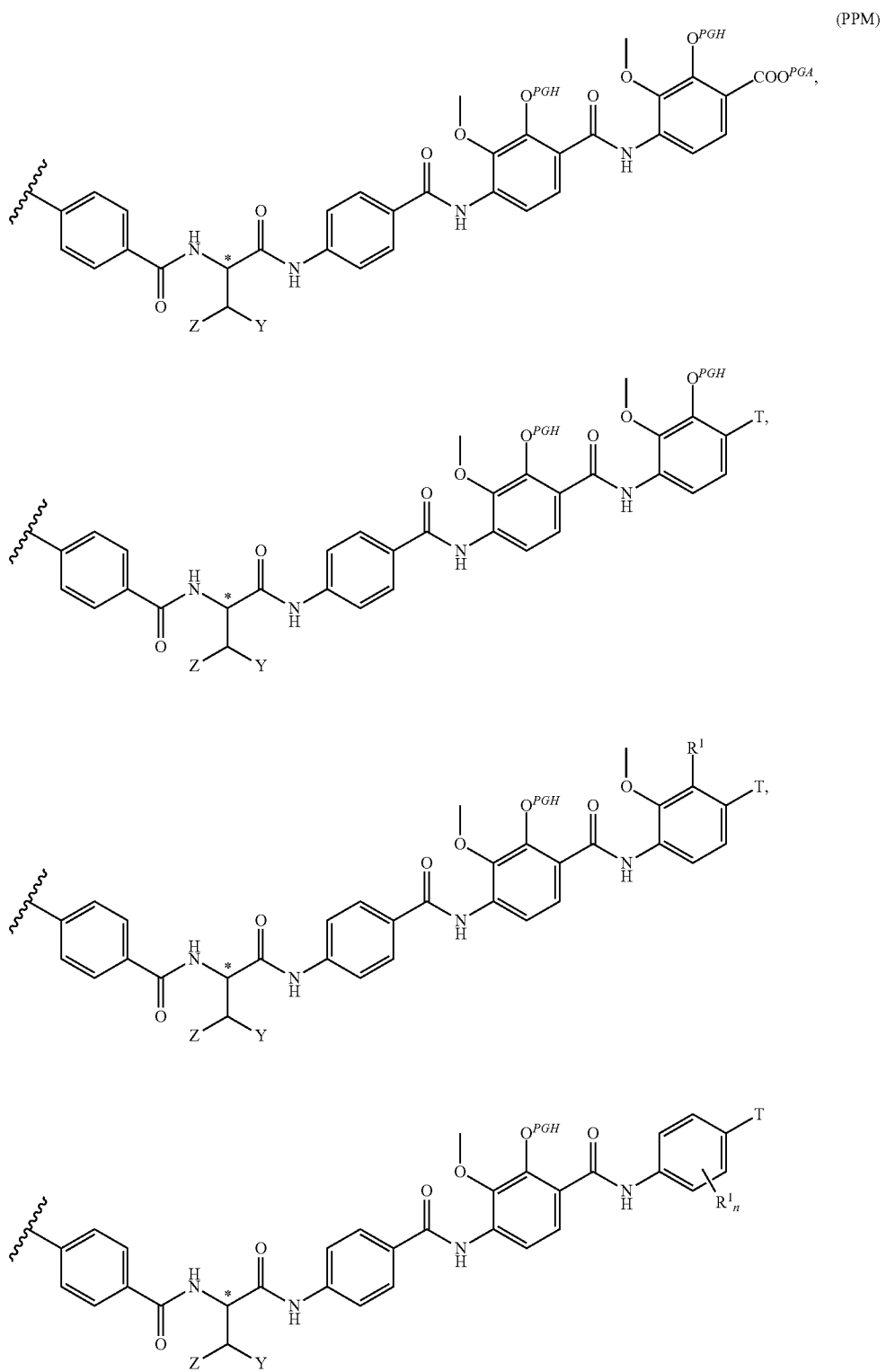

Said building block BB1 and a building block of the general formula

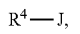 (B1)

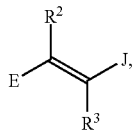 (C1)

E—J, (C2)

 (C3)

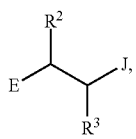 (C4)

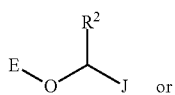 (C5)

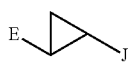 (C6)

wherein
- $COO^{PGA}$ or $O^{PGH}$ signifies a COOH or OH moiety reversibly inactivated by a removable protecting group,
- $CO^{act}$ signifies an activated carboxylic acid moiety,
- J is a first linking function which is formed in such a way as to form a covalent bond selectively with a second linking function G and to provide the linker $D^1$, and
- E, D, $R^2$, $R^3$, $R^4$, Z and Y have the same meaning as defined above, are reacted and yield protected compounds of the general formulas

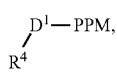 (PB1)

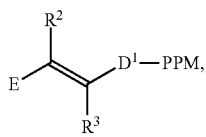 (PC1)

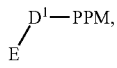 (PC2)

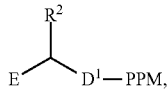 (PC3)

-continued

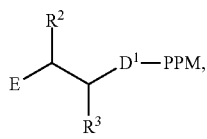 (PC4)

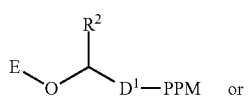 (PC5)

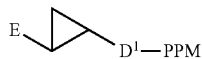 (PC6)

After removal of the protecting groups the compound with a molecular structure as defined by the general formulas

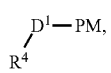 (GB1)

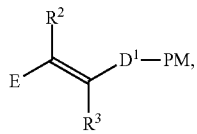 (GC1)

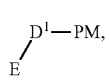 (GC2)

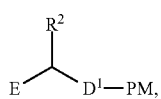 (GC3)

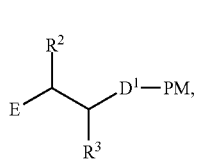 (GC4)

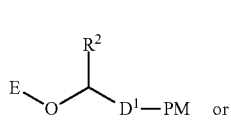 (PC5)

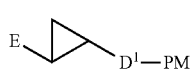 (PC6)

are provided,
with PM being the parent moiety

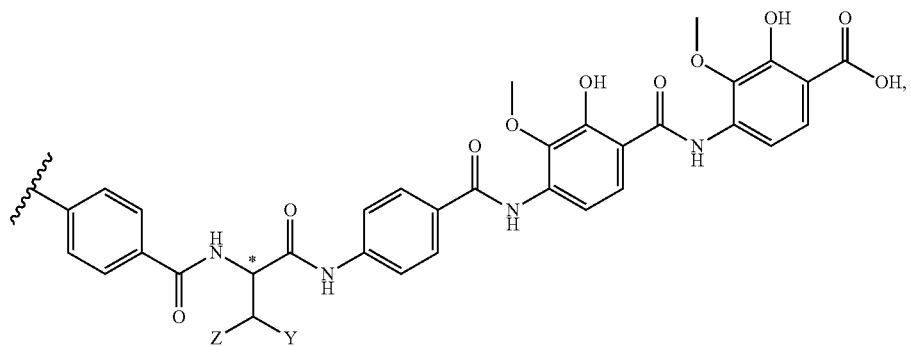
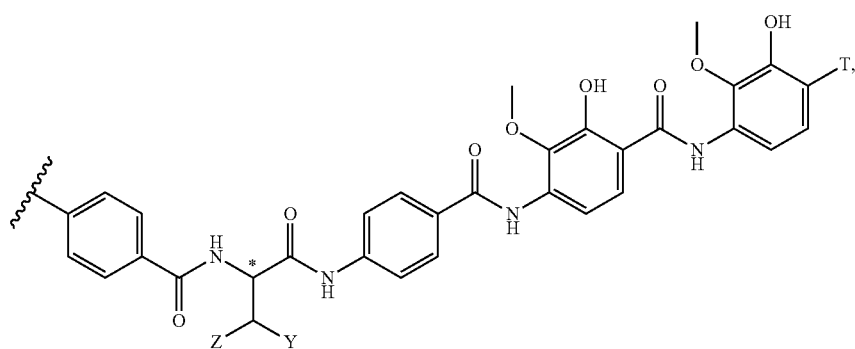
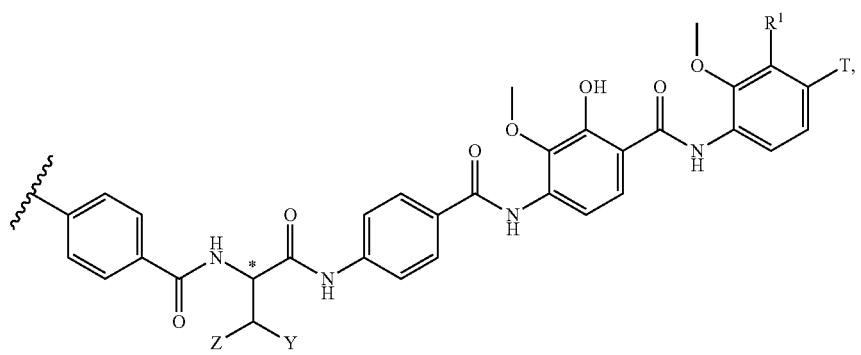
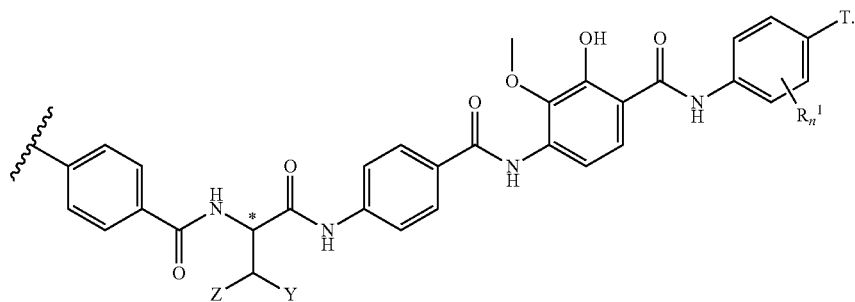

Building blocks B1 and C1 to C6 are known compounds, commercially available or may be produced analogously to known compounds.

Alternatively instead of C6

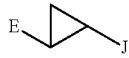
(C6)

the following compound

(C6a)

may be used in the above described manner, wherein the moiety

may be introduced later by a reaction of the double bond according to literature procedure (Davies et al, J. Am. Chem. Soc. 1993, 115, 9468; IUPAC Gold book definition (http://www.iupac.org/goldbook/D01745.Pdf); Kishner et al. J. Russ. Phys. Chem. Soc. 43, 1132 (1911); phenylcyclopropane in Organic Syntheses, Coll. Vol. 5, p. 929 (1973); Vol. 47, p. 98 (1967); Ludger et al "Biosynthesis and Metabolism of Cyclopropane Rings in Natural Compounds" Chem. Rev., 2003, volume 103, pp 1625-1648; Coelho et al. Science 339 (6117): 307-310. doi: 10.1126/science.1231434; Charette et al., A. Org. React. 2001, 58, 1; Paul et al. J. Am. Chem. Soc.; 2006; 128(19) pp 6302-6303).

Particular embodiments of the building blocks B1 and C1 to C4 are depicted below:

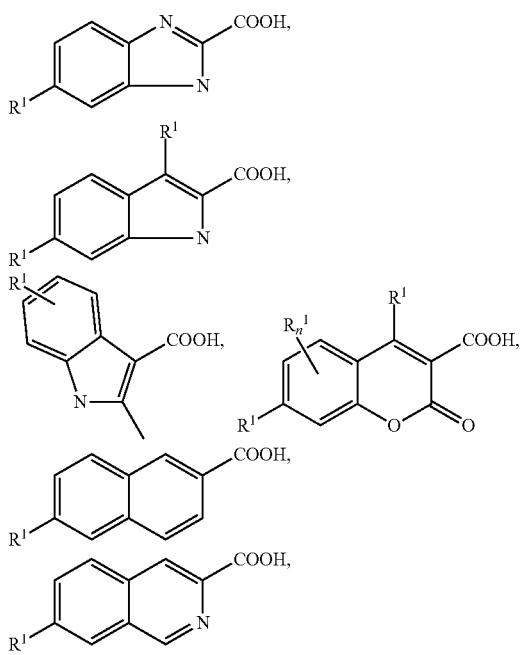

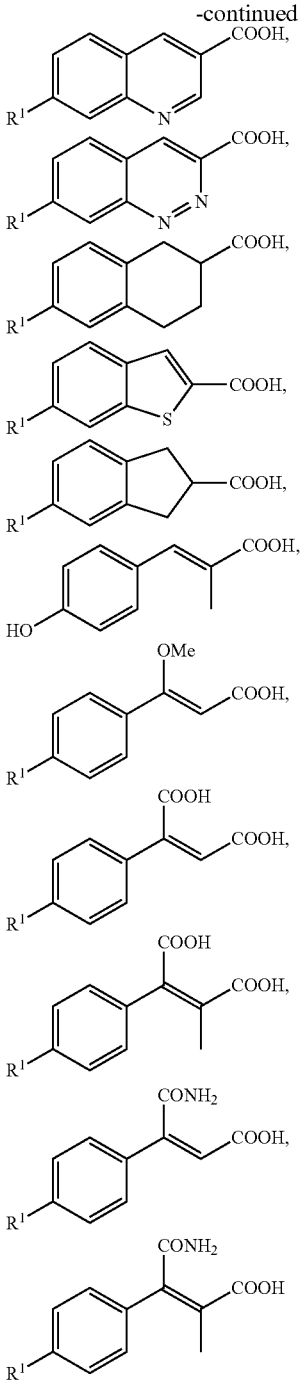

with n of $R^1_n$ being 0, 1, 2, 3 or 4, in particular n of $R^1_n$ being 0, 1, 2 or 3, more particularly n of $R^1_n$ being 1, and with each $R^1$ independently from any other $R^1_n$ being selected from a substituent group S1 or S2.

The connection of two compounds by the first and second linking function (G and J) providing a defined bond (a linker D) between these compounds is known in the art and can be achieved by standard reaction according to basic literature procedures or adapted basic literature procedures. For example, J of one compound may be —$CH_2)_2OH$ and G of another compound may be Cl. The reaction of these compounds in the presence of NaH yields a —$CH_2)_2O$— bond (linker D) between the two compounds providing a space of 3 atoms between these compounds. A reaction of —(C=O)Cl (linking function J) with —NH$_2$ (linking function G) yields a —(C=O)—NH— bond (linker D) providing a space of 3 atoms. Exemplary examples are given further below for one linker D$^1$. Analogue pathways apply for the other linkers D$^2$ to D$^5$.

In case of D$^1$ being

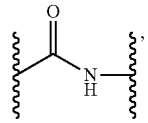, a compound

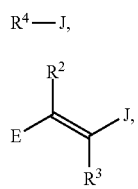

(B1)

(C1)

(C2)

(C3)

(C4)

(C5)

(C6)

(C6a)

with J being COOH or COO$^{act}$ is reacted with a compound of the formula 55

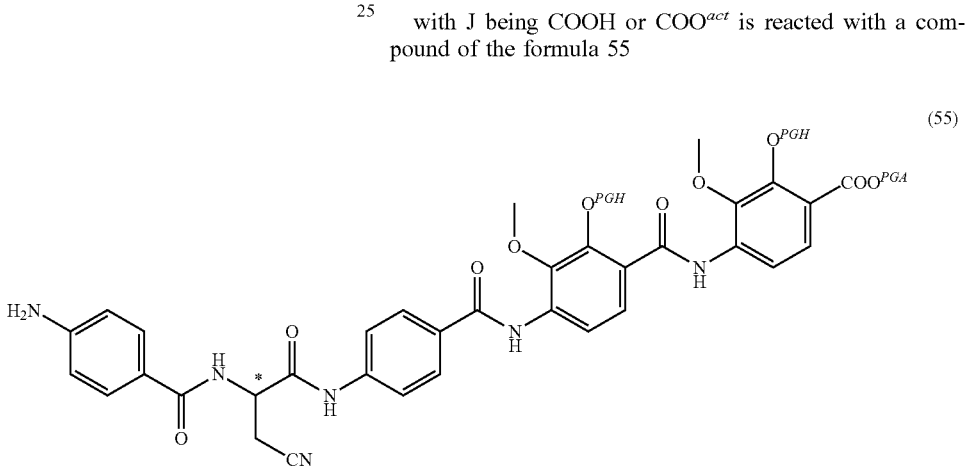

(55)

The above mentioned compounds B1 or C1 to C6 are known compounds, commercially available or may be produced analogously to known compounds.

The synthesis of the invention comprises the compound 55, which is prepared according to the reaction pathway depicted in scheme 1

Scheme 1:

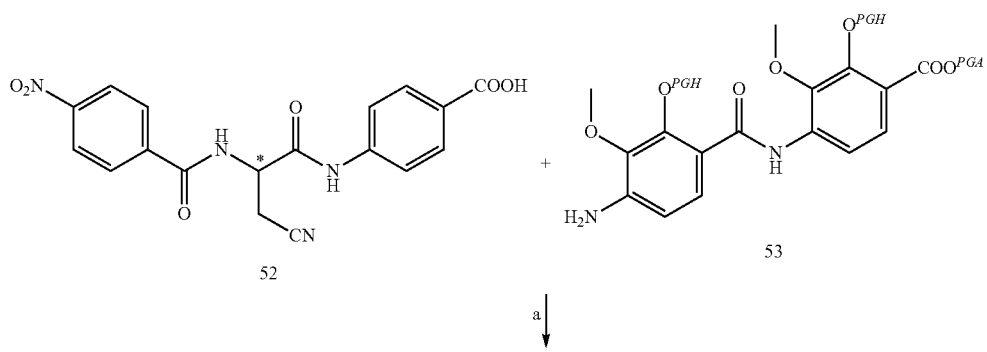

a

-continued

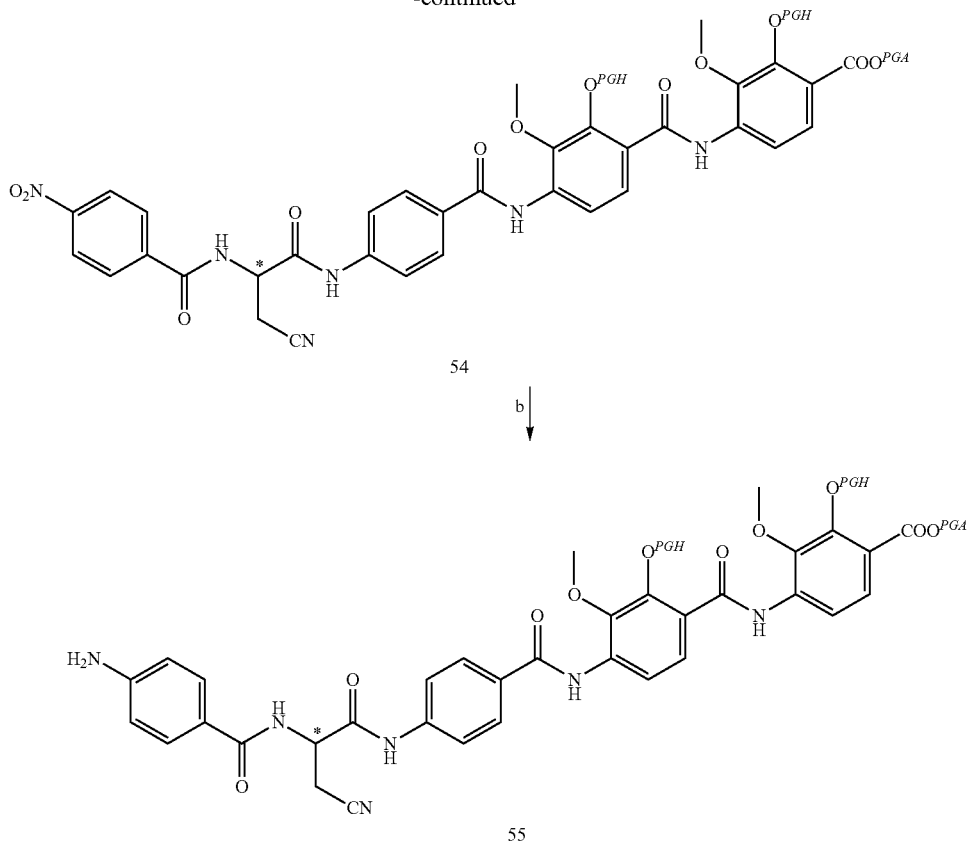

Compound 52 was reacted with compound 53 in the presence of Bis-(trichloromethyl)carbonate (BTC), 2,4,6-Collodine and N,N-diisopropylethylamine (DIPEA) yielding compound 54 (step a). After isolation of compound 54, the NO$_2$-moiety of compound 54 is converted with SnCl$_2$ to the NH$_2$-moiety of compound 55 (step b).

The compound 52 and the compound 53 may be synthesised according to scheme 2 or scheme 3.

In scheme 2 compound 56 was reacted with compound 57 in the presence of N,N'-Dicyclohexyl-methandiimin (DCC) yielding compound 58 (step a). Alternatively 1 O-(7-azabenzotriazol-1-yl)-N,N,N',N'-tetramethyluronium hexafluorophosphate (HATU) and N,N-diisopropyl-ethylamine (DIPEA) may be used. Compound 58 was treated with HCl/Dioxane to obtain compound 59 (step b). Subsequently, Scheme 2:

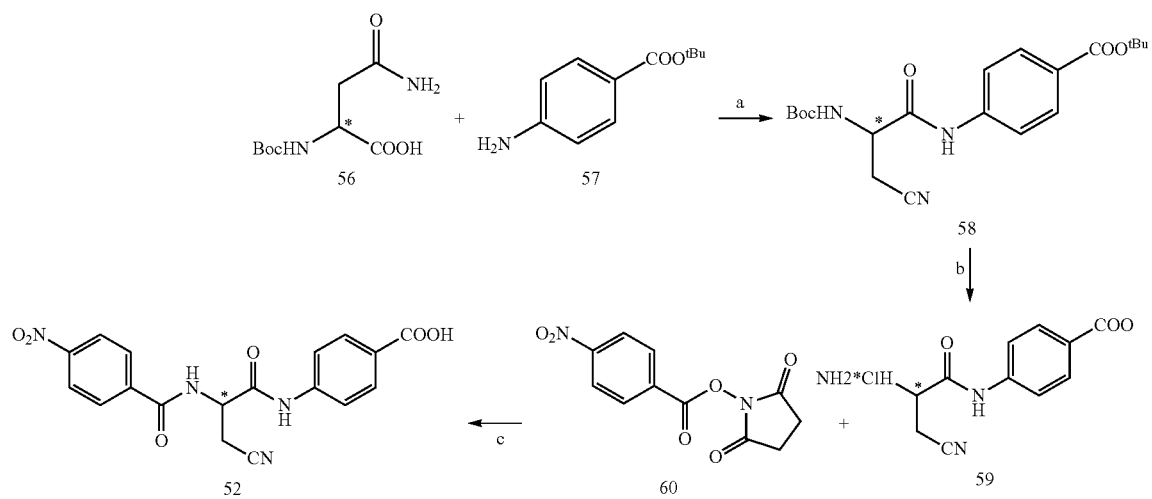

compound 59 was reacted with compound 60 in the presence of triethylamine, yielding compound 53 (step c).

Scheme 3:

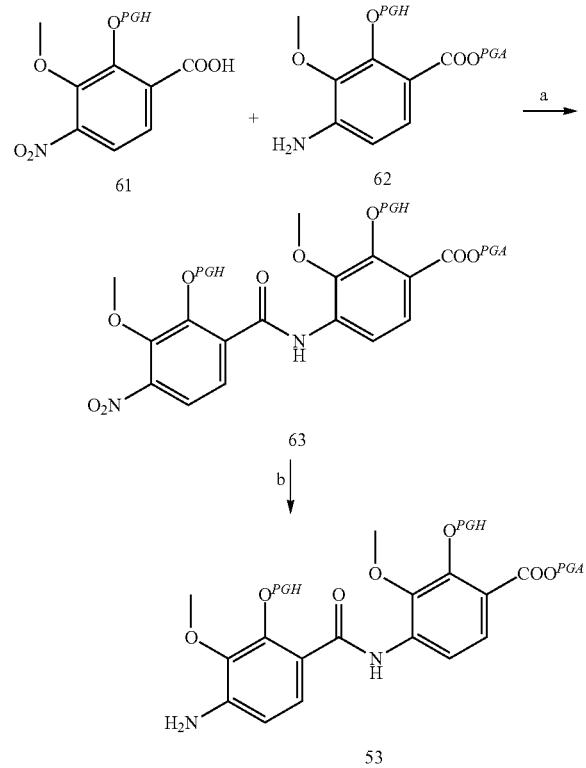

Scheme 3 describes the reaction of compound 61 with compound 62 in the presence of Bis-(trichloromethyl)carbonate (BTC), 2,4,6-Collidine and N,N-diisopropylethylamine (DIPEA), yielding compound 63 (step a). After isolation of compound 63, the $NO_2$-moiety of compound 47 is converted to the $NH_2$-moiety of compound 53 by the use of $SnCl_2$.

Compounds 57, 60, 61 or 62 are known compounds, commercially available or may be produced analogously to known compounds. Compound 60 can be synthesised according to Adamczyk, M., Fino, J., R., Org. Prep. Proced. Int., 2009, 28, 470-474. For example, compound 61 and 62 may be produced by an adapted procedure according to Tichenor et al. (M. S. Tichenor, D. B. Kastrinsky and D. L. Boger, J. Am. Chem. Soc., 2004, 126, 8396). Comparable compounds to 57, 61 or 62 with different substituents on the phenyl moieties may be employed in a similar reaction to provide the respective building blocks comparable to compound 53.

The method of choice of linking these compounds is a selective coupling reaction between the (activated) carboxylic acid moiety $R^4$—COOH or $R^4$—$COO^{act}$ or E-COOH or E-$COO^{act}$ (acid partner), and the amino moiety (amino partner), whereby other functional groups of the amino and acid partner are protected. The reactive hydroxyl groups need to be transitionally (reversibly) protected by any of the many suitable protection groups for hydroxyl groups (PGH) known in the art. Likewise, the carboxylic acid moiety of the amino partner $H_2N$— will be protected by any of the many suitable protection groups (PGA) known in the art for carboxylic acid groups to prevent homopolymer formation.

Furthermore, any amino moiety of the acid partner will likewise be protected by any of the many suitable protection groups for amino groups (PGN) known in the art.

Activation of the carboxylic acid moiety of the acid partner may be applied before the reaction of the acid partner with the amino partner and can be achieved by any of the methods known in the art for increasing the reactivity of carboxylic acids to amide formation with primary amines, in particular reference is made to the activation of the carboxylic acid as discussed.

The reactions are carried out between −30° C. to 80° C., in particular between 25° C. to 60° C. and further in particular between 25 to 30° C.

The PGH protecting groups can be $C_4H_9$ (t-Butyl), para-methoxybenzyl (PMB), benzyl or $CH_2CHCH_2$ (allyl), in particular $CH_2CHCH_2$ (allyl).

The PGA protecting groups can be $C_4H_9$ (t-Butyl), para-methoxybenzyl (PMB), benzyl 9-fluorenylmethyl (Fm) or $CH_2CHCH_2$ (allyl), in particular $CH_2CHCH_2$ (allyl).

The activated carboxyl moiety can be (O-(7-azabenzotriazol-1-yl)-N,N,N',N'-tetramethyluronium hexafluorophosphate) (HATU) ester, achieved by a coupling of the acid with HATU, or Bis-(trichloromethyl)carbonate (BTC) ester, achieved by a coupling of the acid with BTC, or acyl chloride, achieved by a coupling of the acid with $SOCl_2$ or N,N'-Diisopropylcarbodiimide (DIC) ester, achieved by a of the acid coupling with DIC, or N,N'-Dicyclohexylcarbodiimide (DCC) ester, achieved by a coupling of the acid with DCC.

The coupling reactions to the activated carboxyl moiety may be supported by addition of bases selected from (N,N-diisopropylethylamine) (DIPEA), N-methylmorpholine (NMM), 4-dimethylaminopyridine (DMAP), triethylamine (TEA), 2,4,6-trimethylpyridine (sym-collidine), pyridine, N,N'-Diisopropylcarbodiimide (DIC), 2,6-di-tert-butyl-4-dimethylaminopyridine (DBDMAP), in particular from N,N-diisopropylethylamine (DIPEA) or 2,4,6-Trimethylpyridine (sym-collidine). The addition of bases allows a deprotonation of the carboxylic acid and facilitates the reaction to the respective activated carboxylic acid.

The solvent of the reactions is tetrahydrofuran, dioxane, acetonitrile, tert-butyl methyl ether, dichlormethane, chloroform, 1-methyl-2-pyrrolidinone, N,N-dimethylacetamide (DMA), or dimethylformamide, in particular tetrahydrofuran or dimethylformamide. Other solvents may be applied if necessary.

The compound characterized by the general formula 1 is obtained by removal of the protecting groups.

An analogue pathway applies for $D^1$ being

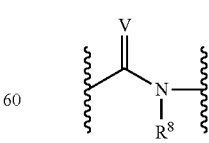

with $R^8$ being selected from —$CH_3$, —$CH_2CH_3$, —$OCH_3$, —$OCF_3$, —$CH_2CF_3$, —$CHFCF_3$, —$CF_2CF_3$, —$CHF_2$, —$CH_2F$ or —$CF_3$, in particular with $R^8$ being $CH_3$, and with V being S or O. Reference is made to the description above.

An analogue pathway applies for D¹ being

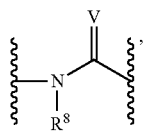

with R⁸ being selected from —H, —CH₃, —CH₂CH₃, —OCH₃, —OCF₃, —CH₂CF₃, —CHFCF₃, —CF₂CF₃, —CHF₂, —CH₂F or —CF₃, in particular R⁸ being selected from H or CH₃, more particularly R⁸ being H, and with V being S, NH or O. Reference is made to the description above, wherein the respective functional groups are switched.

An analogue pathway applies also for D¹ being

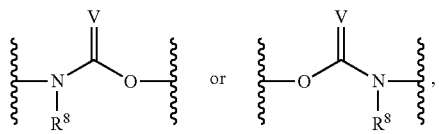

with R⁸ being selected from —H, —CH₃, —CH₂CH₃, —OCH₃, —OCF₃, —CH₂CF₃, —CHFCF₃, —CF₂CF₃, —CHF₂, —CH₂F or —CF₃, in particular with R⁸ being selected from H or CH₃, more particularly R⁸ being H, and with V being S, NH or O. Reference is made to the description above An analogue pathway applies also for D¹ being

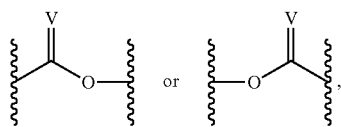

with R⁸ being selected from —H, —CH₃, —CH₂CH₃, —OCH₃, —CH₂CF₃, —CHFCF₃, —CF₂CF₃, —CHF₂, —CH₂F or —CF₃, and with V being S, NH or O. Reference is made to the description above.

An analogue pathway applies also for D being

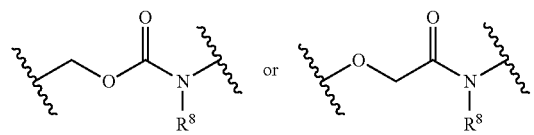

with R⁸ being selected from —H, —CH₃, —CH₂CH₃, —OCH₃, —CH₂CF₃, —CHFCF₃, —CF₂CF₃, —CHF₂, —CH₂F or —CF₃. Reference is made to the description above An analogue pathway applies also for D¹ being

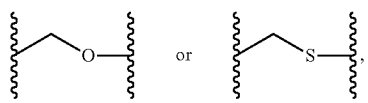

wherein the coupling step is achieved by a Williamson-Ether-Synthesis, a known organic name reaction.

Optionally

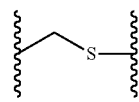

may be oxidized yielding

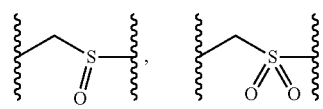 [SMILES: *CS(*)=O ; *CS(*)(=O)=O]

as a linker D¹.

An analogue pathway applies also for D¹ being

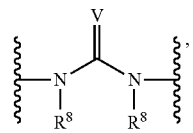

with each R⁸ being selected independently from each other from —H, —CH₃, —CH₂CH₃, —OCH₃, —OCF₃, —CH₂CF₃, —CHFCF₃, —CF₂CF₃, —CHF₂, —CH₂F or —CF₃, in particular with each R⁸ being selected independently from each other from H or CH₃, more particularly each R⁸ being H, and with V being S, NH or O. Reference is made to the description above. Concerning the coupling step reference is made to the description below and the experimental section.

An analogue pathway applies also for D¹ being

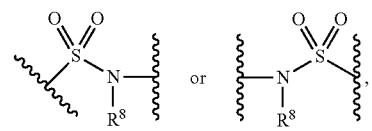

with R⁸ being selected from —H, —CH₃, —CH₂CH₃, —OCH₃, —OCF₃, —CH₂CF₃, —CHFCF₃, —CF₂CF₃, —CHF₂, —CH₂F or —CF₃, in particular with R⁸ being selected from H or CH₃, more particularly R⁸ being H. Reference is made to the description above. Concerning the coupling step reference is made to the description below and the experimental section.

An analogue pathway applies also for $D^1$ being

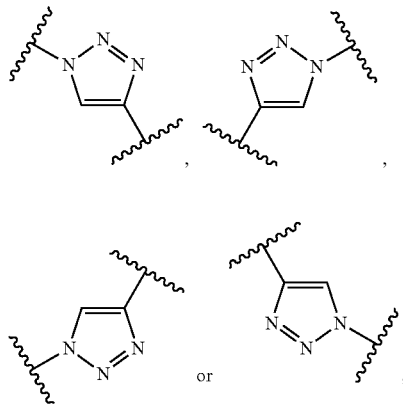

Reference is made to the description above, wherein the coupling step is achieved by a Click reaction, a known organic reaction.

An analogue pathway applies also for D being

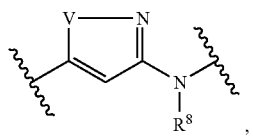

wherein the respective heterocycle is produced with an adapted procedure of Zhang et al. (*Org. Lett.*, 2010, 12 (17), pp 3942-3945), using an aluminum-based Lewis acids promotion for a condensation of substituted α-chloroglycinates with isonitriles or with cyanide ion.

In case of $D^1$ being

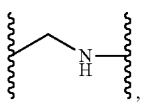

a compound

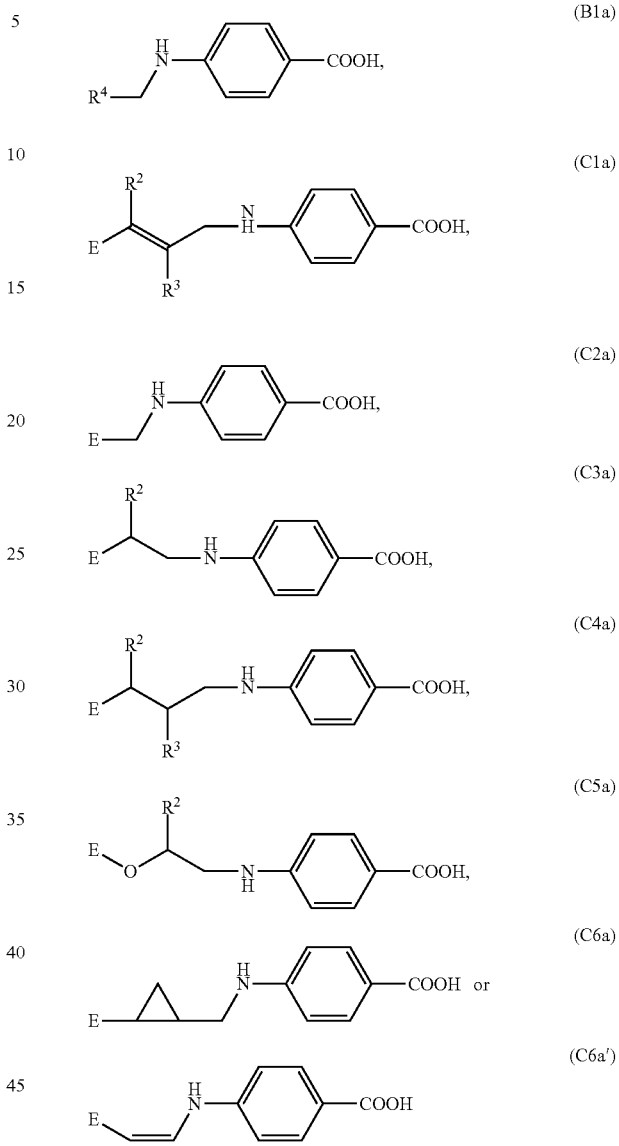

is reacted with a compound of the formula 64

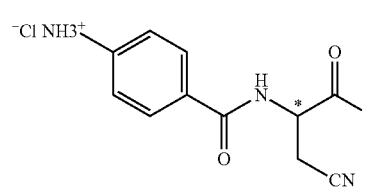

in the presence of an activation reagent and a base, yielding a compound of the general formula 1.

The above mentioned compounds B1a or C1a to C6a are known compounds, commercially available or may be produced analogously to known compounds. Reference is also made to the experimental section.

An analogue pathway applies for $D^1$ being

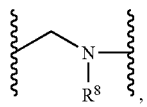

with $R^8$ being selected from —H, —$CH_3$, —$CH_2CH_3$, —$OCH_3$, —$OCF_3$, —$CH_2CF_3$, —$CHFCF_3$, —$CF_2CF_3$, —$CHF_2$, —$CH_2F$ or —$CF_3$, in particular with $R^8$ being selected from H or $CH_3$, more particularly $R^8$ being H. Reference is made to the description above Similar procedures may be applied where E is one of the moieties below

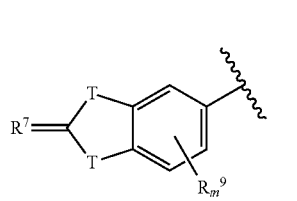

T, T', T'', $R^5$, $R^6$, $R^{6'}$, $R^7$, m or $R^9{}_m$ having the same meaning as defined previously.

The preparation further comprises a compound with n, $R^1$, $R^2$, $R^3$, D, E, Z and Y having the same meaning as defined above.

In case of D being

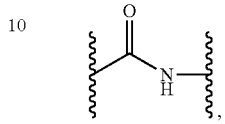

a compound

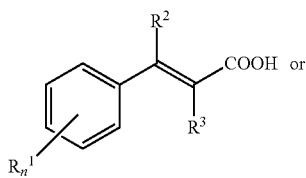

(49)

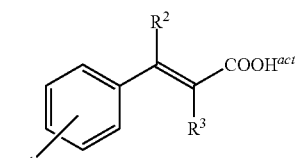

(50)

is reacted with a compound of the formula 39

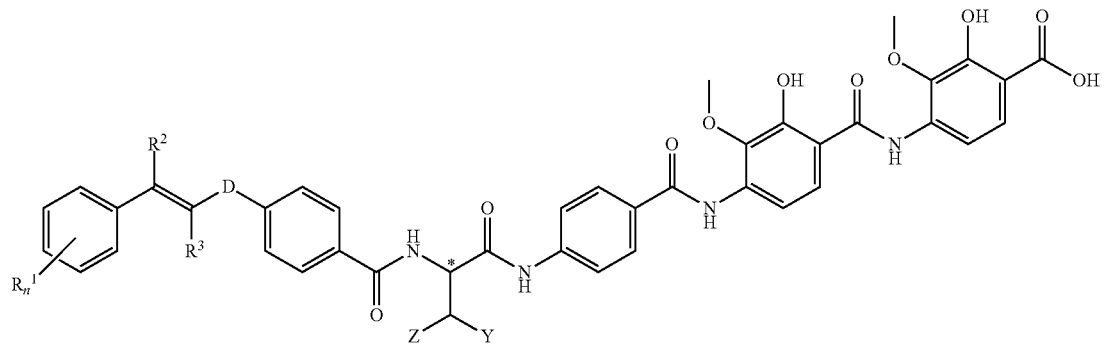

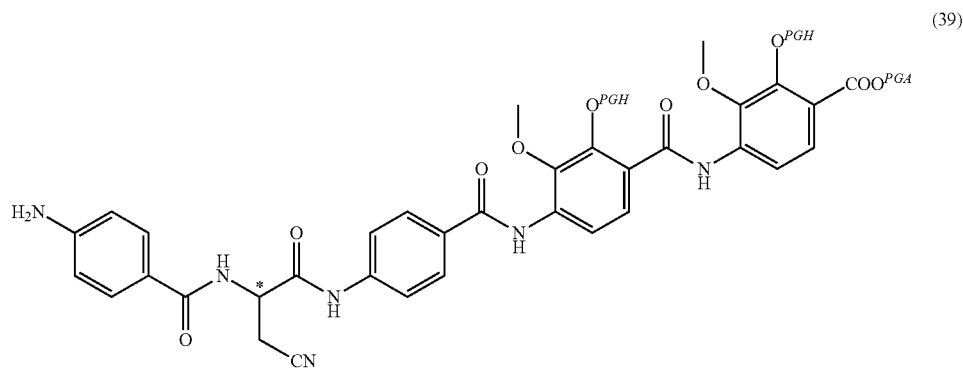
(39)
according to the previously described reaction pathway. One specific example is given in scheme 4. Compound 49, 49a or 50 are known compounds, commercially available or may be produced analogously to known compounds. Other compounds for 49, 49a or 50 may be used in a similar way.
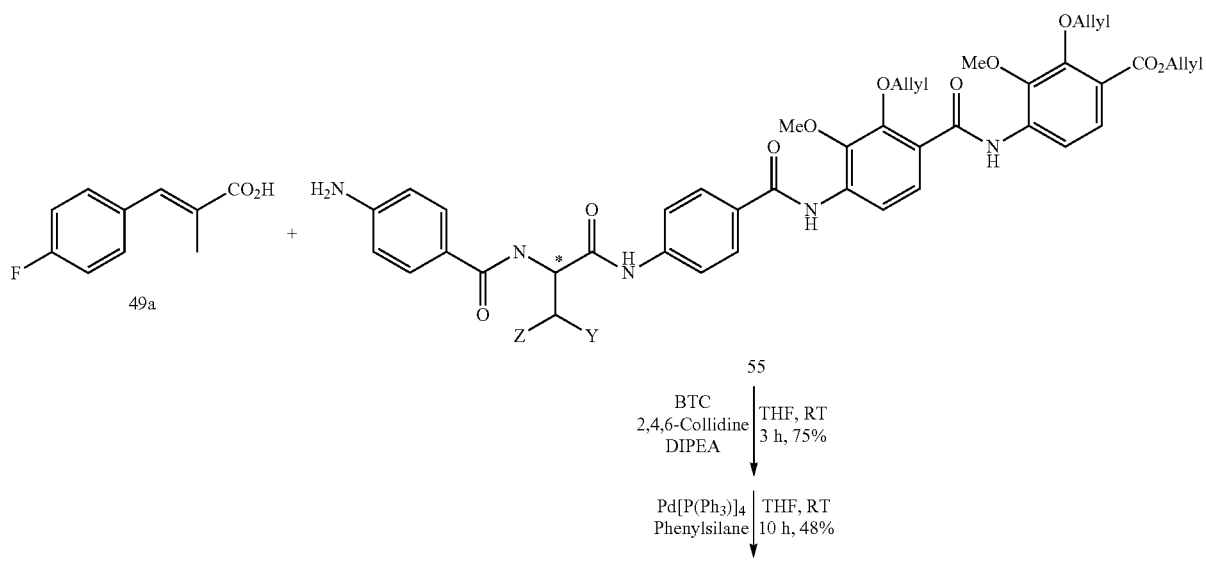
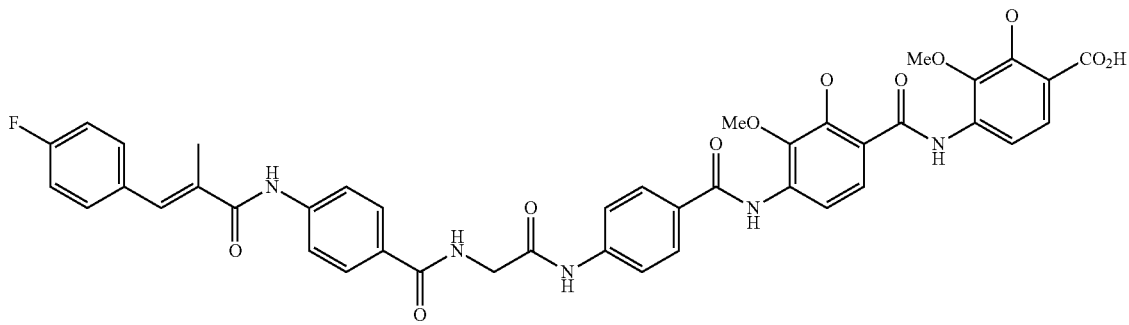

An analogue synthesis may be applied for the moieties below, with J being COOH or COO$^{act}$.

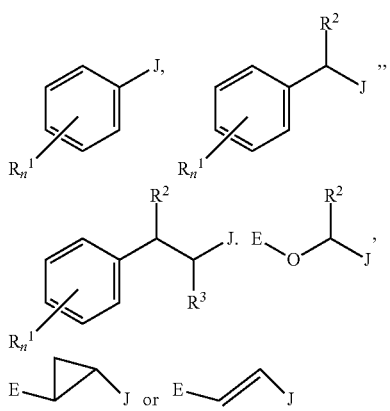

Concerning the reaction pathway with respect to different $D^1$ moieties as listed above reference is made to the previously described pathways with these functional groups $D^1$.

Scheme 1 to 3 or the reaction with compound 48 show exemplary reaction pathways for compounds with Z being H and Y being CN. It is understood that compounds comprising other substituents Y such as —C(=O)OH, —C(=O)OCH$_3$, —C(=O)OCH$_2$CH$_3$, —C(=O)NHCH$_3$, —C(=O)NHCH$_2$CH$_3$, —C(=O)N(CH$_3$)$_2$, —C(=O)N(CH$_2$CH$_3$)$_2$, —C(=O)N(CH$_3$)(CH$_2$CH$_3$) or —C(=O)NH$_2$ can be produced according to a similar reactions pathway as depicted in schemes 1 to 3, whereby reactive moieties —C(=O)(NH$_2$) or —C(=O)OH may be protected (—C(=O)N$^{PGN}$ or —C(=O)O$^{PGA}$ until the global deprotection. The same applies for compounds where Z is —H, —OH, —CH$_3$, —CH$_2$CH$_3$ or —OCH$_3$. Different protecting groups may be applied as discussed above.

It is further understood that the same reaction pathways may be used for different building blocks BC, as described above. Furthermore, The reaction of the two linking functions G and J yielding different D moieties (D1 to D21) may be employed with respect for the other building block (e.g. a connection between building block BE with BF).

Further examples with variations on different building blocks or different linkers D shall further clarify the systematic approach in providing a compound of the general formula 1.

An alternative pathway for building blocks comprising different BB or BD moieties is depicted in scheme 5 and scheme 6

Scheme 5:

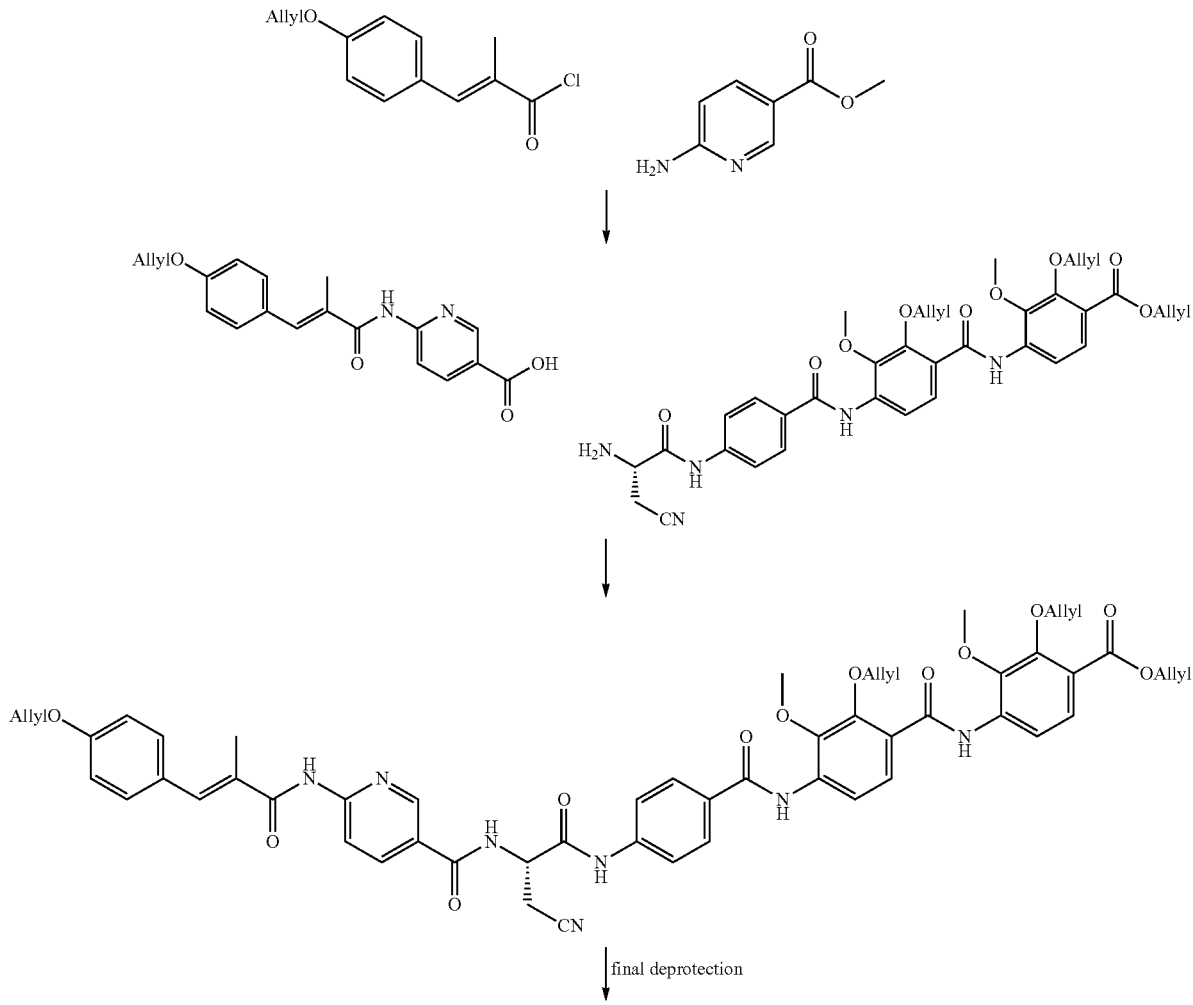

final deprotection

-continued

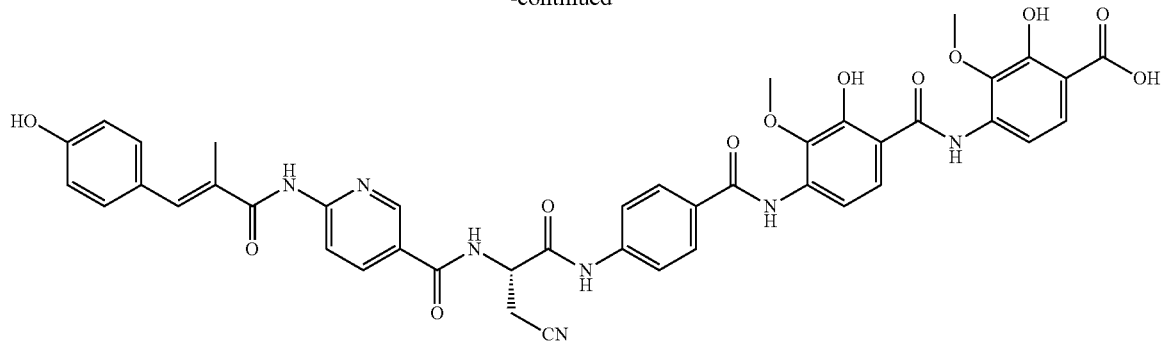

The starting materials may be provided by a reaction of 6-Amineonicotinic acid or allyl protected cinnamic acid with SOCl₂ and are coupled with standard coupling procedures described above providing the a-b- building block in form of an ester. The respective acid is provided by a reaction with Dioxane/H₂O and LiOH. Said acid (a-b-COOH) is reacted with the c-d-e-f building block (the synthesis of this block is described above) in the presence of Triphosgen and Collidin. The final deprotection is achieved with Phenylsilane and [Pd(PPH₃)₄].

Scheme 6: Shows a reaction pathway for providing a building block -b-c-d-. Details are given in the experimental section.

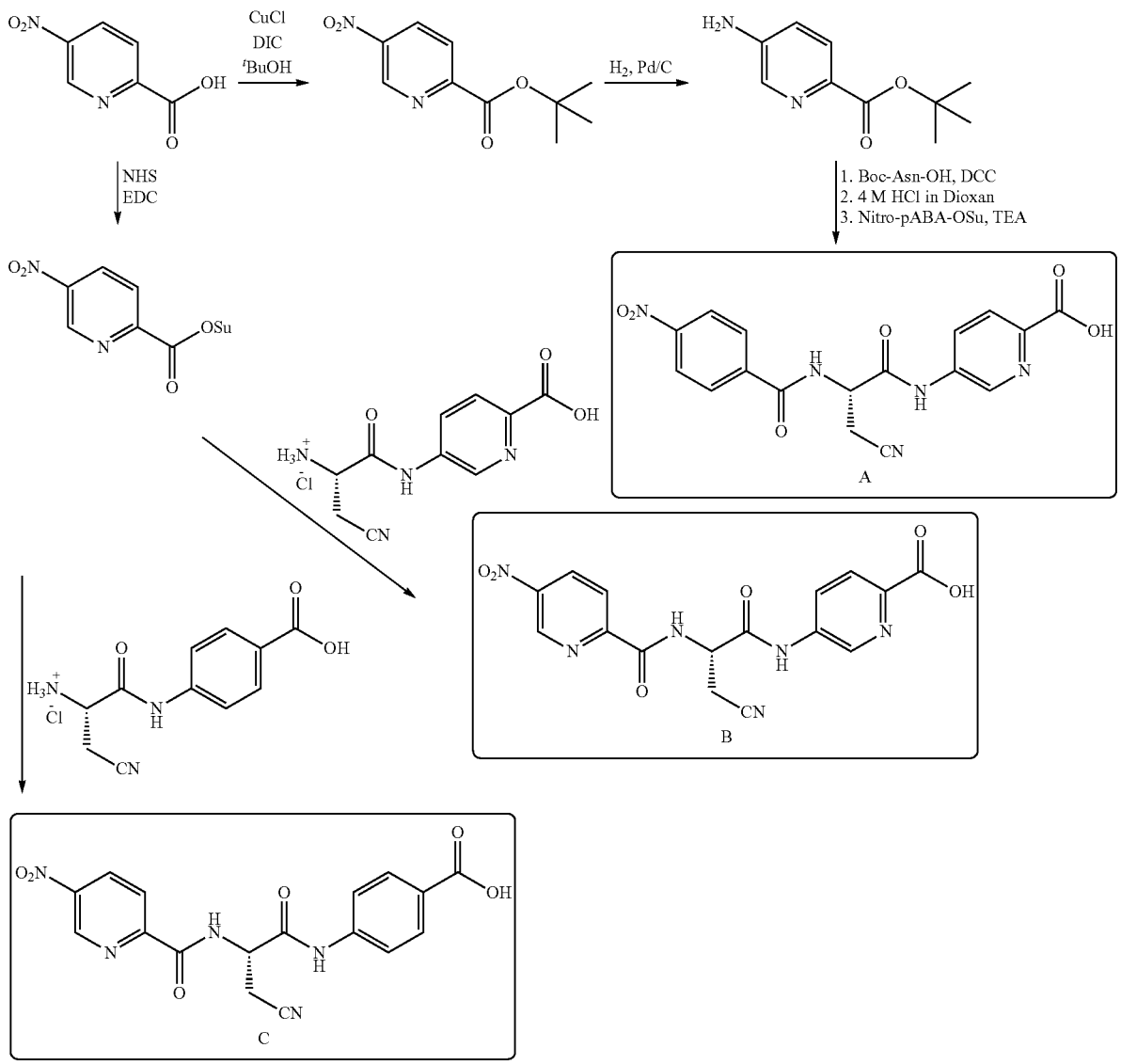

A reaction pathway to the a-b-c-d-e-f backbone starting from the above depicted building blocks -b-c-d- is depicted in scheme 8.

Scheme 8: Shows a reaction pathway to the a-b-c-d-e-f backbone starting from the building blocks -b-c-d- (A, B, C) of scheme 7. The reaction conditions are similar to the previously discussed reduction, coupling and deprotection conditions (see e.g. Scheme 4). Details are given in the experimental section.

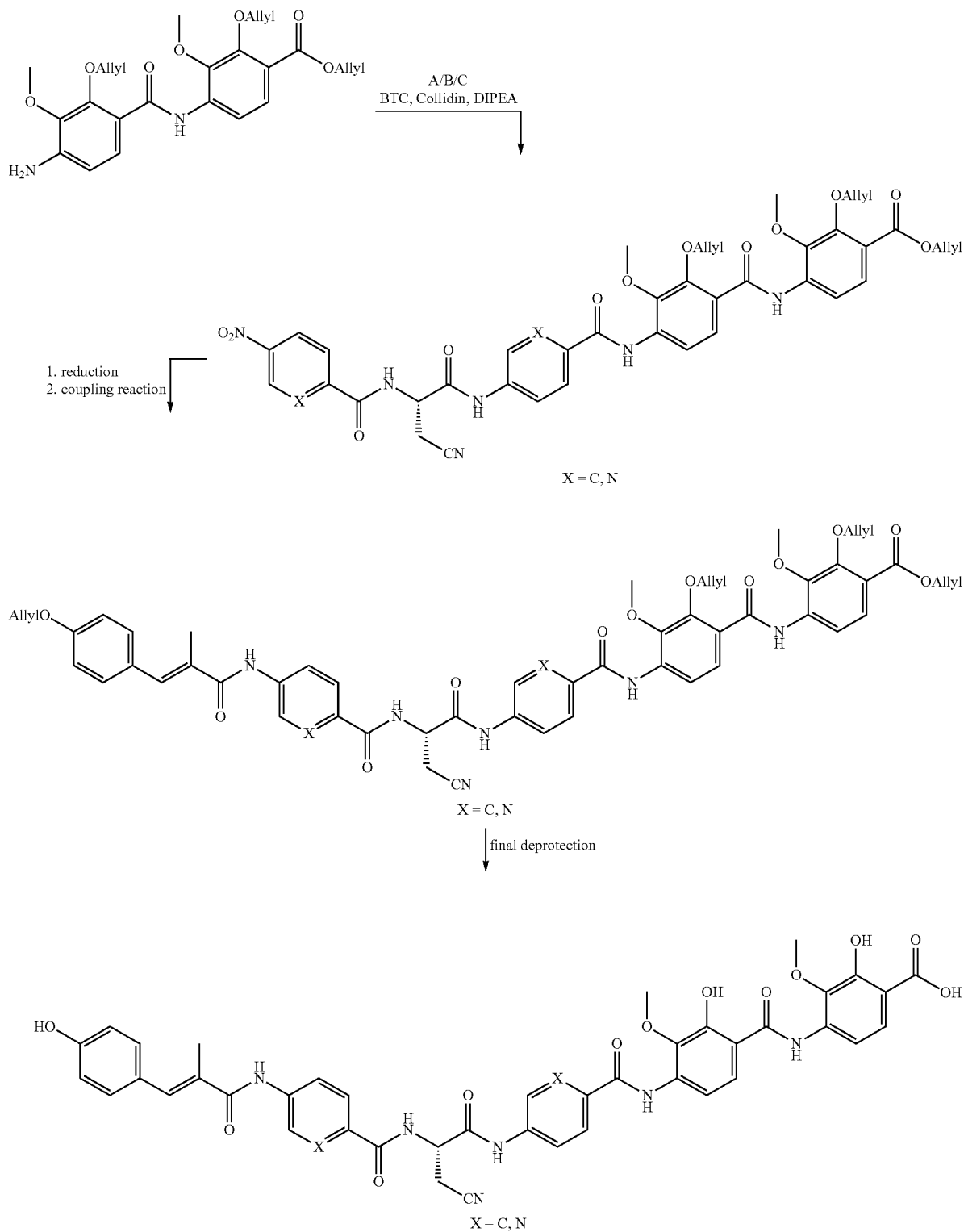

An alternative pathway for building blocks comprising a —SO$_2$— linker different is depicted in scheme 9 and scheme 10. These examples may be applied for other building blocks as well.
Scheme 9:
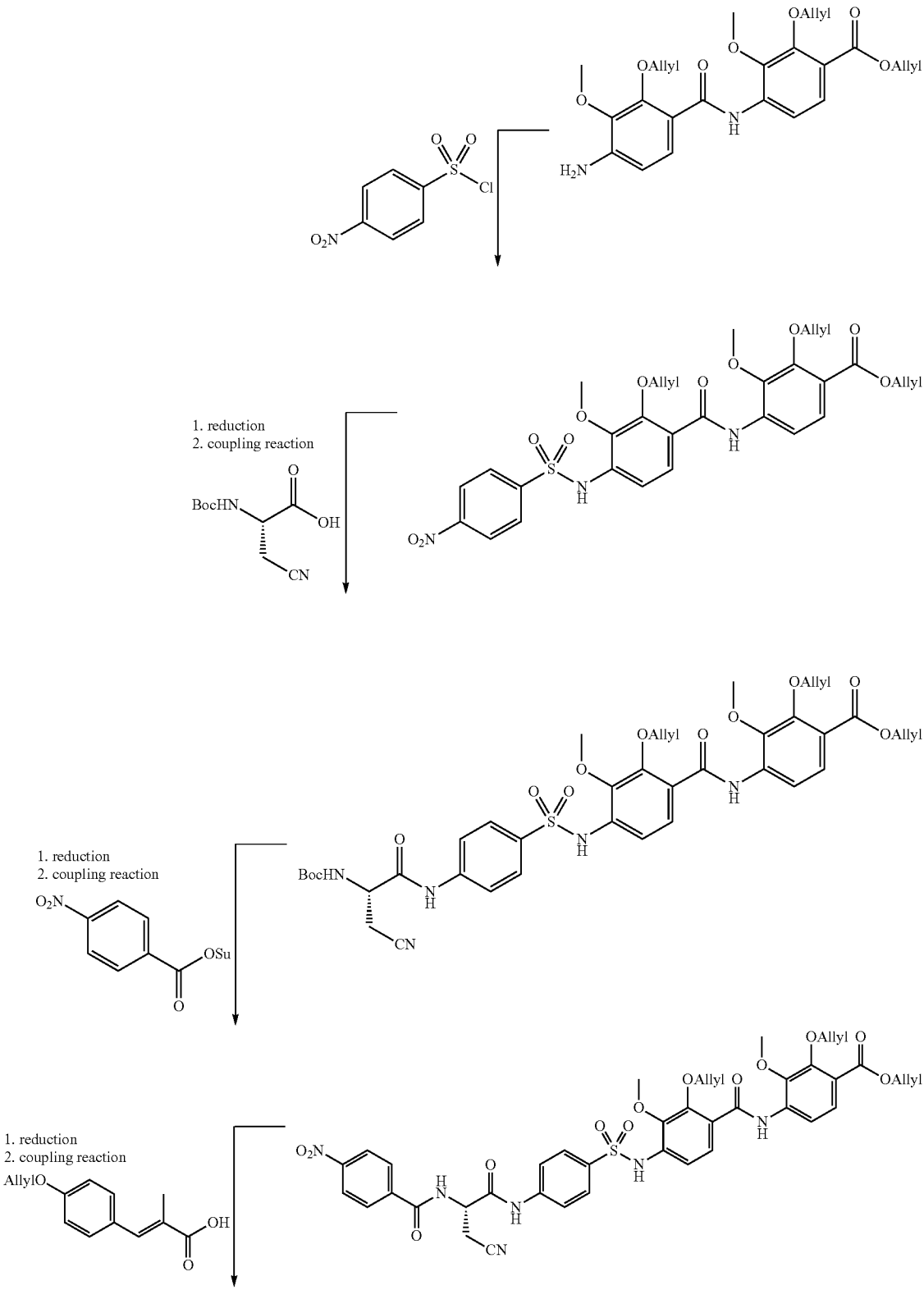

289 290
-continued

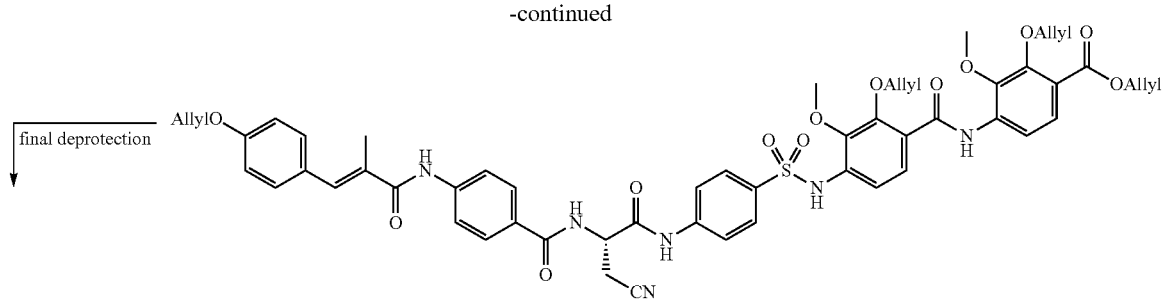

final deprotection ↓

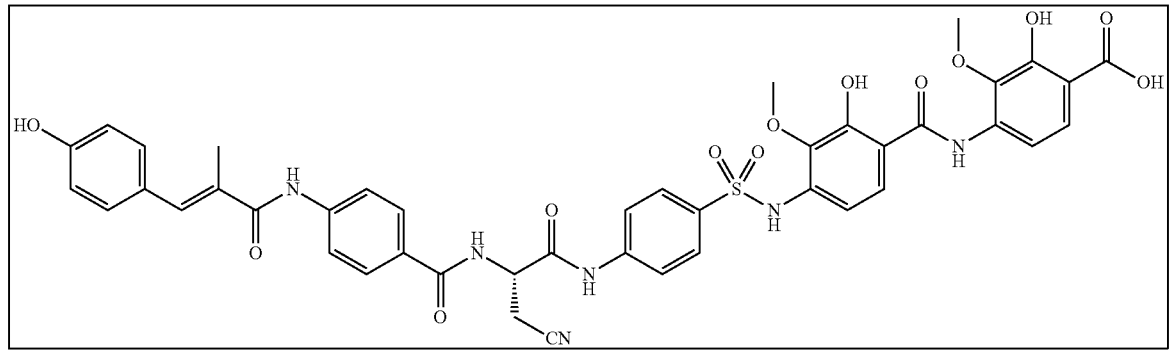

Shows a reaction pathway to the a-b-c-d-e-f backbone comprising a —SO$_2$— linker in place of D$^4$. The reaction conditions are similar to the previously discussed reduction, coupling and deprotection conditions (see e.g. Scheme 4). Details are given in the experimental section.

Scheme 10:

1. Boc deprotection
2. coupling reaction

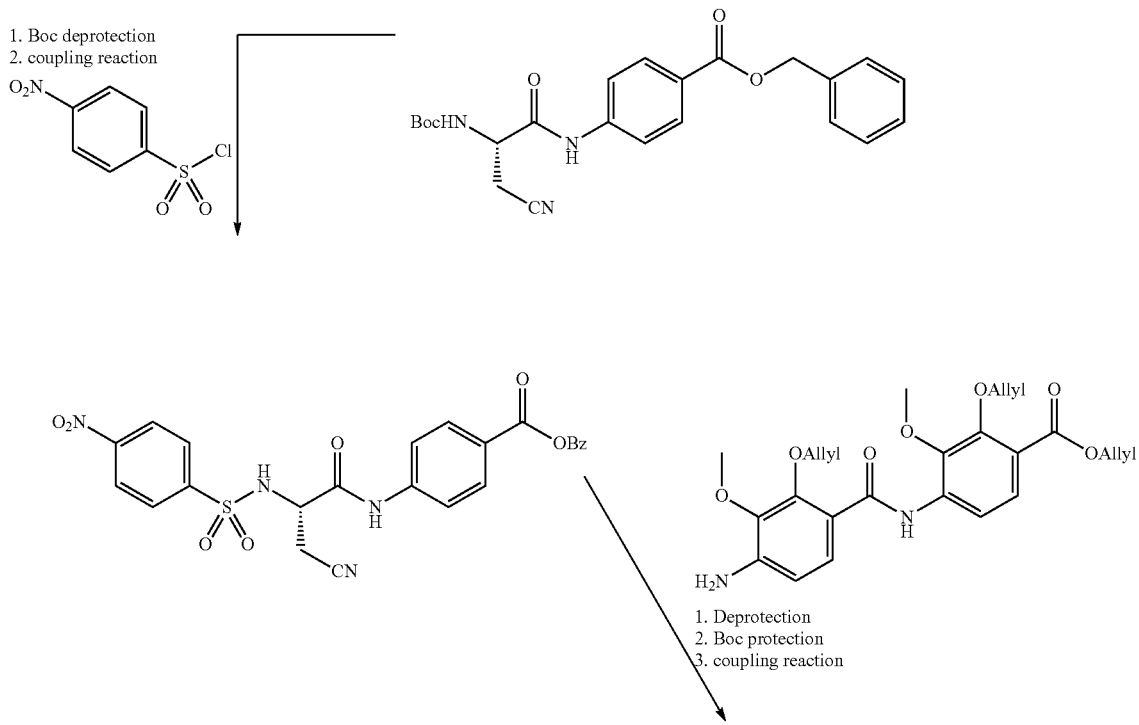

1. Deprotection
2. Boc protection
3. coupling reaction

-continued

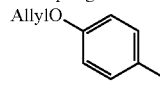
1. Boc deprotection
2. coupling reaction

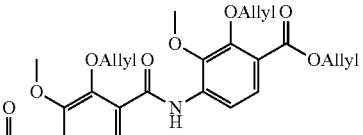

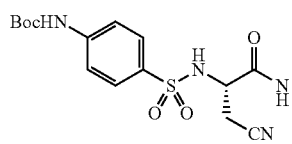

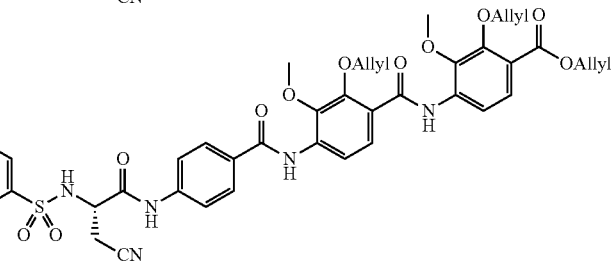

final deprotection

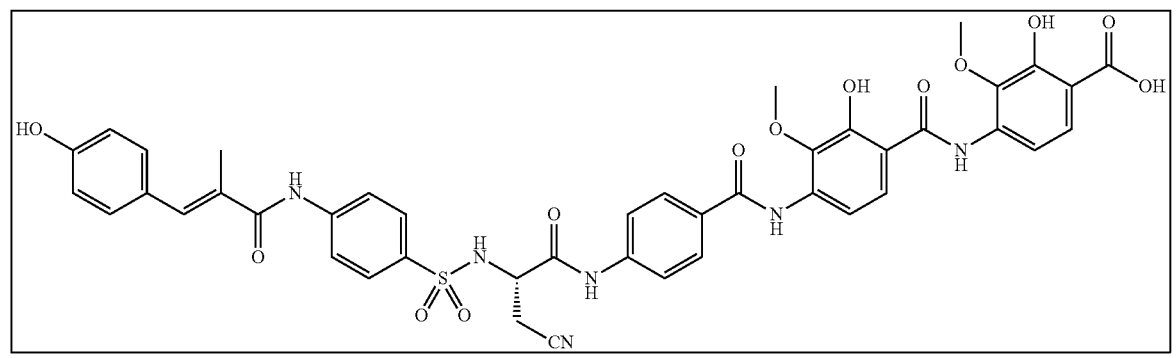

Shows a reaction pathway to the a-b-c-d-e-f backbone comprising a—SO$_2$—
linker in place of D$^2$. The reaction conditions are similar to the previously discussed reduction, coupling and deprotection conditions (see e.g. Scheme 4).
Details are given in the experimental section.

An alternative pathway for building blocks comprising different BC moieties is depicted in scheme 11:

Scheme 11: Compound 65 may be purchased as the respective an amino acid glycine and subsequently protected according to standard procedures. The compound 68 may be used according to scheme 1 to provide an analogue derivative of compound 55, which can be used as an intermediate for the last coupling reaction under similar conditions as described previously, in particular in scheme 4.

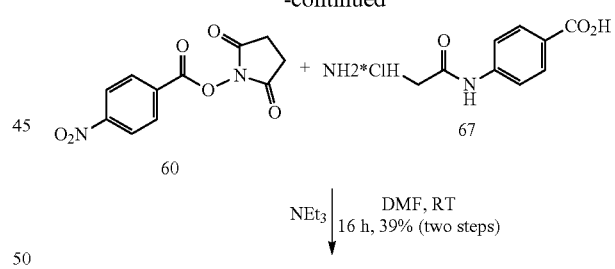

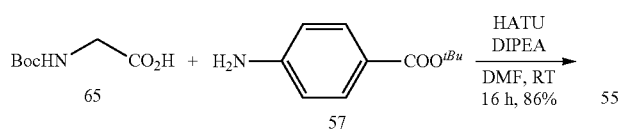

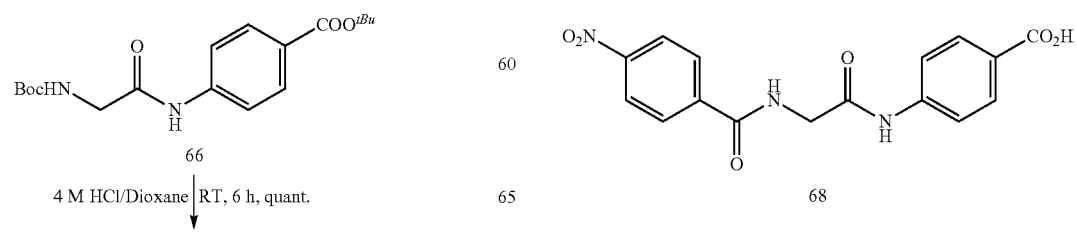

An analogue procedure applies to BC moieties selected from

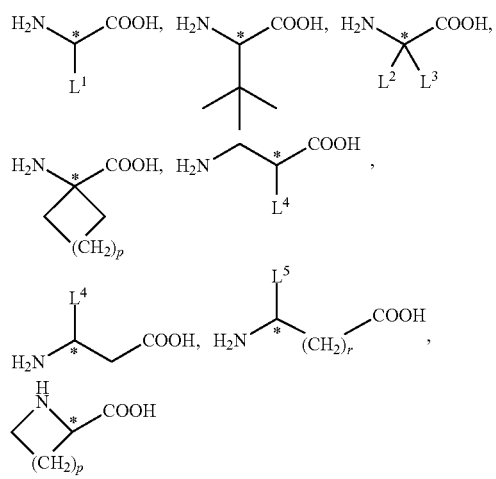

wherein the $NH_2$ or the COOH moieties may be protected by a suitable protecting group and the COOH, in an analogue way as described above, moiety may be activated—if necessary—in an analogue way as described above. These building blocks (comparable to compound 68) may be used according to scheme 1 to provide an analogue derivative of compound 55, which can be used as an intermediate for the last coupling reaction under similar conditions as described previously, in particular in scheme 4.

Examples of synthetic pathways for a few representative compounds are given in the following. Other compounds with comparable BC moieties may be produced analogously.

Derivatives containing building block BC variations are depicted below. If not mentioned otherwise, the reaction conditions are the same or similar to the previously described coupling reactions. Further details could be found in the experimental section.

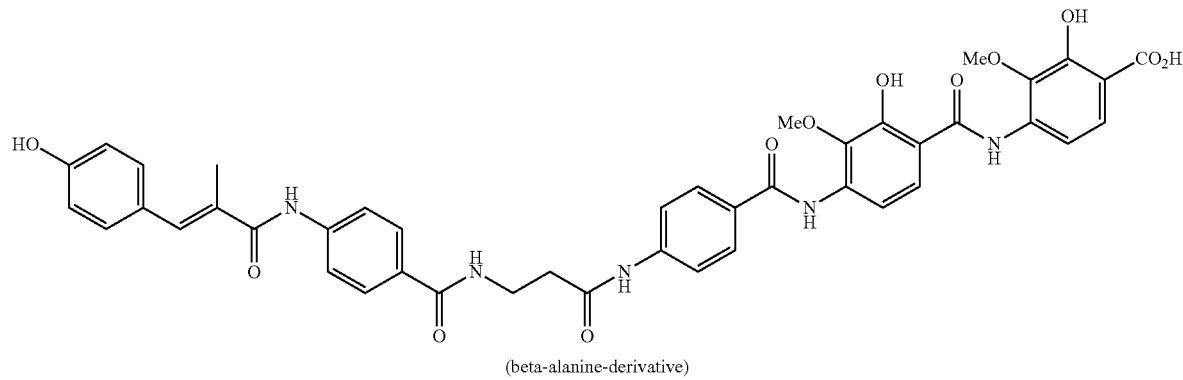

(beta-alanine-derivative)

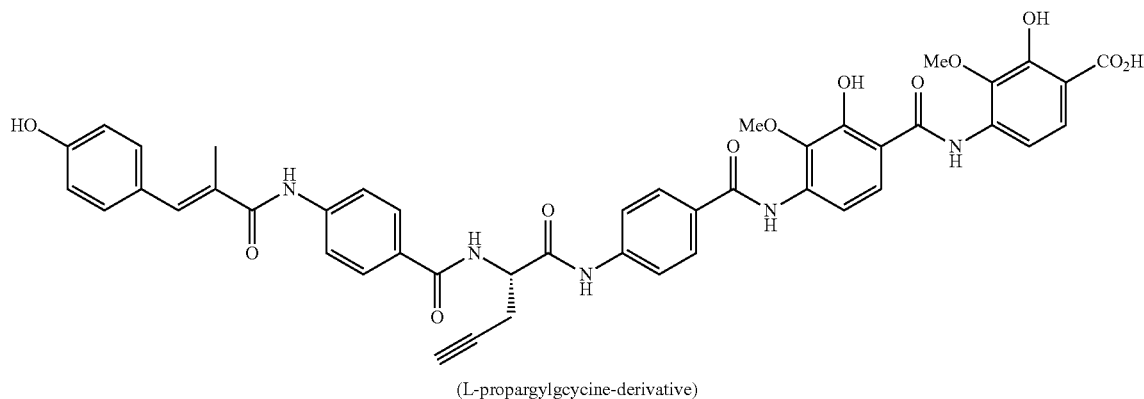

(L-propargylgcycine-derivative)

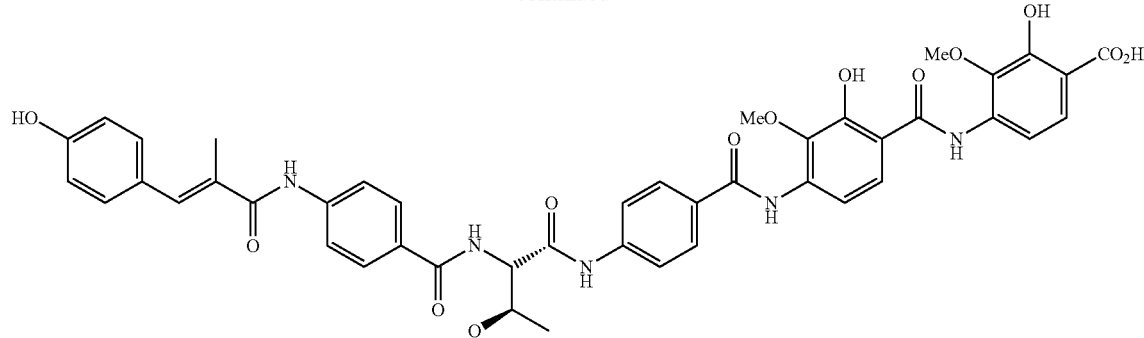
(threonine-derivative)
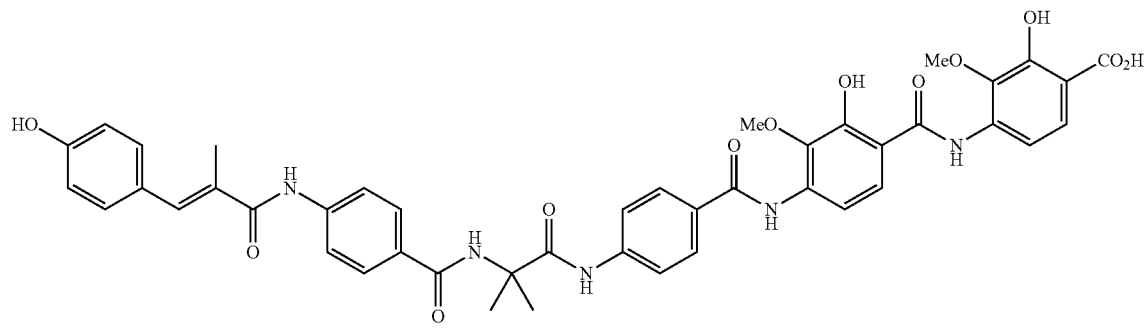
(α-aminoisobutyric acid-derivative)
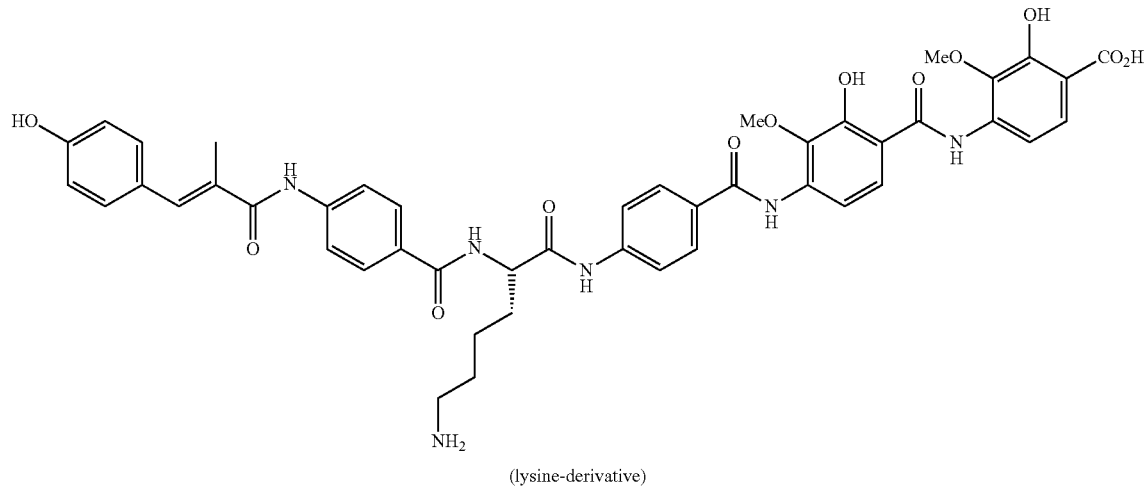
(lysine-derivative)
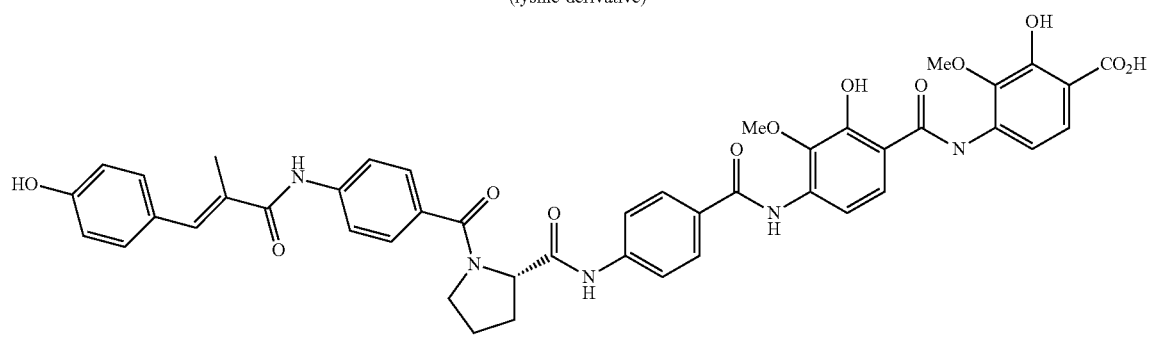
(proline-containing derivative)
may be synthesized as follows.

For beta-alanine-, L-propargylgcycine- and α-aminoisobutyric acid-derivative, the following boc-protected amino acids were used as starting material:

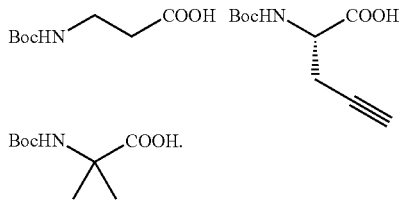

For threonine- and lysine-derivative the following starting materials were used:

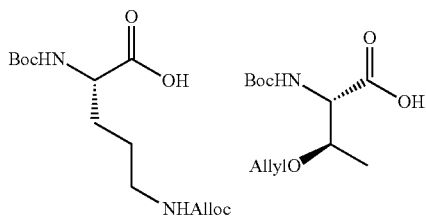

The above mentioned five starting materials were coupled to tert-butyl 4-aminobenzoate using HATU in DMF yielding the corresponding protected dipeptides

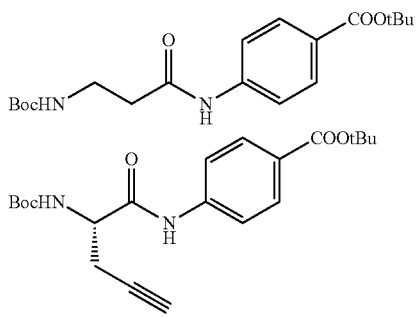

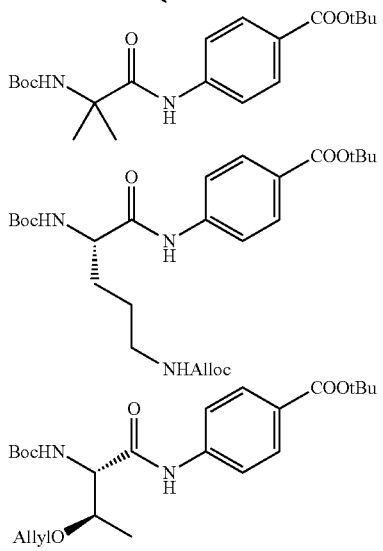

Deprotection of these compounds was carried out using 4 M HCl in dioxanes yielding the following compounds as hydrochlorides.

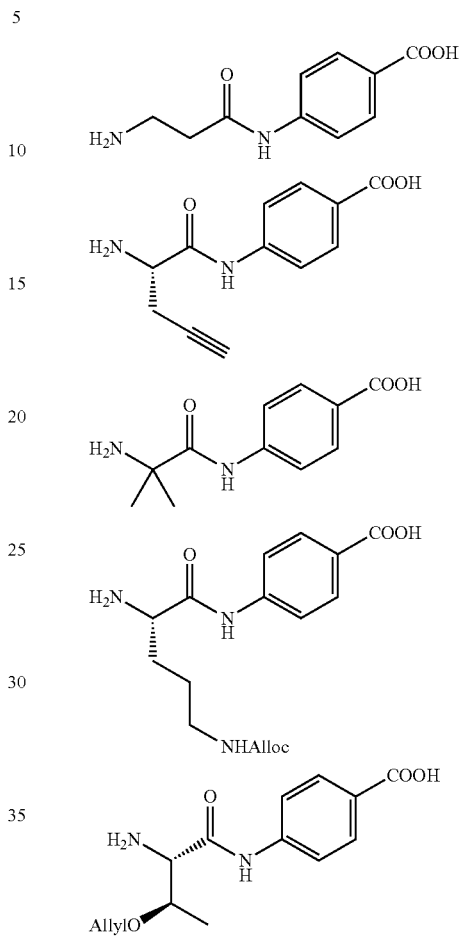

These compounds were coupled to nitro-pABA succinate ester 60 yielding the following tripeptides:

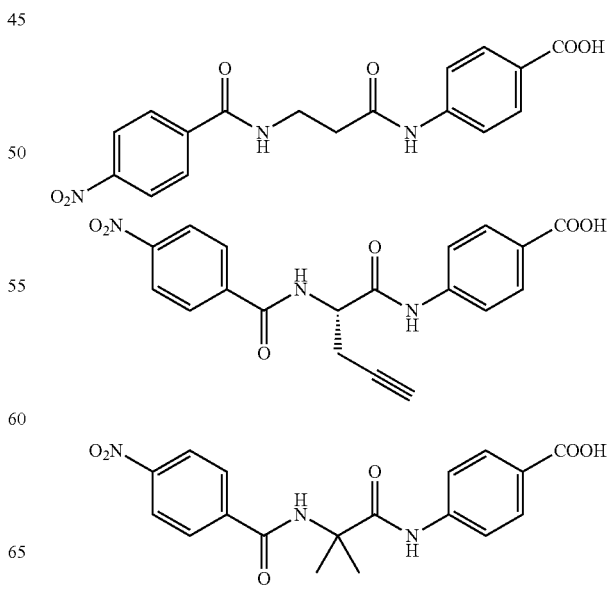

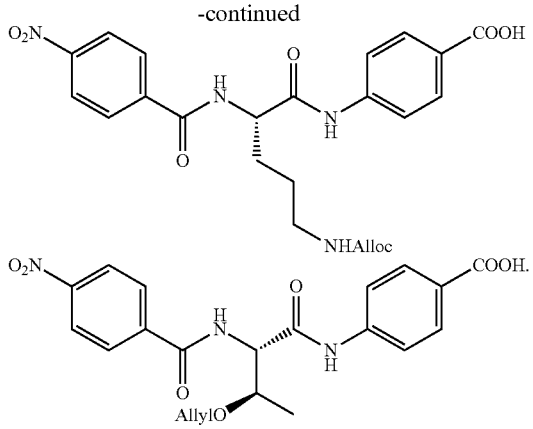

For the proline-containing derivative the following pathway was used:

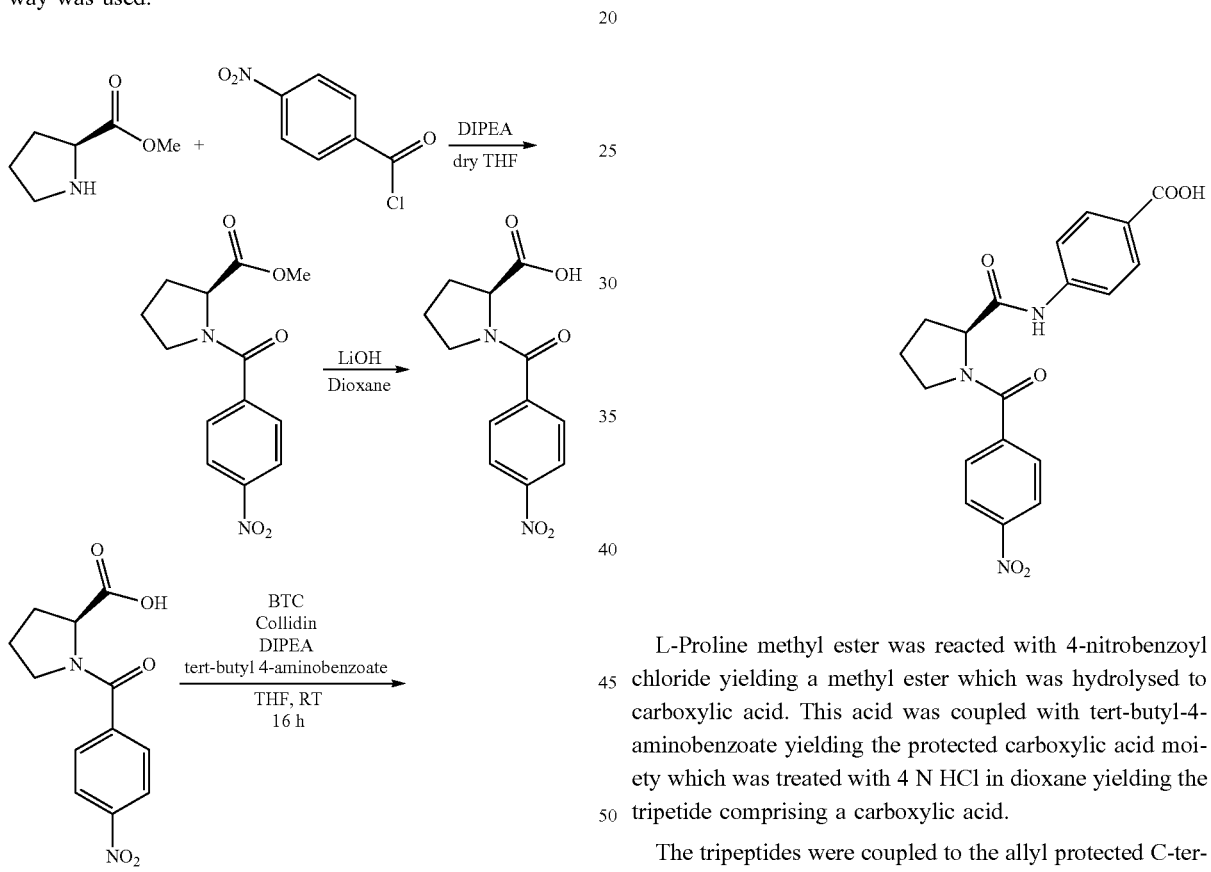

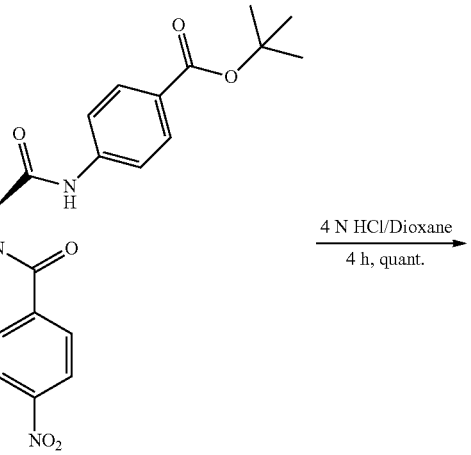

L-Proline methyl ester was reacted with 4-nitrobenzoyl chloride yielding a methyl ester which was hydrolysed to carboxylic acid. This acid was coupled with tert-butyl-4-aminobenzoate yielding the protected carboxylic acid moiety which was treated with 4 N HCl in dioxane yielding the tripetide comprising a carboxylic acid.

The tripeptides were coupled to the allyl protected C-terminal dipeptide compound 53 yielding compounds:

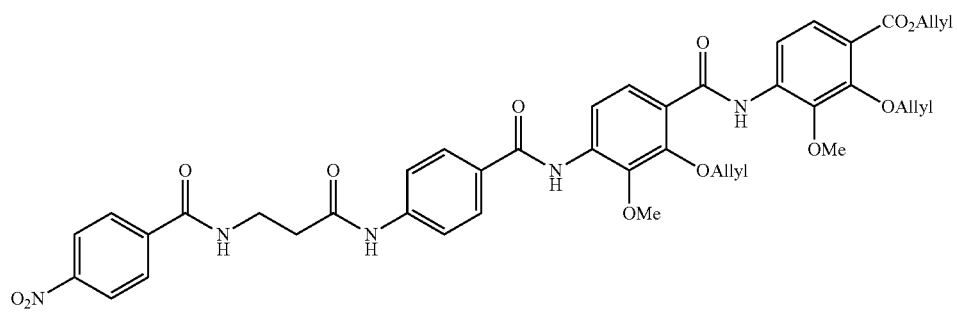

-continued
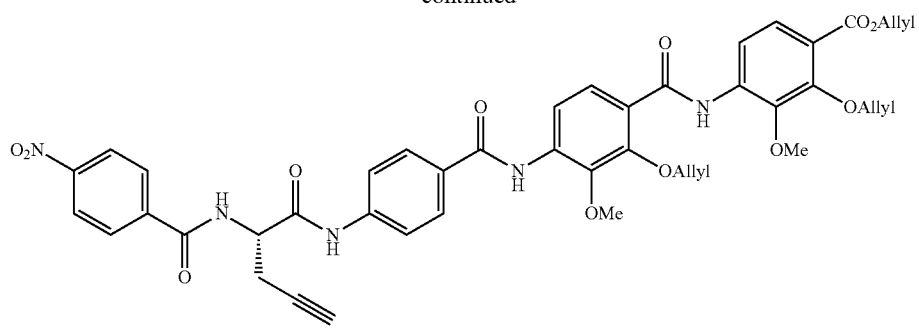
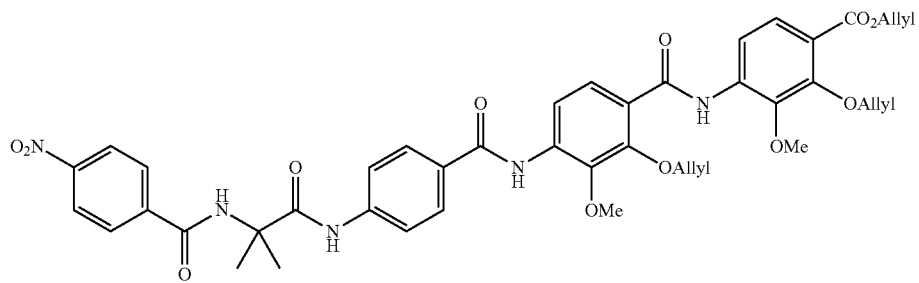
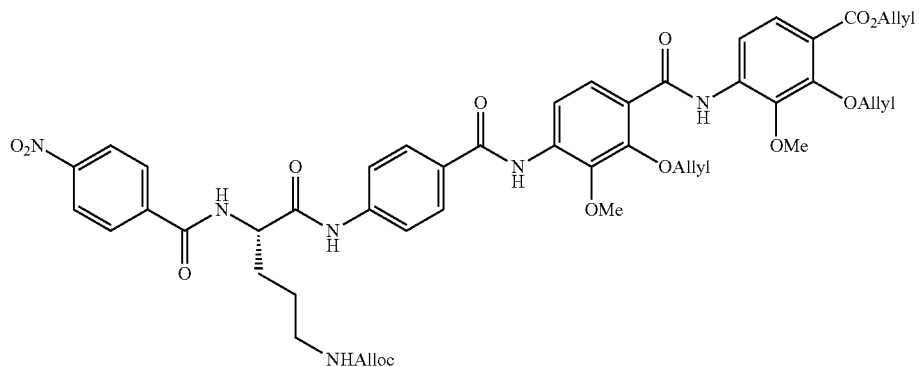
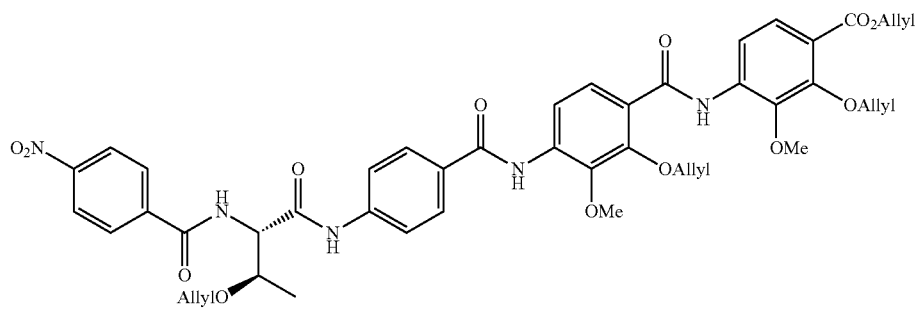
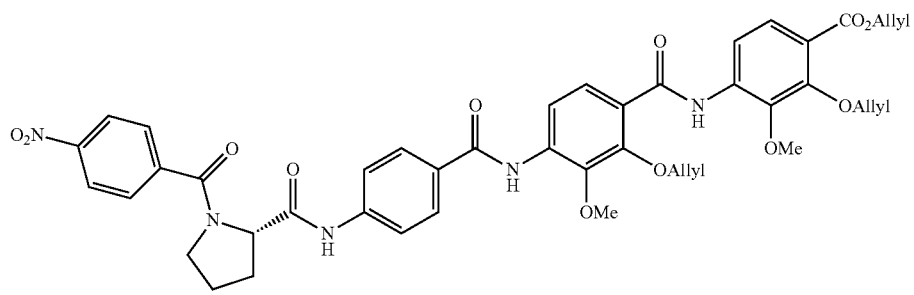

These compounds were reacted with Tin(II) chloride dihydrate yielding the respective terminal NH$_2$ moiety instead of the NO$_2$ moiety, and were subsequently coupled with E)-3-(4-(Allyloxy)phenyl)-2-methylacrylic acid yielding a protected compound of the formula 1. After global deprotection Pd(PPh$_3$)$_4$ and purification via HPLC the beta-alanine-derivative, L-propargylgcycine-derivative, threonine-derivative, α-aminoisobutyric acid-derivative, lysine-derivative or proline-containing derivative, as depicted above, were provided.

Possible ways to obtain derivatives of building blocks, in particular of building blocks BE and BF, are given in scheme 12:

Scheme 12:

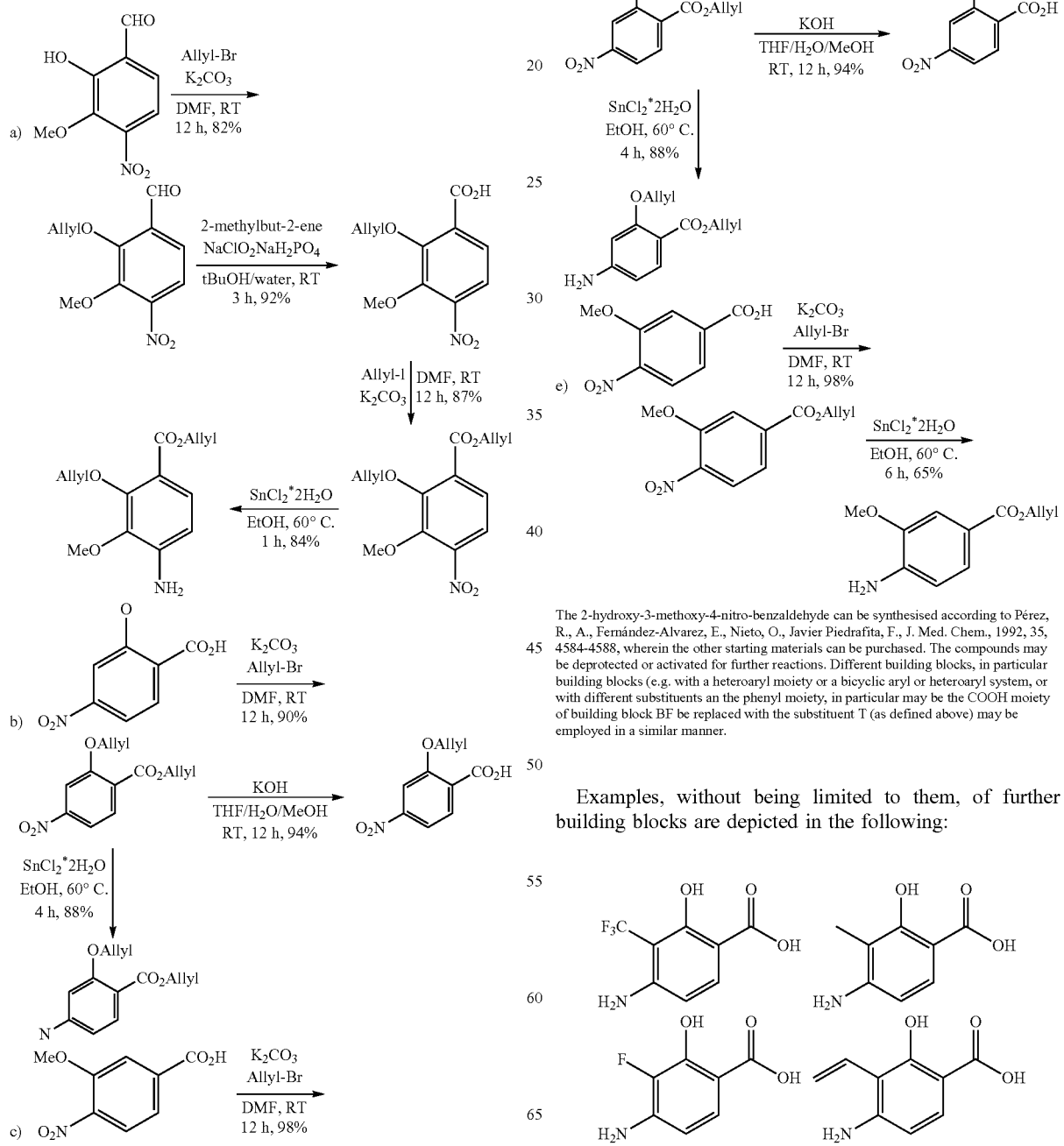

The 2-hydroxy-3-methoxy-4-nitro-benzaldehyde can be synthesised according to Pérez, R., A., Fernández-Alvarez, E., Nieto, O., Javier Piedrafita, F., J. Med. Chem., 1992, 35, 4584-4588, wherein the other starting materials can be purchased. The compounds may be deprotected or activated for further reactions. Different building blocks, in particular building blocks (e.g. with a heteroaryl moiety or a bicyclic aryl or heteroaryl system, or with different substituents an the phenyl moiety, in particular may be the COOH moiety of building block BF be replaced with the substituent T (as defined above) may be employed in a similar manner.

Examples, without being limited to them, of further building blocks are depicted in the following:

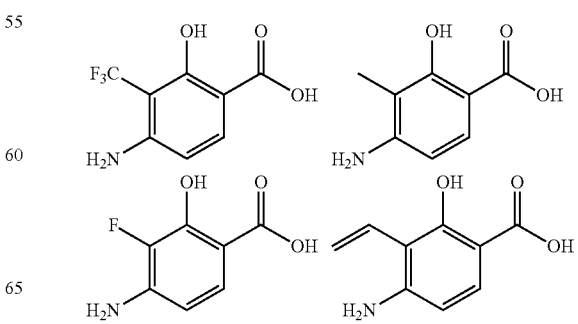

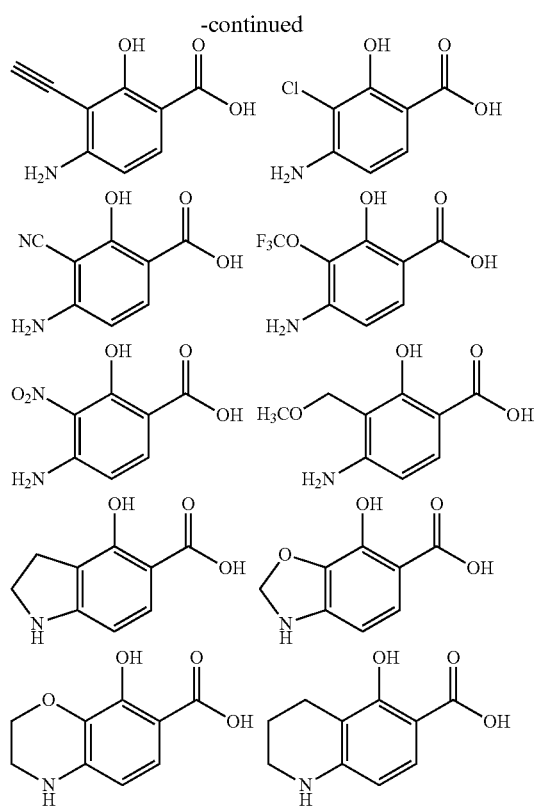
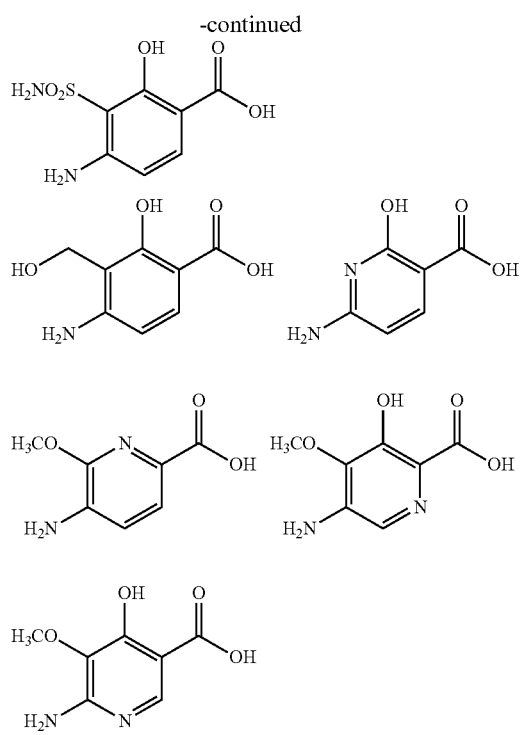
An example for a BA building block comprising a different functional group is given in scheme 13:
Scheme 13:
a)
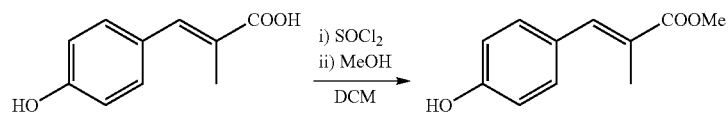
b)
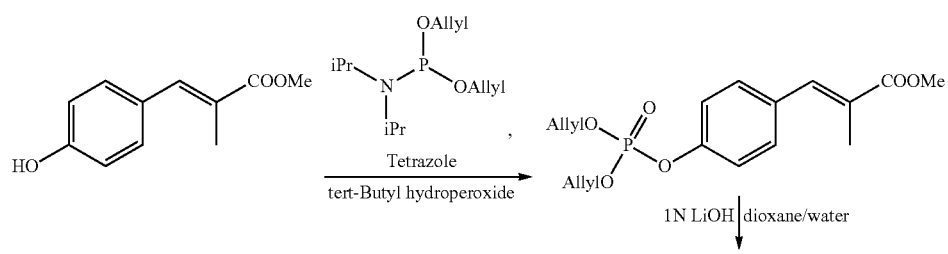
c)
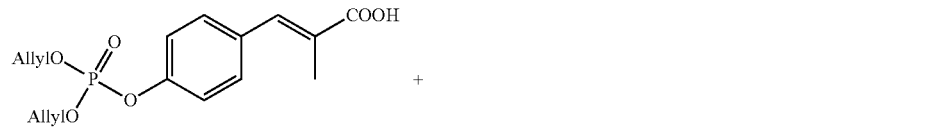

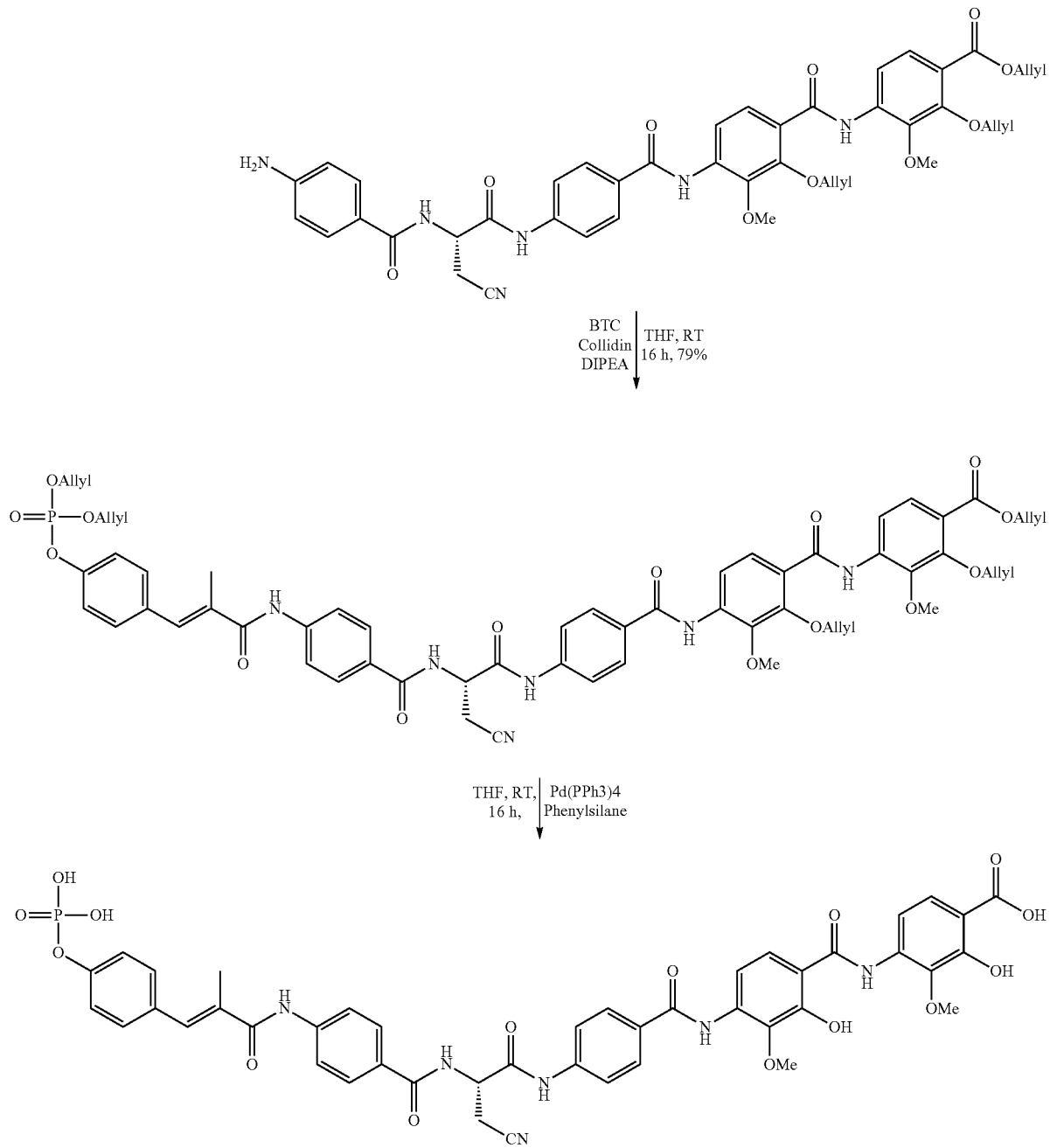

a) To a solution of the cinematic acid in anhydrous DCM was added $SOCl_2$ (1.2 eq) and the mixture was stirred for 3 hours at room temperature. Anhydrous methanol was added (10 eq) and the Mixture was stirred for 10 min. The solvent was removed under reduced pressure. Column chromatography (n-hexane:ethyl acetate 3:1) yielded the ester as a white solid (95%).

b) To a solution of the ester in anhydrous THF was added Tetrazole (3 eq) and Diallyl N,N-diisopropylphosphoramidite (2 eq) at 0° C. The mixture was stirred for 3 hours at room temperature, cooled to 0° C. and tert-Butyl hydroperoxide (3 eq) was slowly added. Stirring was continued for 1 hour at 0° C. The Reaction mixture was poured into a solution of $NaSO_3$ (10%) and extracted three times with ethyl acetate. After drying over $Na_2SO_4$ and filtration, the solvent was removed under reduced pressure. Column chromatography (n-hexane:ethyl acetate 2:1) yielded the allyl protected ester as a clear oil (50%), which was taken up in dioxane/1N LiOH and the mixture was stirred at room temperature for 16 hours. The mixture was acidified to pH 1 with 1N HCl and extracted three times with ethyl acetate. After drying over $Na_2SO_4$ and filtration, the solvent was removed under reduced pressure. Column chromatography (Chloroform:Methanol 100:1) yielded the allyl protected acid as a clear oil (46%).

c) BTC (0.766 eq, 0.0667 mmol, 19.8 mg) was dissolved in dry THF (10 ml) under an atmosphere of argon. The allyl protected acid (2.37 eq, 0.207 mmol, 70 mg) was added. syn-Collidine (8 eq, 0697 mmol, 91μl) was slowly added via syrringe and the white suspension was stirred at room temperature for 20 min. The amine (1 eq, 0.087 mmol, 70 mg) and DIPEA (10 eq, 0.872 mmol, 0.150 ml) were added via syrringe. The reaction mixture was stirred for 12 h at room temperature and quenched by the addition of water. After removing the organic solvent under reduced pressure the aqueous phase was extracted with EtOAc (3 × 50 ml). The organic phase was washed with aqueous HCl solution (5%, 2 × 50 ml), water (1 × 50 ml) and brine (1 × 50 ml). After drying over $Na_2SO_4$ and filtration, the solvent was removed under reduced pressure. Column chromatography (CHCl$_3$:MeOH; 1.5% MeOH) yielded the fully protected compound as an orange oil (78 mg, 79%), which was (1 eq, 0.0534 mmol, 60 mg) with phenylsilane (20 eq, 1.07 mmol, 132μl) dissolved in dry THF under an atmosphere of argon and exclusion of light. Pd[P(Ph)$_3$]$_4$ (1 eq, 0.0534 mmol, 62 mg) was added and the mixture was stirred 12 h at room temperature. After adding 3 drops of acetic acid the solvent was removed under reduced pressure. The final product was isolated after preparative HPCL purification as a white powder Further functional groups may be introduced in the "finished backbone a-b-c-d-e-f according to standard procedures, like fro example oxidation, reduction or halogenations.

In an embodiment the synthesis of compounds with the following molecular structure of formula (2)

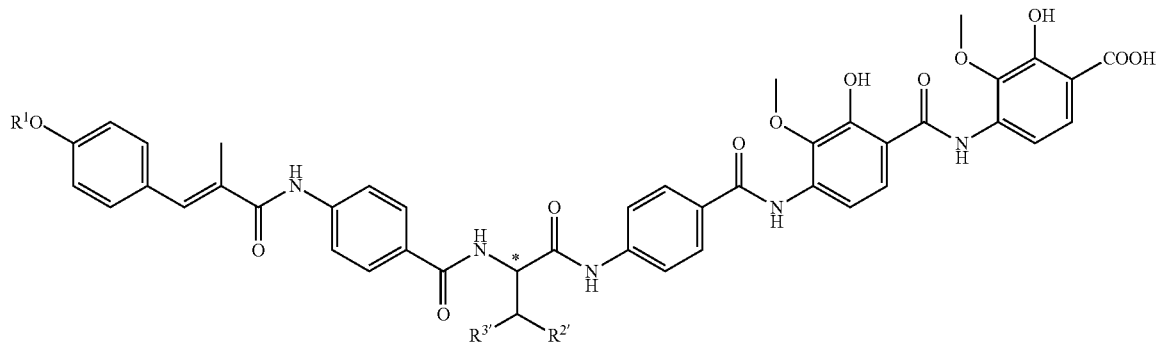

wherein $R^1$ is H or $CO(NH_2)$, $R^{2'}$ is $CO(NH_2)$ or CN, $R^{3'}$ is H or $OCH_3$, and

* indicates a stereo center of a L- or D-enantiomer, which is located on the tertiary carbon atom below the asterisk *, and wherein the compound of the general formula (1) is an essentially pure L-enantiomer, an essentially pure D-enantiomer or a mixture of the L- and D-enantiomer of the same molecular formula, wherein in particular the compound of the general formula (1) is an essentially pure L-enantiomer or an essentially pure D-enantiomer.

may be carried out as described in the following.

In case of the compound of above formula 2 the previously mentioned six building blocks are

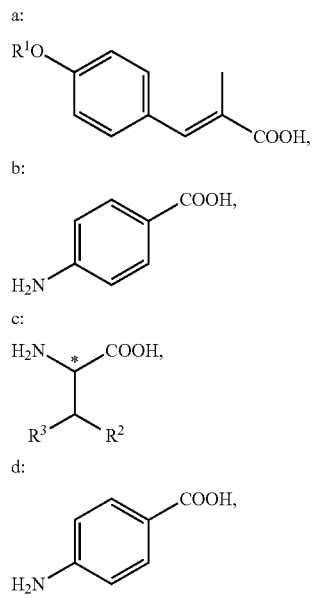

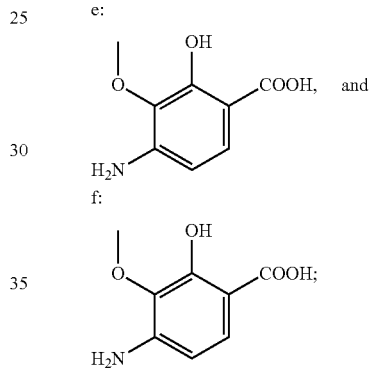

wherein $R^1$ is H or $CO(NH_2)$, $R^2$ is CN or $CO(NH_2)$ and $R^3$ is H or $OCH_3$.

The method of choice of linking these building blocks is a selective coupling reaction between the (activated) carboxylic acid moiety of one block (acid partner), and a amino moiety of another block (amino partner), whereby other functional groups of the amino and acid partner are protected. The reactive hydroxyl groups of block a, e and f need to be transitionally (reversibly) protected by any of the many suitable protection groups for hydroxyl groups (PGH) known in the art. Likewise, the carboxylic acid moiety of the amino partner will be protected by any of the many suitable protection groups (PGA) known in the art for carboxylic acid groups to prevent homopolymer formation. Furthermore, any amino moiety of the acid partner will likewise be protected by any of the many suitable protection groups for amino groups (PGN) known in the art. Additionally, the group $R^1$ will be transitionally (reversibly) protected by a protecting group $R^1PG$, whereby $R^1PG$ is, in case of $R^1$ being H, the protection group for hydroxyl groups PGH ($O^{PGH}$) and, in case of $R^1$ being $—CO(NH_2)$, the protection group for amino groups (PGN) attached to the $—CO(NH_2)$ moiety of $R^1$ ($—CO(N^{PGN})$). Likewise, the group $R^2$ will be, in case of $R^2$ being $CO(NH_2)$, transitionally (reversibly) protected by a protecting group PGN attached to the $—CO(NH_2)$ moiety of $R^{2'}$ ($—CO(N^{PGN})$), whereby in case of $R^2$ being CN no protection group is applied.

Activation of the carboxylic acid moiety of the acid partner may be applied before the reaction of the acid partner with the amino partner and can be achieved by any of the methods known in the art for increasing the reactivity of carboxylic acids to amide formation with primary amines, in particular reference is made to the activation of the carboxylic acid as discussed. Thus, derivatives of the six building blocks are employed as intermediates in the synthesis of the invention as building blocks of the general formula

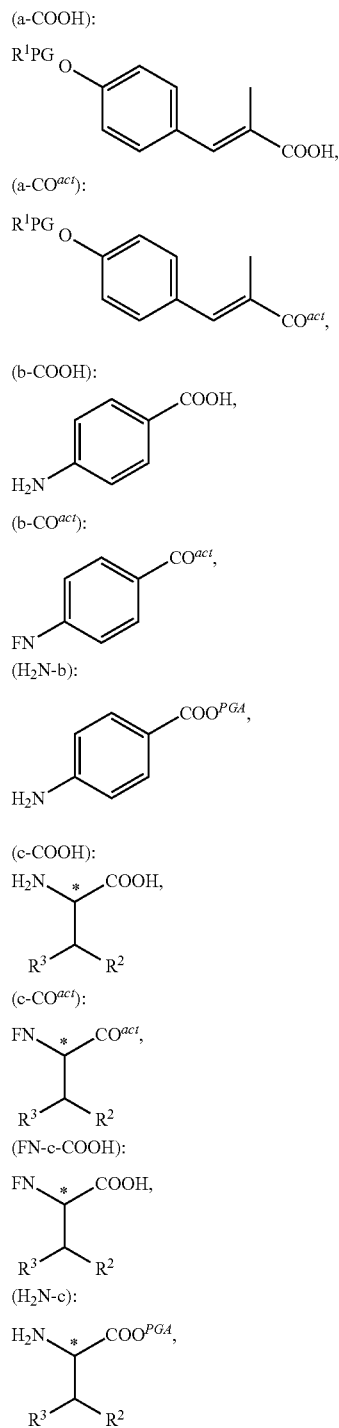

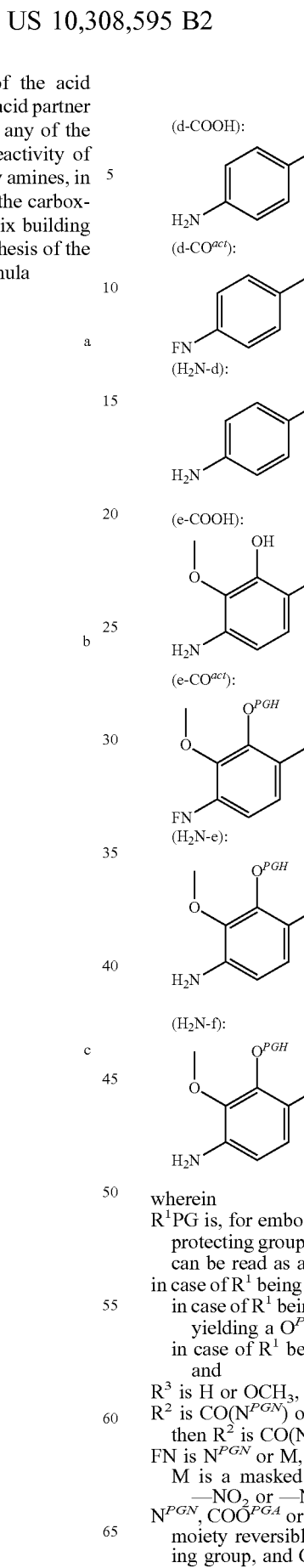

wherein
$R^1PG$ is, for embodiments for which $R^1$ is H, a hydroxyl protecting group PGH, in other words the $O^{R^1PG}$ moiety can be read as an $O^{PGH}$ moiety, or,
in case of $R^1$ being $CO(NH_2)$, a $—CO(N^{PGN})$ moiety, and,
in case of $R^1$ being H, a hydroxyl protecting group PGH yielding a $O^{PGH}$ moiety, or,
in case of $R^1$ being $CO(NH_2)$, a $—CO(N^{PGN})$ moiety, and
$R^3$ is H or $OCH_3$, and
$R^2$ is $CO(N^{PGN})$ or CN, except in case of FN-c-COOH, then $R^2$ is $CO(NH_2)$
FN is $N^{PGN}$ or M, wherein
M is a masked functional group, in particular M is $—NO_2$ or $—N_3$, and wherein,
$N^{PGN}$, $COO^{PGA}$ or $O^{PGH}$ signifies an $NH_2$, COOH or OH moiety reversibly inactivated by a removable protecting group, and $CO^{act}$ signifies an activated carboxylic acid moiety, are employed as intermediates, and i. the carboxylic acid moiety a-COOH or the activated carboxylic acid moiety a-$CO^{act}$ of the acid partner a is linked to the amine moiety $H_2N$-b of the amino partner b, ii. the carboxylic acid moiety b-COOH or the activated carboxylic acid moiety b-$CO^{act}$ of the acid partner b is linked to the amine moiety $H_2N$-c of the amino partner c, iii. the carboxylic acid moiety c-COOH or the activated carboxylic acid moiety c-$CO^{act}$ of the acid partner c is linked to the amine moiety $H_2N$-d of the amino partner d, iv. the carboxylic acid moiety d-COOH or the activated carboxylic acid moiety d-$CO^{act}$ of the acid partner d is linked to the amine moiety $H_2N$-e of the amino partner e, and v. the carboxylic acid moiety e-COOH or the activated carboxylic acid moiety e-$CO^{act}$ of the acid partner e is linked to the amine moiety $H_2N$-f of the amino partner f.

In some embodiments, only the activated carboxylic acid moiety of the acid partner is used in one of the steps i. to v., in particular in all the steps i. to v. is the carboxylic acid moiety of the acid partner activated.

It is apparent to the skilled person that the above coupling reactions i. to v. will not necessarily involve the isolated building blocks in each case, but will take place between combinations of the above mentioned building blocks in order to arrive at the full sequence of six blocks (a-b-c-d-e-f). Therefore, the above is to be understood as a teaching regarding the sequence of blocks, i.e. which block links to which other one through the amino and carboxylic acid moiety. In other words, which block will function as an acid partner and which as an amino partner in the above coupling reactions in order to arrive at the full sequence of six blocks (a-b-c-d-e-f).

For example, the reaction of the acid partner b with the amino partner c will yield a building compound b-c, wherein the amino moiety of the block b and the carboxylic acid moiety of block c are protected. This compound b-c can react as an acid partner as well as an amino partner in subsequent reactions. By removing the protection group of the amino moiety of block b a reaction with an acid partner a can be established, yielding compound a-b-c, wherein the carboxylic acid moiety of block c is protected. After removal of the carboxylic acid moiety of block c compound a-b-c can function as an acid partner for the amino partner d. The same applies to further subsequent reactions in order to arrive at the full sequence of six blocks.

It is further possible that by removing the protection group of the carboxylic acid moiety of block c of the compound b-c, the carboxylic acid moiety of block c will function as an acid partner and a reaction with an amino partner d can be established, yielding compound b-c-d. The amino moiety of the block b and the carboxylic acid moiety of block d of the compound b-c-d are protected. Thus, compound b-c-d can function after the removal of the protection group on the amino moiety of block b or on the carboxylic acid moiety of block d, comparable to compound b-c, as an acid partner for a reaction with the amino partner e or as an amino partner for the reaction with the acid partner a. The same applies to further subsequent reactions in order to arrive at the full sequence of six blocks.

Many ways to achieve the full albicidin sequence a-b-c-d-e-f are possible. The following examples show without being limited to these combinations three further possible combinations such as e+f yielding (e-f), d+(e-f) yielding (d-e-f), c+(d-e-f) yielding (c-d-e-f), a+b yielding (a-b), (a-b)+(c-d-e-f) yielding (a-b-c-d-e-f), b+c yielding (b-c), (b-c)+d yielding (b-c-d), e+f yielding (e-f), (b-c-d)+(e-f) yielding (b-c-d-e-f), a+(b-c-d-e-f) yielding (a-b-c-d-e-f) or c+d yielding (c-d), b+(c-d) yielding (b-c-d), e+f yielding (e-f), (b-c-d)+(e-f) yielding a+(b-c-d-e-f) yielding (a-b-c-d-e-f), whereby the coupling of the respective building blocks may be achieved in a similar manner as discussed in the previous sections.

In embodiments of the synthesis of the invention where one last peptide coupling step is made to arrive at the albicidin backbone (this "last step" may be followed by subsequent reactions to remove protecting groups or to introduce modifications of the reactive groups), this last step of backbone formation can be:

a+b-c-d-e-f, or
a-b+c-d-e-f, or
a-b-c+d-e-f, or
a-b-c-d+e-f, or
a-b-c-d-e+f.

In embodiments of the synthesis of the invention where one peptide coupling step is made to arrive at the albicidin intermediate a-b-c-d-e this step can be:

a+b-c-d-e, or
a-b+c-d-e, or
a-b-c+d-e, or
a-b-c-d+e.

In embodiments of the synthesis of the invention where one peptide coupling step is made to arrive at the albicidin intermediate b-c-d-e-f, this step can be:

b-c-d-e+f, or
b-c-d+e-f, or
b-c+d-e-f, or
b+c-d-e-f.

In embodiments of the synthesis of the invention where one peptide coupling step is made to arrive at the albicidin intermediate b-c-d-e, this step can be:

b-c-d+e, or
b-c+d-e, or
b+c-d-e.

In certain embodiments, a compound (a-b-c-d-e-$CO^{act}$):

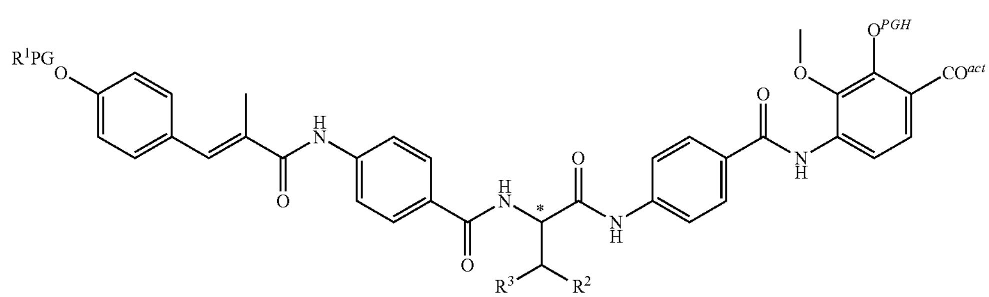

is reacted with compound (H₂N-f), yielding compound a-b-c-d-e-f

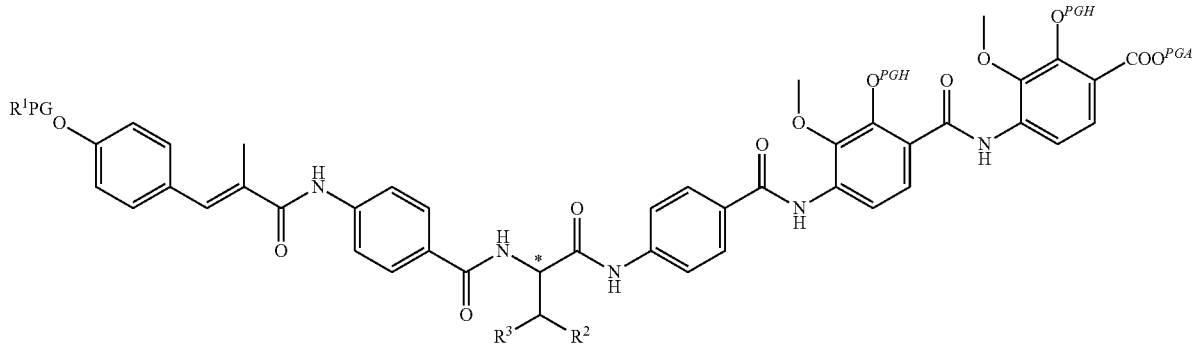

wherein
- R¹PG is, for embodiments for which R¹ is H, a hydroxyl protecting group PGH, in other words the $O^{R^1PG}$ moiety can be read as an $O^{PGH}$ moiety, or,
- in case of R¹ being CO(NH₂), a —CO($N^{PGN}$) moiety, wherein in particular R¹PG is a hydroxyl protecting group PGH with R¹ being H, yielding a $O^{PGH}$ moiety, and
- R³ is H or OCH₃, and
- R² is CO($N^{PGN}$) or CN, and
- $N^{PGN}$, $COO^{PGA}$ or $O^{PGH}$ signifies an NH₂, COOH or OH moiety reversibly inactivated by a removable protecting group, and $CO^{act}$ signifies an activated carboxylic acid moiety, wherein from compound (a-b-c-d-e-f) albicidin is obtained by removal of the protecting groups PGN, PGH and PGA. Alternatively the not activated carboxyl acid moiety a-b-c-d-e-COOH may be used instead of the activated carboxyl moiety a-b-c-d-e-$CO^{act}$.

In certain embodiments, a compound (a-b-c-d-$CO^{act}$):

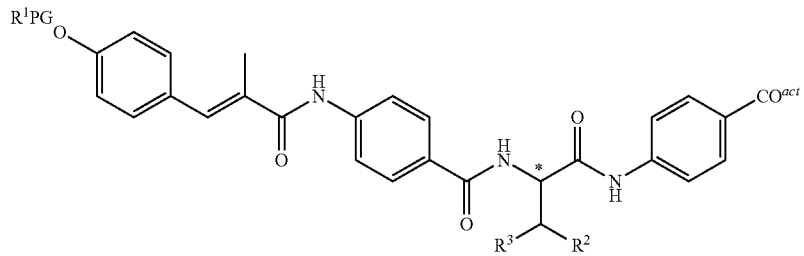

is reacted with a compound (H₂N-e-f):

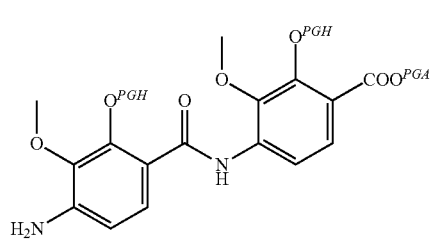

wherein
- R¹PG is, for embodiments for which R¹ is H, a hydroxyl protecting group PGH, in other words the $O^{R^1PG}$ moiety can be read as an $O^{PGH}$ moiety, or,
- in case of R¹ being CO(NH₂), a —CO($N^{PGN}$) moiety, wherein in particular R¹PG is a hydroxyl protecting group PGH with R¹ being H, yielding a $O^{PGH}$ moiety, and
- R³ is H or OCH₃, and
- R² is CO($N^{PGN}$) or CN, and
- $N^{PGN}$, $COO^{PGA}$ or $O^{PGH}$ signifies an NH₂, COOH or OH moiety reversibly inactivated by a removable protecting group, and $CO^{act}$ signifies an activated carboxylic acid moiety, wherein from compound (a-b-c-d-e-f) albicidin is obtained by removal of the protecting groups PGN, PGH and PGA. Alternatively the not activated carboxyl acid moiety a-b-c-d-COOH may be used instead of the activated carboxyl moiety a-b-c-d-$CO^{act}$.

In certain embodiments, a compound (a-b-c-$CO^{act}$)

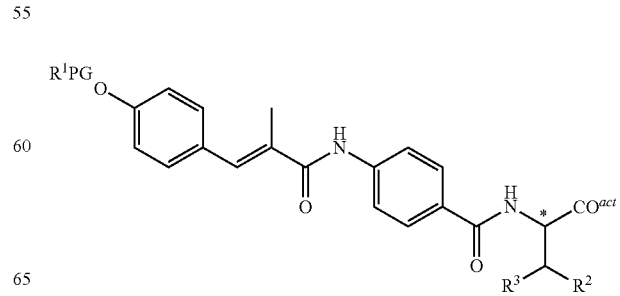

is reacted with a compound (H₂N-d-e-f)

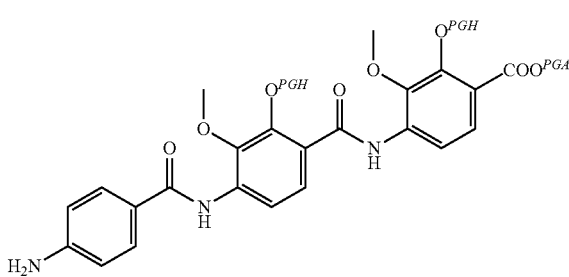

wherein
R¹PG is, for embodiments for which R¹ is H, a hydroxyl protecting group PGH, in other words the $O^{R^1PG}$ moiety can be read as an $O^{PGH}$ moiety, or,
in case of R¹ being CO(NH₂), a —CO($N^{PGN}$) moiety, wherein in particular R¹PG is a hydroxyl protecting group PGH with R¹ being H, yielding a $O^{PGH}$ moiety, and
R³ is H or OCH₃, and
R² is CO($N^{PGN}$) or CN, and
$N^{PGN}$, $COO^{PGA}$ or $O^{PGH}$ signifies an NH₂, COOH or OH moiety reversibly inactivated by a removable protecting group, and $CO^{act}$ signifies an activated carboxylic acid moiety, wherein from compound (a-b-c-d-e-f) albicidin is obtained by removal of the protecting groups PGN, PGH and PGA. Alternatively the not activated carboxyl acid moiety a-b-c-COOH may be used instead of the activated carboxyl moiety a-b-c-$CO^{act}$.

In certain embodiments, a compound (a-b-$CO^{act}$):

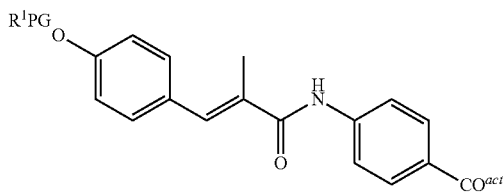

is reacted with a compound (H₂N-c-d-e-f)

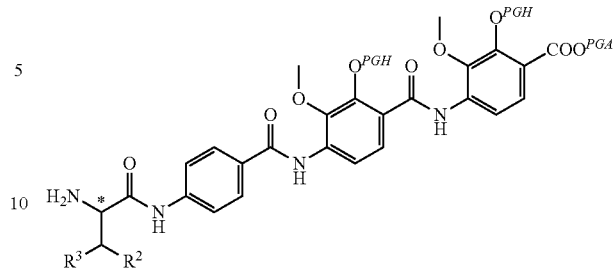

wherein
R¹PG is, for embodiments for which R¹ is H, a hydroxyl protecting group PGH, in other words the $O^{R^1PG}$ moiety can be read as an $O^{PGH}$ moiety, or,
in case of R¹ being CO(NH₂), a —CO($N^{PGN}$) moiety, wherein in particular R¹PG is a hydroxyl protecting group PGH with R¹ being H, yielding a $O^{PGH}$ moiety, and
R³ is H or OCH₃, and
R² is CO($N^{PGN}$) or CN, and
$N^{PGN}$, $COO^{PGA}$ or $O^{PGH}$ signifies an NH₂, COOH or OH moiety reversibly inactivated by a removable protecting group, and $CO^{act}$ signifies an activated carboxylic acid moiety,
wherein from compound (a-b-c-d-e-f) albicidin is obtained by removal of the protecting groups PGN, PGH and PGA. Alternatively the not activated carboxyl acid moiety a-b-COOH may be used instead of the activated carboxyl moiety a-b-$CO^{act}$.

In certain embodiments, compound (a-$CO^{act}$) is reacted with a compound (H₂N-b-c-d-e-f):

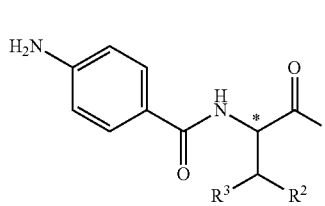

wherein
R¹PG is, for embodiments for which R¹ is H, a hydroxyl protecting group PGH, in other words the $O^{R^1PG}$ moiety can be read as an $O^{PGH}$ moiety, or,
in case of R¹ being CO(NH₂), a —CO($N^{PGN}$) moiety, wherein in particular R¹PG is a hydroxyl protecting group PGH with R¹ being H, yielding a $O^{PGH}$ moiety, and
R³ is H or OCH₃, and
R² is CO($N^{PGN}$) or CN, and
$N^{PGN}$, $COO^{PGA}$ or $O^{PGH}$ signifies an NH₂, COOH or OH moiety reversibly inactivated by a removable protecting group, and $CO^{act}$ signifies an activated carboxylic acid moiety,
wherein from compound (a-b-c-d-e-f) albicidin is obtained by removal of the protecting groups PGN, PGH and PGA as discussed above. Alternatively the not activated carboxyl acid moiety a-COOH may be used instead of the activated carboxyl moiety a-$CO^{act}$.

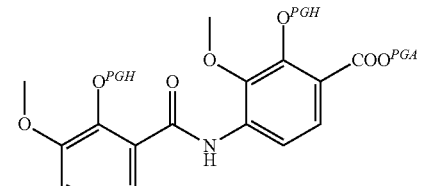

In some embodiments of the synthesis of the invention the peptide coupling steps to arrive at the albicidin backbone can be achieved by using combined building blocks (a-b); (c-d) and (e-f).

In some embodiments, compound (e-$CO^{act}$) is reacted with compound ($H_2N$-f), yielding a compound (e-f):

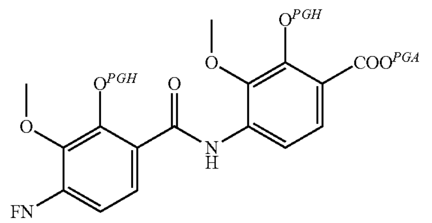

and/or compound (a-$CO^{act}$) is reacted with compound ($H_2N$-b), yielding a compound (a-b):

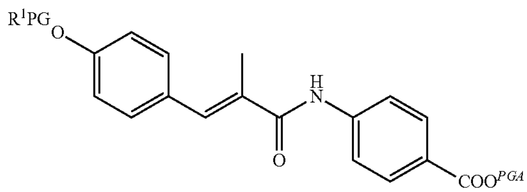

and/or compound (c-$CO^{act}$) is reacted with compound ($H_2N$-d)
yielding a compound (c-d):

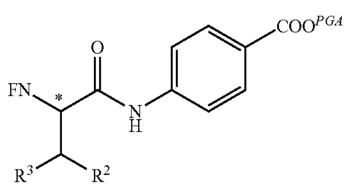

wherein

- $R^1PG$ is, for embodiments for which $R^1$ is H, a hydroxyl protecting group PGH, in other words the $O^{R^1PG}$ moiety can be read as an $O^{PGH}$ moiety, or,
  - in case of $R^1$ being $CO(NH_2)$, a —$CO(N^{PGN})$ moiety, wherein in particular $R^1PG$ is a hydroxyl protecting group PGH with $R^1$ being H, yielding a $O^{PGH}$ moiety, and
- $R^3$ is H or $OCH_3$, and
- $R^2$ is $CO(N^{PGN})$ or CN, and
- $N^{PGN}$, $COO^{PGA}$ or $O^{PGH}$ signifies an $NH_2$, COOH or OH moiety reversibly inactivated by a removable protecting group, and $CO^{act}$ signifies an activated carboxylic acid moiety.

In some embodiments, concerning any step of the synthesis it is possible to use the —COOH building blocks instead of the —$CO^{act}$ building blocks, whereby the —COOH moiety may be activated with a catalytic amount of a proton or a lewis acid, as discussed above.

In some embodiments, the carboxyl protecting group PGA of compound (a-b) is selectively removed, yielding a compound (a-b-COOH):

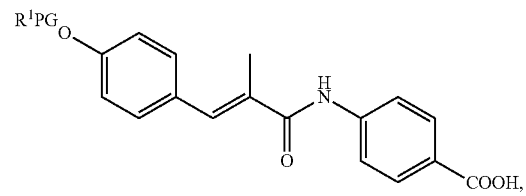 [SMILES: C/C(=C\c1ccc(O)cc1)C(=O)Nc1ccc(C(=O)O)cc1]

and optionally the carboxylic acid moiety of compound (a-b-COOH) is activated, yielding a compound (a-b-$CO^{act}$):

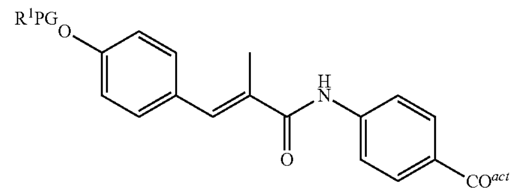

and the carboxyl protecting group of compound (c-d) is selectively removed, yielding a compound (c-d-COOH):

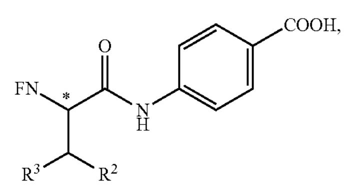

and optionally the carboxylic acid moiety of compound (c-d-COOH) is activated, yielding a compound (c-d-$CO^{act}$):

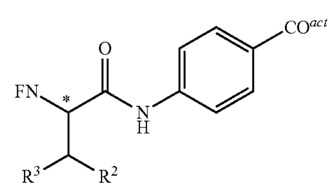

and subsequently compound (c-d-COOH) or compound (c-d-$CO^{act}$) is reacted with ($H_2N$-e-f), yielding a compound (c-d-e-f):

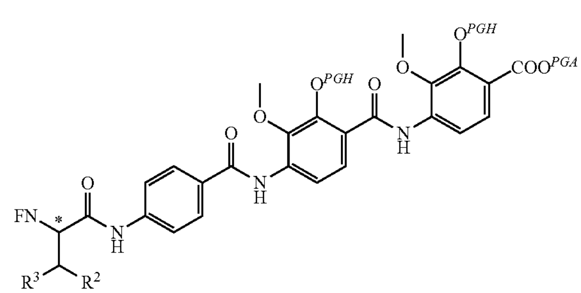

from which the amino-protecting group PGN of FN is selectively removed or the masked functional group M of FN is selectively reduced to —$NH_2$, yielding compound ($H_2N$-c-d-e-f), and (a-b-COOH) or (a-b-$CO^{act}$) is reacted with ($H_2N$-c-d-e-f), yielding compound (a-b-c-d-e-f), from which albicidin is obtained by removal of the protecting groups PGN, PGH and PGA.

In some embodiments, the amino protecting group PGN of compound (c-d) is selectively removed, yielding a compound (H₂N-c-d):

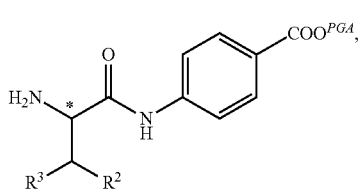

and subsequently, (H₂N-c-d) is reacted with compound (a-b-COOH) or with compound (a-b-CO$^{act}$), yielding a compound (a-b-c-d):

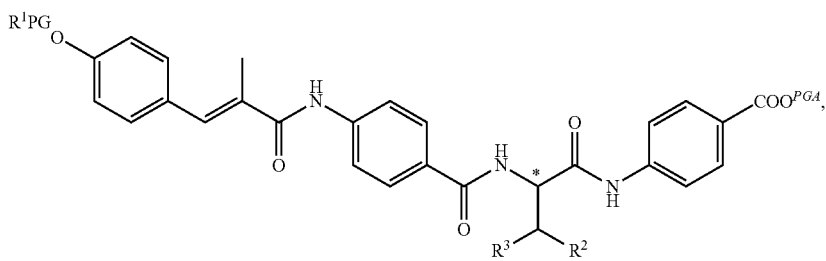

and the carboxyl protecting group PGA of compound (a-b-c-d) is selectively removed, yielding compound (a-b-c-d-COOH):

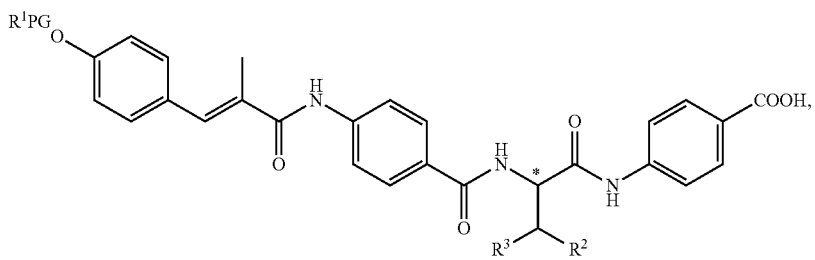

and optionally the carboxylic acid moiety of compound (a-b-c-d-COOH) is activated, yielding compound (a-b-c-d-CO$^{act}$), and subsequently compound (a-b-c-d-COOH) or compound (a-b-c-d-CO$^{act}$) is reacted with compound (H₂N-e-f), yielding compound (a-b-c-d-e-f), from which albicidin is obtained by removal of the protecting groups PGN, PGH and PGA.

In some embodiments, compound (a-b-CO$^{act}$) or compound (a-b-COOH) is reacted with compound (H₂N-c), yielding a compound (a-b-c):

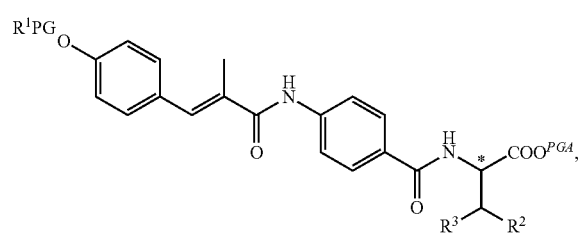

thereafter, the carboxyl protecting group PGA of compound (a-b-c) is selectively removed, yielding a compound (a-b-c-COOH):

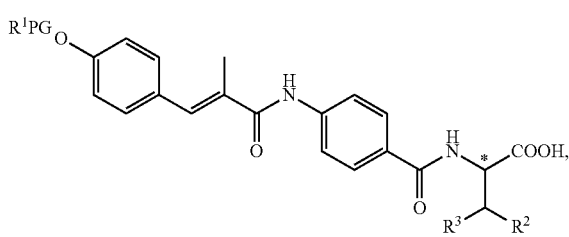

and optionally the carboxylic acid moiety of compound (a-b-c-COOH) is activated, yielding compound (a-b-c-CO$^{act}$), and compound (H₂N-e-f) is reacted with compound (d-COOH) or (d-CO$^{act}$), yielding a compound (d-e-f):

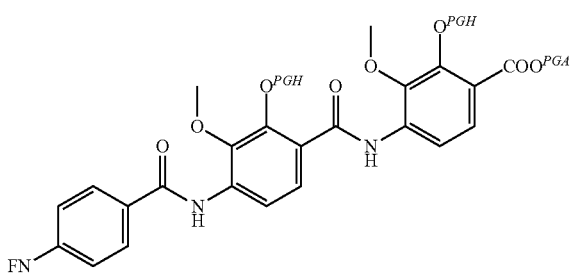

and thereafter, the amino-protecting group PGN of FN of compound (d-e-f) is selectively removed or the masked functional group M of FN of compound (d-e-f) is selectively reduced to —NH$_2$, to render compound (H$_2$N-d-e-f), which is thereafter reacted with compound (a-b-c-COOH) or (a-b-c-CO$^{act}$), yielding compound (a-b-c-d-e-f), from which albicidin is obtained by removal of the protecting groups PGH and PGA.

In some embodiments, compound (H$_2$N-e-f) is reacted with compound (d-CO$^{act}$) or compound (d-COOH), yielding compound (d-e-f), subsequently, the amino-protecting group PGN of FN of compound (d-e-f) is selectively removed or the masked functional group M of FN of compound (d-e-f) is selectively reacted to —NH$_2$, yielding compound (H$_2$N-d-e-f); then compound (H$_2$N-d-e-f) is reacted with compound (c-CO$^{act}$) or compound (c-COOH), yielding compound (c-d-e-f), from which the amino-protecting group PGN is selectively removed, yielding compound (H$_2$N-c-d-e-f), and compound (H$_2$N-c-d-e-f) is reacted with compound (a-b-CO$^{act}$) or compound (a-b-COOH), yielding compound (a-b-c-d-e-f), from which albicidin is obtained by removal of the protecting groups PGN, PGH and PGA.

In some embodiments, compound (H$_2$N-e-f) is further reacted
- with compound (d-COOH) or (d-CO$^{act}$), yielding compound (d-e-f), subsequently, the amino-protecting group PGN of FN of compound (d-e-f) is selectively removed or the masked functional group M of FN of compound (d-e-f) is selectively reacted to —NH$_2$, yielding compound (H$_2$N-d-e-f); then
- compound (H$_2$N-d-e-f) is reacted with compound (c-COOH) or (c-CO$^{act}$), yielding compound (c-d-e-f), from which the amino-protecting group PGN of FN of compound (c-d-e-f) is selectively removed or the masked functional group M of FN of compound (c-d-e-f) is selectively reacted to —NH$_2$, yielding compound (H$_2$N-c-d-e-f), and
- compound (H$_2$N-c-d-e-f) is reacted with compound (a-b-COOH) or (a-b-CO$^{act}$), yielding compound (a-b-c-d-e-f), from which albicidin is obtained by removal of the protecting groups PGN, PGH and PGA.

In some embodiments, compound (b-COOH) or (b-CO$^{act}$) is further reacted
- with compound (H$_2$N-c-d), yielding compound (b-c-d), subsequently, the carboxyl protecting group PGA of compound (b-c-d) is selectively removed, yielding compound (b-c-d-COOH), the carboxylic acid moiety is optionally activated, yielding compound (b-c-d-CO$^{act}$); then
- compound (b-c-d-COOH) or (b-c-d-CO$^{act}$) is further reacted with compound (H$_2$N-e-f), yielding compound (b-c-d-e-f), from which the amino-protecting group PGN of FN of compound (b-c-d-e-f) is selectively removed or the masked functional group M of FN of compound (b-c-d-e-f) is selectively reacted to —NH$_2$, yielding compound (H$_2$N-b-c-d-e-f), and
- compound (H$_2$N-b-c-d-e-f) is reacted with compound (a-COOH) or (a-CO$^{act}$), yielding compound (a-b-c-d- e-f), from which albicidin is obtained by removal of the protecting groups PGN, PGH and PGA.

Alternatively the compound (b-c-d) may be achieved by a reaction of the compound (b-c) with block d in a similar manner.

In some embodiments, compound (FN-c-COOH)

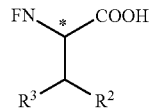

wherein
R$^3$ is H or OCH$_3$, and
R$^2$ is CO(NH$_2$)
FN is N$^{PGN}$ or M, wherein
 M is a masked functional group, in particular M is —NO$_2$ or —N$_3$, further in particular NO$_2$, and wherein, and
N$^{PGN}$ signifies an NH$_2$ moiety reversibly inactivated by a removable protecting group,
is reacted with compound (H$_2$N-d) yielding compound (c-d):

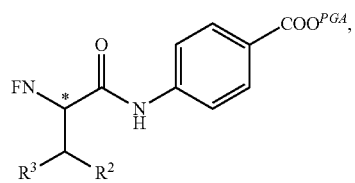

and
compound (c-d) is reacted with compound (H$_2$N-e) yielding compound (c-d-e):

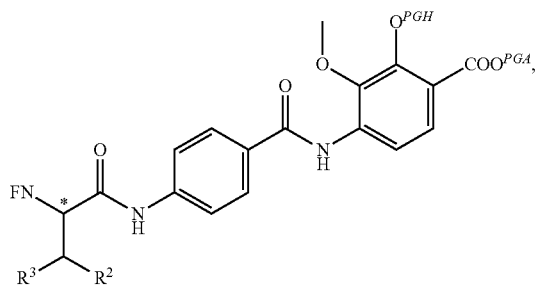

and
compound (c-d-e) is reacted with compound (H$_2$N-f) yielding compound (c-d-e-f)

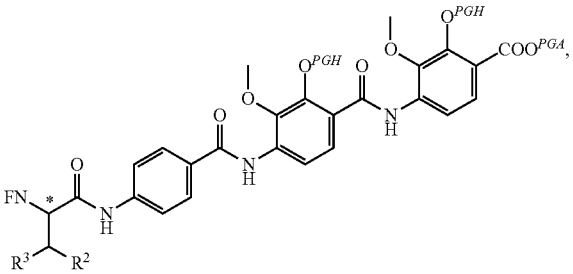

wherein R$^2$ of compound (c-d), (c-d-e) or (c-d-e-f) is, due to the reaction conditions, CN and the protecting group PGA is removed and the COOH-moiety may be activated before the reaction with amino partner, as discussed above. Concerning the combination of the compounds with further building blocks to achieve albicidin (a-b-c-d-e-f) reference is made to the above mentioned methods and combinations.

It is understood that in all the above mentioned embodiments only the activated carboxyl moiety $CO^{act}$ may be used for the reactions of the acid partner with the amino partner.

It is further understood that in all the above mentioned embodiments $R^1PG$ can be a hydroxyl protecting group PGH yielding a $O^{PGH}$ moiety, and, thus, after removal of the protecting group PGH $R_1$ is H.

In some embodiments, the reactions are carried out between −30° C. to 80° C., in particular between 25° C. to 60° C. and further in particular between 25 to 30° C.

In some embodiments, the reactions are carried out between −30° C. to 30° C., in particular between −30° C. and 0° C., in order to suppress racemisation reactions.

In some embodiments, the PGN protecting groups are tert-butyloxycarbonyl (t-Boc), allyloxycarbonyl (Alloc), 9-fluorenylmethoxycarbonyl (Fmoc), para-methoxybenzyl carbamate (Moz) and benzyloxycarbonyl (Z).

In some embodiments, the PGN protecting groups are, in case of a $CO(N^{PGN})$ moiety, in particular for the amide sidechain of asparagine (building block c), 9-Xanthenyl (Xan), Trityl (Trt), 4-Methyltrityl (Mtt), Cyclopropyldimethylcarbinyl (Cpd), 4,4'-Dimethoxybenzhydryl (Mbh), 2,4,6-Trimethoxybenzyl (Tmob).

In some embodiments, the PGH protecting groups are $C_4H_9$ (t-Butyl), para-methoxybenzyl (PMB), benzyl or $CH_2CHCH_2$ (allyl).

In some embodiments, the PGA protecting groups are $C_4H_9$ (t-Butyl), para-methoxybenzyl (PMB), benzyl 9-fluorenylmethyl (Fm) or $CH_2CHCH_2$ (allyl).

In some embodiments, the activated carboxyl moiety is
(O-(7-azabenzotriazol-1-yl)-N,N,N',N'-tetramethyluronium hexafluorophosphate) (HATU) ester, achieved by a coupling with HATU, or
BTC, achieved by a coupling with BTC, or
acyl chloride, achieved by a coupling with $SOCl_2$ or
N,N'-Diisopropylcarbodiimide (DIC) ester, achieved by a coupling with DIC, or
N,N'-Dicyclohexylcarbodiimide (DCC) ester, achieved by a coupling with DCC.

In some embodiments the coupling reactions to the activated carboxyl moiety may be supported by addition of bases selected from (N,N-diisopropylethylamine) (DIEA), N-methylmorpholine (NMM), 4-dimethylaminopyridine (DMAP), triethylamine (TEA), 2,4,6-trimethylpyridin (sym-collidine), pyridine, N,N'-Diisopropylcarbodiimid (DIC), 2,6-di-tert-butyl-4-dimethylaminopyridine (DBDMAP), in particular from N,N-diisopropylethylamine (DIEA) or 2,4,6-Trimethylpyridin (sym-collidine). The addition of bases allows a deprotonation of the carboxylic acid and facilitate the reaction to the respective activated carboxylic acid.

In some embodiments, if an acyl halogenide, in particular an acyl chloride, is used as the activated carboxyl moiety, a base selected from N,N-diisopropylethylamine (DIEA), N-methylmorpholine (NMM), triethylamine (TEA), 4-dimethylaminopyridine (DMAP), 2,4,6-trimethylpyridin (sym-collidine), 2,6-di-tert-butyl-4-dimethylaminopyridine (DB-DMAP), in particular from N,N-diisopropylethylamine) (DIEA), or 2,4,6-trimethylpyridin (sym-collidine), is added in order to prevent a removal of the protecting group due to acidic by-products.

In some embodiments the solvent of the reactions is tetrahydrofuran, dioxane, acetonitrile, tert-butyl methyl ether, dichlormethane, chloroform, 1-methyl-2-pyrrolidinone, N,N-dimethylacetamide (DMA), or dimethylformamide, in particular tetrahydrofuran or dimethylformamide. Other solvents may be applied if necessary.

In the above described synthesis of albicidin of the formula 2 intermediates are used which acan be described by the following formulas:

a. building block a-b:

i. (a-b):

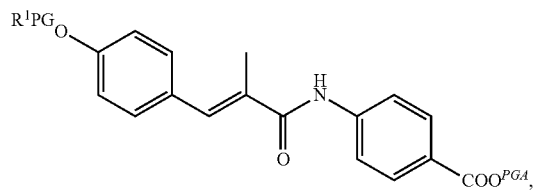

ii. (a-b-COOH):

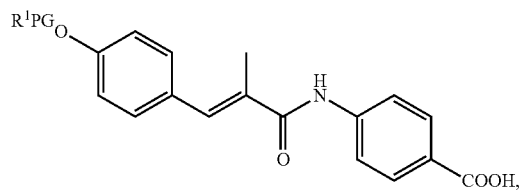

iii. (a-b-$CO^{act}$):

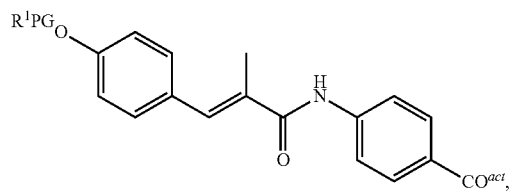

iv. unprotected (a-b):

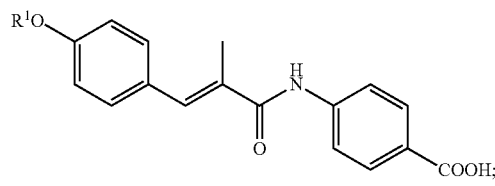

b. building block a-b-c:

i. (a-b-c):

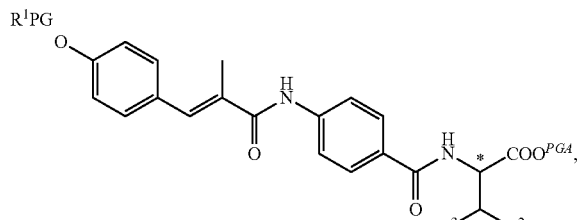

ii. (a-b-c-COOH):

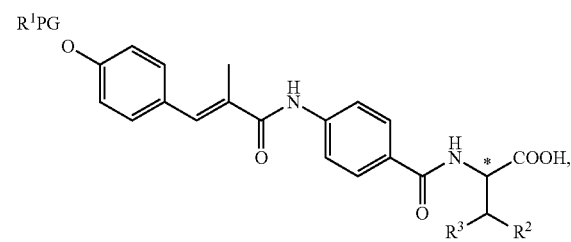

iii. (a-b-c-CO^{act}):
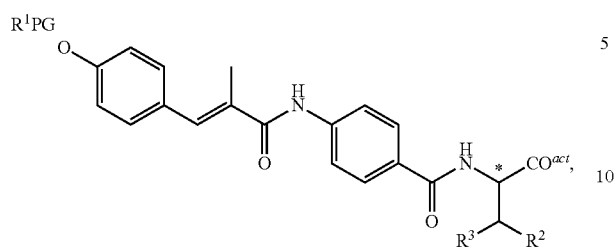
iv. unprotected (a-b-c):
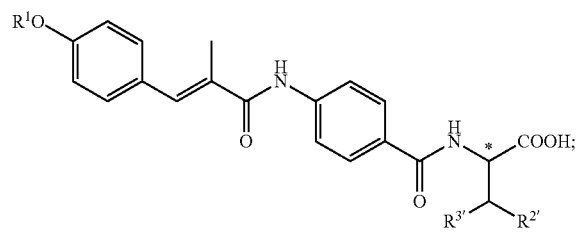
c. building block a-b-c-d:
i. (a-b-c-d):
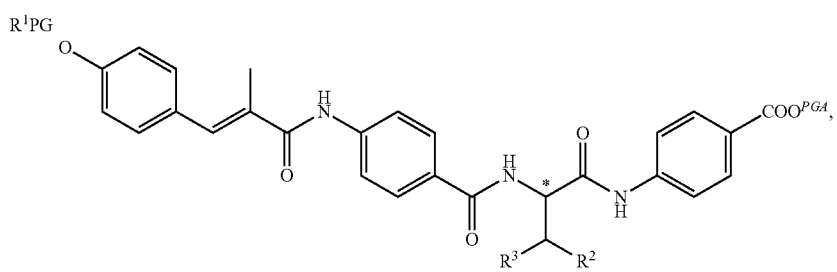
ii. (a-b-c-d-COOH):
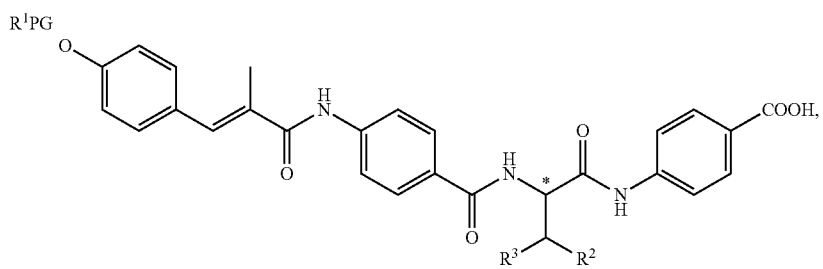
iii. (a-b-c-d-CO^{act}):
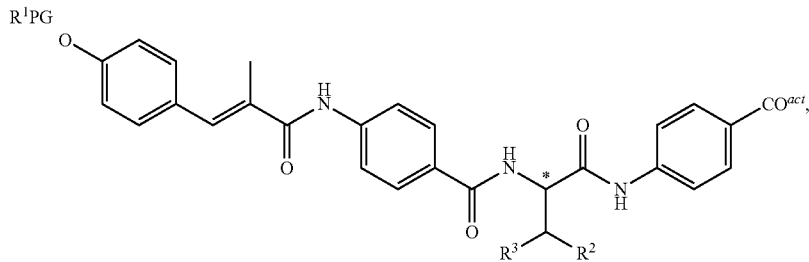
iv. unprotected (a-b-c-d):
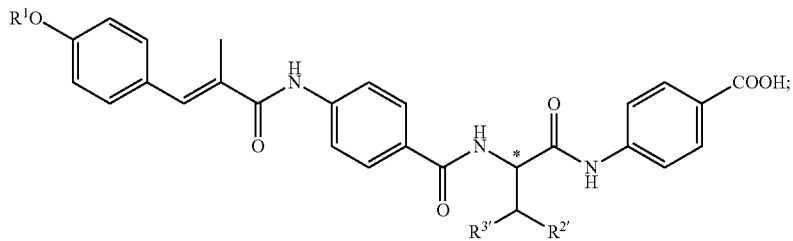

d. building block a-b-c-d-e:
i. (a-b-c-d-e):
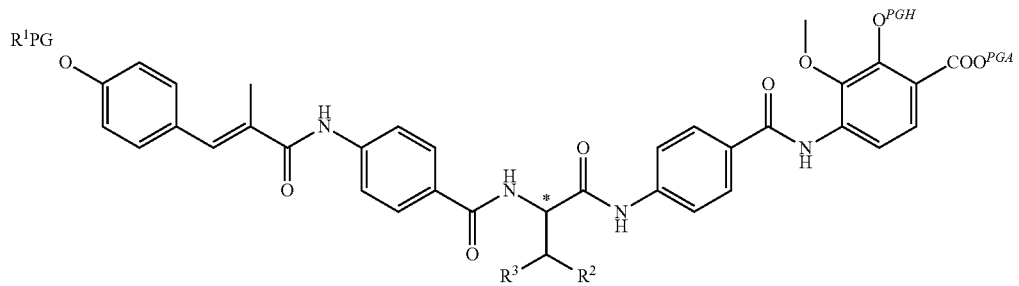
ii. (a-b-c-d-e-COOH):
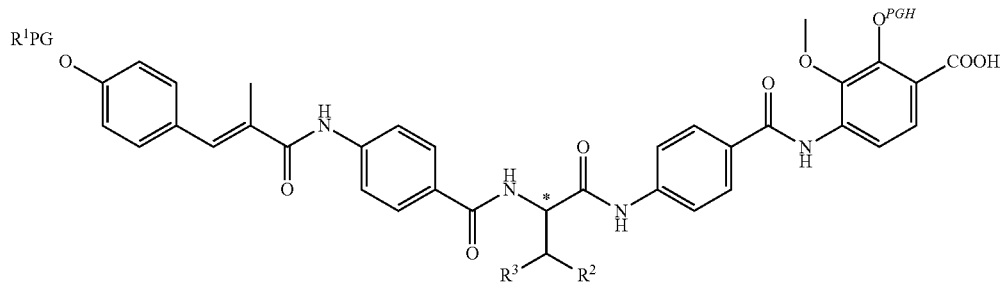
iii. (a-b-c-d-e-CO$^{act}$):
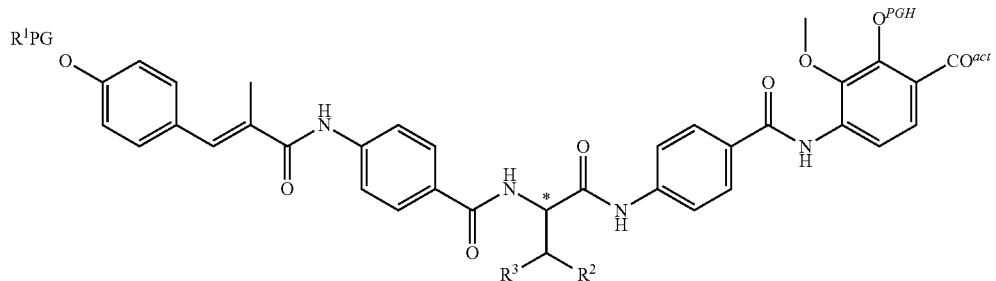
iv. unprotected (a-b-c-d-e):
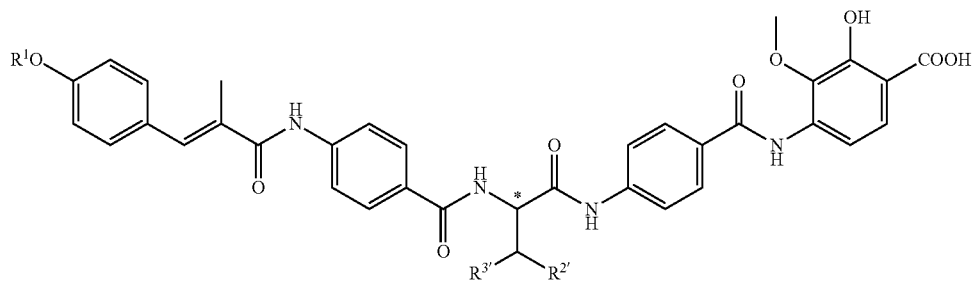
e. a-b-c-d-e-f:
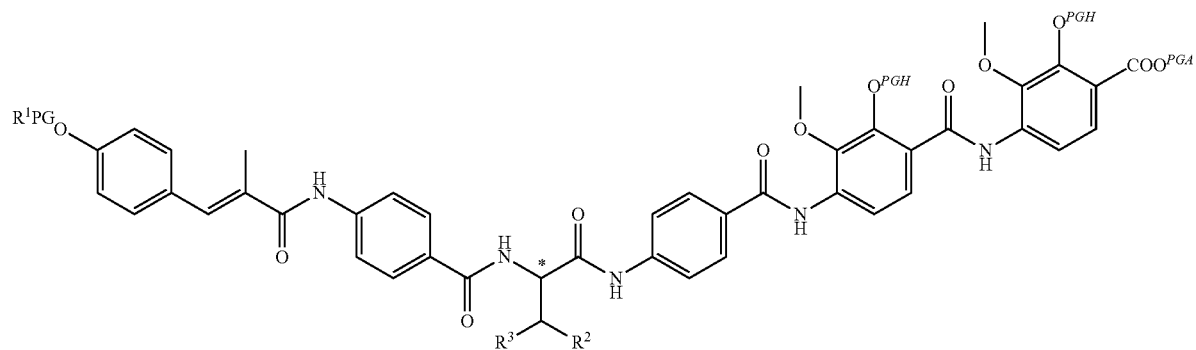

f. building block e-f:
i. (e-f):
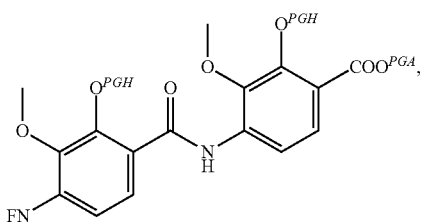
ii. (e-f-COOH):
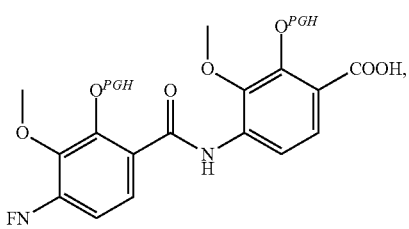
iii. (H₂N-e-f):
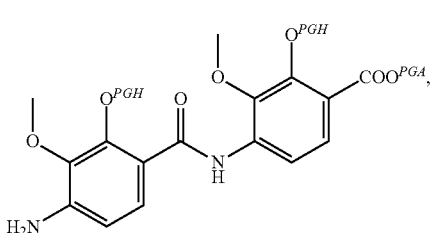
iv. 4-[(4-amino-2-hydroxy-3-methoxy-benzoyl)amino]-2-hydroxy-3-methoxy-benzoic acid (unprotected (e-f))
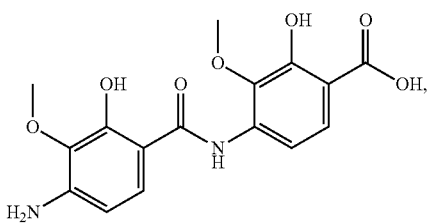
g. building block d-e-f:
i. (d-e-f):
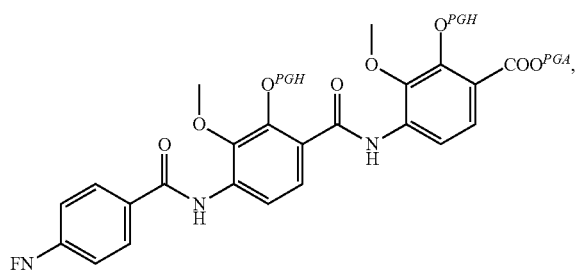
ii. (H₂N-d-e-f):
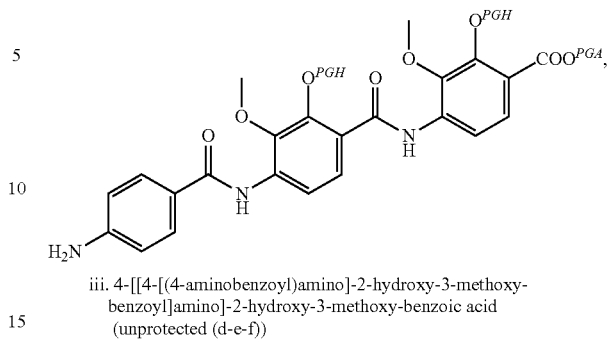
iii. 4-[[4-[(4-aminobenzoyl)amino]-2-hydroxy-3-methoxy-benzoyl]amino]-2-hydroxy-3-methoxy-benzoic acid (unprotected (d-e-f))
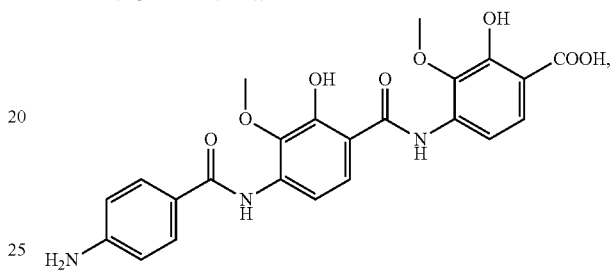
h. building block c-d-e-f:
i. (c-d-e-f):
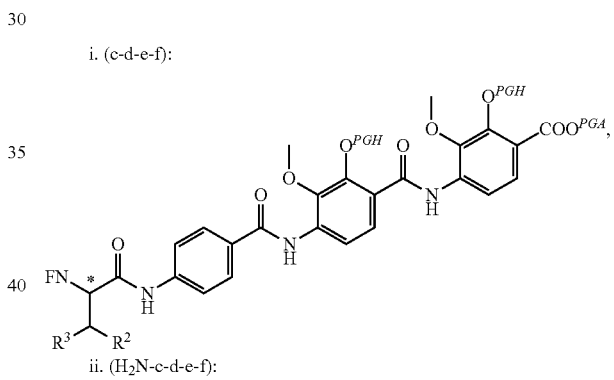
ii. (H₂N-c-d-e-f):
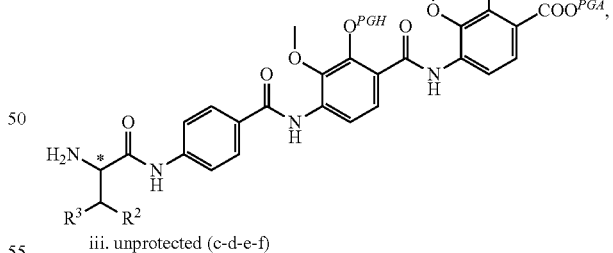
iii. unprotected (c-d-e-f)
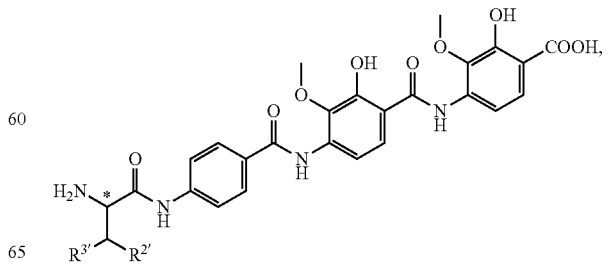

i. building block b-c-d-e-f:
i. (b-c-d-e-f):
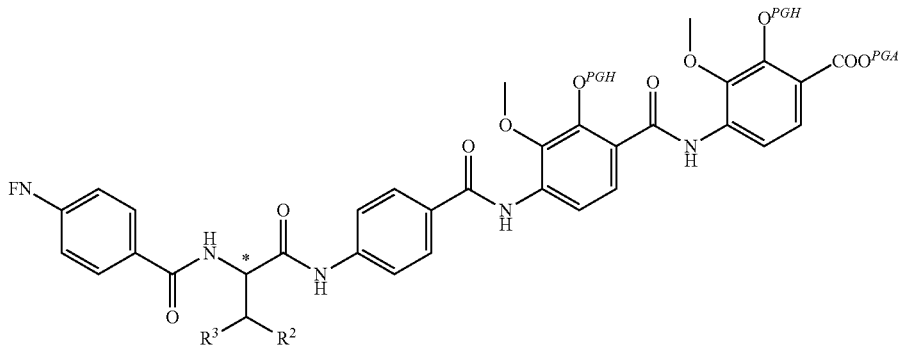
ii. (H₂N-b-c-d-e-f):
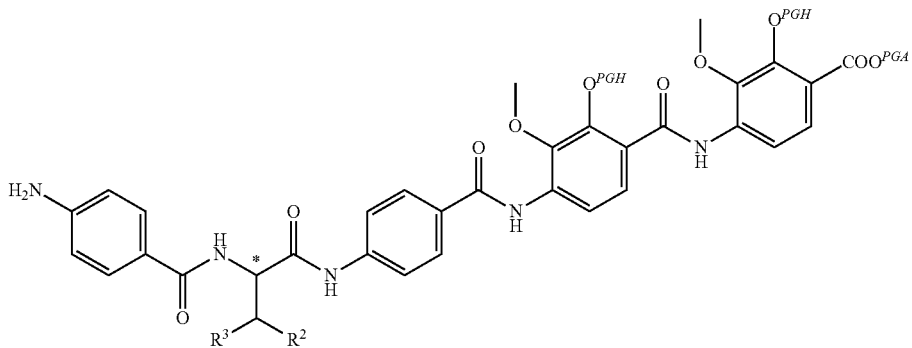
iii. unprotected b-c-d-e-f:
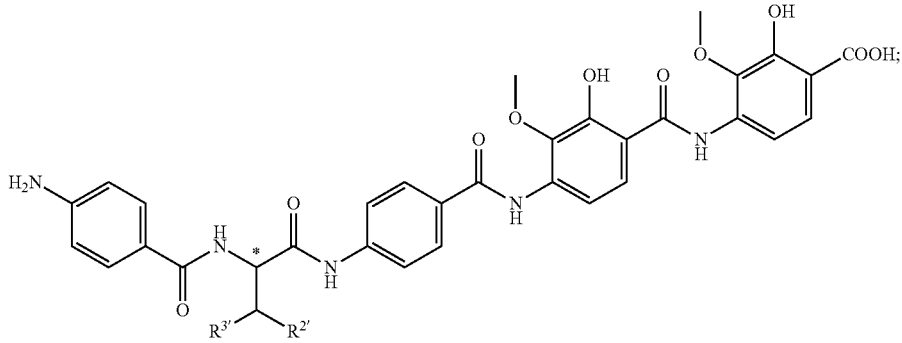
j. building block b-c:
i. (b-c):
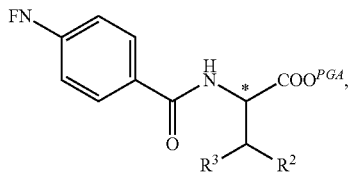
ii. (b-c-COOH):
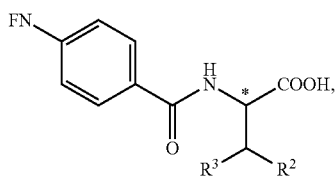
iii. (b-c-CO$^{act}$):
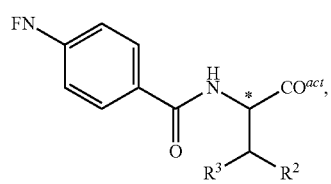
iv. (H₂N-b-c):
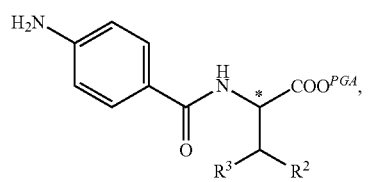

v. unprotected (b-c):
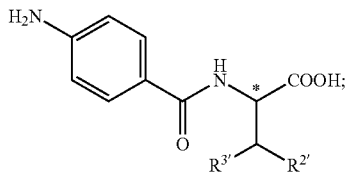
k. building block b-c-d:
i. (b-c-d):
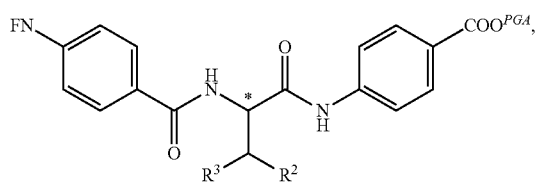
ii. (b-c-d-COOH):
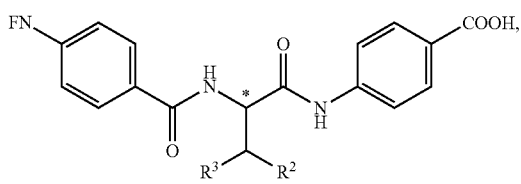
iii. (b-c-d-CO$^{act}$):
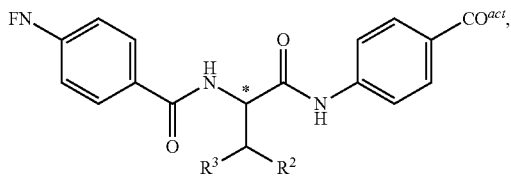
iv. (H$_2$N-b-c-d):
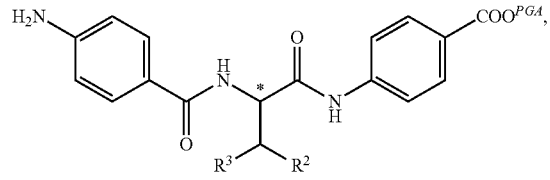
v. unprotected (b-c-d):
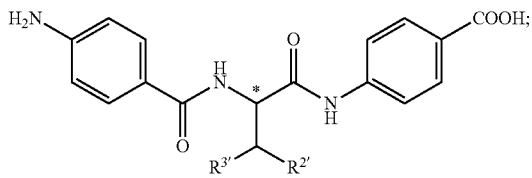
l. building block b-c-d-e:
i. (b-c-d-e):
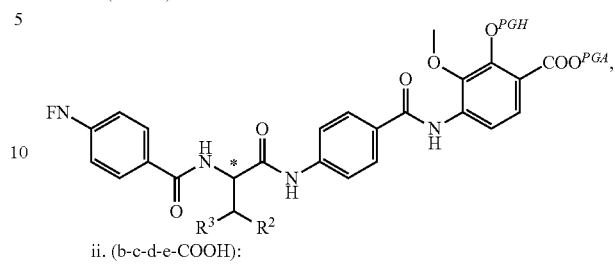
ii. (b-c-d-e-COOH):
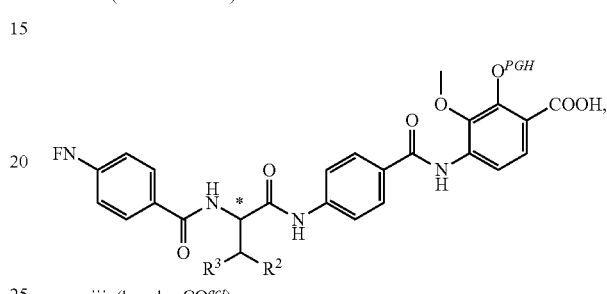
iii. (b-c-d-e-CO$^{act}$):
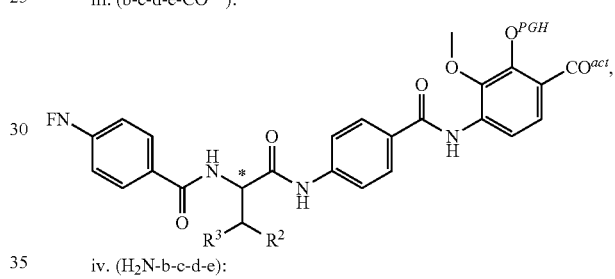
iv. (H$_2$N-b-c-d-e):
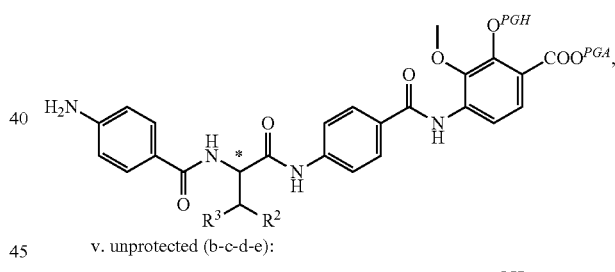
v. unprotected (b-c-d-e):
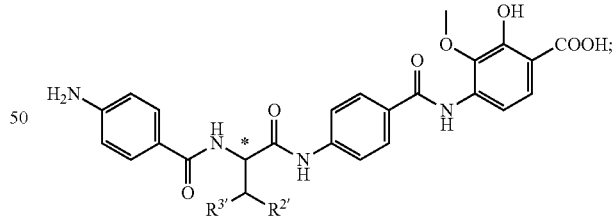
m. building block c-d:
i. (c-d):
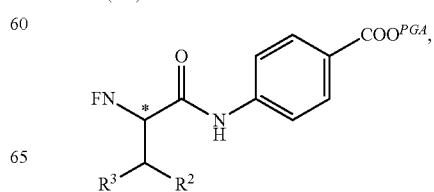

337
-continued ii. (c-d-COOH):

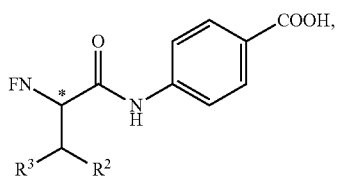

iii. (c-d-CO$^{act}$):

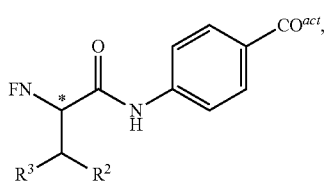

iv. (H$_2$N-c-d):

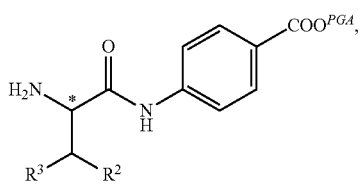

v. unprotected (c-d)

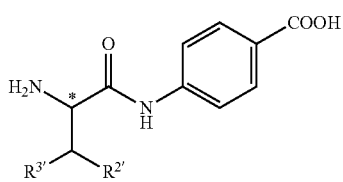

n. building block c-d-e:

i. (c-d-e):

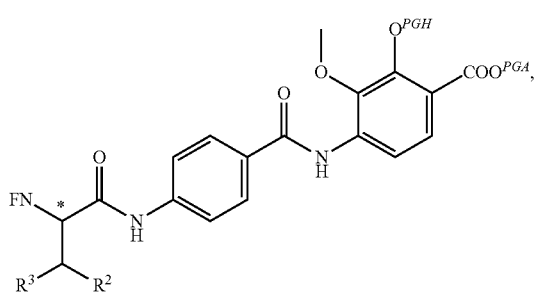

ii. (c-d-e-COOH):

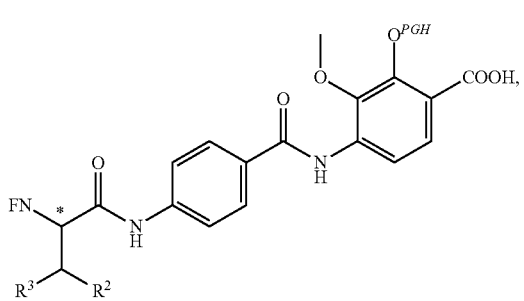

338
-continued iii. (c-d-e-CO$^{act}$):

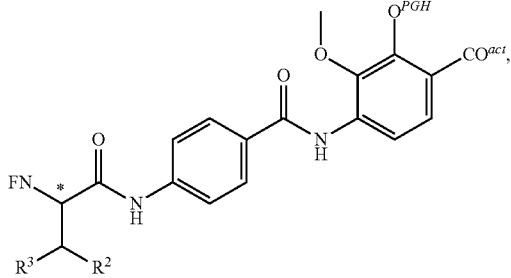

iv. (H$_2$N-c-d-e):

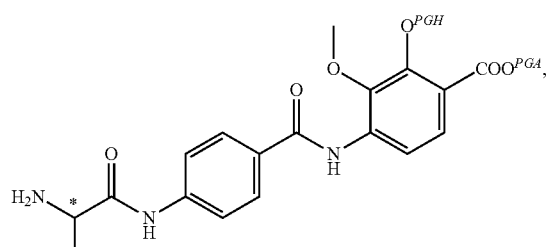

v. unprotected (c-d-e):

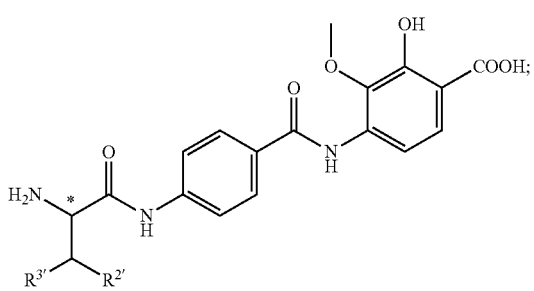

wherein:
R$^1$ is H or CO(NH$_2$),
R$^3$ or R$^{3'}$ is H or OCH$_3$
R$^{2'}$ is CO(NH$_2$) or CN, and wherein
R$^1$PG is,
in case of R$^1$ being H, a hydroxyl protecting group PGH yielding a O$^{PGH}$ moiety, or,
in case of R$^1$ being CO(NH$_2$), a —CO(N$^{PGN}$) moiety, and
R$^2$ is CO(N$^{PGN}$) or CN,
FN is N$^{PGN}$ or M, wherein in particular FN is N$^{PGN}$, wherein
M is a masked functional group, and wherein,
N$^{PGN}$, COO$^{PGA}$ or O$^{PGH}$ signifies an NH$_2$, COOH or OH moiety reversibly inactivated by a removable protecting group, and CO$^{act}$ signifies an activated carboxylic acid moiety, wherein
each PGH independently of any other PGH is a hydroxyl protecting group selected from CH$_2$CHCH$_2$ (allyl), THP (tetrahydropyranyl), SiR'$_3$ (trialkylsilicon), C$_4$H$_9$ (t-Butyl), CH$_2$C$_6$H$_5$ (benzyl), H$_3$CCO (acetyl), CH$_2$C$_6$H$_4$OCH$_3$ (4-methoxybenzyl) or C$_{19}$H$_{15}$ (Triphenylmethyl),
with each R' being independently from any other R' a C$_1$ to C$_4$ alkyl
each PGA independently of any other PGA is a carboxylic protecting group selected from CH$_2$CHCH$_2$ (allyl), THP (tetrahydropyranyl), SiR'3 (trialkylsilicon), or C$_4$H$_9$ (t-Butyl), CH$_2$C$_6$H$_5$ (benzyl), H$_3$CCO (acetyl), CH₂C₆H₄OCH₃ (4-methoxybenzyl) or C₁₉H₁₅ (Triphenylmethyl),
with each R' being independently from any other R' a $C_1$ to $C_4$ alkyl each PGN independently of any other PGN is an amino protecting group selected from t-Butyloxycarbonyl (Boc), (CO)OCH₂C₆H₅ (benzyloxycarbonyl), (CO) OCH₂C₆H₄OCH₃ (4- methoxybenzyloxycarbonyl) or Allyloxycarbonyl (Alloc), M is —NO₂ or —N₃, wherein M is in particular NO₂ each $CO^{act}$ independently from any other $CO^{act}$ is acyl fluoride, acyl chloride, benzotriazole esters or carbodiimide esters, generated by use of the carboxylic acid and coupling agents such as Benzotriazolyloxytris-(dimethylamino)-phosphonium hexafluorophosphate (BOB), Benzotriazol-1-yl-oxy-tripyrrolidino-phosphonium hexafluorophosphate (pyBOP), N,N,N',N'-Tetramethyl-O-(1H-benzo-triazol-1-yl) uronium hexafluorophosphate (HBTU), (O-(7-azabenzotriazol-1-yl)-N,N,N',N'-tetramethyluronium hexafluoro-phosphate) (HATU), N,N-Di-cyclohexylcarbodiimide (DCC), N,N'-Di-isopropylcarbodiimid (DIC), 1-Ethyl-3-(3-dimethylaminopropyl) carbodiimide (EDC).

In some embodiments, concerning the above mentioned intermediates, $R^1$ is H, $R^3$ or $R^{3'}$ is H or OCH₃

$R^{2'}$ is CO(NH₂) or CN, in particular $R^{2'}$ is CN, and wherein $R^1 PG$ is a hydroxyl protecting group PGH yielding a $O^{PGH}$ moiety, and $R^2$ is —CO(N)$^{PGN}$ or CN, in particular $R^2$ is CN FN is $N^{PGN}$ or M, wherein in particular FN is $N^{PGN}$, wherein M is a masked functional group, and wherein, $N^{PGN}$, $COO^{PGA}$ or $O^{PGH}$ signifies an NH₂, COOH or OH moiety reversibly inactivated by a removable protecting group, and $CO^{act}$ signifies an activated carboxylic acid moiety, wherein each PGH independently of any other PGH is a hydroxyl protecting group selected from CH₂CHCH₂ (allyl), THP (tetrahydropyranyl), SiR'₃ (trialkylsilicon), C₄H₉ (t-Butyl), CH₂C₆H₅ (benzyl), H₃CCO (acetyl) or C₁₉H₁₅ (Triphenylmethyl),
with each R' being independently from any other R' a $C_1$ to $C_4$ alkyl each PGA independently of any other PGA is a carboxylic protecting group selected from CH₂CHCH₂ (allyl), THP (tetrahydropyranyl), SiR'₃ (trialkylsilicon), or C₄H₉ (t-Butyl), CH₂C₆H₅ (benzyl) or C₁₉H₁₅ (Triphenylmethyl),
with each R' being independently from any other R' a $C_1$ to $C_4$ alkyl each PGN independently of any other PGN is a amino protecting group selected from t-Butyloxycarbonyl (Boc), (CO)OCH₂C₆H₅ (benzyloxycarbonyl) or Allyloxycarbonyl (Alloc), M is —NO₂ or —N₃, wherein M is in particular NO₂ each $CO^{act}$ independently from any other $CO^{act}$ is acyl fluorid, acyl chloride, benzotriazole esters or carbodiimide esters, generated by use of the carboxylic acid and coupling agents such as Benzotriazolyloxytris-(dimethylamino)-phosphonium hexafluorophosphat (BOB), Benzotriazol-1-yl-oxy-tripyrrolidino-phosphonium hexafluorophosphate (pyBOP), N,N,N',N'-Tetramethyl-O-(1H-benzo-triazol-1-yl) uronium hexafluorophosphate (HBTU), (O-(7-azabenzotriazol-1-yl)-N,N,N',N'-tetramethyluronium hexafluoro-phosphate) (HATU), N,N'-Dicyclohexylcarbodiimide (DCC), N,N'-Diisopropylcarbodiimide (DIC), 1-Ethyl-3-(3-dimethylaminopropyl) carbodiimide (EDC).

Wherever alternatives for single separable features such as, for example, a moiety $R^1$ or $R^{2'}$ or $R^{3'}$ a medical indication specifying a particular pathogen or a particular synthetic route are laid out herein as "embodiments", it is to be understood that such alternatives may be combined freely to form discrete embodiments of the invention disclosed herein.

Scheme 14 depicts a general reaction pathway to the compound beta albicidin from the compound (c-d) over (b-c-d) to compound (b-c-d-e-f) and the unprotected (a-b-c-d-e-f).

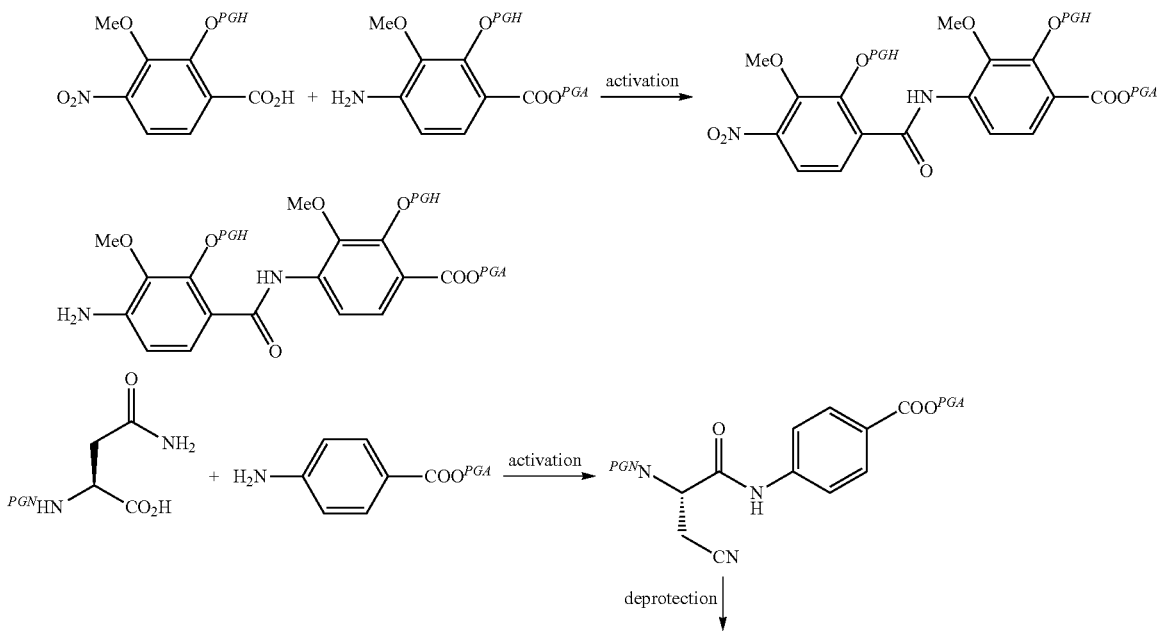

-continued
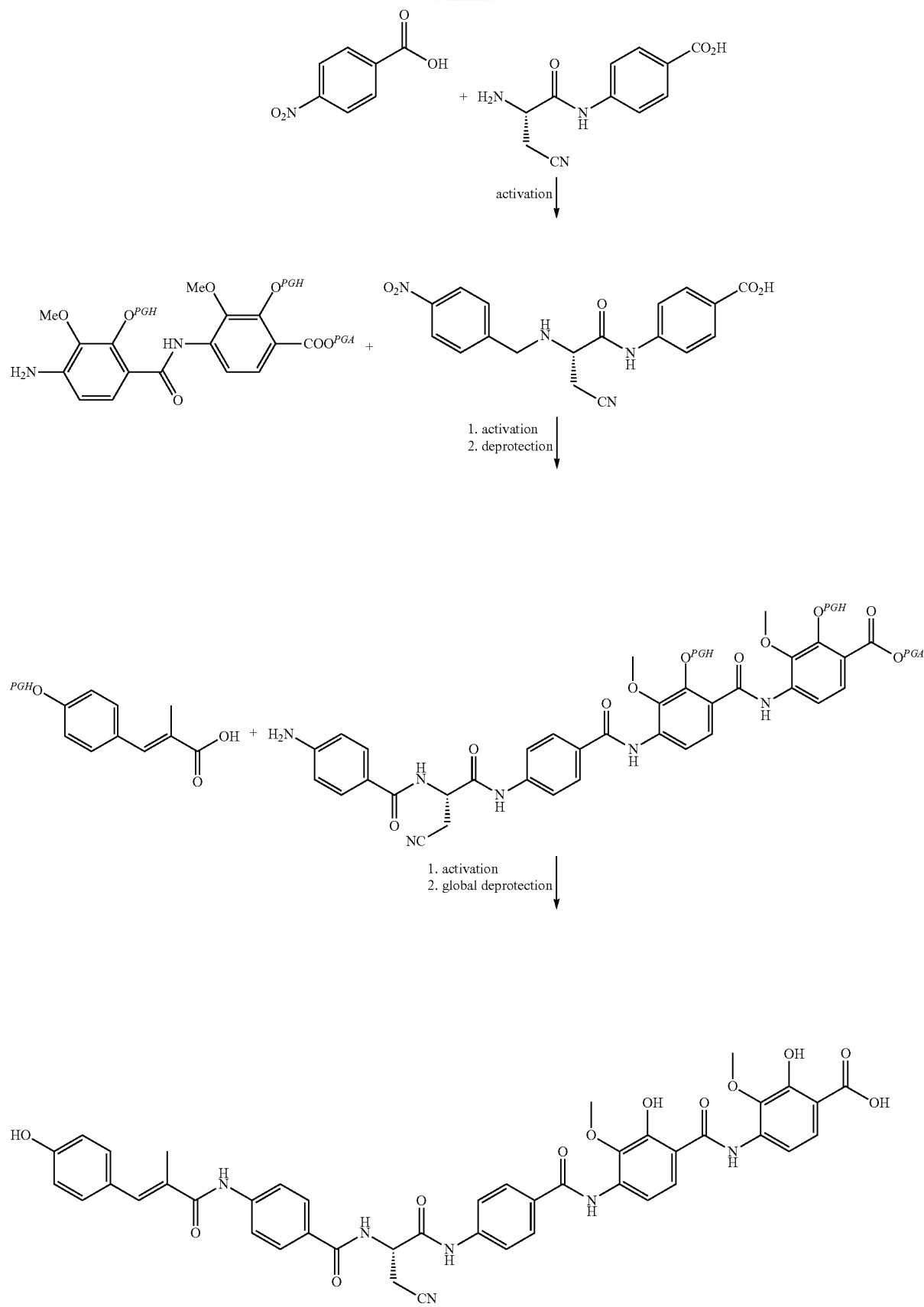

Alternatively, instead of using a reaction between (FN-c-COOH) and (H$_2$N-d) a reaction between (C—COOH) respectively (c-CO$^{act}$) and (H$_2$N-d) may be applied, wherein the CO(NH$_2$) moiety of R$^2$ of building block c is protected (CO)N$^{PGN}$.
Scheme 15 depicts a reaction pathway to the compound (b-c-d) and R$^{2\prime}$ of compound (b-c-d) being CN.
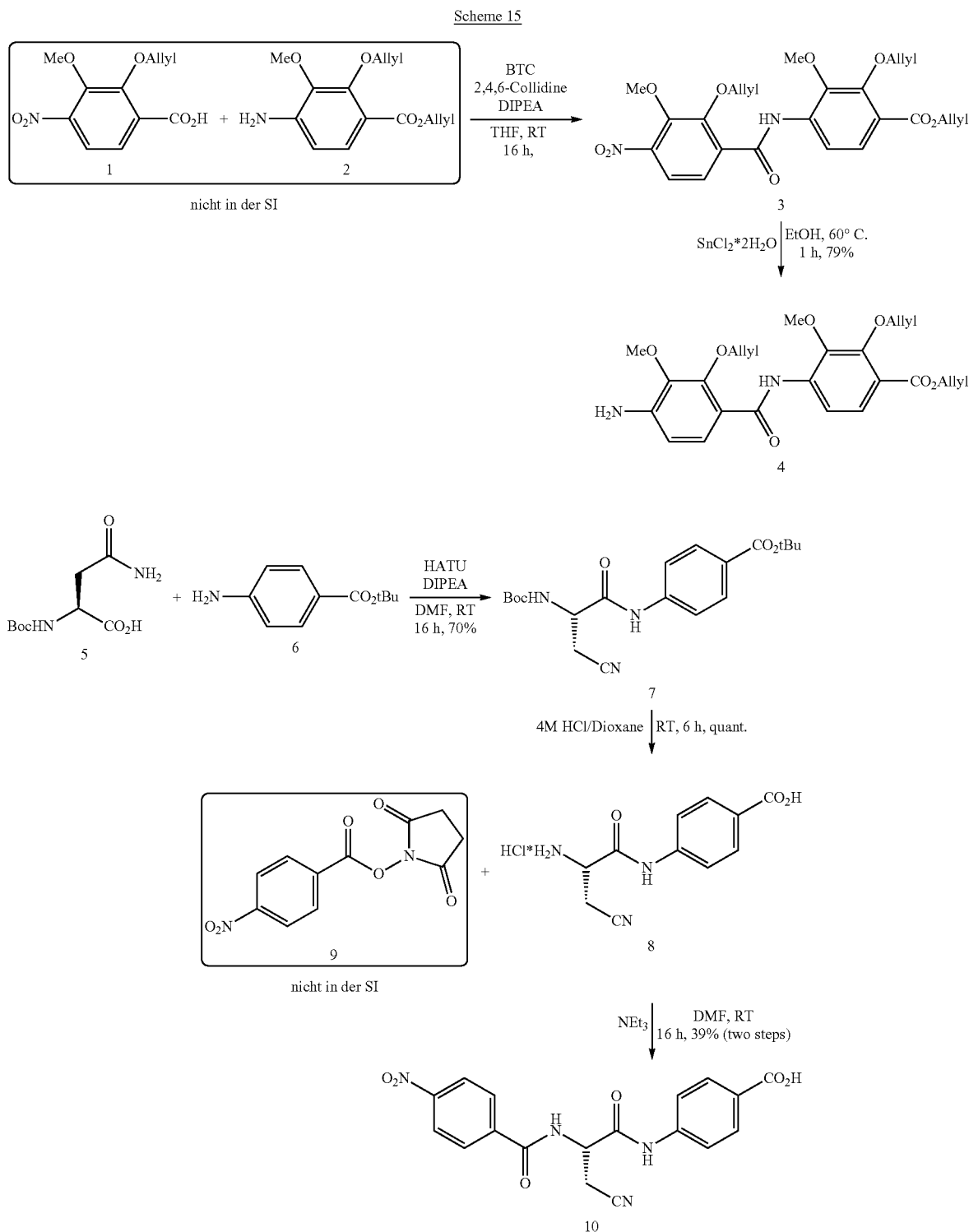

Scheme 16 depicts a reaction pathway to beta-Albicidin from the compound (b-c-d) over the compound (b-c-d-e-f) to the unprotected compound (a-b-c-d-e-f).
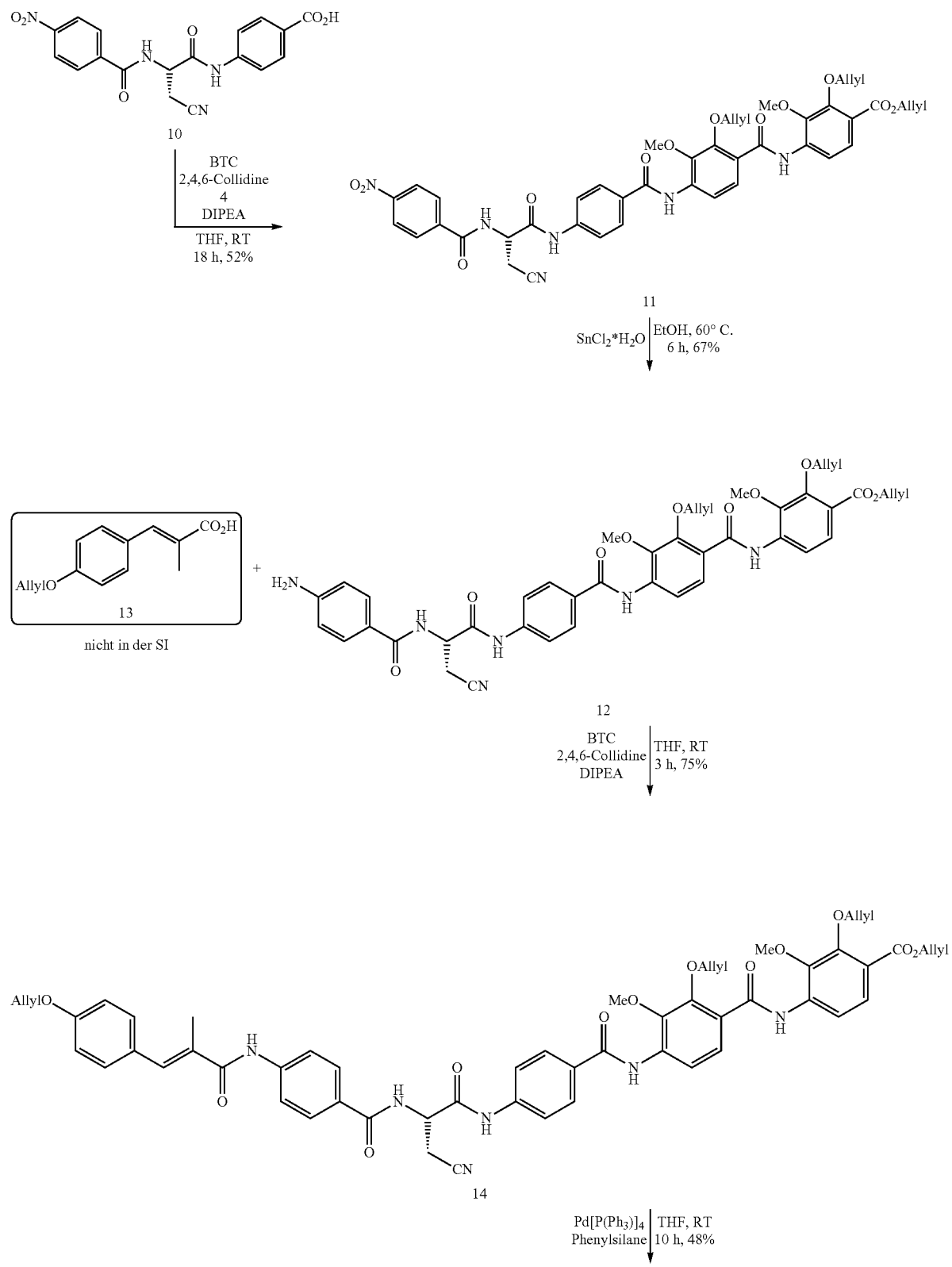

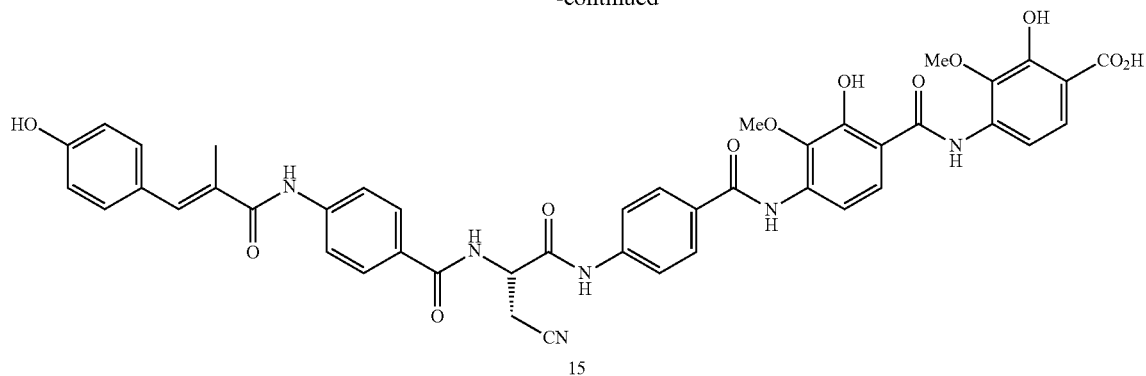
15
Scheme 17 depicts a reaction pathway to beta-Albicidin from the compound (d-e) over the compound (d-e-f), (c-d-e-f) to the unprotected compound (a-b-c-d-e-f).
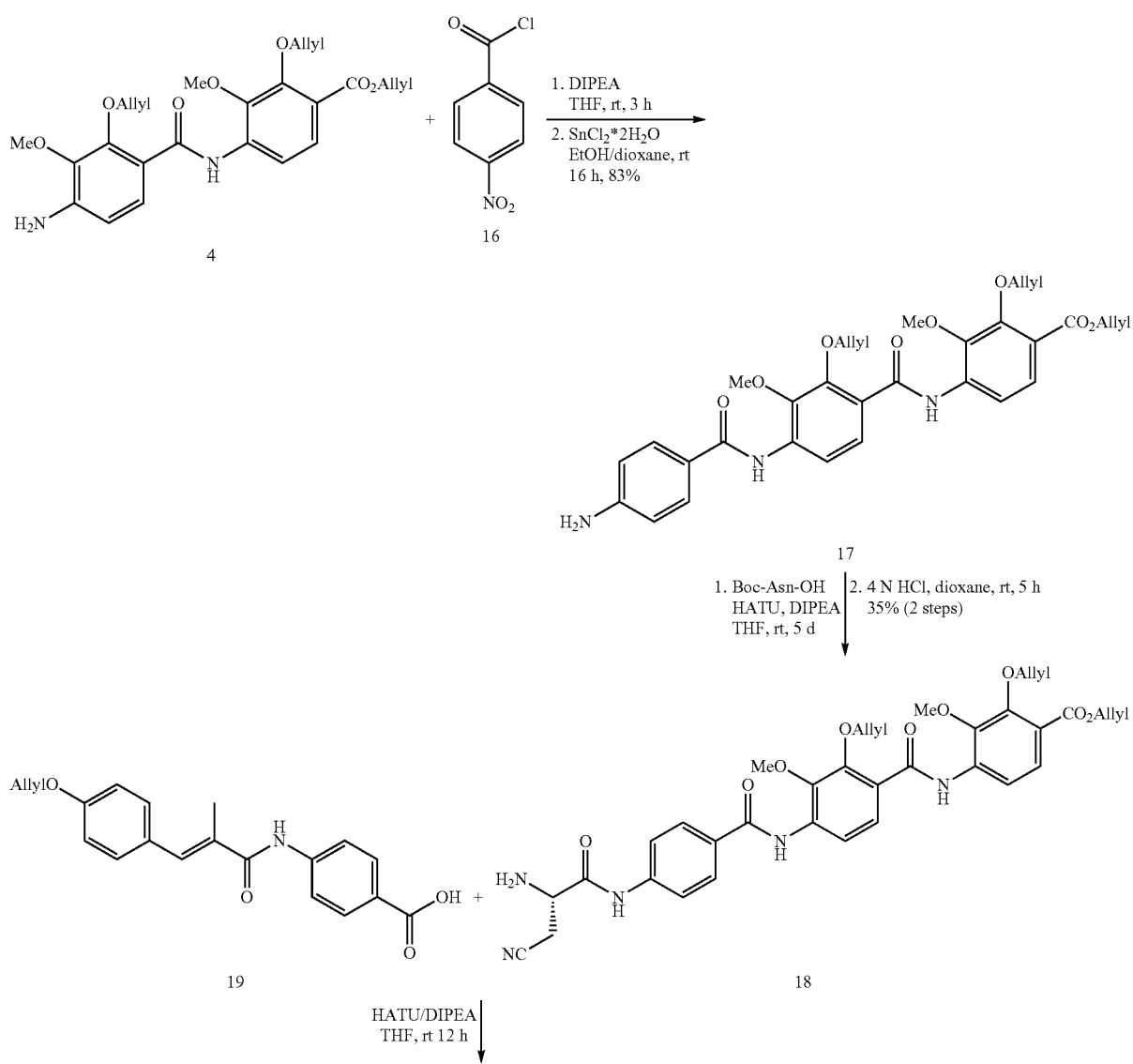

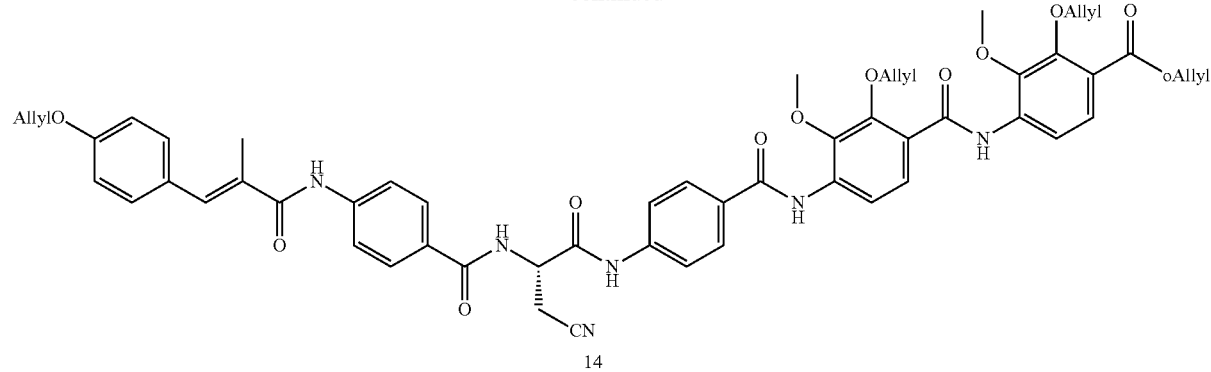
14
It is understood that the compound Carbamoyl-Albicidin can be produced according to a similar reactions pathway as depicted in schemes 14 to 17, whereby the CO(NH$_2$) moiety of building block a is protected ((CO)N$^{PGN}$) until the global deprotection.
Scheme 18
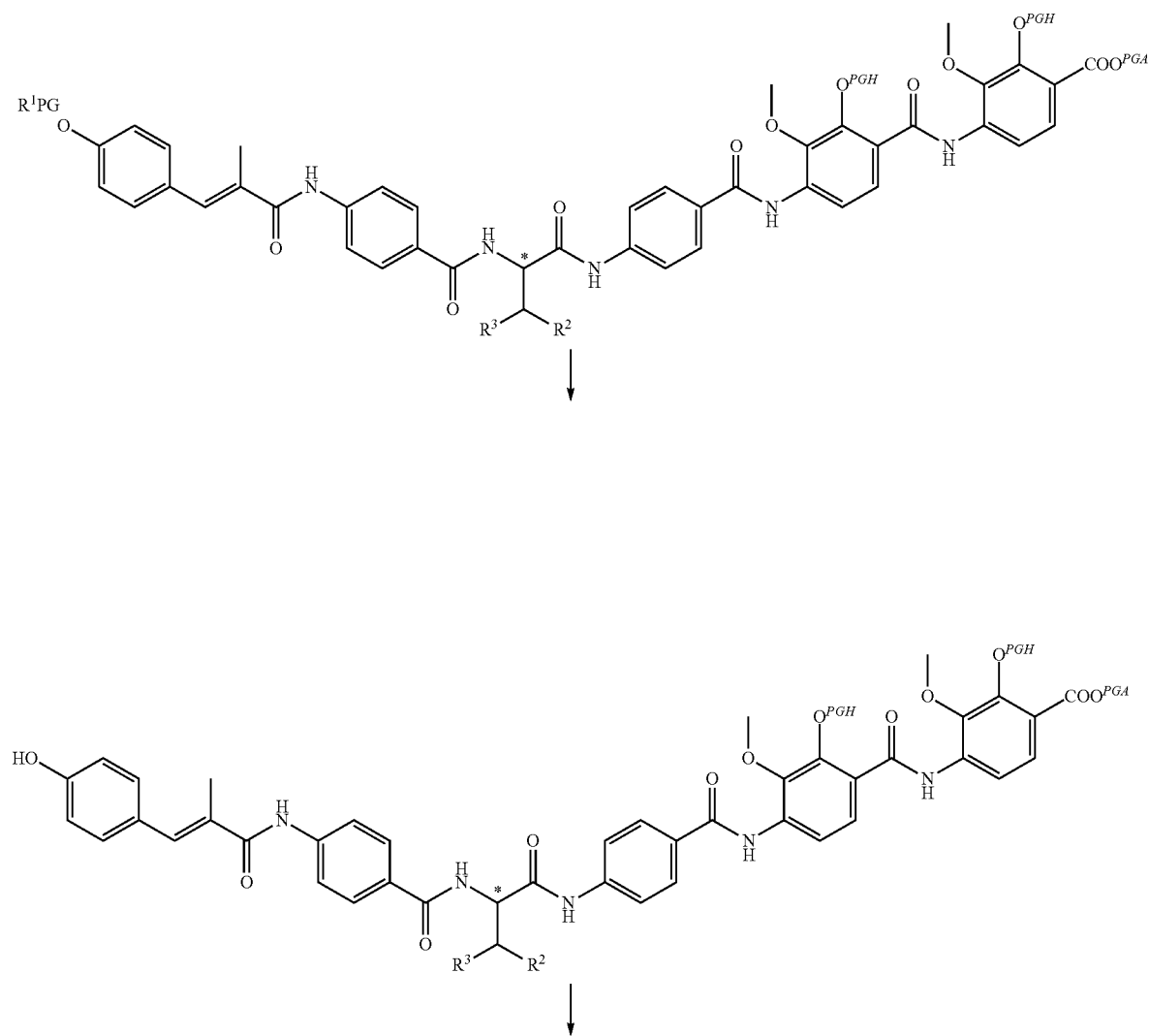

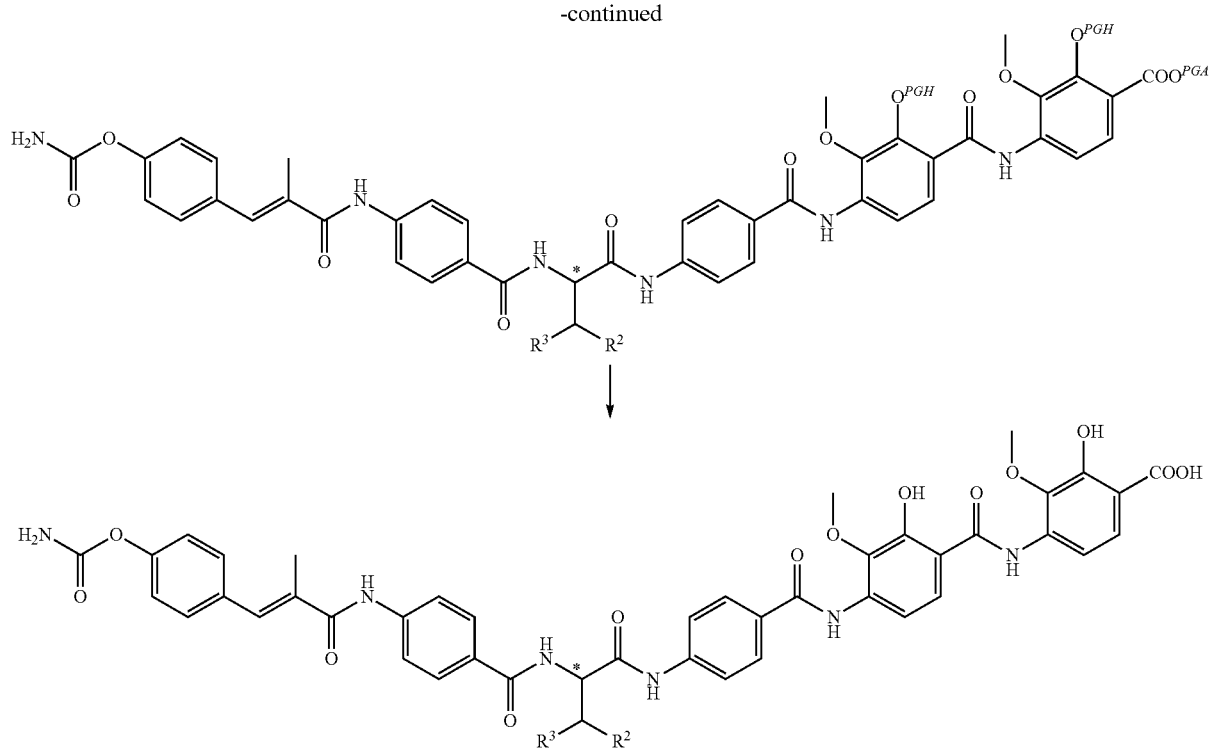

Furthermore, the compound Asn-Albicidin can be produced according to a similar reactions pathway as depicted in schemes 14 to 17, by using a reaction between (C—COOH) respectively (c-CO$^{act}$) and (H$_2$N-d), wherein the CO(NH$_2$) moiety of R$^2$ of building block c is protected (CO)N$^{PGN}$. The same applies to the compound Carbamoyl-Asn-Albicidin, whereby additionally the CO(NH$_2$) moiety of building block a is protected ((CO)N$^{PGN}$) until the global deprotection.

It is understood that the compounds Asn-Albicidin, Carbamoyl-Albicidin, Carbamoyl-Asn-Albicidin, beta-OMe-Albicidin, Asn-OMe-Albicidin, Carbamoyl-OMe-Albicidin or Carbamoyl-OMe-Asn-Albicidin are producible according to a similar pathway as depicted in the schemes 14 to 17, whereby the L building block c comprises the respective substituents R$^1$, R$^2$ and R$^3$.

It is further understood that the compounds Enantio-beta-Albicidin, Enantio-Asn-Albicidin, Enantio-Carbamoyl-Albicidin, Enantio-Carbamoyl-Asn-Albicidin, Enantio-beta-OMe-Albicidin, Enantio-Asn-OMe-Albicidin, Enantio-Carbamoyl-OMe-Albicidin or Enantio-OMe-Carbamoyl-Asn-Albicidin are producible according to a similar pathway as depicted in the schemes 14 to 17, whereby instead of a L building block c moiety a D building block c moiety is used or generated.

These schemes are only exemplary. Different protecting groups, activations, deprotection and combinations of the respective building blocks may be used. Reference is made in particular to the detailed description and specifically mentioned reagents hereinbefore and hereinafter.

It is further possible to transform one of the above mentioned albicidin compounds (or the respective intermediates) in another. For example is it possible to remove selectively the PGH protecting group of the building block a of the compound (a-b-c-d-e-f) and convert the OH-moiety in a carbamoyl-moiety, wherein subsequently the, e.g. Pd-labile, remaining protecting groups will be removed afterwards yielding another albicidin compound (conversion of e.g. beta-Albicidin to Carbamoyl-Albicidin; see scheme 5). Alternatively the beta-Albacidin may be converted to the Asn-albicidin, as described below. Further conversions are also possible and are part of the invention.

Synthesis of Asn-Albicidin from Albicidin

Albicidin (1.2 mg) is dissolved in 0.5 mL THF under argon atmosphere at room temperature 21° C. Then one equivalent of an aqueous solution of LiOH (1 mg/mL) is slowly added via a syringe pump. The resulting suspension is stirred at room temperature for 20 min. Stirring is continued for 3 h at room temperature. the process of hydrolysis is controlled by ESI-mass spectrometry. The organic solvent is removed under reduced pressure and EtOAc is added. The mixture is washed successively with saturated NaHCO$_3$, water and brine. The organic solvent is dried over Na$_2$SO$_4$, filtered and removed under reduced pressure. The product is purified by column chromatography.

Further possible synthetic routes for albicidin are depict in the following schemes 19 and 24.

Scheme 19

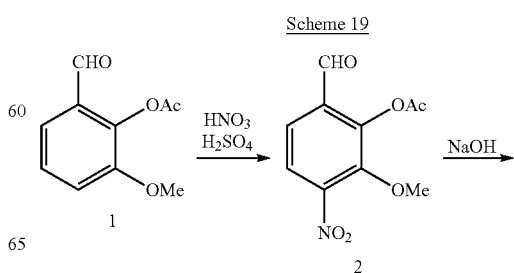

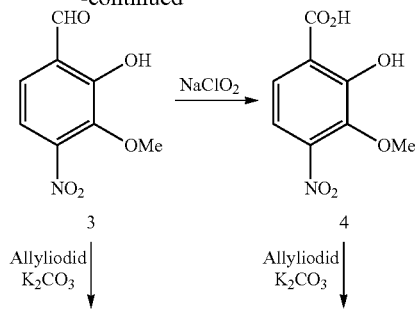
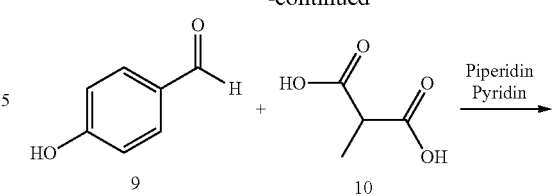
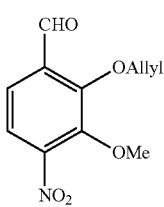
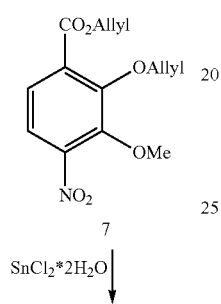
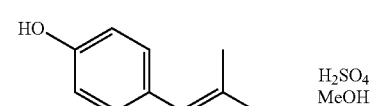
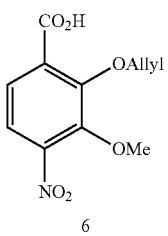
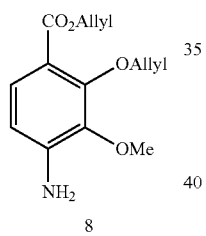
Scheme 20
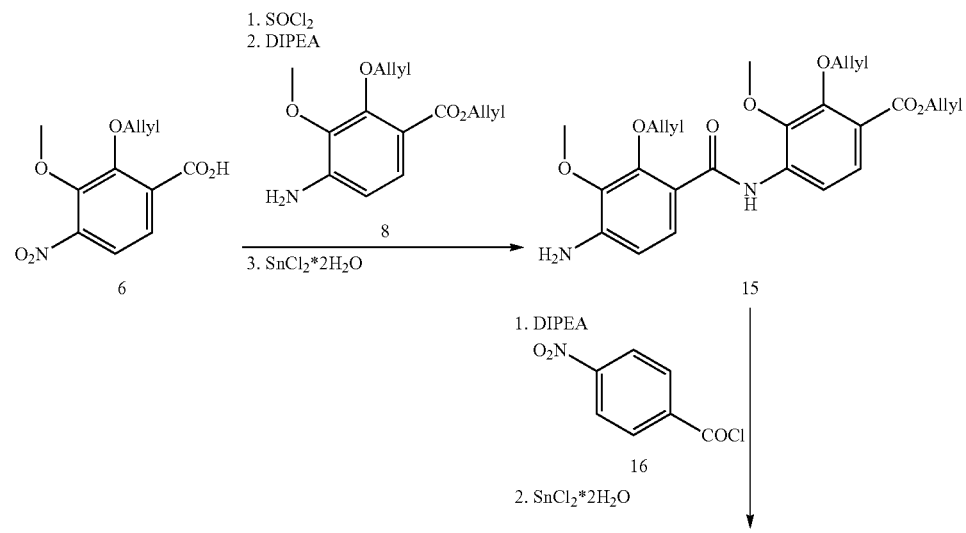

-continued
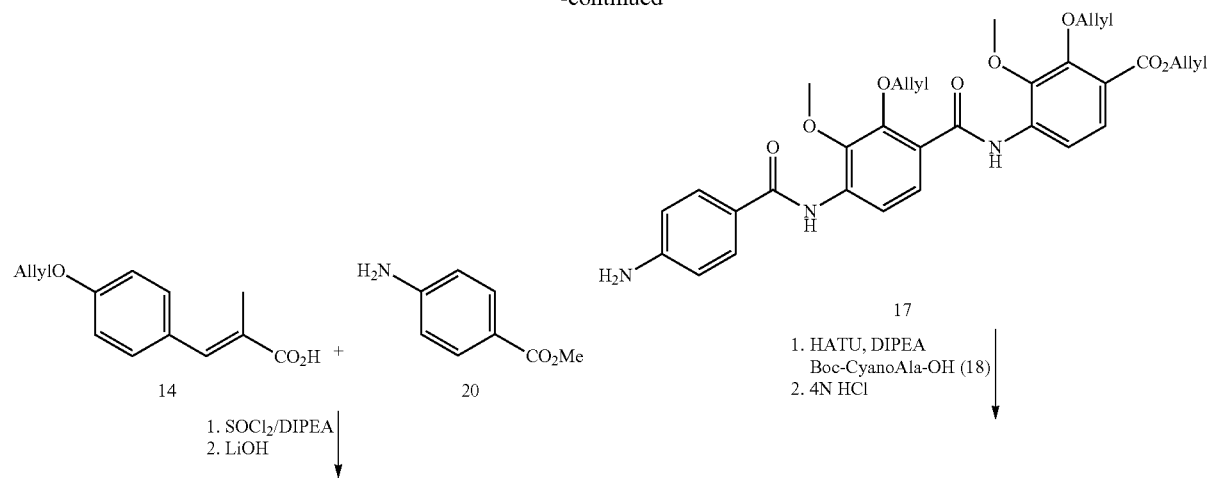
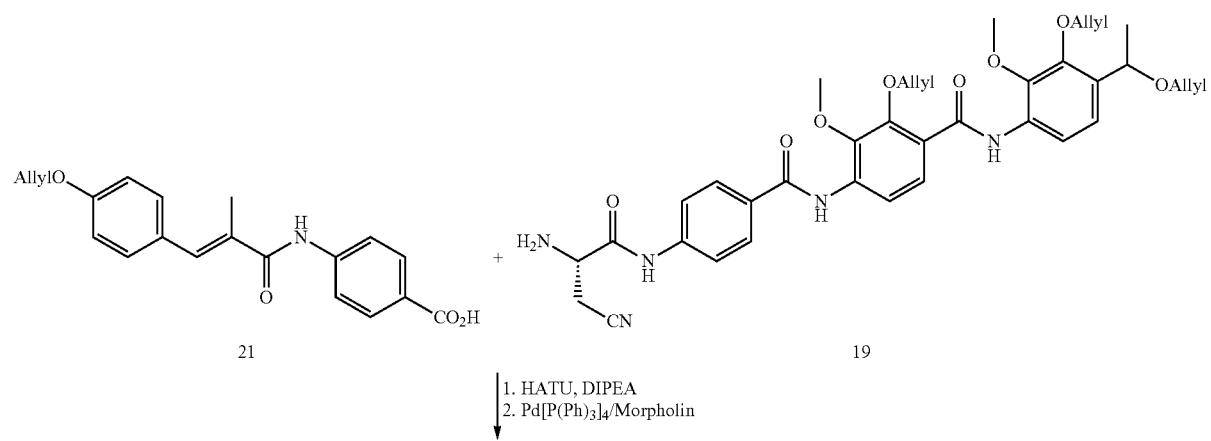
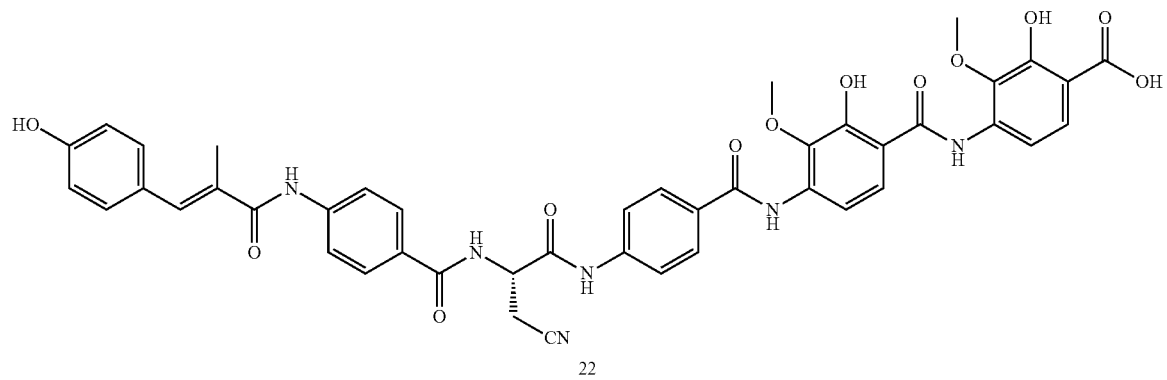 [SMILES: COc1c(NC(=O)c2ccc(NC(=O)c3ccc(NC(=O)[C@H](CC#N)NC(=O)c4ccc(NC(=O)/C(C)=C/c5ccc(O)cc5)cc4)cc3)c(OC)c2O)ccc(C(=O)O)c1O]

Scheme 21
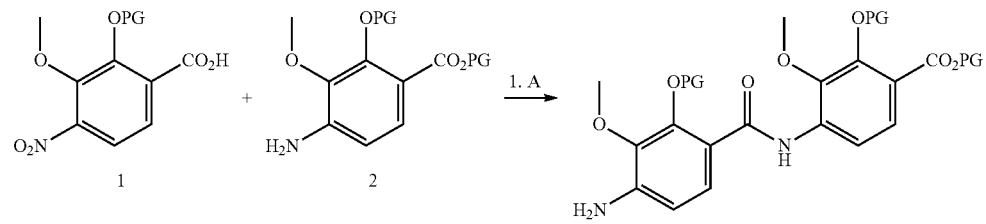
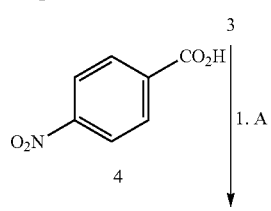
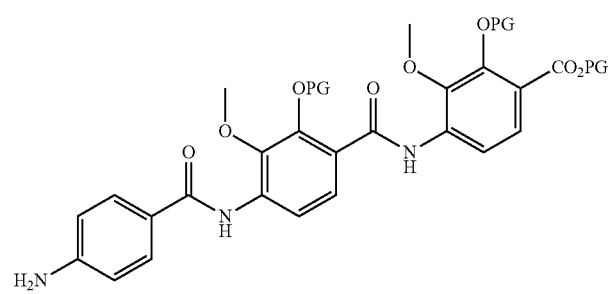
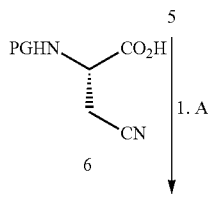
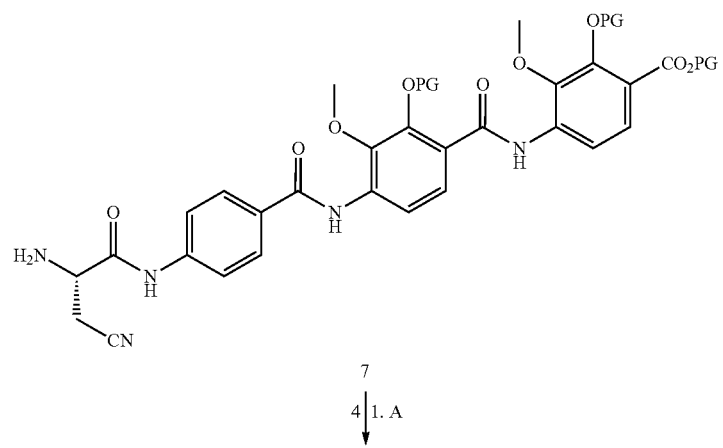

-continued
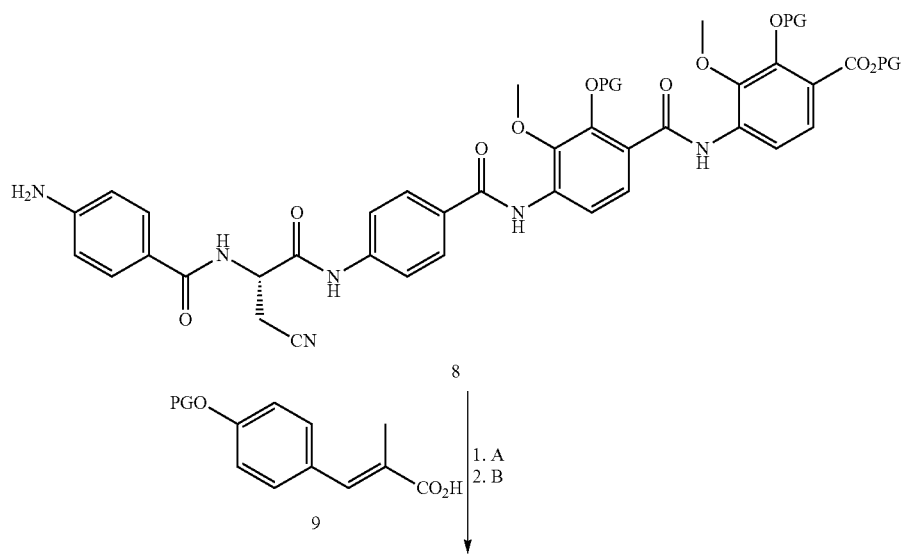
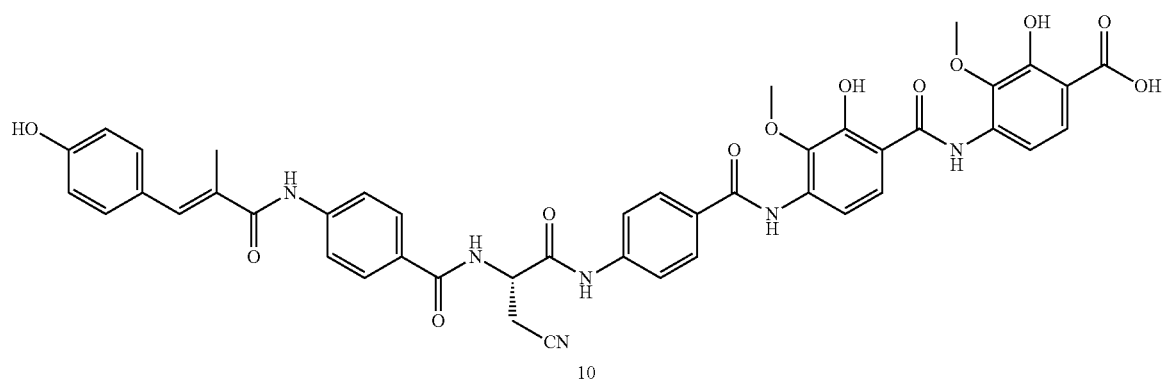
PG = protecting group
Scheme 22
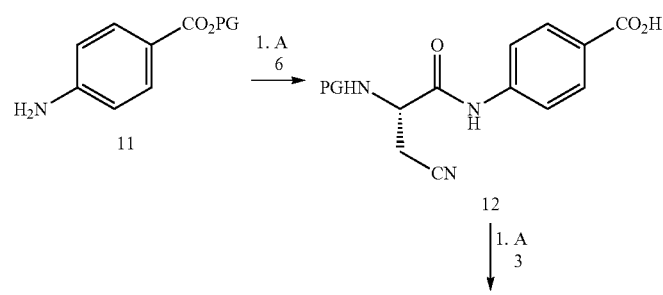

-continued
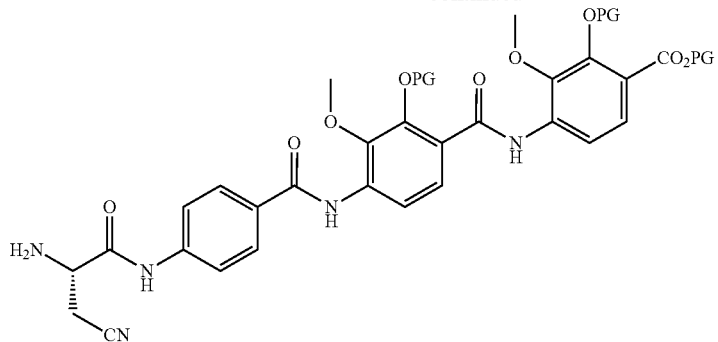
7
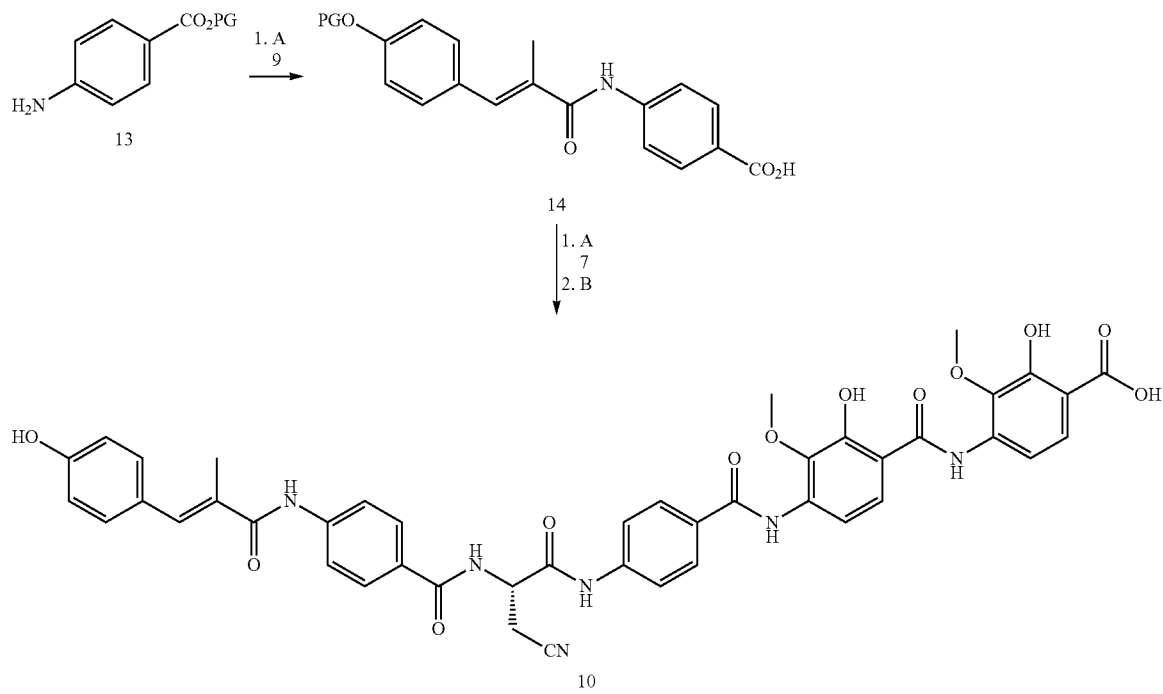
10
PG = protecting group
Scheme 23
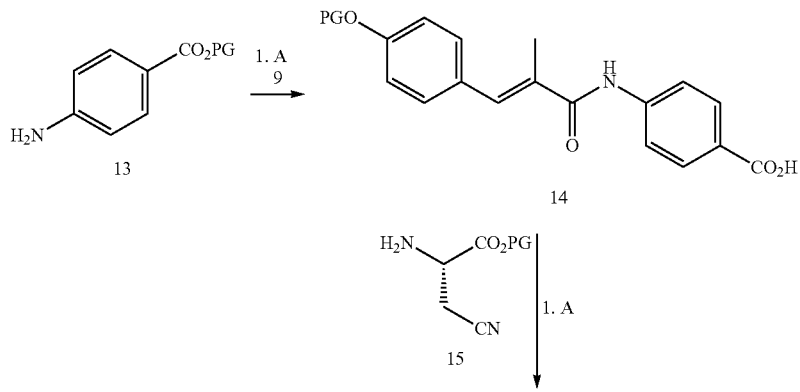

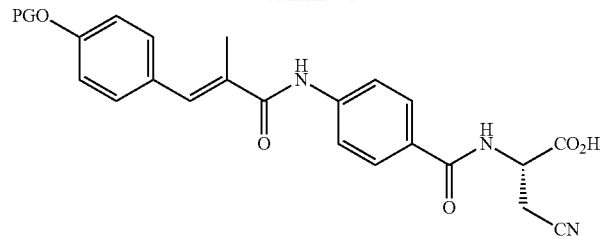
16
1. A
   5
2. B
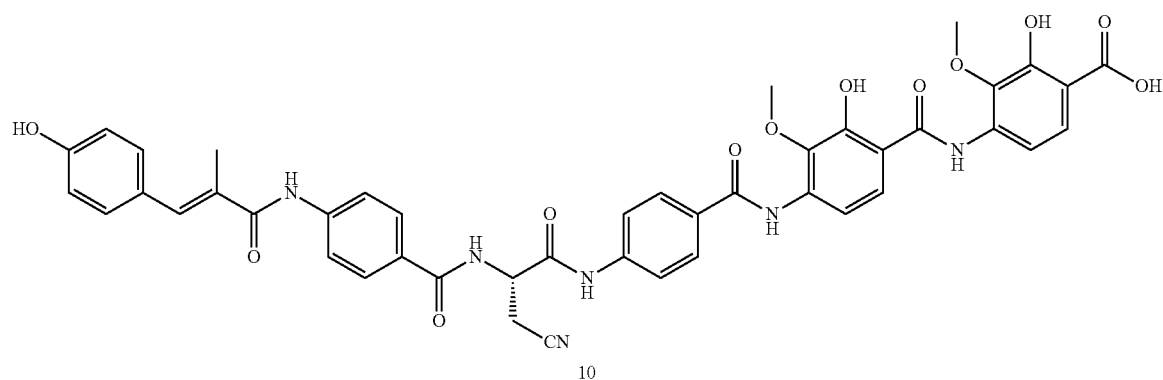
10
PG = protecting group
Scheme 24
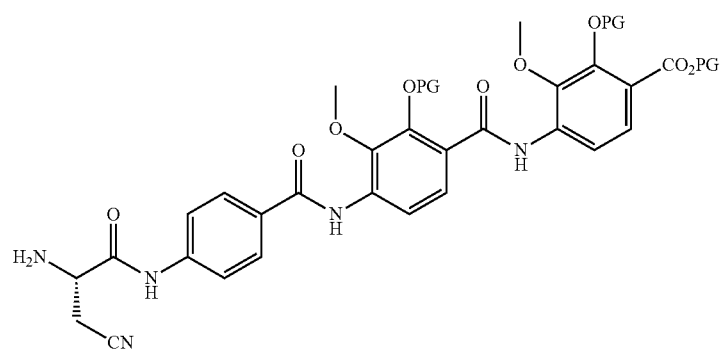
7
1. A
   14
2. B

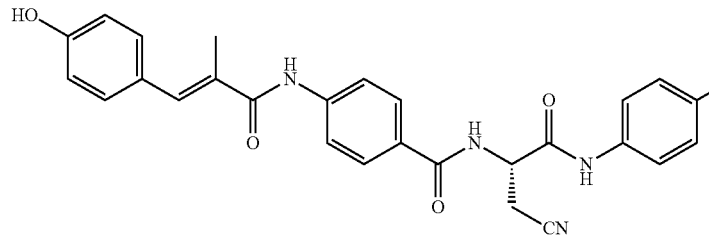

10

PG = protecting group

The spectral analysis of the albicidin derivatives of formula 2 obtained by the just described method is depicted in the FIGS. 1-10 described in detail further below.

General synthetic methods and procedures as applied in the present case are described in the following.

General Procedure for Synthesis of Cinnamic Acids

Method A

The aldehyde (1.00 eq) and the malonic acid (2.00 eq) were dissolved in pyridine and piperidine (2.00 eq) was added. The mixture was stirred at 100° C. for 16 h. After cooling down to room temperature the reaction mixture was poured onto conc. HCl on ice. The precipitated cinnamic acid was filtered and dried in vacuo.

Method B

To a stirred solution of the aldehyde (1.50 eq) and propanoic acid (1.00 eq) in dry THF was slowly added $TiCl_4$ (2.00 eq) at 0° C. The mixture was stirred for 30 min and TEA (4.00 eq) was added. The reaction was allowed to warm up to room temperature and stirred for an additional 48 h. The reaction was quenched with water and the aqueous layer was extracted 3× with DCM. The combined organic layers were dried over $Na_2SO_4$ and the solvent was removed. The crude product was chromatographically purified.

Method C

A mixture of the aldehyde/ketone (1.00 eq), malonic acid (2.00 eq), $SnCl_2.H_2O$ (0.50 eq) and pyridine (2.00 eq) were stirred at 80° C. for 72 h. The mixture was filtered through a pad of celite and the solvent was evaporated. The crude product was chromatographically purified.

Several derivatives of cinnamic acid obtained by at least one of the above described methods are depicted below.

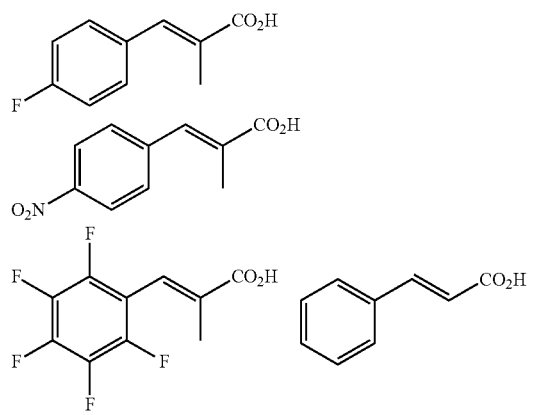

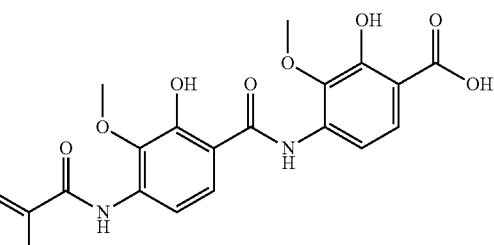

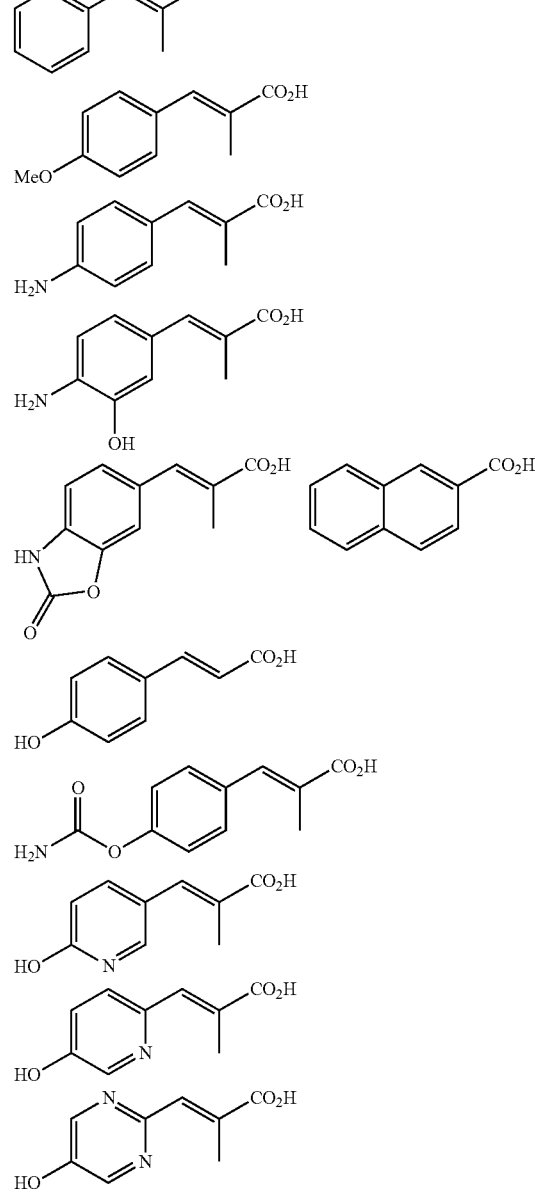

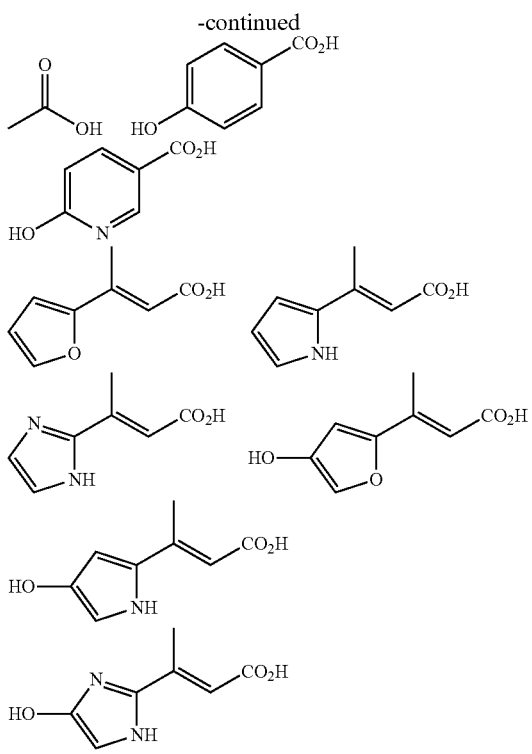

Introduction of an Allylprotecting Group

The cinnamic acid (1.0 eq) was dissolved in DMF and Allylbromide (3.0 eq) and $K_2CO_3$ (3.0 eq) was added. The mixture was stirred at room temperature for 16 h. EtOAc was added and the organic layer was washed with $H_2O$ and brine. After drying over $Na_2SO_4$ the solvent was evaporated. The residue was purified via silica gel column chromatography.

Allyl Deprotection

KOH (2.0 eq) was dissolved in MeOH and added to the protected cinnamic acid. After stirring at room temperature for 12 h the mixture was acidified with conc. HCl. The precipitate was collected and dried in vacuo. If no precipitate was formed the MeOH was removed under reduced pressure and the residue was dissolved again in $H_2O$. The product was extracted with EtOAc. After drying the organic layer over $Na_2SO_4$ the solvent was removed and the product dried in vacuo.

General Procedure for Coupling of an Acid Partner with an Amino Partner:

Method A

Bis-(trichloromethyl)carbonate (1.2 eq) and acid partner (3.5 eq) are dissolved in dry THF under argon atmosphere. 2,4,6-Collidine (8.0 eq) is added slowly via a syringe pump. The resulting suspension is stirred at room temperature for 20 min and a solution of the amino partner (1; 1.0 eq) and DIPEA (10.0 eq) in dry THF is added. Stirring is continued for 3 h at room temperature and the reaction is quenched by addition of water. The organic solvent is removed under reduced pressure and EtOAc is added. The mixture is washed successively with saturated $NaHCO_3$, water and brine. The organic solvent is dried over $Na_2SO_4$, filtered and removed under reduced pressure. The product is purified by crystallisation and column chromatography if necessary (TLC control, HPLC control).

Method B

The acid partner (1 eq) is refluxed in $SOCl_2$ for 2 h. The solvent is removed under reduced pressure and traces of $SOCl_2$ are removed by coevaporation with toluene. The amino partner (1, 1 eq) and a base (e. g. DIPEA, 5 eq) in an organic solvent (e. g. THF, c=0.2 M) are added and the mixture is stirred for 12-16 h. After completion of the reaction (TLC control), the solvent is removed under reduced pressure and the residue is diluted with EtOAc. The organic layer is washed successively with saturated $NaHCO_3$, HCl (5%), water and brine. After drying over $Na_2SO_4$ and filtration the product is isolated by column chromatography or crystallisation.

Method C

Commercially available acid chlorides (carboxylic acid chloride or sulfonic acid chloride; 3 eq) are added to a solution of DIPEA (5 eq) and the amino partner (1, 1 eq). The solution is stirred for 16 h at room temperature and quenched by the addition of water. The organic solvent is removed under reduced pressure and the residue diluted with EtOAc. The organic layer is washed successively with saturated $NaHCO_3$, HCl (5%), water and brine. After drying over $Na_2SO_4$ and filtration the product is isolated by column chromatography or crystallisation.

General Procedure for Coupling an Isocyanate for the Synthesis of Compounds Including an Urea Moiety:

The amine (1 eq) was dissolved in dry THF under an atmosphere of argon. Isocyanate (5 eq) was added and after stirring for 16 h the solvent was removed under reduced pressure. The product was isolated by column chromatography or crystallisation.

General Procedure for Reductive Amination:

Free amine (1.0 eq) and aldehyde (1.0 eq) were dissolved in MeOH and acetic acid (3.5 eq) was added. To this solution $NaBH_3CN$ (1.2 eq) was added and the mixture was stirred for 16 h at room temperature. The reaction mixture was quenched with saturated $NaHCO_3$ solution and extracted with EtOAc. The organic solvent was dried over $Na_2SO_4$, filtered and removed under reduced pressure. The residue was dissolved in 4 N HCl in dioxane. After 5 h of stirring at room temperature the organic solvent was removed under reduced pressure. The residue was dissolved in 10% $NaHCO_3$ and filtrated. Acidification with conc. HCl precipitated the pure carboxylic acid which was isolated by filtration.

General Procedure for Synthesizing Amine Compounds

Carboxylic acid (5 eq) and triethylamine (10 eq) were dissolved in dry DMF HATU (5 eq) was added and the mixture was stirred for 60 min. The amine, dissolved in dry DMF, was added dropwise and the mixture was stirred for 16 h at room temperature. The mixture was diluted with EtOAc and washed successively with brine (3×), 1 N HCl (2×) and saturated $NaHCO_3$ (2×) The organic solvent was dried over $Na_2SO_4$, filtered and removed under reduced pressure. The product was purified by column chromatography or crystallisation.

General Procedure for Converting a Nitro Group into an Amine:

The nitro compound (1 eq) is dissolved in EtOH and $SnCl_2*2H_2O$ (5 eq) and the reaction mixture is stirred at 60° C. until the starting material has disappeared (TLC- and LCMS-monitoring, approximately 4-6 h). The solvent is removed under reduced pressure and the residue diluted with EtOAc. After addition of $NaHCO_3$ (saturated) and separation of the phases, the aqueous phase is further extracted with EtOAc (2×). The combined organic layers are washed with brine (1×), dried over $Na_2SO_4$ and filtered. After removing the solvent under reduced pressure, the product was isolated by column chromatography or crystallisation.

General Procedure for Coupling of an Aldehyde Partner with an Amino Partner Under Reductive Conditions:

The amine (1.0 eq) and aldehyde (1.0 eq) were dissolved in dry THF under argon atmosphere and a catalytic amount of acetic acid was added. After stirring for 60 min at room temperature NaBH$_3$CN (1.3 eq) was added. The reaction mixture was stirred for 3 h at room temperature and another 1.3 eq of NaBH$_3$CN was added and the mixture was stirred for 16 h at room temperature. The reaction was quenched by addition of 1 N HCl and extracted three times with EtOAc. The organic solvent was dried over Na$_2$SO$_4$, filtered and removed under reduced pressure. The product was purified by column chromatography or crystallisation.

General Procedure for Removal of Protection Groups:

A fully protected derivative of the compound according to the formula 1 (1.0 eq) was dissolved in dry THF under argon atmosphere and exclusion of light. Phenylsilane (8.0 eq) and Pd[P(Ph)$_3$]$_4$ (0.5 eq) were added and the reaction mixture was stirred for 10 h at room temperature. AcOH was added, the solvent was removed under reduced pressure and the sample was freeze dried. Purification was achieved by crystallization or preparative HPLC.

General Procedure for Providing Deuterium Atoms in the Structure:

The provision of deuterium instead of hydrogen in a structure is basic knowledge for the expert in the field. For example, deuterium-containing compounds may be synthesized according to known methods (e.g. David S. Wisharta, Brian D. Sykesa, Frederic M. Richards, Biochimica et Biophysica Acta—Protein Structure and Molecular Enzymology, Volume 1164, Issue 1, 1993, Pages 36-46). Furthermore, the respective intermediates may comprise one or more deuterium instead of hydrogen or only deuterium. Thus, by applying the synthesis pathways as discussed above compounds characterized by the general formula 1 are produced, which comprise at least one deuterium in their structure. Such intermediates may be purchased or may be produced to known literature procedures.

Coupling Reactions:

Reaction conditions for coupling primary amines or aryl amines with carboxylic acids to yield amide linkages are known to those of ordinary skill in the art and may be found in any compendium of standard synthetic methods or literature related to the synthesis of peptides and proteins. See e.g., March, J., Advanced Organic Chemistry; Reactions, Mechanisms and Structure, 4th ed., 1992; Larock, Comprehensive Organic Transformations, VCH, New York, 1999; Bodanzsky, Principles of Peptide Synthesis, Springer Verlag, 1984; Bodanzsky, Practice of Peptide Synthesis, Springer Verlag, 1984; Lloyd-Williams et al., Chemical Approaches to the Synthesis of Peptides and Proteins, CRC Press, 1997 (see especially pp. 105-114); and Atherton & Sheppard, Solid Phase Peptide Synthesis: A Practical Approach, IRL Press, 1989). Alternative reactive groups can be utilized, such as compounds exemplified herein after or discussed above, in methods known in the art or described hereinafter.

Protecting Groups

Protection of the N-terminus of a building block with acid labile protecting groups

The amine (1 eq) and di-tert-butyl dicarbonate (1.5 eq) are dissolved in a solvent (e. g. DCM; c=0.2 M) and a base (e. g. NEt$_3$, 3 eq) is added. The mixture is stirred at room temperature for 16 h. After removing the solvent under reduced pressure the product is isolated after column chromatography or crystallisation.

Protection of the N-terminus of a building block methoxybenzylcarbamate protecting group

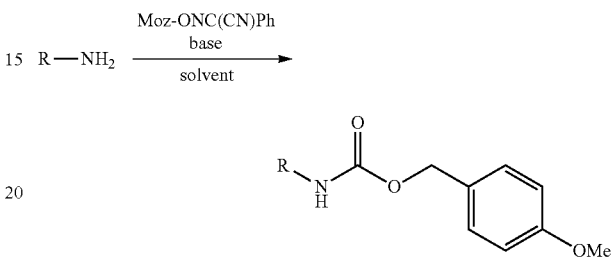

The amine (1 eq) and a base (e. g. NEt$_3$, 1.1 eq) are dissolved in a solvent (e. g. H$_2$O, c=0.2 M) and Moz-ONC(CN)Ph (1 eq) is added in a solvent (e. g. dioxane, c=0.1 M). The mixture is stirred at room temperature for 6-12 h and water is added. The mixture is washed with EtOAc and the aqueous layer is adjusted to pH 2 (5% HCl) and extracted with EtOAc. After drying over Na$_2$SO$_4$ and filtration the organic solvent is removed under reduced pressure. The product is isolated after column chromatography or crystallisation.

Protection of N-terminus with Pd-labile protecting groups

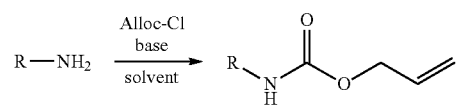

The amine (1 eq) and a base (e. g. pyridine, 3 eq) are dissolved in a solvent (e. g. DCM; c=0.2 M) and slowly allyloxycarbonyl chloride (2 eq) is added. Stirring is continued for 16 h and the reaction mixture is washed successively with HCl (5%) and brine. After drying over Na$_2$SO$_4$, filtration and removal of the solvent the product is isolated by column chromatography or crystallisation.

Protection of phenols with acid labile protecting groups:

The phenol (1 eq) is dissolved in a solvent (e. g. DCM; c=0.2 M) and cooled to −75° C. H$_3$PO$_4$ and BF$_3$*OEt$_2$ and isobutylene (excess) are added and the mixture is stirred 16 h at room temperature. After quenching the reaction by the addition of NH$_4$OH (2 N) and extraction with organic solvent (e. g. DCM) the product is isolated by column chromatography or crystallisation.

Protection of phenols with the methoxybenzyl protecting group:

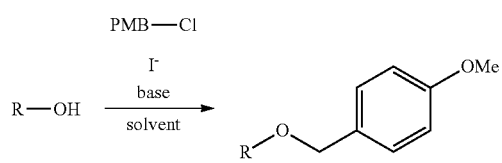

The phenol (1 eq), para-methoxybenzyl chloride (PMB-Cl; 1.1 eq) I$^-$ (e. g. Bu$_4$N—I, 1.1 eq) and a base (e. g. K$_2$CO$_3$, 1.5 eq) are dissolved in a solvent (e. g. acetone; c=0.2 M) and heated to 55° C. for 6-12 h. The solvent is removed under reduced pressure and the residue diluted with EtOAc. The organic phase is washed successively with saturated NaHCO$_3$, HCl (5%) and brine. After drying over Na$_2$SO$_4$ and filtration the organic solvent is removed under reduced pressure. The product is isolated by column chromatography or crystallisation.

Protection of phenols with Pd-labile protecting groups:

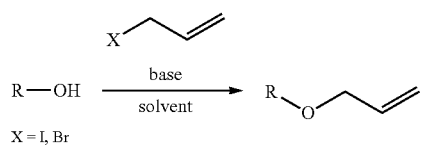

The phenol (1 eq) is dissolved in a solvent (e. g. DMF, c=0.2 M) and a base (e. g. K$_2$CO$_3$, 3 eq) is added. Allylhalogenide (1.5 eq) is added via a syringe pump and stirring is continued at room temperature for 12 h. The solvent is removed under reduced pressure and the product is isolated by column chromatography or crystallisation.

Protection of carboxylic acids with acid labile protecting groups:

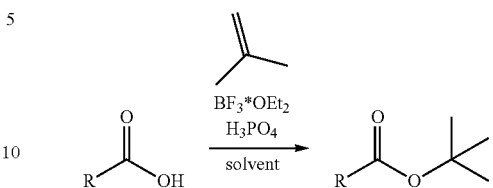

The carboxylic acid (1 eq) is dissolved in a solvent (e. g. DCM; c=0.2 M) and cooled to −75° C. H$_3$PO$_4$ and BF$_3$*OEt$_2$ and isobutylene (excess) are added and the mixture is stirred 16 h at room temperature. After quenching the reaction by the addition of NH$_4$OH (2 N) and extraction with organic solvent (e. g. DCM) the product is isolated by column chromatography or crystallisation.

Protection of carboxylic acids with 4-methoxybenzyl protecting groups:

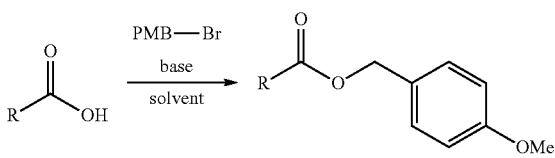

The carboxylic acid (1 eq) and a base (e. g. NEt$_3$, 1 eq) are dissolved in a solvent (e. g. DCM c=0.2 M) and cooled to 0° C. PMB-Br (1 eq) is added and the mixture is stirred 24 h at room temperature. The solution is washed successively with water, saturated NaHCO$_3$, water and brine. After drying over Na$_2$SO$_4$ and filtration the organic solvent is removed under reduced pressure. The product is isolated by column chromatography or crystallisation.

Deprotection

Deprotection of acid labile protecting groups of the N-terminus, of phenols and of carboxylic acids

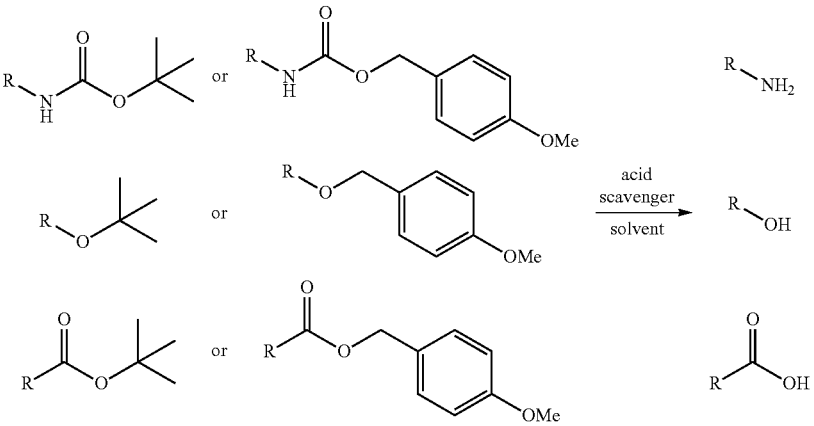

The protected amine, phenol or acid is dissolved in an acid (e. g. TFA—5-95% in DCM) and scavenger (e. g. triethylsilane, 3 eq) is added. Stirring is continued for 12 h (TLC control) and the solvent is removed under reduced pressure. Purification is performed by column chromatography or crystallisation.

Deprotection of Pd-labile protecting groups of the N-terminus of phenols and f the carboxylic acids

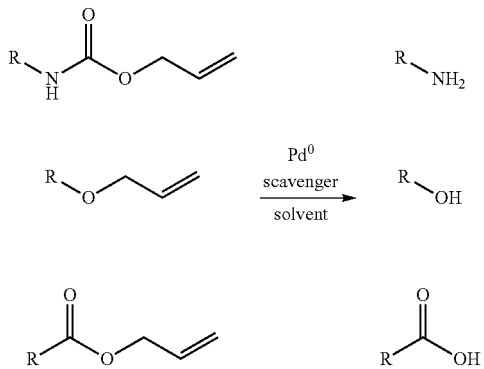

The protected amine (carbamate), phenol (ether) or carboxylic acid (ester) (1 eq) is dissolved in a solvent (e. g. THF), then scavenger (e. g. phenylsilane, 1.5 eq) and $Pd^0$ (e. g. $Pd[P(Ph)_3]_4$, 0.1 eq) are added under argon or nitrogen atmosphere and the exclusion of light. Stirring is continued for 12 h at room temperature and the solvent is removed under reduced pressure. Column chromatography or crystallisation yields the pure product.

While the method illustrated above using acid or Palladium labile protecting groups, a person having ordinary skill in the art will recognize that other protecting groups may be employed. Groups suitable for protecting a wide variety of different functionalities, as well as conditions for their removal, are well known and will be apparent to those of ordinary skill in the art. Specific guidance for selectively protecting a wide variety of functionalities may be found, for example, in Greene & Wuts, Protective Groups in Organic Synthesis, 3rd edition, 1999 ("Greene & Wuts"). Preferred protecting groups are those that may be easily removed. Preferred groups for protecting primary amines and aryl amines are tert-butyloxycarbonyl ("t-Boc"), allyloxycarbonyl (Alloc), 9-fluorenylmethoxycarbonyl ("Fmoc"), para-methoxybenzyl carbamate (Moz) and benzyloxycarbonyl ("Z").

Preferred groups for protecting carboxylic acids are tert-butyl ("t-Bu"), allyl (All), 9-fluorenylmethyl ("Fm"), para-methoxybenzyl (PMB) and benzyl ("Bzl").

Preferred groups for protecting phenols are tert-butyl ("t-Bu"), allyl (All), para-methoxybenzyl (PMB) and benzyl ("Bzl").

Preferred groups for protecting amides are 9-xanthenyl ("Xan"), Trityl (Trt), 4-Methyltrityl (Mtt) and benzyl ("Bzl").

General Methods for Peptide Coupling
Coupling reaction with Bis-(trichloromethyl)carbonate (BTC)

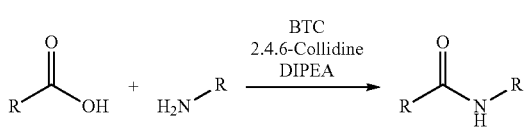

Bis-(trichloromethyl)carbonate (1.2 eq) and carboxylic acid (3.5 eq) are dissolved in dry organic solvent (e. g. THF) under argon atmosphere. 2,4,6-Collidine (8.0 eq) is added slowly via syringe. The resulting suspension is stirred at room temperature for 20 min and a solution of the amine (1.0 eq), DIPEA (10.0 eq) in dry THF is added. Stirring is continued for 3 h at room temperature and the reaction is quenched by addition of water. The organic solvent is removed under reduced pressure and EtOAc is added. The mixture is washed successively with saturated $NaHCO_3$, water and brine. The organic solvent is dried over $Na_2SO_4$, filtered and removed under reduced pressure. The product is purified by column chromatography or crystallisation.

Coupling reaction with (O-(7-azabenzotriazol-1-yl)-N,N,N',N'-tetramethyluronium hexafluorophosphate) (HATU)

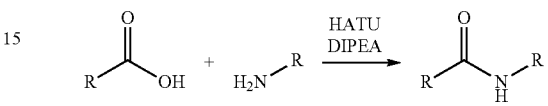

Carboxylic acid (1.1 eq) is dissolved in dry organic solvent (e. g. DMF) and cooled to 0° C. DIPEA (3 eq) and HATU (2 eq) is added. After five minutes the amine (1 eq) is added and stirring was continued for 12 h at room temperature. EtOAc is added and the mixture is washed successively with brine (3×), saturated $NaHCO_3$, 5% HCl, water and brine. After drying over $Na_2SO_4$ and filtration the solvent is removed under reduced pressure. The product is purified by column chromatography or crystallisation.

While the method illustrated above using a peptide coupling in the presence of BTC or HATU, a person having ordinary skill in the art will recognize that other coupling methods may be employed. Peptide coupling methods are well known and will be apparent to those of ordinary skill in the art.

In some embodiments, masked functional group M is $NO_2$ or $N_3$. The reduction of the masked functional group M is carried out under conditions which are state of the art and can be performed by a chemist experienced in the state of the art. The reduction of the nitro group and of the azide group is not limited to the use of hydrogen gas in combination with a catalyst.

The azide or the nitro-group containing compound is dissolved in appropriate solvents as ethyl acetate, acetonitrile, alcohols. A catalyst (Pd, $PtO_2$, 10%/Pd/C) is added under 1 atm hydrogen gas ($H_2$). The reaction stirred preferably at room temperature may be performed between 1 h and 20 h. The application of higher or lower reaction temperatures as well as elevated pressure of hydrogen gas may be applied.

It is understood that other methods exist which are state of the art for reduction: Applying $Fe/CaCl_2$ enables the reduction of nitroarenes by catalytic transfer hydrogenation (S. Chandrappa, T. Vinaya, T. Ramakrishnappa, K. S. Rangappa, *Synlett*, 2010, 3019-3022).

General Methods
Materials:

Commercially available reagents were used throughout the syntheses, without further purification unless otherwise stated; solvents were dried using standard procedures. Unless otherwise specified, reactions were performed under an inert atmosphere of dry nitrogen or argon using absolute solvents purchased from Acros or freshly taken over the PureSolv (Innovative Technologies, USA). Amino acids and coupling reagents were obtained from either IRIS (Marktredwitz, Germany), Novabiochem (Darmstadt, Germany) or Bachem (Basel, Switzerland). Analytical thin layer chromatography was carried out using aluminium-backed plate coated with Merck Kieselgel 60 GF$_{254}$. Plates were visualized under UV light (at □=254 and/or 360 nm) and stained with KMnO$_4$ solution or ninhydrin solution. Flash chromatography was carried out using silica gel 60 (Merck, Darmstadt, Germany). Column chromatography was performed on silica gel (0.04-0.063 mm) purchased from MACHERY-NAGEL GmbH & Co. KG.

Instrumentation and Methods:

$^1$H and $^{13}$C NMR spectra were recorded using Bruker Avance 400, DPX 500, 700 MHz instruments (Bruker, Karlsruhe, Germany) (corresponding $^{13}$C frequencies are 100, 125, 175 MHz); J values are in Hz. The $^{13}$C signals assigned from APT, HSQC and HMBC. Data are reported as parts per million (ppm) downfield shift from tetramethylsilane (TMS) using residual solvent peaks of chloroform (CDCl$_3$, 7.26 ppm and 77.2 ppm) or dimethyl sulfoxide (DMSO-d6, 2.50 ppm and 39.5 ppm) as internal references. Chemical shifts (δ, ppm), multiplicity (br=broad, s=singlet, d=doublet, t=triplet, q=quartet, m=multiplet), coupling constant (J Hz), relative integrals and assignment are quoted where possible.

LCMS/high-resolution mass spectra were recorded on a Orbitrap high resolution mass spectrometer using electrospray ionization (ESI) in positive mode unless otherwise specified.

Analytical Thin Layer Chromatography (TLC) was performed using pre-prepared plates (Merck Kieselgel 60, 0.25 mm F$_{254}$) using UV light (□=254 nm) or ninhydrin stain for visualization. Flash column chromatography was performed using 230-400 mesh Kieselgel 60 silica gel using a mobile phase of the indicated solvents expressed as volume/volume ratios (v/v).

HPLC measurements were performed on a Agilent 1100-HPLC with diode array detection (Agilent, Waldbronn, Germany). Unless otherwise noted the following parameters have been used; Column: Luna C18, 100 A, 100×4.6 mm, 5 um. Gradient: H$_2$O/ACN (A/B)+0.1% HCOOH, starting with 5% B to 100% B in 10 min, holding 2 min 100% B, reconditioning zo 5% B in 3 min, with a constant flow rate of 1 mL/min HPLC-MS/high-resolution mass spectra were recorded on a Exactive Orbitrap high resolution mass spectrometer (Thermo Scientific, Bremen, Germany) using electrospray ionization (ESI) in positive mode unless otherwise specified. Column: Thermo Hypersil-Gold, 50×2.1 mm, 5 um. Gradient: H2O/MeOH (A/B)+0.1% HCOOH, starting with 5% B to 100% B in 6 min, holding for 4 min at 100% B, with a constant flow rate of 0.25 mL/min.

MS/MS experiments were performed on a ESI-Triple-Quadrupol-MS, 6460 series (Agilent Technologies, Waldbronn, Germany).

HPLC-ESI-MS was performed on a LTQ Orbitrap XL (Thermo Fisher Scientific, Waltham, USA) mass spectrometer and an using a Grom-Sil-120-ODS-4-HE column (Grace, Md., USA), length 50 mm, i.d. 2 mm, particle size 3 μm.

Gradient:
Eluent 1: H2O+0.1% HCO2H
Eluent 2: MeCN+0.1% HCO2H
0-10 min: Eluent 2: 20% to 100%
10-13 min: Eluent 2: 100%
13-17 min: Eluent 2: 20%
flow: 0.3 mL/min Circular dichroism (CD) spectra were recorded on a JASCO J-815 CD spectrometer (JASCO, Tokyo, Japan). The parameters are the following: constant temperature at 20° C., cell length 10 mm, range of measurement 700-200 nm, data intervall 0.1 mm, scanning speed 100 nm/min. Each CD-spectrum was accumulated four times. Unless otherwise noted all spectra presented were recorded in DMSO as a solvent. CD-spectra of the albicidins were obtained after subtraction of the blank spectrum (DMSO).

Preparative/semipreparative HPLC for purification was performed with a system from Agilent 1260 Infinity (Agilent, Santa Clara, USA) using a C$_{18}$-RP-Column (Agilent, Santa Clara, USA), length 250 mm, i. d. 21.2 mm, particle size 10 μm.

Isolation Protocol

Isolation protocol was established, testing bioactive fractions by the agar diffusion assay with E. coli. To the fermentation broth of X. axonopodis pv. vesicatoria XAD-7 was added to absorb metabolites from the liquid media. Albicidins were purified from XAD-7 with a MeOH-step-gradient (20%), separating undesirable crude material. The elution of albicidins was achieved with 100% MeOH. The eluted fraction was concentrated in a Genevac Speedvac (Great Britain, Ipswich) and dissolved in MeOH. After centrifugation, the supernatant was used for further purification by preparative HPLC-DAD (at λ=310 nm) on a $C_{18}$ reversed phase column using a linear MeOH-gradient. Albicidins eluted at the $R_t$=33 min. The freeze-dried material was dissolved in 44% THF+1% $CH_3COOH$ and further purified with HPLC-DAD (at 310 nm) using isocratic conditions and $H_2O$/THF as the solvent system on a polymeric reversed phase (PRP) column. Six albicidins eluted under this conditions (FIG. 10). After a last third step albicidins were obtained as white solids. The conditions are shown in Table 1.

TABLE 1

Chromatographic conditions for purification of albicidins with HPLC-DAD.

| | Solvent system (A/B) | Gradient | Column |
|---|---|---|---|
| Step 1 | $H_2O$/MeOH | 35% MeOH + 0.1% HCOOH to 80% MeOH + 0.1% HCOOH in 40 min Flow rate: 15 mL/min | Grace (Germany, Rottenburg-Hailfingen) C18-HPLC GromSil 120 ODS 5 ST, 10 um; 250 × 20 mm |
| Step 2 | $H_2O$/THF | 44% THF + 1% $CH_3OOH$ Isocratic for 80 min Flow rate: 1 mL/min | Hamilton (Switzerland, Bonaduz) PRP-1, 5 um; 305 × 7 mm |
| Step 3 | $H_2O$/CAN + 0.05% TFA | 10% MeOH + 0.1% HCOOH to 80% MeOH + 0.1% HCOOH in 60 min Flow rate: 1 mL/min | Zorbax RX-C18 220 × 4.6 mm |

Liquid cultures of heterologous host *Xanthomonas axonopodis* pv. *vesicatoria* were prepared in plastic falcon tubes of 500 mL, to avoid adsorption sticking of albicidins to the glass surfaces. Cultures were grown under agitation at 28° C., for 5 days, in 72 tubes each containing 200 mL of a modified XaBMM (used for wild-type)/XVM2B (previously used for heterologous host) medium, now called XVM3B medium (see table 2).

TABLE 2

Medium composition per liter for the production of albicidins in *X. axonopodis* pv. *vesicatoria*

|  | *X. axonopodis* pv. *vesicatoria* |
|---|---|
| Medium composition per liter | XVM3B |
| Glycerol | 0.5% (v/v) 6 g/L |
| $K_2HPO_4$ | 0.32 mM |
| $(NH_4)_2SO_4$ | 10 mM |
| $MgSO_4*7H_2O$ | 5 mM |
| Casamino acids | 0.015% |
| $FeSO_4$ | 0.01 mM |
| $CaCl_2$ | 1 mM |
| $KH_2PO_4$ | 0.16 mM |
| NaCl | 20 mM |
| pH | 6.7 |

Unless otherwise specified, reactions were performed under an inert atmosphere of dry nitrogen using absolute solvents, freshly taken over the PureSolv (Innovative Technologies, USA) or purchased from Acros. Amino acids, coupling reagents were obtained from either IRIS (Marktredwitz, Germany), Novabiochem (Darmstadt, Germany) or Bachem (Basel, Switzerland).

Preparation of the Test Substrate

The dry compounds were dissolved in DMSO (1 mg/ml) and the so obtained stock solution was diluted with sterilized Millipore water 1:10 and 1:100

Reference Agents:
Apramycin 1 mg/ml
Chloramphenicol 1 mg/ml
DMSO 100%
$H_2O$

Preparation of the Inoculum

20 μl of cryo stock of each strain were inoculated to 20 ml of Mueller-Hinton medium and grown overnight at 30° C. or 37° C. on a vertical shaker with 160 rpm. The inoculum for the test was adjusted by the 0.5 McFarland Standard ($OD_{625}$ from 0.08 to 0.1)

Strains:
*Staphylococcus aureus* DSM 2569 [gram. Pos.] Medium: MHB/37° C.
*Pseudomonas aeruginosa* DSM1117 [gram. Neg.] Medium: MHB/37° C.
*Bacillus subtilis* DSM10 [gram. Pos.] Medium: MHB/30° C.
*Micrococcus luteus* DSM1790 [gram. Pos.] Medium: MHB/37° C.
*Escherichia coli* $DH_5\alpha$ [gram. Neg.] Medium: MHB/37° C.
*Escherichia coli* albi-res (Montpellier) [gram. Neg.] Medium: MHB/37° C.
*Bacillus megaterium* [gram. Pos.] Medium: MHB/30° C.
*Mycobacterium phlei* DSM750 [gram. Pos.] Medium: MHB/30° C.
*Escherichia coli* K12 (W1130) [gram. Neg.] Medium: MHB/37° C.

DSM 10, 1117 1790 2569 are the order numbers of the "Leibniz-Institut DSMZ-Deutsche Sammlung von Mikroorganismen und Zellkulturen GmbH", one of the largest biological resource centres worldwide (www.dsmz.de)

Preparation of the Test Agar Plates

Every plate is prepared by pouring 10 ml Mueller-Hinton agar into standard petri dishes (diam 94 mm). The so obtained Mueller-Hinton plates are overlayed with 4 ml Mueller-Hinton soft agar containing 100 μl suspension of the test strain.

After the soft agar turned solid, sterile susceptibility test discs were circular placed on the agar and on every test disc 10 μl compound was added. Each concentration is tested in triplicate. The agar dishes were incubated for 18 hours at a temperature of 30° C. or 37° C. Results are obtained by measuring the diameter of inhibition area around each test disc.

EN-ISO Standard Test:

Furthermore, compounds were tested against the following bacteria

*Escherichia coli* (ATCC 25922, 100-2-49 and 100-2-56),
*Salmonella enteritidis* (PEG-10-3-58),
*Pseudomonas aeruginosa* (ATCC 27853 and PEG-10-2-61)
*Staphylococcus aureus* (ATCC 29213 and PEG 10-38-22)

according to EN-ISO standard (ISO 20776-1: 2006. Clinical laboratory testing and in vitro diagnostic test systems—Susceptibility testing of infectious agents and evaluation of performance of antimicrobial susceptibility test devices—Part 1:Reference method for testing the in vitro activity of antimicrobial agents against rapidly growing aerobic bacteria involved in infectious diseases; German version EN ISO 20776-1:2006. Beuth-Verlag, Berlin).

ATCC 25922, 27853, 29213 are the order numbers of the "American Type Culture Collection", a biological resource centre.

Results

Figure 2:
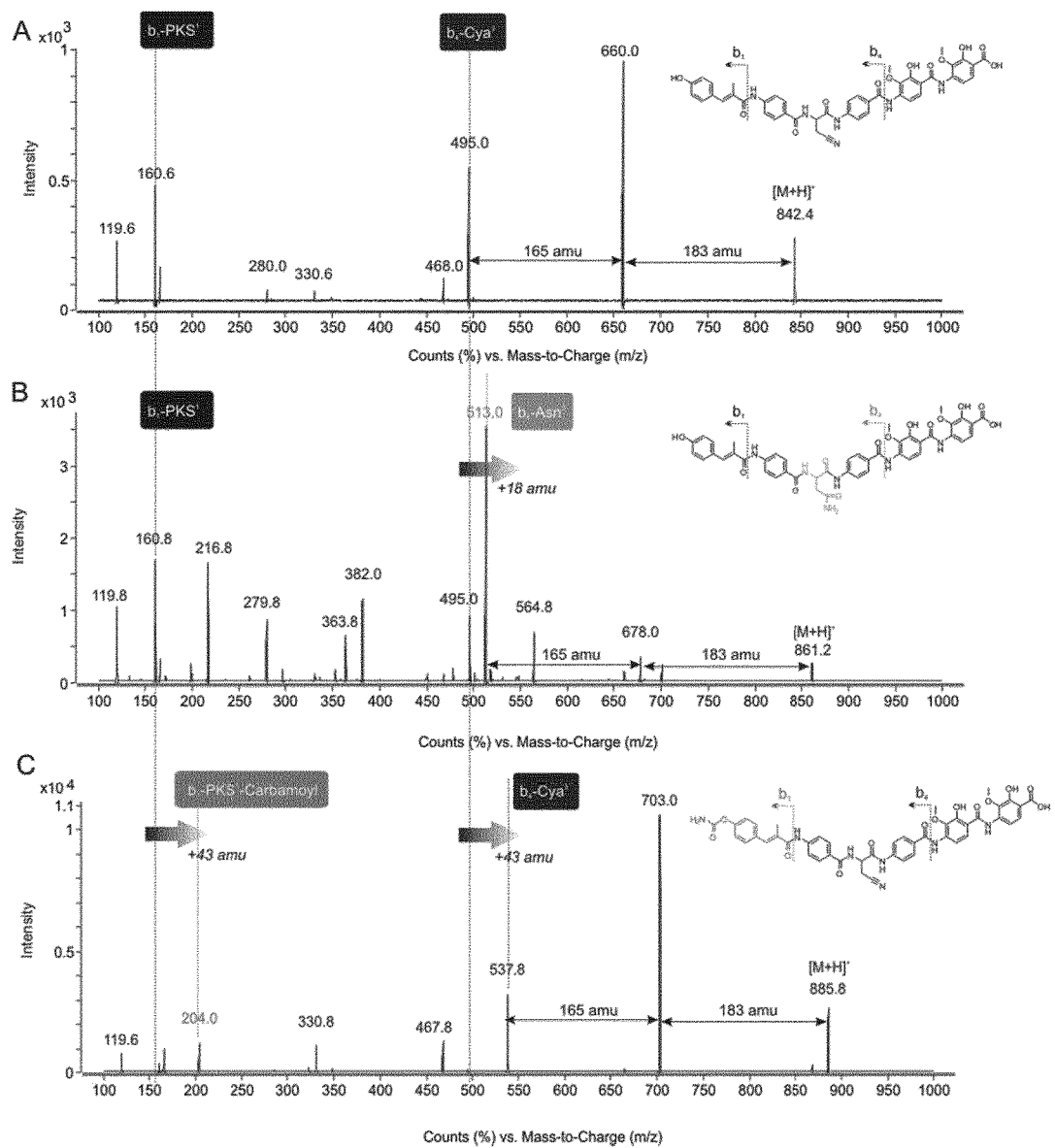

Characterisation of the Natural Occurring L-Albicidin of the General Formula (1L):

The natural occurring L-albicidin of the general formula (1L) were characterised by mass spectrometry (MS and MS2), CD spectroscopy and NMR spectroscopy (1H, 13C) and the molecular formulas of the respective albicidin was determined (see e.g. FIG. 2).

Purification of the Albicidin Compounds

The albicidin compounds were purified by column chromatography or crystallization.

Activity of the Albicidin Compounds

Results are obtained by determining the diameter of inhibition area around each test disc, which could be seen in table 1.

TABLE

Antibacterial activity against selected strains. A = Albicidin; EA = Enantio-Albicidin ("—" no activity detected).

| compound | concentration [mg/ml] | Bacillus subtilis DSM 10 | Bacillus megaterium | Mycobacterium phlei DSM 750 | Micrococcus luteus | Escherichia coli K12 (W1130) |
|---|---|---|---|---|---|---|
| Apramycin | 1 | 2.0 | 3.5 | 2.2 | 1.8 | 1.7 |
| A | 1 | 2.8 | 2.0 | 1.5 | 2.8 | 2.6 |
| A | 0.1 | 1.4 | 1.2 | — | 2.0 | 1.9 |
| EA | 1 | 2.8 | 2.4 | 1.4 | 2.9 | 2.6 |
| EA | 0.1 | 1.8 | 1.4 | 0.6 | 2.0 | 1.9 |
| DMSO | 100% | — | — | — | — | — |
| DMSO | 10% | — | — | — | — | — |
| H$_2$O | 100% | — | — | — | — | — |

Test Agar Plates (Active Substance 1 mg/ml)

Control Substance:

Natural albicidin showed in the same tests a diameter of inhibition of more than 1 cm.

*Staphylococcus aureus* DSM 2569:

Compounds 1 to 5, 7 to 12, 15, 16, 30 and 34 to 36 show a diameter of inhibition of more than 1 cm and more than 2 cm.

*Micrococcus luteus* DSM1790:

Compounds 1 to 5, 9 to 13, 16, 30, 36 and 44 show a diameter of inhibition of more than 1 cm and more than 2 cm.

*Pseudomonas aeruginosa* DSM1117:

Compounds 1 to 5, 7, 10 to 13, 26, 29, 30, 34, 35, 36, 43 and 44 show a diameter of inhibition of more than 1 cm or more than 2 cm.

*Bacillus subtilis* DSM10

Compounds 1 to 5, 7 to 16, 26, 29, 30, 34, 35, 36, 38 to 41, 43 and 44 show a diameter of inhibition of more than 1 cm or more than 3.9 cm

*Escherichia coli* albi-res (Montpellier):

Compounds 1 to 5, 7 to 16, 26, 29, 30, 34, 35, 36, 38 to 41, 43, 44 and 49 show a diameter of inhibition of more than 1 cm or more than 2 cm.

*Escherichia coli* DH$_5$α:

Compounds 1 to 5, 8 to 13, 16, 30, 34, 35, 36 and 44 show a diameter of inhibition of more than 1 cm or more than 2 cm.

EN-ISO Standard Test:

*Escherichia coli* (ATCC 25922, 100-2-49 and 100-2-56):

Compounds 1, 5, 16, 30, 35, 36 and 43 show an activity with good to very good MIC values (minimal inhibitory concentration).

*Salmonella enteritidis* (PEG-10-3-58):

Compounds 1, 5, 16, 30, 35, 36 and 43 show an activity with good to very good MIC values.

*Pseudomonas aeruginosa* (ATCC 27853):

Compounds 1, 5, 30, 35 and 36 show an activity with good to very good MIC values.

*Pseudomonas aeruginosa* (PEG-10-2-61):

Compounds 1, 5 and 36 show an activity with good to very good MIC values.

*Staphylococcus aureus* (ATCC 29213)

Compounds 1, 5, 30 and 36 show an activity with good to very good MIC values.

*Staphylococcus aureus* (PEG 10-38-22)

Compounds 1, 5 and 36 show an activity with good to very good MIC values.

Several of the herein tested strains are of importance for development of antibacterial therapy, particularly due to their resistance breaking potential against ciprofloxacin.

The Infectious Diseases Society of America in the January 2009 highlighted the impact of the ESKAPE pathogens (*Enterococcus faecium, Staphylococcus aureus, Klebsiella pneumoniae, Acinetobacter baumannii, Pseudomonas aeruginosa* and *Enterobacter* species) as a group of particularly troublesome bacteria having the ability to "escape" the effects of current antimicrobial agents [Boucher H W, Talbot G H, Bradley J S, et al Bad bugs, no drugs: no ESKAPE! An update from the Infectious Diseases Society of America. Clin Infect Dis 2009; 48:1-12]. The bacterium *E. coli* is the predominant etiologic pathogen for gram-negative infections and it represents a great total burden of disease. Livermore et al [Livermore D M, Hope R, Brick G, Lillie M, Reynolds R. BSAC Working Parties on Resistance Surveillance. Non-susceptibility trends among Enterobacteriaceae from bacteraemias in the UK and Ireland, 2001-06. J Antimicrob Chemother 2008; 62(Suppl 2):ii41-54.] point out that *E. coli* infections currently account for ~20% of all cases of bacteraemia in the United Kingdom. This rivals the incidence of *S. aureus* infection and is nearly double that associated with any other pathogen. Ciprofloxacin is commonly used for urinary tract and intestinal infections (traveler's diarrhea), used to treat especially tenacious infections. Many bacteria have developed resistance to this drug in recent years, leaving it significantly less effective than it would have been otherwise. Numerous pathogens, including *Staphylococcus aureus*, enterococci, *Streptococcus pyogenes* and *Klebsiella pneumoniae* (quinolone-resistant) now exhibit resistance worldwide.

Synthesis and Characterization

Compound 1

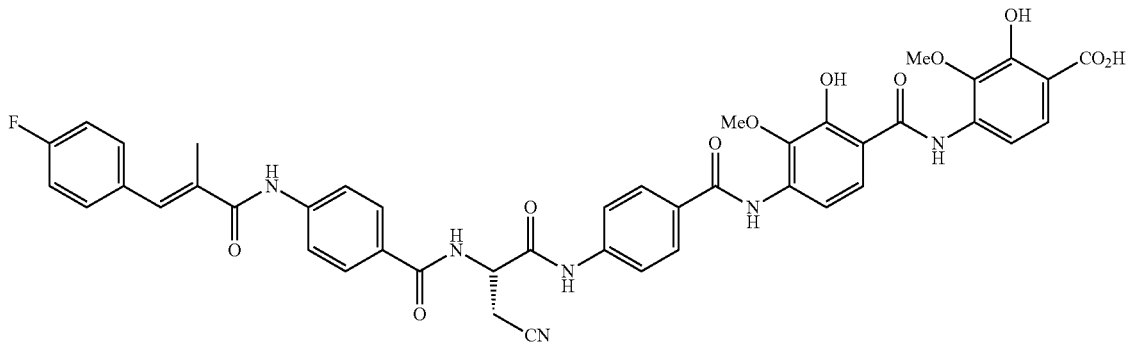

Chemical Formula: $C_{44}H_{37}FN_6O_{11}$

Exact Mass: 844,2504

BTC (1.15 eq, 0.100 mmol, 30 mg) was dissolved in dry THF (5 ml) under an atmosphere of argon. (E)-3-(4-fluorophenyl)-2-methylacrylic acid (3.5 eq, 0.305 mmol, 55 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated $NaHCO_3$ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange oil (76 mg, 91%). The oil (1 eq, 0.069 mmol, 67 mg) and phenylsilane (8 eq, 0.556 mmol, 0.069 ml) were dissolved in dry THF under an atmosphere of argon and exclusion of light. Pd[P(Ph)$_3$]$_4$ (0.5 eq, 0.035 mmol, 40 mg) was added and the mixture was stirred 12 h at room temperature. After adding 3 drops of acetic acid the solvent was removed under reduced pressure. The product was isolated after preparative HPLC purification as a white powder (18 mg, 31%).

$^1$H-NMR (DMSO-d$_6$, 500 MHz): δ [ppm] 2.10 (s, 3H), 3.06 (dd, J$_1$=16.84 Hz, J$_2$=8.72 Hz, 1H), 3.15 (m, 1H), 3.77 (s, 1H), 3.90 (s, 1H), 4.98 (m, 1H), 7.28 (t, J=8.82 Hz, 2H), 7.33 (s, 1H), 7.55 (m, 4H), 7.79 (m, 3H), 7.84 (d, J=8.72 Hz, 2H), 7.93 (d, J=8.72 Hz, 2H), 8.00 (m, 3H), 9.02 (d, J=7.53 Hz, 1H), 9.68 (s, 1H), 10.19 (s, 1H), 10.56 (s, 1H), 11.13 (s, 1H), 11.52 (bs, 1H).

HRMS (ESI): [M–H]$^-$ calculated: 843.2421.

found: 843.2441.

Compound 2

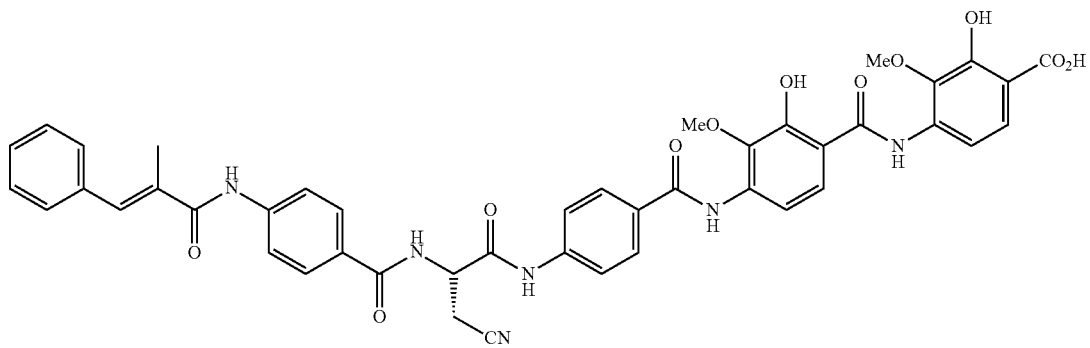

Chemical Formula: $C_{44}H_{38}N_6O_{11}$

Exact Mass: 826,2599

BTC (1.15 eq, 0.100 mmol, 30 mg) was dissolved in dry THF (5 ml) under an atmosphere of argon. (E)-2-methyl-3-phenylacrylic acid (3.5 eq, 0.305 mmol, 49 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated $NaHCO_3$ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange oil (65 mg, 79%). The oil (1 eq, 0.055 mmol, 52 mg) and phenylsilane (8 eq, 0.430 mmol, 0.054 ml) were dissolved in dry THF under an atmosphere of argon and exclusion of light. Pd[P(Ph)$_3$]$_4$ (0.5 eq, 0.027 mmol, 32 mg) was added and the mixture was stirred 12 h at room temperature. After adding 3 drops of acetic acid the solvent was removed under reduced pressure. The product was isolated after preparative HPLC purification as a white powder (16 mg, 35%).

¹H-NMR (DMSO-d₆, 500 MHz): δ [ppm] 2.12 (s, 3H), 3.07 (dd, J₁=16.84 Hz, J₂=8.72 Hz, 1H), 3.15 (m, 1H), 3.77 (s, 3H), 3.91 (s, 3H), 4.98 (m, 1H), 7.36 (m, 2H), 7.46 (m, 4H), 7.57 (m, 2H), 7.79 (m, 3H), 7.86 (d, J=8.72 Hz, 2H), 7.93 (m, 2H), 7.98 (d, J=8.52 Hz, 2H), 8.04 (d, J=8.92 Hz, 1H), 9.02 (d, J=7.73 Hz, 1H), 10.19 (s, 1H), 10.57 (s, 1H), 11.16 (s, 1H), 11.52 (s, 1H).

HRMS (ESI): [M−H]⁻ calculated: 825.2515.
found: 825.2533.

Compound 3 mmol, 46 mg) and phenylsilane (8 eq, 0.395 mmol, 0.049 ml) were dissolved in dry THF under an atmosphere of argon and exclusion of light. Pd[P(Ph)₃]₄ (0.5 eq, 0.025 mmol, 29 mg) was added and the mixture was stirred 12 h at room temperature. After adding 3 drops of acetic acid the solvent was removed under reduced pressure. The product was isolated after preparative HPLC purification as a white powder (7 mg, 18%).

¹H-NMR (DMSO-d₆, 500 MHz): δ [ppm] 3.06 (dd, J₁=16.84 Hz, J₂=8.72 Hz, 1H), 3.15 (m, 1H), 4.98 (m, 1H),

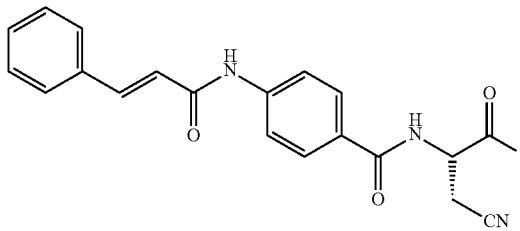
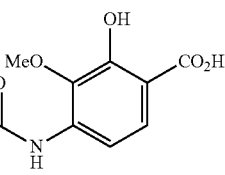

Chemical Formula: $C_{43}H_{36}N_6O_{11}$
Exact Mass: 812,2442

BTC (1.15 eq, 0.100 mmol, 30 mg) was dissolved in dry THF (5 ml) under an atmosphere of argon. Cinnamic acid (3.5 eq, 0.305 mmol, 45 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature 6.85 (d, J=15.66 Hz, 1H), 7.43 (m, 3H), 7.60 (m, 5H), 7.80 (m, 5H), 7.93 (d, J=8.72 Hz, 2H), 7.98 (d, J=8.72 Hz, 2H), 8.05 (d, J=8.92 Hz, 1H), 9.02 (d, J=7.73 Hz, 1H), 9.68 (s, 1H), 10.48 (s, 1H), 10.55 (s, 1H), 11.16 (s, 1H), 11.51 (s, 1H), 11.58 (bs, 1H).

HRMS (ESI): [M−H]⁻ calculated: 811.2358.
found: 811.2373.

Compound 4

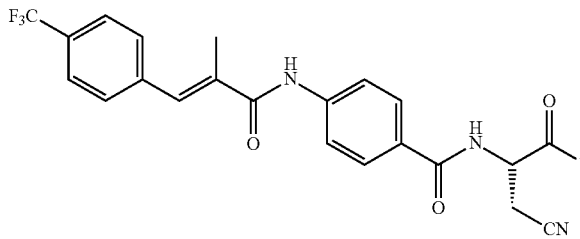

and quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over Na₂SO₄ and filtration, the solvent was removed under reduced pressure. Column chromatography (CHCl₃:MeOH; 1.5% MeOH) yielded the product as an orange oil (80 mg, 99%). The oil (1 eq, 0.049

Chemical Formula: $C_{45}H_{37}F_3N_6O_{11}$
Exact Mass: 894,2472

BTC (1.15 eq, 0.100 mmol, 30 mg) was dissolved in dry THF (5 ml) under an atmosphere of argon. (E)-2-methyl-3-(4-(trifluoromethyl)phenyl)acrylic acid (3.5 eq, 0.305 mmol, 70 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (86 mg, 97%). The oil (1 eq, 0.077 mmol, 78 mg) and phenylsilane (8 eq, 0.614 mmol, 0.076 ml) were dissolved in dry THF under an atmosphere of argon and exclusion of light. Pd[P(Ph)$_3$]$_4$ (0.5 eq, 0.038 mmol, 44 mg) was added and the mixture was stirred 12 h at room temperature. After adding 3 drops of acetic acid the solvent was removed under reduced pressure. The product was isolated after preparative HPLC purification as a white powder (20 mg, 29%).

$^1$H-NMR (DMSO-d$_6$, 400 MHz): δ [ppm] 2.12 (s, 3H), 3.06 (dd, J$_1$=16.79 Hz, J$_2$=8.73 Hz, 1H), 3.15 (m, 1H), 3.76 (s, 3H), 3.90 (s, 3H), 4.97 (m, 1H), 7.39 (s, 1H), 7.55 (m, 2H), 7.68 (d, J=8.06 Hz, 2H), 7.79 (m, 5H), 7.85 (d, J=8.60 Hz, 2H), 7.93 (m, 2H), 7.98 (d, J=8.60 Hz, 2H), 8.03 (d, J=8.87 Hz, 1H), 9.04 (d, J=7.52 Hz, 1H), 9.70 (s, 1H), 10.28 (s, 1H), 10.58 (s, 1H), 11.16 (s, 1H), 11.54 (s, 1H).

HRMS (ESI): [M−H]$^-$ calculated: 893.2389.
found: 893.2410.

Compound 5 amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (56 mg, 66%). The oil (1 eq, 0.057 mmol, 56 mg) and phenylsilane (8 eq, 0.460 mmol, 0.057 ml) were dissolved in dry THF under an atmosphere of argon and exclusion of light. Pd[P(Ph)$_3$]$_4$ (0.5 eq, 0.029 mmol, 33 mg) was added and the mixture was stirred 12 h at room temperature. After adding 3 drops of acetic acid the solvent was removed under reduced pressure. The product was isolated after preparative HPLC purification as a white powder (10 mg, 20%).

$^1$H-NMR (DMSO-d$_6$, 700 MHz): δ [ppm] 3.05 (dd, J$_1$=16.75 Hz, J$_2$=8.82 Hz, 1H), 3.14 (m, 1H), 3.76 (s, 3H), 3.90 (s, 3H), 4.97 (m, 1H), 6.08 (s, 2H), 6.67 (d, J=15.66 Hz, 1H), 6.98 (d, J=7.93 Hz, 1H), 7.15 (D, J=7.93 Hz, 1H), 7.19 (s, 1H), 7.55 (m, 3H), 7.79 (m, 5H), 7.92 (d, J=8.52 Hz, 2H),

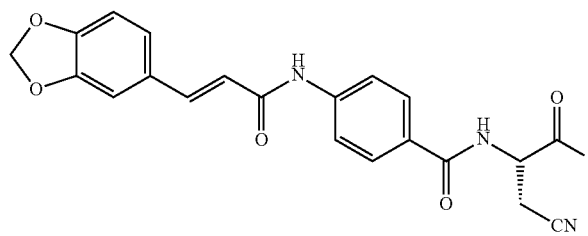

Chemical Formula: C$_{44}$H$_{36}$N$_6$O$_{13}$
Exact Mass: 856,2340

BTC (1.15 eq, 0.100 mmol, 30 mg) was dissolved in dry THF (5 ml) under an atmosphere of argon. (E)-3-(1,3-dihydroisobenzofuran-5-yl)acrylic acid (3.5 eq, 0.305 mmol, 59 mg) was added. syn-Collidine (8 eq, 0.700 mmol, 0.092 ml) was slowly added via syringe and the white suspension was stirred at room temperature for 10 min. The 7.97 (d, J=8.72 Hz, 2H), 8.03 (d, J=8.92 Hz, 1H), 9.00 (d, J=7.53 Hz, 1H), 9.67 (s, 1H), 10.37 (s, 1H), 10.54 (s, 1H), 11.15 (s, 1H), 11.50 (s, 1H), 11.57 (bs, 1H).

HRMS (ESI): [M+H]$^+$ calculated: 857.2413.
found: 857.2422.
[M+Na]$^+$ calculated: 879.2233.
found: 879.2242.

Compound 6

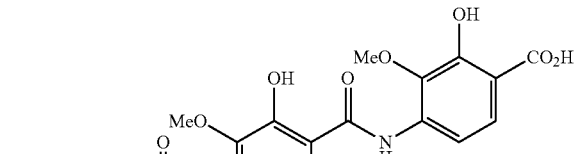

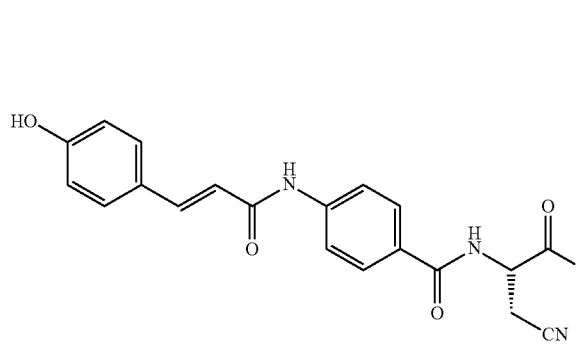

Chemical Formula: $C_{43}H_{36}N_6O_{12}$

Exact Mass: 828,2391

BTC (1.15 eq, 0.100 mmol, 30 mg) was dissolved in dry THF (5 ml) under an atmosphere of argon. (E)-3-(4-(Allyloxy)phenyl)acrylic acid (3.5 eq, 0.305 mmol, 62 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated $NaHCO_3$ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange oil (55 mg, 64%). The oil (1 eq, 0.058 mmol, 57 mg) and phenylsilane (8 eq, 0.462 mmol, 0.057 ml) were dissolved in dry THF under an atmosphere of argon and exclusion of light. $Pd[P(Ph)_3]_4$ (0.5 eq, 0.029 mmol, 33 mg) was added and the mixture was stirred 12 h at room temperature. After adding 3 drops of acetic acid the solvent was removed under reduced pressure. The product was isolated after preparative HPLC purification as a white powder (10 mg, 20%).

$^1$H-NMR (DMSO-$d_6$, 400 MHz): δ [ppm] 3.07 (dd, $J_1$=16.79 Hz, $J_2$=8.73 Hz, 1H), 3.16 (s, 1H), 3.78 (s, 3H), 3.92 (s, 3H), 4.99 (m, 1H), 6.64 (d, J=15.58 Hz, 1H), 6.84 (d, J=8.33 Hz, 2H), 7.54 (m, 5H), 7.80 (m, 5H), 7.93 (d, J=8.87 Hz, 2H), 7.99 (d, J=8.87 Hz, 2H), 8.06 (d, J=8.87 Hz, 1H), 9.03 (d, J=7.52 Hz, 1H), 9.71 (s, 1H), 9.98 (bs, 1H), 10.37 (s, 1H), 10.57 (s, 1H), 11.18 (s, 1H), 11.54 (s, 1H), 11.60 (bs, 1H).

HRMS (ESI): [M−H]$^-$ calculated: 827.2307. found: 827.2331.

Compound 7

Chemical Formula: $C_{41}H_{34}N_6O_{12}$

Exact Mass: 802,2235

BTC (1.15 eq, 0.100 mmol, 30 mg) was dissolved in dry THF (5 ml) under an atmosphere of argon. 4-(Allyloxy)benzoic acid (3.5 eq, 0.305 mmol, 67 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated $NaHCO_3$ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange oil (58 mg, 69%). The oil (1 eq, 0.058 mmol, 56 mg) and phenylsilane (8 eq, 0.466 mmol, 0.057 ml) were dissolved in dry THF under an atmosphere of argon and exclusion of light. $Pd[P(Ph)_3]_4$ (0.5 eq, 0.029 mmol, 34 mg) was added and the mixture was stirred 12 h at room temperature. After adding 3 drops of acetic acid the solvent was removed under reduced pressure. The product was isolated after preparative HPLC purification as a white powder (19 mg, 41%).

$^1$H-NMR (DMSO-$d_6$, 500 MHz): δ [ppm] 3.07 (dd, $J_1$=16.65 Hz, $J_2$=8.72 Hz, 1H), 3.16 (m, 1H), 3.77 (s, 3H), 3.90 (s, 3H), 4.98 (m, 1H), 6.87 (d, J=8.52 Hz, 2H), 7.57 (dd, $J_1$=8.92 Hz, $J_2$=4.56 Hz, 2H), 7.80 (m, 3H), 7.94 (m, 10H), 9.02 (d, J=7.53 Hz, 1H), 9.68 (s, 1H), 10.16 (s, 1H), 10.23 (s, 1H), 10.59 (s, 1H), 11.14 (s, 1H), 11.52 (s, 1H).

HRMS (ESI): [M+H]$^+$ calculated: 803.2308. found: 803.2323.

[M+Na]$^+$ calculated: 825.2127. found: 825.2141.

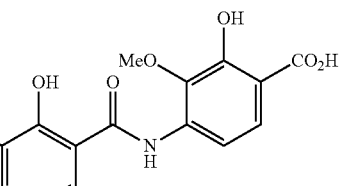

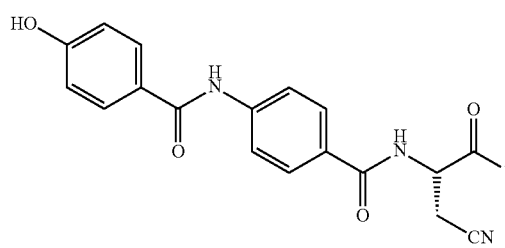

Compound 8

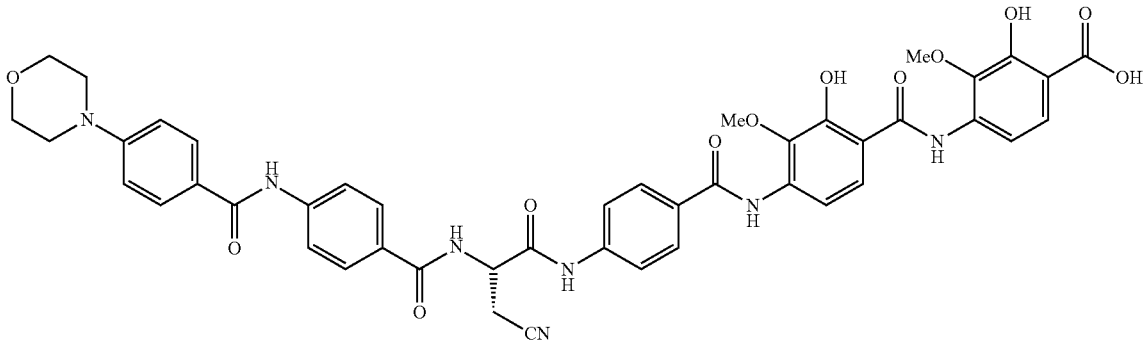

Chemical Formula: $C_{45}H_{41}N_7O_{12}$

Exact Mass: 871,2813

BTC (1.15 eq, 0.100 mmol, 29 mg) was dissolved in dry THF (5 ml) under an atmosphere of argon. 4-Morpholinobenzoic acid (3.5 eq, 0.305 mmol, 63 mg) was added. syn-Collidine (8 eq, 0.697 mmol, 91 µl) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated $NaHCO_3$ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange oil (72 mg, 84%). The oil (1 eq, 0.069 mmol, 68 mg) and phenylsilane (8 eq, 0.552 mmol, 68 µl) were dissolved in dry THF under an atmosphere of argon and exclusion of light. $Pd[P(Ph)_3]_4$ (0.5 eq, 0.035 mmol, 40 mg) was added and the mixture was stirred 12 h at room temperature. After adding 3 drops of acetic acid the solvent was removed under reduced pressure. The product was isolated after preparative HPLC purification as a white powder (6 mg, 10%).

$^1$H-NMR (DMSO-$d_6$, 400 MHz): δ [ppm] 3.07 (dd, $J_1$=16.12, $J_2$=8.87 Hz, 1H), 3.16 (dd, $J_1$=16.12, $J_2$=5.10 Hz, 1H), 3.27 (m, 4H), 3.76 (m, 4H), 3.79 (s, 3H), 3.85 (s, 3H), 4.99 (dd, $J_1$=13.43, $J_2$=7.79 Hz, 1H), 7.05 (d, J=9.40 Hz, 2H), 7.42 (m, 2H), 7.56 (m, 2H), 7.63 (m, 2H), 7.78 (d, J=8.87 Hz, 2H), 7.93 (m, 6H), 8.93 (s, 1H), 9.04 (d, J=7.79 Hz, 1H), 10.22 (s, 1H), 10.58 (s, 1H), 10.64 (s, 1H).

HRMS (ESI): [M+H]$^+$ calculated: 872.2886. found: 872.2882.

Compound 9

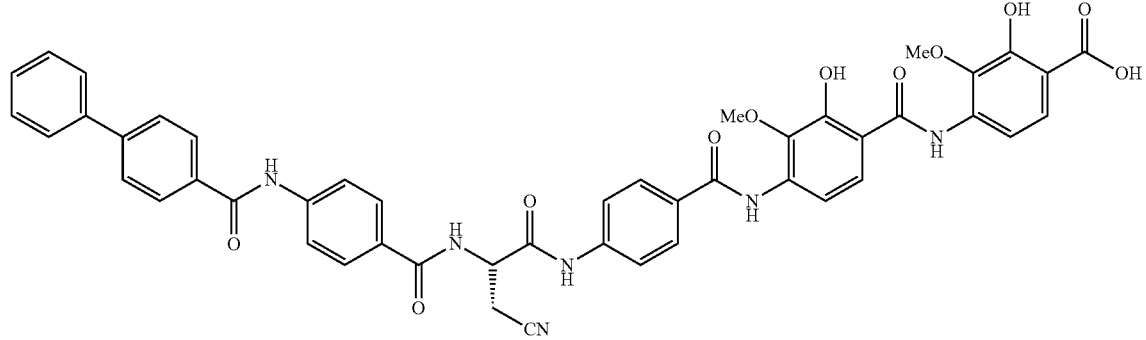

Chemical Formula: $C_{47}H_{38}N_6O_{11}$

Exact Mass: 862,2599

BTC (1.15 eq, 0.100 mmol, 29 mg) was dissolved in dry THF (5 ml) under an atmosphere of argon. Biphenyl-4-carboxylic acid (3.5 eq, 0.305 mmol, 60 mg) was added. syn-Collidine (8 eq, 0.697 mmol, 91 µl) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated $NaHCO_3$ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange oil (60 mg, 70%). The oil (1 eq, 0.055 mmol, 54 mg) and phenylsilane (8 eq, 0.440 mmol, 54 µl) were dissolved in dry THF under an atmosphere of argon and exclusion of light. $Pd[P(Ph)_3]_4$ (0.5 eq, 0.028 mmol, 32 mg) was added and the mixture was stirred 12 h at room temperature. After adding 3 drops of acetic acid the solvent was removed under reduced pressure. The product was isolated after preparative HPLC purification as a white powder (7 mg, 15%).

HRMS (ESI): [M+H]$^+$ calculated: 863.2671. found: 863.2666.

Compound 10

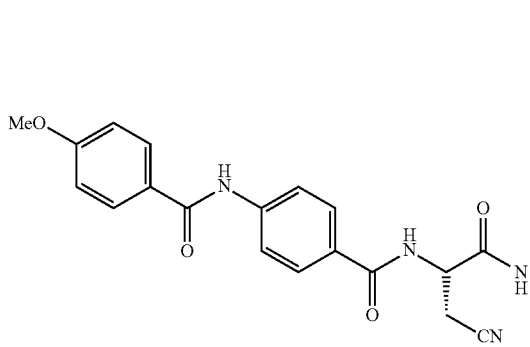

Chemical Formula: $C_{42}H_{36}N_6O_{12}$

Exact Mass: 816,2391

BTC (1.15 eq, 0.100 mmol, 30 mg) was dissolved in dry THF (5 ml) under an atmosphere of argon. 4-Methoxybenzoic acid (3.5 eq, 0.305 mmol, 46 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over Na₂SO₄ and filtration, the solvent was removed under reduced pressure. Column chromatography (CHCl₃:MeOH; 1.5% MeOH) yielded the product as an orange oil (43 mg, 53%). The oil (1 eq, 0.046 mmol, 43 mg) and phenylsilane (8 eq, 0.367 mmol, 0.045 ml) were dissolved in dry THF under an atmosphere of argon and exclusion of light. Pd[P(Ph)₃]₄ (0.5 eq, 0.023 mmol, 26 mg) was added and the mixture was stirred 12 h at room temperature. After adding 3 drops of acetic acid the solvent was removed under reduced pressure. The product was isolated after preparative HPLC purification as a white powder (5 mg, 13%).

¹H-NMR (DMSO-d₆, 700 MHz): δ [ppm]3.08 (m, 1H), 3.17 (m, 1H), 3.78 (s, 3H), 3.83 (s, 1H), 3.86 (s, 3H), 5.00 (s, 1H), 6.55 (bs, 1H), 7.10 (d, J=8.37 Hz, 2H), 7.56 (m, 2H), 7.81 (m, 3H), 7.97 (m, 9H), 9.05 (d, J=7.18 Hz, 1H), 9.68 (s, 1H), 10.35 (s, 1H), 10.58 (s, 1H), 11.06 (s, 1H), 11.54 (s, 1H).

HRMS (ESI): [M−H]⁻ calculated: 815.2307. found: 815.2310.

Compound 11

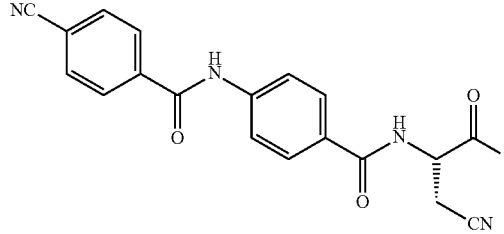

Chemical Formula: $C_{42}H_{33}N_7O_{11}$

Exact Mass: 811,2238

BTC (1.15 eq, 0.100 mmol, 30 mg) was dissolved in dry THF (5 ml) under an atmosphere of argon. 4-Cyanobenzoic acid (3.5 eq, 0.305 mmol, 45 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over Na₂SO₄ and filtration, the solvent was removed under reduced pressure. Column chromatography (CHCl₃:MeOH; 1.5% MeOH) yielded the product as an orange oil (59 mg, 73%). The oil (1 eq, 0.064 mmol, 59 mg) and phenylsilane (8 eq, 0.509 mmol, 0.063 ml) were dissolved in dry THF under an atmosphere of argon and exclusion of light. Pd[P(Ph)₃]₄ (0.5 eq, 0.032 mmol, 37 mg) was added and the mixture was stirred 12 h at room temperature. After adding 3 drops of acetic acid the solvent was removed under reduced pressure. The product was isolated after preparative HPLC purification as a white powder (11 mg, 21%).

¹H-NMR (DMSO-d₆, 500 MHz): δ [ppm] 3.09 (dd, J₁=16.84 Hz, J₂=8.92 Hz, 1H), 3.18 (dd, J₁=17.14 Hz, J₂=5.85 Hz, 1H), 3.79 (s, 3H), 3.91 (s, 3H), 5.01 (m, 1H), 7.02 (s, 1H), 7.12 (s, 1H), 7.22 (s, 2H), 7.57 (d, J=8.72 Hz, 2H), 7.81 (m, 4H), 7.93 (d, J=8.52 Hz, 3H), 7.99 (m, 5H), 8.96 (d, J=8.13 Hz, 2H), 8.14 (d, J=8.32 Hz, 2H), 9.08 (d, J=7.93 Hz, 1H), 9.68 (s, 1H), 10.59 (s, 1H), 10.74 (s, 1H), 11.07 (bs, 1H), 11.55 (bs, 1H).

Compound 12 atmosphere of argon and exclusion of light. Pd[P(Ph)₃]₄ (0.5 eq, 0.039 mmol, 45 mg) was added and the mixture was stirred 12 h at room temperature. After adding 3 drops of acetic acid the solvent was removed under reduced pressure. The product was isolated after preparative HPLC purification as a white powder (43 mg, 65%).

¹H-NMR (DMSO-d₆, 400 MHz): δ [ppm] 3.08 (dd, J₁=16.79 Hz, J₂=9.00 Hz, 1H), m (3.17, 1H), 3.78 (s, 3H),

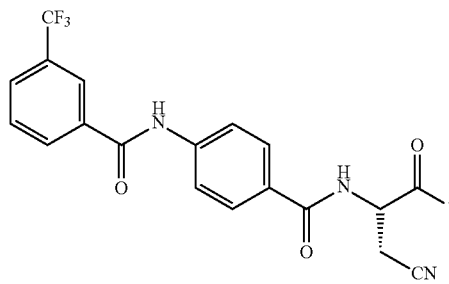
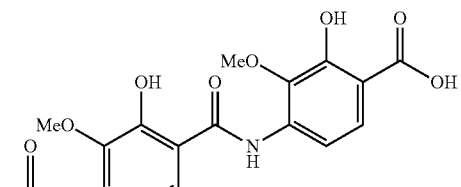

Chemical Formula: $C_{42}H_{33}F_3N_6O_{11}$

Exact Mass: 854.2159

BTC (1.15 eq, 0.100 mmol, 30 mg) was dissolved in dry THF (5 ml) under an atmosphere of argon. 3-(Trifluoromethyl)benzoic acid (3.5 eq, 0.305 mmol, 61 mg) was added. syn-Collidine (8 eq, 0.700 mmol, 0.092 ml) was slowly added via syringe and the white suspension was stirred at 3.91 (s, 3H), 5.00 (m, 1H), 7.58 (m, 2H), 7.81 (m, 4H), 7.99 (m, 8H), 8.31 (m, 2H), 9.09 (d, J=8.09 Hz, 1H), 9.72 (s, 1H), 10.60 (s, 1H), 10.73 (s, 1H), 11.18 (s, 1H), 11.55 (s, 1H).

HRMS (ESI): [M−H]⁻ calculated: 853.2076.
found: 853.2095.

Compound 13

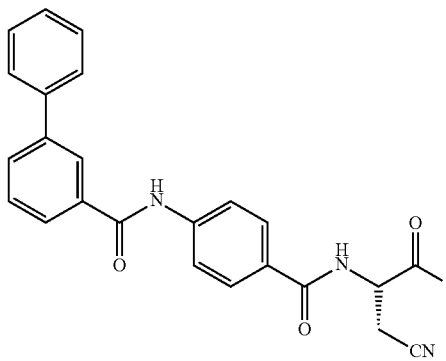

room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over Na₂SO₄ and filtration, the solvent was removed under reduced pressure. Column chromatography (CHCl₃:MeOH; 1.5% MeOH) yielded the product as an orange oil (86 mg, 99%). The oil (1 eq, 0.077 mmol, 75 mg) and phenylsilane (8 eq, 0.617 mmol, 0.076 ml) were dissolved in dry THF under an Chemical Formula: $C_{47}H_{38}N_6O_{11}$ Exact Mass: 862.2599

BTC (1.15 eq, 0.100 mmol, 30 mg) was dissolved in dry THF (5 ml) under an atmosphere of argon. Biphenyl-2-carboxylic acid (3.5 eq, 0.305 mmol, 61 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange oil (86 mg, 99%). The oil (1 eq, 0.079 mmol, 78 mg) and phenylsilane (8 eq, 0.635 mmol, 0.078 ml) were dissolved in dry THF under an atmosphere of argon and exclusion of light. $Pd[P(Ph)_3]_4$ (0.5 eq, 0.040 mmol, 46 mg) was added and the mixture was stirred 12 h at room temperature. After adding 3 drops of acetic acid the solvent was removed under reduced pressure. The product was isolated after preparative HPLC purification as a white powder (35 mg, 51%).

¹H-NMR (DMSO-$d_6$, 400 MHz): δ [ppm] 3.06 (dd, $J_1$=16.66 Hz, $J_2$=8.60 Hz, 1H), 3.15 (m, 1H), 3.78 (s, 3H), 3.92 (s, 1H), 4.98 (m, 1H), 7.29 (m, 1H), 7.37 (t, J=7.52 Hz, 2H), 7.44 (m, 2H), 7.50 (m, 2H), 7.61 (m, 6H), 7.80 (m, 3H), 7.87 (d, J=8.60 Hz, 2H), 7.99 (d, J=8.60 Hz, 2H), 8.06 (d, J=8.87 Hz, 1H), 9.01 (d, J=7.79 Hz, 1H), 9.71 (s, 1H), 10.50 (s, 1H), 10.57 (s, 1H), 11.19 (s, 1H), 11.58 (m, 2H).

HRMS (ESI): [M–H]⁻ calculated: 861.2593. found: 861.2530.

Compound 14

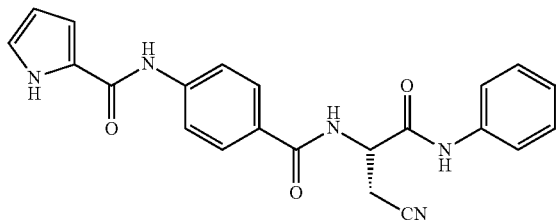

Chemical Formula: $C_{39}H_{33}N_7O_{11}$
Exact Mass: 775.2238

BTC (1.15 eq, 0.100 mmol, 30 mg) was dissolved in dry THF (5 ml) under an atmosphere of argon. 1H-pyrrole-2-carboxylic acid (3.5 eq, 0.305 mmol, 29 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.8% MeOH) yielded the product as an orange solid (54 mg, 69%). The solid (1 eq, 0.058 mmol, 56 mg) and phenylsilane (8 eq, 0.466 mmol, 0.057 ml) were dissolved in dry THF under an atmosphere of argon and exclusion of light. $Pd[P(Ph)_3]_4$ (0.5 eq, 0.029 mmol, 34 mg) was added and the mixture was stirred 12 h at room temperature. After adding 3 drops of acetic acid the solvent was removed under reduced pressure. The product was isolated after preparative HPLC purification as a white powder (17 mg, 38%).

¹H-NMR (DMSO-$d_6$, 400 MHz): δ [ppm] 3.07 (m, 1H), 3.16 (m, 1H), 3.77 (s, 3H), 3.91 (s, 3H), 4.99 (m, 1H), 6.18 (m, 1H), 7.00 (m, 1H), 7.12 (m, 1H), 7.58 (t, J=9.1 Hz, 2H), 7.80 (m, 3H), 7.88 (m, 4H), 7.99 (d, J=8.9 Hz, 2H), 8.06 (d, J=8.9 Hz, 1H), 9.02 (d, J=7.5 Hz, 1H), 9.71 (s, 1H), 9.99 (s, 1H), 10.58 (s, 1H), 11.18 (s, 1H), 11.54 (s, 1H).

HR-MS: [M–H]⁻ calculated: 774.2154.
[M–H]⁻ found: 774.2153.

Compound 15

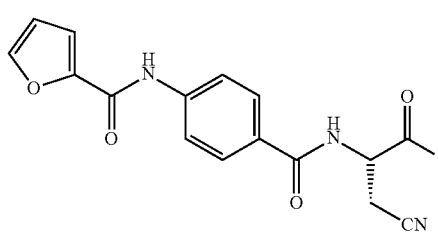

Chemical Formula: $C_{39}H_{32}N_6O_{12}$
Exact Mass: 776.2078

BTC (1.15 eq, 0.100 mmol, 30 mg) was dissolved in dry THF (5 ml) under an atmosphere of argon. Furan-2-carboxylic acid (3.5 eq, 0.305 mmol, 29 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (72 mg, 89%). The oil (1 eq, 0.078 mmol, 70 mg) and phenylsilane (8 eq, 0.625 mmol, 0.077 ml) were dissolved in dry THF under an atmosphere of argon and exclusion of light. Pd[P(Ph)$_3$]$_4$ (0.5 eq, 0.039 mmol, 45 mg) was added and the mixture was stirred 12 h at room temperature. After adding 3 drops of acetic acid the solvent was removed under reduced pressure. The product was isolated after preparative HPLC purification as a white powder (16 mg, 27%).

$^1$H-NMR (DMSO-d$_6$, 400 MHz): δ [ppm] 3.07 (m, 1H), 3.16 (m, 1H), 3.77 (s, 3H), 3.91 (s, 3H), 4.99 (m, 1H), 6.73 (s, 1H), 7.39 (d, J=3.0 Hz, 1H), 7.57 (t, J=8.3 Hz, 2H), 7.80 (m, 3H), 7.94 (m, 6H), 8.04 (d, J=8.6 Hz, 1H), 9.05 (d, J=7.3 Hz, 1H), 9.71 (s, 1H), 10.44 (s, 1H), 10.58 (s, 1H), 11.57 (s, 1H), 11.55 (s, 1H).

HR-MS: [M−H]$^-$ calculated: 775.1994.

[M−H]$^-$ found: 775.1995.

Compound 16

BTC (1.15 eq, 0.100 mmol, 30 mg) was dissolved in dry THF (5 ml) under an atmosphere of argon. Thiazole-4-carboxylic acid (3.5 eq, 0.305 mmol, 34 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an yellow solid (69 mg, 86%). The solid (1 eq, 0.073 mmol, 67 mg) and phenylsilane (8 eq, 0.587 mmol, 0.072 ml) were dissolved in dry THF under an atmosphere of argon and exclusion of light. Pd[P(Ph)$_3$]$_4$ (0.5 eq, 0.037 mmol, 34 mg) was added and the mixture was stirred 12 h at room temperature. After adding 3 drops of acetic acid the solvent was removed under reduced pressure. The product was isolated after preparative HPLC purification as a white powder (21 mg, 38%).

$^1$H-NMR (DMSO-d$_6$, 500 MHz): δ [ppm] 3.07 (dd, J$_1$=16.79 Hz, J$_2$=8.73 Hz, 1H), 3.17 (m, 1H), 3.78 (s, 3H), 3.92 (s, 3H), 4.99 (m, 1H), 7.47 (m, 3H), 7.58 (m, 2H), 7.81 (m, 3H), 7.87 (d, J=8.87 Hz, 2H), 7.94 (m, 2H), 8.00 (d, J=8.60 Hz, 2H), 8.05 (d, J=8.87 Hz, 1H), 9.04 (d, J=7.79 Hz, 1H), 9.71 (s, 1H), 10.22 (s, 1H), 10.59 (s, 1H), 11.17 (s, 1H), 11.54 (s, 1H).

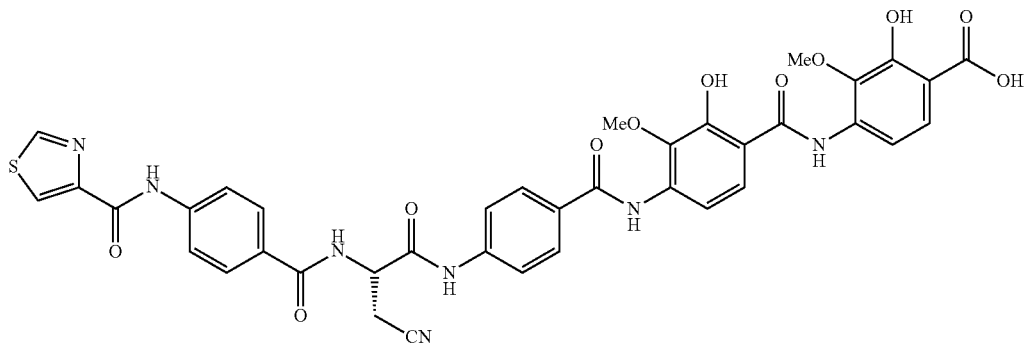

Chemical Formula: C$_{38}$H$_{31}$N$_7$O$_{11}$S

Exact Mass: 793.1802

HRMS (ESI): [M−H]$^+$ calculated: 792.1718.

found: 792.1717.

Compound 17

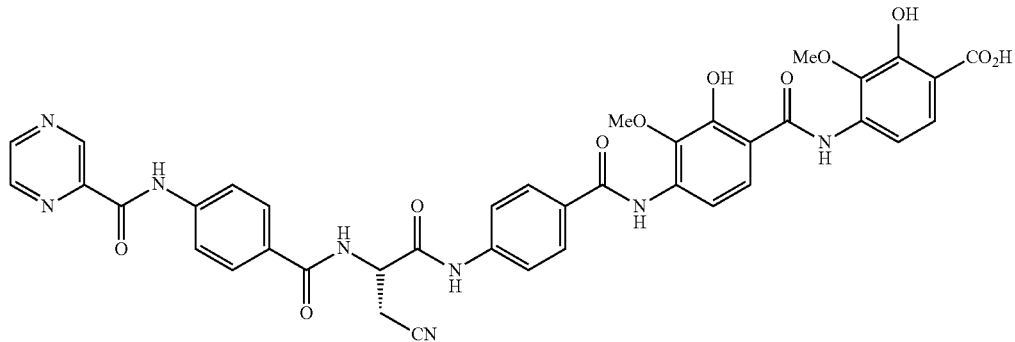

Chemical Formula: $C_{39}H_{32}N_8O_{11}$
Exact Mass: 788,2191

BTC (1.15 eq, 0.100 mmol, 30 mg) was dissolved in dry THF (5 ml) under an atmosphere of argon. Pyrazine-2-carboxylic acid (3.5 eq, 0.305 mmol, 33 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated $NaHCO_3$ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange solid (70 mg, 88%). The solid (1 eq, 0.073 mmol, 67 mg) and phenylsilane (8 eq, 0.590 mmol, 0.073 ml) were dissolved in dry THF under an atmosphere of argon and exclusion of light. Pd[P(Ph)$_3$]$_4$ (0.5 eq, 0.037 mmol, 34 mg) was added and the mixture was stirred 12 h at room temperature. After adding 3 drops of acetic acid the solvent was removed under reduced pressure. The product was isolated after preparative HPLC purification as a white powder (19 mg, 33%).

$^1$H-NMR (DMSO-$d_6$, 400 MHz): δ [ppm] 3.07 (m, 1H), 3.17 (m, 1H), 3.77 (s, 3H), 3.91 (s, 1H), 4.99 (m, 1H), 7.58 (t, J=8.9 Hz, 2H), 7.80 (m, 3H), 7.98 (m, 4H), 8.06 (m, 3H), 8.84 (m, 1H), 8.94 (m, 1H), 9.09 (d, J=7.8 Hz, 1H), 9.32 (s, 1H), 9.71 (s, 1H), 10.58 (s, 1H), 11.00 (s, 1H), 11.18 (s, 1H), 11.54 (s, 1H).

HR-MS: [M+H]$^+$ calculated: 789.2263.
[M+H]$^+$ found: 789.2260.

Compound 18

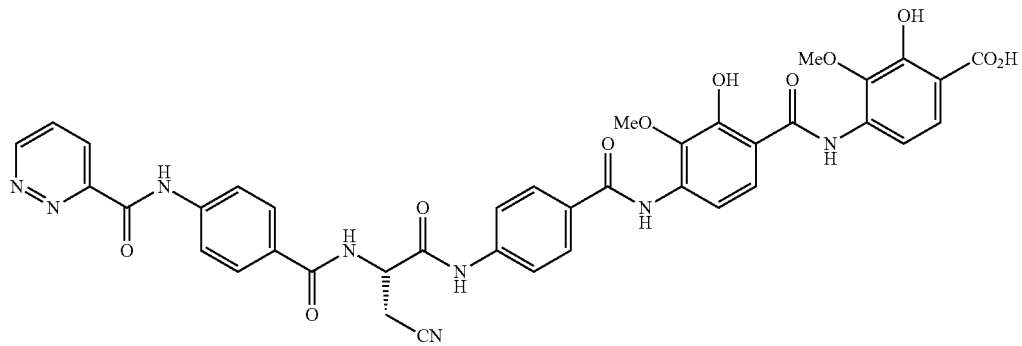

Chemical Formula: $C_{39}H_{32}N_8O_{11}$
Exact Mass: 788,2191

BTC (1.15 eq, 0.100 mmol, 30 mg) was dissolved in dry THF (5 ml) under an atmosphere of argonPyridazine-3-carboxylic acid (3.5 eq, 0.305 mmol, 33 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated $NaHCO_3$ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange oil (58 mg, 73%). The oil (1 eq, 0.058 mmol, 56 mg) and phenylsilane (8 eq, 0.466 mmol, 0.057 ml) were dissolved in dry THF under an atmosphere of argon and exclusion of light. Pd[P(Ph)$_3$]$_4$ (0.5 eq, 0.029 mmol, 34 mg) was added and the mixture was stirred 12 h at room temperature. After adding 3 drops of acetic acid the solvent was removed under reduced pressure.

The product was isolated after preparative HPLC purification as a white powder (7 mg, 15%).

$^1$H-NMR (DMSO-d$_6$, 400 MHz): δ [ppm] 3.08 (m, 1H), 3.17 (m, 1H), 3.77 (s, 3H), 3.91 (s, 3H), 5.00 (m, 1H), 7.57 (t, J=9.0 Hz, 1H), 7.80 (m, 4H), 7.99 (m, 5H), 8.04 (m, 1H), 8.11 (d, J=8.9 Hz), 8.35 (dd, J=1.6 Hz), 9.10 (d, J=7.0 Hz), 9.49 (dd, J$_1$=5.0 Hz, J$_2$=1.5 Hz), 9.71 (s, 1H), 10.59 (s, 1H), 11.18 (s, 1H), 11.34 (s, 1H), 11.54 (s, 1H).

HR-MS: [M−H]$^−$ calculated: 787.2106.

[M−H]$^−$ found: 787.2111.

Compound 19

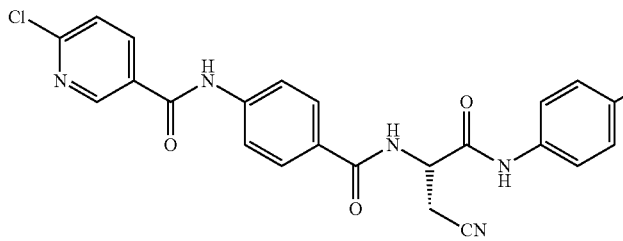

Chemical Formula: C$_{40}$H$_{32}$ClN$_7$O$_{11}$

Exact Mass: 821,1848

BTC (1.15 eq, 0.100 mmol, 30 mg) was dissolved in dry THF (5 ml) under an atmosphere of argon. 6-chloronicotinic acid (3.5 eq, 0.305 mmol, 42 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange solid (73 mg, 89%). The solid (1 eq, 0.075 mmol, 71 mg) and phenylsilane (8 eq, 0.600 mmol, 0.074 ml) were dissolved in dry THF under an atmosphere of argon and exclusion of light. Pd[P(Ph)$_3$]$_4$ (0.5 eq, 0.038 mmol, 44 mg) was added and the mixture was stirred 12 h at room temperature. After adding 3 drops of acetic acid the solvent was removed under reduced pressure. The product was isolated after preparative HPLC purification as a white powder (4 mg, 7%).

$^1$H-NMR (DMSO-d$_6$, 400 MHz): δ [ppm] 3.07 (m, 1H), 3.16 (m, 1H), 3.77 (s, 3H), 3.91 (s, 3H), 4.99 (m, 1H), 6.18 (m, 1H), 7.00 (m, 1H), 7.12 (m, 1H), 7.58 (t, J=9.1 Hz, 2H), 7.80 (m, 3H), 7.88 (m, 4H), 7.99 (d, J=8.9 Hz, 2H), 8.06 (d, J=8.9 Hz, 1H), 9.02 (d, J=7.5 Hz, 1H), 9.71 (s, 1H), 9.99 (s, 1H), 10.58 (s, 1H), 11.18 (s, 1H), 11.54 (s, 1H).

HR-MS: [M−H]$^−$ calculated: 774.2154.

[M−H]$^−$ found: 774.2153.

Compound 20

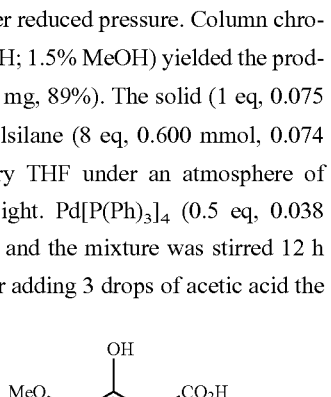

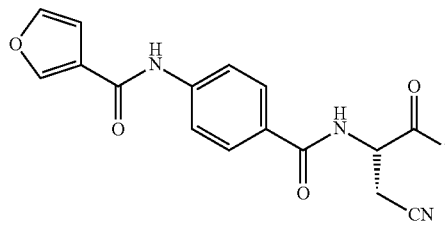

Chemical Formula: C$_{39}$H$_{32}$N$_6$O$_{12}$

Exact Mass: 776,2078

BTC (1.15 eq, 0.100 mmol, 30 mg) was dissolved in dry THF (5 ml) under an atmosphere of argon. Furan-3-carboxylic acid (3.5 eq, 0.305 mmol, 29 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (72 mg, 92%). The oil (1 eq, 0.078 mmol, 70 mg) and phenylsilane (8 eq, 0.625 mmol, 0.077 ml) were dissolved in dry THF under an atmosphere of argon and exclusion of light. Pd[P(Ph)$_3$]$_4$ (0.5 eq, 0.039 mmol, 45 mg) was added and the mixture was stirred 12 h at room temperature. After adding 3 drops of acetic acid the solvent was removed under reduced pressure. The product was isolated after preparative HPLC purification as a white powder (6 mg, 10%).

$^1$H-NMR (DMSO-d$_6$, 400 MHz): δ [ppm] 3.08 (dd, J=8, 6 Hz, 1H), 3.16 (dd, J=5.4 Hz, 1H), 3.77 (s, 3H), 3.91 (s, 3H), 4.99 (m, 1H), 7.02 (d, J=1.3 Hz, 1H), 7.57 (m, 1H), 7.82 (m, 6H), 7.97 (m, 5H), 8.05 (d, J=8.9 Hz, 1H), 8.43 (s, 1H), 9.05 (d, J=7.3 Hz, 1H), 9.71 (s, 1H), 10.17 (s, 1H), 10.58 (s, 1H), 11.18 (s, 1H), 11.54 (s, 1H).

HR-MS: [M–H]$^-$ calculated: 775.1994.

[M–H]$^-$ found: 775.2000.

Compound 21 syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange solid (79 mg, 98%). The oil (1 eq, 0.087 mmol, 79 mg) and phenylsilane (8 eq, 0.693 mmol, 0.085 ml) were dissolved in dry THF under an atmosphere of argon and exclusion of light. Pd[P(Ph)$_3$]$_4$ (1.0 eq, 0.087 mmol, 100 mg) was added and the mixture was stirred 12 h at room temperature. After adding 3 drops of acetic acid the solvent was removed under reduced pressure. The product was isolated after preparative HPLC purification as a white powder (20 mg, 29%).

$^1$H-NMR (DMSO-d$_6$, 400 MHz): δ [ppm] 3.07 (m, 1H), 3.17 (m, 1H), 3.77 (s, 3H), 3.91 (s, 1H), 4.99 (m, 1H), 7.25 (t, J=1.1, 1H), 7.57 (d, 1H), 7.80 (m, 3H), 7.89 (m, 4H), 7.98 (m, 4H), 8.04 (m, 4H), 8.07 (d, J=2.7 Hz, 1H) 9.06 (d, J=7.8 Hz, 1H), 9.70 (s, 1H), 10.47 (s, 1H), 10.58 (s, 1H), 11.16 (s, 1H), 11.53 (s, 1H).

HR-MS: [M–H]$^-$ calculated: 791.17660.

[M–H]$^-$ found: 791.17853.

Compound 22

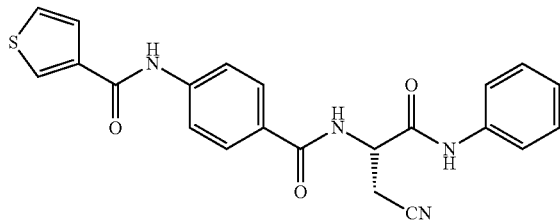
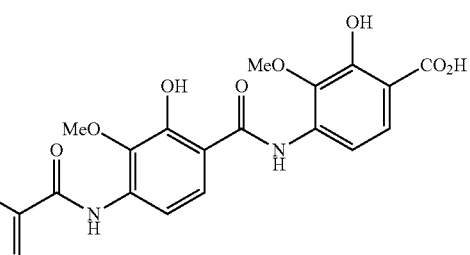

Chemical Formula: C$_{39}$H$_{32}$N$_6$O$_{11}$S

Exact Mass: 792,1850

BTC (1.15 eq, 0.100 mmol, 30 mg) was dissolved in dry THF (5 ml) under an atmosphere of argon. Thiophene-3-carboxylic acid (3.5 eq, 0.305 mmol, 34 mg) was added.

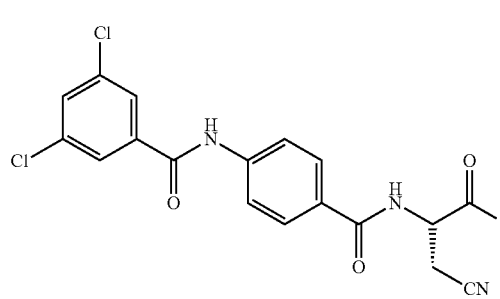
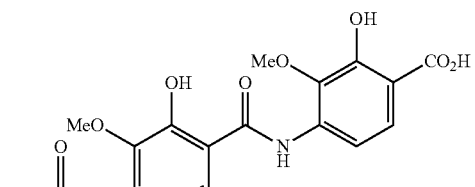

405

Chemical Formula: C₄₁H₃₂Cl₂N₆O₁₁

Exact Mass: 854,1506

The amine (1 eq, 0.087 mmol, 70 mg) and DIPEA (7 eq, 0.611 mmol, 0.100 ml) were dissolved in dry THF (5 ml) under an atmosphere of argon. 3,5-Dichlorobenzoyl chloride (5 eq, 0.436 mmol, 91 mg) was added an the reaction mixture was stirred for 12 hours and the reaction was quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over Na₂SO₄ and filtration, the solvent was removed under reduced pressure. Column chromatography (CHCl₃:MeOH; 1.5% MeOH) yielded the product as an orange oil (82 mg, 99%). The oil (1 eq, 0.075 mmol, 73 mg) and phenylsilane (8 eq, 0.375 mmol, 0.046 ml) were dissolved in dry THF under an atmosphere of argon and exclusion of light. Pd[P(Ph)₃]₄ (0.5 eq, 0.037 mmol, 43 mg) was added and the mixture was stirred 12 h at room temperature. After adding 3 drops of acetic acid the solvent was removed under reduced pressure. The product was isolated after preparative HPLC purification as a white powder (18 mg, 28%).

¹H-NMR (DMSO-d₆, 400 MHz): δ [ppm] 3.08 (dd, J₁=16.79 Hz, J₂=8.73 Hz, 1H), 3.17 (m, 1H), 3.78 (s, 3H), 3.92 (s, 3H), 5.00 (m, 1H), 7.58 (m, 2H), 7.81 (m, 3H), 7.91 (m, 3H), 8.01 (m, 7H), 9.09 (d, J=7.79 Hz, 1H), 9.70 (s, 1H), 10.59 (s, 1H), 10.67 (s, 1H), 11.17 (s, 1H), 11.54 (s, 1H).

HRMS (ESI): [M−H]⁻ calculated: 853.1422.

found: 853.1459.

Compound 23

406

Chemical Formula: C₄₁H₃₃FN₆O₁₁

Exact Mass: 804,2191

The amine (1 eq, 0.087 mmol, 70 mg) and DIPEA (7 eq, 0.611 mmol, 0.100 ml) were dissolved in dry THF (5 ml) under an atmosphere of argon. 4-Fluorobenzoyl chloride (5 eq, 0.436 mmol, 69 mg) was added an the reaction mixture was stirred for 12 hours and the reaction was quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over Na₂SO₄ and filtration, the solvent was removed under reduced pressure. Column chromatography (CHCl₃:MeOH; 1.5% MeOH) yielded the product as an orange oil (78 mg, 97%). The oil (1 eq, 0.081 mmol, 75 mg) and phenylsilane (8 eq, 0.651 mmol, 0.080 ml) were dissolved in dry THF under an atmosphere of argon and exclusion of light. Pd[P(Ph)₃]₄ (0.5 eq, 0.041 mmol, 47 mg) was added and the mixture was stirred 12 h at room temperature. After adding 3 drops of acetic acid the solvent was removed under reduced pressure. The product was isolated after preparative HPLC purification as a white powder (6 mg, 9%).

¹H-NMR (DMSO-d₆, 400 MHz): δ [ppm] 3.01 (dd, J₁=16.79 Hz, J₂=8.73 Hz, 1H), 3.10 (m, 1H), 4.93 (m, 1H), 7.33 (m, 2H), 7.50 (d, J=8.87 Hz, 2H), 7.73 (m, 3H), 7.93 (m, 9H), 9.00 (d, J=7.79 Hz, 1H), 9.63 (s, 1H), 10.45 (s, 1H), 10.52 (s, 1H), 11.06 (s, 1H), 11.47 (s, 1H).

HRMS (ESI): [M−H]⁻ calculated: 803.2108.

found: 803.2130.

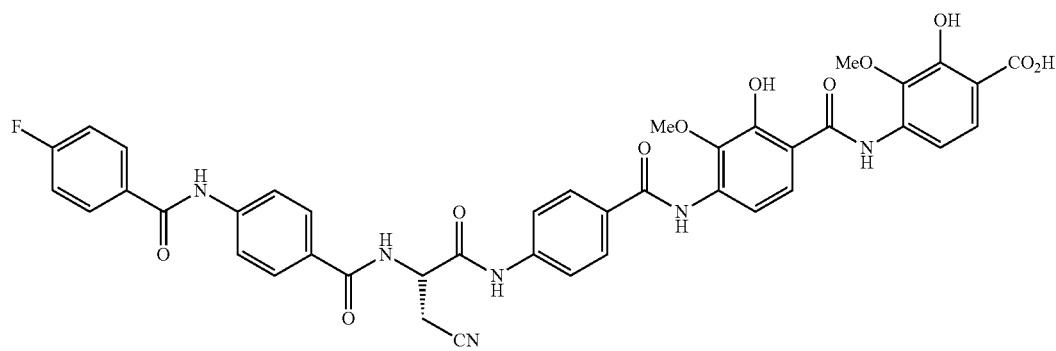

Compound 24

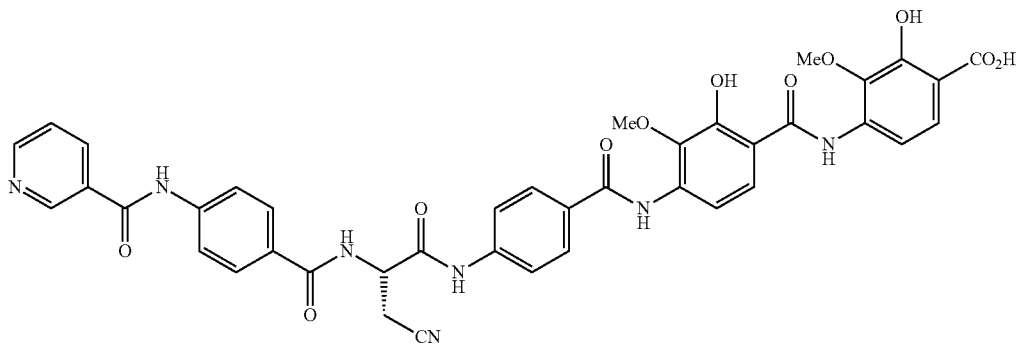

Chemical Formula: C₄₀H₃₃N₇O₁₁

Exact Mass: 787,2238

BTC (1.15 eq, 0.100 mmol, 30 mg) was dissolved in dry THF (5 ml) under an atmosphere of argon. Nicotinic acid (3.5 eq, 0.305 mmol, 66 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over Na₂SO₄ and filtration, the solvent was removed under reduced pressure. Column chromatography (CHCl₃:MeOH; 1.5% MeOH) yielded the product as an yellow solid (64 mg, 80%). The solid (1 eq, 0.068 mmol, 62 mg) and phenylsilane (8 eq, 0.546 mmol, 0.066 ml) were dissolved in dry THF under an atmosphere of argon and exclusion of light. Pd[P(Ph)₃]₄ (0.5 eq, 0.034 mmol, 39 mg) was added and the mixture was stirred 12 h at room temperature. After adding 3 drops of acetic acid the solvent was removed under reduced pressure. The product was isolated after preparative HPLC purification as a white powder (6 mg, 12%).

¹H-NMR (DMSO-d₆, 400 MHz): δ [ppm] 3.08 (m, 1H), 3.17 (m, 1H), 3.78 (s, 3H), 3.92 (s, 3H), 5.00 (m, 1H), 7.58 (m, 4H), 7.80 (dd, J₁=8.60 Hz, J₂=6.18 Hz, 3H), 7.92 (m, 2H), 7.99 (m, 5H), 8.06 (d, J=8.9 Hz, 1H), 8.33 (d, J=7.8 Hz, 1H) 9.08 (d, J=7.3 Hz, 1H), 9.71 (s, 1H), 10.59 (s, 1H), 10.70 (s, 1H), 11.18 (s, 1H), 11.54 (s, 1H).

HR-MS: [M–H]⁻ calculated: 786.21543.

[M–H]⁻ found: 786.21777.

Compound 25

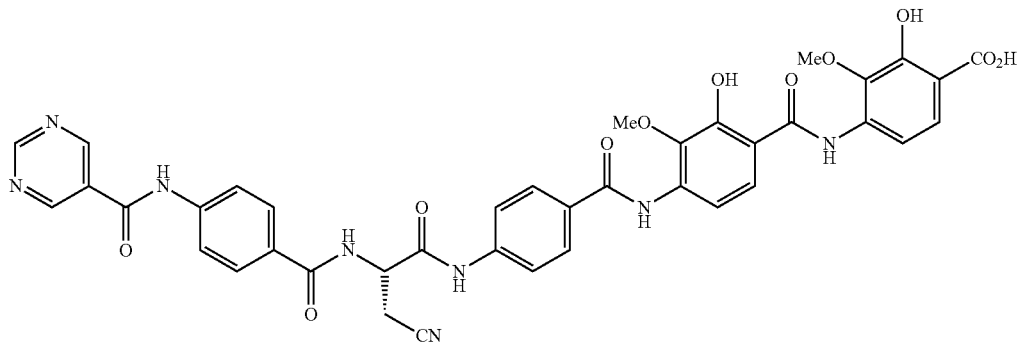

Chemical Formula: C₃₉H₃₂N₈O₁₁

Exact Mass: 788,2191

BTC (1.15 eq, 0.100 mmol, 30 mg) was dissolved in dry THF (5 ml) under an atmosphere of argon. Pyrimidine-5-carboxylic acid (3.5 eq, 0.305 mmol, 67 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over Na₂SO₄ and filtration, the solvent was removed under reduced pressure. Column chromatography (CHCl₃:MeOH; 1.5% MeOH) yielded the product as an yellow solid (55 mg, 65%). The solid (1 eq, 0.058 mmol, 53 mg) and phenylsilane (8 eq, 0.467 mmol, 0.057 ml) were dissolved in dry THF under an atmosphere of argon and exclusion of light. Pd[P(Ph)₃]₄ (0.5 eq, 0.029 mmol, 34 mg) was added and the mixture was stirred 12 h at room temperature. After adding 3 drops of acetic acid the solvent was removed under reduced pressure. The product was isolated after preparative HPLC purification as a white powder (9 mg, 20%).

¹H-NMR (DMSO-d₆, 400 MHz): δ [ppm] 3.08 (m, 1H), 3.17 (dd, J₁=17.1 Hz, J₂=5.2 Hz, 1H), 3.77 (s, 3H), 3.92 (s, 3H), 4.99 (m, 1H), 7.56 (d, J=8.9 Hz, 1H), 7.81 (m, 3H), 7.91 (d, J=8.9 Hz, 2H), 7.99 (d, J=8.4 Hz, 5H) 8.32 (d, J=9.4 Hz, 1H), 9.11 (d, J=7.5 Hz, 1H), 9.32 (s, 2H), 9.39 (s, 1H), 9.70 (s, 1H), 10.61 (s, 1H), 10.87 (s, 1H), 11.15 (s, 1H), 11.57 (s, 1H).

HR-MS: [M–H]⁻ calculated: 787.21068.
[M–H]⁻ found: 787.21283.

Compound 26

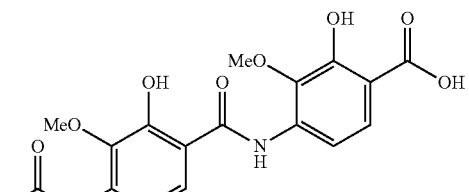
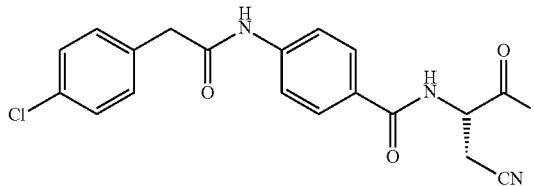

Chemical Formula: $C_{42}H_{35}ClN_6O_{11}$
Exact Mass: 834,2052

BTC (1.15 eq, 0.100 mmol, 30 mg) was dissolved in dry THF (5 ml) under an atmosphere of argon. 2-(4-Chlorophenyl)acetic acid (3.5 eq, 0.305 mmol, 52 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over Na₂SO₄ and filtration, the solvent was removed under reduced pressure. Column chromatography (CHCl₃:MeOH; 1.5% MeOH) yielded the product as an orange oil (35 mg, 42%). The oil (1 eq, 0.037 mmol, 35 mg) and phenylsilane (8 eq, 0.293 mmol, 0.036 ml) were dissolved in dry THF under an atmosphere of argon and exclusion of light. Pd[P(Ph)₃]₄ (0.5 eq, 0.018 mmol, 21 mg) was added and the mixture was stirred 12 h at room temperature. After adding 3 drops of acetic acid the solvent was removed under reduced pressure. The product was isolated after preparative HPLC purification as a white powder (7 mg, 23%).

¹H-NMR (DMSO-d₆, 400 MHz): δ [ppm] 3.05 (m, 1H), 3.15 (m, 1H), 3.70 (s, 2H), 3.77 (s, 3H), 3.91 (s, 3H), 4.97 (m, 1H), 7.38 (m, 4H), 7.57 (d, J=8.33 Hz, 2H), 7.76 (m, 5H), 7.96 (m, 5H), 9.02 (d, J=5.91 Hz, 1H), 9.69 (s, 1H), 10.46 (s, 1H), 10.57 (s, 1H), 11.15 (s, 1H), 11.54 (bs, 1H).

HRMS (ESI): [M–H]⁻ calculated: 833.1969.
found: 833.1962.

Compound 27

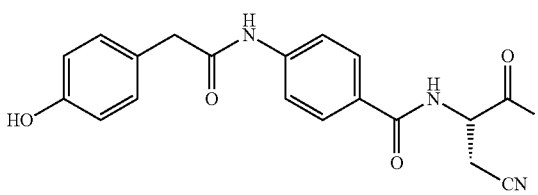

Chemical Formula: $C_{42}H_{36}N_6O_{12}$
Exact Mass: 816,2391

BTC (1.15 eq, 0.100 mmol, 30 mg) was dissolved in dry THF (5 ml) under an atmosphere of argon. 2-(4-(Allyloxy)phenyl)acetic acid (3.5 eq, 0.305 mmol, 59 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over Na₂SO₄ and filtration, the solvent was removed under reduced pressure. Column chromatography (CHCl₃:MeOH; 1.5% MeOH) yielded the product as an orange oil (68 mg, 80%). The oil (1 eq, 0.072 mmol, 70 mg) and phenylsilane (8 eq, 0.576 mmol, 0.071 ml) were dissolved in dry THF under an atmosphere of argon and exclusion of light. Pd[P(Ph)₃]₄ (0.5 eq, 0.036 mmol, 42 mg) was added and the mixture was stirred 12 h at room temperature. After adding 3 drops of acetic acid the solvent was removed under reduced pressure. The product was isolated after preparative HPLC purification as a white powder (30 mg, 51%).

¹H-NMR (DMSO-d₆, 700 MHz): δ [ppm] 3.05 (dd, $J_1$=16.79 Hz, $J_2$=8.73 Hz, 1H), 3.15 (m, 1H), 3.54 (s, 2H), 3.78 (s, 3H), 3.92 (s, 3H), 4.97 (m, 1H), 6.71 (d, J=8.60 Hz, 2H), 7.13 (d, J=8.60 Hz, 2H), 7.58 (m, 2H), 7.71 (d, J=8.87 Hz, 2H), 7.80 (m, 3H), 7.90 (d, J=8.87 Hz, 2H), 7.99 (d, J=8.87 Hz, 2H), 8.05 (d, J=8.87 Hz, 1H), 9.01 (d, J=7.79 Hz, 1H), 9.28 (s, 1H), 9.70 (s, 1H), 10.35 (s, 1H), 10.57 (s, 1H), 11.18 (s, 1H), 11.53 (s, 1H).

HRMS (ESI): [M−H]⁻ calculated: 815.2307.
found: 815.2321.
Compound 28 added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO₃ solution (2×50 ml), aqueous HCl solution (5%, 2×50 ml), water (1×50 ml) and brine (1×50 ml). After drying over Na₂SO₄ and filtration, the solvent was removed under reduced pressure. Column chromatography (CHCl₃:MeOH; 1.5% MeOH) yielded the product as an orange oil (60 mg, 74%). The oil (1 eq, 0.057 mmol, 54 mg) and phenylsilane (8 eq, 0.456 mmol, 0.056 ml) were dissolved in dry THF under an atmosphere of argon and exclusion of light. Pd[P(Ph)₃]₄ (0.5 eq, 0.029 mmol, 33 mg) was added and the mixture was stirred 12 h at room temperature. After adding 3 drops of acetic acid the solvent was removed under reduced pressure. The product was isolated after preparative HPLC purification as a white powder (23 mg, 49%).

¹H-NMR (DMSO-d₆, 400 MHz): δ [ppm] 3.06 (dd, $J_1$=16.79 Hz, $J_2$=8.73 Hz, 1H), 3.15 (m, 1H), 3.69 (s, 2H), 3.78 (s, 3H), 3.92 (s, 3H), 4.97 (m, 1H), 7.16 (m, 2H), 7.37 (m, 2H), 7.58 (m, 2H), 7.72 (d, J=8.06 Hz, 2H), 7.80 (m, 3H), 7.91 (d, J=8.60 Hz, 2H), 7.99 (d, J=8.60 Hz, 2H), 8.06

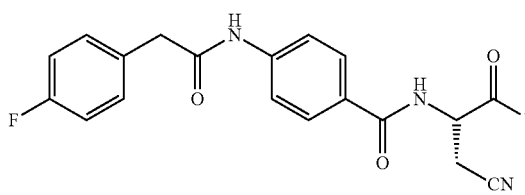

Chemical Formula: C₄₂H₃₅FN₆O₁₁
Exact Mass: 818.2348

BTC (1.15 eq, 0.100 mmol, 30 mg) was dissolved in dry THF (5 ml) under an atmosphere of argon. 2-(4-Fluorophenyl)acetic acid (3.5 eq, 0.305 mmol, 47 mg) was added. syn-Collidine (8 eq, 0.700 mmol, 0.092 ml) was slowly (d, J=8.87 Hz, 1H), 9.02 (d, J=7.79 Hz, 1H), 9.70 (s, 1H), 10.45 (s, 1H), 10.57 (s, 1H), 11.18 (s, 1H), 11.53 (s, 1H), 11.60 (bs, 1H).

HRMS (ESI): [M−H]⁻ calculated: 817.2264.
found: 817.2283.
Compound 29

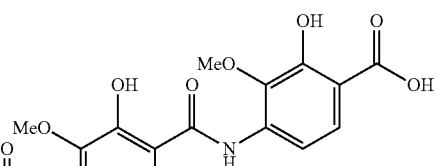

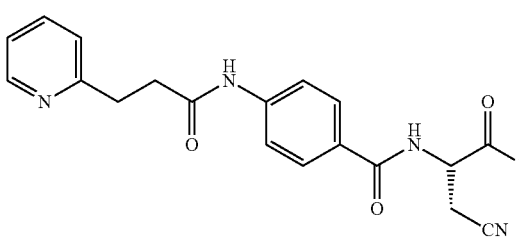

413

Chemical Formula: C$_{42}$H$_{37}$N$_7$O$_{11}$

Exact Mass: 815,2551

BTC (1.15 eq, 0.100 mmol, 30 mg) was dissolved in dry THF (5 ml) under an atmosphere of argon. 3-(Pyridin-2-yl) propanoic acid (3.5 eq, 0.305 mmol, 46 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (47 mg, 58%). The oil (1 eq, 0.047 mmol, 44 mg) and phenylsilane (8 eq, 0.377 mmol, 0.046 ml) were dissolved in dry THF under an atmosphere of argon and exclusion of light. Pd[P(Ph)$_3$]$_4$ (0.5 eq, 0.024 mmol, 27 mg) was added and the mixture was stirred 12 h at room temperature. After adding 3 drops of acetic acid the solvent was removed under reduced pressure. The product was isolated after preparative HPLC purification as a white powder (8 mg, 21%).

$^1$H-NMR (DMSO-d$_6$, 400 MHz): δ [ppm] 2.74 (s, 2H), 3.10 (m, 4H), 3.77 (s, 3H), 3.91 (s, 3H), 4.97 (m, 1H), 7.63 (m, 6H), 7.84 (m, 6H), 8.02 (m, 4H), 9.01 (d, J=7.25 Hz, 1H), 9.70 (s, 1H), 10.24 (s, 1H), 10.57 (s, 1H), 11.18 (s, 1H), 11.55 (s, 1H).

HRMS (ESI): [M−H]$^-$ calculated: 814.2467.
found: 814.2487.

Compound 30

414

Chemical Formula: C$_{42}$H$_{36}$N$_6$O$_{12}$

Exact Mass: 816,2391

BTC (1.15 eq, 0.100 mmol, 30 mg) was dissolved in dry THF (5 ml) under an atmosphere of argon. 2-Phenoxyacetic acid (3.5 eq, 0.305 mmol, 46 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (73 mg, 90%). The oil (1 eq, 0.070 mmol, 66 mg) and phenylsilane (8 eq, 0.561 mmol, 0.069 ml) were dissolved in dry THF under an atmosphere of argon and exclusion of light. Pd[P(Ph)$_3$]$_4$ (0.5 eq, 0.024 mmol, 27 mg) was added and the mixture was stirred 12 h at room temperature. After adding 3 drops of acetic acid the solvent was removed under reduced pressure. The product was isolated after preparative HPLC purification as a white powder (11 mg, 19%).

$^1$H-NMR (DMSO-d$_6$, 400 MHz): δ [ppm] 3.06 (m, 1H), 3.16 (m, 1H), 3.77 (s, 3H), 3.91 (s, 3H), 4.74 (s, 2H), 4.98 (m, 1H), 6.99 (m, 3H), 7.32 (m, 3H), 7.79 (m, 4H), 7.93 (d, J=8.06 Hz, 2H), 7.99 (d, J=8.60 Hz, 2H), 8.05 (d, J=8.60 Hz, 1H), 9.05 (d, J=6.98 Hz, 1H), 9.70 (s, 1H), 10.37 (s, 1H), 10.58 (s, 1H), 11.17 (s, 1H), 11.54 (s, 1H).

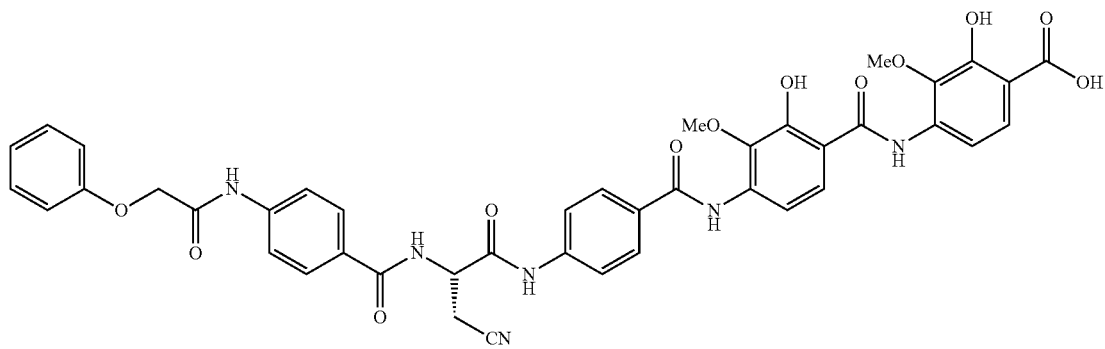

Compound 31

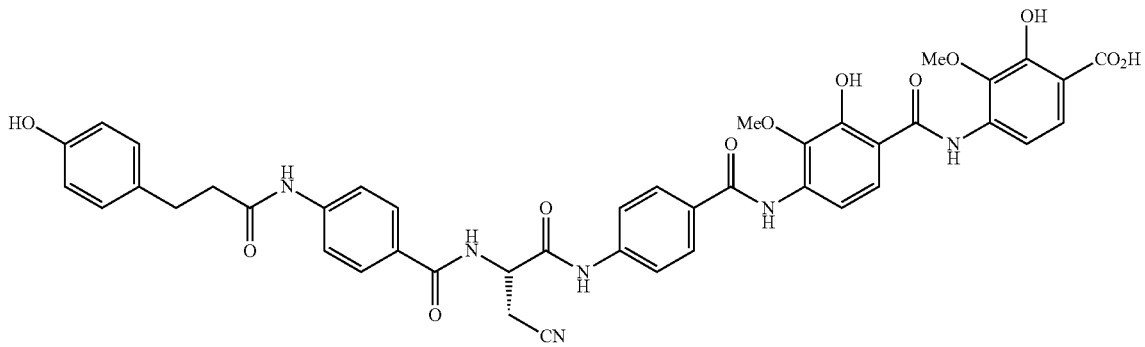

Chemical Formula: C$_{43}$H$_{38}$N$_6$O$_{12}$
Exact Mass: 830,2548

BTC (1.15 eq, 0.100 mmol, 30 mg) was dissolved in dry THF (5 ml) under an atmosphere of argon. 3-(4-(Allyloxy)phenyl)propanoic acid (3.5 eq, 0.305 mmol, 63 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (84 mg, 97%). The oil (1 eq, 0.080 mmol, 79 mg) and phenylsilane (8 eq, 0.640 mmol, 0.079 ml) were dissolved in dry THF under an atmosphere of argon and exclusion of light. Pd[P(Ph)$_3$]$_4$ (0.5 eq, 0.040 mmol, 46 mg) was added and the mixture was stirred 12 h at room temperature. After adding 3 drops of acetic acid the solvent was removed under reduced pressure. The product was isolated after preparative HPLC purification as a white powder (13 mg, 20%).

$^1$H-NMR (DMSO-d$_6$, 400 MHz): δ [ppm] 2.59 (t, J=7.79 Hz, 2H), 2.80 (t, J=7.52 Hz, 2H), 3.06 (dd, J$_1$=16.92 Hz, J$_2$=8.60 Hz, 1H), 3.15 (m, 1H), 3.77 (s, 3H), 3.92 (s, 3H), 4.97 (m, 1H), 6.66 (d, J=8.33 Hz, 2H), 7.03 (d, J=8.33 Hz, 2H), 7.58 (m, 2H), 7.70 (d, J=8.60 Hz, 2H), 7.80 (m, 3H), 7.90 (d, J=8.87 Hz, 2H), 7.99 (d, J=8.87 Hz, 2H), 8.06 (d, J=8.87 Hz, 1H), 9.01 (d, J=8.06 Hz, 1H), 9.17 (bs, 1H), 9.71 (s, 1H), 10.17 (s, 1H), 10.57 (s, 1H), 11.19 (s, 1H), 11.54 (s, 1H), 11.61 (bs, 1H).

HRMS (ESI): [M−H]$^−$ calculated: 829.2464.
found: 829.2483.

Compound 32

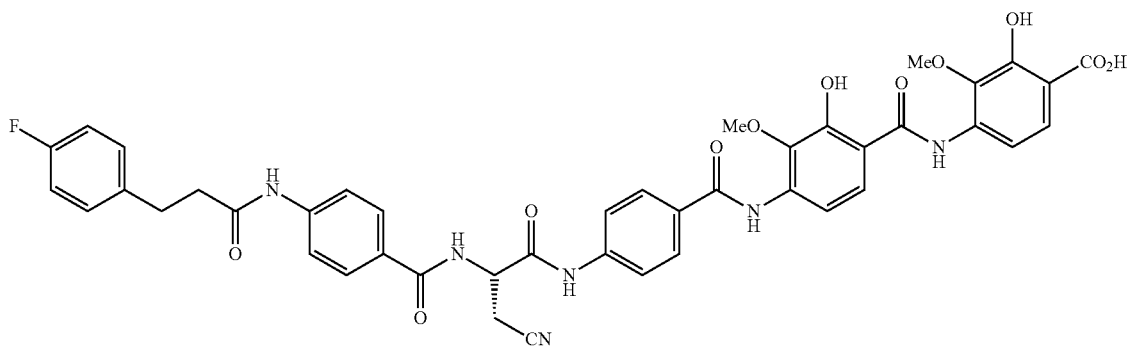

Chemical Formula: C$_{43}$H$_{37}$FN$_6$O$_{11}$
Exact Mass: 832,2504

BTC (1.15 eq, 0.100 mmol, 30 mg) was dissolved in dry THF (5 ml) under an atmosphere of argon. 3-(4-Fluorophenyl)propanoic acid (3.5 eq, 0.305 mmol, 51 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (72 mg, 87%). The oil (1 eq, 0.071 mmol, 67 mg) and phenylsilane (8 eq, 0.566 mmol, 0.070 ml) were dissolved in dry THF under an atmosphere of argon and exclusion of light. Pd[P(Ph)$_3$]$_4$ (0.5 eq, 0.035 mmol, 41 mg) was added and the mixture was stirred 12 h at room temperature. After adding 3 drops of acetic acid the solvent was removed under reduced pressure. The product was isolated after preparative HPLC purification as a white powder (29 mg, 49%).

$^1$H-NMR (DMSO-$d_6$, 400 MHz): δ [ppm] 2.66 (d, J=7.66 Hz, 2H), 2.91 (d, J=7.52 Hz, 2H), 3.06 (dd, J$_1$=16.79 Hz, J$_2$=8.73 Hz, 1H), 3.15 (m, 1H), 3.78 (s, 3H), 3.92 (s, 3H), 4.97 (m, 1H), 7.11 (m, 2H), 7.29 (m, 2H), 7.58 (m, 2H), 7.70 (d, J=8.87 Hz, 2H), 7.80 (m, 3H), 7.90 (d, J=8.60 Hz, 2H), 7.99 (d, J=8.60 Hz, 2H), 8.06 (d, J=8.87 Hz, 1H), 9.01 (d, J=7.79 Hz, 1H), 9.71 (s, 1H), 10.20 (s, 1H), 10.57 (s, 1H), 11.18 (s, 1H), 11.54 (s, 1H), 11.65 (bs, 1H).

HRMS (ESI): [M−H]$^-$ calculated: 831.2421.
found: 831.2437.
Compound 34 ml) were dissolved in dry THF under an atmosphere of argon and exclusion of light. Pd[P(Ph)$_3$]$_4$ (0.5 eq, 0.019 mmol, 22 mg) was added and the mixture was stirred 12 h at room temperature. After adding 3 drops of acetic acid the solvent was removed under reduced pressure. The product was isolated after preparative HPLC purification as a white powder (4 mg, 13%).

$^1$H-NMR (DMSO-$d_6$, 400 MHz): δ [ppm] 0.85 (m, 4H), 1.20 (m, 7H), 3.05 (m, 1H), 3.12 (m, 1H), 3.75 (s, 3H), 3.84 (s, 3H), 4.95 (m, 1H), 7.51 (d, J=8.60 Hz, 2H), 7.68 (d, J=8.87 Hz, 3H), 7.76 (m, 3H), 7.87 (d, J=8.87 Hz, 2H), 7.96 (d, J=8.60 Hz, 2H), 8.97 (d, J=7.79 Hz, 1H), 9.63 (s, 1H), 10.12 (s, 1H), 10.55 (s, 1H), 10.82 (bs, 1H).

HRMS (ESI): [M+H]$^+$ calculated: 781.2828.
found: 781.2837.
[M+Na]$^+$ calculated: 803.2647.
found: 803.2654.
Compound 35

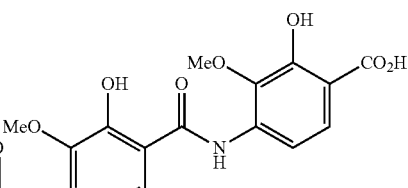

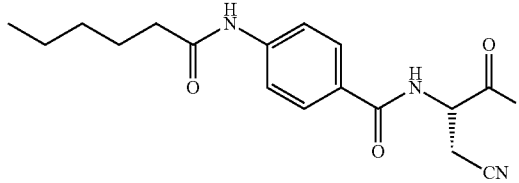

Chemical Formula: $C_{40}H_{40}N_6O_{11}$
Exact Mass: 780,2755

BTC (1.15 eq, 0.100 mmol, 30 mg) was dissolved in dry THF (5 ml) under an atmosphere of argon. Hexanoic acid (3.5 eq, 0.305 mmol, 35 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (39 mg, 50%). The oil (1 eq, 0.039 mmol, 35 mg) and phenylsilane (8 eq, 0.311 mmol, 0.038

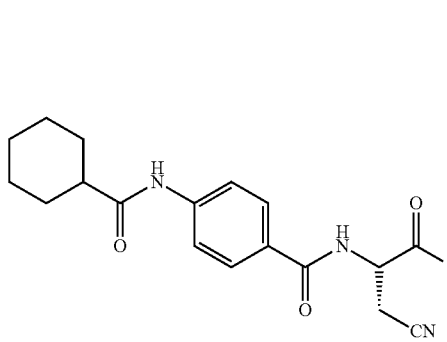

Chemical Formula: $C_{41}H_{40}N_6O_{11}$
Exact Mass: 792,2755

BTC (1.15 eq, 0.100 mmol, 30 mg) was dissolved in dry THF (5 ml) under an atmosphere of argon. Cyclohexanecarboxylic acid (3.5 eq, 0.305 mmol, 40 mg) was added. syn-Collidine (8 eq, 0.700 mmol, 0.092 ml) was slowly added via syringe and the white suspension was stirred at room temperature for 10 min. The amine (1 eq, 0.087 mmol, 70 mg) and DIPEA (10 eq, 0.872 mmol, 0.150 ml) were added via syringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (61 mg, 77%). The oil (1 eq, 0.062 mmol, 57 mg) and phenylsilane (8 eq, 0.500 mmol, 0.062 ml) were dissolved in dry THF under an atmosphere of argon and exclusion of light. Pd[P(Ph)$_3$]$_4$ (0.5 eq, 0.031 mmol, 36 mg) was added and the mixture was stirred 12 h at room temperature. After adding 3 drops of acetic acid the solvent was removed under reduced pressure. The product was isolated after preparative HPLC purification as a white powder (9 mg, 18%).

$^1$H-NMR (DMSO-d$_6$, 400 MHz): δ [ppm] 1.10 (m, 2H), 1.20 (m, 2H), 1.34 (m, 2H), 1.59 (m, 1H), 1.72 (m, 4H), 2.99 (dd, J$_1$=16.66 Hz, J$_2$=8.87 Hz, 1H), 3.08 (m, 1H), 3.71 (s, 3H), 3.84 (s, 1H), 4.90 (m, 1H), 7.50 (d, J=8.87 Hz, 2H), 7.66 (d, J=8.60 Hz, 2H), 7.73 (m, 3H), 7.82 (d, J=8.87 Hz, 2H), 7.92 (m, 3H), 8.93 (d, J=7.79 Hz, 1H), 9.63 (s, 1H), 10.03 (s, 1H), 10.51 (s, 1H), 11.06 (s, 1H), 11.47 (bs, 1H).

HRMS (ESI): [M+H]$^+$ calculated: 793.2822.
found: 793.2836.
[M+Na]$^+$ calculated: 815.2647.
found: 815.2654.

Compound 36 under an atmosphere of argon. AdCOCl (5 eq, 0.436 mmol, 87 mg) was added an the reaction mixture was stirred for 12 hours and the reaction was quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (73 mg, 87%). The oil (1 eq, 0.071 mmol, 69 mg) and phenylsilane (8 eq, 0.568 mmol, 0.070 ml) were dissolved in dry THF under an atmosphere of argon and exclusion of light. Pd[P(Ph)$_3$]$_4$ (0.5 eq, 0.036 mmol, 41 mg) was added and the mixture was stirred 12 h at room temperature. After adding 3 drops of acetic acid the solvent was removed under reduced pressure. The product was isolated after preparative HPLC purification as a white powder (33 mg, 55%).

$^1$H-NMR (DMSO-d$_6$, 700 MHz): δ [ppm] 1.72 (s, 6H), 1.94 (s, 6H), 2.04 (s, 3H), 3.07 (m, 1H), 3.16 (m, 1H), 3.79 (s, 3H), 3.92 (s, 3H), 4.99 (m, 1H), 7.59 (m, 2H), 7.81 (m, 5H), 7.91 (d, J=8.37 Hz, 2H), 8.00 (d, J=8.37 Hz, 2H), 8.05 (d, J=8.67 Hz, 1H), 9.00 (d, J=7.78 Hz, 1H), 9.39 (s, 1H), 9.70 (s, 1H), 10.58 (s, 1H), 11.70 (s, 1H), 11.54 (s, 1H).

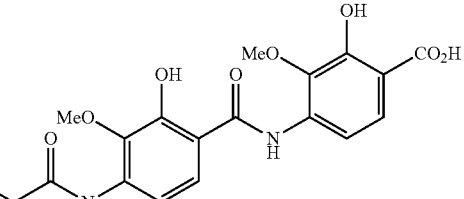

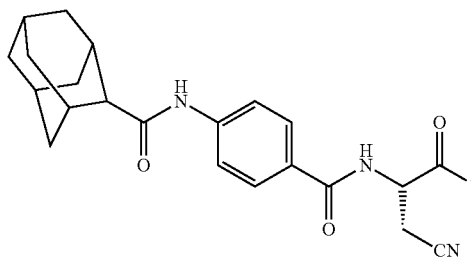

Chemical Formula: C$_{45}$H$_{44}$N$_6$O$_{11}$
Exact Mass: 844.3068

The amine (1 eq, 0.087 mmol, 70 mg) and DIPEA (7 eq, 0.611 mmol, 0.100 ml) were dissolved in dry THF (5 ml)

HRMS (ESI): [M+H]$^+$ calculated: 845.3141.
found: 845.3134.
[M+Na]$^+$ calculated: 867.2960.
found: 867.2954.

Compound 37

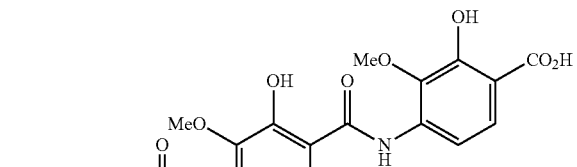

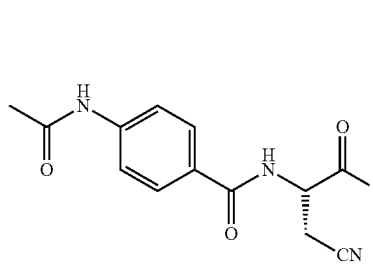

Chemical Formula: $C_{36}H_{32}N_6O_{11}$

Exact Mass: 724,2129

The amine (1 eq, 0.087 mmol, 70 mg) and DIPEA (7 eq, 0.611 mmol, 0.100 ml) were dissolved in dry THF (5 ml) under an atmosphere of argon. Acetyl chloride (5 eq, 0.436 mmol, 34 mg) was added an the reaction mixture was stirred for 12 hours and the reaction was quenched by the addition of water. After removing the organic solvent under reduced pressure the aqueous phase was extracted with EtOAc (3×50 ml). The organic phase was washed with saturated $NaHCO_3$ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange oil (40 mg, 54%). The oil (1 eq, 0.057 mmol, 48 mg) and phenylsilane (8 eq, 0.455 mmol, 0.056 ml) were dissolved in dry THF under an atmosphere of argon and exclusion of light. $Pd[P(Ph)_3]_4$ (0.5 eq, 0.028 mmol, 33 mg) was added and the mixture was stirred 12 h at room temperature. After adding 3 drops of acetic acid the solvent was removed under reduced pressure. The product was isolated after preparative HPLC purification as a white powder (2 mg, 5%).

$^1$H-NMR (DMSO-$d_6$, 800 MHz): δ [ppm] 2.09 (s, 3H), 3.07 (dd, $J_1$=16.17 Hz, $J_2$=8.40 Hz, 1H), 3.16 (m, 1H), 3.78 (s, 3H), 3.93 (s, 3H), 4.98 (m, 1H), 7.58 (d, J=8.68 Hz, 1H), 7.60 (d, J=8.68 Hz, 1H), 7.70 (d, J=8.68 Hz, 2H), 7.81 (m, 3H), 7.91 (d, J=9.59 Hz, 2H), 8.00 (d, J=8.98 Hz, 2H), 8.06 (d, J=8.96 Hz, 1H), 9.00 (d, J=8.40 Hz, 1H), 9.70 (s, 1H), 10.22 (s, 1H), 10.57 (s, 1H), 11.17 (s, 1H), 11.54 (s, 1H).

HRMS (ESI): [M+H]$^+$ calculated: 725.2202.
found: 725.2209.
[M+Na]$^+$ calculated: 747.2021.
found: 747.2027.

Compound 38

Cyclopropanecarbonyl chloride (5 eq, 0.436 mmol, 39.5 µl) was added via syringe to a solution of amine (1 eq, 0.087 mmol, 70 mg) and DIPEA (5 eq, 0.436 mmol, 76 µl) under an atmosphere of argon. The reaction mixture was stirred for 12 h at room temperature and quenched by the addition of water. After removing the organic solvent under reduced pressure the aqueous phase was extracted with EtOAc (3×50 ml). The organic phase was washed with saturated $NaHCO_3$ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange oil (64 mg, 84%). The oil (1 eq, 0.069 mmol, 60 mg) and phenylsilane (8 eq, 0.552 mmol, 68 µl) were dissolved in dry THF under an atmosphere of argon and exclusion of light. $Pd[P(Ph)_3]_4$ (0.5 eq, 0.035 mmol, 40 mg) was added and the mixture was stirred 12 h at room temperature. After adding 3 drops of acetic acid the solvent was removed under reduced pressure. The product was isolated after preparative HPLC purification as a white powder (15 mg, 29%).

$^1$H-NMR (DMSO-$d_6$, 500 MHz): δ [ppm] 0.83 (m, 4H), 1.83 (m, 1H), 3.07 (dd, $J_1$=17.24, $J_2$=9.12 Hz, 1H), 3.16 (dd, $J_1$=16.84, $J_2$=6.14 Hz, 1H), 3.78 (s, 3H), 3.91 (s, 3H), 4.97 (dd, $J_1$=14.27, $J_2$=8.32 Hz, 1H), 7.58 (t, J=8.82 Hz, 2H), 7.72 (d, J=8, 72 Hz, 2H), 7.80 (t, J=8.50 Hz, 3H), 7.90 (d, J=8.72 Hz, 2H), 7.98 (d, J=8.52 Hz, 2H), 8.04 (d, J=8.92 Hz, 1H), 9.00 (d, J=7.73 Hz, 1H), 9.68 (s, 1H), 10.51 (s, 1H), 10.61 (s, 1H), 11.16 (s, 1H), 11.52 (s, 1H).

HRMS (ESI): [M+H]$^+$ calculated: 751.2358.
found: 751.2358.

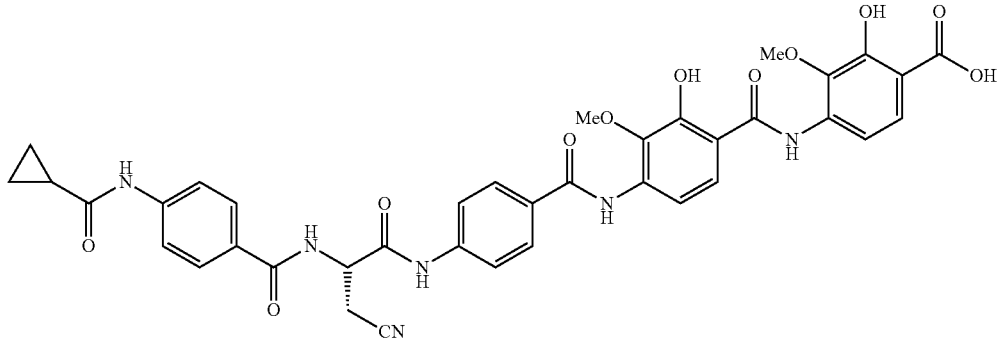

Chemical Formula: $C_{38}H_{34}N_6O_{11}$

Exact Mass: 750,2286

[M+Na]$^+$ calculated: 773.2178.
found: 773.2178.

Compound 39

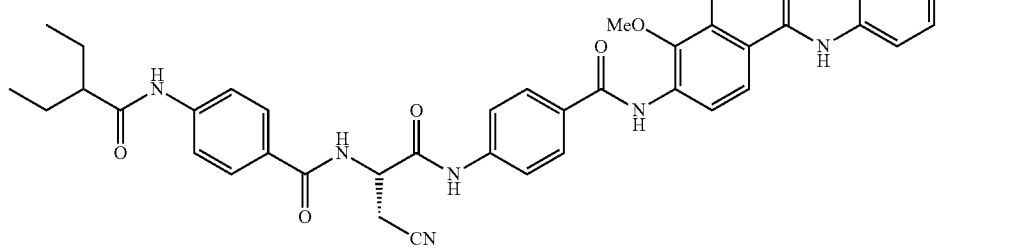

Chemical Formula: $C_{40}H_{40}N_6O_{11}$
Exact Mass: 780,2755

2-Ethylbutanoyl chloride (5 eq, 0.436 mmol, 59.70) was added via syringe to a solution of amine (1 eq, 0.087 mmol, 70 mg) and DIPEA (5 eq, 0.436 mmol, 76 µl) under an atmosphere of argon. The reaction mixture was stirred for 12 h at room temperature and quenched by the addition of water. After removing the organic solvent under reduced pressure the aqueous phase was extracted with EtOAc (3×50 ml). The organic phase was washed with saturated $NaHCO_3$ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange oil (75 mg, 96%). The oil (1 eq, 0.078 mmol, 70 mg) and phenylsilane (8 eq, 0.624 mmol, 77 µl) were dissolved in dry THF under an atmosphere of argon and exclusion of light. $Pd[P(Ph)_3]_4$ (0.5 eq, 0.039 mmol, 45 mg) was added and the mixture was stirred 12 h at room temperature. After adding 3 drops of acetic acid the solvent was removed under reduced pressure. The product was isolated after preparative HPLC purification as a white powder (32 mg, 53%).

$^1$H-NMR (DMSO-$d_6$, 500 MHz): δ [ppm] 0.86 (t, J=7.43 Hz, 6H), 1.46 (m, 2H), 1.57 (m, 2H), 2.26 (m, 1H), 3.06 (dd, $J_1$=17.04, $J_2$=8.72 Hz, 1H), 3.15 (dd, $J_1$=16.64, $J_2$=5.35 Hz, 1H), 3.78 (s, 3H), 3.91 (s, 3H), 4.98 (dd, $J_1$=13.67, $J_2$=8.13 Hz, 1H), 7.57 (d, J=8.72 Hz, 1H), 7.75 (d, J=8.72 Hz, 2H), 7.79 (d, J=8.72 Hz, 1H), 7.81 (d, J=9.12 Hz, 1H), 7.90 (d, J=8.72 Hz, 2H), 7.98 (d, J=8.52 Hz, 2H), 8.04 (d, J=8.52 Hz, 1H), 8.98 (d, J=7.53 Hz, 1H), 9.68 (s, 1H), 10.13 (s, 1H), 10.55 (s, 1H), 11.15 (s, 1H), 11.52 (s, 1H).

HRMS (ESI): [M+H]$^+$ calculated: 781.2826.
found: 781.2828.
[M+Na]$^+$ calculated: 803.2647.

Compound 40

Trimethylacetyl chloride (5 eq, 0.436 mmol, 53.70) was added via syringe to a solution of amine (1 eq, 0.087 mmol, 70 mg) and DIPEA (5 eq, 0.436 mmol, 76 µl) under an atmosphere of argon. The reaction mixture was stirred for 12 h at room temperature and quenched by the addition of water. After removing the organic solvent under reduced pressure the aqueous phase was extracted with EtOAc (3×50 ml). The organic phase was washed with saturated $NaHCO_3$ solution (2×50 ml), aqueous HCl solution (5%, 2×50 ml), water (1×50 ml) and brine (1×50 ml). After drying over $Na_2SO_4$ and filtration, the solvent was removed under reduced pressure. Column chromatography ($CHCl_3$:MeOH; 1.5% MeOH) yielded the product as an orange oil (52 mg, 67%). The oil (1 eq, 0.054 mmol, 48 mg) and phenylsilane (8 eq, 0.432 mmol, 53 µl) were dissolved in dry THF under an atmosphere of argon and exclusion of light. $Pd[P(Ph)_3]_4$ (0.5 eq, 0.027 mmol, 31 mg) was added and the mixture was stirred 12 h at room temperature. After adding 3 drops of acetic acid the solvent was removed under reduced pressure. The product was isolated after preparative HPLC purification as a white powder (15 mg, 36%).

$^1$H-NMR (DMSO-$d_6$, 400 MHz): δ [ppm] 1.24 (s, 9H), 3.06 (dd, $J_1$=16.39, $J_2$=8.33 Hz, 1H), 3.13 (dd, $J_1$=16.79, $J_2$=5.24 Hz, 1H), 3.77 (s, 3H), 3.91 (s, 3H), 4.97 (dd, $J_1$=13.70, $J_2$=7.52 Hz, 1H), 7.56 (d, J=8.87 Hz, 2H), 7.79 (m, 5H), 7.90 (d, J=8.60 Hz, 2H), 7.99 (d, J=8.33 Hz, 2H), 8.04 (d, J=8.60 Hz, 1H), 9.01 (d, J=7.52 Hz, 1H), 9.46 (s, 1H), 9.71 (s, 1H), 10.59 (s, 1H), 11.17 (s, 1H), 11.55 (s, 1H).

HRMS (ESI): [M+H]$^+$ calculated: 767.2671.
found: 767.2670.

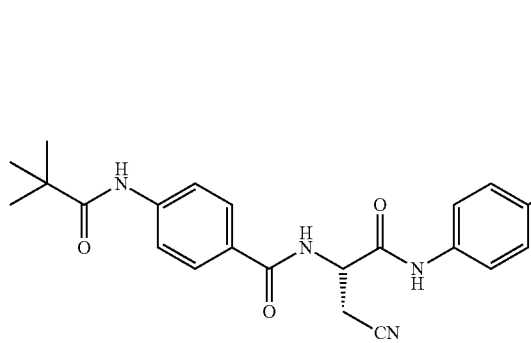
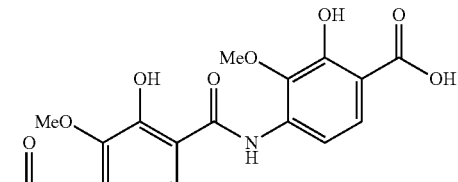

Chemical Formula: $C_{39}H_{38}N_6O_{11}$
Exact Mass: 766,2599

[M+Na]$^+$ calculated: 789.2491.
found: 789.2490.

Compound 41

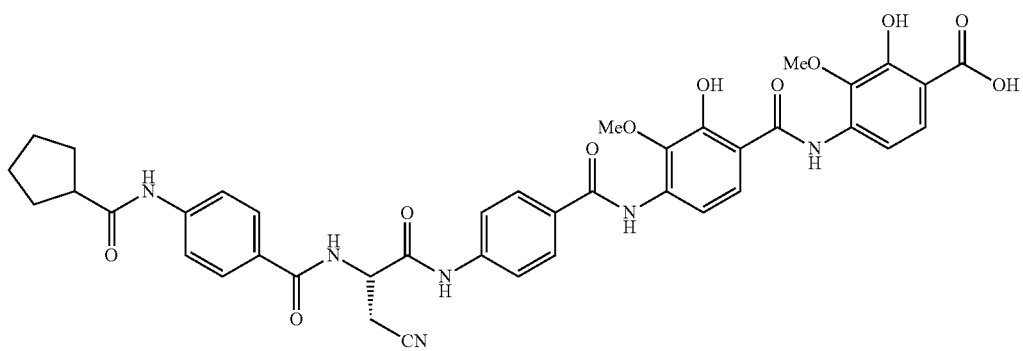

Chemical Formula: C$_{40}$H$_{38}$N$_6$O$_{11}$
Exact Mass: 778,2599

Cyclopentanecarbonyl chloride (5 eq, 0.436 mmol, 53 µl) was added via syringe to a solution of amine (1 eq, 0.087 mmol, 70 mg) and DIPEA (5 eq, 0.436 mmol, 76 µl) under an atmosphere of argon. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (67 mg, 86%). The oil (1 eq, 0.069 mmol, 62 mg) and phenylsilane (8 eq, 0.552 mmol, 68 µl) were dissolved in dry THF under an atmosphere of argon and exclusion of light. Pd[P(Ph)$_3$]$_4$ (0.5 eq, 0.035 mmol, 40 mg) was added and the mixture was stirred 12 h at room temperature. After adding 3 drops of acetic acid the solvent was removed under reduced pressure. The product was isolated after preparative HPLC purification as a white powder (2 mg, 4%).

$^1$H-NMR (DMSO-d$_6$, 400 MHz): δ [ppm] 1.56 (m, 2H), 1.70 (m, 4H), 1.86 (m, 2H), 2.80 (m, 1H), 3.06 (dd, J$_1$=16.92, J$_2$=8.87 Hz, 1H), 3.15 (dd, J$_1$=16.79, J$_2$=4.70 Hz, 1H), 3.77 (s, 3H), 3.89 (s, 3H), 4.97 (dd, J$_1$=14.24, J$_2$=7.79 Hz, 1H), 7.55 (d, J=8.60 Hz, 2H), 7.63 (m, 1H), 7.73 (d, J=8.60 Hz, 2H), 7.79 (t, J=7.80 Hz, 3H), 7.89 (d, J=8.60 Hz, 2H), 7.98 (d, J=8.87 Hz, 2H), 9.01 (d, J=7.25 Hz, 1H), 9.69 (s, 1H), 10.16 (s, 1H), 10.58 (s, 1H), 11.03 (s, 1H), 11.56 (s, 1H).

HRMS (ESI): [M+H]$^+$ calculated: 779.2671.
found: 779.2672.
[M+Na]$^+$ calculated: 801.2491.
found: 801.2487.

Compound 42

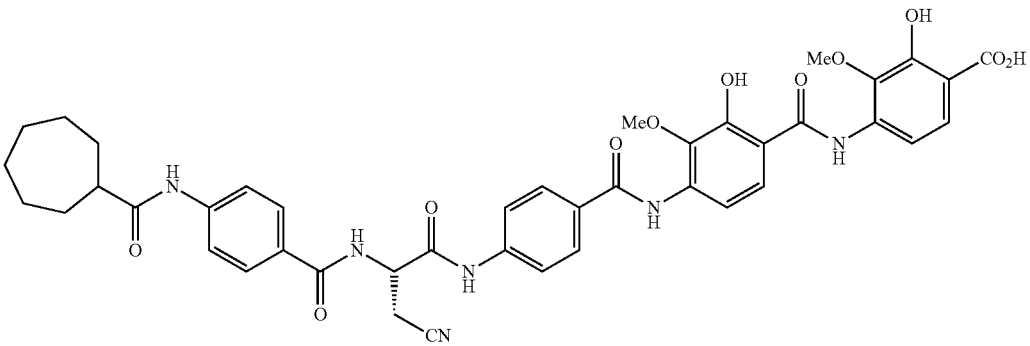

Chemical Formula: C$_{42}$H$_{42}$N$_6$O$_{11}$
Exact Mass: 806,2912

BTC (2.9 eq, 0.253 mmol, 75 mg) was dissolved in dry THF (5 ml) under an atmosphere of argon. Cycloheptanecarboxylic acid (9 eq, 0.785 mmol, 112 mg) was added. syn-Collidine (8 eq, 0.697 mmol, 91 µl) was slowly added via syringe and the white suspension was stirred at room temperature for 10 min. The amine (1 eq, 0.087 mmol, 70 mg) and DIPEA (10 eq, 0.872 mmol, 0.150 ml) were added via syrringe. The reaction mixture was stirred for 12 h at room temperature and quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (48 mg, 60%). The oil (1 eq, 0.049 mmol, 45 mg) and phenylsilane (8 eq, 0.392 mmol, 48 µl) were dissolved in dry THF under an atmosphere of argon and exclusion of light. Pd[P(Ph)$_3$]$_4$ (0.5 eq, 0.025 mmol, 28 mg) was added and the mixture was stirred 12 h at room temperature. After adding 3 drops of acetic acid the solvent was removed under reduced pressure. The product was isolated after preparative HPLC purification as a white powder (10 mg, 25%).

$^1$H-NMR (DMSO-d$_6$, 400 MHz): δ [ppm] 1.54 (m, 4H), 1.72 (m, 4H), 1.84 (m, 4H), 2.54 (m, 1H), 3.06 (dd, J$_1$=17.19, J$_2$=9.13 Hz, 1H), 3.13 (dd, J$_1$=16.92, J$_2$=5.37 Hz, 1H), 3.77 (s, 3H), 3.90 (s, 3H), 4.97 (dd, J$_1$=13.97, J$_2$=8.06 Hz, 1H), 7.56 (d, J=8.87 Hz, 2H), 7.71 (d, J=8.87 Hz, 2H), 7.79 (m, 4H), 7.89 (d, J=8.60 Hz, 2H), 7.98 (d, J=8.60 Hz, 2H), 9.00 (d, J=7.79 Hz, 1H), 9.70 (s, 1H), 10.08 (s, 1H), 10.58 (s, 1H), 11.11 (s, 1H), 11.55 (s, 1H).

HRMS (ESI): [M−H]$^-$ calculated: 805.2839.
found: 805.2826.

Compound 43

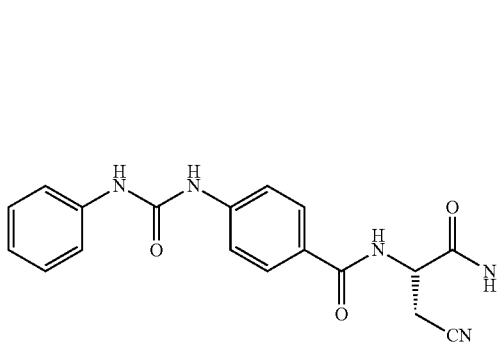

Chemical Formula: $C_{41}H_{35}N_7O_{11}$
Exact Mass: 801.2395

The amine (1 eq, 0.087 mmol, 70 mg) and phenyl isocyanate (5 eq, 0.435 mmol, 0.047 ml) were dissolved in dry THF (5 ml) under an atmosphere of argon. The reaction mixture was stirred at room temperature for 12 h and another portion of phenyl isocyanate (5 eq, 0.435 mmol, 0.047 ml) was added. The solvent was removed under reduced pressure. Column chromatography ($CHCl_3$:MeOH; 1.5% MeOH) yielded the product as an orange oil (78 mg, 97%). The oil (1 eq, 0.073 mmol, 67 mg) and phenylsilane (8 eq, 0.584 mmol, 0.072 ml) were dissolved in dry THF under an atmosphere of argon and exclusion of light. $Pd[P(Ph)_3]_4$ (0.5 eq, 0.036 mmol, 42 mg) was added and the mixture was stirred 12 h at room temperature. After adding 3 drops of acetic acid the solvent was removed under reduced pressure. The product was isolated after preparative HPLC purification as a white powder (8 mg, 14%).

$^1$H-NMR (DMSO-$d_6$, 500 MHz): δ [ppm] 3.08 (dd, $J_1$=16.84, 4.12=8.72 Hz, 1H), 3.16 (m, 1H), 3.79 (s, 3H), 3.93 (s, 3H), 4.99 (m, 1H), 7.00 (t, J=7.43 Hz, 1H), 7.30 (t, J=7.83 Hz, 2H), 7.48 (d, J=7.93 Hz, 2H), 7.59 (m, 4H), 7.81 (m, 3H), 7.91 (d, J=8.52 Hz, 2H), 8.00 (d, J=8.72 Hz, 2H), 8.06 (d, J=8.92 Hz, 1H), 8.79 (s, 1H), 8.97 (d, J=7.73 Hz, 1H), 9.02 (s, 1H), 9.69 (s, 1H), 10.56 (s, 1H), 11.17 (s, 1H), 11.53 (s, 1H), 11.60 (bs, 1H).

HRMS (ESI): [M+H]$^+$ calculated: 802.2461.
found: 802.2467.
[M+Na]$^+$ calculated: 824.2287.
found: 824.2279.

Compound 44

Amino derivative (1.0 eq, 0.062 mmol, 50 mg) and biphenyl-4-carbaldehyde (1 eq, 0.062 mmol, 11 mg) were dissolved in dry THF under argon atmosphere and a catalytic amount of acetic acid was added. After stirring this solution for 60 min $NaBH_3CN$ (1.3 eq, 0.081 mmol, 5 mg) was added. After 3 h of stirring at room temperature another 1.3 eq of $NaBH_3CN$ was added and the Mixture was stirred for 16 h. The reaction was quenched by addition of 1 N HCl and extracted three times with EtOAc. The organic solvent was dried over $Na_2SO_4$, filtered and removed under reduced pressure. Column chromatography ($CHCl_3$:MeOH; 1.5% MeOH) yielded the product as an orange oil (55 mg, 62%). The oil (1 eq, 0.059 mmol, 50 mg) and phenylsilane (8 eq, 0.472 mmol, 58 μl) were dissolved in dry THF under an atmosphere of argon and exclusion of light. $Pd[P(Ph)_3]_4$ (0.5 eq, 0.030 mmol, 35 mg) was added and the mixture was stirred 12 h at room temperature. After adding 3 drops of acetic acid the solvent was removed under reduced pressure. The product was isolated after preparative HPLC purification as a white powder (8 mg, 16%).

$^1$H-NMR (DMSO-$d_6$, 400 MHz): δ [ppm] 3.02 (dd, $J_1$=17.19, $J_2$=9.13 Hz, 1H), 3.11 (dd, $J_1$=16.79, $J_2$=5.51 Hz, 1H), 3.77 (s, 3H), 3.90 (s, 3H), 4.40 (d, J=5.37 Hz, 2H), 4.92 (dd, $J_1$=13.97, $J_2$=8.06 Hz, 1H), 6.65 (d, J=8.87 Hz, 2H), 7.44 (d, J=8.06 Hz, 4H), 7.63 (d, J=6.72 Hz, 2H), 7.65 (d, J=5.91 Hz, 2H), 7.70 (d, J=8.87 Hz, 2H), 7.78 (m, 4H), 7.92 (d, J=8.33 Hz, 2H), 7.97 (d, J=8.87 Hz, 2H), 8.01 (d, J=8.33 Hz, 1H), 8.64 (d, J=7.52 Hz, 1H), 9.69 (s, 1H), 10.51 (s, 1H), 11.07 (s, 1H), 11.57 (s, 1H).

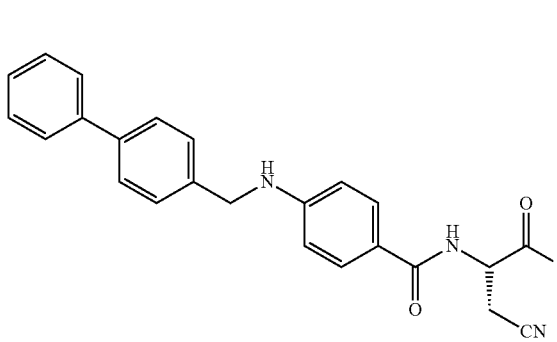

Chemical Formula: $C_{47}H_{40}N_6O_{10}$
Exact Mass: 848.2806

HRMS (ESI): [M+H]$^+$ calculated: 849.2879.
found: 849.2878.

Compound 48

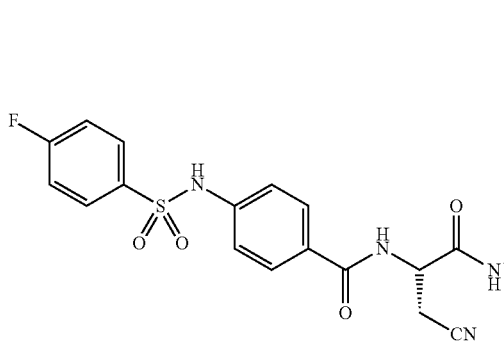

Chemical Formula: C$_{40}$H$_{33}$FN$_6$O$_{12}$S
Exact Mass: 840,1861

The amine (1 eq, 0.087 mmol, 70 mg) and DIPEA (7 eq, 0.611 mmol, 0.100 ml) were dissolved in dry THF (5 ml) under an atmosphere of argon. 4-Fluorobenzene-1-sulfonyl chloride (5 eq, 0.435 mmol, 84 mg) was added and the reaction mixture was stirred for 12 hours and the reaction was quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (62 mg, 89%). The oil (1 eq, 0.072 mmol, 58 mg) and phenylsilane (8 eq, 0.576 mmol, 71 µl) were dissolved in dry THF under an atmosphere of argon and exclusion of light. Pd[P(Ph)$_3$]$_4$ (0.5 eq, 0.036 mmol, 42 mg) was added and the mixture was stirred 12 h at room temperature. After adding 3 drops of acetic acid the solvent was removed under reduced pressure. The product was isolated after preparative HPLC purification as a white powder (23 mg, 38%).

$^1$H-NMR (DMSO-d$_6$, 700 MHz): δ [ppm] 3.02 (dd, J$_1$=16.75, J$_2$=8.68 Hz, 1H), 3.12 (dd, J$_1$=16.75, J$_2$=5.39 Hz, 1H), 3.78 (s, 3H), 3.92 (s, 3H), 4.94 (dd, J$_1$=13.76, J$_2$=8.08 Hz, 1H), 7.21 (d, J=8.68 Hz, 2H), 7.41 (t, J=8.68 Hz, 2H), 7.58 (t, J=8.40 Hz, 2H), 7.76 (d, J=8.38 Hz, 2H), 7.81 (m, 3H), 7.88 (dd, J$_1$=8.68, J$_2$=5.09 Hz, 2H), 7.97 (d, J=8.68 Hz, 2H), 8.03 (d, J=8.68 Hz, 1H), 8.95 (d, J=7.78 Hz, 1H), 9.63 (s, 1H), 10.47 (s, 1H), 10.68 (s, 1H), 11.12 (s, 1H), 11.47 (s, 1H).

HRMS (ESI): [M+H]$^+$ calculated: 841.1934.
found: 841.1929.
[M+Na]$^+$ calculated: 863.1753.
found: 863.1746.

Compound 49

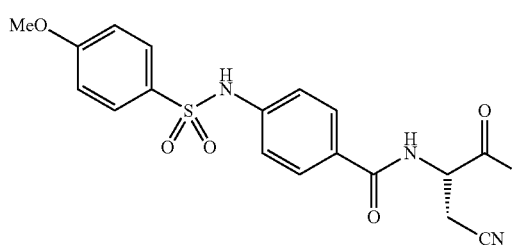

Chemical Formula: C$_{41}$H$_{36}$N$_6$O$_{13}$S
Exact Mass: 852,2061

The amine (1 eq, 0.087 mmol, 70 mg) and DIPEA (7 eq, 0.611 mmol, 0.100 ml) were dissolved in dry THF (5 ml) under an atmosphere of argon. 4-Methoxy-sulfonic carbonyl chloride (3 eq, 0.262 mmol, 54 mg) was added an the reaction mixture was stirred for 12 hours and the reaction was quenched by the addition of water. After removing the organic solvent under reduced pressure the aqueous phase was extracted with EtOAc (3×50 ml). The organic phase was washed with saturated NaHCO$_3$ solution (2×50 ml), aqueous HCl solution (5%, 2×50 ml), water (1×50 ml) and brine (1×50 ml). After drying over Na$_2$SO$_4$ and filtration, the solvent was removed under reduced pressure. Column chromatography (CHCl$_3$:MeOH; 1.5% MeOH) yielded the product as an orange oil (23 mg, 26%). The oil (1 eq, 0.022 mmol, 22 mg) and phenylsilane (8 eq, 0.181 mmol, 0.022 ml) were dissolved in dry THF under an atmosphere of argon and exclusion of light. Pd[P(Ph)$_3$]$_4$ (0.5 eq, 0.011 mmol, 13 mg) was added and the mixture was stirred 12 h at room temperature. After adding 3 drops of acetic acid the solvent was removed under reduced pressure. The product was isolated after preparative HPLC purification as a white powder (9 mg, 46%).

$^1$H-NMR (DMSO-d$_6$, 700 MHz): δ [ppm] 3.02 (dd, J$_1$=16.75, J$_2$=8.68 Hz, 1H), 3.12 (dd, J$_1$=16.75, J$_2$=5.39 Hz, 1H), 3.78 (s, 3H), 3.92 (s, 3H), 4.94 (dd, J$_1$=13.76, J$_2$=8.08 Hz, 1H), 7.21 (d, J=8.68 Hz, 2H), 7.41 (t, J=8.68 Hz, 2H), 7.58 (t, J=8.40 Hz, 2H), 7.76 (d, J=8.38 Hz, 2H), 7.81 (m, 3H), 7.88 (dd, J$_1$=8.68, 4.12=5.09 Hz, 2H), 7.97 (d, J=8.68 Hz, 2H), 8.03 (d, J=8.68 Hz, 1H), 8.95 (d, J=7.78 Hz, 1H), 9.63 (s, 1H), 10.47 (s, 1H), 10.68 (s, 1H), 11.12 (s, 1H), 11.47 (s, 1H).

HRMS (ESI): [M+H]$^+$ calculated: 841.1934.
found: 841.1929.
[M+Na]$^+$ calculated: 863.1753.
found: 863.1746.

Compound 50

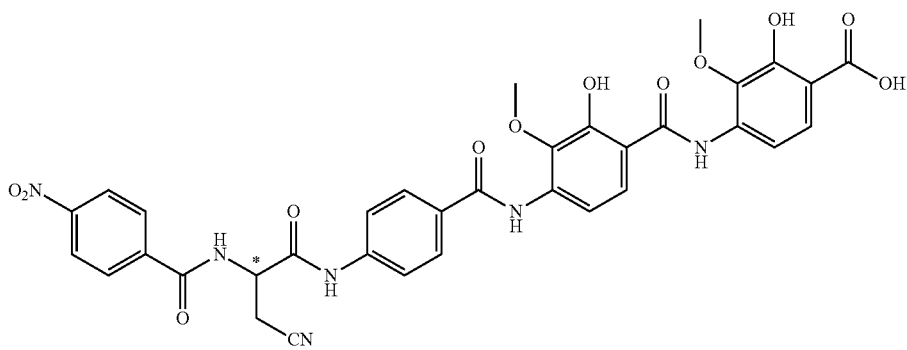

General Deprotection of Compound 53

$^1$H-NMR (DMSO-d$_6$, 500 MHz): δ [ppm] 3.08 (dd, J$_1$=16.84 Hz, J$_2$=8.72 Hz, 1H), 3.18 (m, 1H), 3.77 (s, 3H), 3.90 (s, 3H), 5.02 (m, 1H), 7.55 (d, J=8.92 Hz, 2H), 7.79 (m, 3H), 7.97 (m, 3H), 8.17 (d, J=8.72 Hz, 2H), 8.37 (d, J=8.72 Hz, 2H), 9.53 (d, J=7.53 Hz, 1H), 9.68 (s, 1H), 10.62 (s, 1H), 11.09 (s, 1H), 11.54 (bs, 1H).

HRMS (ESI): [M+H]$^+$ calculated: 713.1838.
found: 713.1862.

Compound 51

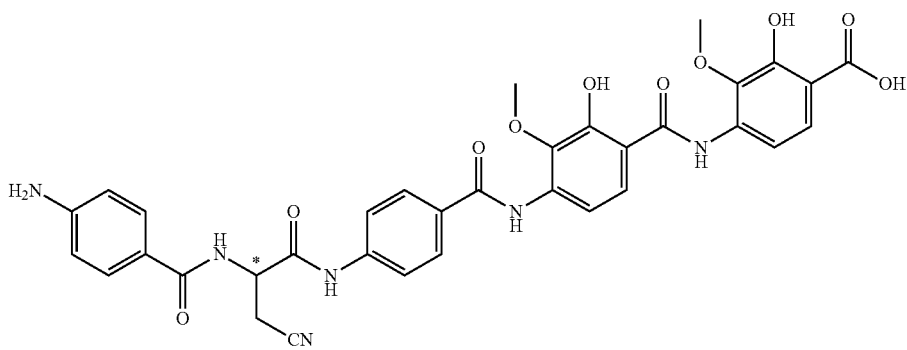 [SMILES: COc1c(NC(=O)c2ccc(NC(=O)c3ccc(NC(=O)C(CC#N)NC(=O)c4ccc([N+](=O)[O-])cc4)cc3)c(OC)c2O)ccc(C(=O)O)c1O]

General Deprotection of Compound 54

$^1$H-NMR (DMSO-d$_6$, 500 MHz): δ [ppm] 3.03 (d, J$_1$=16.84 Hz, J$_2$=8.72 Hz, 1H), 3.11 (m, 1H), 3.77 (s, 3H), 3.91 (s, 3H), 4.92 (m, 1H), 6.63 (d, J=8.52 Hz, 2H), 7.33 (m, 1H), 7.58 (m, 3H), 7.68 (d, J=8.52 Hz, 2H), 7.79 (m, 3H), 7.97 (d, J=8.52 Hz, 2H), 8.05 (d, J=8.92 Hz, 1H), 8.64 (d, J=7.73 Hz, 1H), 9.68 (s, 1H), 10.51 (s, 1H), 11.17 (s, 1H), 11.53 (bs, 1H).

HRMS (ESI): [M+H]$^+$ calculated: 683.2096.
found: 683.2123.
[M+Na]$^+$ calculated: 705.1916.
found: 705.1940.

Compound 52

(S)-4-(3-Cyano-2-(4-nitrobenzamido)propanamido)benzoic acid

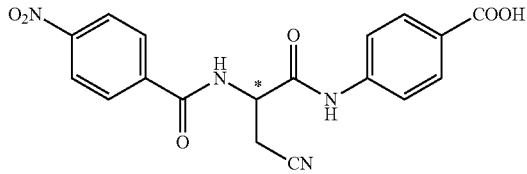 [SMILES: N#CCC(NC(=O)c1ccc([N+](=O)[O-])cc1)C(=O)Nc1ccc(C(=O)O)cc1]

(S)-tert-Butyl 4-(2-(tert-butoxycarbonylamino)-3-cyano-propanamido)benzoate (56) (1.0 eq, 0.81 mmol, 314 mg) was dissolved in HCl/dioxane (4 M, 5 mL) and the reaction mixture was stirred at room temperature until cleavage of the Boc group and tert-butyl ester was completed (LC/MS monitoring, approximately 6 hours). The solvent was removed under reduced pressure and the residue resolved in dry DMF (10 mL) under argon atmosphere. Triethylamine (3.0 eq, 2.42 mmol, 0.73 mL) and 2,5-dioxopyrrolidin-1-yl 4-nitrobenzoate (1.1 eq, 0.89 mmol, 234 mg) were added and the mixture was stirred at room temperature for 16 h. EtOAc (50 mL) was added and the mixture was washed successively with brine (3×25 mL), saturated NaHCO₃ solution (2×25 mL), HCl (5%, 2×25 mL) and brine (1×25 mL). The organic phase was dried over Na₂SO₄, filtered and the solvent was removed under reduced pressure. Column chromatography (CHCl₃:CH₃OH-9:0.5) yielded the product as a white solid (119 mg, 39%)

Compound 53

Allyl 2-(allyloxy)-4-(2-(allyloxy)-4-amino-3-methoxybenzamido)-3-methoxybenzoate

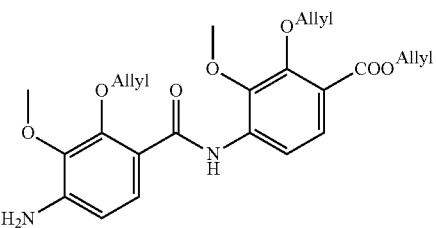

Allyl 2-(allyloxy)-4-(2-(allyloxy)-3-methoxy-4-nitrobenzamido)-3-methoxybenzoate (63) (1.0 eq, 2.41 mmol, 1.2 g) and SnCl₂*2H₂O (7.0 eq, 16.86 mmol, 3.8 g) were dissolved in EtOH (40 mL) and stirred at 60° C. for 1 h. The solution was concentrated under reduced pressure and diluted with water (100 mL). The pH was adjusted to 8-9 by adding saturated NaHCO₃ solution and the aqueous suspension was extracted with EtOAc (3×250 mL). The phases were separated and the organic phase was washed with brine (1×250 mL), dried over Na₂SO₄ and filtered. After removing the solvent under reduced pressure, column chromatography (H:EA-3:1) yielded the product as an orange oil (892 mg, 79%).

Compound 54

(S)-Allyl 2-(allyloxy)-4-(2-(allyloxy)-4-(4-(3-cyano-2-(4-nitrobenzamido)propanamido)benzamido)-3-methoxybenzamido)-3-methoxybenzoate

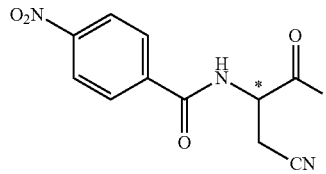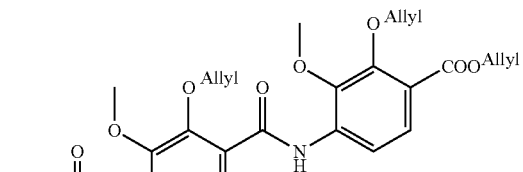

Bis-(trichloromethyl)carbonate (0.5 eq, 0.13 mmol, 37 mg) and (S)-4-(3-Cyano-2-(4-nitrobenzamido)propanamido)benzoic acid (52) (1.5 eq, 0.38 mmol, 146 mg) were dissolved in dry THF (3 mL) under argon atmosphere. 2,4,6-Collidine (8.0 eq, 2.04 mmol, 270 □L) was added slowly via syringe. The resulting suspension was stirred at room temperature for 1 h and a solution of (53) (1.0 eq, 0.26 mmol, 119 mg), DIPEA (10.0 eq, 2.55 mmol, 430 □ L) in dry THF (2 mL) was added. Stirring was continued for 20 h at room temperature and the reaction was quenched by addition of MeOH (2 mL). The organic solvent was removed under reduced pressure and EtOAc (20 mL) was added. The mixture was washed successively with saturated NaHCO₃ (2×10 mL), HCl (5%, 2×10 mL), water (1×10 mL) and brine (1×10 mL). The organic solvent was dried over Na₂SO₄, filtered and removed under reduced pressure. Purification by column chromatography (H:EA-1:1) yielded the product as a white solid (115 mg, 54%).

Compound 55

(S)-Allyl 2-(allyloxy)-4-(2-(allyloxy)-4-(4-(2-(4-aminobenzamido)-3-cyanopropanamido)benzamido)-3-methoxybenzamido)-3-methoxybenzoate

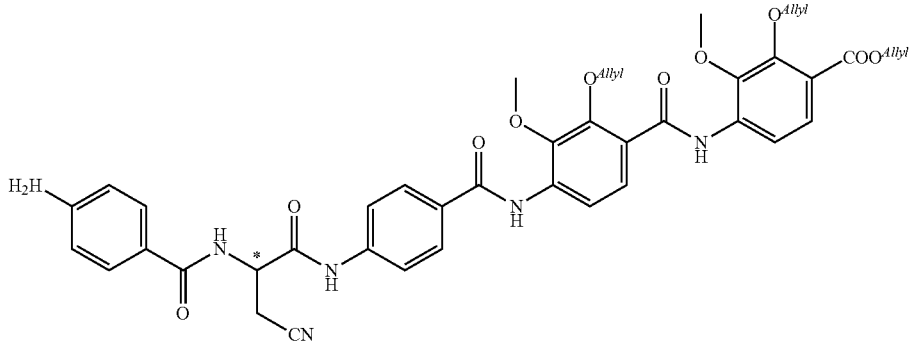

(S)-Allyl 2-(allyloxy)-4-(2-(allyloxy)-4-(4-(3-cyano-2-(4-nitrobenzamido) propanamido)benzamido)-3-methoxybenzamido)-3-methoxybenzoate (54) (1.0 eq, 0.13 mmol, 106 mg) and SnCl$_2$*2H$_2$O (5.0 eq, 0.63 mmol, 143 mg) were dissolved in EtOH (10 mL) and stirred at 60° C. for 6 h. The solution was concentrated under reduced pressure and diluted with water (10 mL). The pH was adjusted to 8-9 by adding saturated NaHCO$_3$ solution and the aqueous suspension was extracted with EtOAc (3×50 mL). The phases were separated and the organic phase was washed with brine (1×25 mL), dried over Na$_2$SO$_4$ and filtered. After removing the solvent under reduced pressure, column chromatography (CHCl$_3$:CH$_3$OH-9:0.3) yielded the product as a slightly yellow solid (69 mg, 67%).

Compound 56

(S)-tert-Butyl 4-(2-(tert-butoxycarbonylamino)-3-cyanopropanamido)benzoate

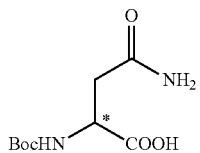 [SMILES: CC(C)(C)OC(=O)NC(CC(N)=O)C(=O)O]

Method A:
Boc-L-Asn-OH (1.0 eq, 4.31 mmol, 1.0 g), DIPEA (5.0 eq, 21.53 mmol, 3.7 mL) and HATU (2.0 eq, 8.61 mmol, 3.3 g) were dissolved in dry DMF (40 mL) under argon atmosphere. After stirring for 10 min at room temperature tert-butyl 4-aminobenzoate (1.0 eq, 4.31 mmol, 0.8 g) was added and stirring was continued for 19 h. EtOAc (200 mL) was added and the mixture was washed successively with brine (3×80 mL), saturated NaHCO$_3$ solution (2×80 mL), HCl (5%, 2×80 mL) and brine (1×80 mL). The organic phase was dried over MgSO$_4$, filtered and the solvent was removed under reduced pressure. Column chromatography (H:EA-4:1) yielded the product as a white solid (1.4 g, 84%).

Method B:
Boc-L-Asn-OH (1.0 eq, 4.31 mmol, 1.0 g), DIPEA (5.0 eq, 21.53 mmol, 3.7 mL) and HATU (2.0 eq, 8.61 mmol, 3.3 g) were dissolved in dry DMF (40 mL) under argon atmosphere. After stirring for 10 min at room temperature tert-butyl 4-aminobenzoate (1.0 eq, 4.31 mmol, 0.8 g) was added and stirring was continued for 19 h. EtOAc (200 mL) was added and the mixture was washed successively with brine (3×80 mL), saturated NaHCO$_3$ solution (2×80 mL), HCl (5%, 2×80 mL) and brine (1×80 mL). The organic phase was dried over MgSO$_4$, filtered and the solvent was removed under reduced pressure. Column chromatography (H:EA-4:1) yielded the product as a white solid (1.4 g, 84%).

Boc-L-Asn-OH (2.0 eq, 2.07 mmol, 481 mg) and DCC (4.0 eq, 4.14 mmol, 854 mg) are dissolved in dry DMF (10 mL) under an atmosphere of argon. tert-butyl 4-aminobenzoate (1.0 eq, 1.04 mmol, 200 mg) is added and the reaction mixture is stirred at room temperature for 12 h. EtOAc (50 mL) is added and the mixture is washed with brine (3×20 mL). The mixture was washed successively with brine (3×80 mL), saturated NaHCO$_3$ solution (2×20 mL), HCl (5%, 2×20 mL) and brine (1×20 mL). The organic phase was dried over MgSO$_4$, filtered and the solvent was removed under reduced pressure. Column chromatography (H:EA-4:1) yielded the product as a white solid (331 mg, 65%).

Compound 63

Allyl 2-(allyloxy)-4-(2-(allyloxy)-3-methoxy-4-nitrobenzamido)-3-methoxybenzoate

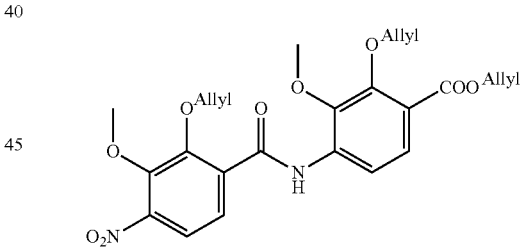

Bis-(trichloromethyl)carbonate (0.5 eq, 1.31 mmol, 388 mg) and 2-(allyloxy)-3-methoxy-4-nitrobenzoic acid (1.5 eq, 4.01 mmol, 1014 mg) were dissolved in dry THF (25 mL) under argon atmosphere. 2,4,6-Collidine (8.0 eq, 21.38 mmol, 2.8 mL) was added slowly via syringe. The resulting suspension was stirred at room temperature for 15 min and a solution of allyl 2-(allyloxy)-4-amino-3-methoxybenzoate (1.0 eq, 2.67 mmol, 703 mg), DIPEA (10.0 eq, 26.72 mmol, 4.5 mL) in dry THF (25 mL) was added. Stirring was continued for 11 h at room temperature and the reaction was quenched by addition of water (10 mL). The organic solvent was removed under reduced pressure and EtOAc (70 mL) was added. The mixture was washed successively with saturated NaHCO$_3$ (2×25 mL), HCl (5%, 2×25 mL), water (1×25 mL) and brine (1×25 mL). The organic solvent was dried over Na$_2$SO$_4$, filtered and removed under reduced pressure. Purification by column chromatography (heaxane (H): ethyl acetate (EA); H:EA-8:1) yielded the product as a slightly yellow oil (1.2 g, 91%).

Compound 64

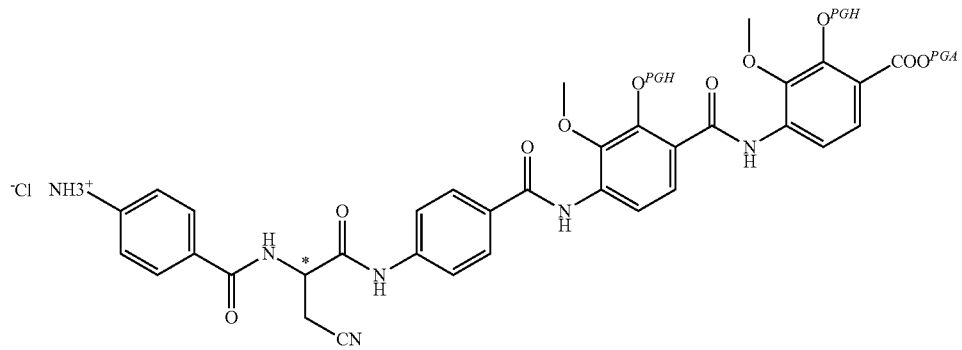

Free amine (1.0 eq) and aldehyde (1.0 eq) were dissolved in MeOH and acetic acid (3.5 eq) was added. To this solution NaBH$_3$CN (1.2 eq) was added and the mixture was stirred for 16 h at room temperature. The reaction mixture was quenched with saturated NaHCO$_3$ solution and extracted with EtOAc. The organic solvent was dried over Na$_2$SO$_4$, filtered and removed under reduced pressure. The residue was dissolved in 4 N HCl in dioxane. After 5 h of stirring at room temperature the organic solvent was removed under reduced pressure. The residue was dissolved in 10% NaHCO$_3$ and filtrated. Acidification with conc. HCl precipitated the pure carboxylic acid which was isolated by filtration Compound 66

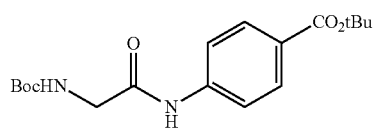

Boc-Gly-OH (2.0 eq, 20.8 mmol, 3.64 g), DIPEA (5.0 eq, 52.0 mmol, 8.8 mL) and HATU (1.9 eq, 19.8 mmol, 7.51 g) were dissolved in dry DMF (200 mL) under argon atmosphere. After stirring for 10 min at room temperature tert-butyl 4-aminobenzoate (1.0 eq, 10.4 mmol, 2.00 g) was added and stirring was continued for 18 h. EtOAc (400 mL) was added and the mixture was washed successively with brine (3×160 mL), saturated NaHCO$_3$ solution (2×160 mL), HCl (5%, 2×160 mL) and brine (1×160 mL). The organic phase was dried over Na$_2$SO$_4$, filtered and the solvent was removed under reduced pressure. Column chromatography (H:EA-5:2) yielded the product as a white solid (3.15 g, 86%).

$^1$H-NMR (dmso-d$_6$, 400 MHz): δ [ppm] 1.38 (s, 3H), 1.52 (s, 3H), 3.73 (d, J=6.18 Hz, 2H), 7.07 (t, J=6.04 Hz, 1H), 7.68 (d, J=8.60 Hz, 2H), 7.84 (d, J=8.87 Hz, 2H), 10.23 (s, 1H).

HRMS (ESI): [M+H]$^+$ calculated: 351.1914.
found: 351.1911.
[M+Na]$^+$ calculated: 373.1734.
found: 373.1729.

Compound 68

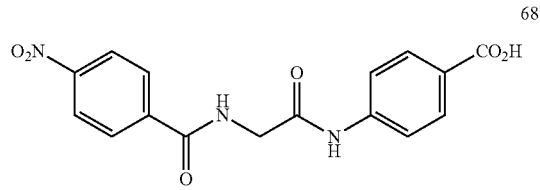 [SMILES: O=C(CNC(=O)c1ccc([N+](=O)[O-])cc1)Nc1ccc(C(=O)O)cc1]

Compound (66) (1.0 eq, 8.57 mmol, 3.0 g) was dissolved in HCl/dioxane (4 M, 20 mL) and the reaction mixture was stirred at room temperature until cleavage of the boc group and tert-butyl ester was completed (LC/MS monitoring, approximately 6 hours). The solvent was removed under reduced pressure and the residue resolved in dry DMF (25 mL) under argon atmosphere. Triethylamine (2.0 eq, 17.14 mmol, 2.4 mL) and 2,5-dioxopyrrolidin-1-yl 4-nitrobenzoate (1.1 eq, 9.43 mmol, 2.5 g) were added and the mixture was stirred at room temperature for 16 h. EtOAc (300 mL) was added and the mixture was washed successively with HCl (5%, 1×100 mL) and brine (3×100 mL). The product was filtered and lyophilized and obtained as a white solid (1.6 g, 54%, two steps).

$^1$H-NMR (dmso-d$_6$, 400 MHz): δ [ppm] 4.14 (d, J=5.64 Hz, 2H), 7.73 (d, J=8.87 Hz, 2H), 7.90 (d, J=8.60 Hz, 2H), 8.14 (d, J=9.13 Hz, 2H), 8.35 (d, J=8.87 Hz, 2H), 9.27 (t, J=5.78 Hz, 1H), 10.48 (s, 1H), 12.56 (bs, 1H).

HRMS (ESI): [M+H]$^-$ calculated: 342.0721.
found: 342.0718.

Compound 69

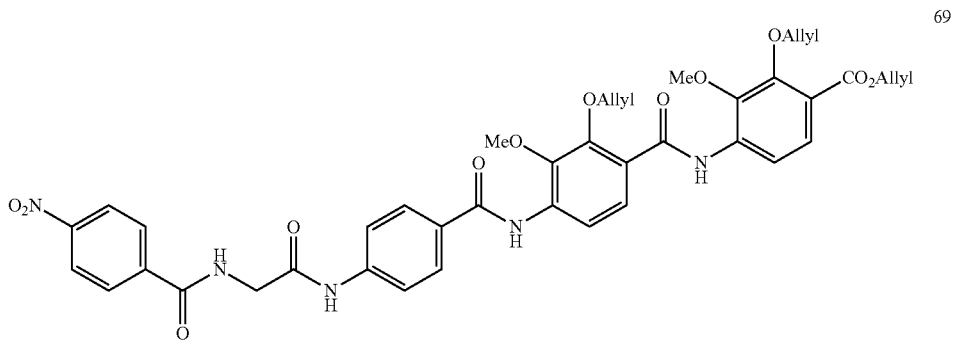

Bis-(trichloromethyl)carbonate (1.15 eq, 0.61 mmol, 182 mg) and (68) (3.5 eq, 1.87 mmol, 641 mg) were dissolved in dry THF (15 mL) under argon atmosphere. 2,4,6-Collidine (8.0 eq, 4.27 mmol, 0.6 mL) was added slowly via syringe. The resulting suspension was stirred at room temperature for 1 h and a solution of (53) (1.0 eq, 0.53 mmol, 250 mg), DIPEA (10.0 eq, 5.34 mmol, 0.9 mL) in dry THF (10 mL) was added. Stirring was continued for 20 h at room temperature and the reaction was quenched by addition of water (10 mL). The organic solvent was removed under reduced pressure and EtOAc (50 mL) was added. The mixture was washed successively with saturated $NaHCO_3$ (2×20 mL), HCl (5%, 2×20 mL), water (1×20 mL) and brine (1×20 mL). The organic solvent was dried over $Na_2SO_4$, filtered and removed under reduced pressure. Purification by column chromatography (C:M-18:1) yielded the product as a white solid (228 mg, 54%).

$^1$H-NMR (dmso-$d_6$, 400 MHz): δ [ppm] 3.92 (s, 3H), 3.93 (s, 3H), 4.16 (d, J=5.91 Hz, 2H), 4.45 (d, J=5.64 Hz, 2H), 4.78 (d, J=5.64 Hz, 2H), 4.80 (d, J=6.18 Hz, 2H), 5.27 (m, 3H), 5.40 (m, 3H), 6.08 (m, 3H), 7.57 (d, J=8.87 Hz, 1H), 7.80 (m, 3H), 7.93 (d, J=8.87 Hz, 1H), 7.98 (d, J=8.87 Hz, 2H), 8.15 (d, J=8.87 Hz, 2H), 8.33 (d, J=8.87 Hz, 1H), 8.37 (d, J=8.87 Hz, 2H), 9.27 (t, J=5.78 Hz, 1H), 10.46 (s, 1H), 10.66 (s, 1H).

HRMS (ESI): [M+H]$^+$ calculated: 794.2668.
found: 794.2678.
[M+Na]$^+$ calculated: 816.2487.
found: 816.2497.

Compound 70

Compound (69) (1.0 eq, 0.26 mmol, 200 mg) and $SnCl_2*2H_2O$ (7.0 eq, 1.80 mmol, 400 mg) were dissolved in EtOH (10 mL) and stirred at 60° C. for 3 h when another portion of $SnCl_2*2H_2O$ (3.5 eq, 0.90 mmol, 200 mg) and the stirring continued for another 3 h. The solution was concentrated under reduced pressure and diluted with EtOAc (200 mL). Saturated $NaHCO_3$ solution (400 mL) was added and extracted with EtOAc (2×300 mL). The phases were separated and the organic phase was washed with brine (1×400 mL), dried over $Na_2SO_4$ and filtered. After removing the solvent under reduced pressure, column chromatography ($CHCl_3$:$CH_3OH$-1.5% MeOH) yielded the product as a slightly yellow solid (140 mg, 71%).

$^1$H-NMR (dmso-$d_6$, 400 MHz): δ [ppm] 3.92 (s, 3H), 3.93 (s, 3H), 4.04 (d, J=5.91 Hz, 2H), 4.54 (d, J=5.91 Hz, 2H), 4.79 (m, 4H), 5.33 (m, 6H), 5.67 (s, 2H), 6.08 (m, 3H), 6.57 (d, J=8.60 Hz, 2H), 7.57 (d, J=8.87 Hz, 1H), 7.63 (d, J=8.60 Hz, 2H), 7.79 (m, 3H), 7.95 (m, 3H), 8.34 (d, J=8.87 Hz, 1H), 8.40 (t, J=5.78 Hz, 1H), 9.66 (s, 1H), 10.35 (s, 1H), 10.66 (s, 1H).

HRMS (ESI): [M+H]$^+$ calculated: 764.2926.
found: 764.2941.

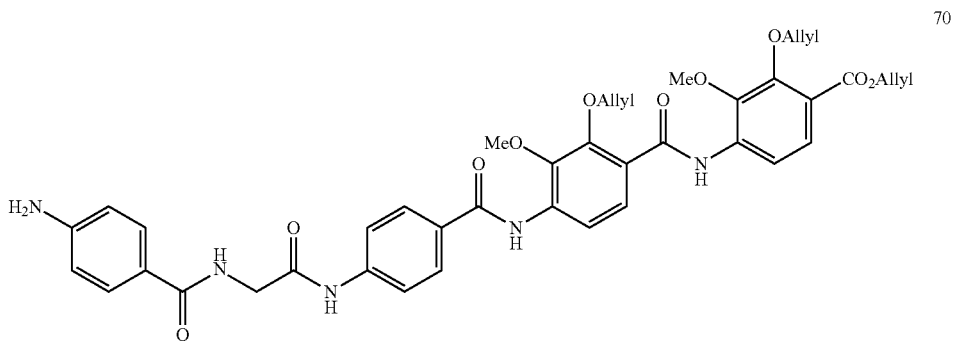

Compound 70

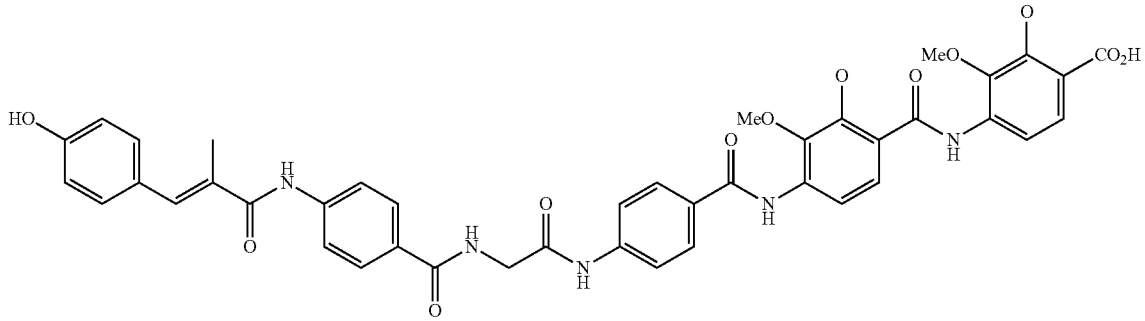

BTC (2.0 eq, 0.19 mmol, 56 mg) was dissolved in dry THF (5 ml) under an atmosphere of argon. (E)-3-(4-(allyloxy)phenyl)-2-methylacrylic acid (6.0 eq, 0.56 mmol, 123 mg) was added. syn-Collidine (8.0 eq, 0.94 mmol, 0.1 ml) was slowly added via syrringe and the white suspension was stirred at room temperature for 20 min. 18 (1 eq, 0.09 mmol, 72 mg) and DIPEA (10 eq, 1.13 mmol, 0.19 ml) dissolved in dry THF (5 mL) were added via syrringe. The reaction mixture was stirred for 4 h at room temperature and quenched by the addition of water. After removing the organic solvent under reduced pressure the aqueous phase was extracted with EtOAc (3×40 ml). The organic phase was washed with saturated $NaHCO_3$ solution (2×25 ml), aqueous HCl solution (5%, 2×25 ml), water (1×25 ml) and brine (1×25 ml). After drying over $Na_2SO_4$ and filtration, the solvent was removed under reduced pressure. Column chromatography ($CHCl_3$:MeOH; 1.5% MeOH) yielded the product as an orange oil (61 mg, 67%). The oil (1 eq, 0.06 mmol, 56 mg) and phenylsilane (8 eq, 0.47 mmol, 0.057 mL) were dissolved in dry THF (5 mL) under an atmosphere of argon and exclusion of light. $Pd[P(Ph)_3]_4$ (0.5 eq, 0.03 mmol, 34 mg) was added and the mixture was stirred 12 h at room temperature. After adding 3 drops of acetic acid the solvent was removed under reduced pressure. The product was isolated by preparative HPLC purification as a white powder (8 mg, 17%).

$^1$H-NMR (DMSO-$d_6$, 700 MHz): δ [ppm] 2.12 (s, 3H), 3.78 (s, 3H), 3.92 (s, 3H), 4.11 (d, J=5.31 Hz, 2H), 6.85 (d, J=8.47, 2H), 7.27 (s, 1H), 7.36 (d, J=8.47 Hz, 2H), 7.59 (t, J=9.28 Hz, 2H), 7.81 (m, 5H), 7.89 (d, J=9.59 Hz, 2H), 7.98 (d, J=7.77 Hz, 2H), 8.07 (d, J=9.03 Hz, 1H), 8.81 (t, J=5.39 Hz, 1H), 9.71 (s, 1H), 9.80 (s, 1H), 8.81 (s, 1H), 10.42 (s, 1H), 11.20 (s, 1H), 11.56 (s, 1H), 11.63 (bs, 1H).

HRMS (ESI): [M−H]$^-$ calculated: 802.2355.
found: 802.2362.

Compound 71

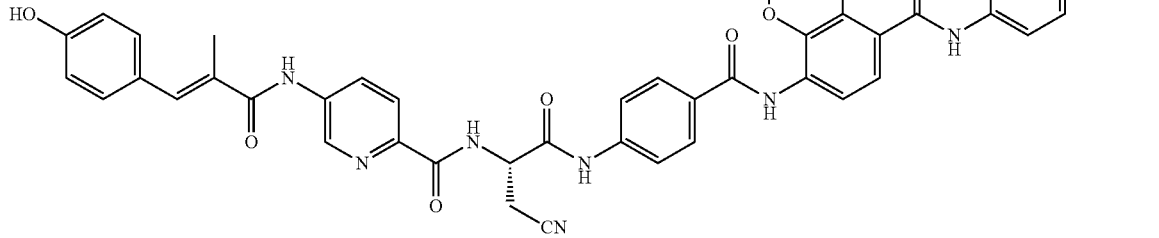

Chemical Formula: $C_{43}H_{37}N_7O_{12}$
Exact Mass: 843,2500

Allyl 2-allyloxy-4-[[2-allyloxy-4-[[4-[[(2S)-2-[[5-[[(E)-3-(4-allyloxyphenyl)-2-methyl-prop-2-enoyl]amino]pyridine-2-carbonyl]amino]-3-cyano-propanoyl]amino]benzoyl]amino]-3-methoxy-benzoyl]amino]-3-methoxy-benzoate (65 mg, 0.065 mmol, 1.00 eq), was dissolved in THF (5 ml). Phenylsilane (56 mg, 64 μl, 0.518 mmol, 8.00 eq) and [Pd(PPh$_3$)$_4$] (38 mg, 0.032 mmol, 0.50 eq) were added and the mixture was stirred for 16 h. After adding 3 drops of acetic acid the solvent was removed and the crude product was purified via HPLC chromatography to give the product as a white solid (42%).

$^1$H-NMR (400 MHz, DMSO-$d_6$): 3.21-3.27 (m, 2H), 3.77 (s, 3H), 3.91 (s, 3H), 5.02-5.07 (m, 1H), 6.85 (d, J=8.6 Hz, 2H), 7.34 (s, 1H), 7.38 (d, J=8.6 Hz, 2H), 7.55-7.60 (m, 3H), 7.76-7.82 (m, 2H), 7.99 (d, J=8.6 Hz, 2H), 8.04-8.09 (m, 2H), 8.36-8.39 (m, 1H), 9.02 (s, 1H), 9.18 (d, J=8.1 Hz, 1H), 9.73 (s, 1H), 10.40 (s, 1H), 11.19 (s, 1H), 11.55 (s, 1H)

HR-MS: calc.: [M+H]$^+$: 844.2549.
found: [M+H]$^+$: 844.2573.

Compound 72

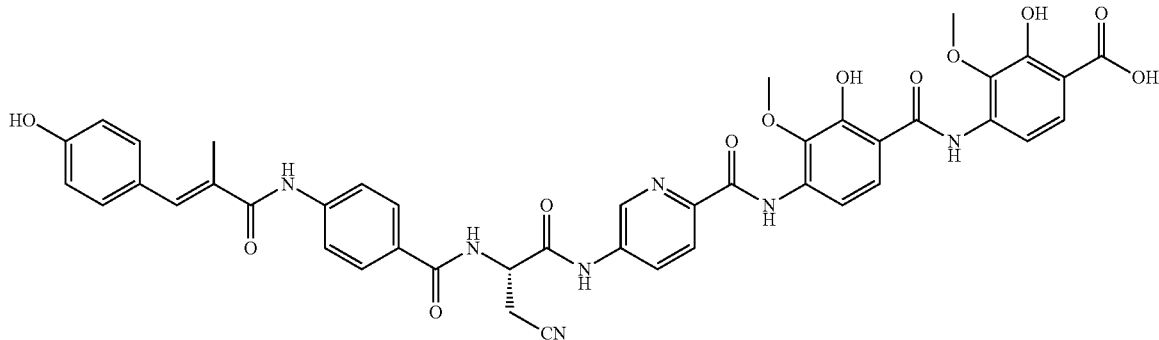 [SMILES: COc1c(NC(=O)c2ccc(NC(=O)c3ccc(NC(=O)[C@H](CC#N)NC(=O)c4ccc(NC(=O)/C(C)=C/c5ccc(O)cc5)cc4)cn3)c(OC)c2O)ccc(C(=O)O)c1O]

Chemical Formula: $C_{43}H_{37}N_7O_{12}$
Exact Mass: 843,2500

Allyl 2-allyloxy-4-[[2-allyloxy-4-[[5-[[(2S)-2-[[4-[[(E)-3-(4-allyloxyphenyl)-2-methyl-prop-2-enoyl]amino]benzoyl]amino]-3-cyano-propanoyl]amino]pyridine-2-carbonyl]amino]-3-methoxy-benzoyl]amino]-3-methoxy-benzoate (1.00 eq) was dissolved in THF. Phenylsilane (8.00 eq) and [Pd(PPh$_3$)$_4$] (0.50 eq) were added and the mixture was stirred for 16 h. After adding 3 drops of acetic acid the solvent was removed and the crude product was purified via HPLC chromatography to give the product as a solid.

Compound 73

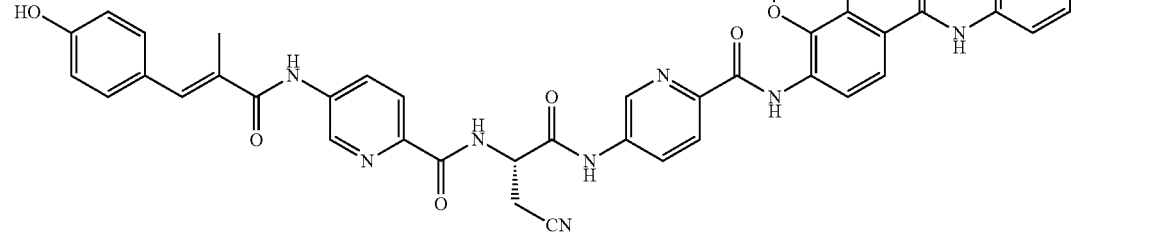

Chemical Formula: $C_{42}H_{36}N_8O_{12}$
Exact Mass: 844,2453

Allyl 2-allyloxy-4-[[2-allyloxy-4-[[5-[[(2S)-2-[[5-[[(E)-3-(4-allyloxyphenyl)-2-methyl-prop-2-enoyl]amino]pyridine-2-carbonyl]amino]-3-cyano-propanoyl]amino]pyridine-2-carbonyl]amino]-3-methoxy-benzoyl]amino]-3-methoxy-benzoate (1.00 eq) was dissolved in THF. Phenylsilane (8.00 eq) and [Pd(PPh$_3$)$_4$] (0.50 eq) were added and the mixture was stirred for 16 h. After adding 3 drops of acetic acid the solvent was removed and the crude product was purified via HPLC chromatography to give the product as a solid.

Compound 74

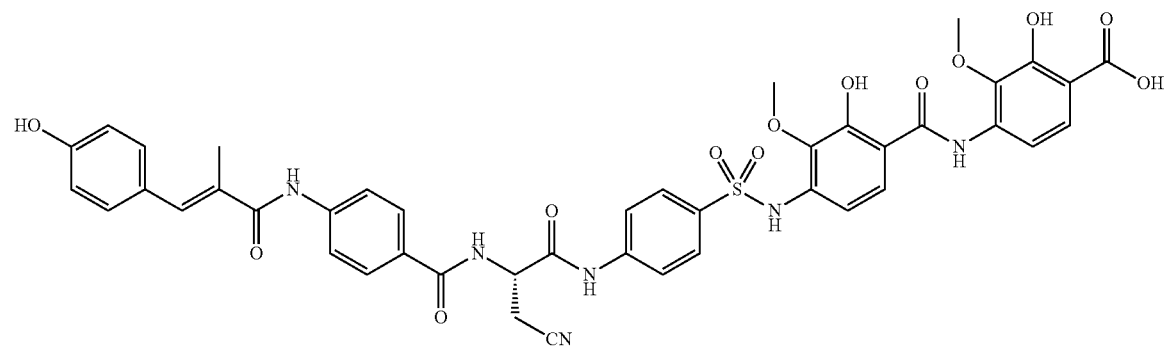 [SMILES: COc1c(NC(=O)c2ccc(NS(=O)(=O)c3ccc(NC(=O)[C@H](CC#N)NC(=O)c4ccc(NC(=O)/C(C)=C/c5ccc(O)cc5)cc4)cc3)c(OC)c2O)ccc(C(=O)O)c1O]

Chemical Formula: $C_{43}H_{38}N_6O_{13}S$
Exact Mass: 878,2218

Allyl 2-allyloxy-4-[[2-allyloxy-4-[[4-[[(2S)-2-[[4-[[(E)-3-(4-allyloxyphenyl)-2-methyl-prop-2-enoyl]amino]benzoyl]amino]-3-cyano-propanoyl (1.00 eq) was dissolved in THF. Phenylsilane (8.00 eq) and [Pd(PPh$_3$)$_4$] (0.50 eq) were added and the mixture was stirred for 16 h. After adding 3 drops of acetic acid the solvent was removed and the crude product was purified via HPLC chromatography to give the product as a solid.
Compound 75

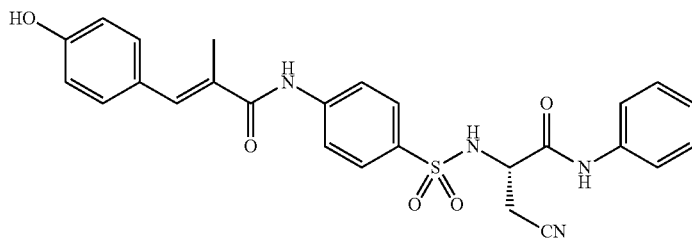

Chemical Formula: $C_{43}H_{38}N_6O_{13}S$
Exact Mass: 878,2218

Allyl 2-allyloxy-4-[[2-allyloxy-4-[[4-[[(2S)-2-[[4-[[(E)-3-(4-allyloxyphenyl)-2-methyl-prop-2-enoyl]amino]phenyl]sulfonylamino]-3-cyano-propanoyl]amino]benzoyl]amino]-3-methoxy-benzoyl]amino]-3-methoxy-benzoate (1.00 eq) was dissolved in THF. Phenylsilane (8.00 eq) and [Pd(PPh$_3$)$_4$] (0.50 eq) were added and the mixture was stirred for 16 h. After adding 3 drops of acetic acid the solvent was removed and the crude product was purified via HPLC chromatography to give the product as a solid.
Compound 76

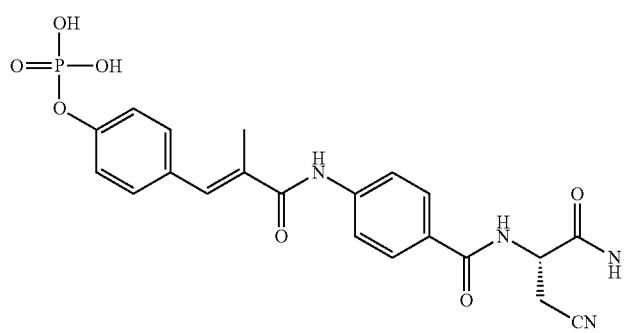

Allyl 2-allyloxy-4-[[2-allyloxy-4-[[4-[[(2S)-3-cyano-2-[[4-[[(E)-3-(4-diallyloxyphosphoryloxy phenyl)-2-methyl-prop-2-enoyl]amino]benzoyl]amino]propanoyl]amino]benzoyl]amino]-3-methoxy-benzoyl]amino]-3-methoxy-benzoate (1 eq, 0.0534 mmol, 60 mg) with phenylsilane (20 eq, 1.07 mmol, 132 µl) dissolved in dry THF under an atmosphere of argon and exclusion of light. Pd[P(Ph)$_3$]$_4$ (1 eq, 0.0534 mmol, 62 mg) was added and the mixture was stirred 12 h at room temperature. After adding 3 drops of acetic acid the solvent was removed under reduced pressure. The final product was isolated after preparative HPCL purification as a white powder Starting Materials Allyl 2-(allyloxy)-4-nitrobenzoate

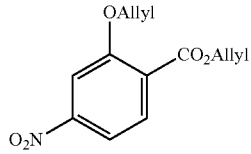

2-Hydroxy-4-nitrobenzoic acid (1.0 eq, 27.32 mmol, 5.0 g) was dissolved in DMF (150 mL) and K$_2$CO$_3$ (4.0 eq, 109.28 mmol, 15.1 g) were added. Allyl-Br (3.0 eq, 81.96 mmol, 7.1 mL) were slowly added via syringe and the reaction mixture was stirred 12 h at room temperature. It was diluted with EtOAc (200 mL) and washed with brine (3×100 mL). The organic solvent was dried over Na$_2$SO$_4$, filtered and purified by column chromatography (H:EE-10:1). The product was isolated as an orange oil (6.5 g, 90%).
$^1$H-NMR (dmso-d$_6$, 400 MHz): δ [ppm] 4.80 (m, 4H), 5.27 (m, 2H), 5.42 (m, 2H), 6.01 (m, 2H), 7.87 (m, 3H).
HRMS (ESI): [M+H]$^+$ calculated: 264.0866.
found: 264.0869.

2-(Allyloxy)-4-nitrobenzoic acid

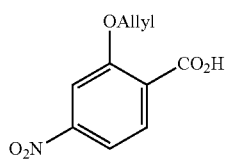

Allyl 2-(allyloxy)-4-nitrobenzoate (1.0 eq, 3.72 mmol, 1.0 g) was dissolved in THF (50 mL) and MeOH (75 mL). KOH (5.0 eq, 18.58 mmol, 1.0 g) dissolved in $H_2O$ (50 mL) was added and the reaction mixture was stirred at room temperature for 23 h. The organic solvents were removed and the aqueous phase acidified with HCl (5%) and the product was filtered and freeze dried. The product was isolated as a white solid (775 mg, 94%).

$^1$H-NMR (dmso-$d_6$, 500 MHz): δ [ppm] 4.81 (d, J=4.76 Hz, 2H), 5.30 (m, 1H), 5.49 (m, 1H), 6.05 (m, 1H), 7.84 (m, 3H).

HRMS (ESI): [M−H]$^-$ calculated: 222.0397. found: 222.0400.

Allyl 2-(allyloxy)-4-aminobenzoate

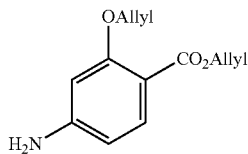

Allyl 2-(allyloxy)-4-nitrobenzoate (1.0 eq, 3.80 mmol, 1.0 g) was dissolved in EtOH (20 mL), $SnCl_2$*$2H_2O$ (5.0 eq, 19.0 mmol, 4.3 g) was added and the reaction mixture was stirred at 60° C. for 4 h. The solvent was removed under reduced pressure and the residue diluted with EtOAc (100 mL). Saturated $NaHCO_3$-solution (300 mL) was added and after phase separation the aqueous phase was extracted with EtOAc (2×200 mL). The organic solvent was washed with brine (1×400 mL), dried over $Na_2SO_4$, filtered and removed under reduced pressure. The product was obtained after column chromatography (H:EE-3:1) as a yellow oil (779 mg, 88%).

$^1$H-NMR (dmso-$d_6$, 400 MHz): δ [ppm] 4.49 (m, 2H), 4.63 (m, 2H), 5.22 (m, 2H), 5.35 (m, 1H), 5.53 (m, 1H), 6.01 (m, 4H), 6.18 (m, 2H), 7.55 (d, J=8.33 Hz, 1H).

HRMS (ESI): [M+H]$^+$ calculated: 234.1125. found: 234.1115.

Allyl 3-methoxy-4-nitrobenzoate

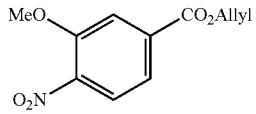

3-Methoxy-4-nitrobenzoic acid (1.0 eq, 5.07 mmol, 1.0 g) and $K_2CO_3$ (2.0 eq, 10.15 mmol, 1.4 g) were dissolved in DMF (20 mL) and Allyl-Br (1.2 eq, 6.09 mmol, 0.5 mL) was added. The reaction mixture was stirred at room temperature for 20 h and diluted with EtOAc (100 mL). Water (100 mL) was added and the phases were separated. The organic phase was washed with brine (3×100 mL), dried over $Na_2SO_4$, filtered and removed under reduced pressure. The product was obtained after column chromatography (H:EE-10:1) as a colorless oil (1.2 g, 98%).

$^1$H-NMR (dmso-$d_6$, 400 MHz): δ [ppm] 4.00 (s, 3H), 4.86 (m, 2H), 5.31 (m, 1H), 5.43 (m, 1H), 6.06 (m, 1H), 7.69 (dd, $J_1$=8.33 Hz, $J_2$=1.61 Hz, 1H), 7.78 (d, J=1.34 Hz, 1H), 8.00 (d, J=8.33 Hz, 1H).

HRMS (ESI): [M+Na]$^+$ calculated: 260.0529. found: 260.0236.

Allyl 4-amino-3-methoxybenzoate

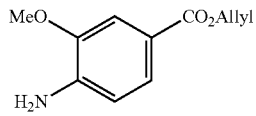

Allyl 3-methoxy-4-nitrobenzoate (1.0 eq, 4.64 mmol, 1.1 g) and $SnCl_2$*$2H_2O$ (5.0 eq, 23.20 mmol, 5.2 g) were dissolved in EtOH (50 mL). The reaction mixture was stirred for 6 h at 60° C. and the solvent was removed under reduced pressure. The residue was diluted with EtOAc (100 mL) and saturated $NaHCO_3$ (50 mL) was added. After separating the phases, the aqueous phase was extracted with EtOAc (100 mL). The combined organic layers were washed with brine (1×200 mL), dried over $Na_2SO_4$ and filtered. After removing the solvent under reduced pressure the product was obtained after column chromatography (H:EE-3:1) as a brown oil (720 mg, 75%).

$^1$H-NMR (dmso-$d_6$, 400 MHz): δ [ppm] 3.81 (s, 3H), 4.71 (m, 2H), 5.23 (m, 1H), 5.36 (m, 1H), 5.67 (s, 2H), 6.02 (s, 1H), 6.66 (d, J=8.33 Hz, 1H), 7.31 (d, J=1.61 Hz, 1H), 7.42 (dd, $J_1$=8.19 Hz, $J_2$=1.75 Hz, 1H).

HRMS (ESI): [M+H]$^+$ calculated: 208.0968. found: 208.0965.

2-(Allyloxy)-3-methoxy-4-nitrobenzaldehyde

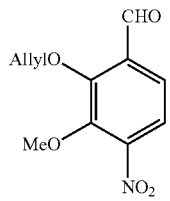

2-Hydroxy-3-methoxy-4-nitrobenzaldehyde (1.0 eq, 72 mmol, 14.25 g) was dissolved in DMF (400 mL) and $K_2CO_3$ (2.0 eq, 145 mmol, 20.00 g) was added. Allyl bromide (1.5 eq, 108 mmol, 9.4 mL) was added via syringe and the mixture was stirred at room temperature for 12 h. EtOAc (500 mL) was added and the mixture was washed with brine (3×200 mL). After drying over $Na_2SO_4$ and filtration the solvent was removed under reduced pressure. Purification by column chromatography (H:EA-10:1) yielded the product as an orange oil (14.0 g, 82%).

$^1$H-NMR (dmso-$d_6$, 400 MHz): δ [ppm] 3.95 (s, 3H), 4.71 (s, 2H), 5.29 (dd, $J_1$=10.48 Hz, $J_2$=1.61 Hz, 1H), 5.41 (dd, $J_1$=17.19 Hz, $J_2$=1.34 Hz, 1H), 6.12 (m, 1H), 7.61 (d, J=8.60 Hz, 1H), 7.74 (d, J=8.33 Hz, 1H), 10.28 (s, 1H).

HRMS (ESI): [M+H]$^+$ calculated: 238.0710. found: 238.0750.

2-(Allyloxy)-3-methoxy-4-nitrobenzoic acid

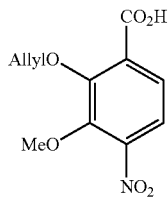

2-(Allyloxy)-3-methoxy-4-nitrobenzaldehyde (1.0 eq, 5.87 mmol, 1.39 g) was dissolved in tBuOH (44 mL) and 2-methylbut-2-ene (1.2 mL/mmol) and NaClO$_2$ (1.2 eq, 7.04 mmol, 0.8 g-80%) in NaH$_2$PO$_4$ (0.5 M in water, 7 mL) was added. The mixture was stirred at room temperature for 3 h and the solvent was removed under reduced pressure. After diluting with water the pH was adjusted to 2 (5% HCl). After cooling the precipitate was filtered and dried. The product was obtained as a white solid (1.4 g, 92%).

$^1$H-NMR (dmso-d$_6$, 400 MHz): δ [ppm] 3.90 (s, 3H), 4.57 (s, 2H), 5.24 (dd, 1H, J$_1$=10.34 Hz, J$_2$=1.48 Hz, 1H), 5.37 (dd, J$_1$=17.19 Hz, J$_2$=1.61 Hz, 1H), 6.03 (m, 1H), 7.52 (d, J=8.60 Hz, 1H), 7.67 (d, J=8.60 Hz, 1H).

HRMS (ESI): [M+H]$^+$ calculated: 254.0659.
found: 254.0662.

Allyl 2-(allyloxy)-3-methoxy-4-nitrobenzoate

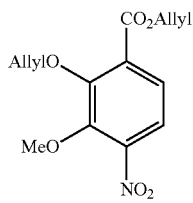

2-(Allyloxy)-3-methoxy-4-nitrobenzoic acid (1.0 eq, 1.76 mmol, 445 mg) was dissolved in DMF (10 mL) and K$_2$CO$_3$ (2.0 eq, 3.52 mmol, 486 mg) was added. Allyl iodide (1.5 eq, 2.66 mmol, 0.24 mL) was added via syringe and the mixture was stirred at room temperature for 12 h. EtOAc (100 mL) was added and the mixture was washed with brine (3×30 mL). After drying over Na$_2$SO$_4$ and filtration the solvent was removed under reduced pressure. Purification by column chromatography (H:EA-12:1) yielded the product as an orange oil (471 mg, 87%).

$^1$H-NMR (dmso-d$_6$, 400 MHz): δ [ppm] 3.92 (s, 3H), 4.56 (d, J=5.91 Hz, 1H), 4.80 (d, J=5.37 Hz, 1H), 5.32 (m, 4H), 6.02 (m, 2H), 7.58 (d, J=8.60 Hz, 1H), 7.71 (d, J=8.60 Hz, 1H).

HRMS (ESI): [M+H]$^+$ calculated: 294.0972.
found: 294.0990.

Allyl 2-(allyloxy)-4-amino-3-methoxybenzoate

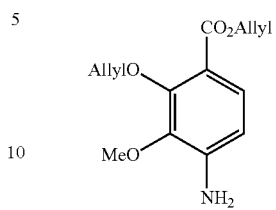

Allyl 2-(allyloxy)-3-methoxy-4-nitrobenzoate (1.0 eq, 1.61 mmol, 471 mg) and SnCl$_2$*2H$_2$O (5.0 eq, 8.04 mmol, 1.81 g) were dissolved in EtOH (20 mL) and stirred at 60° C. for 1 h. The solution was concentrated under reduced pressure and diluted with water (50 mL). The pH was adjusted to 8-9 by adding saturated NaHCO$_3$ solution and the aqueous suspension was extracted with EtOAc (3×100 mL). The phases were separated and the organic phase was washed with brine (1×100 mL), dried over Na$_2$SO$_4$ and filtered. After removing the solvent under reduced pressure, column chromatography (H:EA-8:1) yielded the product as an orange oil (355 mg, 84%).

$^1$H-NMR (dmso-d$_6$, 400 MHz): δ [ppm] 3.67 (s, 3H), 4.43 (m, 2H), 4.64 (m, 2H), 5.19 (m, 2H), 5.34 (m, 2H), 5.77 (s, 2H), 6.01 (m, 2H), 6.44 (d, J=8.60 Hz, 1H), 7.33 (d, J=8.60 Hz, 1H).

HRMS (ESI): [M+H]$^+$ calculated: 264.1230.
found: 264.1233.

(E)-Allyl 3-(4-(allyloxy)phenyl)-2-methylacrylate

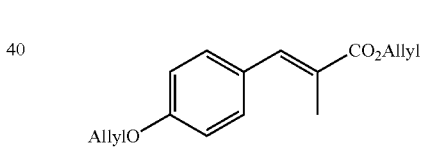

(E)-3-(4-hydroxyphenyl)-2-methyl-prop-2-enoic acid (1.0 eq, 5.60 mmol, 1.0 g), which can be synthesised according to Yamamoto, A., Nakamura, K., Furukawa, K., Konishi, Y., Ogino, T., Higashiura, K., Yago, H., Okamoto, K., Otsuka, M., Chem. Pharm. Bull., 2002, 50, 47-52, was dissolved in DMF (50 mL) and K$_2$CO$_3$ (3.0 eq, 16.8 mmol, 2.32 g) was added. Allyl iodide (3.0 eq, 16.8 mmol, 1.53 mL was added via syringe and the mixture was stirred at room temperature for 12 h. EtOAc (150 mL) was added and the mixture was washed with brine (3×50 mL). After drying over Na$_2$SO$_4$ and filtration the solvent was removed under reduced pressure. Purification by column chromatography (H:EA-12:1-->4:1)) yielded the product as an orange oil (1.3 g, 90%).

$^1$H-NMR (dmso-d$_6$, 400 MHz): δ [ppm] 2.08 (s, 3H), 4.62 (d, J=4.61 Hz, 2H), 4.68 (d, J=5.37 Hz, 2H), 5.32 (m, 4H), 6.03 (m, 2H), 7.02 (d, J=8.87 Hz, 1H), 7.47 (d, J=8.87 Hz, 1H), 7.60 (s, 1H).

HRMS (ESI): [M+H]$^+$ calculated: 259.1329.
found: 259.1335.

(E)-3-(4-(Allyloxy)phenyl)-2-methylacrylic acid

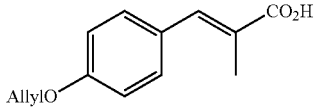

(E)-Allyl 3-(4-(allyloxy)phenyl)-2-methylacrylate (1.0 eq, 1.93 mmol, 500 mg) and KOH (2.0 eq, 3.86 mmol, 217 mg) were dissolved in MeOH (10 mL) and stirred for 16 h at room temperature. The solvent was removed under reduced pressure and the residue suspended in HCl (1 M, 10 mL). The aqueous phase was extracted with EtOAc (3×25 mL). The combined organic layers were washed with brine (1×25 mL), dried over $Na_2SO_4$ and filtered. The product was obtained as a slightly brown-white solid (384 mg, 87%).

$^1$H-NMR (dmso-$d_6$, 400 MHz): δ [ppm] 2.03 (s, 3H), 4.61 (m, 2H), 5.27 (m, 1H), 5.41 (m, 1H), 6.06 (m, 1H), 7.01 (d, J=8.87 Hz, 1H), 7.44 (d, J=8.60 Hz, 1H), 7.55 (s, 1H), 12.38 (s, 1H).

HRMS (ESI): [M+H]$^+$ calculated: 219.1016.
found: 219.1034.

(E)-Allyl 3-(4-(allyloxy)phenyl)-2-methylacrylate

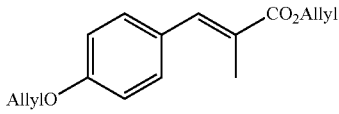

E)-3-(4-(Allyloxy)phenyl)-2-methylacrylic acid (1.0 eq, 5.60 mmol, 1.0 g) was dissolved in DMF (50 mL) and $K_2CO_3$ (3.0 eq, 16.8 mmol, 2.32 g) was added. Allyl iodide (3.0 eq, 16.8 mmol, 1.53 mL was added via syringe and the mixture was stirred at room temperature for 12 h. EtOAc (150 mL) was added and the mixture was washed with brine (3×50 mL). After drying over $Na_2SO_4$ and filtration the solvent was removed under reduced pressure. Purification by column chromatography (H:EA-12:1-->4:1)) yielded the product as an orange oil (1.3 g, 90%).

$^1$H-NMR (dmso-$d_6$, 400 MHz): δ [ppm] 2.08 (s, 3H), 4.62 (d, J=4.61 Hz, 2H), 4.68 (d, J=5.37 Hz, 2H), 5.32 (m, 4H), 6.03 (m, 2H), 7.02 (d, J=8.87 Hz, 1H), 7.47 (d, J=8.87 Hz, 1H), 7.60 (s, 1H).

HRMS (ESI): [M+H]$^+$ calculated: 259.1329.
found: 259.1335.

2,5-dioxopyrrolidin-1-yl 4-nitrobenzoate

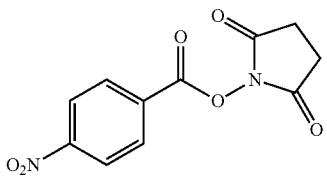 [SMILES: O=C(ON1C(=O)CCC1=O)c1ccc([N+](=O)[O-])cc1]

2,5-dioxopyrrolidin-1-yl 4-nitrobenzoate can be synthesised according to Adamczyk, M., Fino, J., R., *Org. Prep. Proced. Int.*, 2009, 28, 470-474.

Allyl 2-(allyloxy)-4-(2-(allyloxy)-3-methoxy-4-nitrobenzamido)-3-methoxybenzoate

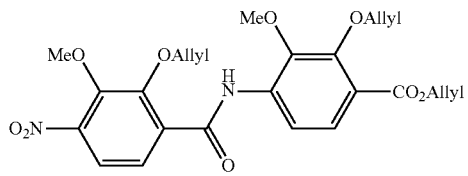

Bis-(trichloromethyl)carbonate (0.5 eq, 1.31 mmol, 388 mg) and 2-(allyloxy)-3-methoxy-4-nitrobenzoic acid (1.5 eq, 4.01 mmol, 1014 mg) were dissolved in dry THF (25 mL) under argon atmosphere. 2,4,6-Collidine (8.0 eq, 21.38 mmol, 2.8 mL) was added slowly via syringe. The resulting suspension was stirred at room temperature for 15 min and a solution of allyl 2-(allyloxy)-4-amino-3-methoxybenzoate (1.0 eq, 2.67 mmol, 703 mg), DIPEA (10.0 eq, 26.72 mmol, 4.5 mL) in dry THF (25 mL) was added. Stirring was continued for 11 h at room temperature and the reaction was quenched by addition of water (10 mL). The organic solvent was removed under reduced pressure and EtOAc (70 mL) was added. The mixture was washed successively with saturated $NaHCO_3$ (2×25 mL), HCl (5%, 2×25 mL), water (1×25 mL) and brine (1×25 mL). The organic solvent was dried over $Na_2SO_4$, filtered and removed under reduced pressure. Purification by column chromatography (H:EA-8:1) yielded the product as a slightly yellow oil (1.2 g, 91%).

$^1$H-NMR (dmso-$d_6$, 500 MHz): δ [ppm] 3.90 (s, 3H), 3.99 (s, 3H), 4.53 (d, J=4.53 Hz, 2H), 4.76 (d, J=4.76 Hz, 2H), 4.78 (d, J=5.35 Hz, 2H), 5.27 (m, 3H), 5.41 (m, 3H), 6.07 (m, 3H), 7.57 (d, J=8.72 Hz, 1H), 7.74 (d, J=8.72 Hz, 1H), 7.79 (d, J=8.52 Hz, 1H), 8.21 (d, J=8.72 Hz, 1H), 10.43 (s, 1H).

HRMS (ESI): [M+H]$^+$ calculated: 499.1711.
found: 499.1701.
[M+Na]$^+$ calculated: 521.1530.
found: 521.1520.

Allyl 2-(allyloxy)-4-(2-(allyloxy)-4-amino-3-methoxybenzamido)-3-methoxybenzoate

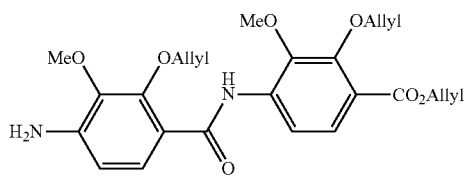

Allyl 2-(allyloxy)-4-(2-(allyloxy)-3-methoxy-4-nitrobenzamido)-3-methoxybenzoate (1.0 eq, 2.41 mmol, 1.2 g) and $SnCl_2*2H_2O$ (7.0 eq, 16.86 mmol, 3.8 g) were dissolved in EtOH (40 mL) and stirred at 60° C. for 1 h. The solution was concentrated under reduced pressure and diluted with water (100 mL). The pH was adjusted to 8-9 by adding saturated $NaHCO_3$ solution and the aqueous suspension was extracted with EtOAc (3×250 mL). The phases were separated and the organic phase was washed with brine (1×250 mL), dried over $Na_2SO_4$ and filtered. After removing the solvent under reduced pressure, column chromatography (H:EA-3:1) yielded the product as an orange oil (892 mg, 79%).

$^1$H-NMR (dmso-d$_6$, 400 MHz): δ [ppm] 3.76 (s, 3H), 3.91 (s, 3H), 4.54 (d, J=5.75 Hz, 2H), 4.78 (m, 4H), 5.26 (dd, J$_1$=17.54 Hz, J$_2$=10.40, 3H), 5.41 (m, 3H), 5.87 (s, 2H), 6.08 (m, 3H), 6.58 (d, J=8.72 Hz, 1H), 7.54 (d, J=8.92 Hz, 1H), 7.59 (d, J=8.92 Hz, 1H), 8.36 (d, J=8.92 Hz, 1H), 10.64 (s, 1H).

HRMS (ESI): [M+H]$^+$ calculated: 469.1969.
found: 469.1958.
[M+Na]$^+$ calculated: 491.1789.
found: 491.1778.

(S)-tert-Butyl 4-(2-(tert-butoxycarbonylamino)-3-cyanopropanamido)benzoate

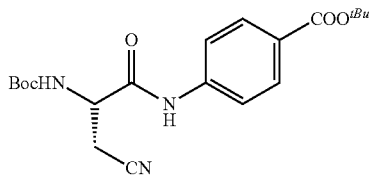

Boc-L-Asn-OH (2.0 eq, 34.44 mmol, 8.0 g) and DCC (4.0 eq, 68.87 mmol, 14.2 g) were dissolved in dry DMF (150 mL) under argon atmosphere. After stirring for 10 min at room temperature tert-butyl 4-aminobenzoate (1.0 eq, 17.22 mmol, 3.9 g) was added and stirring was continued for 19 h. EtOAc (400 mL) was added and the mixture was washed successively with brine (3×150 mL), saturated NaHCO$_3$ solution (2×150 mL), HCl (5%, 2×150 mL) and brine (1×150 mL). The organic phase was dried over Na$_2$SO$_4$, filtered and the solvent was removed under reduced pressure. Column chromatography (H:EA-4:1) yielded the product as a white solid (4.2 g, 57%).

$^1$H-NMR (dmso-d$_6$, 400 MHz): δ [ppm] 1.40 (s, 9H), 1.53 (s, 9H), 2.83 (dd, J$_1$=16.92 Hz, 1H), 2.99 (dd, J$_1$=16.92 Hz, J$_2$=5.10 Hz, 1H), 4.46 (dd, J$_1$=13.70 Hz, J$_2$=8.86 Hz, 1H), 7.58 (d, J=7.79 Hz, 1H), 7.71 (d, J=8.60 Hz, 2H), 7.87 (d, J=8.60 Hz, 2H), 10.48 (s, 1H).

HRMS (ESI): [M+H]$^+$ calculated: 390.2034.
found: 390.2017.
[M+Na]$^+$ calculated: 412.1843.
found: 412.1834.

(S)-4-(3-Cyano-2-(4-nitrobenzamido)propanamido)benzoic acid

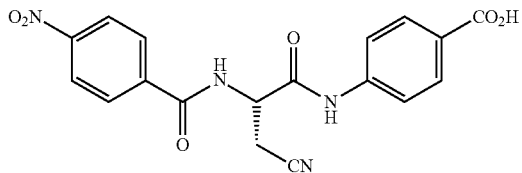

(S)-tert-Butyl 4-(2-(tert-butoxycarbonylamino)-3-cyanopropanamido)benzoate (1.0 eq, 0.81 mmol, 314 mg) was dissolved in HCl/dioxane (4 M, 5 mL) and the reaction mixture was stirred at room temperature until cleavage of the boc group and tert-butyl ester was completed (LC/MS monitoring, approximately 6 hours). The solvent was removed under reduced pressure and the residue resolved in dry DMF (10 mL) under argon atmosphere. Triethylamine (3.0 eq, 2.42 mmol, 0.73 mL) and 2,5-dioxopyrrolidin-1-yl 4-nitrobenzoate (1.1 eq, 0.89 mmol, 234 mg) were added and the mixture was stirred at room temperature for 16 h. EtOAc (50 mL) was added and the mixture was washed successively with brine (3×25 mL), saturated NaHCO$_3$ solution (2×25 mL), HCl (5%, 2×25 mL) and brine (1×25 mL). The organic phase was dried over Na$_2$SO$_4$, filtered and the solvent was removed under reduced pressure. Column chromatography (CHCl$_3$:CH$_3$OH-9:0.5) yielded the product as a white solid (119 mg, 39%).

$^1$H-NMR (dmso-d$_6$, 400 MHz): δ [ppm] 3.06 (dd, J$_1$=16.92 Hz, J$_2$=8.60 Hz, 1H), 3.17 (dd, J$_1$=16.92 Hz, J$_2$=5.37 Hz, 1H), 5.01 (m, 1H), 7.74 (d, J=8.87 Hz, 1H), 7.92 (d, J=8.87 Hz, 1H), 8.16 (d, J=9.13 Hz, 1H), 8.38 (d, J=8.87 Hz, 1H), 9.53 (d, J=7.79 Hz, 1H), 10.61 (s, 1H).

HRMS (ESI): [M+H]$^+$ calculated: 383.0986.
found: 390.0974.

Methyl-6-amineonicotinate

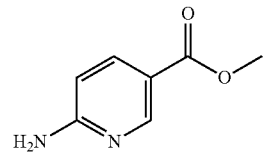

Chemical Formula: C$_7$H$_8$N$_2$O$_2$
Exact Mass: 152,0586

6-Amineonicotinic acid (1.00 g, 7.246 mmol, 1.00 eq) was dissolved in abs. MeOH (40 ml) and cooled to 0° C. SOCl$_2$ (2.587 g, 1.70 ml, 21.739 mmol, 3.00 eq) was added and the reaction mixture was allowed to warm up to room temperature. After stirring for 16 h the solvent was evaporated to give the product as a pale yellow solid (60%).

$^1$H-NMR (400 MHz, DMSO-d$_6$): 3.75 (s, 3H), 6.43-6.46 (dd, J$_1$=8.7 Hz, J$_2$=0.7 Hz, 1H), 6.84 (s, 2H), 7.81-7.83 (dd, J$_1$=8.9 Hz, J$_2$=2.4 Hz, 1H), 8.50 (d, J=2.1 Hz, 1H), $^{13}$C-NMR (100.6 MHz, DMSO-d$_6$): 51.36, 107.13, 113.19, 137.60, 151.04, 162.52, 165.72

HR-MS: calc.: [M+H]$^+$ 153.0659.
found: [M+H]$^+$ 153.0654.

Methyl 6-[[(E)-3-(4-allyloxyphenyl)-2-methyl-prop-2-enoyl]amino]pyridine-3-carboxylate

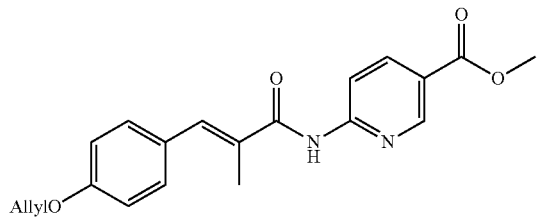

Chemical Formula: C$_{20}$H$_{20}$N$_2$O$_4$
Exact Mass: 352,1423

The Allyl protected cinnamic acid (200 mg, 0.917 mmol, 1.00 eq) was dissolved in DCM (10 ml) and a catalytic amount of DMF (100 µl) was added. SOCl$_2$ (545 mg, 0.36 ml, 4.579 mmol, 5.00 eq) was added dropwise and the mixture was stirred for 16 h. The solvents were removed and the residue redissolved in DMF. Methyl-6-aminonicotinate (139 mg, 0.917 mmol, 1.00 eq) was dissolved in DMF and added. After stirring for another 16 h the mixture was diluted with EE and the organic layer was washed 3× with 1 N HCl, sat. NaHCO$_3$ and brine. The organic layer was dried over Na$_2$SO$_4$ and the solvent was evaporated. The crude product was chromatographically purified to give the product as a pale yellow solid.

6-[[(E)-3-(4-allyloxyphenyl)-2-methyl-prop-2-enoyl]amino]pyridine-3-carboxylic acid

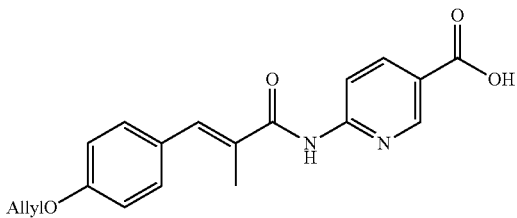

Chemical Formula: C$_{19}$H$_{18}$N$_2$O$_4$
Exact Mass: 338,1267

Methyl 6-[[(E)-3-(4-allyloxyphenyl)-2-methyl-prop-2-enoyl]amino]pyridine-3-carboxylate (1.00 eq) was dissolved in Dioxane/H$_2$O (1:1) and LiOH (3.00 eq) was added. The mixture was stirred for 4 h. The Dioxane was removed and the aqueous layer acidified with conc. HCl. The aqueous layer was extracted 3× with EE and the combined organic layers were dried over Na$_2$SO$_4$. The solvent was evaporated to give the product.

Allyl 2-allyloxy-4-[[2-allyloxy-4-[[4-[[(2S)-2-[[6-[[(E)-3-(4-allyloxyphenyl)-2-methyl-prop-2-enoyl]amino]pyridine-3-carbonyl]amino]-3-cyano-propanoyl]amino]benzoyl]]

Chemical Formula: C$_{55}$H$_{53}$N$_7$O$_{12}$
Exact Mass: 1003,3752

6-[[(E)-3-(4-allyloxyphenyl)-2-methyl-prop-2-enoyl]amino]pyridine-3-carboxylic acid (1.50 eq) was dissolved in THF. Triphosgen (0.50 eq) and Collidin (8.00 eq) were added and stirred for 20 min. The aminee (1.00 eq) and DIPEA (10.00 eq) were dissolved in THF and added to mixture. After stirring for 16 h the mixture was diluted with EE and the organic layer was washed 3× with 1 N HCl, sat. NaHCO$_3$ and brine. After drying the organic layer over Na$_2$SO$_4$ the solvent was removed and the crude product was chromatographically purified to give the product.

4-[[(2S)-3-cyano-2-[(5-nitropyridine-2-carbonyl)amino]propanoyl]amino]benzoic acid

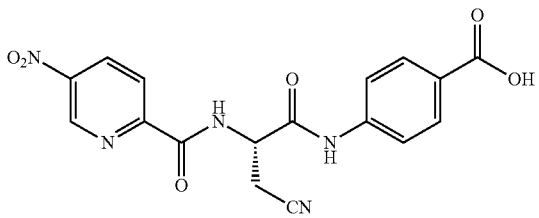

Chemical Formula: C$_{17}$H$_{13}$N$_5$O$_6$
Exact Mass: 383,0866

(S)-1-((4-carboxyphenyl)amineo)-3-cyano-1-oxopropan-2-amineium chloride (424 mg, 1.58 mmol, 1.00 eq) was dissolved in abs. DMF (10 ml) and TEA (479 mg, 665 µl, 4.74 mmol, 3.00 eq) was slowly added. 2,5-dioxopyrrolidin-1-yl 5-nitropicolinate (440 mg, 1.66 mmol, 1.05 eq) was dissolved in DMF (10 ml) and added to the reaction mixture. After stirring for 16 h at room temperature the mixture was diluted with EE (50 ml) and the organic layer was washed 4× with 1 N HCl and brine. The solvent was evaporated and the crude product was chromatographically purified (Hex: EE 1:1) to give the product as a pale yellow solid (78%).

$^1$H-NMR (400 MHz, DMSO-d$_6$): 3.19-3.28 (m, 2H), 5.04-5.10 (m, 1H), 7.72 (d, J=8.9 Hz, 2H), 7.92 (d, J=8.6 Hz, 2H), 8.32 (d, J=8.6 Hz, 1H), 8.79-8.82 (dd, J$_1$=8.6 Hz, J$_2$=2.4 Hz, 1H), 9.46 (d, J=2.4 Hz, 1H), 9.55 (d, J=8.3 Hz, 1H), 10.53 (s, 1H), 12.73 (br, 1H)

$^{13}$C-NMR (100.6 MHz, DMSO-d$_6$): 20.30, 50.08, 117.96, 118.99, 123.12, 125.78, 130.35, 133.54, 142.31, 144.04, 145.92, 152.98, 162.54, 166.80, 167.37

HR-MS: calc.: [M−H]$^-$ 382.0782.
found: [M−H]$^-$ 382.0789.

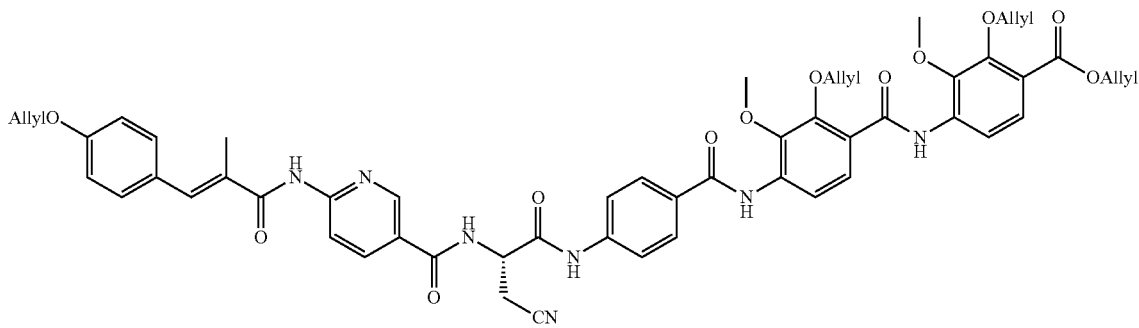

Allyl 2-allyloxy-4-[[2-allyloxy-4-[[4-[[(2S)-3-cyano-2-[(5-nitropyridine-2-carbonyl)amino]propanoyl]amino]benzoyl]amino]-3-methoxy-benzoyl]amino]-3-methoxy-benzoate

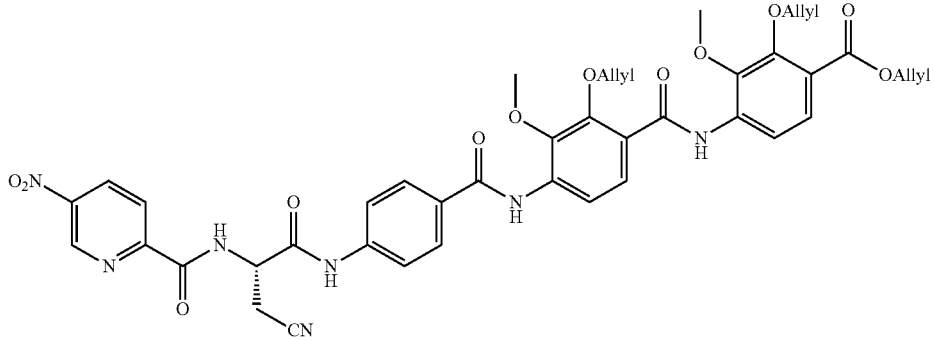

Chemical Formula: $C_{42}H_{39}N_7O_{12}$
Exact Mass: 833,2657

(S)-4-(3-cyano-2-(5-nitropicolinamido)propanamido)benzoic acid (404 mg, 1.05 mmol, 2.00 eq) was dissolved in THF (20 ml), BTC (104 mg, 0.35 mmol, 0.66 eq) and Collidin (510 mg, 558 µl, 4.22 mmol, 8.00 eq) was added and stirred 20 min at room temperature. Allyl 2-(allyloxy)-4-(2-(allyloxy)-4-amineo-3-methoxybenzamido)-3-methoxybenzoate (246 mg, 0.52 mmol, 1.00 eq) and DIPEA (679 mg, 940 µl, 5.27 mmol, 10.00 eq) were dissolved in THF (10 ml) and added to the reaction mixture. After stirring for 16 h the mixture was diluted with EE (50 ml) and washed 3× with 1 N HCl, sat. NaHCO₃ and brine. After drying over Na₂SO₄ the solvent was evaporated. The crude product was chromatographically purified (Hex:EE 1:1) to give the product as a yellow solid (69%).

¹H-NMR (400 MHz, DMSO-d₆): 3.24-3.29 (m, 2H), 3.91 (s, 3H), 3.93 (s, 3H), 4.53-4.55 (m, 2H), 4.76-4.81 (m, 4H), 5.06-5.12 (m, 1H), 5.23-5.31 (m, 3H), 5.36-5.44 (m, 3H), 5.99-6.16 (m, 3H), 7.57 (d, J=8.6 Hz, 1H), 7.77 (d, J=8.6 Hz, 2H), 7.80 (d, J=8.9 Hz, 1H), 7.90-7.92 (m, 1H), 7.99 (d, J=8.9 Hz, 2H), 8.32-8.35 (m, 2H), 8.80-8.83 (m, 1H), 9.48 (dd, J₁=2.6 Hz, J₂=0.7 Hz, 1H), 9.57 (d, J=8.6 Hz, 1H), 9.70 (s, 1H), 10.55 (s, 1H), 10.65 (s, 1H)

HR-MS: calc.: [M+H]⁺ 834.2729.
found: [M+H]⁺ 804.2900.

Allyl 2-allyloxy-4-[[2-allyloxy-4-[[4-[[(2S)-2-[(5-aminopyridine-2-carbonyl)amino]-3-cyano-propanoyl]amino]benzoyl]amino]-3-methoxy-benzoyl]amino]-3-methoxy-benzoate Chemical Formula: $C_{42}H_{41}N_7O_{10}$
Exact Mass: 803,2915

(S)-allyl2-(allyloxy)-4-(2-(allyloxy)-4-(4-(3-cyano-2-(5-nitropicolinamido)propanamido)benzamido)-3-methoxy-benzamido)-3-methoxybenzoate (335 mg, 0.402 mmol, 1.00 eq) was dissolved in EtOH (30 ml) and SnCl₂.H₂O was added. The mixture was stirred at 60° C. for 6 h. The solvent was evaporated and the residue was redissolved in EE. The organic layer was washed with sat. NaHCO₃ and the aqueous layer extracted twice with EE. The organic layer was washed with brine, dried over Na₂SO₄ and evaporated. The crude product was chromatographically purified (CHCl₃: MeOH 9:0.1) to give the product as a yellow solid (60%).

¹H-NMR (400 MHz, DMSO-d₆): 3.18-3.23 (m, 1H), 3.27-3.32 (m, 1H), 3.91 (s, 3H), 3.93 (s, 3H), 4.53-4.55 (m, 2H), 4.77-4.81 (m, 4H), 4.99-5.04 (m, 1H), 5.23-5.31 (m, 3H), 5.36-5.44 (m, 3H), 5.99-6.16 (m, 3H), 7.29 (dd, J₁=7.72 Hz, J₂=2.6 Hz, 1H), 7.57 (d, J=8.6 Hz, 1H), 7.76-7.81 (m, 3H), 7.91 (dd, J₁=8.7 Hz, J₂=2.8 Hz, 2H), 7.99 (d, J=8.6 Hz, 2H), 8.18 (d, J=2.4 Hz, 1H), 8.33 (d, J=8.9 Hz, 1H), 8.85 (d, J=1.6 Hz, 1H), 8.93 (d, J=8.3 Hz, 1H), 9.14 (s, 1H), 9.69 (s, 1H), 10.56 (s, 1H), 10.65 (s, 1H)

HR-MS: calc.: [M+H]⁺ 804.2988.
found: [M+H]⁺ 804.2900.

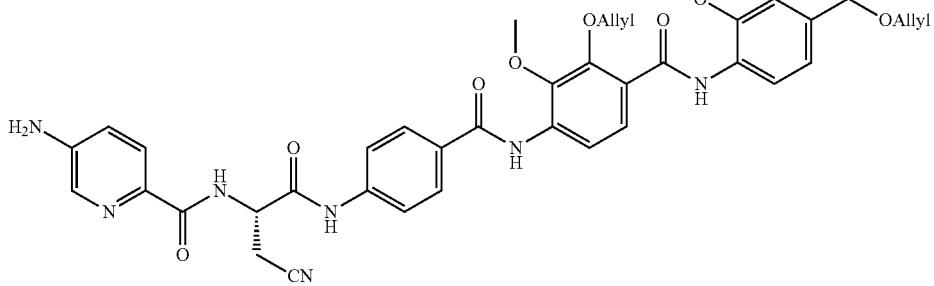

Allyl 2-allyloxy-4-[[2-allyloxy-4-[[4-[[(2S)-2-[[5-[[(E)-3-(4-allyloxyphenyl)-2-methyl-prop-2-enoyl]amino]pyridine-2-carbonyl]amino]-3-cyano-propanoyl]amino]benzoyl]amino]-3-methoxy-benzoyl]amino]-3-methoxy-benzoate

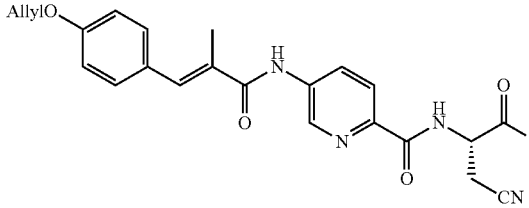

Chemical Formula: C$_{55}$H$_{53}$N$_{7}$O$_{12}$
Exact Mass: 1003,3752

(E)-3-(4-(allyloxy)phenyl)-2-methylacrylic acid (42 mg, 0.194 mmol, 3.00 eq) was dissolved in THF. BTC (19 mg, 0.065 mmol, 1.00 eq) and Collidin (63 mg, 69 µl, 0.518 mmol, 8.00 eq) were added and the mixture was stirred at room temperature. After 20 min (S)-allyl 2-(allyloxy)-4-(2-(allyloxy)-4-(4-(2-(5-aminepicolinamido)-3-cyanopropanamido)benzamido)-3-methoxybenzamido)-3-methoxybenzoate (52 mg, 0.065 mmol, 1.00 eq) and DIPEA (83 mg, 116 µl, 0.647 mmol, 10.00 eq) were dissolved in THF, added to the reaction mixture and stirred for an additional 16 h. The reaction mixture was diluted with EE and washed 3× with 1 N HCl, sat. NaHCO$_3$ and brine. After drying over Na$_2$SO$_4$ the solvent was removed. The crude product was chromatographically purified (CHCl$_3$:MeOH 9:0.2) to give the product as a yellow solid (95%).

$^1$H-NMR (400 MHz, DMSO-d$_6$): 2.15 (s, 3H), 3.91 (s, 3H), 3.93 (s, 3H), 4.53-4.55 (m, 2H), 4.60-4.63 (m, 2H), 4.76-4.81 (m, 4H), 5.01-5.08 (m, 1H), 5.26-5.29 (m, 4H), 5.38-5.44 (m, 4H), 6.00-6.10 (m, 4H), 7.04-7.06 (m, 2H), 7.46-7.49 (m, 2H), 7.56-7.58 (m, 1H), 7.77-7.82 (m, 3H), 7.91-7.93 (m, 1H), 7.98-8.01 (m, 2H), 8.07-8.09 (m, 1H), 8.33 (d, J=8.9 Hz, 1H), 8.36-8.39 (dd, J$_1$=8.6 Hz, J$_2$=2.1 Hz, 1H), 9.03 (d, J=2.6 Hz, 1H), 9.18 (d, J=9.1 Hz, 1H), 9.71 (s, 1H), 10.43 (s, 1H), 10.58 (s, 1H), 10.66 (s, 1H)

HR-MS: calc.: [M+H]$^+$: 1004.3825.
found: [M+H]$^+$: 1004.3842.

tert-butyl 5-nitropyridine-2-carboxylate

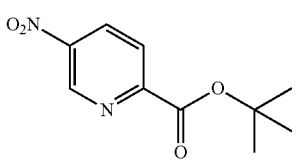

Chemical Formula: C$_{10}$H$_{12}$N$_2$O$_4$
Exact Mass: 224,0797

DIC (3.00 eq), tBuOH (4.00 eq) and CuCl (0.02 eq) were stirred under an Argon-athmosphere at room temperature for 5 d. The mixture was filtered through a pad of celite and diluted with DCM (4:1). 5-Nitropicolinic acid (1.00 g, 5.952 mmol, 1.00 eq) was dissolved in DMF (20 ml) and the activated tBuOH was added via a dropping funnel. After stirring for 4 h at room temperature the mixture was cooled to 0° C. Hexane (40 ml) was added and it was stirring for an additional 30 min. The mixture was filtered through celite and the filtrate was washed 3× with H$_2$O. The solvent was removed and the crude product was chromatographically purified (Hex/EE 5:1) to give the product as a white solid (70%).

$^1$H-NMR (400 MHz, DMSO-d$_6$): 1.58 (s, 9H), 8.21-8.23 (dd, J$_1$=8.6 Hz, J$_2$=0.8 Hz, 1H), 8.72-8.75 (dd, J$_1$=8.6 Hz, J$_2$=2.7 Hz, 1H), 9.44-9.45 (d, J=2.6 Hz, 1H)

$^{13}$C-NMR (100.6 MHz, DMSO-d$_6$): 27.62, 82.75, 125.17, 133.07, 144.73, 152.81, 160.74, 174.17

HR-MS: calc.: [M+H]$^+$: 225.0870.
found: [M+H]$^+$: 255.0872.

tert-butyl 5-aminopyridine-2-carboxylate

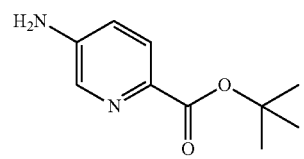 [SMILES: CC(C)(C)OC(=O)c1ccc([N+](=O)[O-])cn1]

Chemical Formula: C$_{10}$H$_{14}$N$_2$O$_2$
Exact Mass: 194,1055

Tert-Butyl-5-nitro-picolinate (822 mg, 3.67 mmol) was dissolved in EE/MeOH (9:1) (20 ml) and Pd/C 10% (82 mg) was added. The mixture was stirred at room temperature under a Hydrogen-atmosphere for 5 h. The mixture was filtrated through a pad of celite and the solvents were evaporated to give the product as an white solid (90%).

$^1$H-NMR (400 MHz, DMSO-d$_6$): 1.50 (s, 9H), 6.08 (s, 2H), 6.89 (dd, J$_1$=8.6 Hz, J$_2$=2.7 Hz, 1H), 7.68 (d, J=8.6 Hz, 1H), 7.95 (d, J=2.7 Hz, 1H)

$^{13}$C-NMR (100.6 MHz, DMSO-d$_6$): 27.95, 79.57, 118.07, 126.09, 135.55, 135.60, 147.72, 164.06

HR-MS: calc.: [M+H]$^+$: 195.1128.
found: [M+H]$^+$: 195.1128.

tert-butyl 5-[[(2S)-2-(tert-butoxycarbonylamino)-3-cyano-propanoyl]amino]pyridine-2-carboxylate

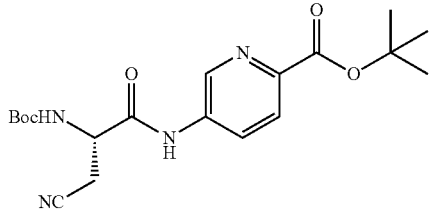 [SMILES: CC(C)(C)OC(=O)N[C@@H](CC#N)C(=O)Nc1ccc(C(=O)OC(C)(C)C)nc1]

Chemical Formula: $C_{19}H_{26}N_4O_5$
Exact Mass: 390,1903

Tert-butyl-5-amineo-picolinate (727 mg, 3.747 mmol, 1.00 eq) and Boc-Asn-OH (1.739 g, 7.495 mmol, 2.00 eq) were dissolved in DMF (30 ml) and DCC (3.092 g, 14.989 mmol, 4.00 eq) was added. After stirring for 16 h at room temperature the mixture was filtrated and the filtrate diluted with EE (60 ml). The organic layer was washed 3× with 1 N HCl, sat. NaHCO$_3$ and brine. The organic layer was dried over Na$_2$SO$_4$ and the solvent was removed. The crude product was chromatographically purified (Hex/EE 1:2) to give the product as a white solid (60%).

$^1$H-NMR (400 MHz, DMSO-d$_6$): 1.41 (s, 9H), 1.54 (s, 9H), 6.08 (s, 2H), 6.89 (dd, J$_1$=8.6 Hz, J$_2$=2.7 Hz, 1H), 7.68 (d, J=8.6 Hz, 1H), 7.95 (d, J=2.7 Hz, 1H)

$^{13}$C-NMR (100.6 MHz, DMSO-d$_6$): 27.95, 79.57, 118.07, 126.09, 135.60, 147.72, 164.06

[(1S)-2-[(6-carboxy-3-pyridyl)amino]-1-(cyanomethyl)-2-oxo-ethyl]ammonium chloride

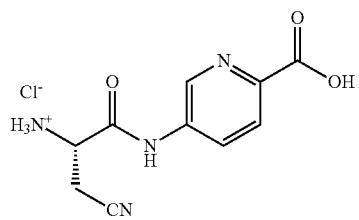 [SMILES: [Cl-] ; N#CC[C@H]([NH3+])C(=O)Nc1ccc(C(=O)O)nc1]

Chemical Formula: $C_{10}H_{11}N_4O_3^+$
Exact Mass: 235,0826

Tert-butyl 5-[[(2S)-2-(tert-butoxycarbonylamino)-3-cyano-propanoyl]amino]pyridine-2-carboxylate (900 mg, 2.310 mmol) was dissolved in 4 M HCl in Dioxane (20 ml). The solution was stirred at room temperature for 5 h. The solvent was evaporated and the product dried in vacuo (quant.).

5-[[(2S)-3-cyano-2-[(4-nitrobenzoyl)amino]propanoyl]amino]pyridine-2-carboxylic acid

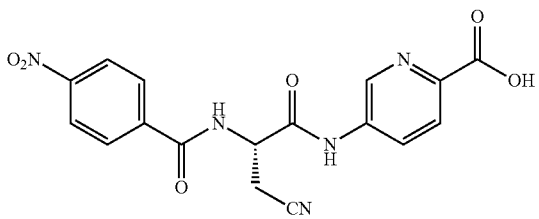

Chemical Formula: $C_{17}H_{13}N_5O_6$
Exact Mass: 383,0866

[(1S)-2-[(6-carboxy-3-pyridyl)amino]-1-(cyanomethyl)-2-oxo-ethyl]ammonium chloride (1.00 eq) was dissolved in DMF and TEA (3.00 eq) was added dropwise. 2,5-Dioxopyrrolidin-1-yl-4-nitrobenzoate (1.05 eq) was dissolved in DMF and added to the mixture. After stirring at room temperature for 16 h the mixture was diluted with EE and washed 4× with 1 N HCl and brine. The organic layer was dried over Na$_2$SO$_4$ and the solvent was removed. The crude product was chromatographically purified to give the product as a yellow solid.

Allyl 2-allyloxy-4-[[2-allyloxy-4-[[5-[[(2S)-3-cyano-2-[(4-nitrobenzoyl)amino]propanoyl]amino]pyridine-2-carbonyl]amino]-3-methoxy-benzoyl]amino]-3-methoxy-benzoate

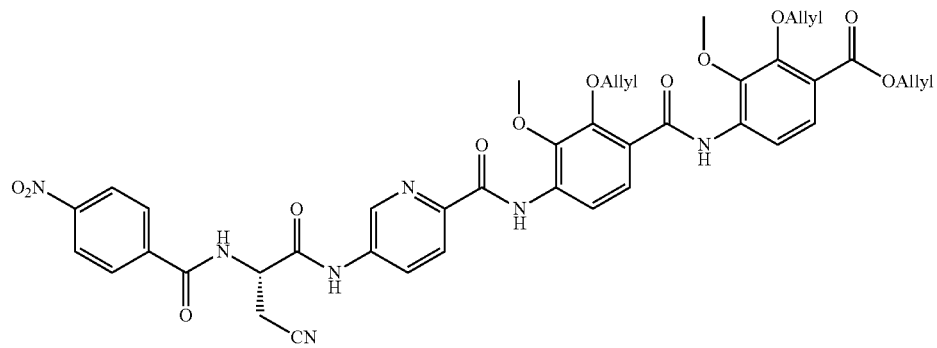

Chemical Formula: C₄₂H₃₉N₇O₁₂

Exact Mass: 833.2657

5-[[(2S)-3-cyano-2-[(4-nitrobenzoyl)amino]propanoyl]amino]pyridine-2-carboxylic acid (2.00 eq) was dissolved in THF and Triphosgen (0.66 eq) and Collidin (8.00 eq) were added. The mixture was stirred at room temperature for 40 min. The amine (1.00 eq) and DIPEA (10.00 eq) were dissolved in THF, added to the mixture and it was stirred for an additional 16 h at room temperature. The reaction was diluted with EE and washed 3× with 1 N HCl, sat. NaHCO₃ and brine. After drying over Na₂SO₄ the solvent was removed. The crude product was chromatographically purified to give the product as a yellow solid.

Allyl 2-allyloxy-4-[[2-allyloxy-4-[[5-[[(2S)-2-[(4-aminobenzoyl)amino]-3-cyano-propanoyl]amino]pyridine-2-carbonyl]amino]-3-methoxy-benzoyl]amino]-3-methoxy-benzoate Chemical Formula: C₅₅H₅₃N₇O₁₂

Exact Mass: 1003.3752

The cinnamic acid (3.00 eq) was dissolved in THF. Triphosgen (1.00 eq) and Collidin (8.00 eq) were added and it was stirred for 15 min. Allyl 2-allyloxy-4-[[2-allyloxy-4-[[5-[[(2S)-2-[(4-aminobenzoyl)amino]-3-cyano-propanoyl]amino]pyridine-2-carbonyl]amino]-3-methoxy-benzoyl]amino]-3-methoxy-benzoate (1.00 eq) and DIPEA (10.00 eq) were dissolved in THF and added to the mixture. After stirring for 16 h the mixture was diluted with EE and the organic layer was washed 3× with 1 N HCl, sat. NaHCO₃ and brine. After drying over Na₂SO₄ the solvent was removed. The crude product was chromatographically purified to give the product as a yellow solid.

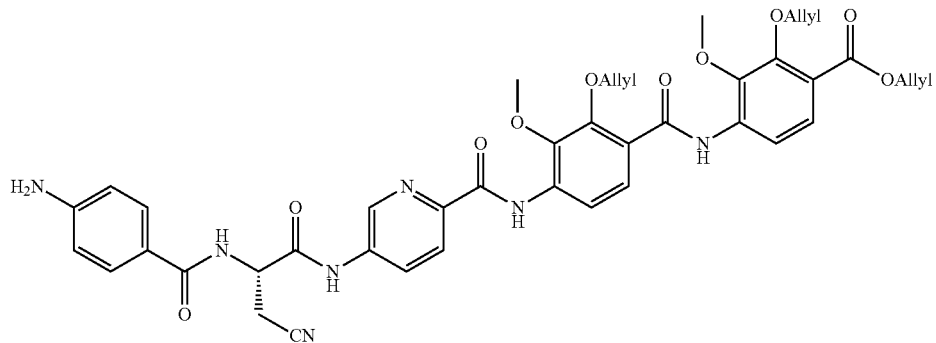

Chemical Formula: C₄₂H₄₁N₇O₁₀

Exact Mass: 803.2915

Allyl 2-allyloxy-4-[[2-allyloxy-4-[[5-[[(2S)-3-cyano-2-[(4-nitrobenzoyl)amino]propanoyl]amino]pyridine-2-carbonyl]amino]-3-methoxy-benzoyl]amino]-3-methoxy-benzoate (1.00 eq) was dissolved in EtOH and SnCl₂·H₂O (5.00 eq) was added. The mixture was stirred at 60° C. for 6 h. The solvent was removed and the residue uptaken in EE. Sat. NaHCO₃ was added and the aqueous layer was extracted 3× with EE. The combined organic layers were dried over Na₂SO₄ and the solvent was removed. The crude product was chromatographically purified to give the product as a yellow solid.

Allyl 2-allyloxy-4-[[2-allyloxy-4-[[5-[[(2S)-2-[[4-[[(E)-3-(4-allyloxyphenyl)-2-methyl-prop-2-enoyl]amino]benzoyl]amino]-3-cyano-propanoyl]amino]pyridine-2-carbonyl]amino]-3-methoxy-benzoyl]amino]-3-methoxy-benzoate 5-[[(2S)-3-cyano-2-[(5-nitropyridine-2-carbonyl)amino]propanoyl]amino]pyridine-2-carboxylic acid

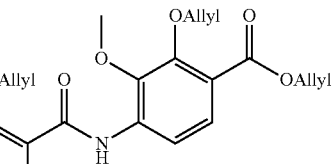

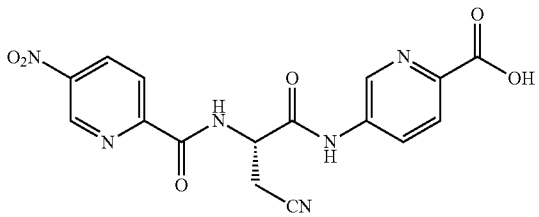 [SMILES: N#CC[C@H](NC(=O)c1ccc([N+](=O)[O-])cn1)C(=O)Nc1ccc(C(=O)O)nc1]

Chemical Formula: C₁₆H₁₂N₆O₆

Exact Mass: 384.0818

The amine (1.00 eq) was dissolved in DMF and TEA (3.00 eq) was added dropwise. 2,5-Dioxopyrrolidin-1-yl-5nitropicolinate (1.05 eq) was dissolved in DMF and added to the mixture. After stirring at room temperature for 16 h the mixture was diluted with EE and washed 4× with 1 N HCl

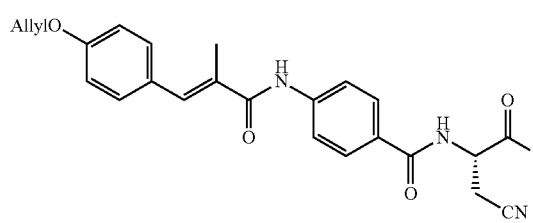

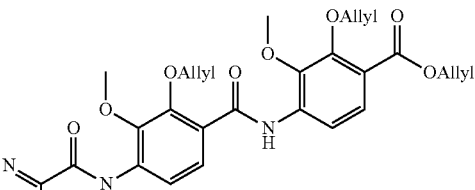

and brine. The organic layer was dried over Na$_2$SO$_4$ and the solvent was removed. The crude product was chromatographically purified to give the product as a yellow solid.

Allyl 2-allyloxy-4-[[2-allyloxy-4-[[5-[[(2S)-3-cyano-2-[(5-nitropyridine-2-carbonyl)amino]propanoyl]amino]pyridine-2-carbonyl]amino]-3-methoxy-benzoyl]amino]-3-methoxy-benzoate

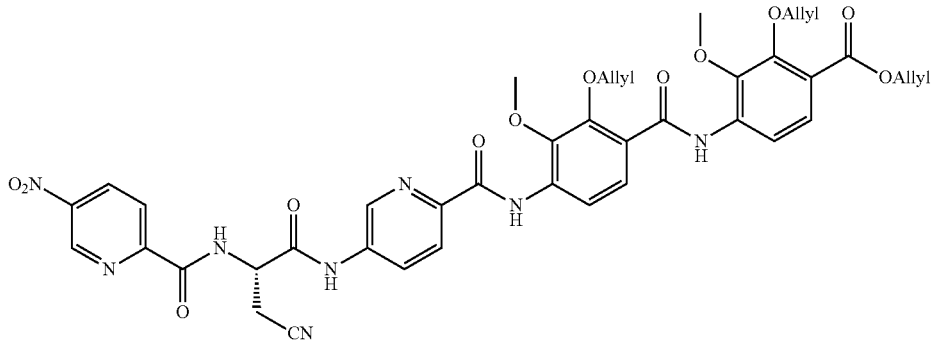

Chemical Formula: C$_{41}$H$_{38}$N$_8$O$_{12}$
Exact Mass: 834,2609

5-[[(2S)-3-cyano-2-[(5-nitropyridine-2-carbonyl)amino]propanoyl]amino]pyridine-2-carboxylic acid (2.00 eq) was dissolved in THF and Triphosgen (0.66 eq) and Collidin (8.00 eq) were added. The mixture was stirred at room temperature for 40 min. The amine (1.00 eq) and DIPEA (10.00 eq) were dissolved in THF, added to the mixture and it was stirred for an additional 16 h at room temperature. The reaction was diluted with EE and washed 3× with 1 N HCl, sat. NaHCO$_3$ and brine. After drying over Na$_2$SO$_4$ the solvent was removed. The crude product was chromatographically purified to give the product as a yellow solid.

Allyl 2-allyloxy-4-[[2-allyloxy-4-[[5-[[(2S)-2-[(5-aminopyridine-2-carbonyl)amino]-3-cyano-propanoyl]amino]pyridine-2-carbonyl]amino]-3-methoxy-benzoyl]amino]-3-methoxy-benzoate

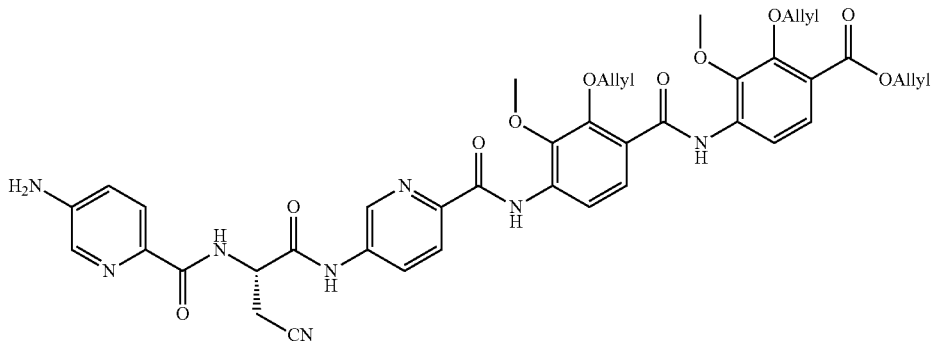

Chemical Formula: C$_{41}$H$_{40}$N$_8$O$_{10}$
Exact Mass: 804,2867

5-[[(2S)-3-cyano-2-[(5-nitropyridine-2-carbonyl)amino]propanoyl]amino]pyridine-2-carboxylic acid (1.00 eq) was dissolved in EtOH and SnCl$_2$.H$_2$O (5.00 eq) was added. The mixture was stirred at 60° C. for 6 h. The solvent was removed and the residue uptaken in EE. Sat. NaHCO$_3$ was added and the aqueous layer was extracted 3× with EE. The combined organic layers were dried over Na$_2$SO$_4$ and the solvent was removed. The crude product was chromatographically purified to give the product as a yellow solid.

Allyl 2-allyloxy-4-[[2-allyloxy-4-[[5-[[(2S)-2-[[5-[[(E)-3-(4-allyloxyphenyl)-2-methyl-prop-2-enoyl]amino]pyridine-2-carbonyl]amino]-3-cyano-propanoyl]amino]pyridine-2-carbonyl]amino]-3-methoxy-benzoyl]amino]-3-methoxy-benzoate

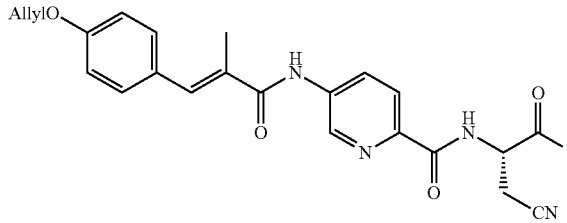

Chemical Formula: $C_{54}H_{52}N_8O_{12}$
Exact Mass: 1004,3705

The cinnamic acid (3.00 eq) was dissolved in THF. Triphosgen (1.00 eq) and Collidin (8.00 eq) were added and it was stirred for 15 min. Allyl 2-allyloxy-4-[[2-allyloxy-4-[[5-[[(2S)-2-[(5-aminopyridine-2-carbonyl)amino]-3-cyano-propanoyl]amino]pyridine-2-carbonyl]amino]-3-methoxy-benzoyl]amino]-3-methoxy-benzoate (1.00 eq) and DIPEA (10.00 eq) were dissolved in THF and added to the mixture. After stirring for 16 h the mixture was diluted with EE and the organic layer was washed 3× with 1 N HCl, sat. NaHCO₃ and brine. After drying over Na₂SO₄ the solvent was removed. The crude product was chromatographically purified to give the product as a yellow solid.

Allyl 2-allyloxy-4-[[2-allyloxy-3-methoxy-4-[(4-nitrophenyl)sulfonylamino]benzoyl]amino]-3-methoxy-benzoate

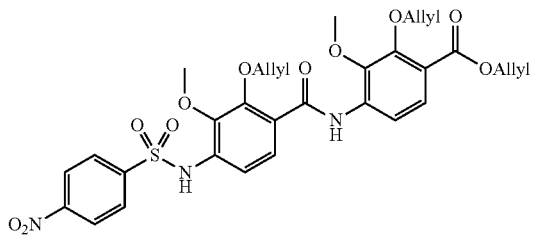

Chemical Formula: $C_{31}H_{31}N_3O_{11}S$
Exact Mass: 653,1679

The amine (500 mg, 1.068 mmol, 1.00 eq) was dissolved in DCM and DMAP (100 mg, w/w 10%) and Pyridin (2.5 ml) were added. 4-Nitrobenzene-1-sulfonyl chloride (710 mg, 3.205 mmol, 3.00 eq) was added and it was stirred at room temperature for 72 h. The mixture was washed 3× with 1 N HCl and brine. After drying over Na₂SO₄ the solvent was removed. The crude product was chromathographically (Hex/EE 3:1) purified to give the product as a yellow solid.

¹H-NMR (400 MHz, DMSO-d₆): 3.59 (s, 3H), 3.87 (s, 3H), 4.50-4.52 (m, 2H), 4.63-4.65 (m, 2H), 4.75-4.76 (m, 2H), 5.24-5.28 (m, 2H), 5.34-5.42 (m, 2H), 5.92-6.12 (m, 3H), 7.29 (d, J=8.9 Hz, 1H), 7.54 (d, J=8.9 Hz, 1H), 7.69 (d, J=8.9 Hz, 1H), 8.09 (d, J=8.9 Hz, 2H), 8.26 (d, J=8.9 Hz, 1H), 8.42 (d, J=8.9 Hz, 2H), 10.51 (s, 1H), 10.59 (s, 1H)

¹³C-NMR (100.6 MHz, DMSO-d₆): 59.76, 60.95, 65.11, 114.87, 117.86, 118.14, 120.21, 120.38, 124.70, 126.24, 128.30, 132.45, 132.61, 133.93, 136.37, 142.52, 144.59, 149.74, 149.91, 151.06, 162.17, 164.44, 172.51

HR-MS: calc.: [M+H]⁺.
found: [M+H]⁺.

Allyl 2-allyloxy-4-[[2-allyloxy-4-[(4-aminophenyl)sulfonylamino]-3-methoxy-benzoyl]amino]-3-methoxy-benzoate

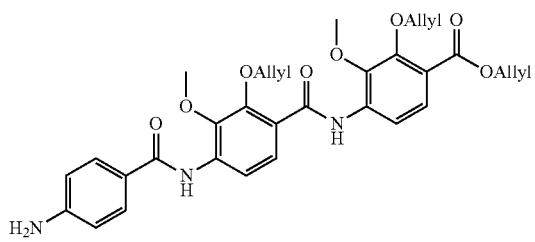

Chemical Formula: $C_{31}H_{33}N_3O_9S$
Exact Mass: 623,1938

Allyl 2-allyloxy-4-[[2-allyloxy-3-methoxy-4-[(4-nitrophenyl)sulfonylamino]benzoyl]amino]-3-methoxy-benzoate (320 mg, 0.490 mmol, 1.00 eq), was dissolved in EtOH (30 ml) and and SnCl₂.H₂O (554 mg, 2.45 mmol, 5.00 eq) was added. The mixture was stirred at 60° C. for 6 h. The solvent was removed and the residue uptaken in EE. Sat. NaHCO₃ was added and the aqueous layer was extracted 3× with EE. The combined organic layers were dried over Na₂SO₄ and the solvent was removed. The crude product was chromatographically (Hex/EE 1:1) purified to give the product as a yellow solid (90%).

¹H-NMR (400 MHz, DMSO-d₆): 3.64 (s, 3H), 3.88 (s, 3H), 4.50-4.52 (m, 2H), 4.67-4.69 (m, 2H), 4.75-4.76 (m, 2H), 5.24-5.30 (m, 2H), 5.34-5.42 (m, 2H), 5.96-6.12 (m, 3H), 6.04 (s, 2H), 6.55 (d, J=8.6 Hz, 2H), 7.32 (d, J=9.1 Hz, 1H), 7.48 (d, J=8.6 Hz, 2H), 7.54 (d, J=8.9 Hz, 1H), 7.67 (d, J=8.9 Hz, 1H), 8.28 (d, J=8.9 Hz, 1H), 9.69 (s, 1H), 10.54 (s, 1H)

¹³C-NMR (100.6 MHz, DMSO-d₆): 60.85, 60.98, 65.09, 74.54, 74.84, 112.51, 114.75, 115.13, 117.85, 118.13, 120.18, 120.24, 121.65, 124.20, 125.73, 126.27, 128.88, 132.51, 132.63, 133.95, 136.39, 136.53, 142.42, 142.88, 149.70, 151.07, 153.18, 162.27, 164.45

HR-MS: calc.: [M+H]⁺: 624.2010.
found: [M+H]⁺: 624.2018.

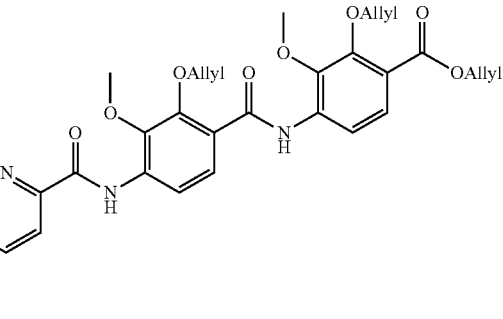

Allyl 2-allyloxy-4-[[2-allyloxy-4-[[4-[[(2S)-2-(tert-butoxycarbonylamino)-3-cyano-propanoyl]amino]phenyl]sulfonylamino]-3-methoxy-benzoyl]amino]-3-methoxy-benzoate

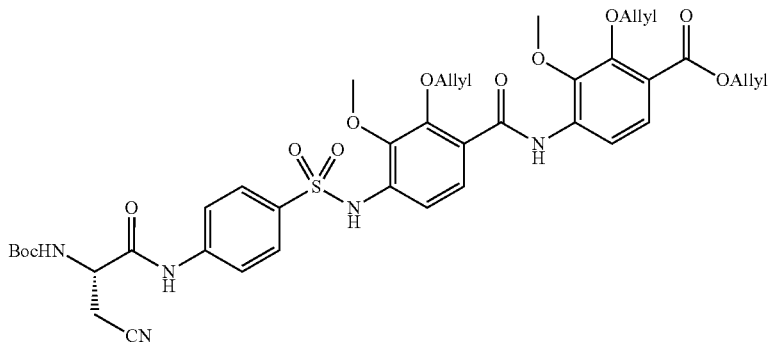

Chemical Formula: $C_{40}H_{45}N_5O_{12}S$

Exact Mass: 819,2785

The amine (1.00 eq) and Boc-Asn-OH (2.00 eq) were dissolved in DMF. DCC (4.00 eq) was added and the mixture was stirred at room temperature for 72 h. The mixture was diluted with EE and washed with 3× with 1 N HCl, sat. NaHCO$_3$ and brine. After drying over Na$_2$SO$_4$ the solvent was evaporated. The crude product was chromatographically purified to give the product as a yellow solid.

[(1S)-2-[4-[[3-allyloxy-4-[(3-allyloxy-4-allyloxycarbonyl-2-methoxy-phenyl)carbamoyl]-2-methoxy-phenyl]sulfamoyl]anilino]-1-(cyanomethyl)-2-oxo-ethyl]ammonium chloride

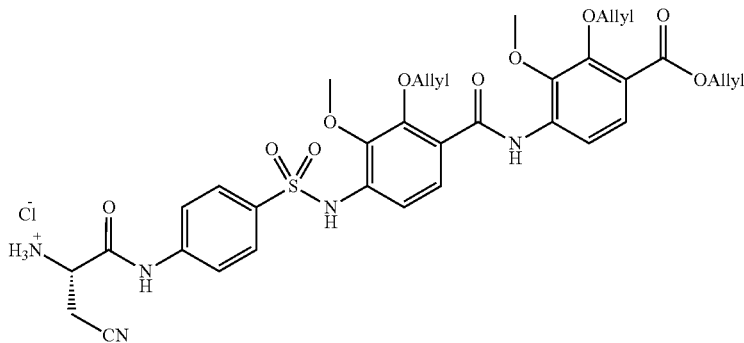

Chemical Formula: $C_{35}H_{38}N_5O_{10}S^+$

Exact Mass: 720,2334

Allyl 2-allyloxy-4-[[2-allyloxy-4-[[4-[[(2S)-2-(tert-butoxycarbonylamino)-3-cyano-propanoyl]amino]phenyl]sulfonylamino]-3-methoxy-benzoyl]amino]-3-methoxy-benzoate was dissolved in 4 M HCl in Dioxane and stirred for 1 h. The solvent was removed and the product dried in vacuo.

Allyl 2-allyloxy-4-[[2-allyloxy-4-[[4-[[(2S)-3-cyano-2-[(4-nitrobenzoyl)amino]propanoyl]amino]phenyl]sulfonylamino]-3-methoxy-benzoyl]amino]-3-methoxy-benzoate

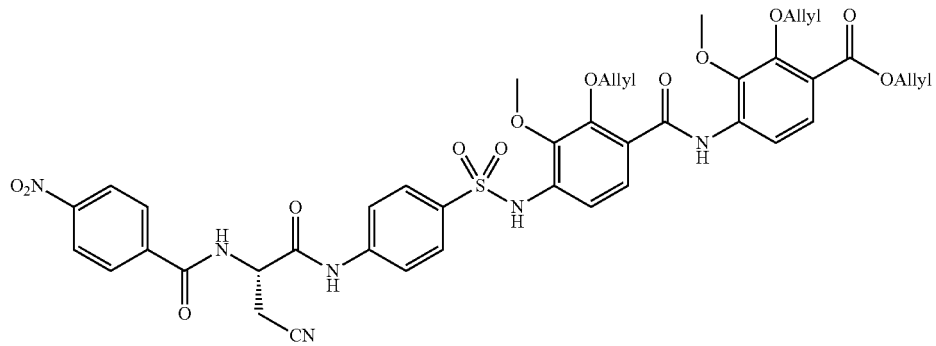

Chemical Formula: $C_{42}H_{40}N_6O_{13}S$
Exact Mass: 868,2374

The amine (1.00 eq) was dissolved in DMF and TEA (3.00 eq) was added dropwise. 2,5-Dioxopyrrolidin-1-yl-4-nitrobenzoate (1.05 eq) was dissolved in DMF and added to the mixture. After stirring at room temperature for 16 h the mixture was diluted with EE and washed 4× with 1 N HCl and brine. The organic layer was dried over $Na_2SO_4$ and the solvent was removed. The crude product was chromatographically purified to give the product as a yellow solid.

Allyl 2-allyloxy-4-[[2-allyloxy-4-[[4-[[(2S)-2-[(4-aminobenzoyl)amino]-3-cyano-propanoyl]amino]phenyl]sulfonylamino]-3-methoxy-benzoyl]amino]-3-methoxy-benzoate

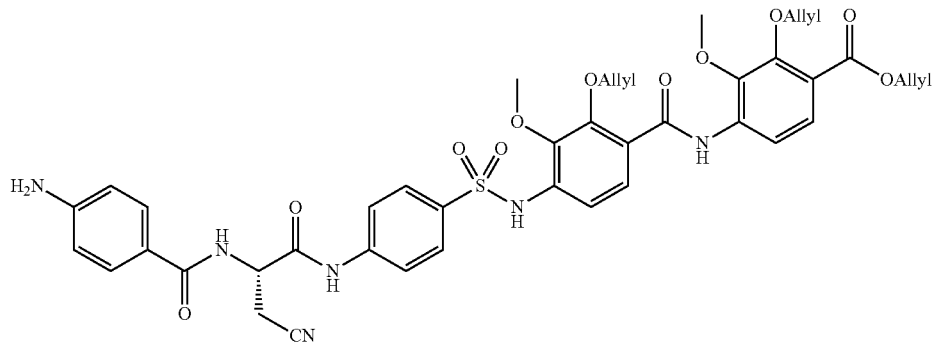

Chemical Formula: $C_{42}H_{42}N_6O_{11}S$
Exact Mass: 838,2632

Allyl 2-allyloxy-4-[[2-allyloxy-4-[[4-[[(2S)-3-cyano-2-[(4-nitrobenzoyl)amino]propanoyl]amino]phenyl]sulfonylamino]-3-methoxy-benzoyl]amino]-3-methoxy-benzoate (1.00 eq), was dissolved in EtOH and $SnCl_2.H_2O$ 5.00 eq) was added. The mixture was stirred at 60° C. for 6 h. The solvent was removed and the residue uptaken in EE. Sat. $NaHCO_3$ was added and the aqueous layer was extracted 3× with EE. The combined organic layers were dried over $Na_2SO_4$ and the solvent was removed. The crude product was chromatographically purified to give the product as a yellow solid.

Allyl 2-allyloxy-4-[[2-allyloxy-4-[[4-[[(2S)-2-[[4-[[(E)-3-(4-allyloxyphenyl)-2-methyl-prop-2-enoyl]amino]benzoyl]amino]-3-cyano-propanoyl

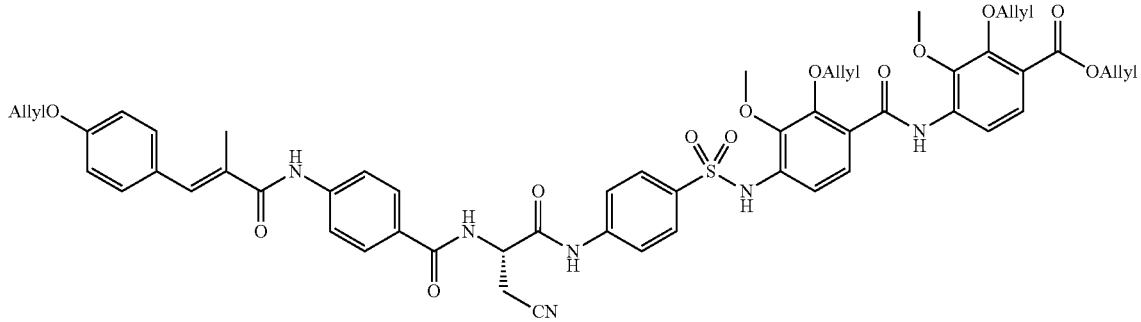

Chemical Formula: $C_{55}H_{54}N_6O_{13}S$
Exact Mass: 1038,3470

The cinnamic acid (3.00 eq) was dissolved in THF. Triphosgen (1.00 eq) and Collidin (8.00 eq) were added and it was stirred for 15 min. Allyl 2-allyloxy-4-[[2-allyloxy-4-[[4-[[(2S)-2-[(4-aminobenzoyl)amino]-3-cyano-propanoyl]amino]phenyl]sulfonylamino]-3-methoxy-benzoyl]amino]-3-methoxy-benzoate (1.00 eq) and DIPEA (10.00 eq) were dissolved in THF and added to the mixture. After stirring for 16 h the mixture was diluted with EE and the organic layer was washed 3× with 1 N HCl, sat. NaHCO₃ and brine. After drying over Na₂SO₄ the solvent was removed. The crude product was chromatographically purified to give the product as a yellow solid.

[(1S)-2-(4-benzyloxycarbonylanilino)-1-(cyanomethyl)-2-oxo-ethyl]ammonium

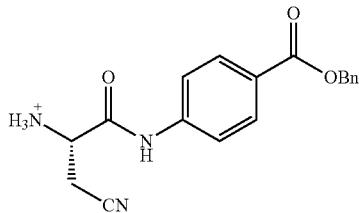 [SMILES: N#CC[C@H](N)C(=O)Nc1ccc(C(=O)OCc2ccccc2)cc1]

Chemical Formula: $C_{18}H_{18}N_3O_3^+$
Exact Mass: 324,1343

The Boc-protected amine (1.49 g, 3.45 mmol) was dissolved in 4 M HCl in Dioxane (20 ml). After stirring for 1 h at room temperature the solvent was evaporated and the product dried in vacuo (quant.).

benzyl 4-[[(2S)-3-cyano-2-[(4-nitrophenyl)sulfonylamino]propanoyl]amino]benzoate

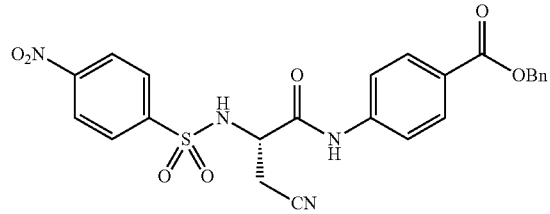 [SMILES: N#CC[C@H](NS(=O)(=O)c1ccc([N+](=O)[O-])cc1)C(=O)Nc1ccc(C(=O)OCc2ccccc2)cc1]

Chemical Formula: $C_{24}H_{20}N_4O_7S$
Exact Mass: 508,1053

The amine (400 mg, 1.11 mmol, 1.00 eq) was dissolved in DCM (20 ml). DMAP (50 mg, 3.88 mmol, 3.50 eq) and Pyridine (2 ml), followed by 4-nitrobenzene-1-sulfonyl chloride (741 mg, mmol, 3.00 eq). The reaction was stirred at room temperature for 72 h and subsequently washed 3× with 1 N HCl and brine. After drying over Na₂SO₄ the solvent was evaporated and the crude product chromatographically purified (Hex/EE 2:1) to give the desired product as a yellow solid (60%).

4-[[(2S)-2-[(4-aminophenyl)sulfonylamino]-3-cyano-propanoyl]amino]benzoic acid

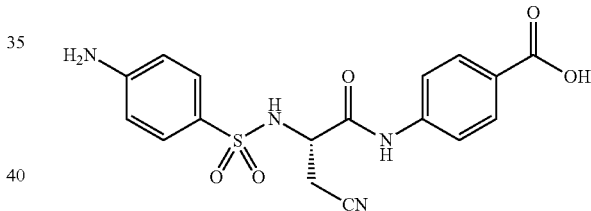

Chemical Formula: $C_{17}H_{16}N_4O_5S$
Exact Mass: 388,0841

The peptide was dissolved in EE/MeOH 9:1 and Pd/C 10% (w/w 10%) was added. Under a Hydrogen-atmosphere it was stirred at room temperature for 2 h. The reaction mixture was filtered through a pad of celite. After drying over Na₂SO₄ the solvent was evaporated to give the product.

4-[[(2S)-2-[[4-(tert-butoxycarbonylamino)phenyl]sulfonylamino]-3-cyano-propanoyl]amino]benzoic acid

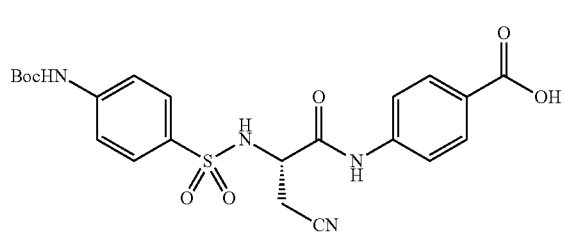 [SMILES: CC(C)(C)OC(=O)Nc1ccc(S(=O)(=O)N[C@@H](CC#N)C(=O)Nc2ccc(C(=O)O)cc2)cc1]

Chemical Formula: $C_{22}H_{24}N_4O_7S$
Exact Mass: 488,1366

The amineoacid (1.00 eq) was dissolved in dioxane/H$_2$O and K$_2$CO$_3$ (2.20 eq) and Boc$_2$O (1.10 eq) were added. After stirring at room temperature for 16 h the Dioxane was removed. The aqueous layer was extracted with MTBE. Subsequently the aqueous layer was acidified with 2 M HCl and extracted 3× with EE. After drying the combined organic layers over Na$_2$SO$_4$ the solvents was evaporated to give the product.

Allyl 2-allyloxy-4-[[2-allyloxy-4-[[4-[[(2S)-2-[[4-(tert-butoxycarbonylamino)phenyl]sulfonylamino]-3-cyano-propanoyl]amino]benzoyl]amino]-3-methoxy-benzoyl]amino]-3-methoxy-benzoate

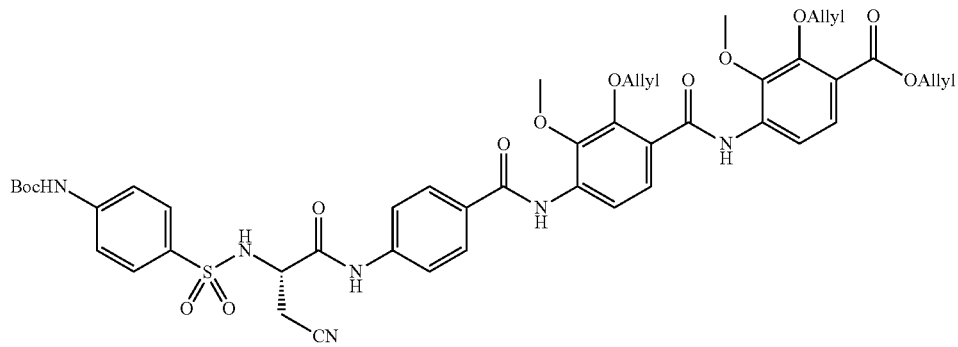

Chemical Formula: C$_{47}$H$_{50}$N$_6$O$_{13}$S
Exact Mass: 938,3157

4-[[(2S)-2-[[4-(tert-butoxycarbonylamino)phenyl]sulfonylamino]-3-cyano-propanoyl]amino]benzoic acid (2.00 eq) was dissolved in THF and Triphosgen (0.66 eq) and Collidin (8.00 eq) were added. The mixture was stirred at room temperature for 40 min. The amine (1.00 eq) and DIPEA (10.00 eq) were dissolved in THF, added to the mixture and it was stirred for an additional 16 h at room temperature. The reaction was diluted with EE and washed 3× with 1 N HCl, sat. NaHCO$_3$ and brine. After drying over Na$_2$SO$_4$ the solvent was removed. The crude product was chromatographically purified to give the product as a yellow solid.

[4-[[(1S)-2-[4-[[3-allyloxy-4-[(3-allyloxy-4-allyloxycarbonyl-2-methoxy-phenyl)carbamoyl]-2-methoxy-phenyl]carbamoyl]anilino]-1-(cyanomethyl)-2-oxo-ethyl]sulfamoyl]phenyl]ammonium

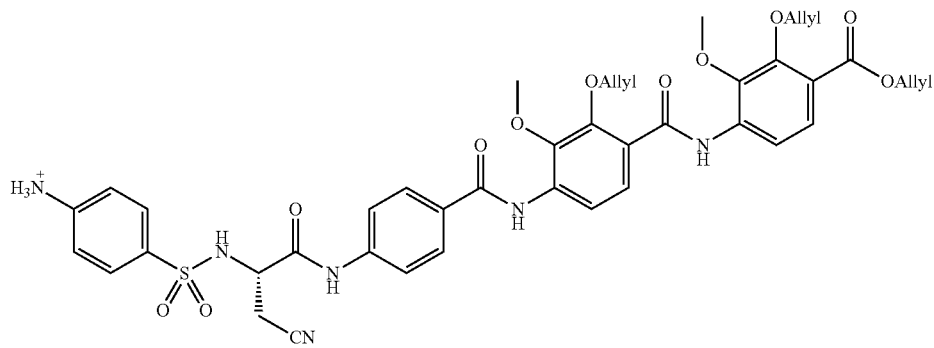

Chemical Formula: C$_{42}$H$_{43}$N$_6$O$_{11}$S$^+$
Exact Mass: 839,2705

The Boc-protected amine was dissolved in 4 M HCl in Dioxane. After stirring for 1 h at room temperature the solvent was evaporated and the product dried in vacuo.

Allyl 2-allyloxy-4-[[2-allyloxy-4-[[4-[[(2S)-2-[[4-[[(E)-3-(4-allyloxyphenyl)-2-methyl-prop-2-enoyl]amino]phenyl]sulfonylamino]-3-cyano-propanoyl]amino]benzoyl]amino]-3-methoxy-benzoyl]amino]-3-methoxy-benzoate

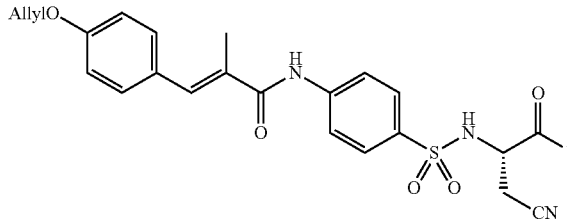
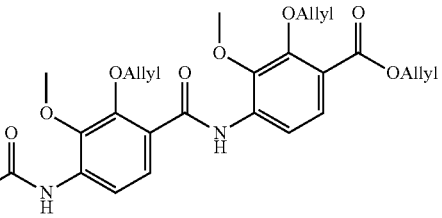

Chemical Formula: $C_{55}H_{54}N_6O_{13}S$
Exact Mass: 1038,3470

The cinnamic acid (3.00 eq) was dissolved in THF. Triphosgen (1.00 eq) and Collidin (8.00 eq) were added and it was stirred for 15 min. The amine (1.00 eq) and DIPEA (10.00 eq) were dissolved in THF and added to the mixture. After stirring for 16 h the mixture was diluted with EE and the organic layer was washed 3× with 1 N HCl, sat. NaHCO₃ and brine. After drying over Na₂SO₄ the solvent was removed. The crude product was chromatographically purified to give the product as a yellow solid.

(S,E)-Allyl 2-(allyloxy)-4-(2-(allyloxy)-4-(4-(2-(4-(3-(4-(allyloxy)phenyl)-2-methylacrylamido)benzamido)-3-cyanopropanamido)benzamido)-3-methoxybenzamido)-3-methoxybenzoate methoxybenzamido)-3-methoxybenzoate (12) (12) (1.0 eq, 0.09 mmol, 69 mg), DIPEA (10.0 eq, 0.86 mmol, 146 µL) in dry THF (3 mL) was added. Stirring was continued for 3 h at room temperature and the reaction was quenched by addition of water (2 mL). The organic solvent was removed under reduced pressure and EtOAc (20 mL) was added. The mixture was washed successively with saturated NaHCO₃ (3×10 mL), water (1×10 mL) and brine (1×10 mL). The organic solvent was dried over Na₂SO₄, filtered and removed under reduced pressure. Purification by column chromatography (CHCl₃-2% MeOH) yielded the product as a slightly yellow oil (64 mg, 75%).

$R_f$ (CHCl₃:CH₃OH-9:0.5)=0.15
¹H-NMR (dmso-d₆, 500 MHz): δ [ppm] 2.14 (s, 3H), 3.08 (dd, J₁=16.75 Hz, J₂=8.82 Hz, 1H), 3.17 (dd, J₁=16.84 Hz, J₂=5.35 Hz, 1H), 3.93 (s, 3H), 3.94 (s, 3H), 4.55 (d, J=5.55 Hz, 2H), 4.63 (d, J=5.15 Hz, 2H), 4.78 (d, J=5.35 Hz, 2H), 4.81 (d, J=6.14 Hz, 2H), 5.00 (dd, J₁=13.87 Hz, J₂=8.13 Hz, 1H), 5.28 (m, 4H), 5.41 (m, 4H), 6.09 (m, 4H), 7.05 (d, J=8.72 Hz, 2H), 7.32 (s, 1H), 7.46 (d, J=8.72 Hz, 2H), 7.58

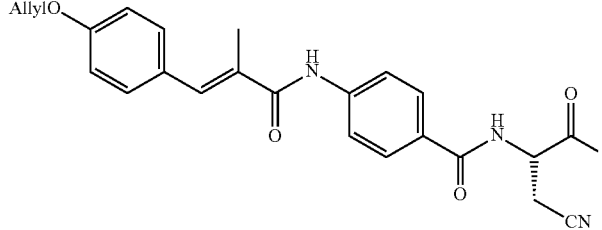
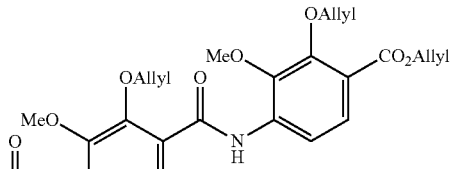

Bis-(trichloromethyl)carbonate (1.2 eq, 0.10 mmol, 29 mg) and (E)-3-(4-(allyloxy)phenyl)-2-methylacrylic acid (3.5 eq, 0.30 mmol, 66 mg) were dissolved in dry THF (2 mL) under argon atmosphere. 2,4,6-Collidine (8.0 eq, 0.69 mmol, 91 µL) was added slowly via syringe. The resulting suspension was stirred at room temperature for 20 min and a solution of (S)-Allyl 2-(allyloxy)-4-(2-(allyloxy)-4-(4-(2-(4-aminobenzamido)-3-cyanopropanamido)benzamido)-3-

(d, J=8.72 Hz, 1H), 7.81 (m, 3H), 7.86 (d, J=8.72 Hz, 2H), 7.94 (m, 3H), 8.00 (d, J=8.72 Hz, 2H), 8.34 (d, J=8.72 Hz, 1H), 9.03 (d, J=7.53 Hz, 1H), 9.69 (s, 1H), 10.15 (s, 1H), 10.59 (s, 1H), 10.66 (s, 1H).

HRMS (ESI): [M+H]⁺ calculated: 1003.3873.
found: 1003.3880.
[M+Na]⁺ calculated: 1025.3692.
found: 1025.3697.

(S,E)-4-(4-(4-(3-cyano-2-(4-(3-(4-hydroxyphenyl)-2-methylacrylamido)benzamido) propanamido)benzamido)-2-hydroxy-3-methoxybenzamido)-2-hydroxy-3-methoxybenzoic acid (albicidin)

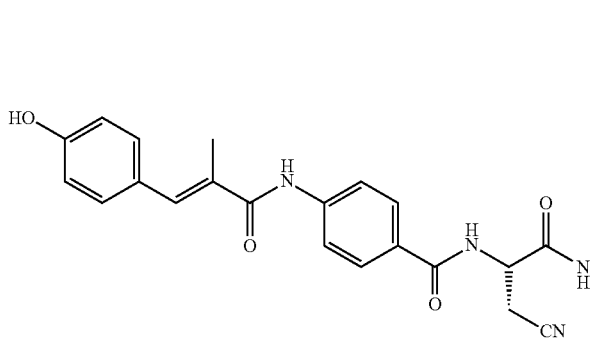

(S,E)-Allyl 2-(allyloxy)-4-(2-(allyloxy)-4-(4-(2-(4-(3-(4-(allyloxy)phenyl)-2-methylacrylamido)benzamido)-3-cyanopropanamido)benzamido)-3-methoxybenzamido)-3-methoxybenzoate (14) (1.0 eq, 30 µmol, 30 mg) was dissolved in dry THF (5 mL) under argon atmosphere and exclusion of light. Phenylsilane (8.0 eq, 239 µmol, 30 µl) and Pd[P(Ph)$_3$]$_4$ (0.5 eq, 15 µmol, 17 mg) were added and the reaction mixture was stirred for 10 hours at room temperature. AcOH (1 mL) was added, the solvent was removed under reduced pressure and the sample was freeze dried. Purification was achieved by preparative HPLC and yielded the product as a white solid (12 mg, 48%).

$^1$H-NMR (THF-d$_8$, 500 MHz): δ 2.05 (s, 3H), 3.01 (dd, J$_1$=16.84 Hz, J$_2$=8.72 Hz, 1H), 3.09 (m, 1H), 3.71 (s, 3H), 3.84 (s, 3H), 4.92 (m, 1H), 6.78 (d, J=8.32 Hz, 2H), 7.21 (s, 1H), 7.29 (d, J=8.32 Hz, 2H), 7.50 (d, J=8.92 Hz, 2H), 7.74 (m, 3H), 7.78 (d, J=8.52 Hz, 2H), 7.86 (m, 2H), 7.94 (m, 3H), 8.96 (d, J=7.53 Hz, 1H), 9.63 (s, 1H), 9.72 (s, 1H), 10.04 (s, 1H), 10.52 (s, 1H), 11.08 (s, 1H), 11.48 (s, 1H).

HRMS (ESI): [M−H]$^-$ calculated: 841.2460.
found: 841.2440.

Allyl 2-(allyloxy)-4-((2-(allyloxy)-3-methoxy-4-(4-nitrobenzamido)benzoyl)oxy)-3-methoxybenzoate

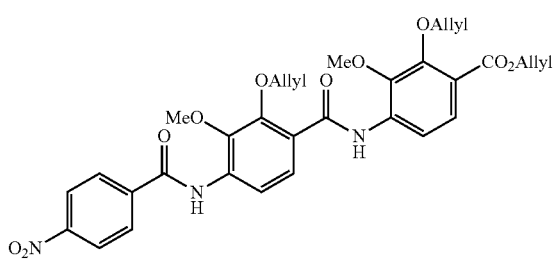

Allyl 2-(allyloxy)-4-(2-(allyloxy)-4-amino-3-methoxybenzamido)-3-methoxybenzoate (4) (1.0 eq, 0.49 mmol, 210 mg) was dissolved in dry THF and DIPEA (7.0 eq, 3.14 mmol, 533 µl) and p-nitro benzoic acid chloride (3.0 eq, 1.34 mmol, 250 mg) was added under argon atmosphere. The solution was stirred for 18 h at room temperature. The solvent was removed under reduced pressure and the crude product was purified by column chromatography (H:EA-4:1) to yield the product as a yellow solid (84 mg, 30%).

R$_f$(H:EA-3:1)=0.19

$^1$H-NMR (CDCl$_3$, 400 MHz): δ [ppm] 3.99 (s, 3H), 4.06 (s, 3H), 4.57-4.60 (m, 2H), 4.77 (d, J=6.42 Hz 2H), 4.81 (dt, J$_1$=5.73 Hz, J$_2$=1.34 Hz, 2H), 5.23-5.45 (m, 6H), 6.00-6.21 (m, 3H), 7.69 (d, J=8.9 Hz, 1H), 8.06-8.09 (m, 3H), 8.38-8.41 (m, 2H), 8.45 (dd, J$_1$=9.14 Hz, J$_2$=3.15 Hz, 2H), 8.69 (s, 1H).

HRMS (ESI): [M+H]$^+$ calculated: 618.2082.
found: 618.2075.
[M+Na]$^+$ calculated: 640.1902.
found: 640.1896.

Allyl 2-(allyloxy)-4-(2-(allyloxy)-4-(4-aminobenzamido)-3-methoxybenzamido)-3-methoxybenzoate

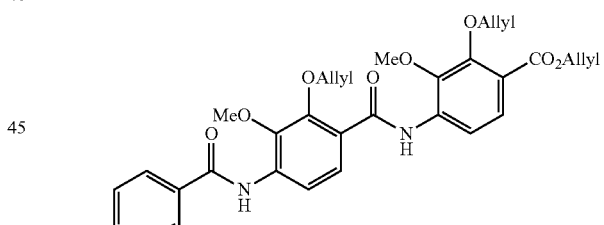

Allyl 2-(allyloxy)-4-((2-(allyloxy)-3-methoxy-4-(4-nitrobenzamido)benzoyl)oxy)-3-methoxy benzoate (20) (1.0 eq, 0.13 mmol, 82 mg) was dissolved in ethanol/dioxane (1:1, 1.8 mL) and SnCl$_2$.H$_2$O (5.0 eq, 0.66 mmol, 150 mg) was added. The solution was stirred for 17 h at room temperature. 1 M KOH was added, the aqueous phase was extracted with EtOAc, the combined organic layers were washed with brine and dried over Na$_2$SO$_4$. The solvent was removed under reduced pressure and the crude product was purified by column chromatography (H:EA-1:1) to yield the product as a yellow solid (65 mg, 83%).

R$_f$(H:EA-1:1)=0.23
HRMS (ESI): [M+H]$^+$ calculated: 588.2340.
found: 588.2338.
[M+Na]$^+$ calculated: 610.2160.
found: 610.2158.

(S)-allyl 2-(allyloxy)-4-(2-(allyloxy)-4-(4-(2-((tert-butoxycarbonyl)amino)-3-cyanopropanamido)benzamido)-3-methoxybenzamido)-3-methoxybenzoate

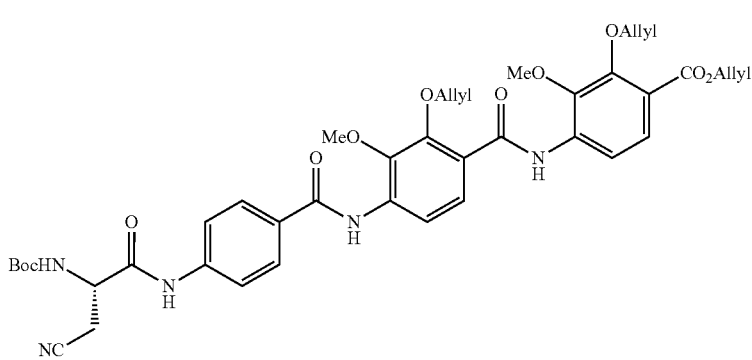

21

Allyl 2-(allyloxy)-4-(2-(allyloxy)-4-(4-aminobenzamido)-3-methoxybenzamido)-3-methoxy benzoate (17) (1.0 eq, 0.095 mmol, 56 mg) was dissolved in dry DMF under argon atmosphere. Boc-Asn-OH (3.0 eq, 0.29 mmol, 67 mg), HATU (6.1 eq, 0.58 mmol, 220 mg) and DIPEA (7 eq, 0.67 mmol, 113 µl) were added. The mixture was stirred at room temperature for 14 h. EtOAc was added and the organic layer was washed with saturated $NH_4Cl$ solution, saturated $NaHCO_3$ solution, brine and dried over $Na_2SO_4$. The solvent was removed under reduced pressure and the crude product was purified by column chromatography ($CHCl_3$:$CH_3OH$-9:0.2) to yield the product as a yellow, viscous oil. Since the product still contained impurities after chromatography the yield was determined after the last coupling step.

$R_f$(C:M-9:0.2)=0.08
HRMS (ESI): [M+Na]$^+$ calculated: 806.3008.
found: 806.3007.

(S)-allyl 2-(allyloxy)-4-(2-(allyloxy)-4-(4-(2-amino-3-cyanopropanamido)benzamido)-3-methoxybenzamido)-3-methoxybenzoate (S)-allyl 2-(allyloxy)-4-(2-(allyloxy)-4-(4-(2-((tert-butoxycarbonyl)amino)-3-cyanopropanamido)benzamido)-3-methoxybenzamido)-3-methoxybenzoate (21) was dissolved in dioxane and 4 M HCl in dioxane was added. The mixture was stirred at room temperature for 1.5 h. The solvent was removed under reduced pressure and the crude product was used for the next step without further purification. The yield was determined after the last coupling step.

$R_f$(C:M-9:1)=0.34
HRMS (ESI): [M+H]$^+$ calculated: 684.2664.
found: 684.2674.
[M+Na]$^+$ calculated: 706.2484.
found: 706.2492.

(E)-Methyl 4-(3-(4-(allyloxy)phenyl)-2-methylacrylamido)benzoate

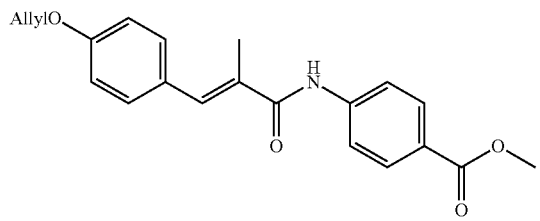

22

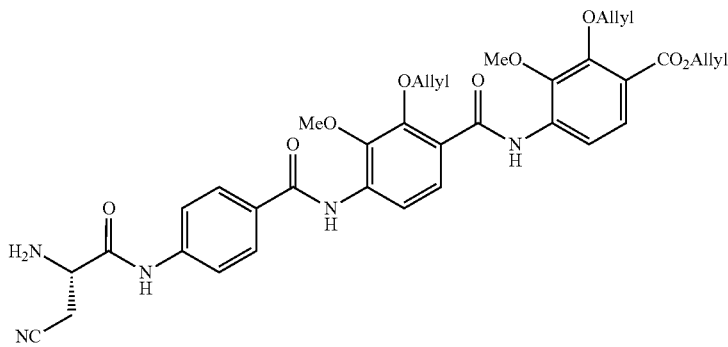

18

(E)-3-(4-allyloxyphenyl)-2-methyl-prop-2-enoic acid (13) (1.0 eq, 0.72 mmol, 157 mg) was dissolved in dry DCM under argon atmosphere and thionyl chloride (10.0 eq, 7.20 mmol, 522 µL) was added The solution was stirred at room temperature for 20 h. The solvent and thionyl chloride were removed under reduced pressure. The residue was dissolved in dry THF and methyl 4-aminobenzoate (0.7 eq, 0.48 mmol, 73 mg) and DIPEA (8.0 eq, 5.76 mmol, 976 µL) were added. The mixture was stirred at room temperature for 20 h, DCM was added and the organic layer was washed with saturated NH$_4$Cl solution and brine and dried over MgSO$_4$. The solvent vas evaporated and the crude product was purified using reversed phase flash chromatography (water/MeOH) to yield the product as a white solid (121 mg, 71%).

R$_f$ (CHCl$_3$:CH$_3$OH-100:1)=0.71

$^1$H-NMR (dmso-d$_6$, 400 MHz): δ [ppm] 2.12 (d, J$_1$=0.9 Hz, 3H), 3.83 (s, 3H), 4.60-4.63 (m, 2H), 5.25-5.30 (m, 1H), 5.38-5.45 (m, 1H), 6.00-6.10 (m, 1H), 7.01-7.05 (m, 2H), 7.29 (s, 1H), 7.44-7.46 (m, 2H), 7.86-7.95 (m, 4H), 10.23 (s, 1H).

HRMS (ESI): [M+H]$^+$ calculated: 352.1543.
found: 352.1550.
[M+Na]$^+$ calculated: 374.1363.
found: 374.1370.

(E)-4-(3-(4-(allyloxy)phenyl)-2-methylacrylamido) benzoic acid

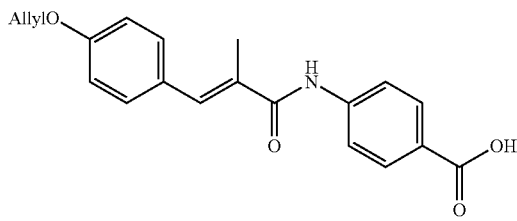

(E)-Methyl 4-(3-(4-(allyloxy)phenyl)-2-methylacrylamido)benzoate (22) (1 eq, 0.34 mmol, 121 mg) was dissolved in THF (2 mL). 0.5 M LiOH in water (2.5 eq, 0.86 mmol, 1.7 mL) was added. The mixture was stirred at room temperature for 20 h, then acidified to pH 2 and extracted with EtOAc. The combined organic layers were washed with water and brine, dried over MgSO$_4$ and the solvent was evaporated to yield the product as a white solid (99 mg, 85%).

R$_f$ (CHCl$_3$:CH$_3$OH-9:1)=0.35

$^1$H-NMR (dmso-d$_6$, 400 MHz): δ [ppm] 2.12 (d, J$_1$=0.98 Hz, 3H), 4.61 (d, J=5.2 Hz, 2H), 5.28 (dd, J$_1$=10.2 Hz, J$_2$=1.5 Hz, 1H), 5.42 (dd, J$_1$=17.3 Hz, J$_2$=1.5 Hz, 1H), 6.02-6.10 (m, 1H), 7.03 (d, J=8.7, 2H), 7.29 (s, 1H), 7.45 (d, J=8.7 Hz, 2H), 7.83-7.92 (m, 4H), 10.18 (s, 1H).

HRMS (ESI): [M−H]$^-$ calculated: 336.1241.
found: 336.1237.

SHORT DESCRIPTION OF THE FIGURES

Figure 4:
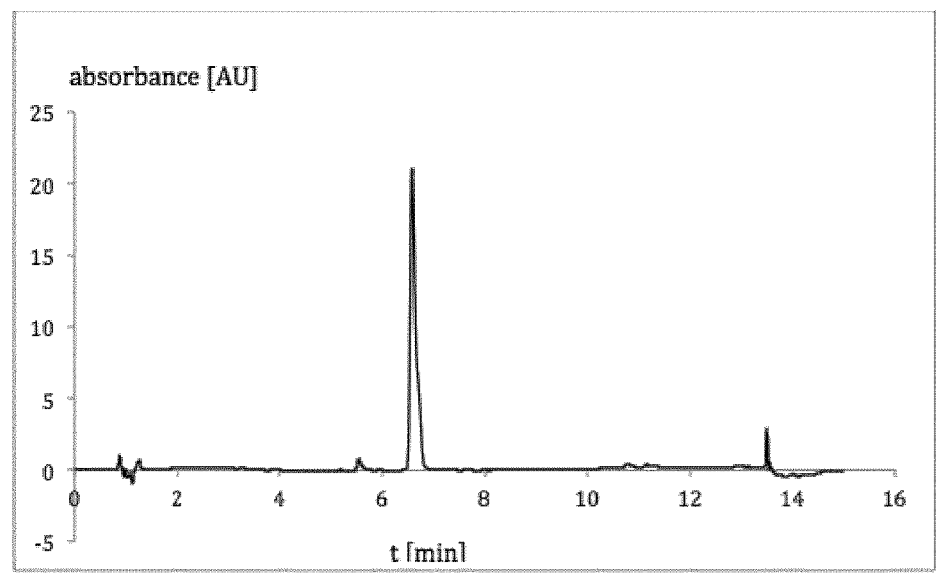
Figure 5:
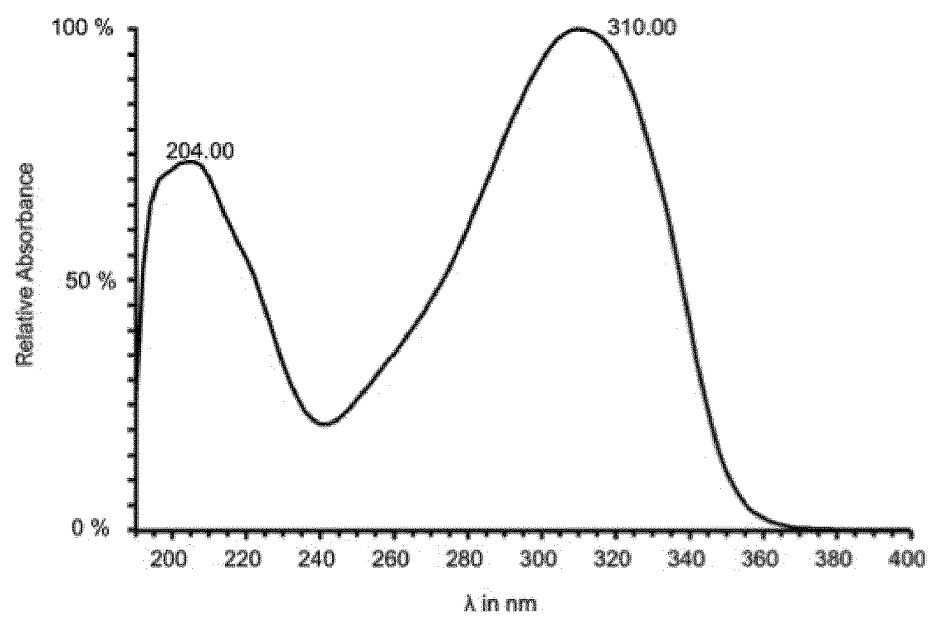
Figure 6:
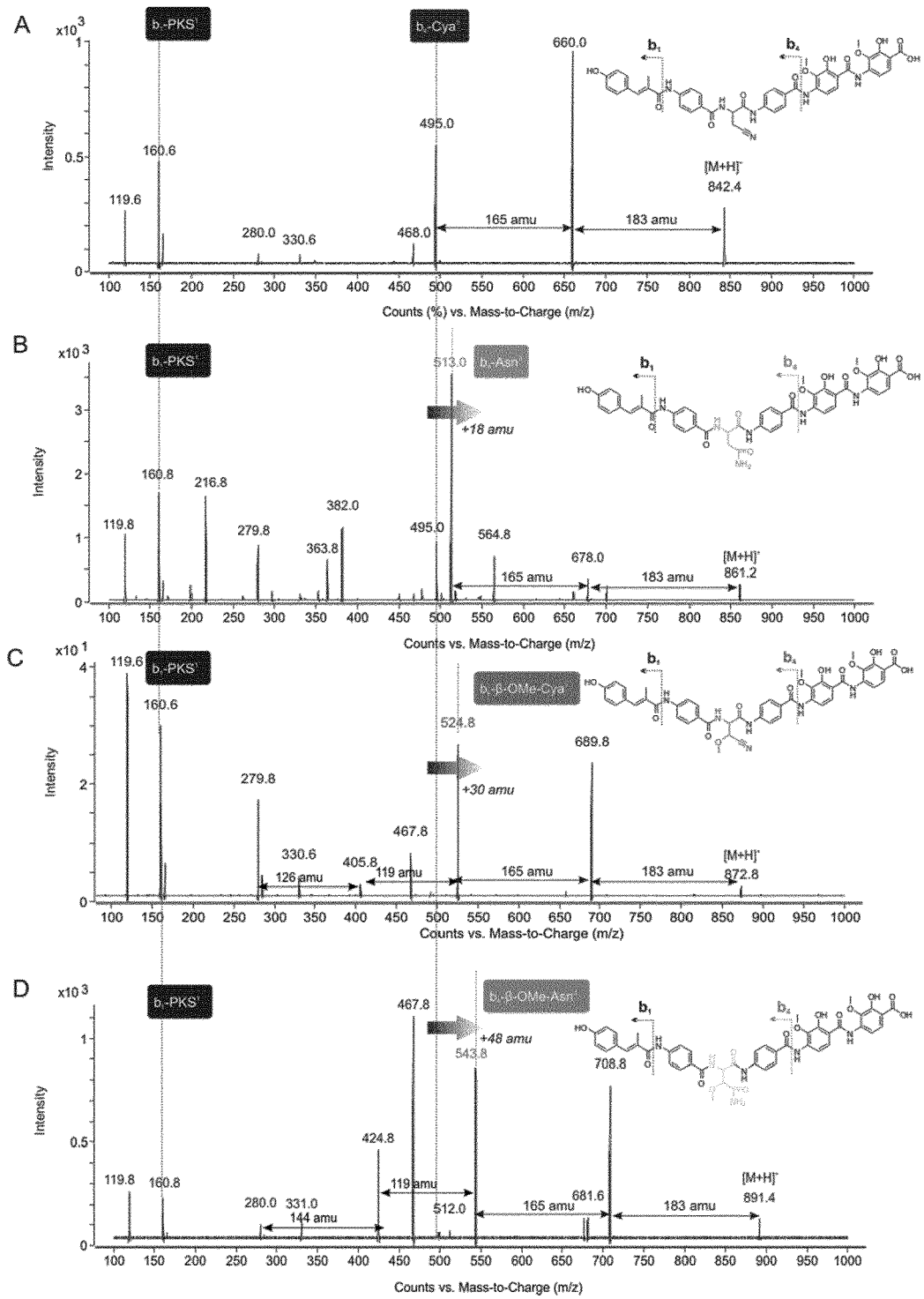
Figure 7:
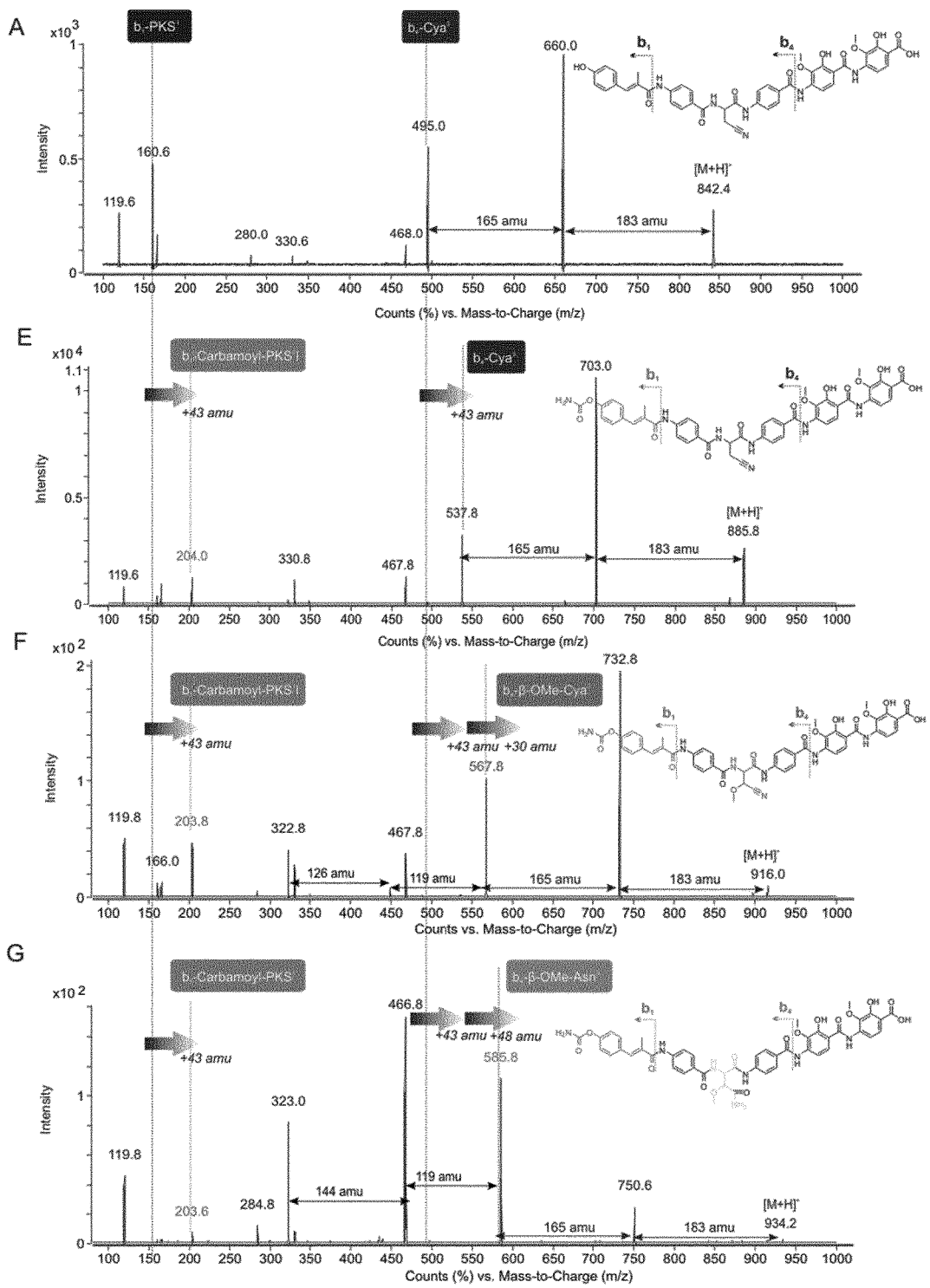
Figure 8:
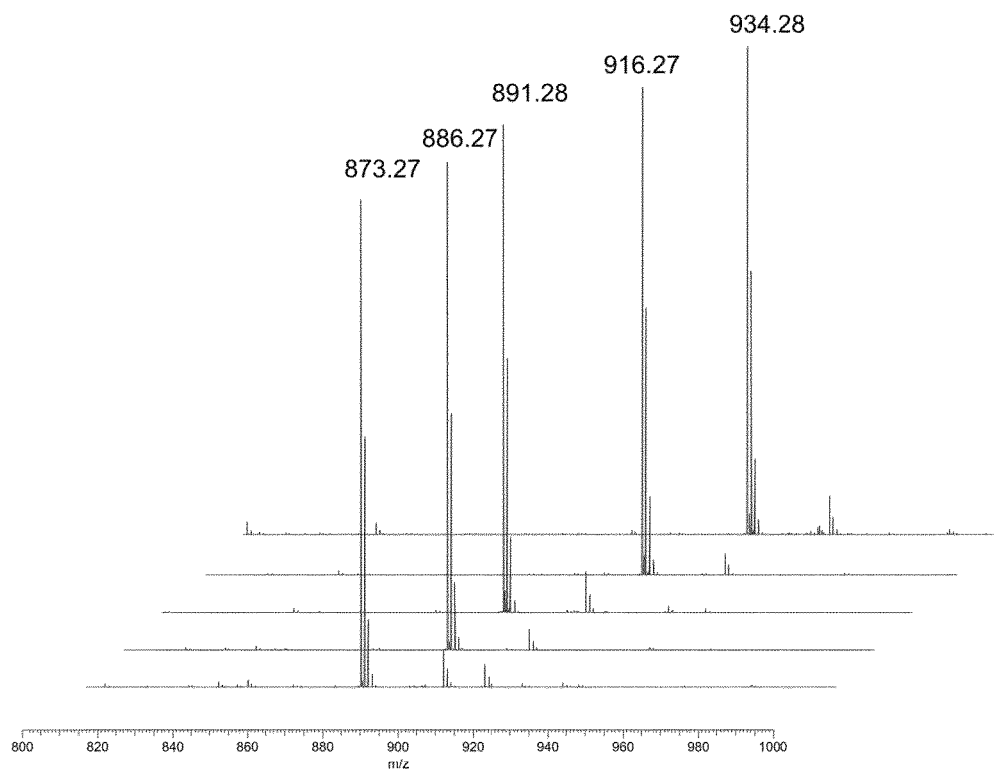
Figure 9:
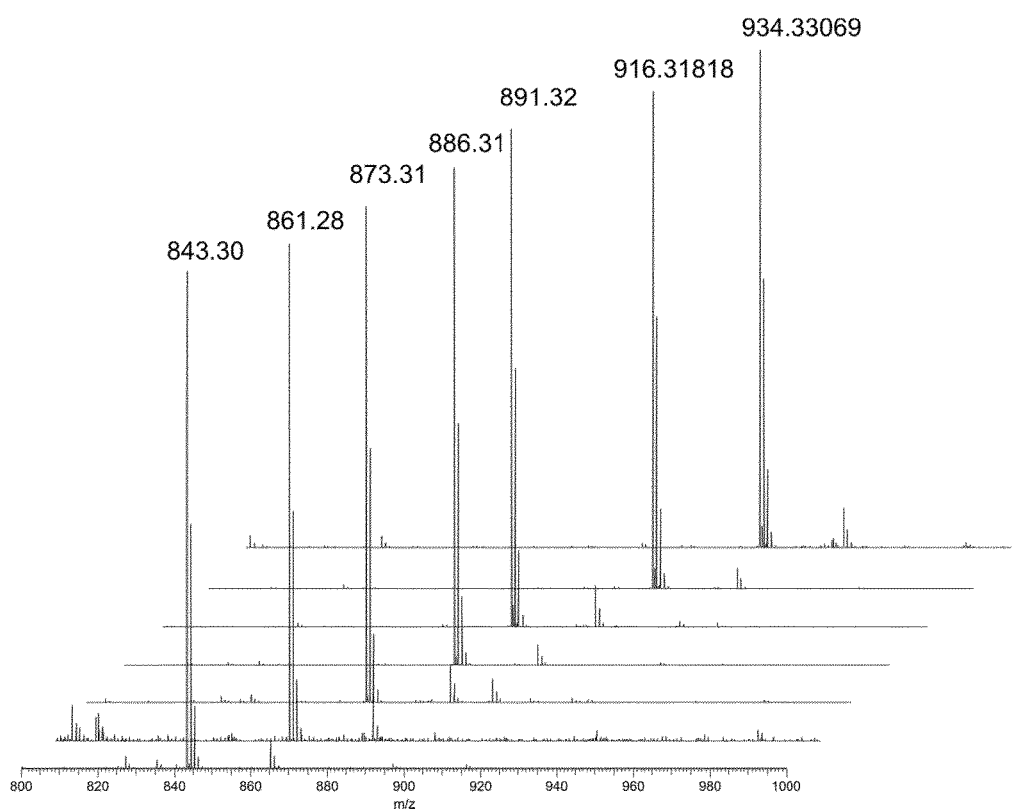
Figure 10:
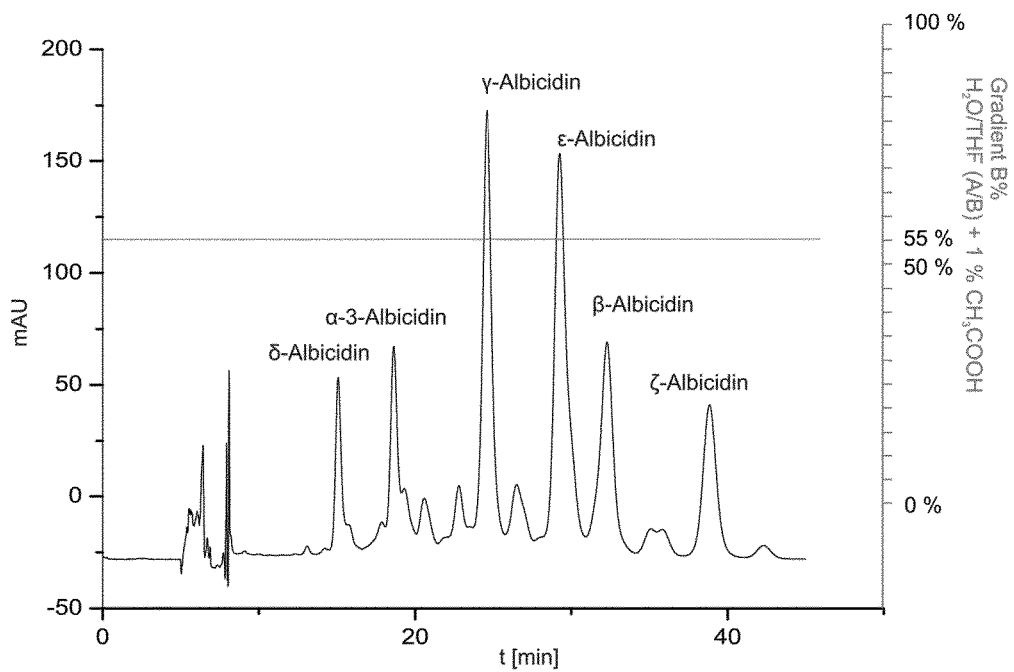

FIG. 1 shows a comparison of $^1$H-NMR spectra of natural beta-Albicidin and synthesized beta-Albicidin measured with a Bruker Avancell 700 MHz spectrometer. A) natural beta-Albicidin in d8-THF (50 µl) B) synthesized beta-Albicidin d8-THF (500 µl);

FIG. 2 shows a HPLC-LR-ESI-(+)-MS$^2$ experiment with A) beta-Albicidin (natural). B) Asn-Albicidin (natural) and C) Carbamoyl-Albicidin (natural) determining the structure of the compounds. HPLC-DAD-LR-ESI-(+)-MS/MS data were recorded on a triple quad mass spectrometer (ESI-Triple-Quadrupol-MS, 6460 series, Agilent Technologies, Waldbronn, Germany; Collision energy 10 eV);

FIG. 3A shows a CD spectra of beta-Albicidin (natural);
FIG. 3B shows a UV spectra of beta-Albicidin (natural);
FIG. 3C shows a CD spectra of beta-Albicidin (synthesized);
FIG. 3D shows a UV spectra of beta-Albicidin (synthesized);
FIG. 3E shows a CD spectra of Enantio-beta-Albicidin (synthesized);
FIG. 3F shows a UV spectra of Enantio-beta-Albicidin (synthesized);
FIG. 4 shows a HPLC-DAD-Chromatogram (Agilent 1100) of beta-(L)-Albicidin (λ=280 nm);
FIG. 5 shows a UV spectrum of the beta-(L)-albicidin measured on the Exactive Orbitrap HPLC-MS instrument (HPLC-DAD photodiode array detection, Agilent 1100 HPLC).
FIG. 6 shows HPLC-LR-ESI-(+)-MS/MS data: A) beta-Albicidin m/z=843.3 [M+H]$^+$; B) Asn-OMe-Albicidin m/z=861.28 [M+H]$^+$; C) beta-OMe-Albicidin m/z=873.31 [M+H]$^+$; D) Asn-OMe-Albicidin m/z=891.32 [M+H]$^+$. HPLC-DAD-LR-ESI-(+)-MS/MS data were recorded on a triple quad mass spectrometer (ESI-Triple-Quadrupol-MS, 6460 series, Agilent Technologies, Waldbronn, Germany; Collision energy 10 eV).
FIG. 7 shows HPLC-LR-ESI-(+)-MS/MS data: A) beta-Albicidin m/z=843.3 [M+H]$^+$; E) Carbamoyl-Albicidin m/z=886.31 [M+H]$^+$; F) Carbamoyl-OMe-Albicidin m/z=916.31 [M+H]$^+$; G) Carbamoyl-OMe-Asn-Albicidin m/z=934.33 [M+H]$^+$. HPLC-DAD-LR-ESI-(+)-MS/MS data were recorded on a triple quad mass spectrometer (ESI-Triple-Quadrupol-MS, 6460 series, Agilent Technologies, Waldbronn, Germany; Collision energy 10 eV).
FIG. 8 shows HR-ESI-(+)-Orbitrap-MS data: beta-OMe-Albicidin m/z=873.31 [M+H]$^+$; Carbamoyl-Albicidin m/z=886.31 [M+H]$^+$; Asn-OMe-Albicidin m/z=891.32 [M+H]$^+$; Carbamoyl-OMe-Albicidin m/z=916.31 [M+H]$^+$; Carbamoyl-OMe-Asn-Albicidin m/z=934.33 [M+H]$^+$.
FIG. 9 shows the High-resolution-ESI-(+)-Orbitrap-MS analysis performed on a Orbitrap XL LC-MS (Thermo Fisher Scientific GmbH, Bremen). beta-Albicidin m/z=843.30 [M+H]$^+$; Asn-OMe-Albicidin m/z=861.28 [M+H]$^+$; beta-OMe-Albicidin m/z=873.31 [M+H]$^+$; Carbamoyl-Albicidin m/z=886.31 [M+H]$^+$; Asn-OMe-Albicidin m/z=891.32 [M+H]$^+$; Carbamoyl-OMe-Albicidin m/z=916.31 [M+H]$^+$; Carbamoyl-OMe-Asn-Albicidin m/z=934.33 [M+H]$^+$.
FIG. 10 shows a HPLC-DAD-Chromatogram at 310 nm after the step 2 purification protocol, summarized in Table 1. R$_t$15 min=Carbamoyl-OMe-Asn-Albicidin (labeled δ-albicidin); R$_t$18 min=Asn-OMe-Albicidin (labeled α-3-albicidin); R$_t$24 min=Carbamoyl-Albicidin (labelled γ-albicidin); R$_t$29 min=Carbamoyl-OMe-Albicidin (labelled ε-albicidin); R$_t$32 min=beta-Albicidin (labelled β-Albicidin); R$_t$38 min=beta-OMe-Albicidin (labelled ξ-albicidin).
FIG. 11 shows a Table of biological test results of synthetic albicidin in comparison to natural albicidin synthesized by heterologous expression. The microbiological assay described by Zhang et al., (J Appl Microbiol., 1998, 85, 1023-8) was used to study cross-resistance between synthetic albicidin (10) and the natural product albicidin purified from albicidin heterologous host developed by Vivien et al. (Antimicrob Agents Chemother., 2007, 51, 1549-52). Several Escherichia coli strains expressing a wide range of albicidin resistance determinants were used for this microbiological bioassay: strain DH5aAlbr (a spontaneous albicidin-resistant DH5a derivative; Rott et al., (J. Bacteriol., 1996, 178, 4590-4596.) and strains harboring albD (an albicidin-detoxifying gene, Zhang and Birch (*Proc. Natl. Acad. Sci. USA*, 1997, 94, 9984-9989.), alb14 (an albicidin efflux pump gene conferring albicidin resistance in *E. coli*, Bostock et al., (*J. Appl. Microbiol.*, 2006, 101, 151-160.), alb19 (a McbG gene conferring albicidin resistance in *E. coli*, Hashimi et al. (*Antimicrob. Agents Chemother.*, 2007, 51, 181-187.), or sbmC (a microcin B17 resistance gene, Baquero et al. (*Mol. Microbiol.*, 1995, 18, 301-311.). The resistance pattern was exactly the same for both toxins (synthetic albicidin (10) and the natural product albicidin purified from albicidin heterologous host), confirming that both toxins exhibit the same mode of action.

PREPARATIONS OF ALBICIDIN DERIVATIVES

According to another aspect, the invention relates to preparations of an antibiotically active compound having a molecular structure as defined by formula 1, characterized in that the purity of the preparation is greater than 95%, 97%, 99%, 99.5% or 99.9%.

In some embodiments, the purity of the preparation is about 99%.

In some embodiments, the purity of the preparation is greater than 99%.

In some embodiments, the purity of the preparation is greater than 99.5%.

In some embodiments, the purity of the preparation is greater than 99.9%.

Similarly, a dosage form for the prevention or treatment of bacterial infection is provided, comprising a compound or preparation according to any of the above described aspects or embodiments of the invention. Dosage forms may be for enteral administration, such as nasal, buccal, rectal, transdermal or oral administration, or as an inhalation form or suppository. Alternatively, parenteral administration may be used, such as subcutaneous, intravenous, intrahepatic or intramuscular injection forms. Optionally, a pharmaceutically acceptable carrier and/or excipient may be present.

According to another aspect, the invention relates to a pharmaceutical preparation of an antibiotically active compound having a molecular structure as defined by formula 1 as active ingredient, characterized in that said pharmaceutical preparation is essentially free of (has a content of less than 5%, 3%, 1%, 0.5%, 0.1% (w/w)) contaminants.

In some embodiments, the pharmaceutical preparation has a content of less than 1% (w/w) contaminants.

In some embodiments, the pharmaceutical preparation has a content of less than 0.5% (w/w) contaminants.

In some embodiments, the pharmaceutical preparation has a content of less than 0.1% (w/w) contaminants.

In some embodiments, the pharmaceutical preparation is essentially free of contaminants.

According to a further aspect, the invention relates to an isolated antibiotically active compound having a molecular structure as defined by formula 1, or to a pharmaceutical preparation of at least one antibiotically active compound having a molecular structure as defined by formula 1 as active ingredient for use in a method of treatment of disease, particularly in a method for the treatment of bacterial infections.

In some embodiments, the pharmaceutical preparation of at least one antibiotically active compound comprises one essentially pure enantiomer according to the general formula 1L or 1D.

In some embodiments, the pharmaceutical preparation of an antibiotically active compound comprises a mixture of L- or D-enantiomers selected independently from each other from the compounds of the general formula 1.

In some embodiments, the pharmaceutical preparation of an antibiotically active compound comprises mixture of the L-enantiomer and the respective D-enantiomer according to the general formula 1L and 1D, wherein Z and Y of the general formula 1L are the same as Z and Y of the general formula 1D, thus, pharmaceutical preparation comprises a mixture of the L- and D-enantiomer with the same molecular formula.

In some embodiments, the pharmaceutical preparation of at least one antibiotically active albicidin compound comprises one essentially pure enantiomer selected from the group of beta-Albicidin or Asn-Albicidin.

In some embodiments, the pharmaceutical preparation of at least one antibiotically active albicidin compound comprises one essentially pure enantiomer selected from the group of Enantio-beta-Albicidin or Enantio-Asn-Albicidin.

In some embodiments, the pharmaceutical preparation comprises beta-Albicidin as N essentially pure enantiomer.

In some embodiments, the pharmaceutical preparation comprises Enantio-beta-Albicidin as N essentially pure enantiomer.

In some embodiments, the pharmaceutical preparation of an antibiotically active albicidin compound comprises a mixture of L- or D-enantiomers selected from the group of beta-Albicidin, Asn-Albicidin, Carbamoyl-Albicidin, Carbamoyl-Asn-Albicidin, beta-OMe-Albicidin, Asn-OMe-Albicidin, Carbamoyl-OMe-Albicidin, Carbamoyl-OMe-Asn-Albicidin, Enantio-beta-Albicidin, Enantio-Asn-Albicidin, Enantio-Carbamoyl-Albicidin, Enantio-Carbamoyl-Asn-Albicidin, Enantio-beta-OMe-Albicidin, Enantio-Asn-OMe-Albicidin, Enantio-Carbamoyl-OMe-Albicidin or Enantio-OMe-Carbamoyl-Asn-Albicidin. This includes also the previously discussed diastereoisomers (1L1, 1L2, 1D1, 1D2), which are not specifically mentioned due to simplicity reasons.

In some embodiments, the pharmaceutical preparation of an antibiotically active albicidin compound comprises a mixture of L-Enantiomers selected from the group of beta-Albicidin, Asn-Albicidin Carbamoyl-Albicidin, Carbamoyl-Asn-Albicidin, beta-OMe-Albicidin, Asn-OMe-Albicidin, Carbamoyl-OMe-Albicidin, Carbamoyl-OMe-Asn-Albicidin.

In some embodiments, the pharmaceutical preparation of an antibiotically active albicidin compound comprises a mixture of D-Enantiomers selected from the group of Enantio-beta-Albicidin, Enantio-Asn-Albicidin, Enantio-Carbamoyl-Albicidin, Enantio-Carbamoyl-Asn-Albicidin Enantio-beta-OMe-Albicidin, Enantio-Asn-OMe-Albicidin, Enantio-Carbamoyl-OMe-Albicidin or Enantio-OMe-Carbamoyl-Asn-Albicidin.

In some embodiments, the pharmaceutical preparation of an antibiotically active albicidin compound comprises mixture of the L-enantiomer and the respective D-enantiomer according to the general formula (1L) and (1D), wherein $R^{1'}$, $R^{2'}$ and $R^{3'}$ of the general formula (1L) are the same as $R^{1'}$, $R^{2'}$ and $R^{3'}$ of the general formula (1D), thus, pharmaceutical preparation comprises a mixture of the L- and D-enantiomer with the same molecular formula.

In some embodiments, the pharmaceutical preparation of an antibiotically active albicidin compound comprises mixture of beta-Albicidin and Enantio-beta-Albicidin, or
Asn-Albicidin and Enantio-Asn-Albicidin.

In some embodiments, the pharmaceutical preparation of an antibiotically active albicidin compound comprises mixture of
beta-Albicidin and Enantio-beta-Albicidin.

In some embodiments, the bacterial infection is an infection by a gram-negative bacterium.

In some embodiments, the bacterial infection is an infection by a gram-negative bacterium of the genus *Acinetobacter, Bordatella, Borellia, Brucella, Camphylobacter, Chlamydia, Chlamydophila, Enterobacter, Escherichia, Francisella, Haemophilus, Helicobacter, Klebisella, Legionella, Leptospira, Morganella, Moraxella, Neisseria, Proteus, Pseudomonas, Rickettsia, Shigella, Salmonella, Stenotrophomonas, Treponema* or *Yersinia*.

In some embodiments, the bacterial infection is an infection by a gram-negative bacterium of the genus *Bacteroides, Escherichia, Enterobacter, Salmonella, Klebisella, Pseudomonas, Haemophilus, Serratia, Shigella, Proteus* or *Morganella*.

In some embodiments, the bacterial infection is an infection by a gram-negative bacterium selected from the group of *Acinetobacter baumannii, Bacteriodis fragilis, Bordatella pertussis, Borrelia burgdorferi, Brucella abortus, Brucella abortus, Brucella canis, Brucella melitensis, Brucella suis, Campylobacter jejuni, Chlamydia pneumoniae, Chlamydia trachomatis, Chlamydophila psittaci, Enterobacter aerogenes, Enterobacter cloacae, Enterobacter sakazakii, Cronobacter sakazakii, Escherichia coli, Francisella tularensis, Haemophilus influenzae, Helicobacter pylori, Klebisella pneumonia, Legionella pneumophila, Leptospira interrogans, Moraxella catarrhalis, Morganella morganii, Moraxella lacunata, Moraxella bovis, Neisseria gonorrhoeae, Neisseria meningitidis, Proteus vulgaris, Proteus mirabilis, Pseudomonas aeruginosa, Rickettsia rickettsii, Salmonella typhi, Salmonella enteritidis, Serratia marcescens, Shigella sonnei, Stenotrophomonas maltophilia, Treponema pallidum, Vibrio cholerae* or *Yersinia pestis*.

In some embodiments, the bacterial infection is an infection by a gram-negative bacterium selected from the group of *Escherichia coli, Enterobacter aerogenes, Enterobacter cloacae, Enterobacter sakazakii, Cronobacter sakazakii, Salmonella typhi, Klebisella pneumonia, Pseudomonas aeruginosa, Haemophilus influenza, Shigella sonnei, Proteus vulgaris, Proteus mirabilis* or *Morganella morganii*.

In some embodiments, the bacterial infection is an infection by a gram-positive bacterium.

In some embodiments, the bacterial infection is an infection by a gram-positive bacterium of the genus *Bacillus, Clostridium, Corynebacterium, Enterococcus, Listeria, Micrococcus, Staphylococcus* or *Streptococcus*.

In some embodiments, the bacterial infection is an infection by a gram-positive bacterium of the genus of *Staphylococcus, Streptococcus, Bacillus* or *Micrococcus*.

In some embodiments, the bacterial infection is an infection by a gram-positive bacterium selected from the group of *Bacillus anthracis, Clostridium botulinum, Clostridium difficile, Clostridium perfringens, Clostridium tetani, Corynebacterium diphtheriae, Enterococcus faecalis, Enterococcus faecium, Listeria monocytogenes, Staphylococcus aureus, Staphylococcus epidermidis, Staphylococcus saprophyticus, Streptococcus agalactiae, Streptococcus pneumoniae* or *Streptococcus pyogenes*.

In some embodiments, the bacterial infection is an infection by a gram-positive bacterium selected from the group of *Staphylococcus aureus, Staphylococcus epidermidis, Streptococcus pyogenes, Bacillus subtilis, Bacillus megaterium* or *Micrococcus luteus*.

In some embodiments, the bacterial infection is an infection by a bacterium of the family of Mycobacteriaceae, in particular a *Mycobacterium*, further in particular an infection by one of *Mycobacterium tuberculosis, Mycobacterium leprae, Mycobacterium ulcerans* or *Mycobacterium avium*.

In some embodiments, the bacterial infection is an infection by a bacterium of the family of Mycoplasmataceae, in particular of the genus *Mycoplasma*, further in particular an infection by *Mycoplasma pneumonia*.

In some embodiments, the bacterial infection is an infection by a bacterium resistant to a fluoroquinolone antibiotic. In some embodiments, the bacterium is resistant to the fluroquinolone antibiotic ciprofloxacin, levofloxacin or trovafloxacin.

The invention claimed is:

1. A compound having formula (23)

(formula 23)

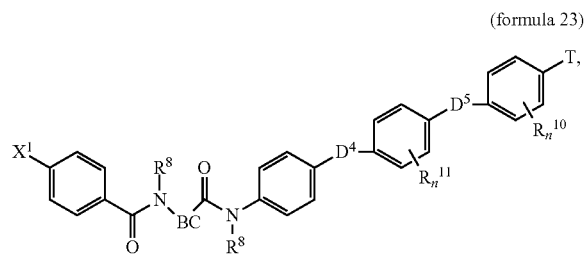

a. with $X^1$ being BA-D1 with BA being selected from (BA1)

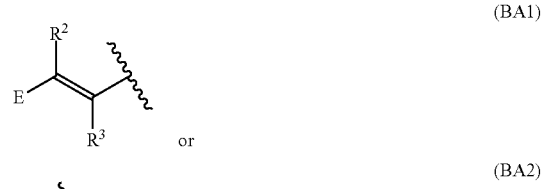

or (BA2)

with $R^2$ and $R^3$ being selected, where applicable, independently from each other from —H, —F, —CN, —OH, a substituted or unsubstituted $C_1$-$C_3$ alkyl, a substituted or unsubstituted $C_1$-$C_3$ alkoxy or a $C_1$-$C_3$ haloalkyl, with E being
a substituted or unsubstituted $C_1$-$C_{16}$ alkyl, a substituted or unsubstituted $C_1$-$C_{16}$ alkoxy, a substituted or unsubstituted $C_1$-$C_{16}$ carboxy, a substituted or unsubstituted $C_2$-$C_{16}$ alkenyl, a substituted or unsubstituted $C_2$-$C_{16}$ alkynyl, or a $C_1$-$C_{16}$ haloalkyl, —
a substituted or unsubstituted $C_3$-$C_{10}$ cycloalkyl or a substituted or unsubstituted $C_3$-$C_{10}$ halo cycloalkyl,
a substituted or unsubstituted $C_3$-$C_{10}$ heterocycle or a substituted or unsubstituted $C_3$-$C_{10}$ halo heterocycle,
a substituted or unsubstituted $C_5$-$C_{10}$ heteroaryl, or

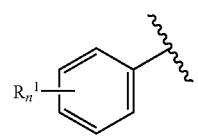

with n of $R^1_n$ being 0, 1, 2, 3, 4, or 5, and
with each $R^1$ independently from any other $R^1$ being selected from the group consisting of —OH, —F, —Cl, —Br, —I, —CCH, —CN, —N3, —OCH3, —OCF3, —NH2, —NHCH3, —N(CH3)2, —CH3, —CH2—CH3, —CF3, —OCONH2 or —NO2, B(ORa)(ORb), —(CH2)m—Ra, —(CH2)m—ORa, —(CH2)m—C(=O)Ra, —(CH2)m—C(=O)ORa, —(CH2)m—OC(=O) Ra, —(CH2)m—OC(=O)ORa, —(CH2)m—OC(=O)NRaRb, —(CH2)m—C(=O)NRaRb, —(CH2)m—C(=O)NRaRb, —(CH2)m—C(=O)NRb(ORa), —(CH2)m—C(=S)Ra, —(CH2)m—C(=S)ORa, —(CH2)m—OC(=S) Ra, —(CH2)m—OC(=S)ORa, —(CH2)m—OC(=S)NRaRb, —(CH2)m—C(=S)NRaRb, —(CH2)m—SRa, —(CH2)m—S(=O)Ra, —(CH2)m—S(O2)Ra, —(CH2)m—S(O2)ORa, —(CH2)m—OS(O2)Ra, —(CH2)m—OS(O2)ORa, —(CH2)m—NRaRb, —(CH2)m—NRcC(=O)Ra, —(CH2)m—NRcC(=O)NRaRb, —(CH2)m—NRcC(=O)ORa, —(CH2)m—NRcC(=S)Ra, —(CH2)m—NRcC(=S)NRaRb, —(CH2)m—NRcC(=S)ORa, —(CH2)m—NRcS(O2)Ra, —(CH2)m—P(=O)(ORb)(ORa), —(CH2)m—P(=O)(ORb)(Ra) or —(CH2)m—S(O2)NRbRa, —(CH2)m—O—C(=O)—(M)—C(=O)OH, —(CH2)m—O—C(=O)—(M)—C(=O)ORa, —(CH2)m—O—C(=O)—(M)—Ra, —(CH2)m—O—(CH2)q—P(=O)(Rba)(Raa), —(CH2)m—C(=O)O—(CH2)q—P(=O)(Rba)(Raa), —(CH2)m—C(=O)O—(CH2)q—S(O2)OH or —(CH2)m—C(=O)O—(CH2)q—S(O2)ORa, with Raa being selected independently from each other being —Ra or —ORa, with Rba being selected independently from each other being —Rb or —ORb, with M being a substituted or unsubstituted C1-C8 alkyl, with m being selected from 0, 1 or 2, with q being selected from 0, 1 or 2, and with each Ra, Rb or Rc being selected independently from each other from
hydrogen, —CN,
a substituted or unsubstituted C1-C16 alkyl, a substituted or unsubstituted C1-C16 alkoxy, a substituted or unsubstituted C1-C16 carboxy, a substituted or unsubstituted C2-C16 alkenyl, a substituted or unsubstituted C2-C16 alkynyl, or a C1-C16 haloalkyl, a substituted or unsubstituted C3-C10 cycloalkyl, or a substituted or unsubstituted C3-C10 halo cycloalkyl,
a substituted or unsubstituted C3-C10 cycloalkyl or a substituted or unsubstituted C3-C10 halo cycloalkyl,
a substituted or unsubstituted C3-C10 heterocycle or a substituted or unsubstituted C3-C10 halo heterocycle,
a substituted or unsubstituted C5-C10 heteroaryl,
a substituted or unsubstituted C6-C10 aryl;

b. with BC being selected from

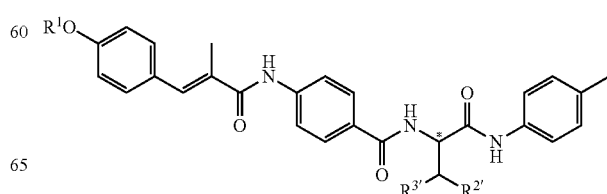

with Y being selected from —CN, —C(=O)OH, —C(=O)OCH3, —C(=O)OCH2CH3, —C(=O)NHCH3, —C(=O)NHCH2CH3, —C(=O)N(CH3)2, —C(=O)N(CH2CH3)2, —C(=O)N(CH3)(CH2CH3), —CF3 or —C(=O)NH2, and with Z being selected from —H, —OH, —CH3, —CH2CH3, —OCH3, —NH2, —NHCH3, —N(CH3)2, —N(CH3)3+;

c. with each $R^8$ being
—H, or, with each $R^8$ being selected independently from each other from —H, —CH3, —CH2CH3;

d. with n of $R^{10}_n$ being 1 or 2; and
with each $R^{10}$ independently from any other $R^{10}$ being selected from
—OH, —F, —Cl, —Br, I, —CCH, —CN, —N3, —OCH3, —OCF3, —NH2, —NHCH3, —N(CH3)2, —CH3, —CH2—CH3, —CF3, or —NO2;

e. with n of $R^{11}_n$ being 0, 1, 2, 3 or 4,
with each $R^{11}$ being selected independently from any other from any other $R^{11}$ from —OH, —F, —Cl, —Br, —I, —CCH, —CN, —N3, —OCH3, —OCF3, NH2, —NHCH3, —N(CH3)2, —CH3, —CH2CH3, —CH2OCH3, —CHCH2, —CH2OH, —SO2NH2, —SO2N(CH3)2, —SO2NHCH3, —CH3, —CF3, or —NO2;

f. with T being selected from
—OH, —F, —Cl, —Br, I, —CCH, —CN, —N3, —OCH3, —OCF3, —NH2, —NHCH3, —N(CH3)2, —CH3, —CH2—CH3, —CF3 or —NO2,
—(CH2)m—C(=O)OR$^a$, —(CH2)m—S(O2)OR$^a$, with m being selected from 0, 1 or 2, with R$^a$ being hydrogen,
a substituted or unsubstituted $C_1$-$C_{16}$ alkyl, a substituted or unsubstituted $C_2$-$C_{16}$ alkenyl, a substituted or unsubstituted $C_2$-$C_{16}$ alkynyl, or a $C_1$-$C_{16}$ haloalkyl, or a substituted or unsubstituted $C_3$-$C_{10}$ cycloalkyl or a substituted or unsubstituted $C_3$-$C_{10}$ halo cycloalkyl;

g. with D1, D4 and D5 being each independently from each other from

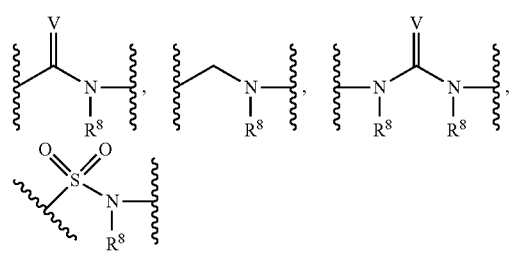

wherein
each $R^8$ being —H, or with each $R^8$ being selected independently from each other from —H, —CH3, —CH2CH3, and
V being O;

h. wherein the compounds of formulae (2a) is disclaimed:

(2a)

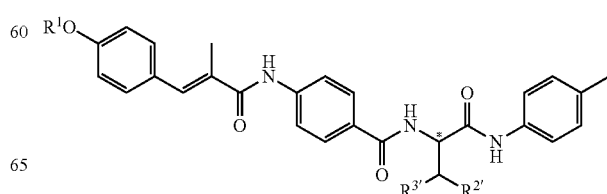

-continued

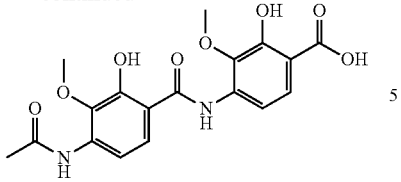

5 wherein $R^1$ is H or $CO(NH_2)$, $R^{2\prime}$ is $CO(NH_2)$ or CN, $R^{3\prime}$ is H or $OCH_3$.

2. The compound according to claim 1 having formulae 21

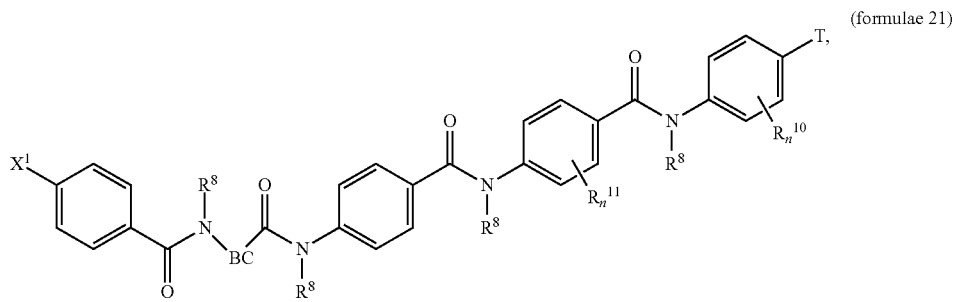

(formulae 21)

wherein $X^1$, BC, $R^8$, $R^{11}{}_n$, $R^{10}{}_n$ and T have the meaning as recited in claim 1.

3. The compound according to claim 1 having formulae 25

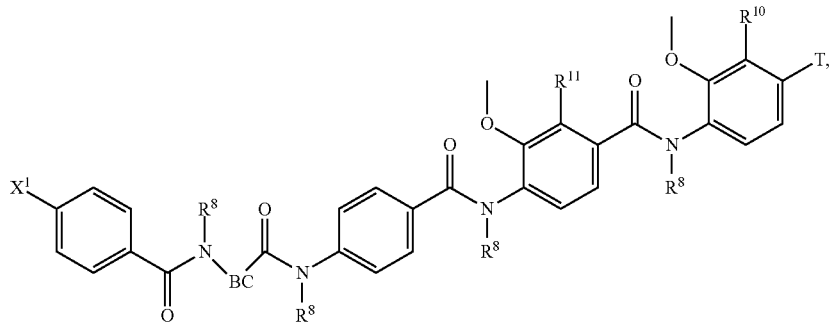

(formulae 25)

wherein $X^1$, BC, $R^8$, $R^{11}$, $R^{10}$ and T have the meaning as recited in claim 1 and E is

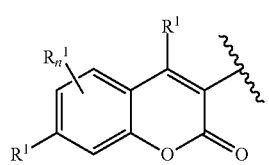

with n of $R^1{}_n$ being 0 or 1, and
with each $R^1$ independently from any other $R^1$ being selected from —OH or —$CH_3$.

4. A compound selected from the group consisting of:

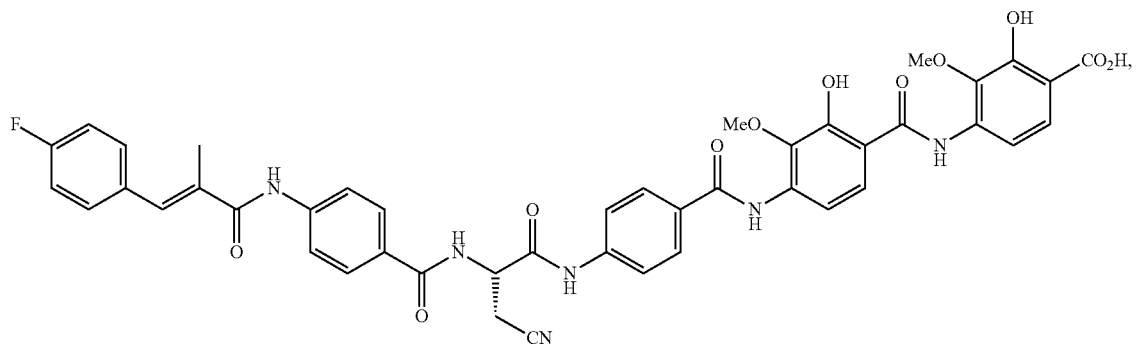
1
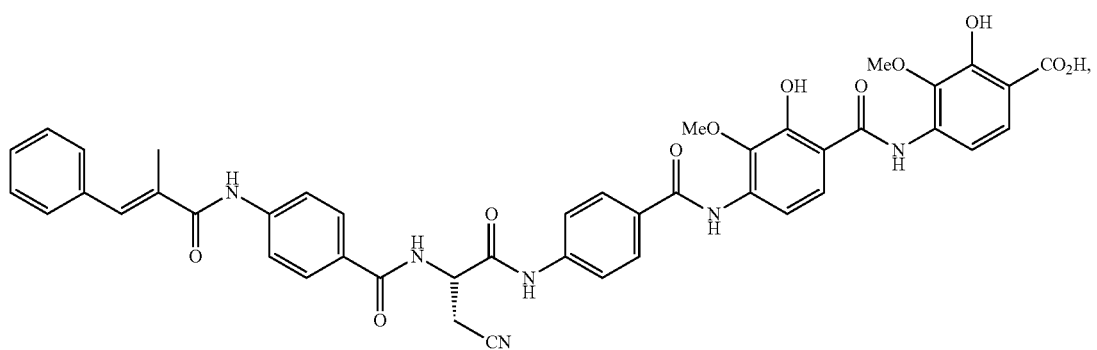
2
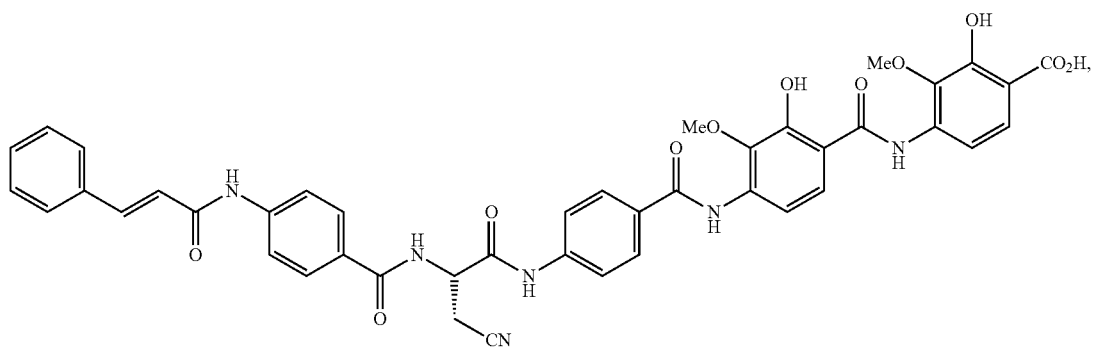
3
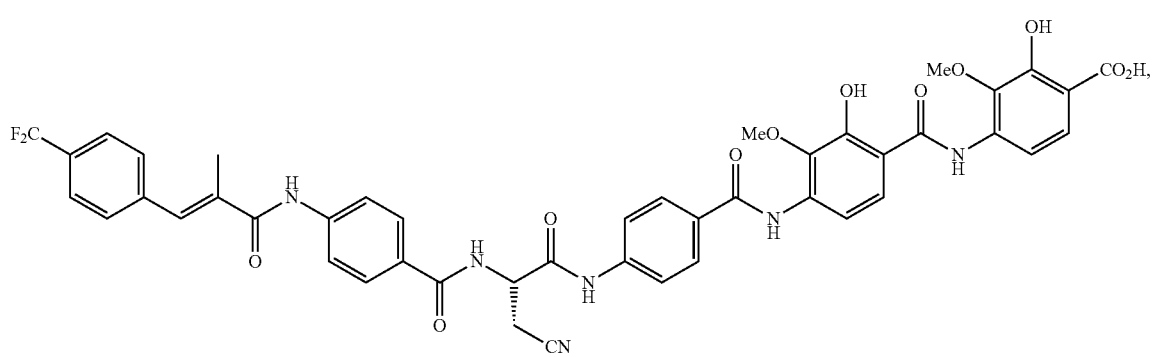
4

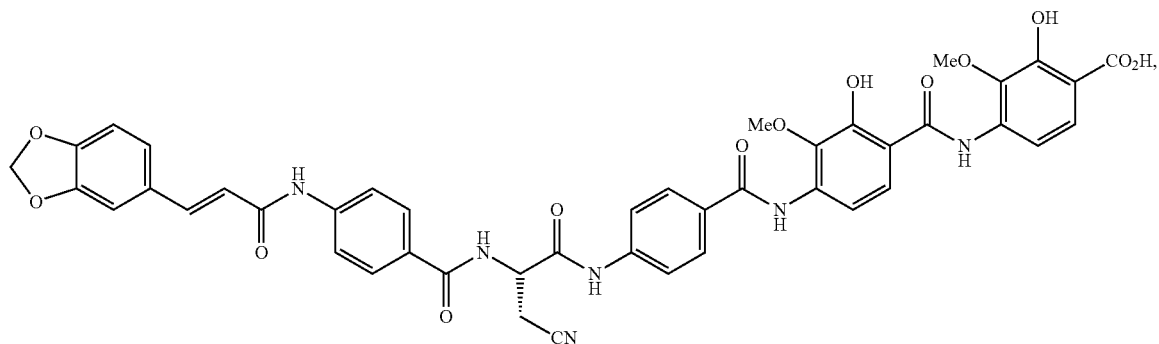
5
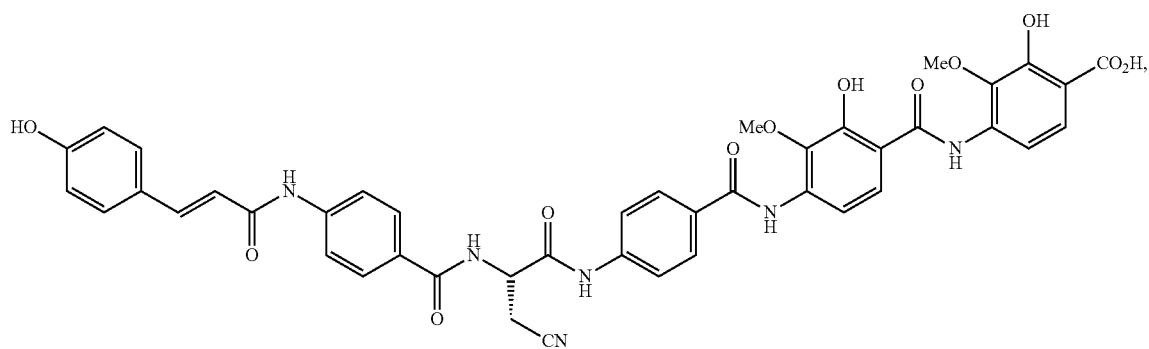
6
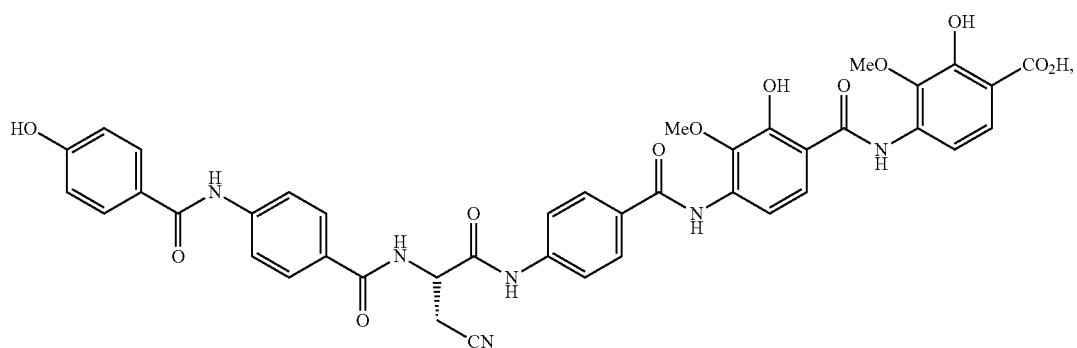
7
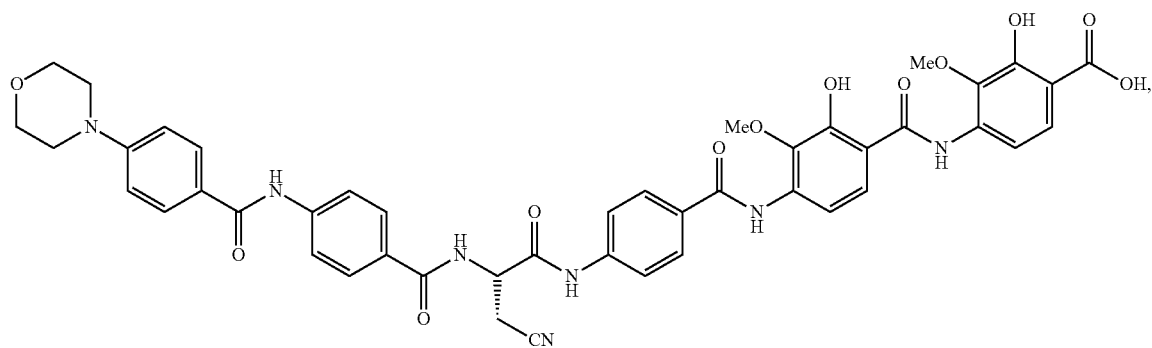
8

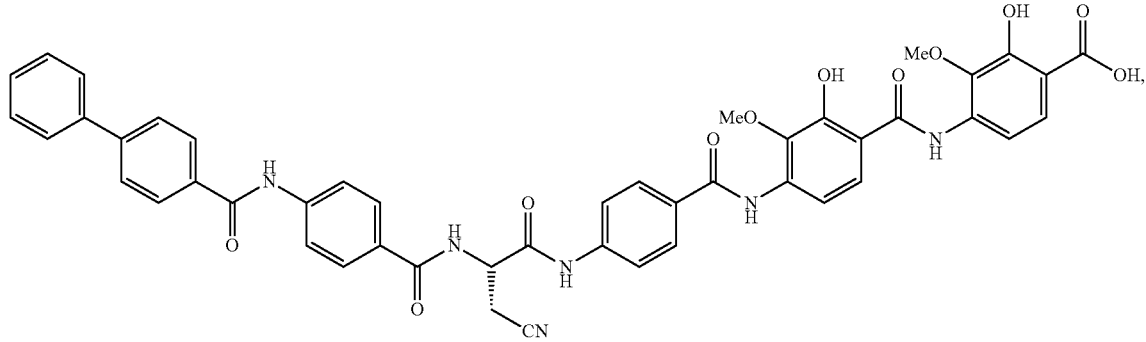
9
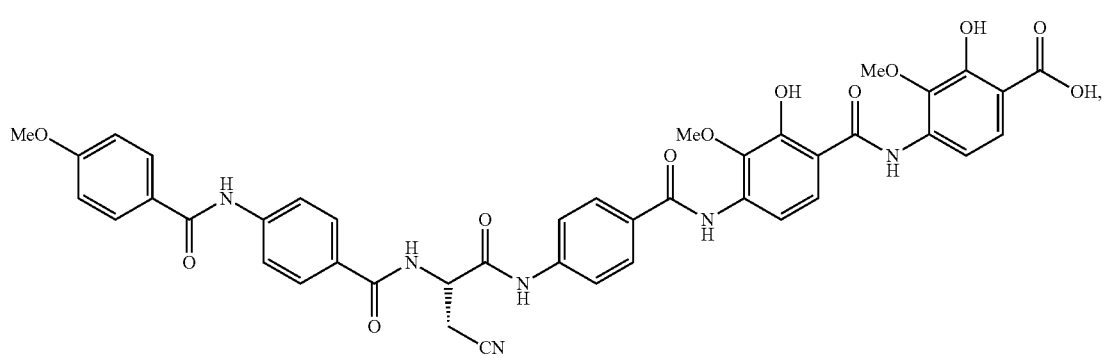
10
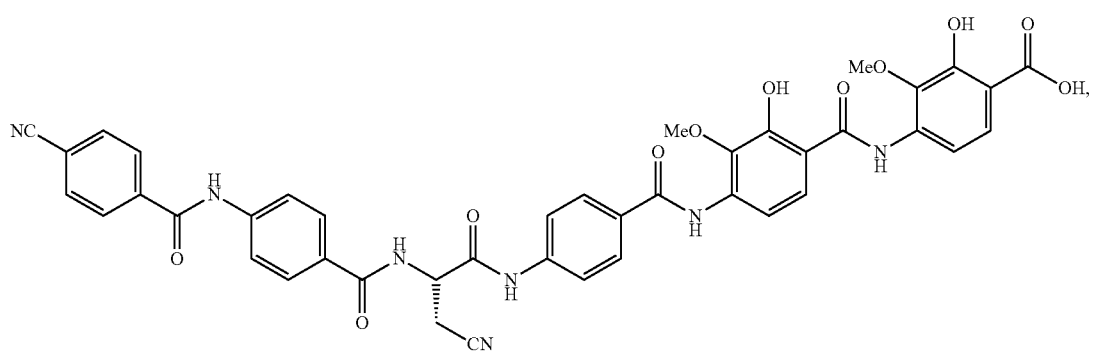
11
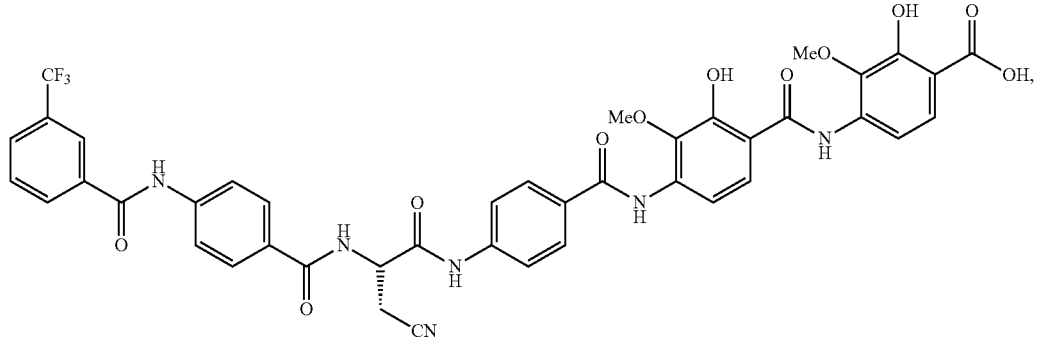
12

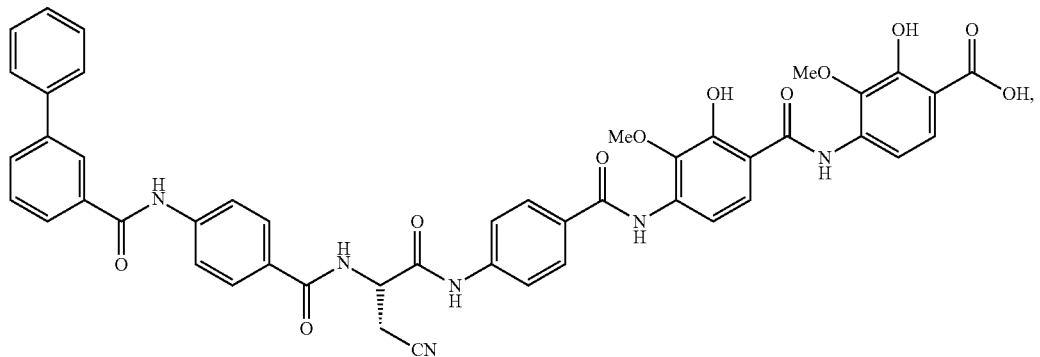
13
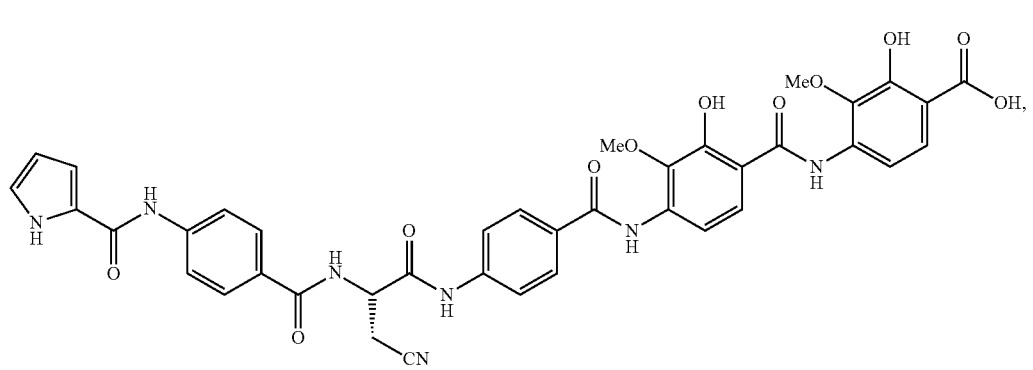
14
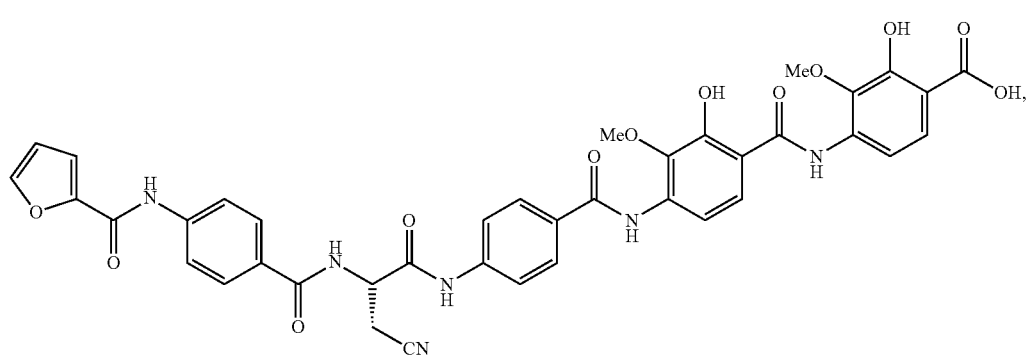
15
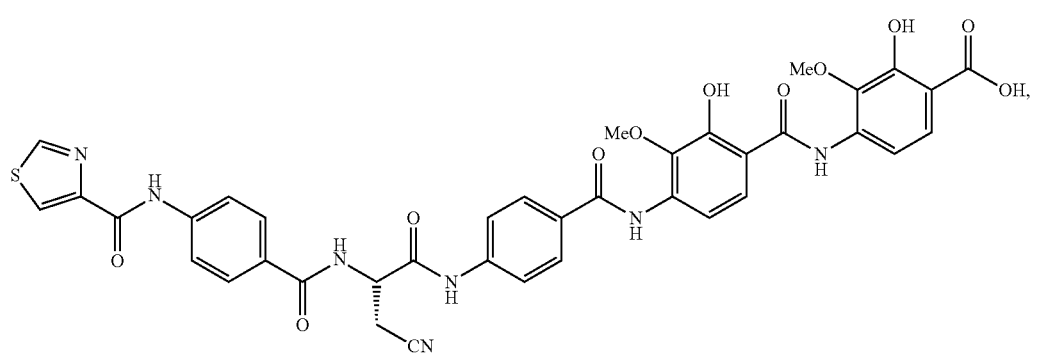
16

-continued
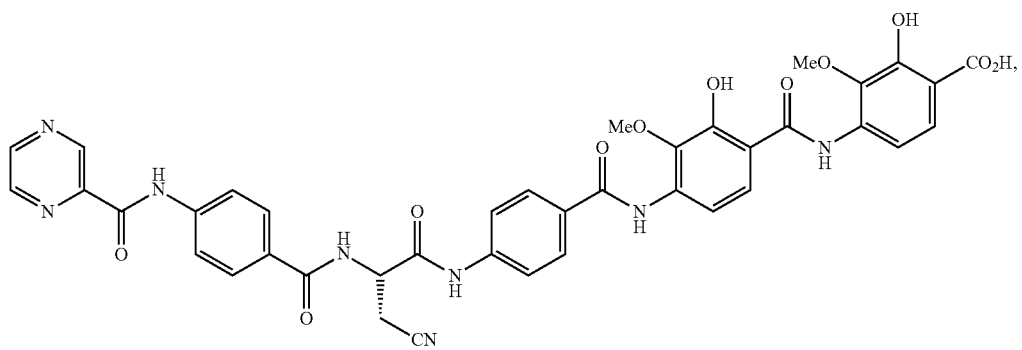
17
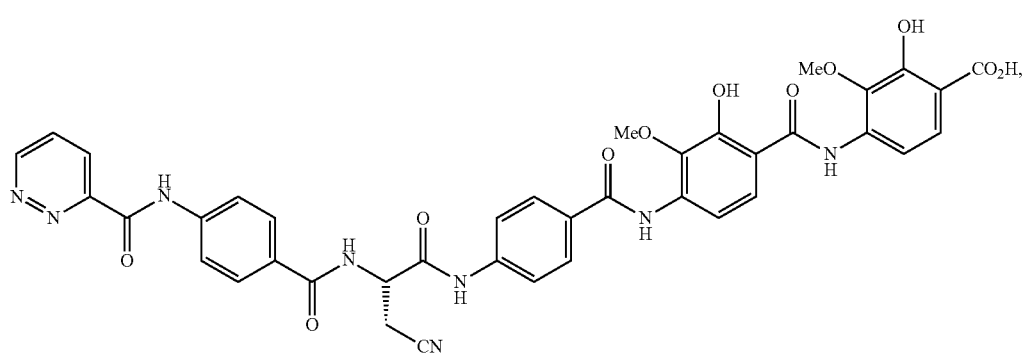
18
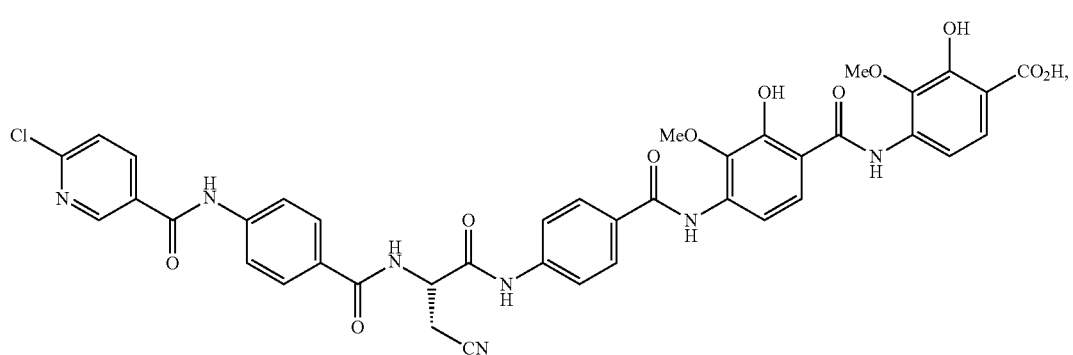
19
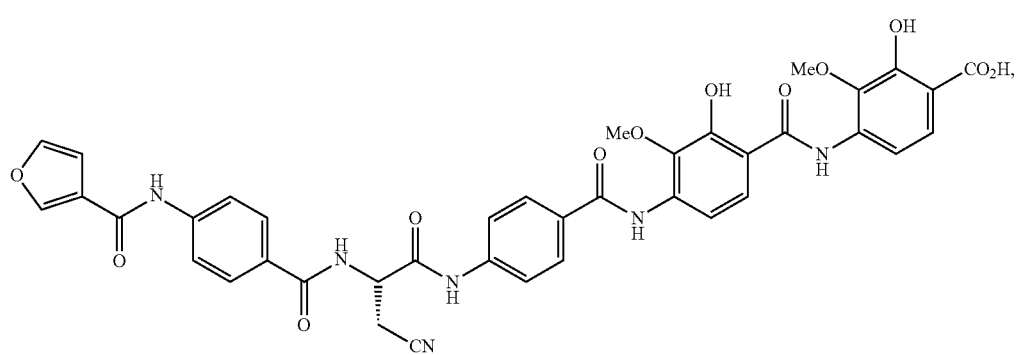
20

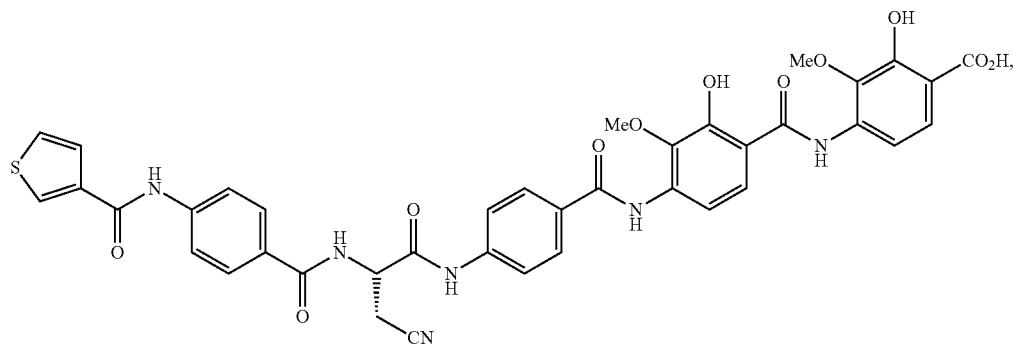
21
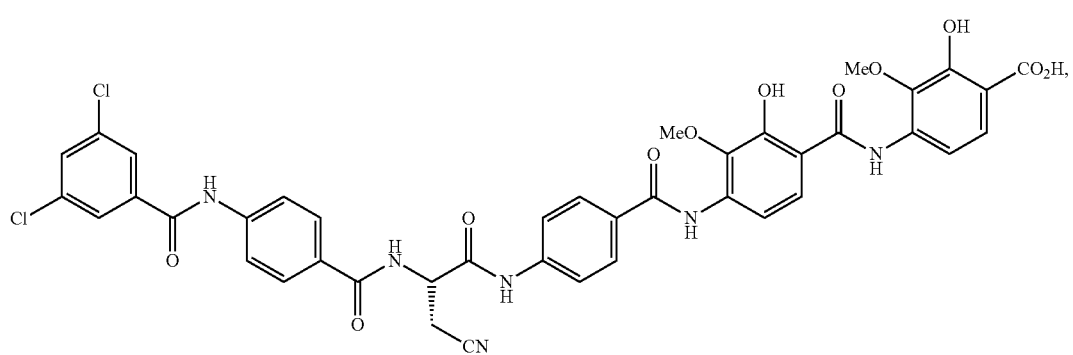
22
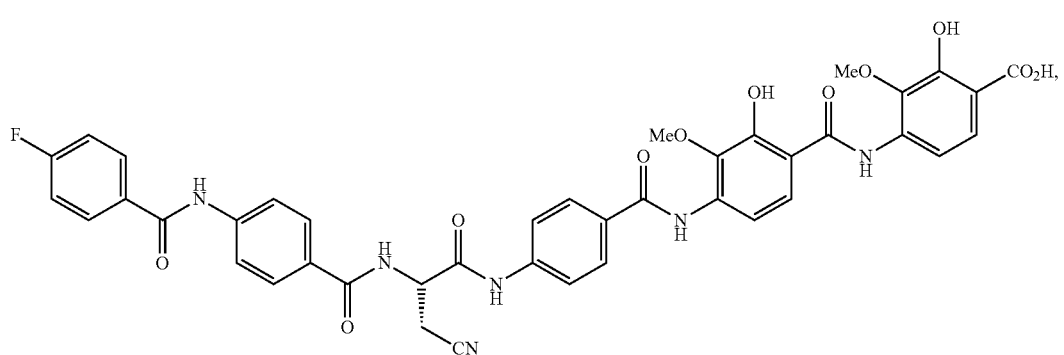
23
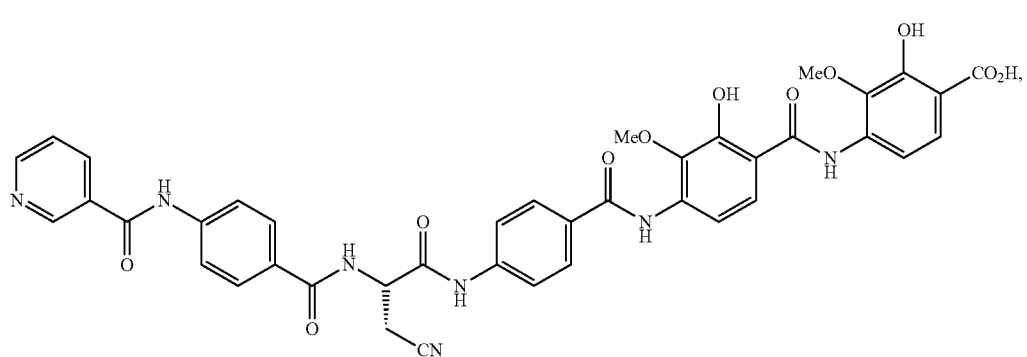
24

-continued
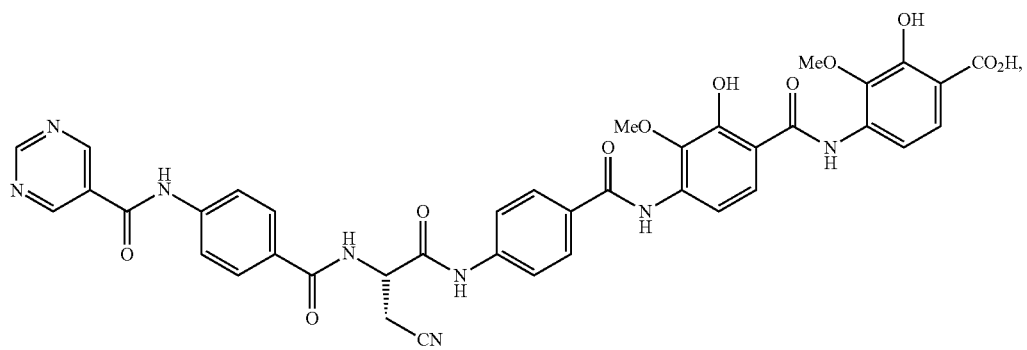
25
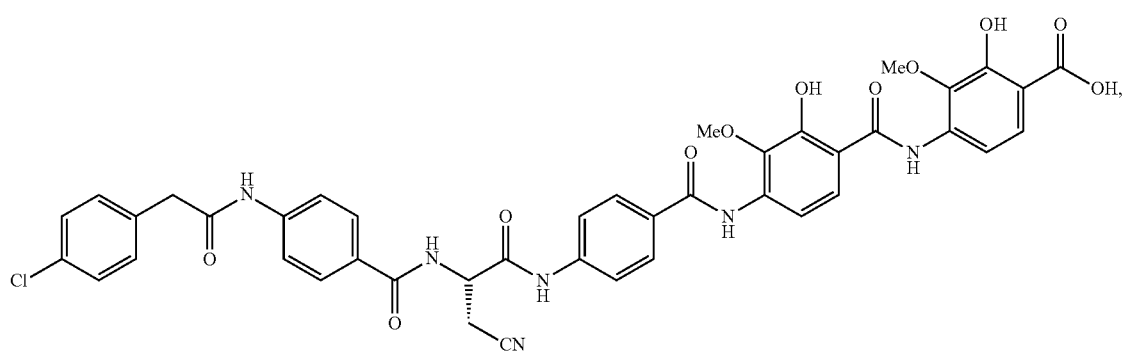
26
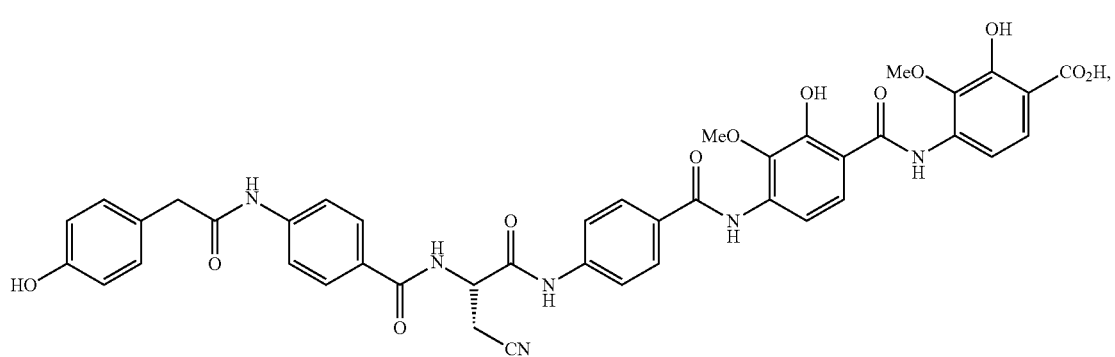
27
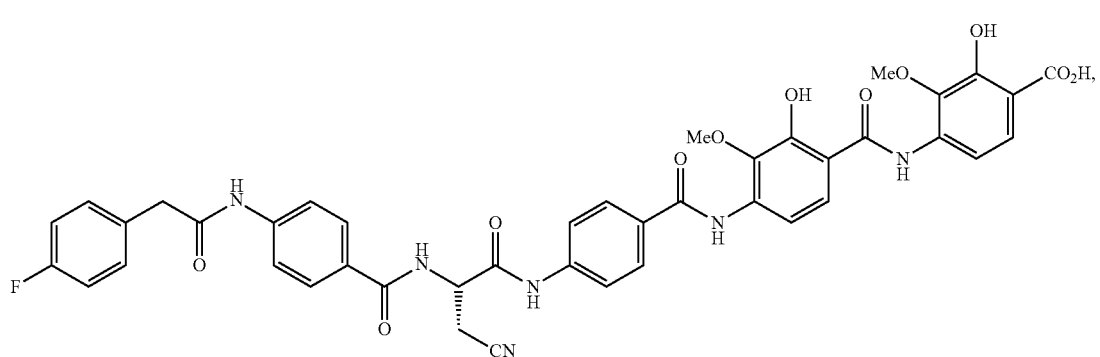
28

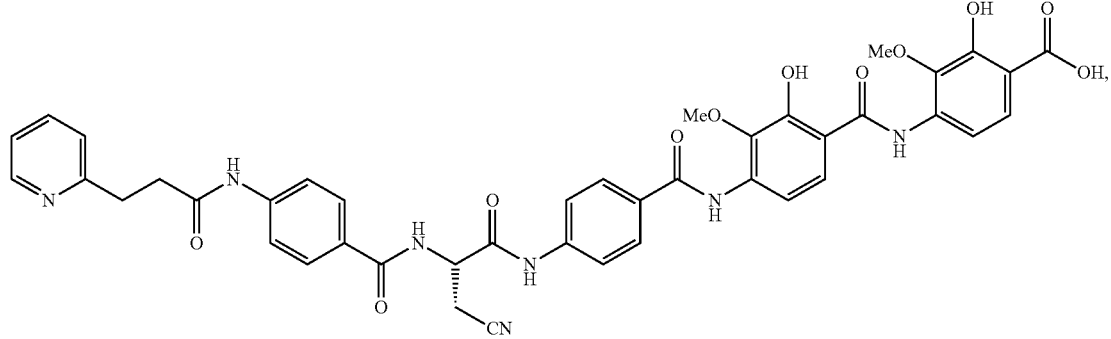
29
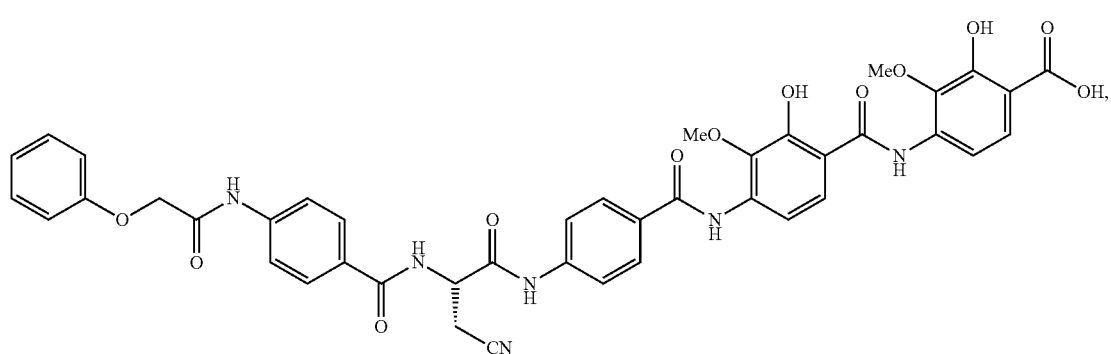
30
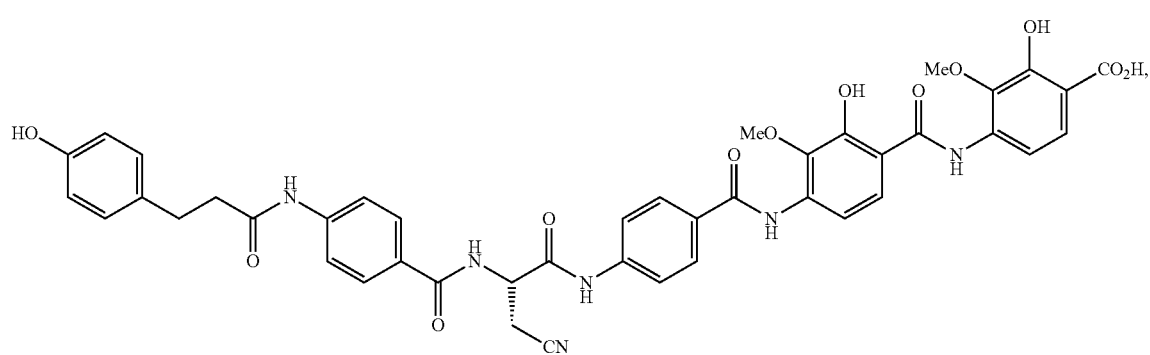
31
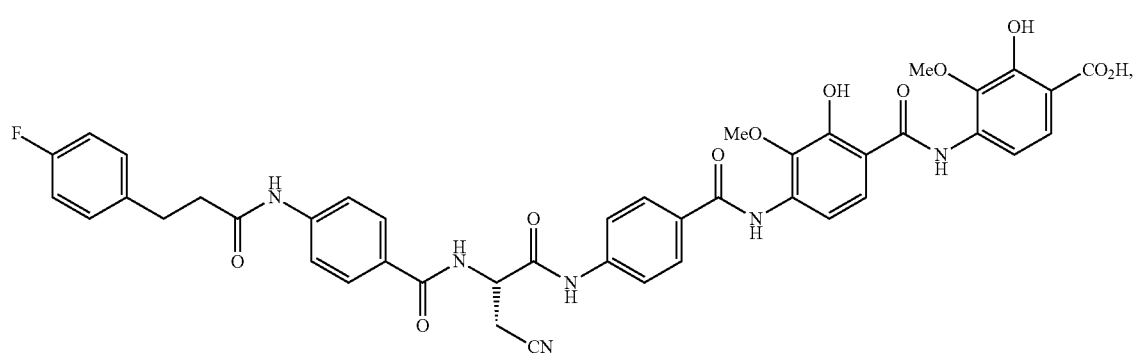
32

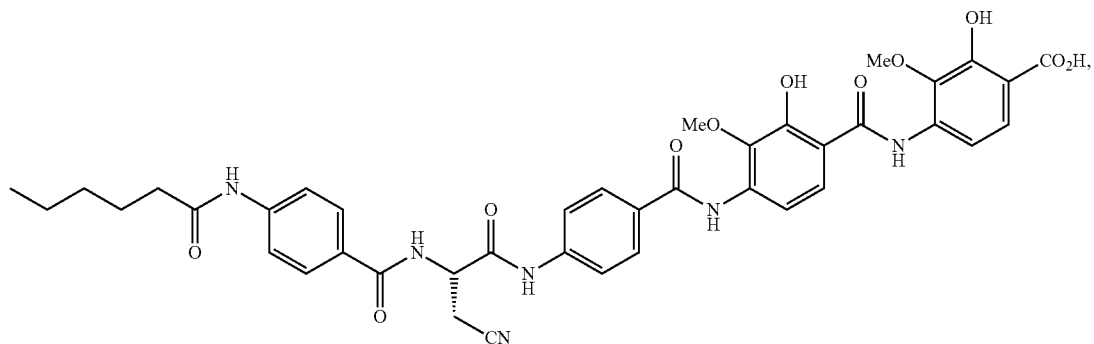
34
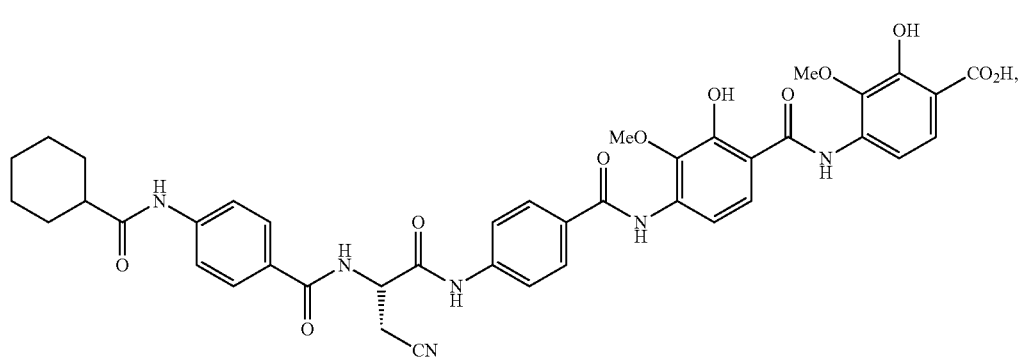
35
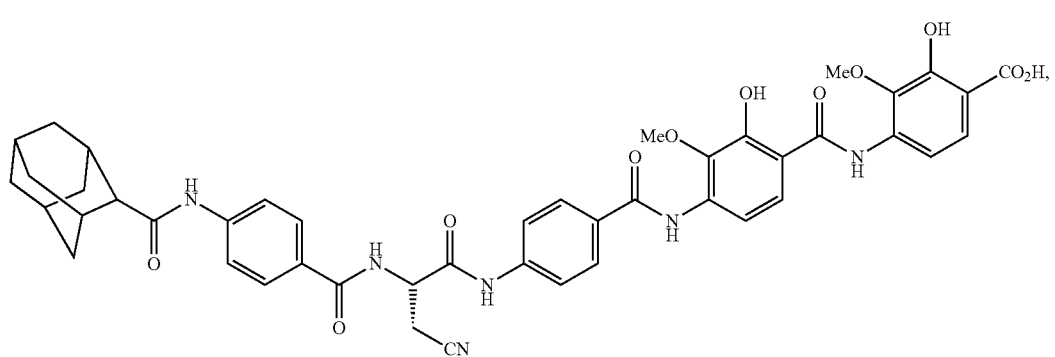
36
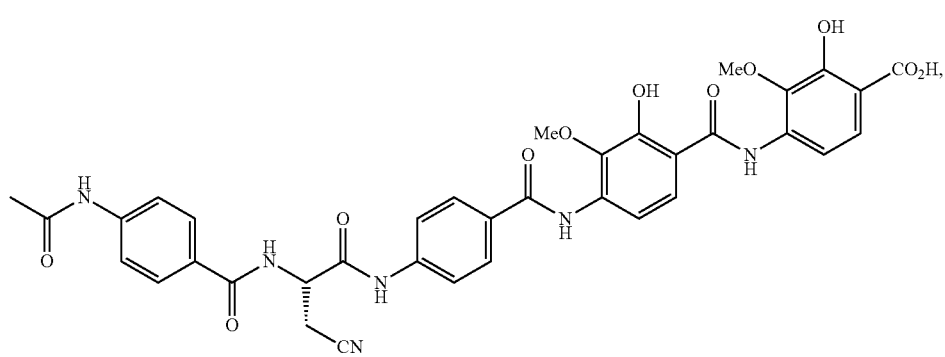
37

-continued
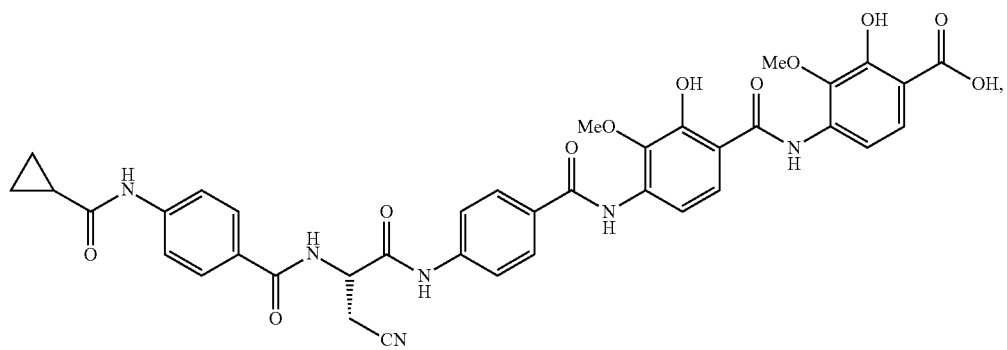
38
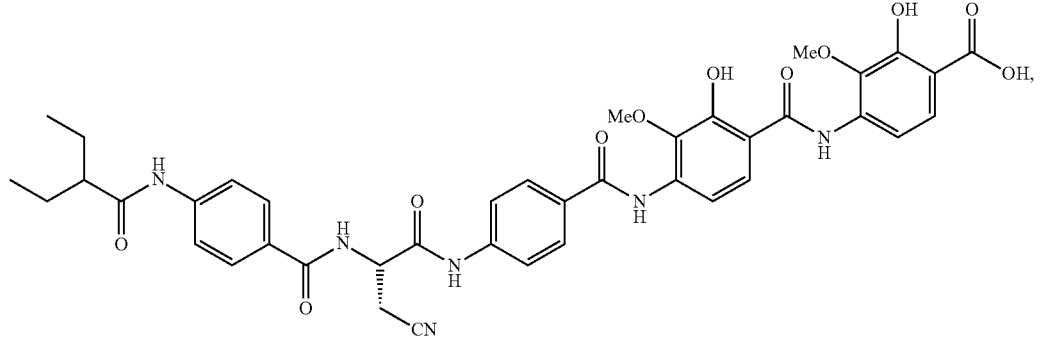
39
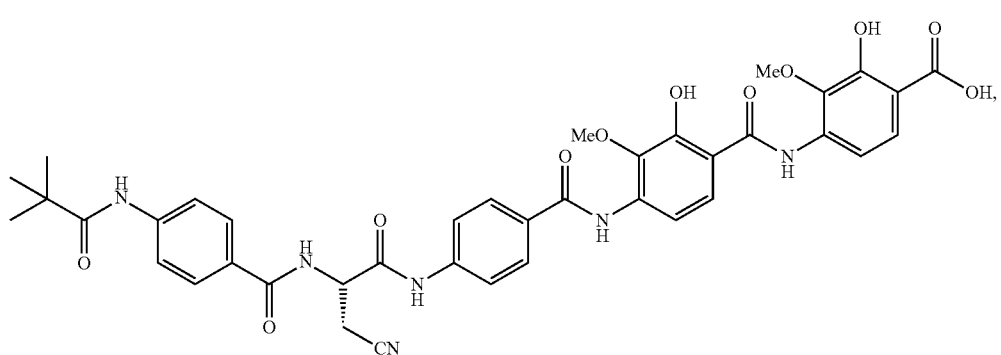
40
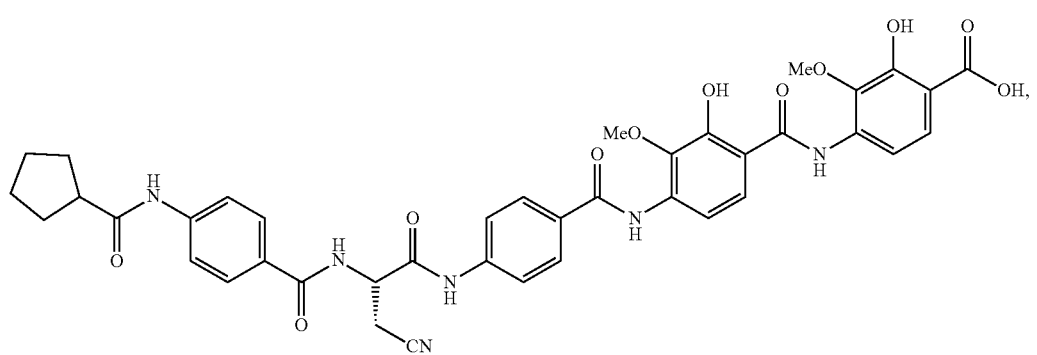
41

42
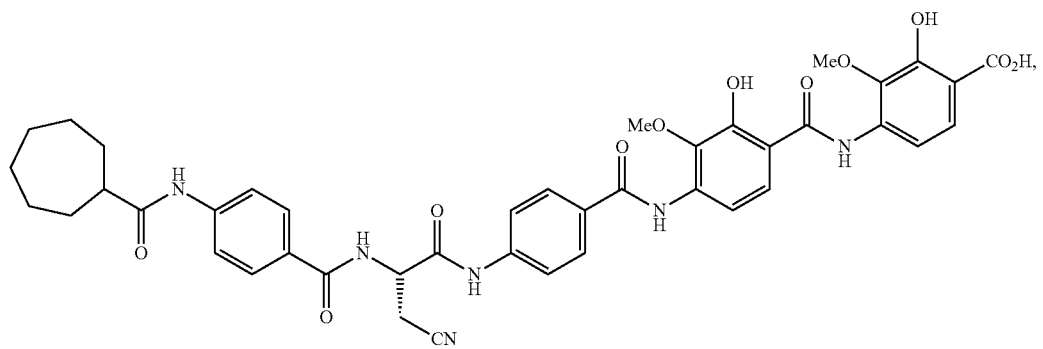
43
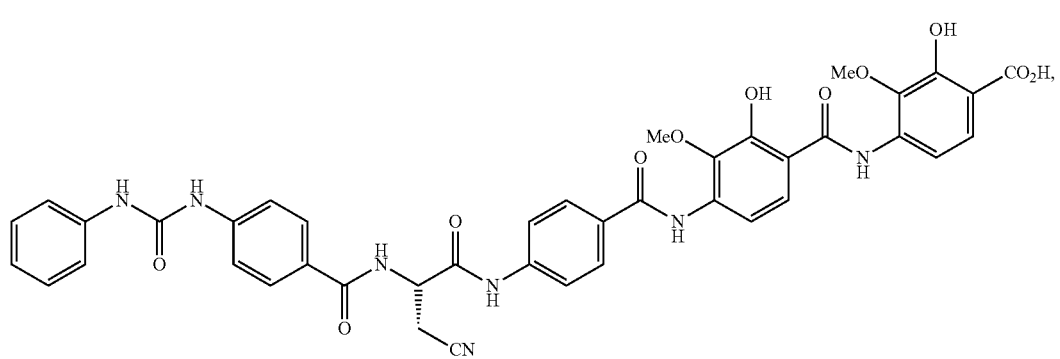
44
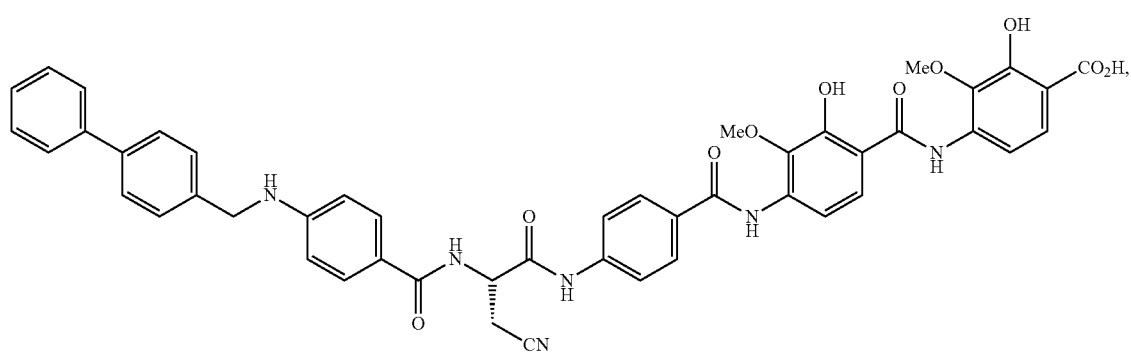
48
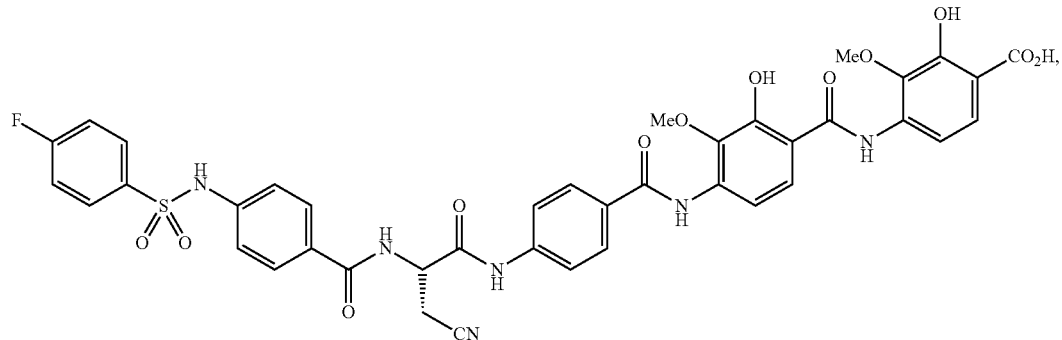

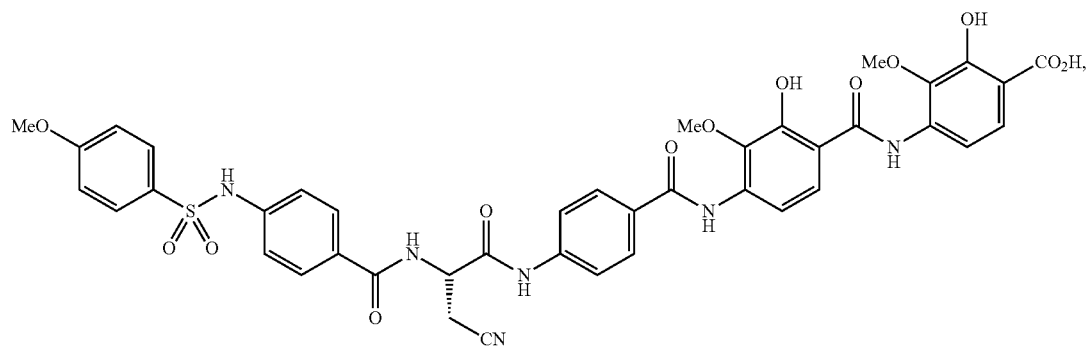
49
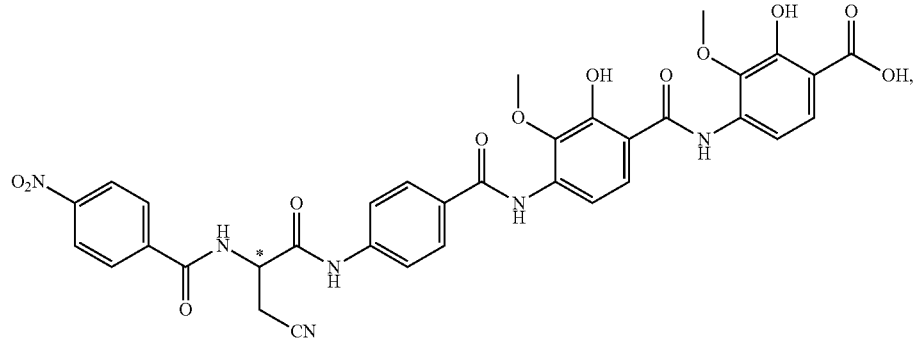
50
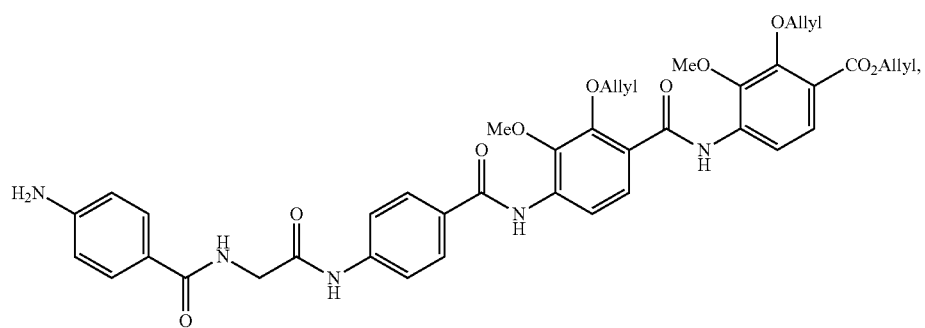
70a
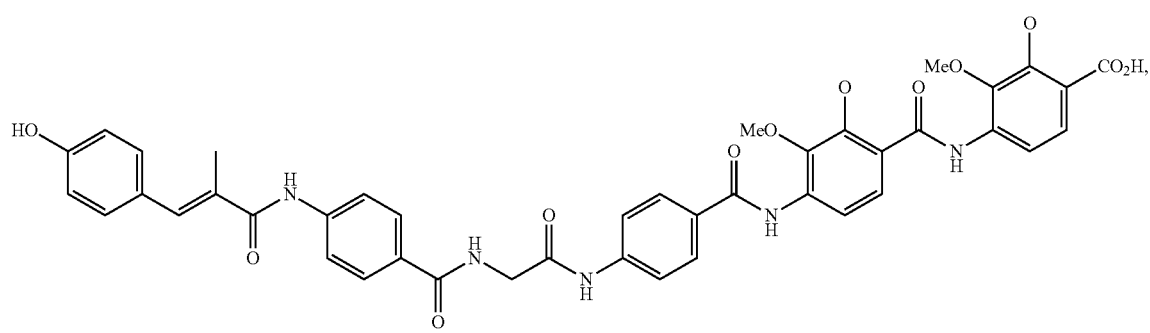
70b

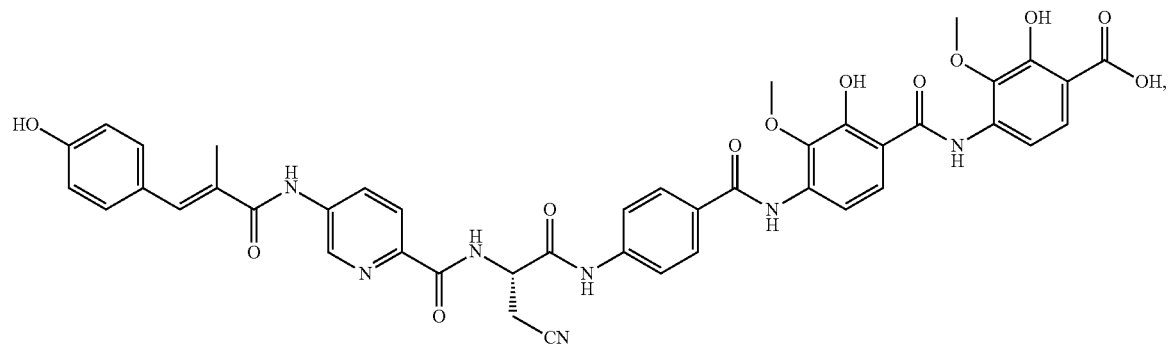
71
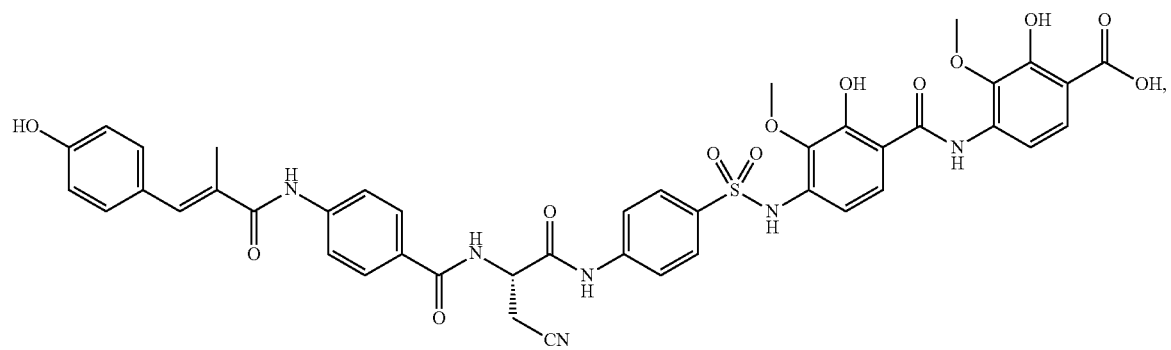
74
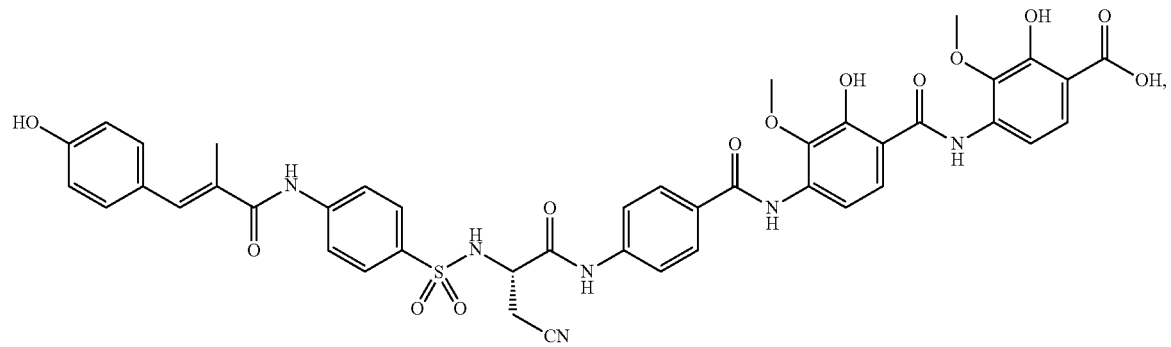
75
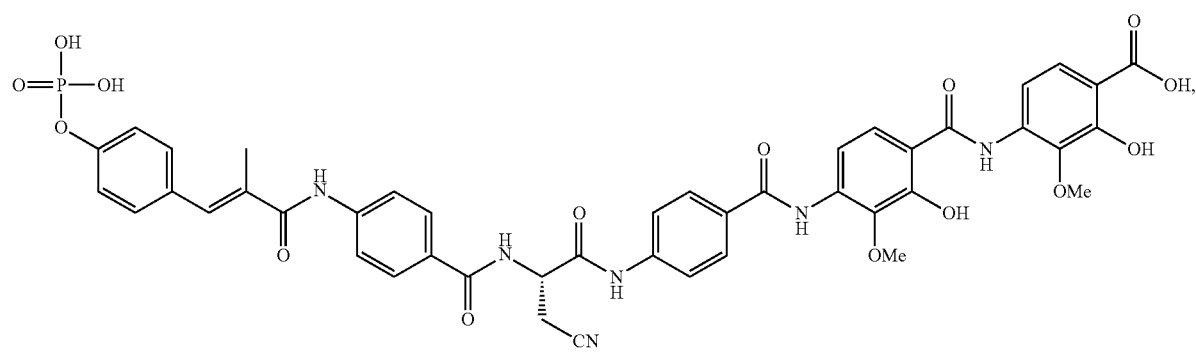
76

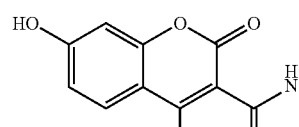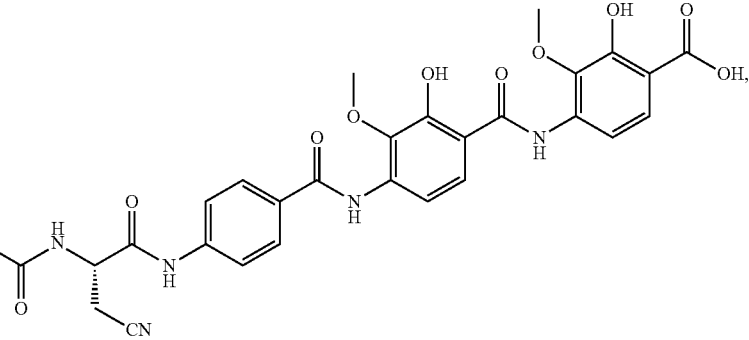
78
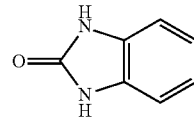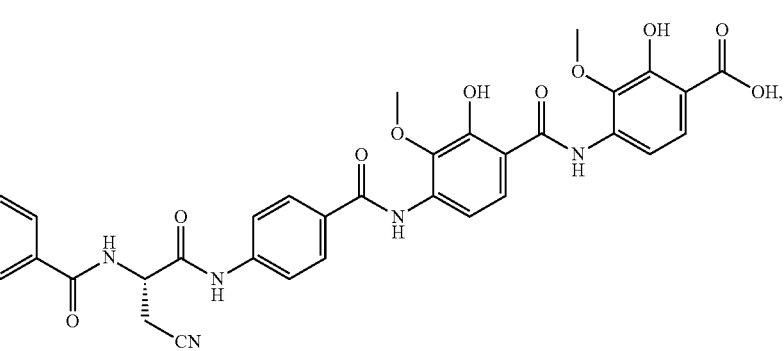
79
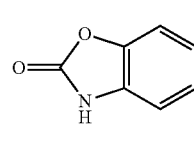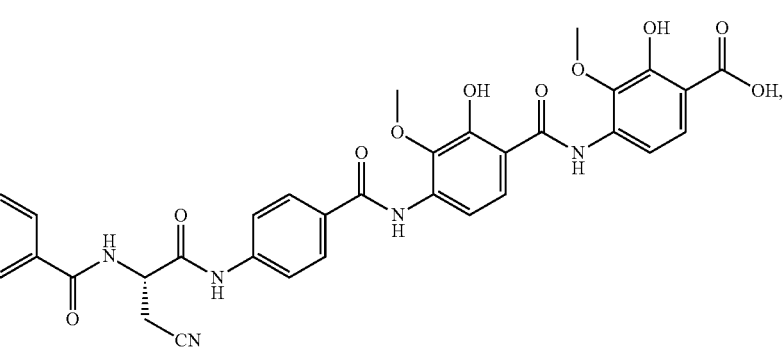
80
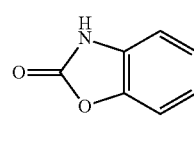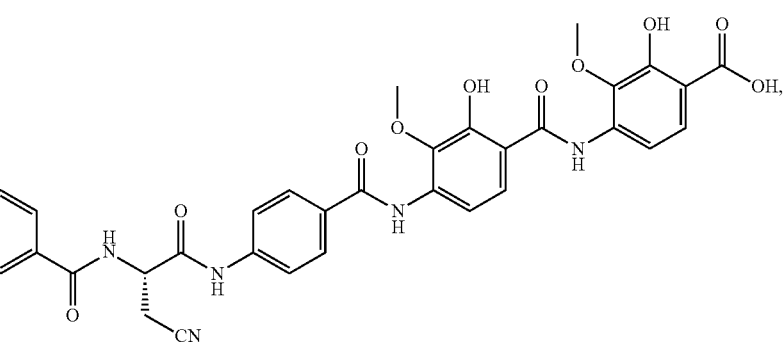
81

82
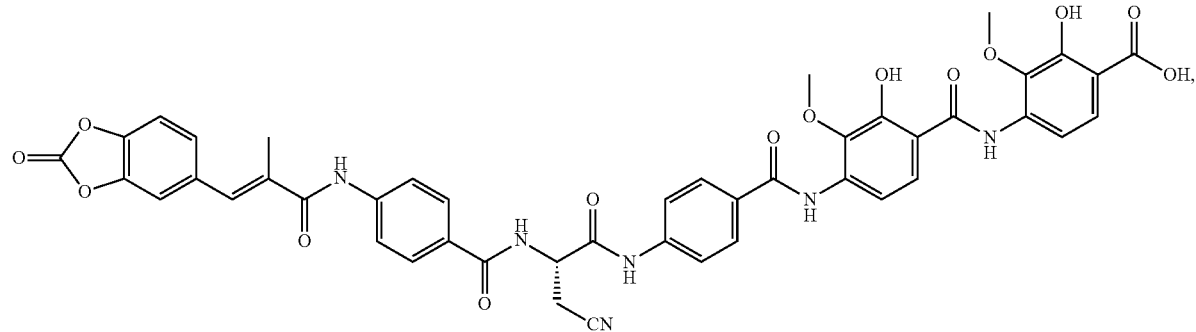
83
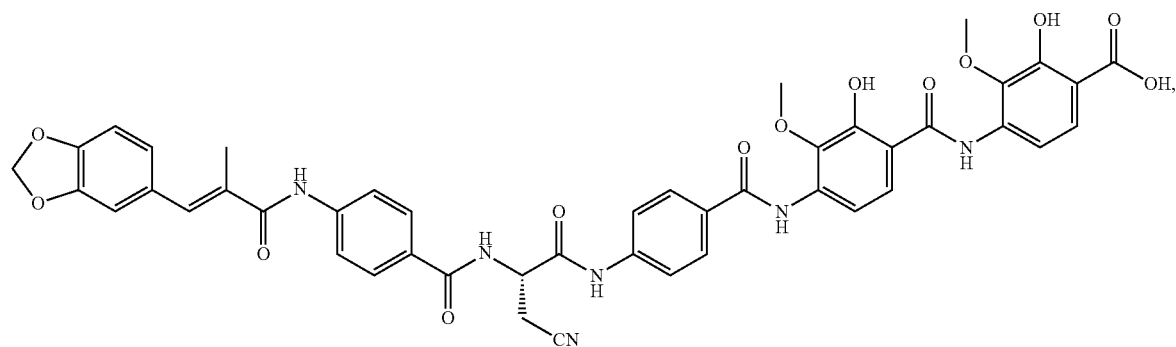
84
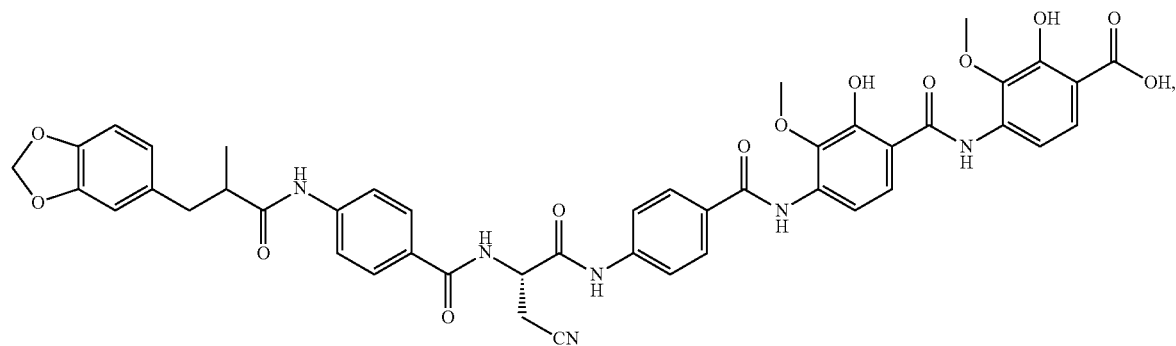
85
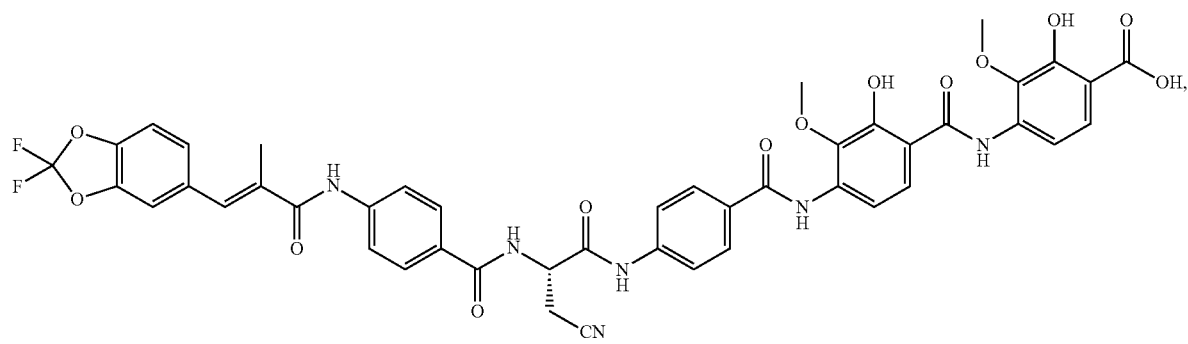

86
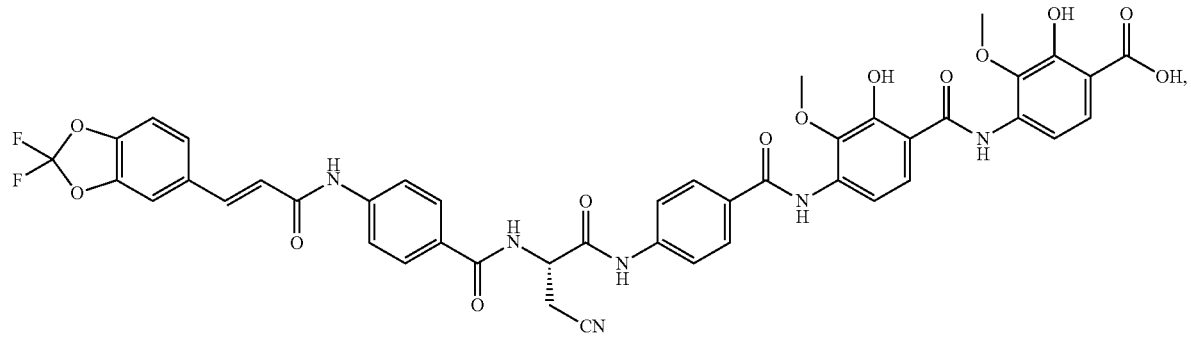
87
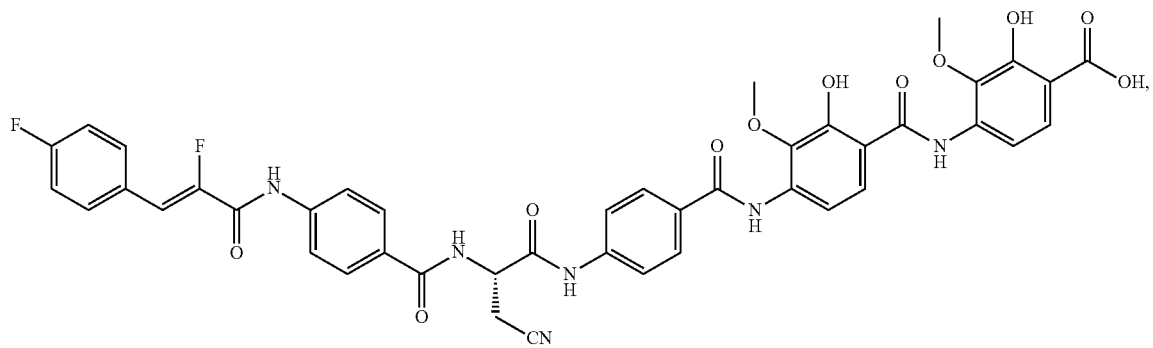
88
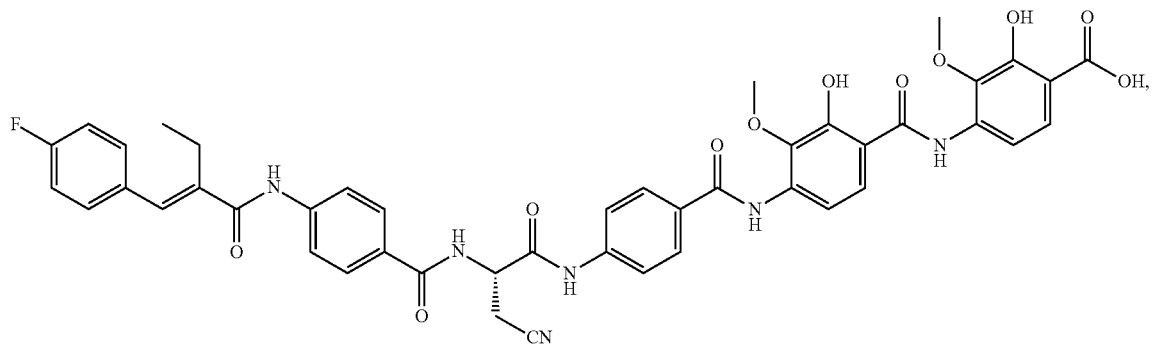
89
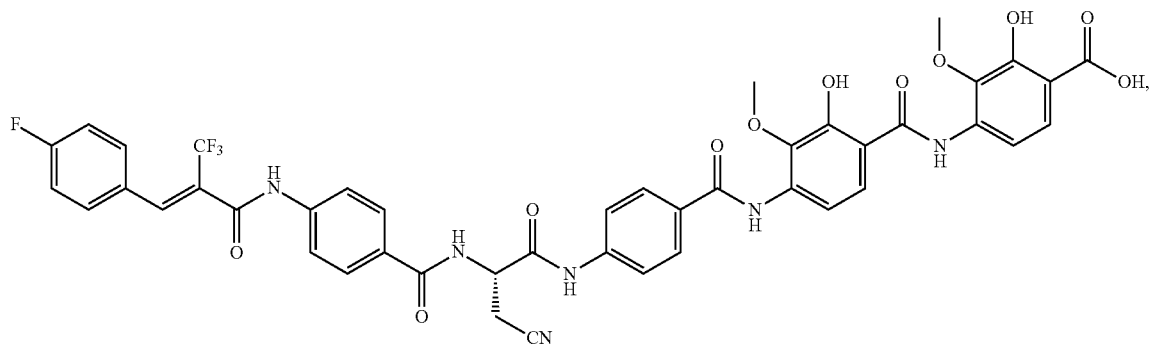

90
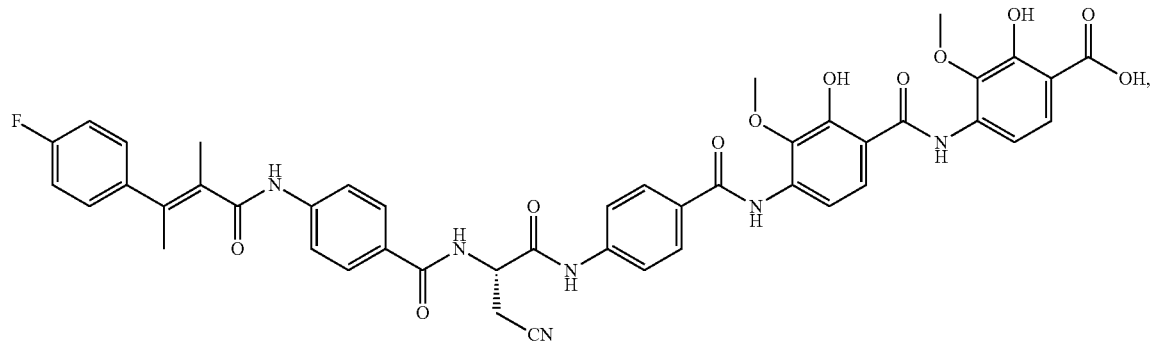
91
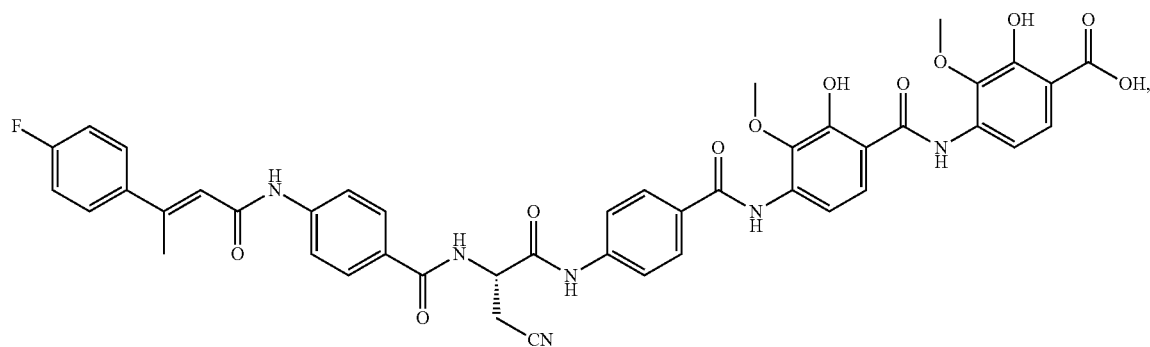
92
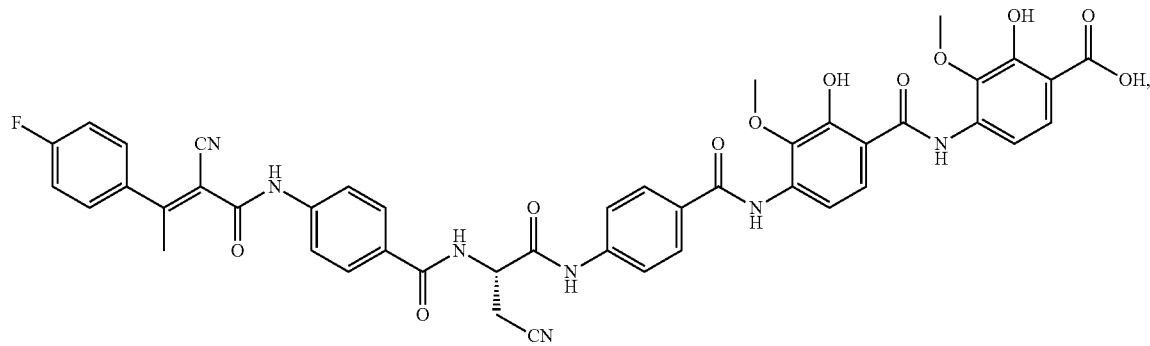
94
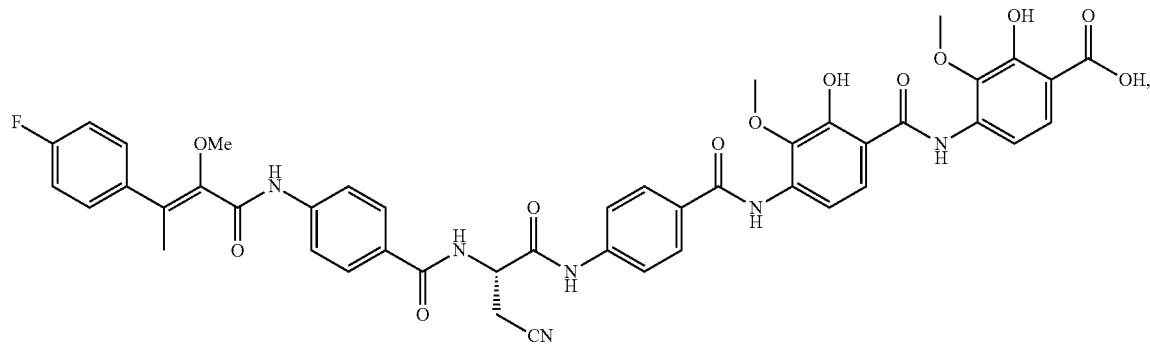

-continued
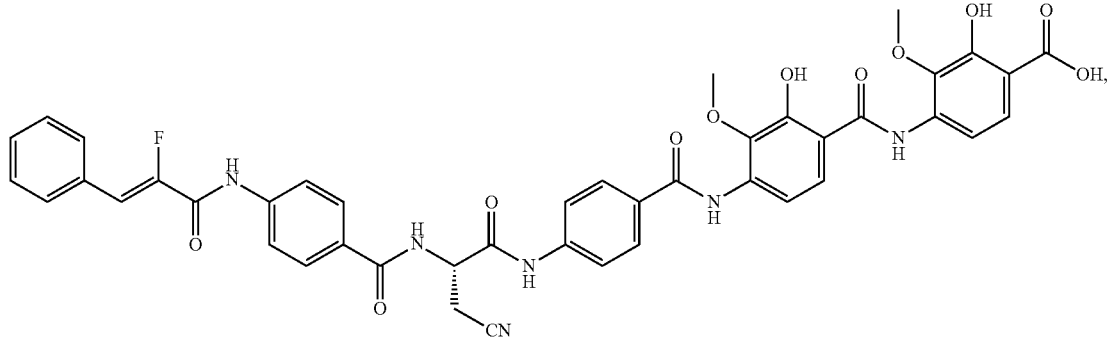
95
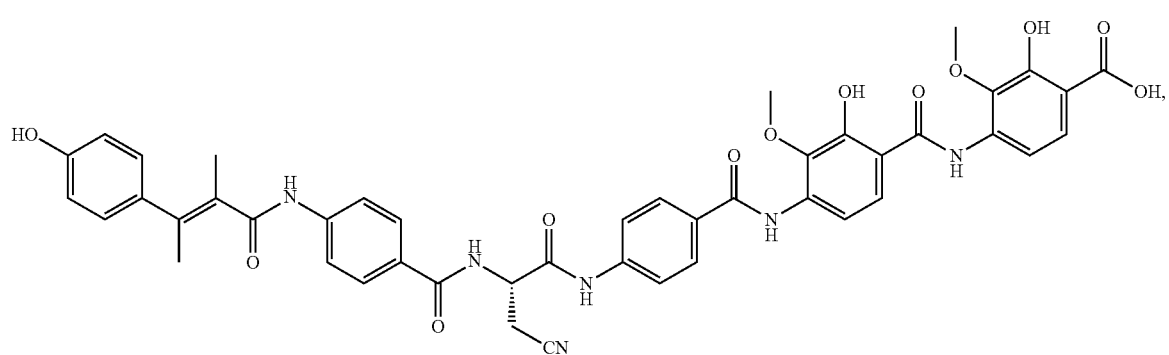
96
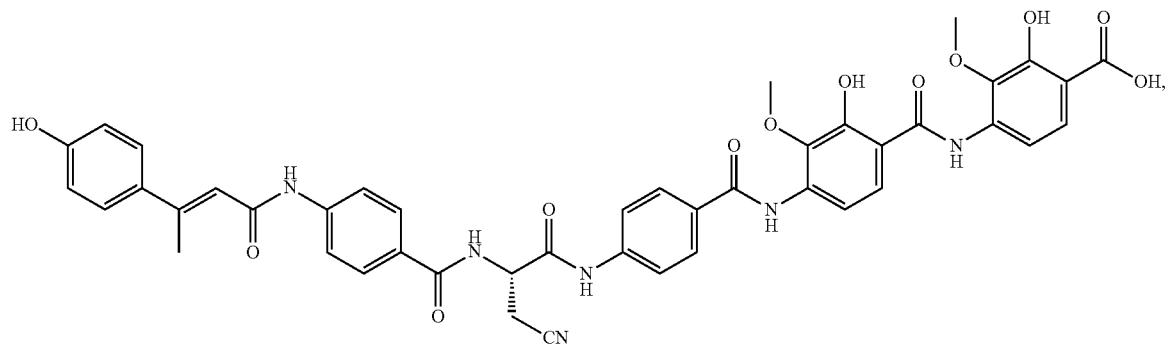
97
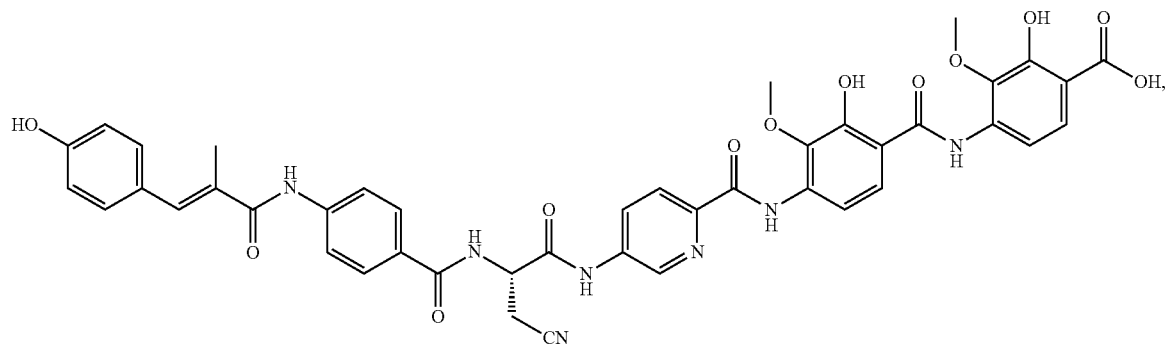
98

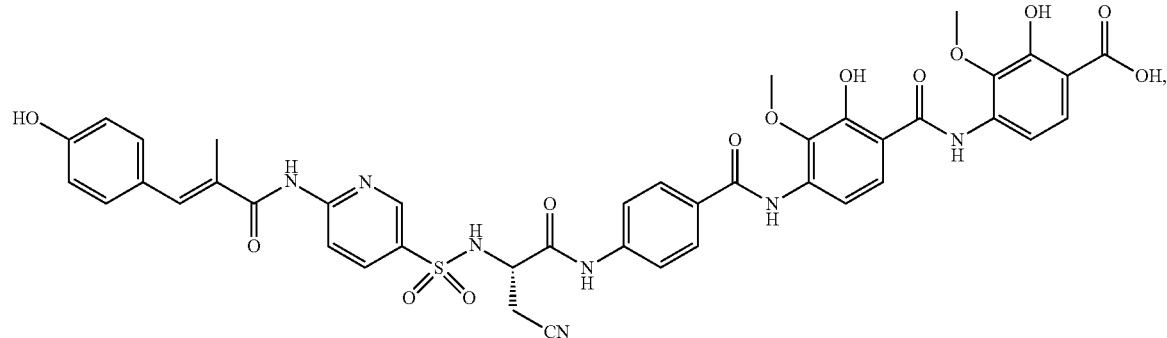
101
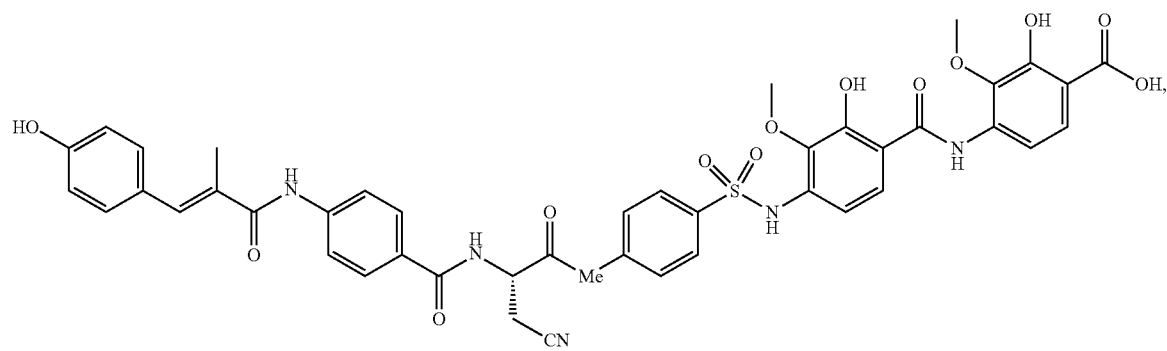
102
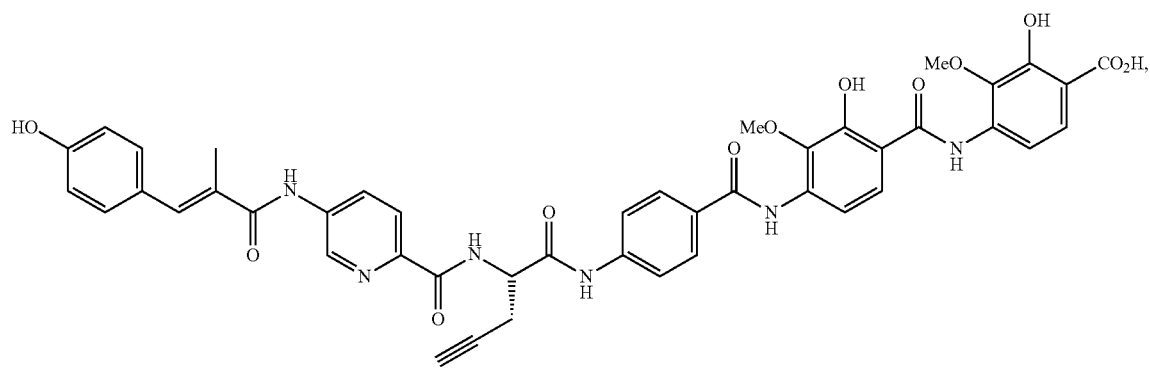
103
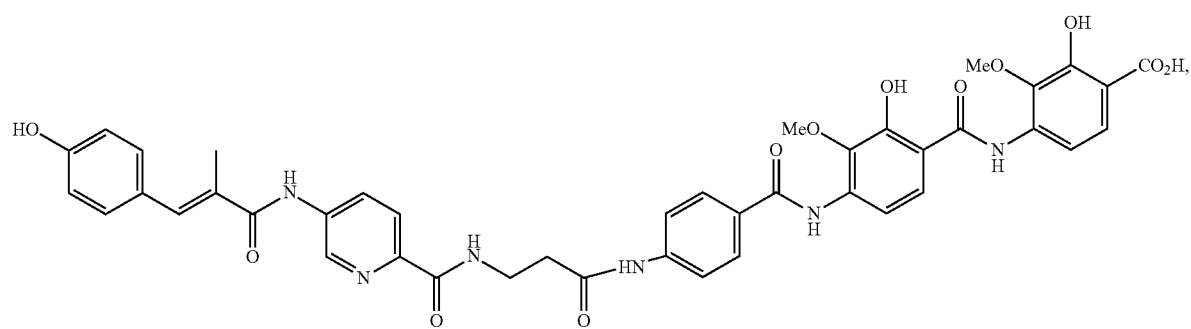
104

105
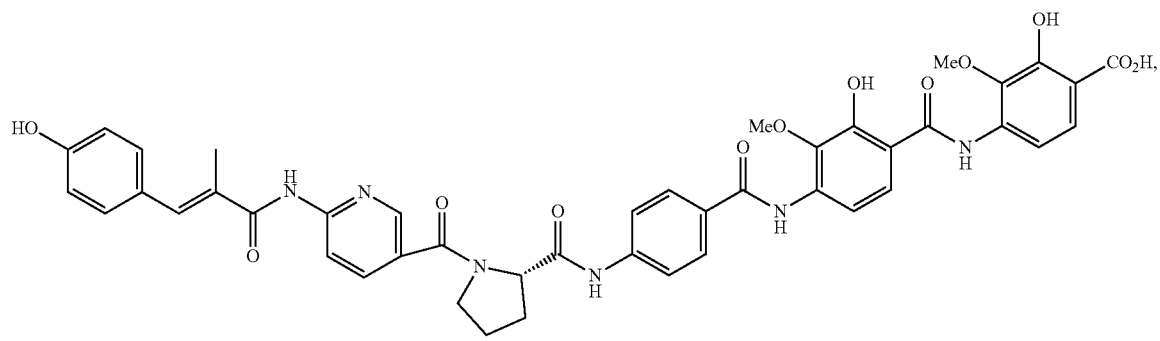
106
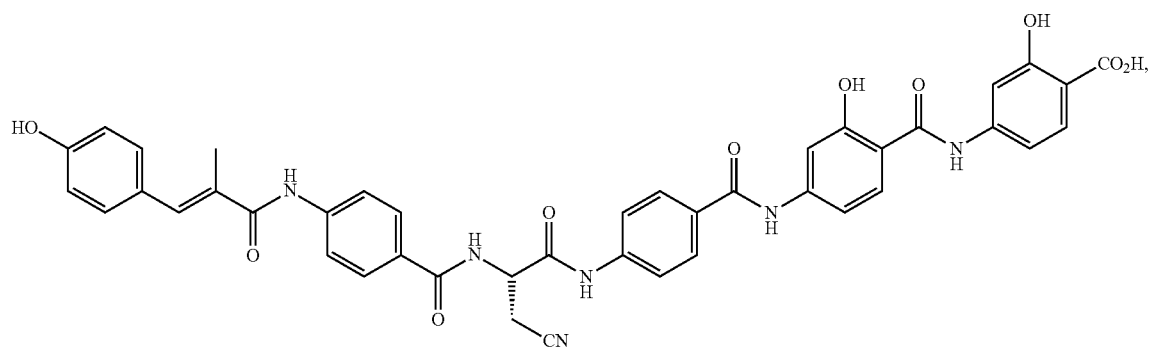
107
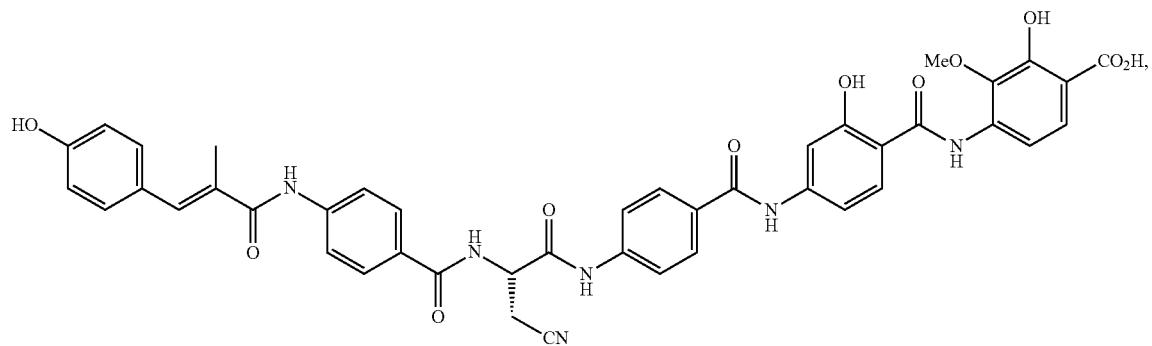
108
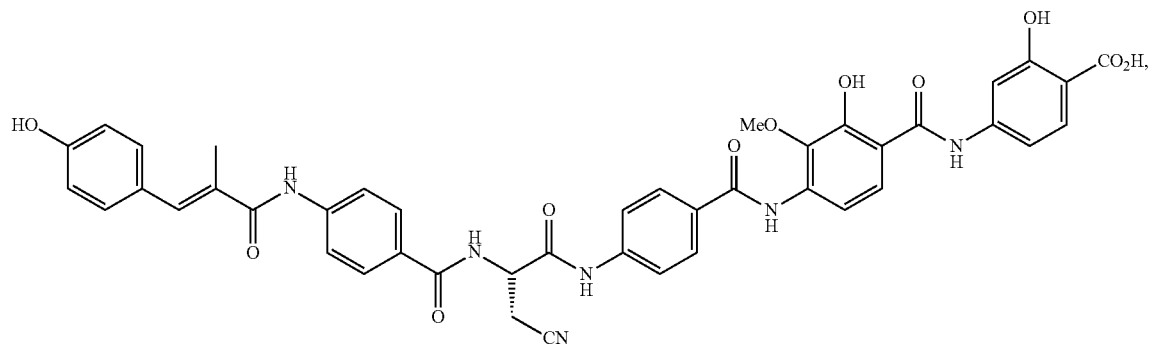

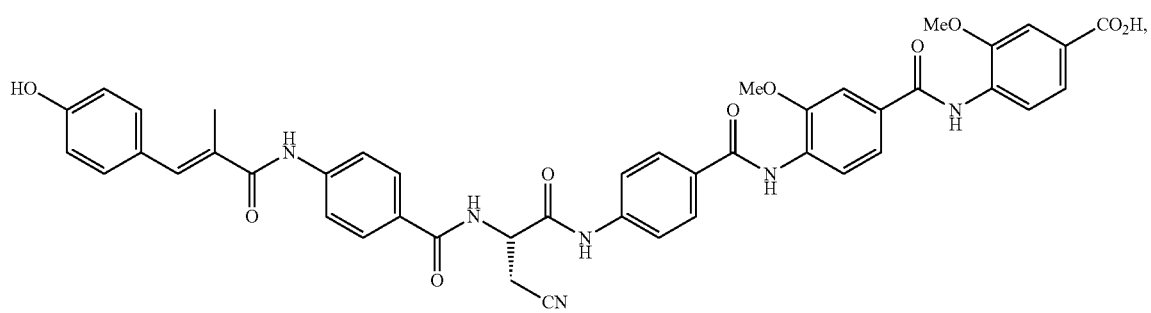
109
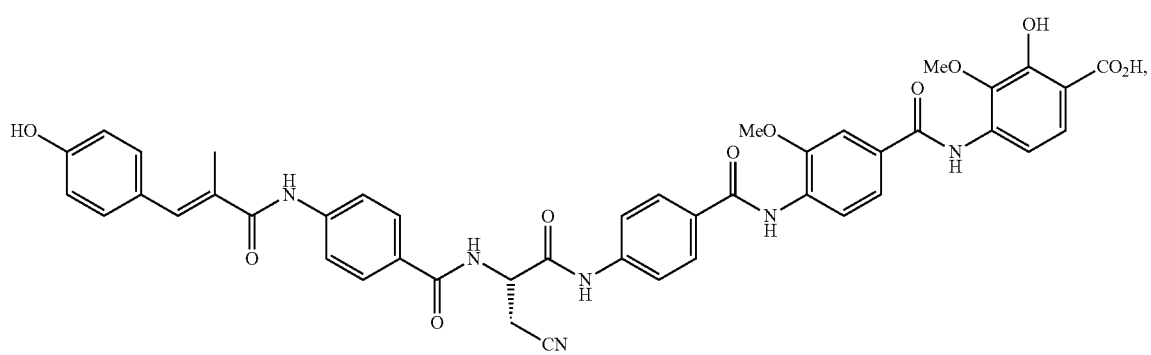
110
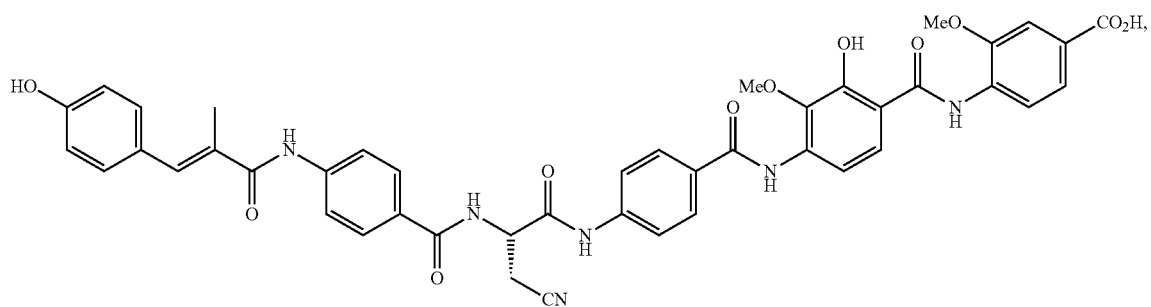
111
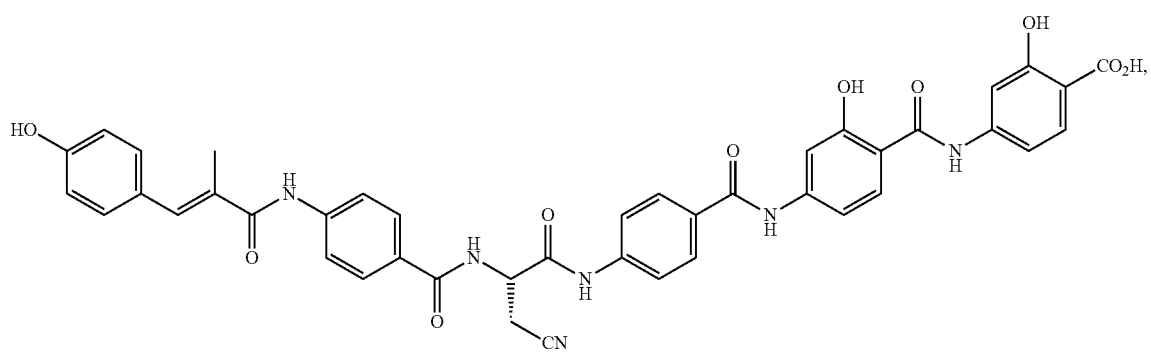
112

113
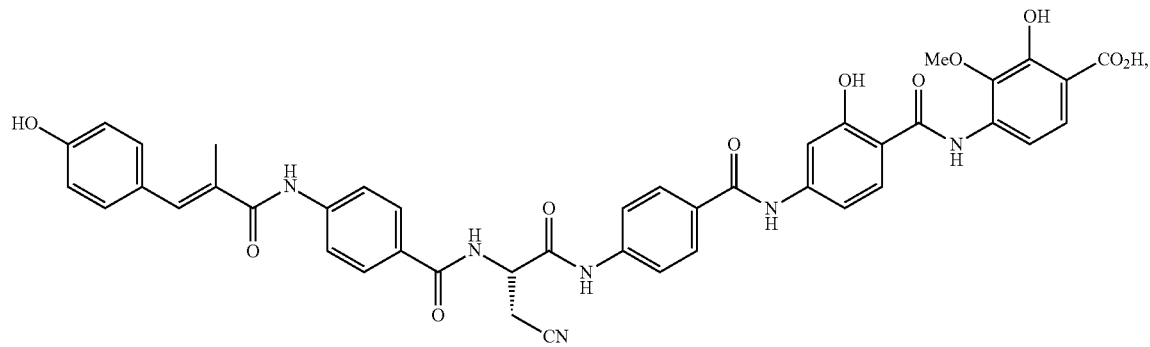
114
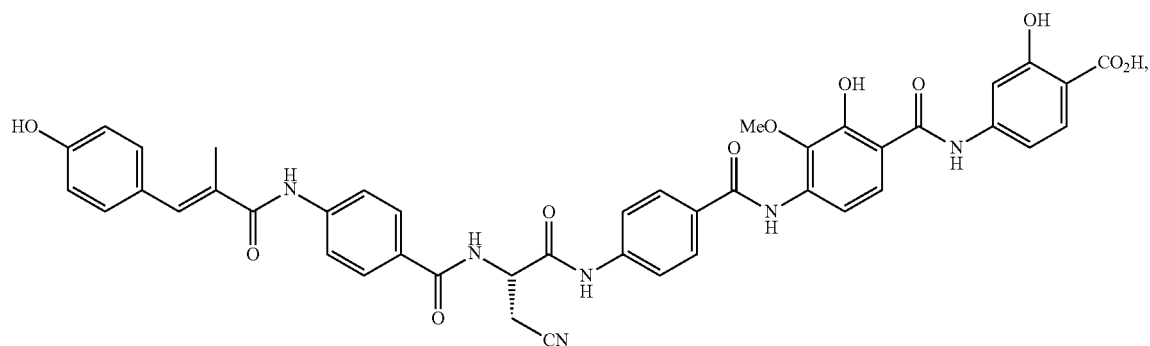
115
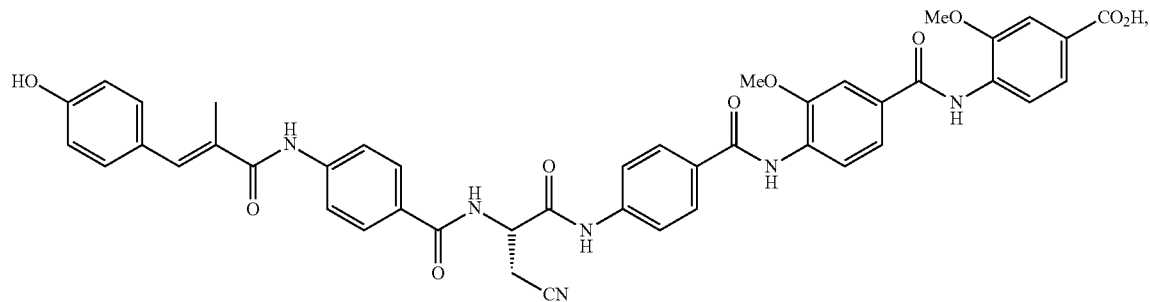
116
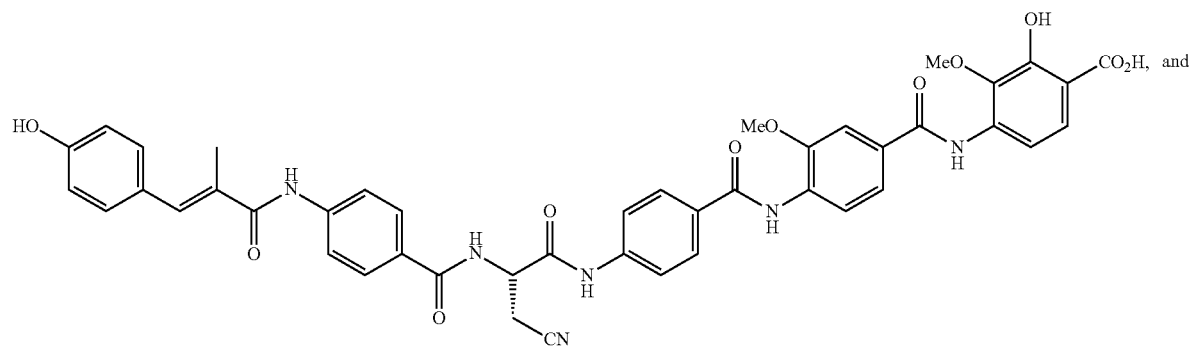
and

117

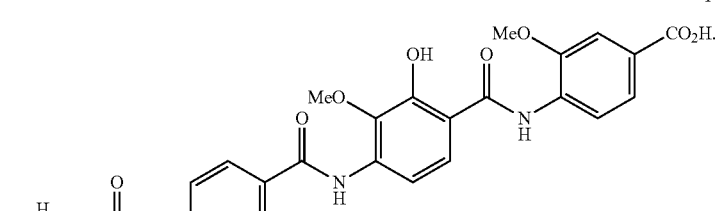

5. The compound of claim 1, wherein E is

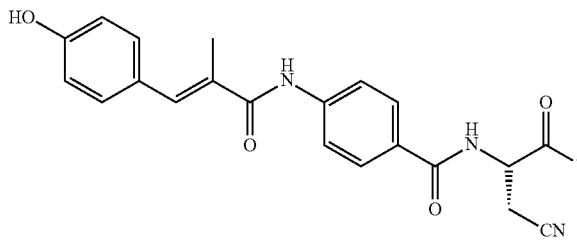

with n of $R^1_n$ being 0 or 1, and
with each $R^1$ independently from any other $R^1$ being selected from —OH or —CH$_3$.

6. The compound of claim 1, wherein E is selected from the group consisting of (I)
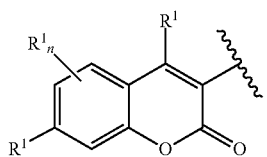

(II)
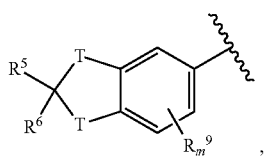

(III)
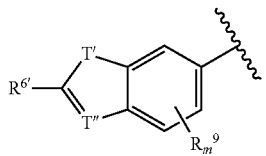

(IV)
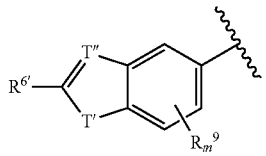

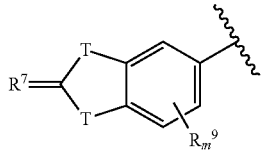

with m of $R^9_m$ being 0, and
with each T being selected independently from each other from —C(CH$_3$)$_2$, —NH, —S or —O,
with T' being selected from —O, —S or —NH,
with T" being =N,
with $R^5$ and $R^6$ being selected independently from each other from —H, —F or —CH$_3$,
with $R^{6'}$ being selected from —OH, —OCH$_3$, —OCH$_2$CH$_3$ or —CH$_3$, and
with $R_7$ being =O.

7. The compound of claim 1, wherein
$R^2$ and $R^3$ is selected independently from each other from —H, —F, —CN, —CH$_3$, —CH$_2$CH$_3$, —OCH$_3$, —OCH$_2$CH$_3$, —OCH$_2$CH$_2$CH$_3$, —OCH(CH$_3$)$_2$, —OCF$_3$, —CH$_2$CF$_3$, —CHFCF$_3$, —CF$_2$CF$_3$, —CHF$_2$, —CH$_2$F or —CF$_3$;
Z is H and Y is CN or —C(=O)NH$_2$;
each $R^8$ is selected independently from each other from H or CH$_3$;
M is an unsubstituted C$_1$-C$_8$ alkyl;
m is 0 or 1;
q is 0 or 1; and
each $R^a$, $R^b$ or $R^c$ are selected independently from each other from a substituted or unsubstituted C$_1$-C$_8$ alkyl, a substituted or unsubstituted C$_1$-C$_8$ alkoxy, a substituted or unsubstituted C$_2$-C$_8$ alkenyl, a substituted or unsubstituted C$_2$-C$_8$ alkynyl, a substituted or unsubstituted C$_1$-C$_8$ haloalkyl, a substituted or unsubstituted C$_4$-C$_{10}$ heterocycle or a substituted or unsubstituted C$_4$-C$_{10}$ halo heterocycle.

8. The compound of claim 1, wherein
n of $R^1_n$ is 0, 1, 2 or 3;
M is an unsubstituted C$_1$-C$_8$ alkyl;
m is 0 or 1;
q is 0 or 1; and
each $R^a$, $R^b$ or $R^c$ are selected independently from each other from a substituted or unsubstituted C$_1$-C$_8$ alkyl, a substituted or unsubstituted C$_1$-C$_8$ alkoxy, a substituted or unsubstituted C$_2$-C$_8$ alkenyl, a substituted or unsubstituted C$_2$-C$_8$ alkynyl, a substituted or unsubstituted C$_1$-C$_8$ haloalkyl, a substituted or unsubstituted C$_4$-C$_{10}$ heterocycle or a substituted or unsubstituted C$_4$-C$_{10}$ halo heterocycle.

9. The compound of claim 1, wherein
n of $R^{10}_n$ being 1 or 2; and
with each $R^{10}$ independently from any other $R^{10}$ being selected from —OH, —OCH$_3$.

10. The compound of claim 1, wherein n of $R^{11}_n$ is
2 and each $R^{11}$ independently from any other $R^{11}$ is —OH, or —OCH$_3$,
1 and $R^{11}$ is —OH, or
1 and $R^{11}$ is —OCH$_3$.

11. The compound according to claim 1 wherein T is —CO$_2$H.

12. The compound of claim 1, wherein the compound is used to treat a bacterial infection by *Salmonella enteritidis, Pseudomonas aeruginosa, Staphylococcus auereus, Escherichia coli, Bacillus sbutillis, Micrococcus luteus, Bacillus megaterium*, or *Myobacterium phlei*.

13. A compound selected from the group consisting of:

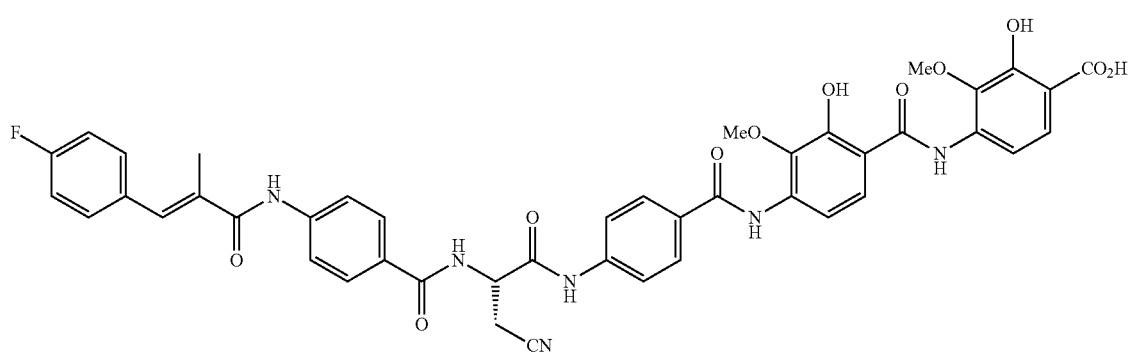
1
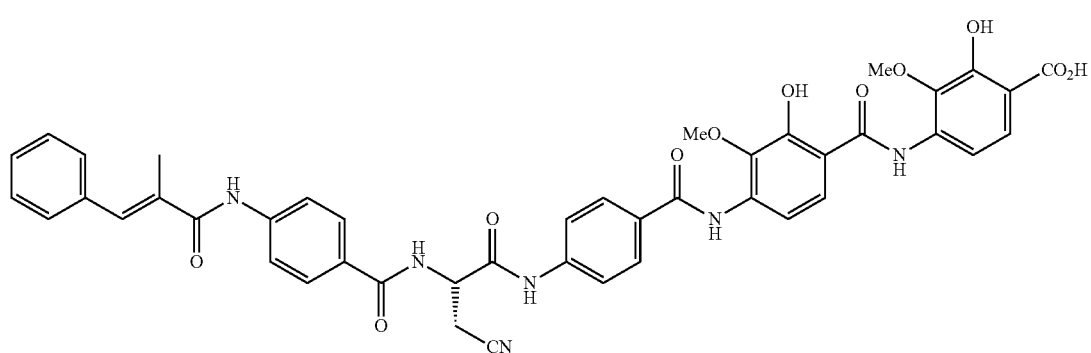
2
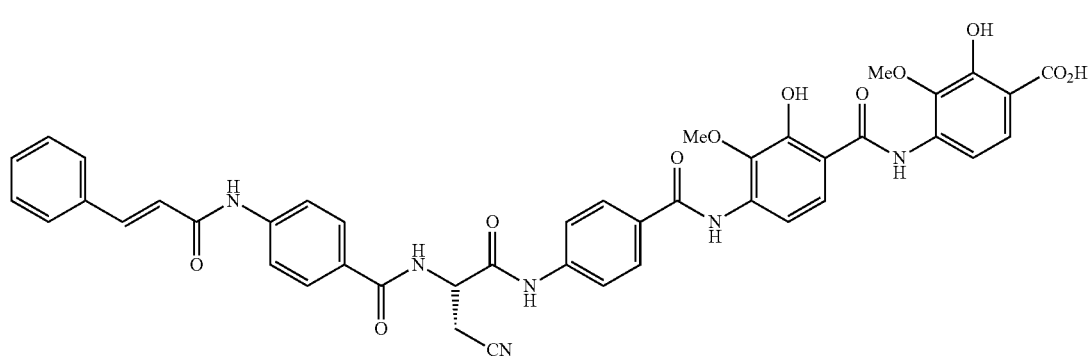
3
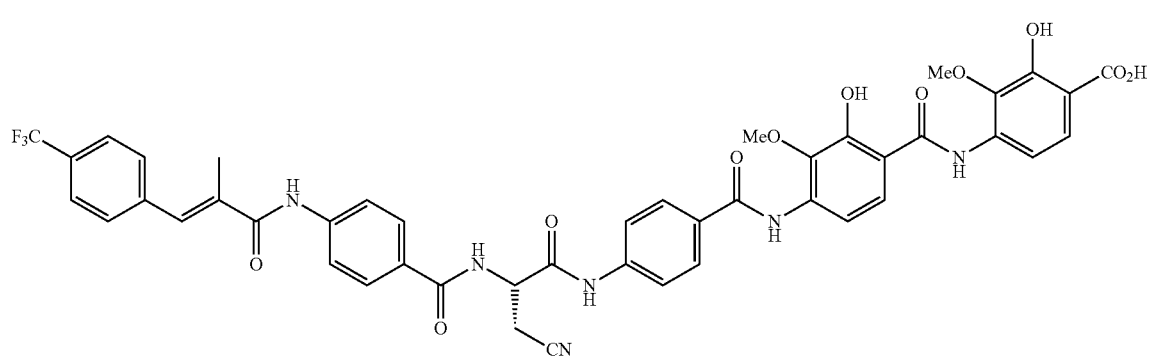
4

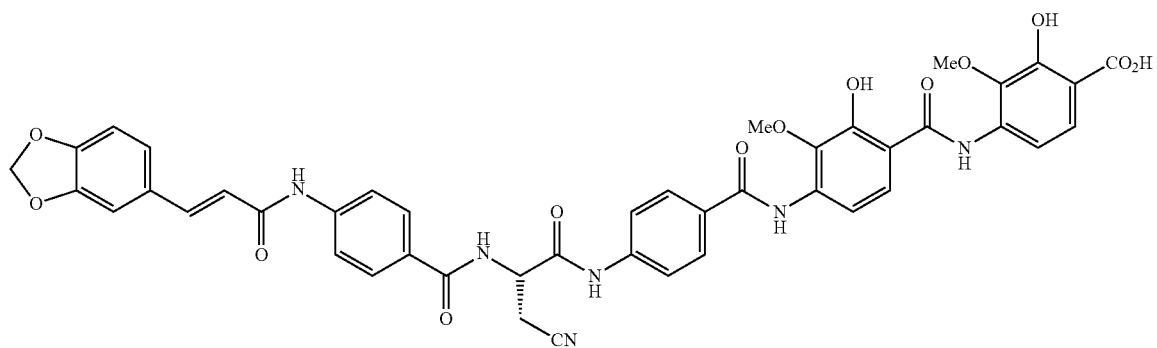
5
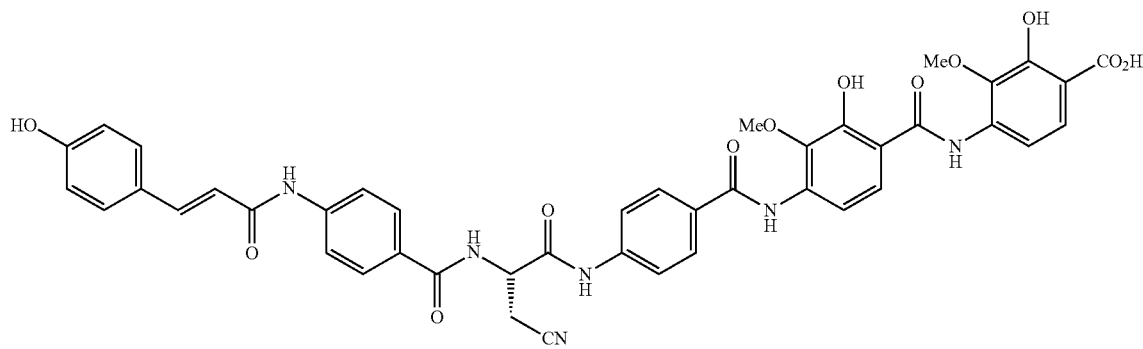
6
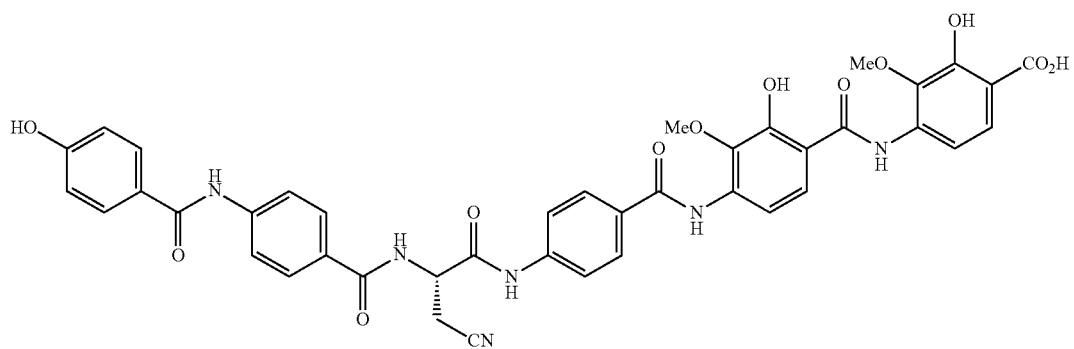
7
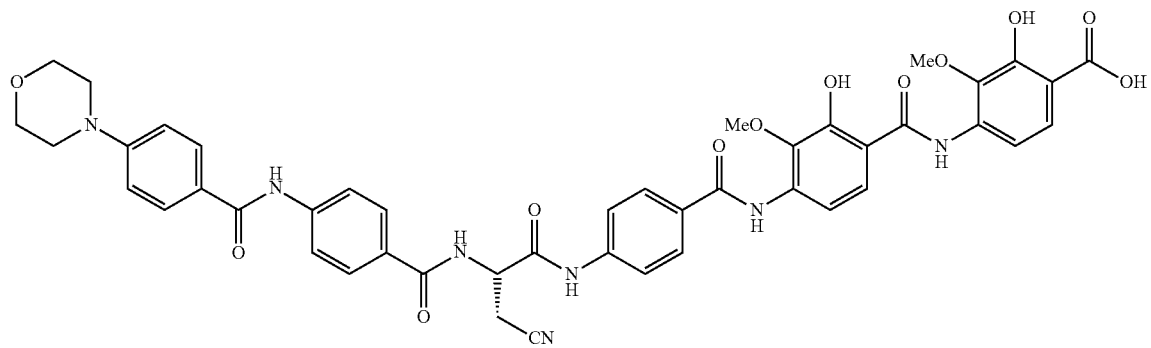
8

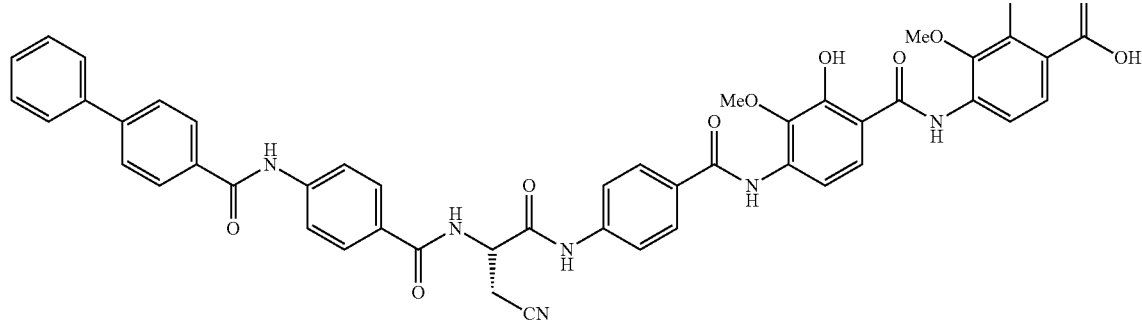
9
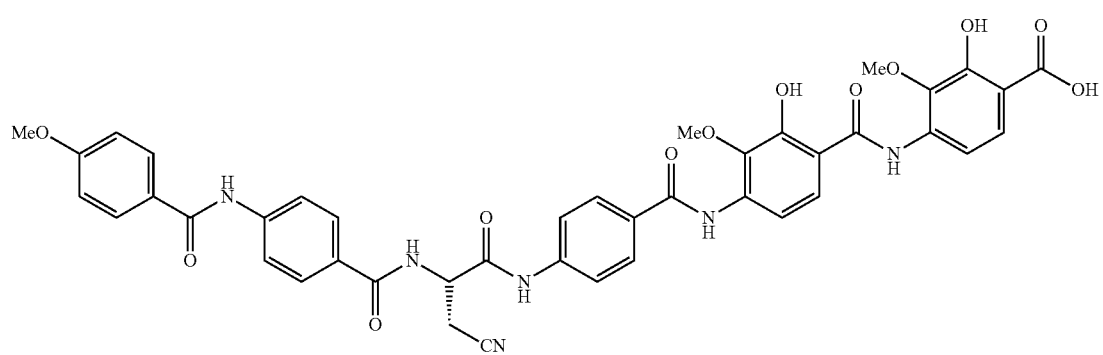
10
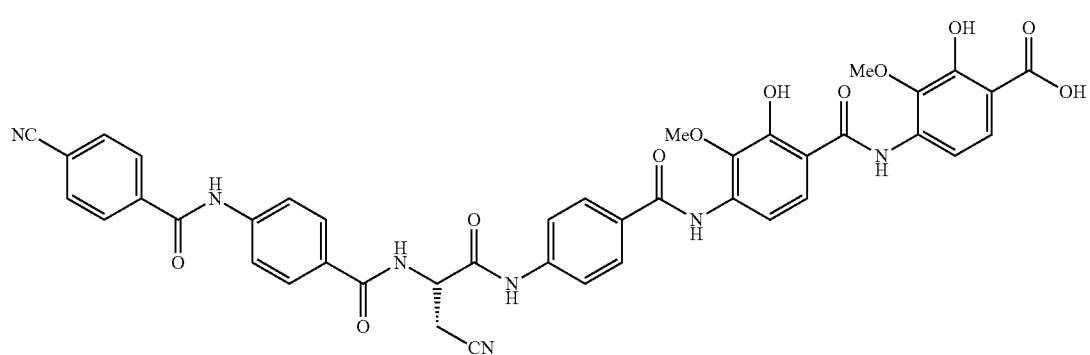
11
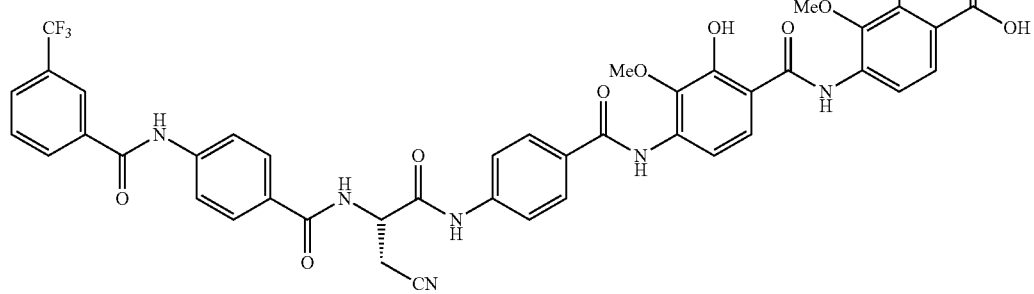
12

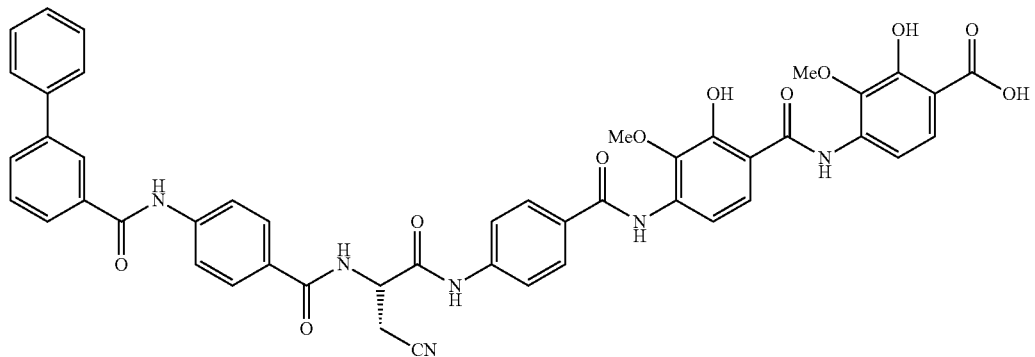
13
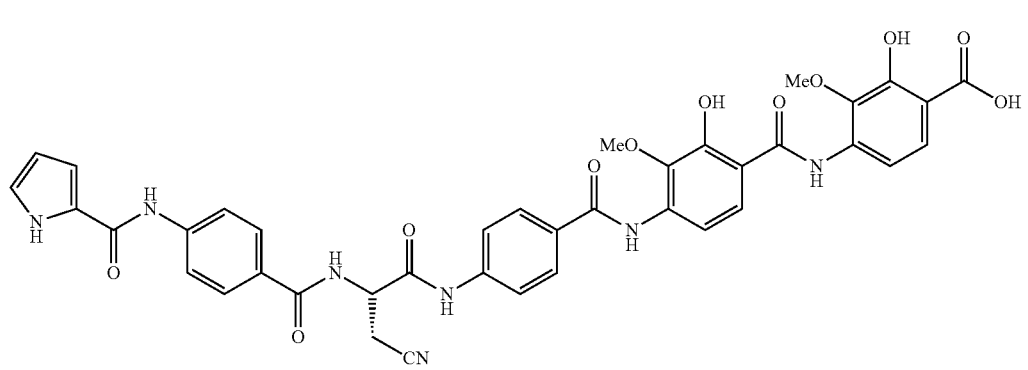
14
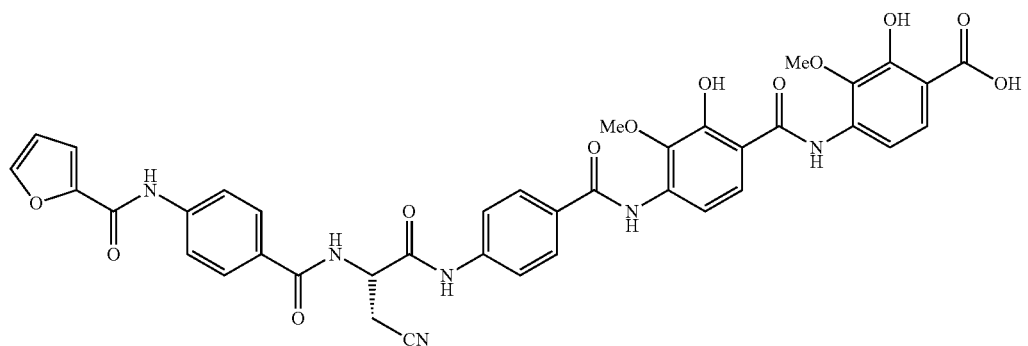
15
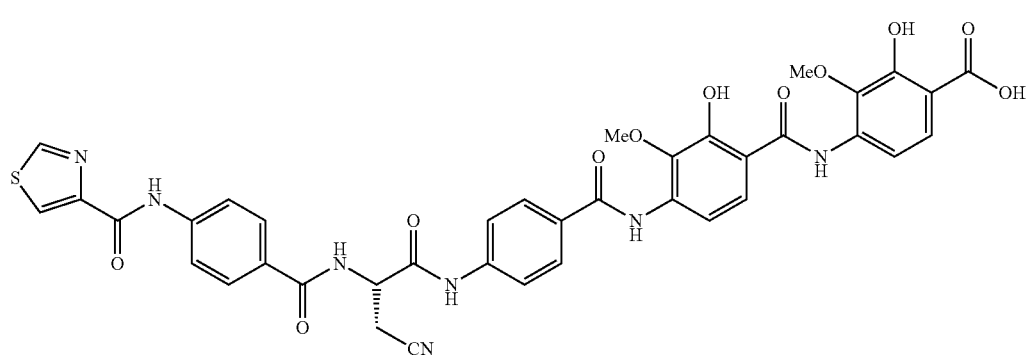
16

-continued
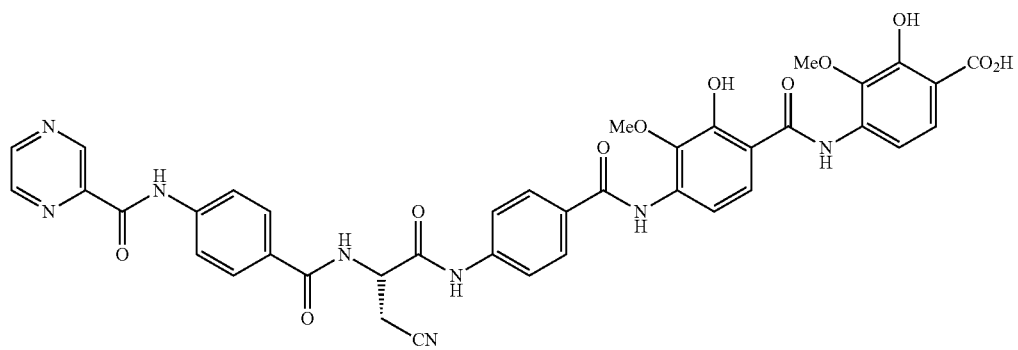
17
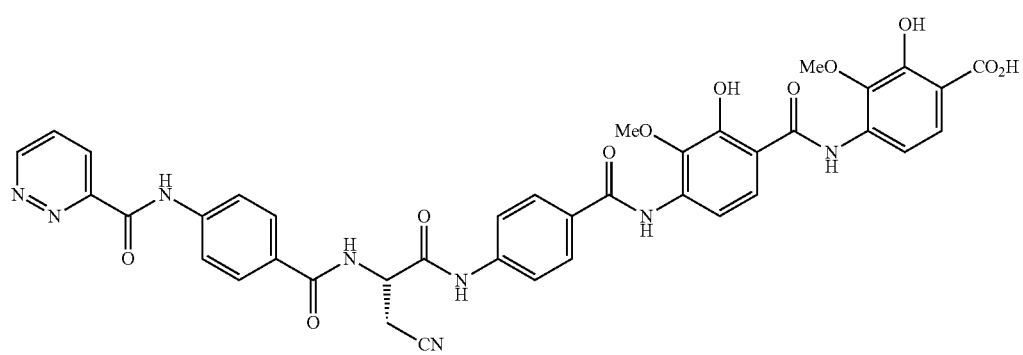
18
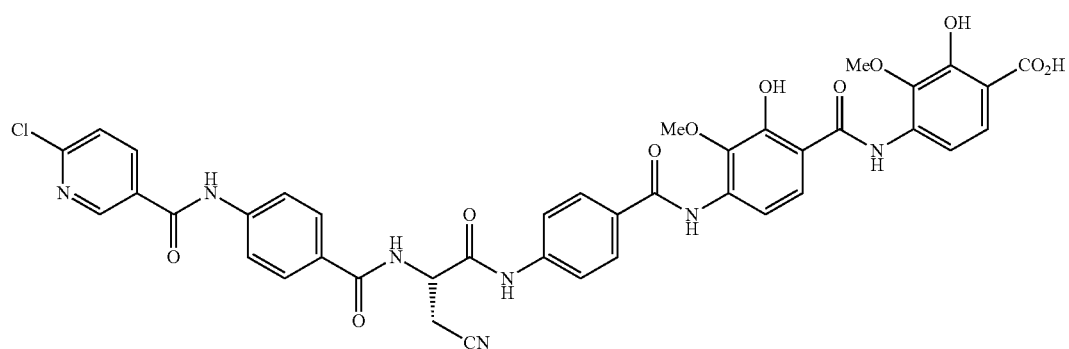
19
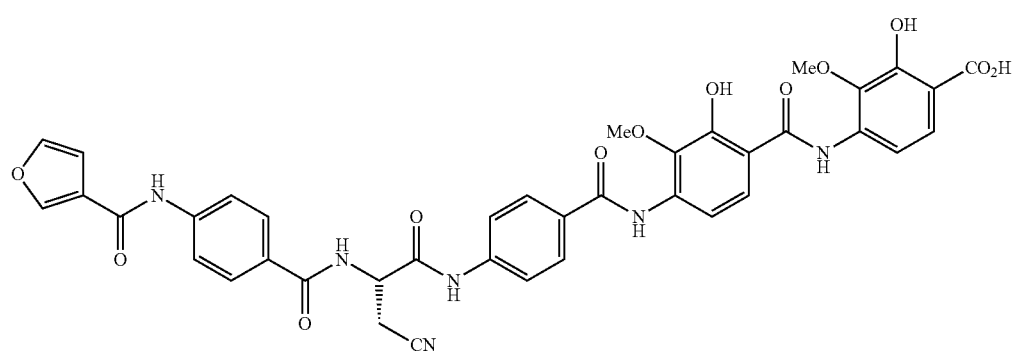
20

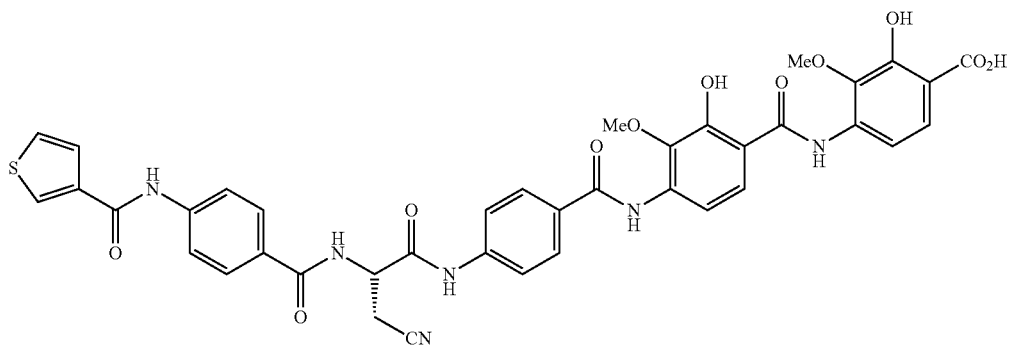
21
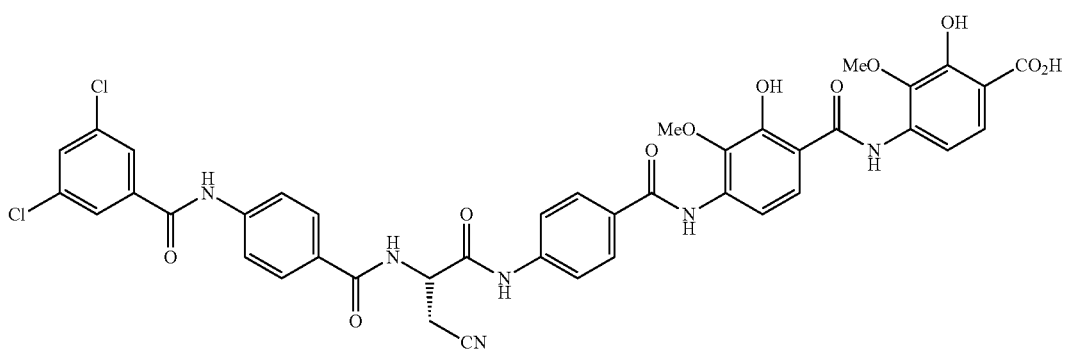
22
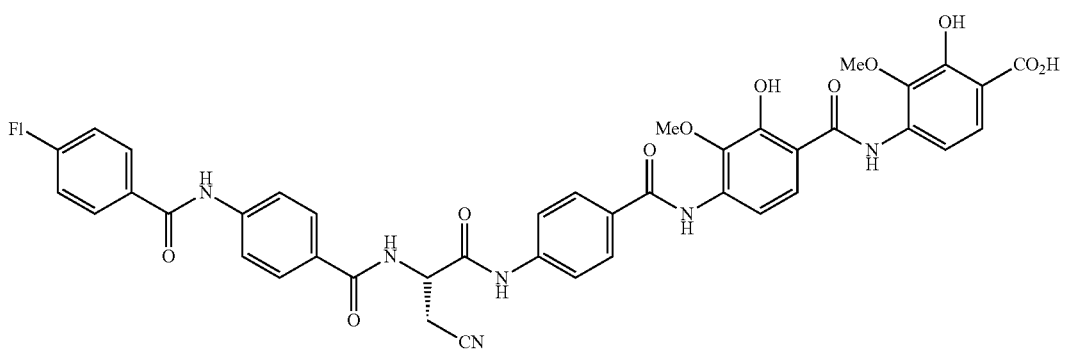
23
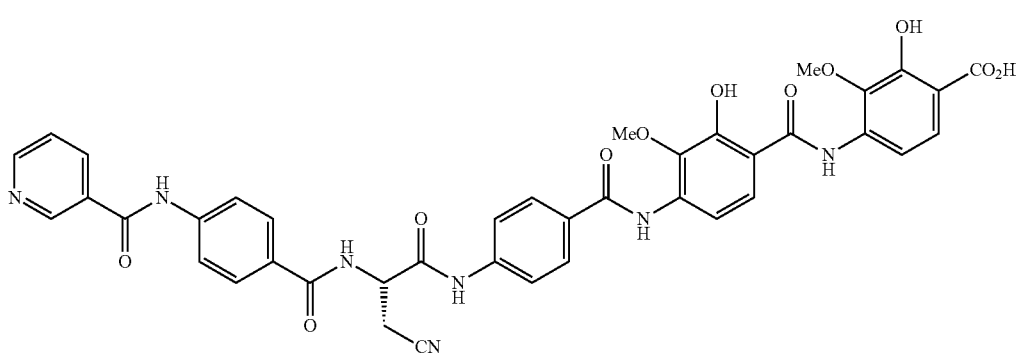
24

25
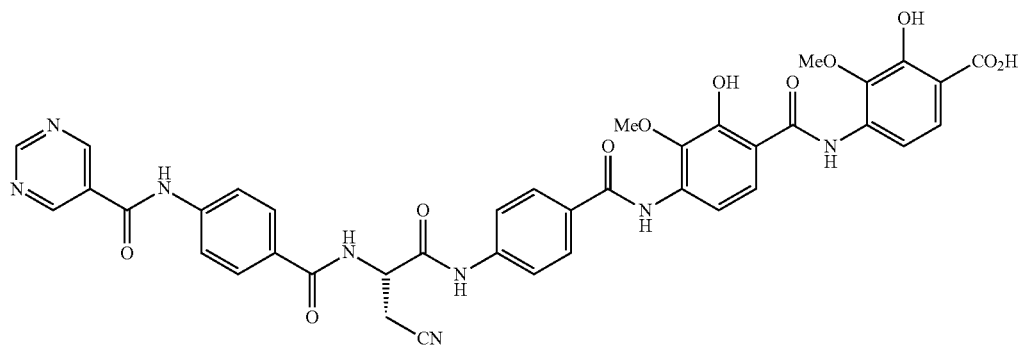
26
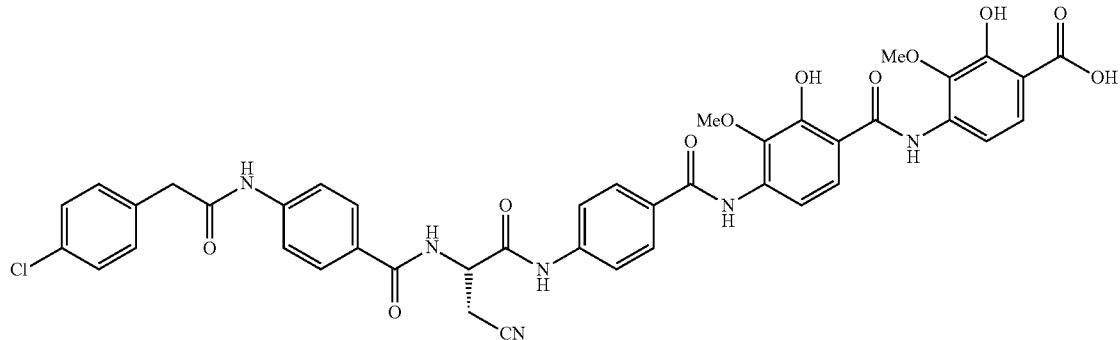
27
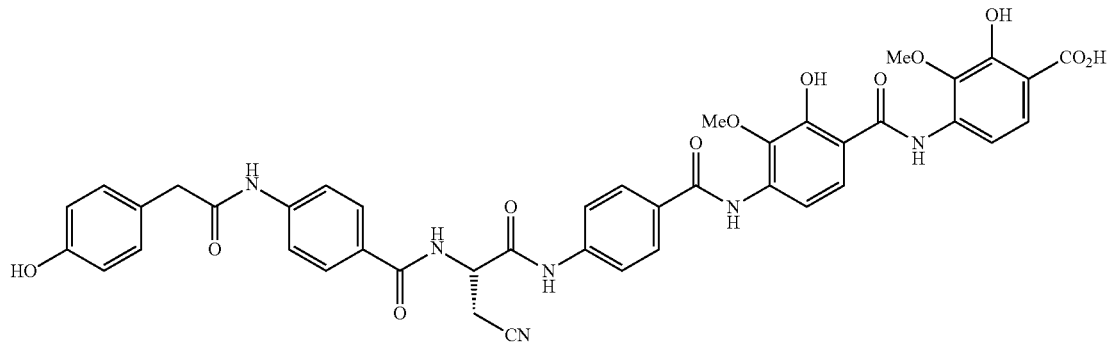
28
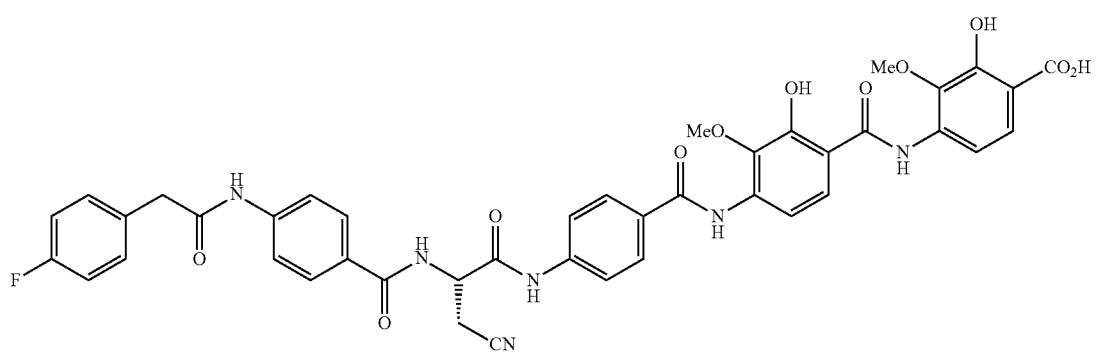

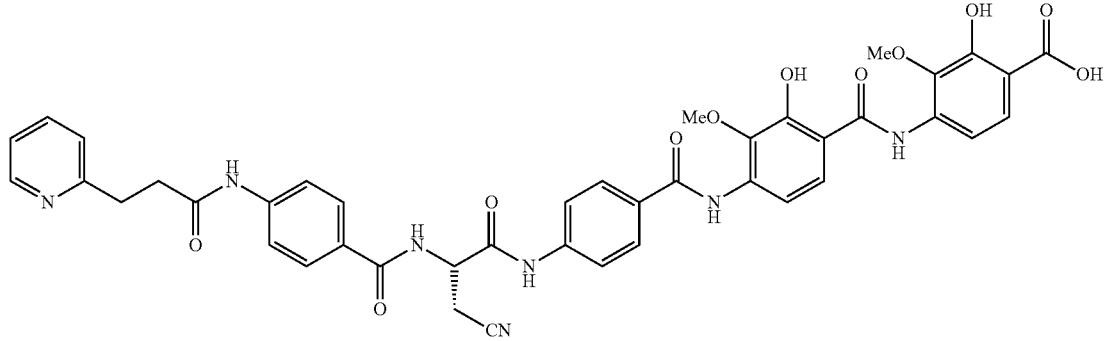
29
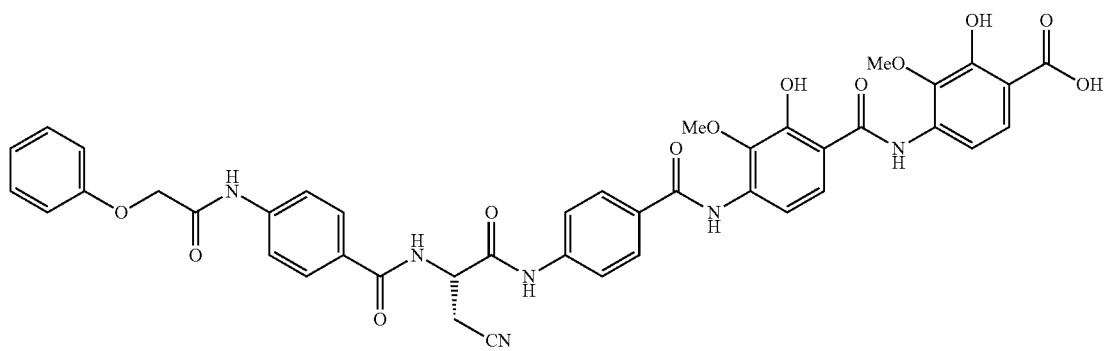
30
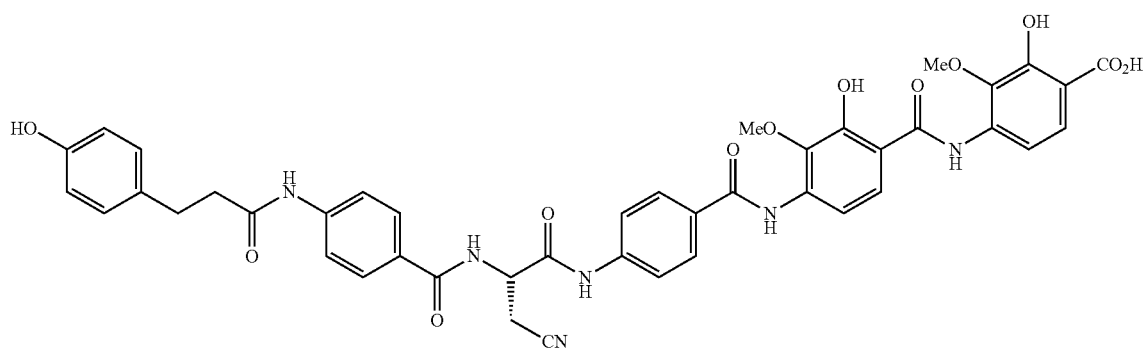
31
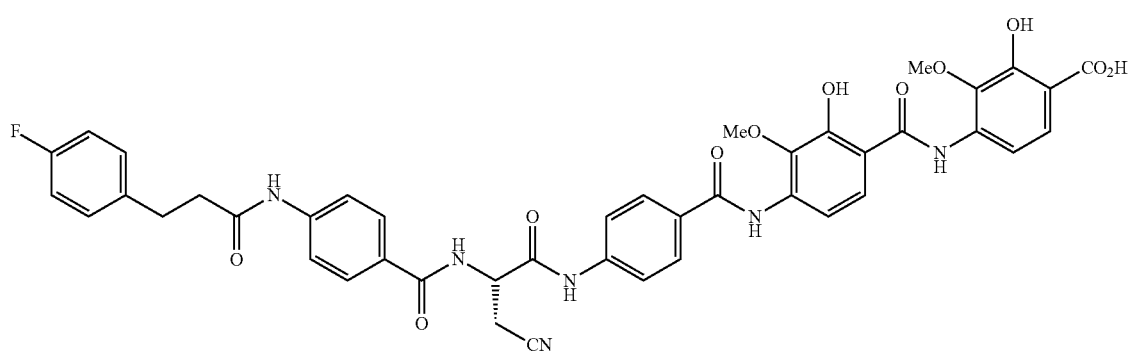
32

34
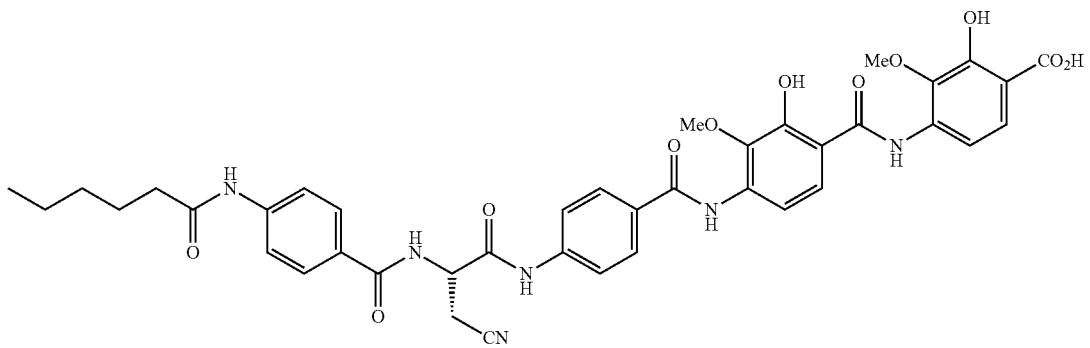
35
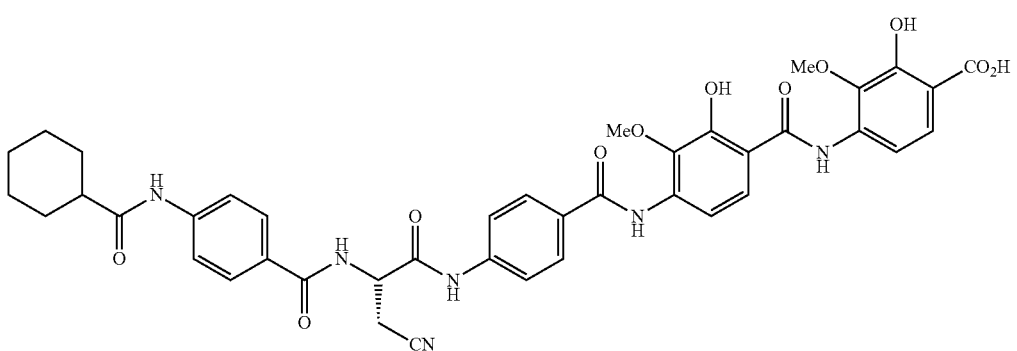
36
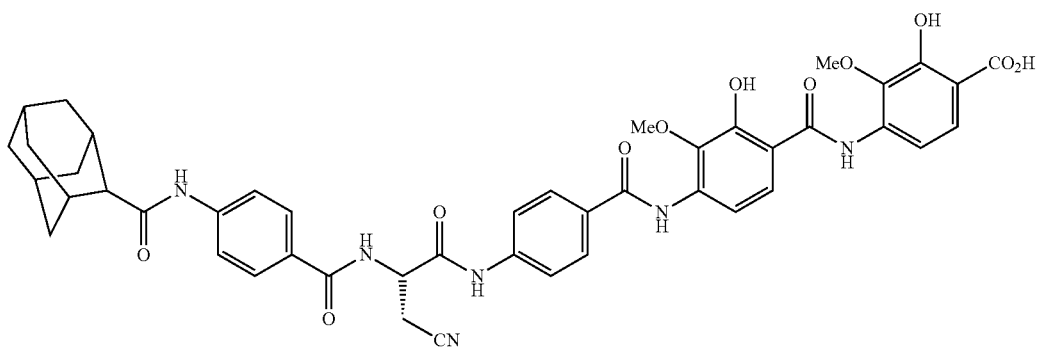
37
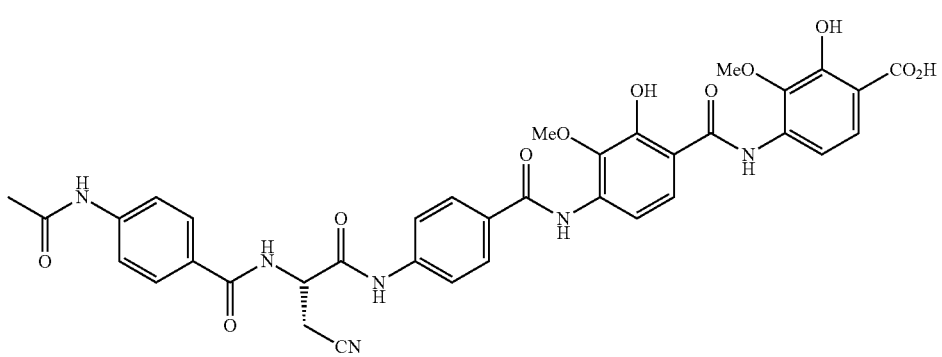

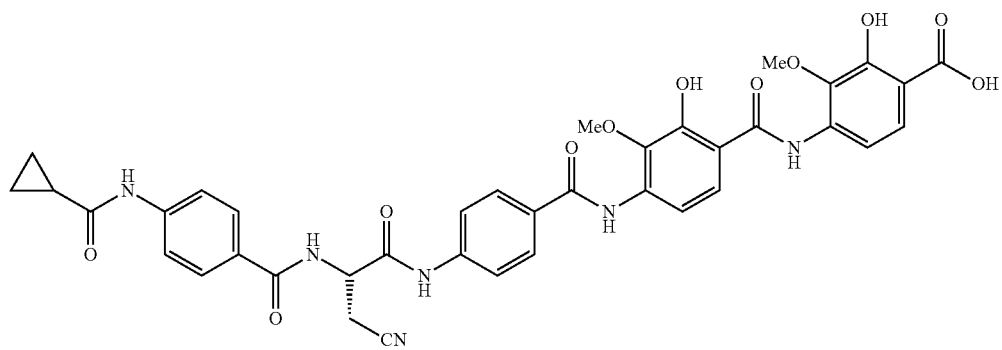
38
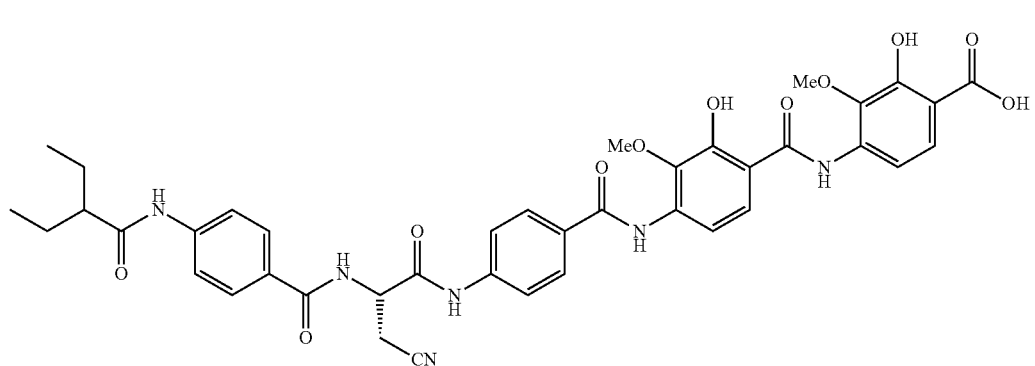
39
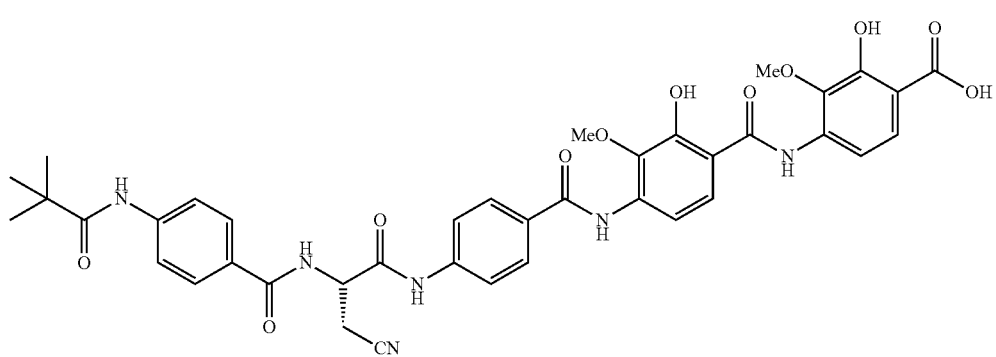
40
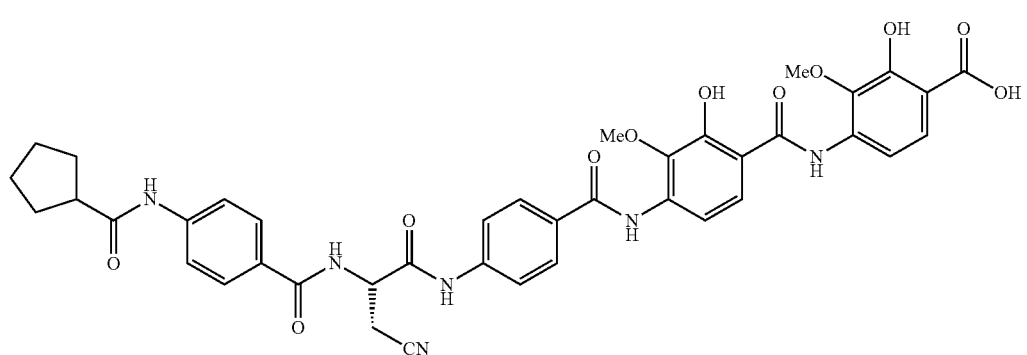
41

-continued
42
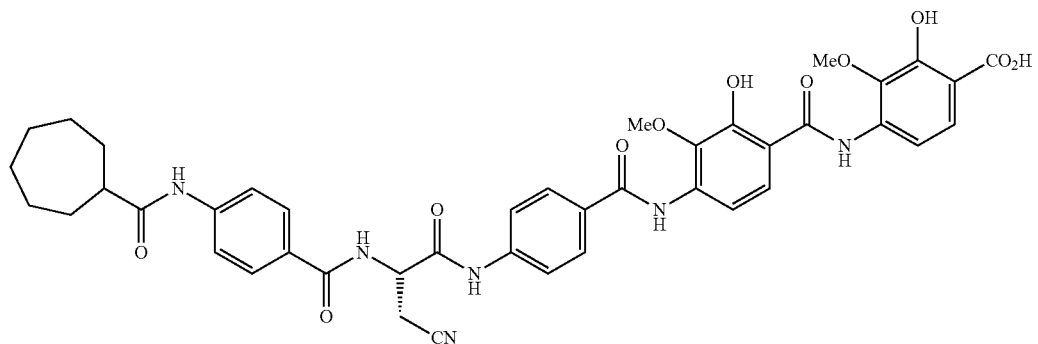
43
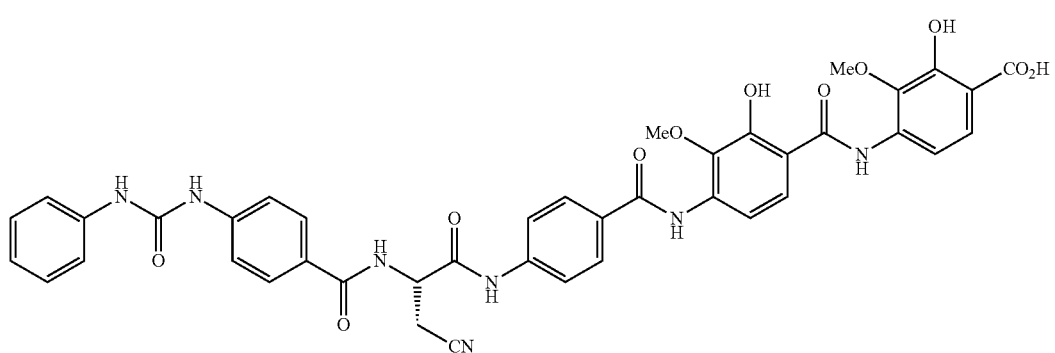
48
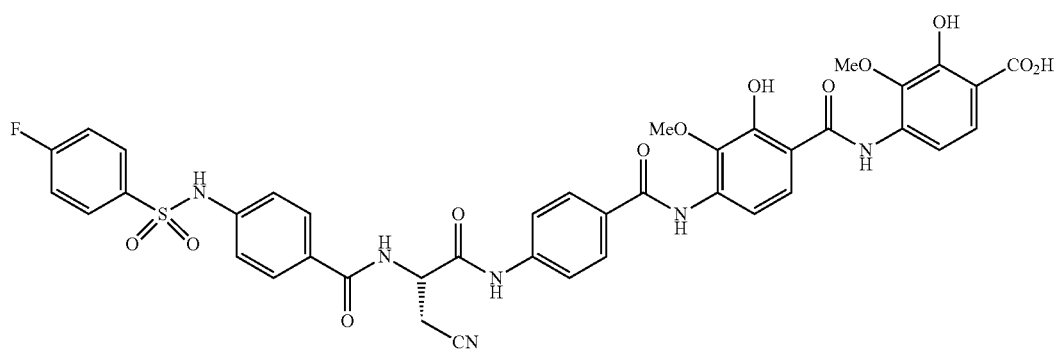
49
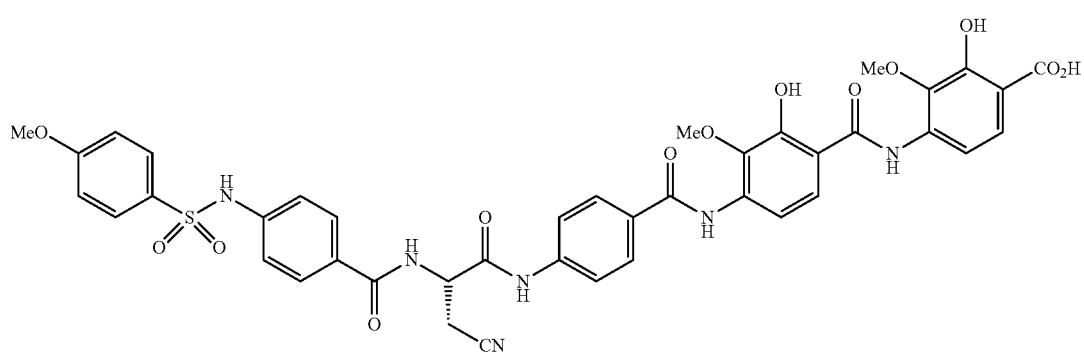

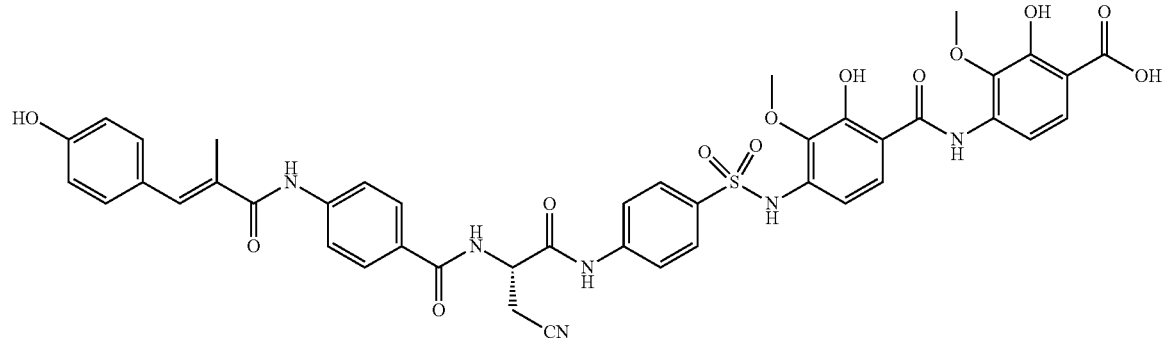
74
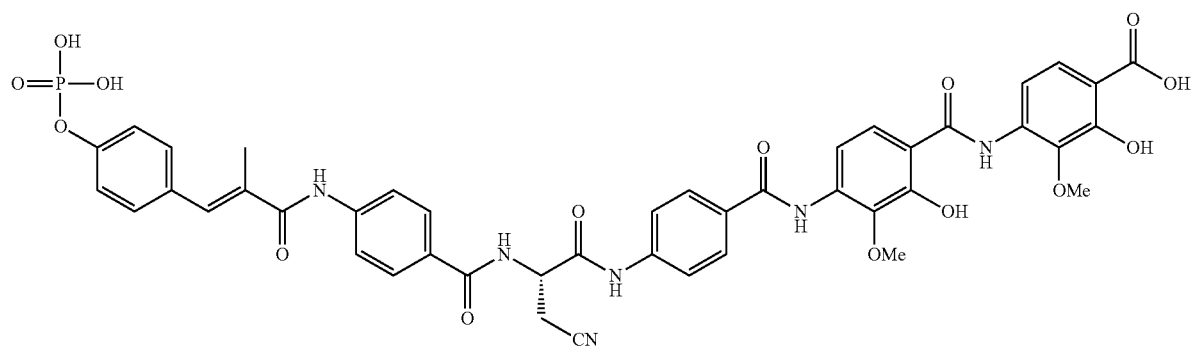
76
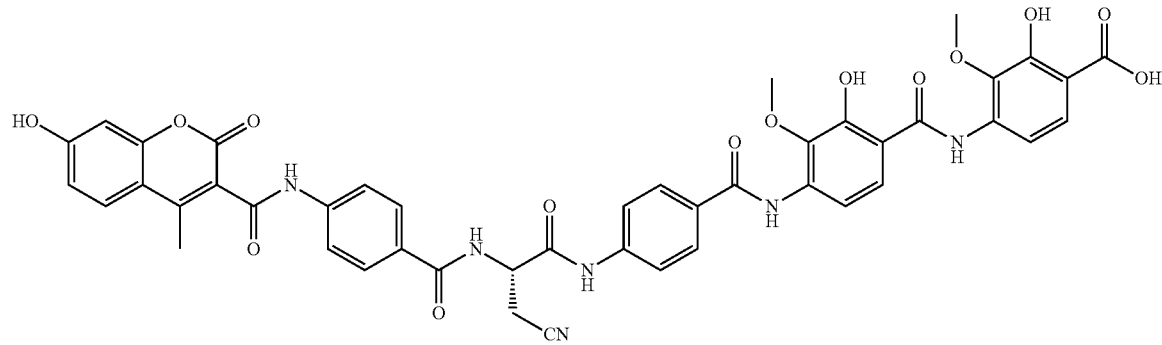
78
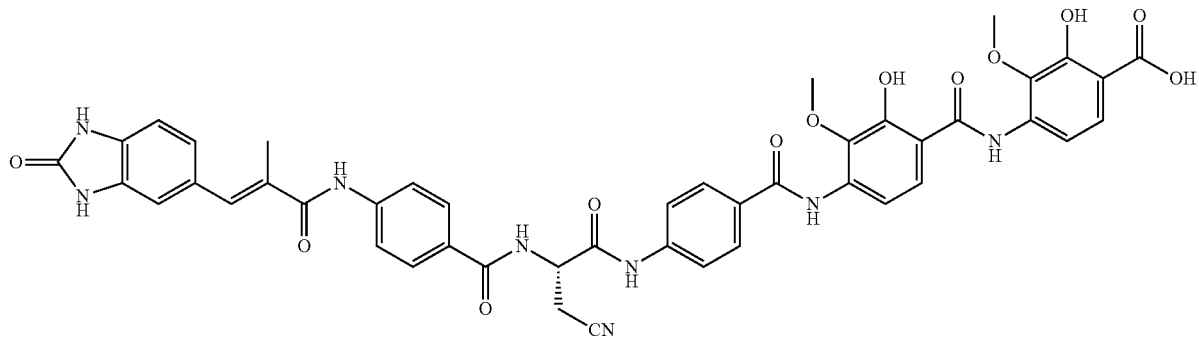
79

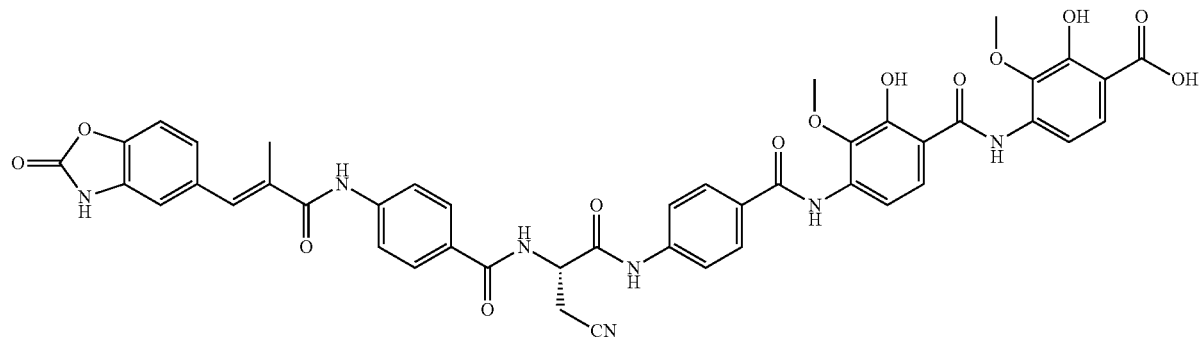
80
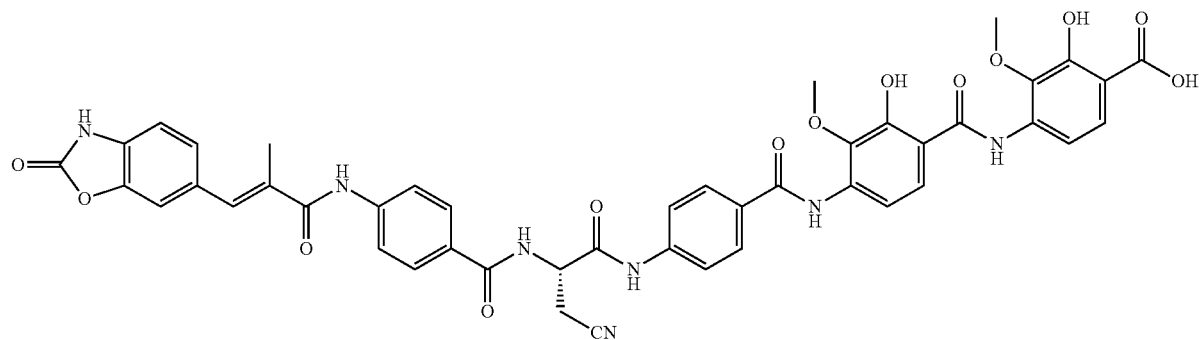
81
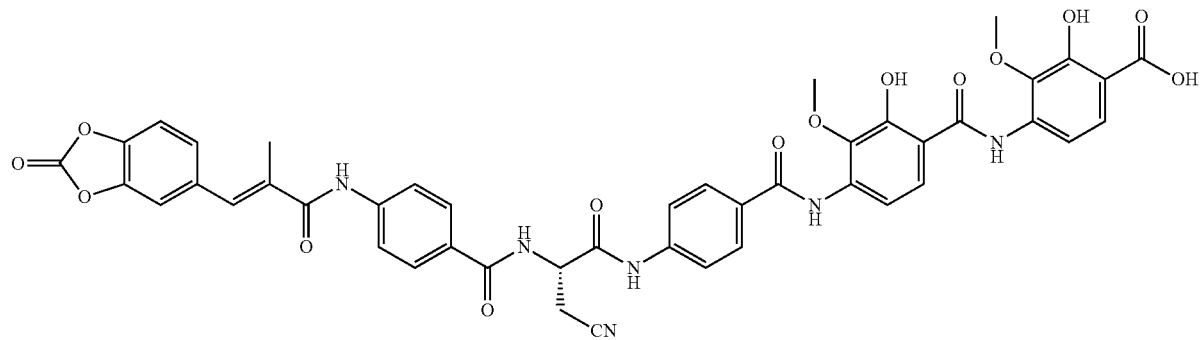
82
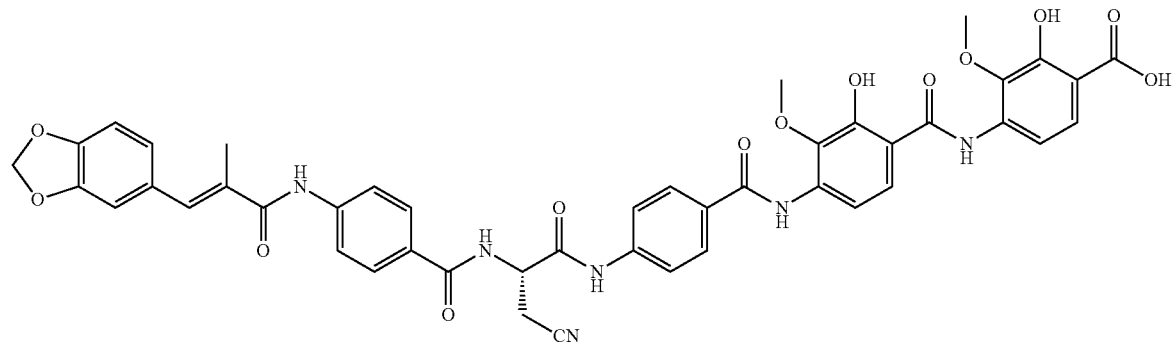
83

84
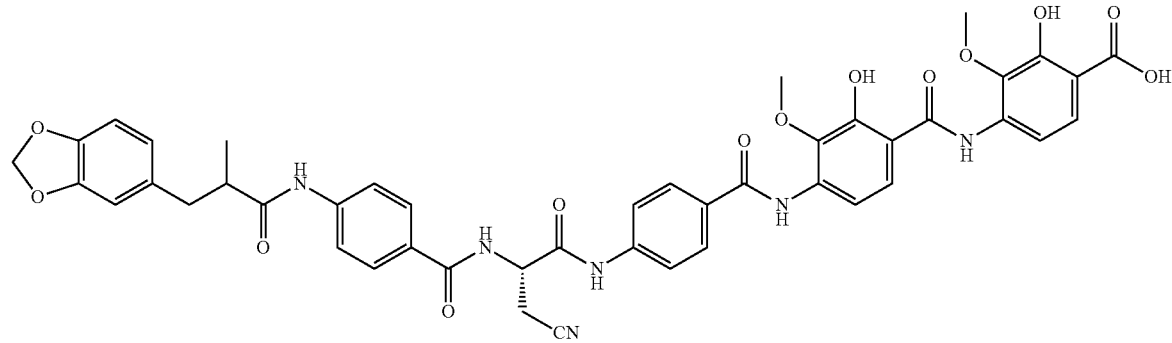
85
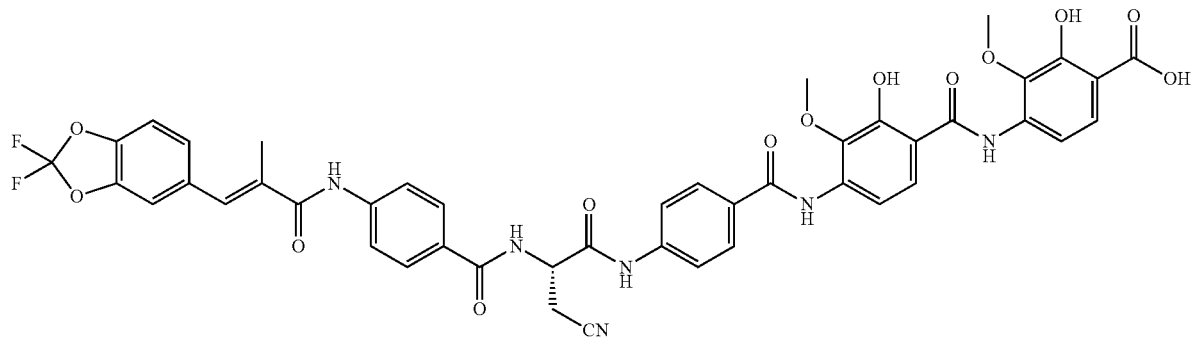
86
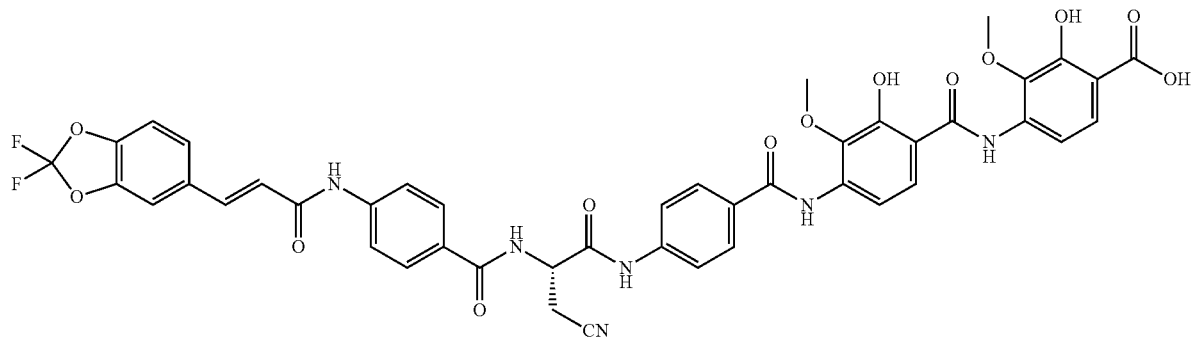
87
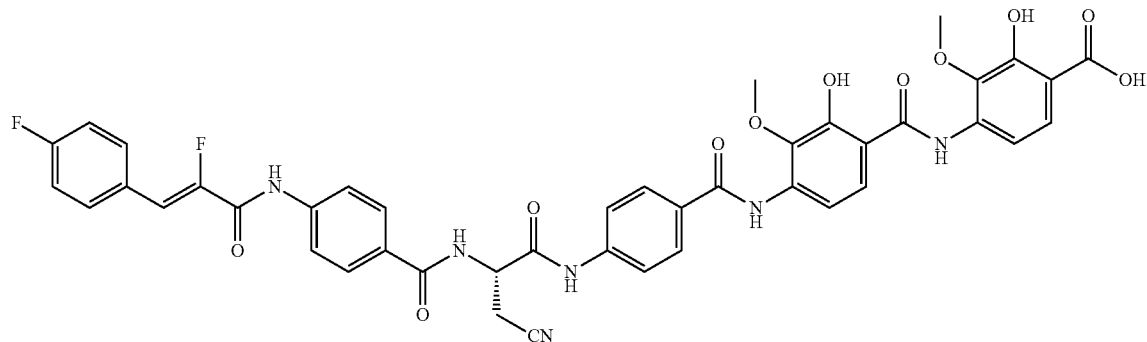

88
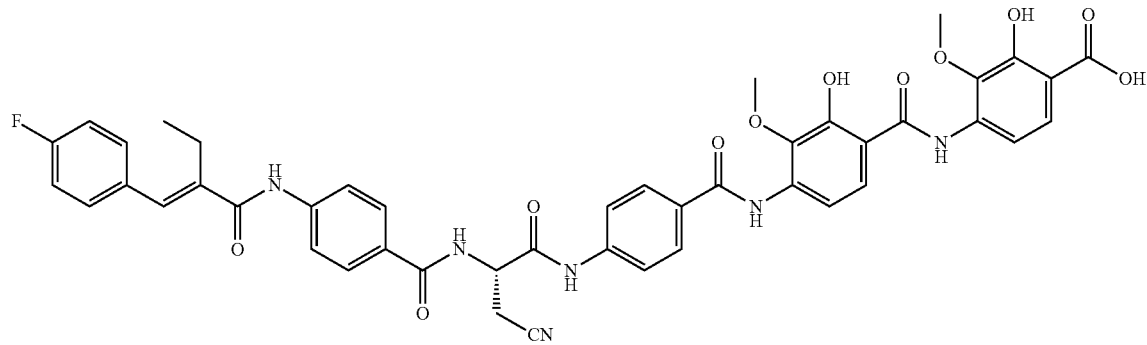
89
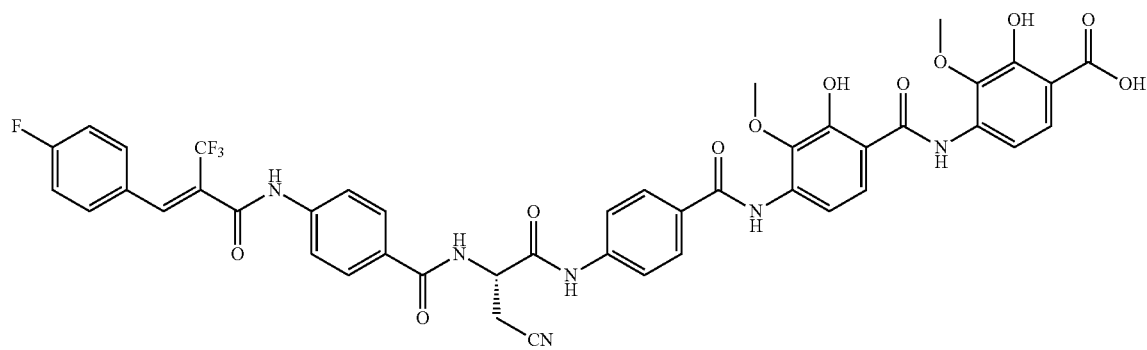
90
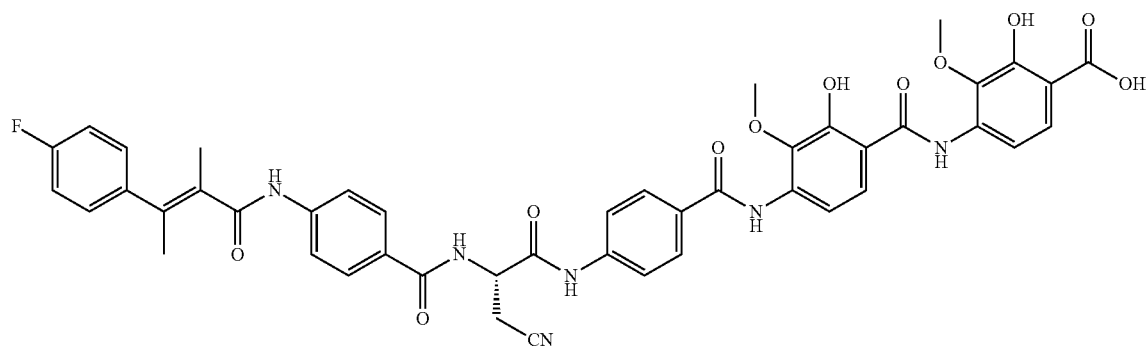
91
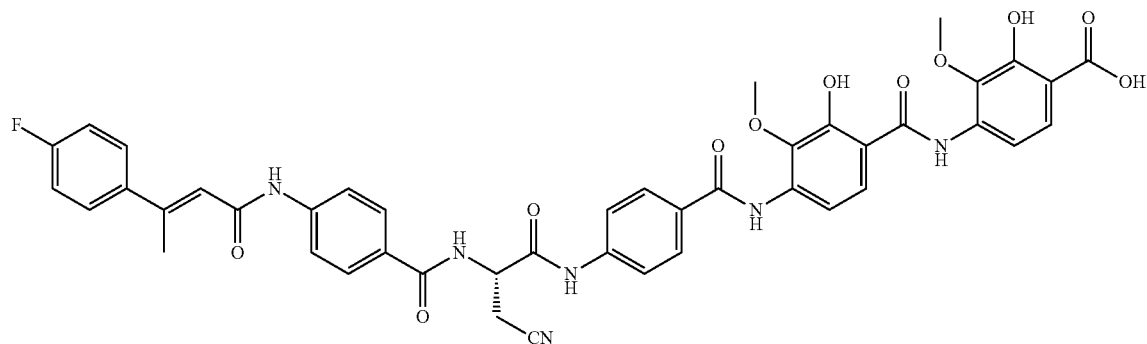

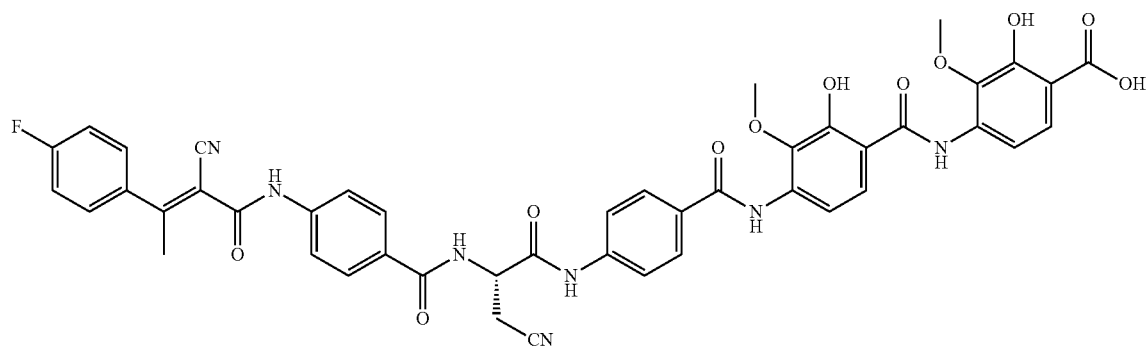
92
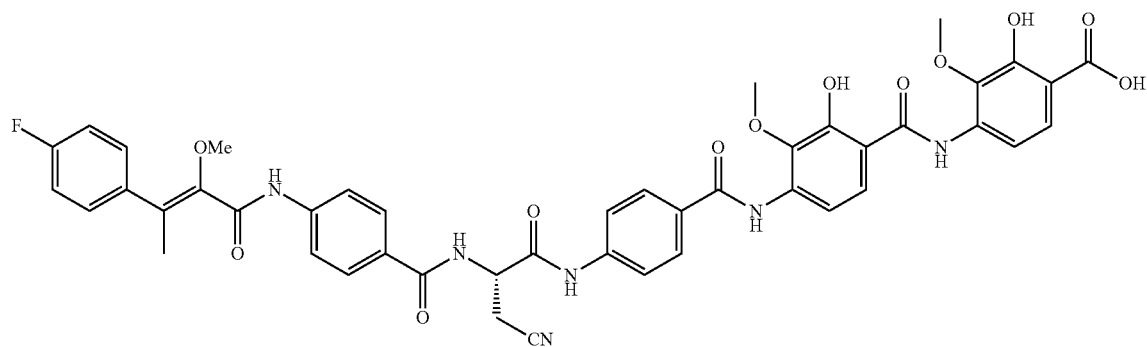
93
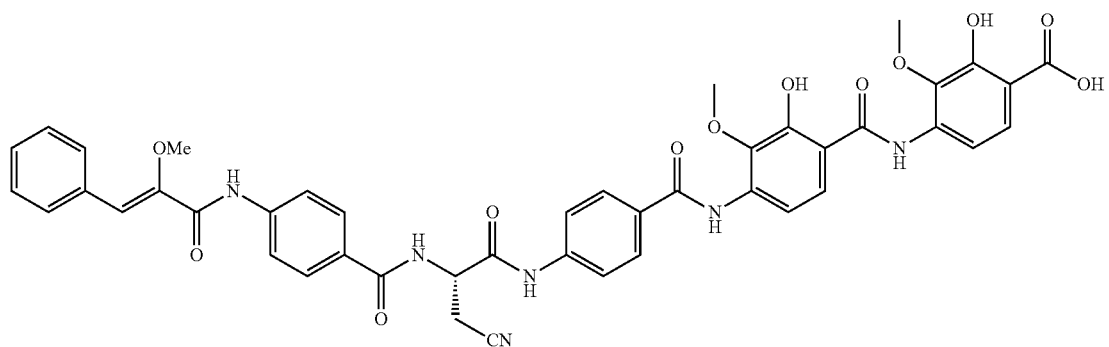
94
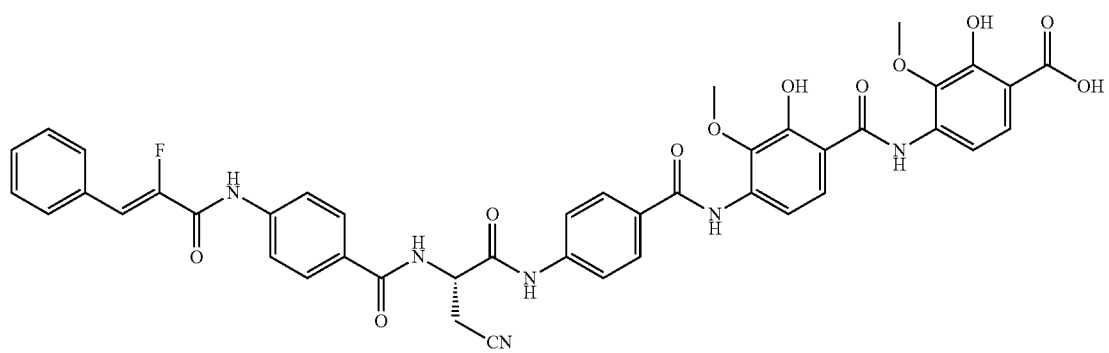
95

96
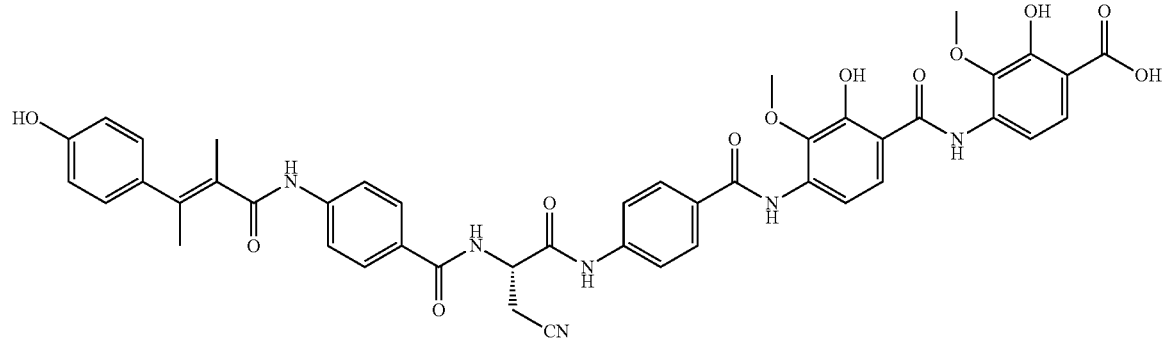
97
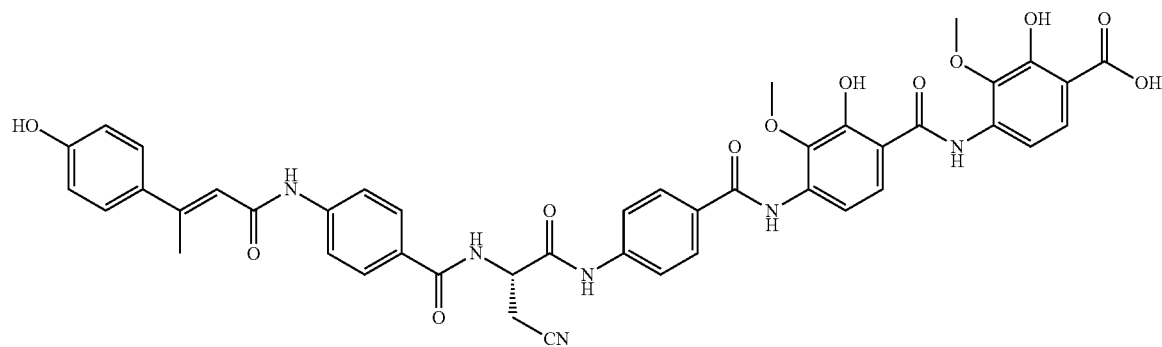
102
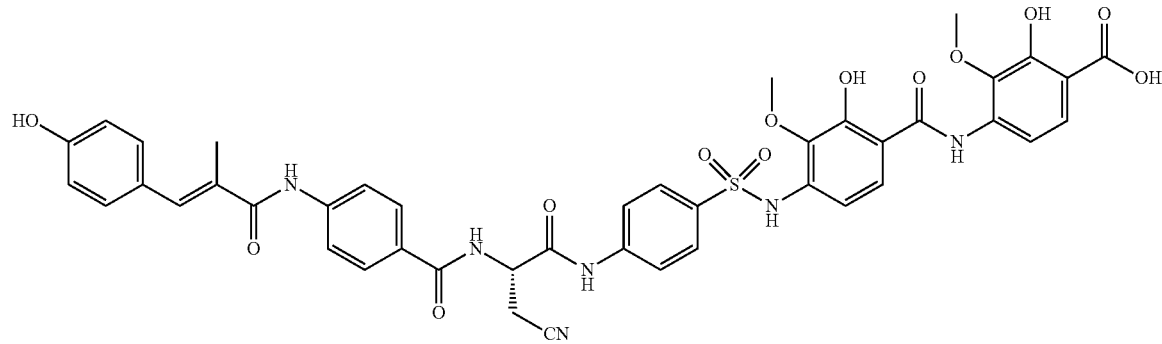
103
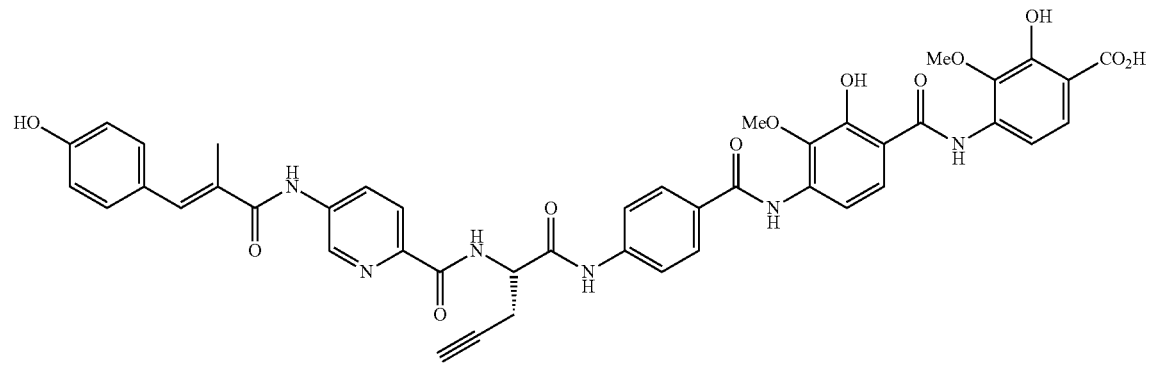

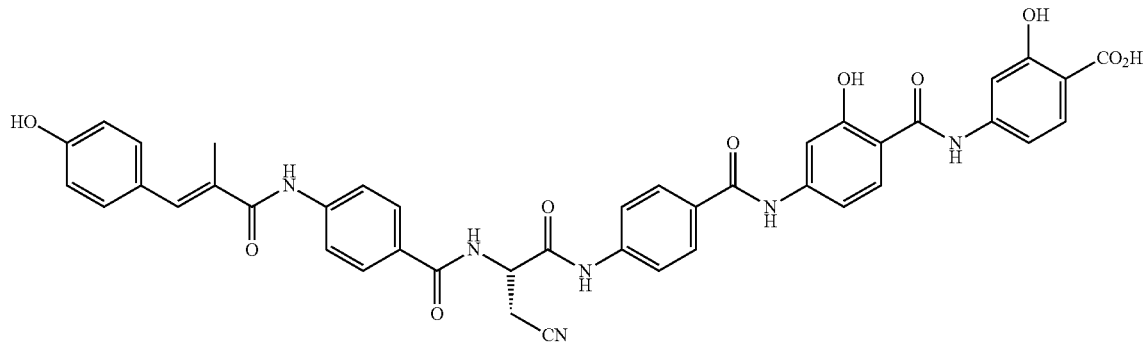
106
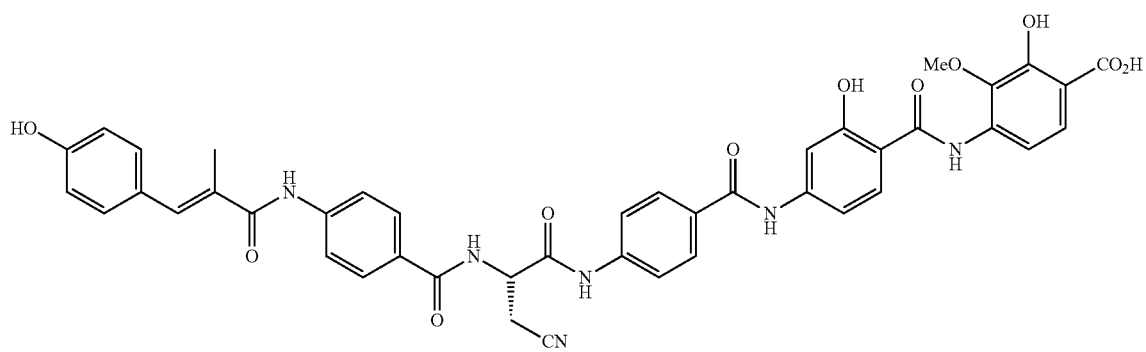
107
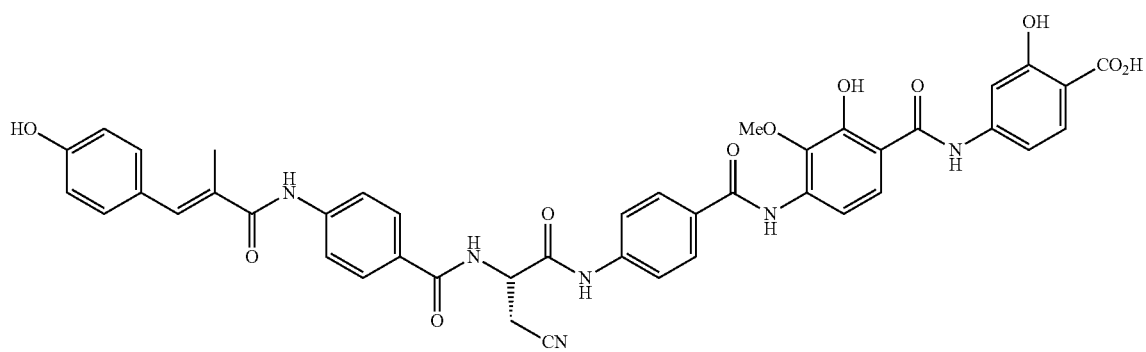
108
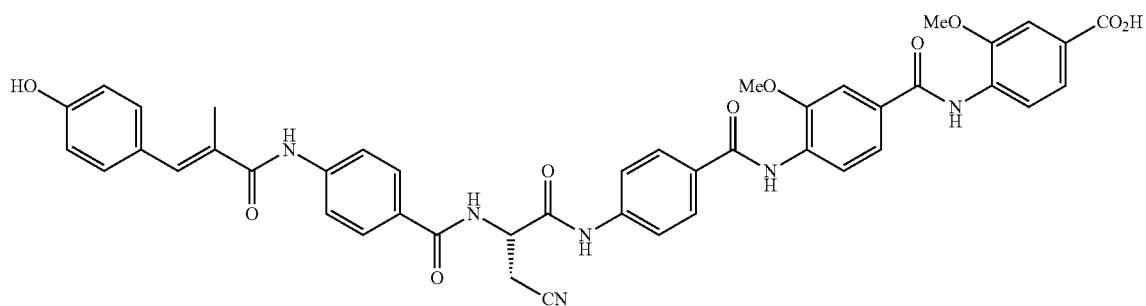
109

-continued
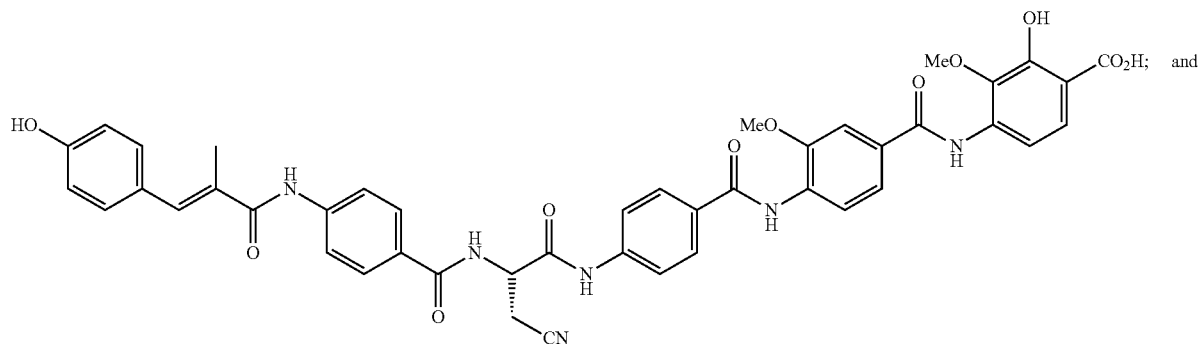
110
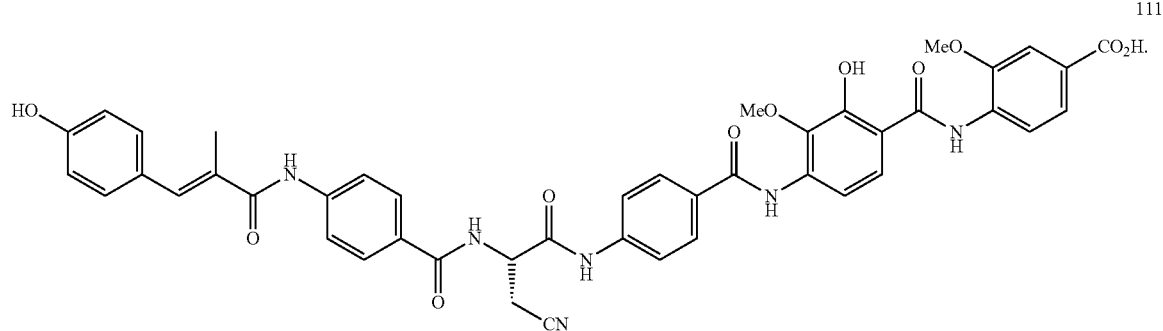
111
14. A compound selected from the group consisting of:
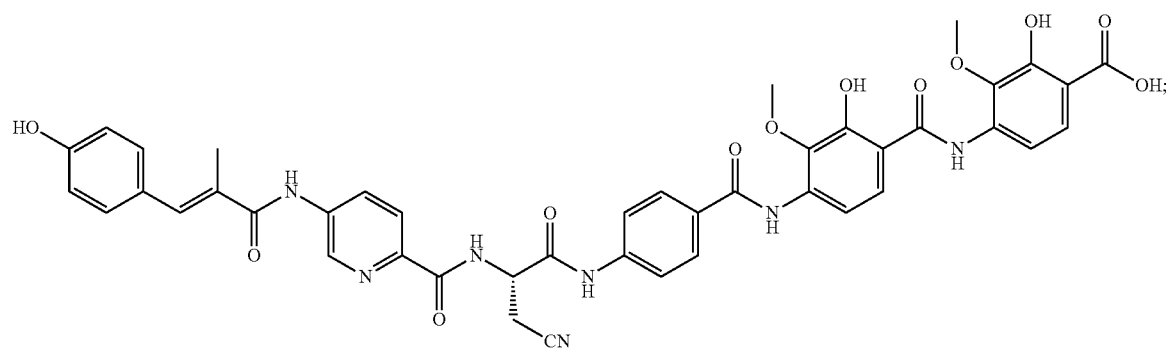
71
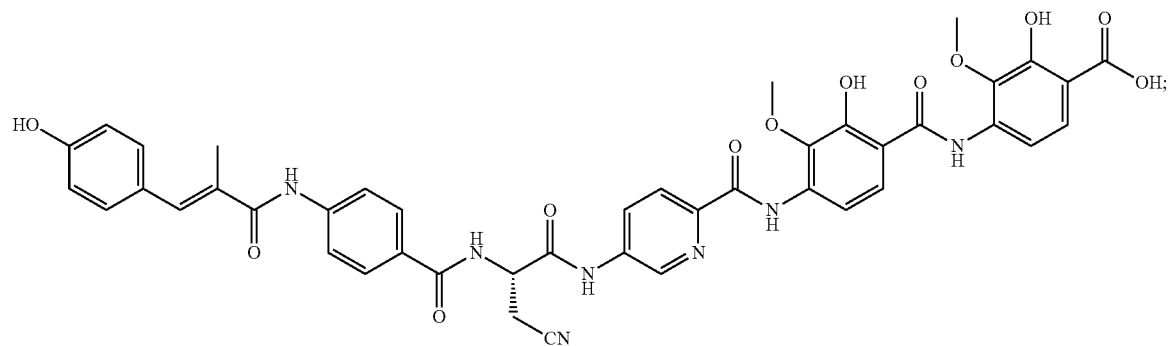
98

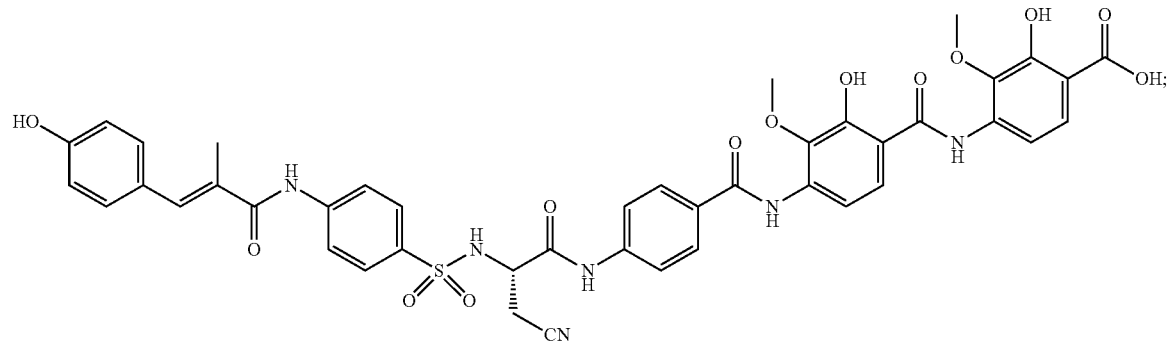
75
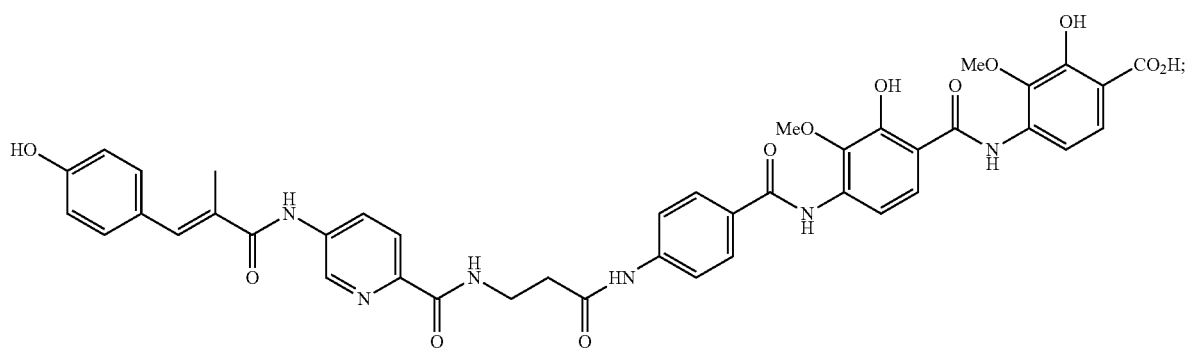
104
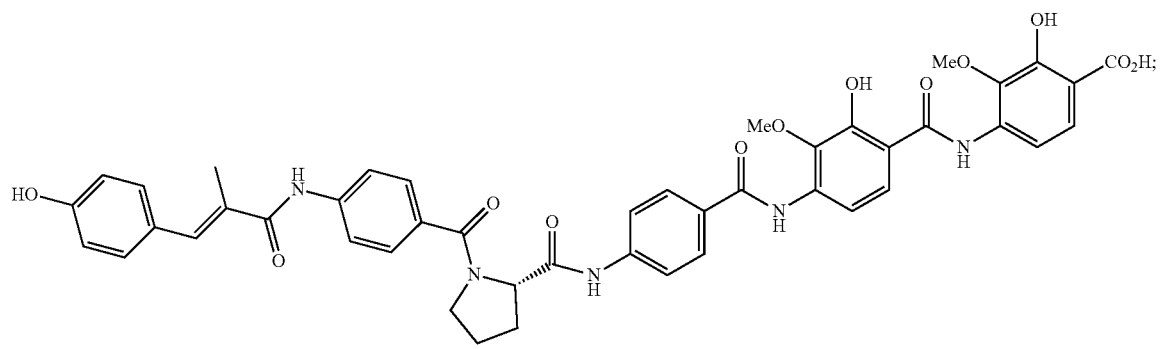
105
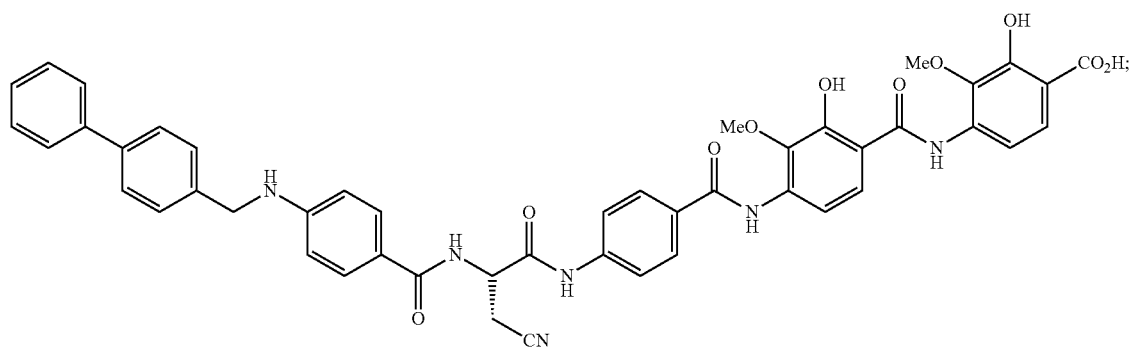
44

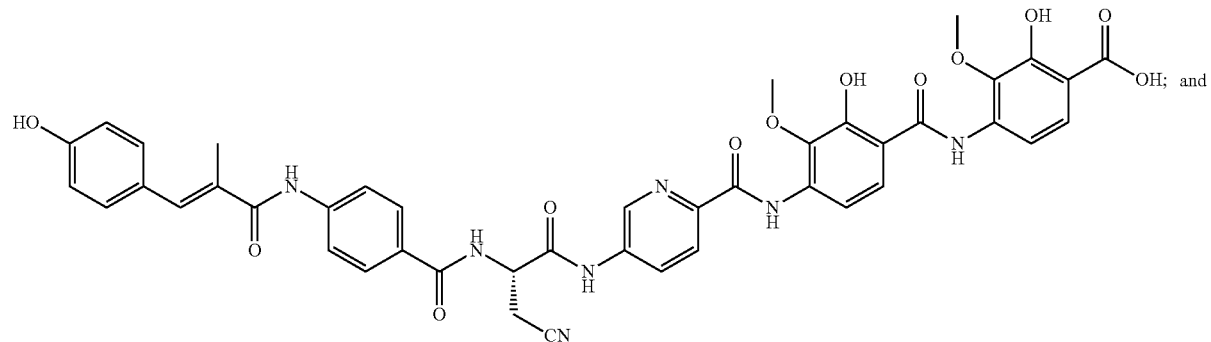
72
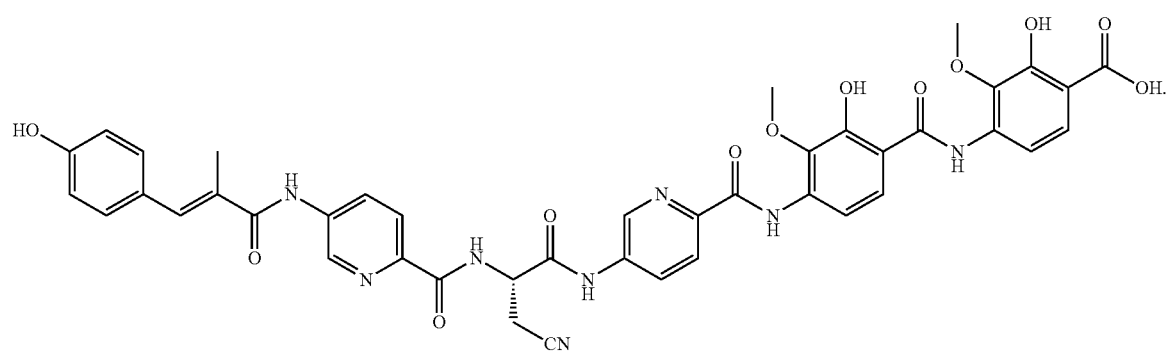
73
* * * * *